(12) United States Patent
Andrews et al.

(10) Patent No.: US 8,273,774 B2
(45) Date of Patent: Sep. 25, 2012

(54) PHENOXYPYRIDINYLAMIDE COMPOUNDS

(75) Inventors: Glen Andrews, Loughborough (GB); Rhona Jane Cox, Loughborough (GB); Christopher De Savi, Loughborough (GB); Premji Meghani, Loughborough (GB); Hitesh Jayantilal Sanganee, Loughborough (GB); Daniel Jon Warner, Loughborough (GB)

(73) Assignee: AstraZeneca AB, Södertälje (SE)

( * ) Notice: Subject to any disclaimer, the term of this patent is extended or adjusted under 35 U.S.C. 154(b) by 456 days.

(21) Appl. No.: 12/471,599

(22) Filed: May 26, 2009

(65) Prior Publication Data

US 2010/0041638 A1 Feb. 18, 2010

Related U.S. Application Data

(60) Provisional application No. 61/128,939, filed on May 27, 2008.

(51) Int. Cl.
*A61K 31/44* (2006.01)
*C07D 213/62* (2006.01)

(52) U.S. Cl. ........................ 514/350; 546/298
(58) Field of Classification Search ........................ None
See application file for complete search history.

(56) References Cited

U.S. PATENT DOCUMENTS

2004/0102472 A1 5/2004 Albaneze-Walker et al.

FOREIGN PATENT DOCUMENTS

| EP | 0260817 | 3/1988 |
| WO | WO93/19068 | 9/1993 |
| WO | WO98/02162 | 1/1998 |
| WO | WO99/07704 | 2/1999 |
| WO | WO 9924404 | * 5/1999 |
| WO | WO00/45800 | 8/2000 |
| WO | WO02/094823 | 11/2002 |
| WO | WO2004/047836 | 6/2004 |
| WO | WO2004/048374 | 6/2004 |
| WO | WO2004/105698 | 12/2004 |
| WO | WO2007/050576 | 5/2007 |
| WO | WO2007/101213 | 9/2007 |

OTHER PUBLICATIONS

Pages (Expert Opinion on Therapeutic Patents, 2009, 19(11), 1501-1519.*

* cited by examiner

*Primary Examiner* — Noble Jarrell
(74) *Attorney, Agent, or Firm* — Fish & Richardson P.C.

(57) ABSTRACT

The present invention provides a compound of a formula (I):

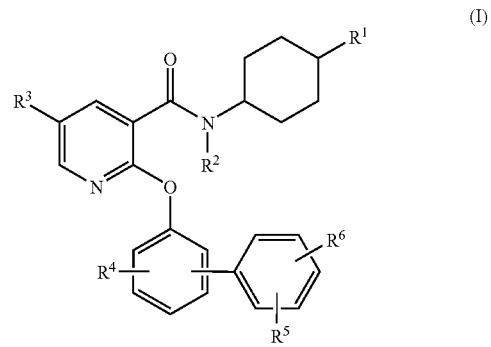

(I)

wherein the variables are defined herein; to a process for preparing such a compound; and to the use of such a compound in the treatment of a PDE4 mediated disease state.

20 Claims, No Drawings

PHENOXYPYRIDINYLAMIDE COMPOUNDS

This application claims the benefit under 35 U.S.C. §119(e) of U.S. Provisional Application No. 61/128,939 filed on 27 May 2008, which is incorporated herein by reference in its entirety.

The present invention concerns phenoxypyridinylamide derivatives having pharmaceutical activity, to processes for preparing such derivatives, to pharmaceutical compositions comprising such derivatives and to the use of such derivatives as active therapeutic agents.

Pharmaceutically active pyridopyrimidine derivatives are disclosed in EP-A-0260817, WO 98/02162, WO 93/19068, WO 00/45800 and WO 2007/101213.

Pharmaceutically active 1,4-dihydro-1,8-naphthyridines are disclosed in WO 2007/050576, WO 2004/105698, US 2004/0102472, WO 2004/048374, WO 2004/047836, WO 02/094823 and WO 99/07704.

Phosphodiesterases (PDEs) work by converting cAMP or cGMP to AMP and GMP, or the inactive nucleotide forms incapable of activating downstream signalling pathways. The inhibition of PDEs leads to the accumulation of cAMP or cGMP, and subsequent activation of downstream pathways. PDEs comprise a large family of second messengers with 11 families and over 50 isoforms. In addition splice variants have been described for each isoform. The PDEs can be cAMP-specific (PDE4, 7, 8, 10), cGMP specific (PDE5, 6, 9) or have dual specificity (PDE1, 2, 3, 11).

cAMP is generated from ATP at the inner leaflet of the plasma membrane through the action of GPCR-regulated adenylate cyclase. Once cAMP is generated, the only way to terminate the signal is through phosphodiesterase action, degrading cAMP into 5'-AMP. Increased concentrations of cAMP are translated into cellular responses mainly by activation of cAMP-dependent protein kinase (PKA). The specific activity of PKA is in part regulated by the sub-cellular localization of PKA, which limits the phosphorylation of PKA to substrates in its near vicinity. The downstream events caused by activation of PKA appear poorly elucidated and involve many components in the initiation of signalling cascades. PDE4s have been shown to have abundant roles in regulating cell desensitisation, adaptation, signal cross-talk, cAMP compartmentalization and feedback loops, and are major regulators of cAMP homeostasis.

The physiological role implicated for elevated cAMP levels include: 1) broad suppression the activity of many immunocompetent cells; 2) induction of airway smooth muscle relaxation; 3) suppression of smooth muscle mitogenesis; and, 4) has beneficial modulatory effects on the activity of pulmonary nerves.

PDE4 has been found to be the predominant cAMP metabolising isozyme family in immune and inflammatory cells and, along with the PDE3 family, a major contributor to cAMP metabolism in airway smooth muscle.

Over the last two decades significant attention has been devoted into the development of PDE4 selective inhibitors for the treatment of inflammatory and immune disorders including asthma, rhinitis, bronchitis, COPD, arthritis and psoriasis. A number of compounds (for example rolipram, tibenelast and denbufylline) have been reported to have impressive effects in animal models of inflammation, especially pulmonary inflammation.

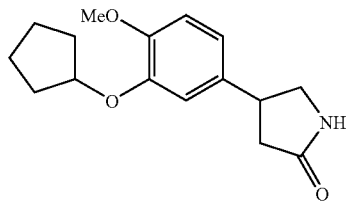

Rolipram

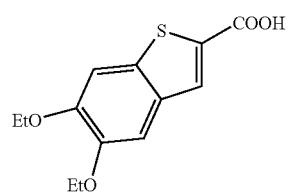

Tibenelast

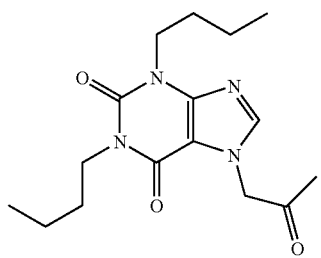

Denbufylline

Unfortunately the clinical utility of these inhibitors has been limited by PDE4 related side-effects, including nausea, vomiting and gastric acid secretion. Recently a second generation of PDE4 inhibitors (for example cilomilast, roflumilast and AWD 12-281) has been described having significantly reduced risk of emetic side effects in animal models of emesis, thus providing the potential for an increased therapeutic ratio.

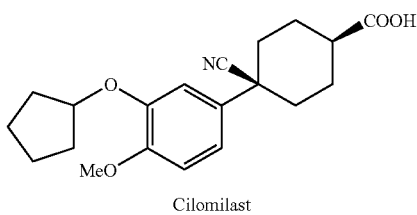

Cilomilast

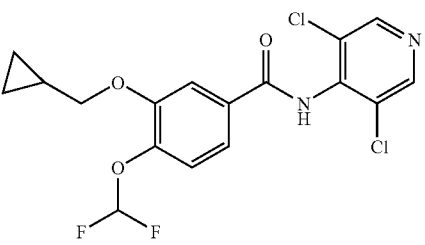

Roflumilast

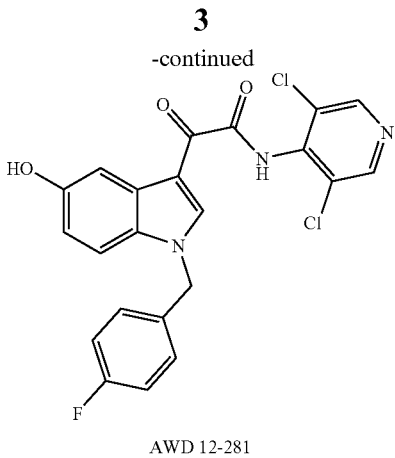

AWD 12-281

The present invention discloses novel phenoxypyridinylamide derivatives that are inhibitors of human PDE4 and are thereby useful in therapy.

The present invention provides a compound of formula (I):

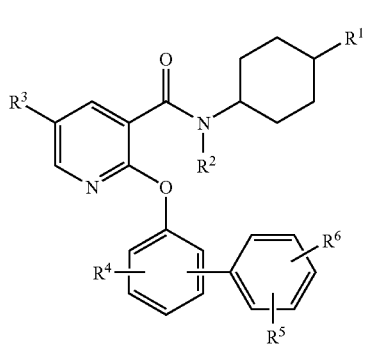

(I)

wherein:
$R^1$ is $NR^7C(O)R^8$, $NR^7S(O)_2R^8$ or $NR^9R^{10}$;
$R^2$ is hydrogen or $C_{1-6}$ alkyl;
$R^3$ is hydrogen, halogen, $C_{1-4}$ alkyl or $C_{1-4}$ alkoxy;
$R^4$ is hydrogen, halogen, cyano, hydroxy, $C_{1-4}$ alkyl, $C_{1-4}$ alkoxy, $CF_3$, $OCF_3$, $C_{1-4}$ alkylthio, $S(O)(C_{1-4}$ alkyl), $S(O)_2$($C_{1-4}$ alkyl), $CO_2H$ or $CO_2(C_{1-4}$ alkyl);
$R^5$ is $C_{1-6}$ alkyl (substituted by $NR^{11}R^{12}$ or heterocyclyl), $C_{1-6}$ alkoxy (substituted by $NR^{11}R^{12}$ or heterocyclyl), $C_{3-6}$ cycloalkyl (substituted by $NR^{11}R^{12}$ or heterocyclyl) or heterocyclyl; provided that if $R^5$ includes a heterocyclyl then said heterocyclyl comprises one or more ring nitrogen atoms; and that if said heterocyclyl is bonded directly via a ring nitrogen either: to the alkyl, alkoxy or cycloalkyl of $R^5$, or to the phenyl ring of formula (I) to which $R^5$ is directly bonded, then said heterocyclyl either has at least two ring heteroatoms, or has an $NR^{46}R^{47}$ substituent;
$R^6$ is hydrogen, halogen, cyano, hydroxy, SH, $C_{1-4}$ alkyl, $C_{1-4}$ alkoxy, $CF_3$, $OCF_3$, $C(O)H$, $C_{1-6}$ alkylthio, $S(O)(C_{1-6}$ alkyl), $S(O)_2(C_{1-6}$ alkyl), $CO_2H$, $CO_2(C_{1-6}$ alkyl), $NR^{13}R^{14}$, $C_{1-6}$ alkyl (optionally substituted by halogen, OH, $CO_2H$, $NR^{15}R^{16}$, NHC(O)O($C_{1-6}$ alkyl), $OS(O)_2(C_{1-6}$ alkyl) or heterocyclyl), $C_{1-6}$ alkoxy (optionally substituted by halogen, OH, $CO_2H$, $NR^{15}R^{16}$ or heterocyclyl), $C_{3-6}$ cycloalkyl (optionally substituted halogen, OH, $CO_2H$, $NR^{15}R^{16}$ or heterocyclyl) or heterocyclyl;
$R^7$ is hydrogen or $C_{1-6}$ alkyl (optionally substituted by $NR^{26}R^{27}$);

$R^8$ is $C_{1-6}$ alkyl {optionally substituted by hydroxyl, $C_{1-6}$ alkoxy, $NR^{21}R^{22}$, heterocyclyl {optionally substituted by oxo, hydroxy, $C_{1-6}$ alkyl, $CO_2(C_{1-6}$ alkyl), aryl, heteroaryl, aryl($C_{1-4}$ alkyl), heterocyclyl or $C(O)(C_{1-4}$ alkyl)phenyl}, aryl, heteroaryl, $C_{3-7}$ cycloalkyl, $C_{3-7}$ cycloalkyl($C_{1-4}$ alkyl), $CO_2H$, $CO_2(C_{1-6}$ alkyl), aryl($C_{1-4}$ alkoxy), aryl($C_{1-4}$ alkylthio), $S(O)_2(C_{1-6}$ alkyl), NHC(O)heteroaryl or NHC(O)$R^{23}$}, $C_{1-6}$ alkoxy, $C_{3-6}$ cycloalkyl {optionally substituted by hydroxyl, $NR^{24}R^{25}$ or $C_{1-6}$ alkyl}, heterocyclyl {optionally substituted by oxo, hydroxy, $C_{1-6}$ alkyl, amino, aryl, heteroaryl, aryl($C_{1-4}$ alkyl), heteroaryl($C_{1-4}$ alkyl), heterocyclyl or $C(O)(C_{1-4}$ alkyl)phenyl}, aryl($C_{1-4}$ alkyl) {substituted by amino($C_{1-4}$ alkyl)}, aryl or heteroaryl;
$R^9$ is hydrogen, $C_{1-6}$ alkyl (optionally substituted by aryl or heteroaryl), aryl or heteroaryl;
$R^{10}$ is hydrogen, $C_{1-6}$ alkyl (optionally substituted by hydroxyl, $C_{1-6}$ alkoxy, aryl, aryloxy, phenyl($C_{1-6}$ alkoxy), heteroaryl, $C_{3-10}$ cycloalkyl, $CO_2H$, $CO_2(C_{1-6}$ alkyl), NHC(O)O($C_{1-6}$ alkyl) or NHC(O)$R^{23}$), $C_{1-6}$ alkoxy, $C_{3-6}$ cycloalkyl (optionally substituted by hydroxy, $C_{1-6}$ alkyl, phenyl, phenyl($C_{1-6}$ alkyl), heteroaryl or heteroaryl($C_{1-6}$ alkyl)), heterocyclyl (optionally substituted by $C_{1-6}$ alkyl, $C(O)NH_2$ or phenyl($C_{1-6}$ alkyl)), aryl or heteroaryl;
$R^{21}$ and $R^{22}$ are, independently, hydrogen, $C_{1-6}$ alkyl or phenyl($C_{1-4}$ alkyl);
$R^{23}$ is $C_{1-6}$ alkyl or phenyl;
the foregoing phenyl, aryl and heteroaryl moieties of $R^5$, $R^8$, $R^9$, $R^{10}$, $R^{23}$, $R^{21}$ and $R^{22}$ are, independently, optionally substituted by: halogen, cyano, nitro, $CF_3$, hydroxy, $S(O)_qR^{26}$, $OC(O)NR^{27}R^{28}$, $NR^{29}R^{30}$, $NR^{31}C(O)R^{32}$, $NR^{33}C(O)NR^{34}R^{35}$, $S(O)_2NR^{36}R^{37}$, $NR^{38}S(O)_2R^{39}$, $C(O)NR^{40}R^{41}$, $C(O)R^{42}$, $CO_2R^{43}$, $NR^{44}CO_2R^{45}$, $OC(O)(C_{1-6}$ alkyl), $C_{1-6}$ alkyl, $C_{1-6}$ hydroxyalkyl, $C_{1-6}$ haloalkyl, $C_{1-6}$ alkoxy($C_{1-6}$)alkyl, amino($C_{1-4}$ alkyl), di($C_{1-6}$)alkylamino($C_{1-6}$)alkyl, $C_{1-6}$ alkoxy, $C_{1-6}$ haloalkoxy, hydroxyl ($C_{1-6}$ alkoxy), heterocyclyl ($C_{1-6}$ alkoxy), $C_{1-6}$ alkoxy($C_{1-6}$)alkoxy, amino($C_{1-4}$ alkoxy), $C_{1-4}$ alkylamino($C_{1-4}$ alkoxy) (itself optionally substituted by phenyl), di($C_{1-4}$ alkyl)amino($C_{1-4}$ alkoxy), $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, heterocyclyl, heterocyclyl($C_{1-4}$ alkyl), phenyl, phenyl($C_{1-4})$alkyl, phenoxy, phenylthio, phenyl($C_{1-4}$) alkoxy, heteroaryl, heteroaryl($C_{1-4})$alkyl, heteroaryloxy or heteroaryl($C_{1-4})$alkoxy; wherein any of the immediately foregoing phenyl and heteroaryl moieties are optionally substituted with halogen, hydroxy, nitro, $S(O)_r(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), NHC(O)($C_{1-4}$ alkyl), $NH(O)_2(C_{1-4}$ alkyl), $C(O)(C_{1-4}$ alkyl), $CF_3$ or $OCF_3$;
q and r are, independently, 0, 1 or 2;
unless otherwise stated heterocyclyl is optionally substituted by OH, $C_{1-6}$ alkyl, $C_{3-7}$ cycloalkyl, $NR^{47}$, ($C_{1-6}$ alkyl)OH or ($C_{1-6}$ alkyl)$NR^{48}R^{49}$, $NR^{50}CO_2(C_{1-6}$ alkyl), $CO_2(C_{1-6}$ alkyl), $C(O)(C_{1-6}$ alkyl), $C(O)$heterocyclyl, heteroaryl, ($C_{1-6}$ alkyl)$C(O)NR^{51}R^{52}$, ($C_{1-6}$ alkyl)$C(O)NR^{53}R^{54}$, ($C_{1-6}$ alkyl)$C(O)$ heterocyclyl or heterocyclyl;
$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ are, independently, $C_{1-6}$ alkyl {optionally substituted by halogen, hydroxy or $C_{1-6}$ alkoxy}, $CH_2(C_{2-6}$ alkenyl), phenyl {itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), NHC(O)($C_{1-4}$ alkyl), $NH(O)_2(C_{1-4}$ alkyl), C(O)(C$_{1-4}$ alkyl), CF$_3$ or OCF$_3$} or heteroaryl {itself optionally substituted by halogen, hydroxy, nitro, NH$_2$, NH(C$_{1-4}$ alkyl), N(C$_{1-4}$ alkyl)$_2$, S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$, cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$, CO$_2$H, CO$_2$(C$_{1-4}$ alkyl), NHC(O)(C$_{1-4}$ alkyl), NH(O)$_2$(C$_{1-4}$ alkyl), C(O)(C$_{1-4}$ alkyl), CF$_3$ or OCF$_3$}; R$^{27}$, R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{40}$, R$^{41}$, R$^{42}$, R$^{43}$, R$^{44}$ and R$^{45}$ can also be hydrogen;

R$^{12}$, R$^{14}$R$^{15}$, R$^{25}$, R$^{47}$ and R$^{49}$ are, independently, hydrogen, C$_{1-6}$ alkyl (optionally substituted by hydroxy, C$_{1-6}$ alkoxy, C$_{1-6}$ alkylthio, C$_{3-7}$ cycloalkyl (optionally substituted by hydroxy) or NR$^{55}$R$^{56}$), C$_{3-7}$ cycloalkyl (optionally substituted by hydroxy(C$_{1-6}$ alkyl)) or heterocyclyl (optionally substituted by C$_{1-6}$ alkyl);

R$^{11}$, R$^{13}$, R$^{16}$, R$^{24}$, R$^{26}$, R$^{27}$, R$^{46}$, R$^{48}$, R$^{50}$, R$^{51}$, R$^{52}$, R$^{53}$, R$^{54}$, R$^{55}$ and R$^{56}$ are, independently, hydrogen or C$_{1-6}$ alkyl;

or a N-oxide thereof; or a pharmaceutically acceptable salt thereof.

Certain compounds of the present invention can exist in different isomeric forms (such as enantiomers, diastereomers, geometric isomers or tautomers). The present invention covers all such isomers and mixtures thereof in all proportions. Enantiomerically pure forms are particularly desired. When in solid crystalline form a compound of formula (I) can be in the form of a co-crystal with another chemical entity and the invention encompasses all such co-crystals.

A pharmaceutically acceptable salt of a compound of formula (I) includes a salt prepared from a pharmaceutically acceptable non-toxic base, such as an inorganic or organic base. A salt derived from an inorganic base is, for example, an aluminium, calcium, potassium, magnesium, sodium or zinc salt. A salt derived from an organic base is, for example, a salt of a primary, secondary or tertiary amine, such as arginine, betaine, benzathine, caffeine, choline, chloroprocaine, cycloprocaine, N',N'-dibenzylethylenediamine, diethanolamine, diethylamine, 2-diethyl-aminoethanol, 2-dimethylaminoethanol, ethanolamine, ethylendiamine, N-ethyl-morpholine, N-ethyl piperidine, glucamine, glucosamine, histidine, hydrabamine, isopropylamine, lysine, meglumine, morpholine, piperazine, piperidine, polyamine resins, procaine, purines, tertiary butylamine, theobromine, triethylamine, trimethylamine, tripropylamine, tromethamine or thanolamine.

A pharmaceutically acceptable salt of a compound of formula (I) also includes a quaternary ammonium salt, for example where an amine group in a compound of formula (I) reacts with a C$_{1-10}$ alkyl halide (for example a chloride, bromide or iodide) to form a quaternary ammonium salt.

A pharmaceutically acceptable salt also includes a salt of pharmaceutically acceptable organic acid, such as a carboxylic or sulphonic acid, for example: an acetate, adipate, alginate, ascorbate, aspartate, benzenesulphonate (besylate), benzoate, butyrate, camphorate, camphorsulphonate (such as [(1S,4R)-7,7-dimethyl-2-oxobicyclo[2.2.1]hept-1-yl]methanesulfonic acid salt), camsylate, citrate, p-chlorobenzenesulphonate, cyclopentate, 2,5-dichlorobesyalte, digluconate, edisylate (ethane-1,2-disulfonate or ethane-1-(sulfonic acid)-2-sulfonate), esylate, ethanesulphonate, fumarate, formate, 2-furoate, 3-furoate, gluconate, glucoheptanate, glutamate, glutarate, glycerophosphate, glycolate, heptanoate, hexanoate, hippurate, 2-hydroxyethane sulfonate, lactate, lactobionate, laurate, malate, maleate, malonate, mandelate, methanesulphonate, 2-naphthalenesulfonate, napadisylate (naphthalene-1,5-disulfonate or naphthalene-1-(sulfonic acid)-5-sulfonate), nicotinate, oleate, orotate, oxalate, pantothenate, pamoate, pamoic, pectinate, 3-phenylpropionate, pivalate, propionate, pivolate, pyruvate, saccharinate, salicylate, stearate, succinate, tartrate, p-toluenesulphonate, trans-cinnamic acid, trifluoroacetate, xinafoate, xinofolate, xylate (p-xylene-2-sulphonic acid), undecanoate, 2-mesitylenesulphonate, 2-naphthalenesulphonate, D-mandelate, L-mandelate, 2,5-dichlorobenzenesulphonate, cinnamate or benzoate; or a salt of an inorganic acid such as a hydrobromide, hydrochloride, hydroiodide, sulphate, bisulfate, phosphate, nitrate, hemisulfate, thiocyanate, persulfate, phosphate or sulphonate salt. In another aspect of the invention the stoichiometry of the salt is, for example, a hemi-salt, or a mono- or di-salt or tri-salt.

A pharmaceutically acceptable salt of a compound of formula (I) can be prepared in situ during the final isolation and purification of a compound, or by separately reacting the compound or N-oxide with a suitable organic or inorganic acid and isolating the salt thus formed.

In one aspect of the invention acid addition salts are, for example, a hydrochloride, dihydrochloride, hydrobromide, phosphate, sulfate, acetate, diacetate, fumarate, maleate, malonate, succinate, tartrate, citrate, methanesulfonate or p-toluenesulfonate, camphorsulfonate (such as [(1S,4R)-7,7-dimethyl-2-oxobicyclo[2.2.1]hept-1-yl]methanesulfonic acid salt). An alternative acid addition salt is a trifluoroacetate salt.

Alternatively, a suitable salt can be a quaternary ammonium salt formed by the reaction of a primary, secondary or tertiary amine group in a compound of formula (I) with, for example, a C$_{1-6}$ alkyl halide (such as methyl iodide or methyl bromide).

The compounds of the invention may exist as solvates (such as hydrates) and the present invention covers all such solvates.

Halogen includes fluorine, chlorine, bromine and iodine. Halogen is, for example, fluorine or chlorine.

Alkyl moieties are straight or branched chain and are, for example, methyl, ethyl, n-propyl, iso-propyl or tert-butyl. Haloalkyl is, for example C$_2$F$_5$, CF$_3$ or CHF$_2$. Alkoxy is, for example, methoxy or ethoxy; and haloalkoxy is, for example OCF$_3$ or OCHF$_2$.

Alkenyl is, for example, vinyl or prop-2-enyl. Alkynyl is, for example, propargyl.

Cycloalkyl is a mono- or bi-cyclic ring system which is saturated or unsaturated but not aromatic. It is, for example, cyclopropyl, cyclobutyl, cyclopentyl, cyclohexyl or bicyclo [3.1.1]heptenyl. C$_{3-7}$ Cycloalkyl(C$_{1-4}$ alkyl) is, for example, cyclopentylCH$_2$. Cycloalkyloxy is, for example, cyclopropyloxy, cyclopentyloxy or cyclohexyloxy. Cycloalkylalkoxy is, for example, (cyclopropyl)methoxy or 2-(cyclopropyl)ethoxy.

Heterocyclyl is a non-aromatic 4-8-membered ring optionally fused to one or more other non-aromatic rings and optionally fused to a benzene ring, comprising at least one heteroatom selected from the group comprising nitrogen, oxygen and sulphur. Heterocyclyl is, for example, azetidinyl, pyrrolidinyl, piperidinyl, piperazinyl, isoindolyl, morpholinyl, thiomorpholinyl, homomorpholinyl, homopiperazinyl, 3,8-diazabicyclo[3.2.1]octyl, 8-azabicyclo[2.2.2]octyl, 2-oxa-6-azabicyclo[5.4.0]undeca-7,9,11-trienyl, 7-oxa-10-azabicyclo[4.4.0]deca-1,3,5-trienyl, 6-thia-1,4-diazabicyclo[3.3.0]octa-4,7-dienyl, tetrahydropyranyl, azabicyclo[3.2.1]octyl, 1,2,3,4-tetrahydroquinolinyl, 1,4-diazepinyl, quinuclidinyl, 9-oxa-2,8-diazaspiro[4.4]non-7-enyl, 1,2-dihydroquinazolinyl, 2,4,10-triazabicyclo[4.4.0]deca-1,3,5,8-tetraenyl or 2-oxa-5-aza-bicyclo[4.4.0]deca-7,9,11-trienyl or azepinyl, homopiperazinyl, 1,4-oxazepinyl or 1-azabicyclo[2.2.2]octyl.

Hydroxyalkyl is, for example, $CH_2OH$; $C_{1-6}$ alkoxy($C_{1-6}$) alkyl is, for example $CH_3OCH_2$; and, $C_{1-6}$ alkoxy($C_{1-6}$) alkoxy is, for example, $CH_3OCH_2O$. Dialkylaminoalkyl is, for example $(CH_3)_2NCH_2$ or $(CH_3)(CH_3CH_2)NCH_2$. Amino ($C_{1-4}$ alkyl) is, for example, $CH_2NH_2$. Amino($C_{1-4}$ alkoxy) is, for example, $OCH_2NH_2$. $C_{1-4}$ Alkylamino($C_{1-4}$ alkoxy) is, for example, $CH_3NHCH_2O$.

Aryl is, for example, phenyl or naphthyl. In one aspect aryl is phenyl. Aryl($C_{1-4}$ alkyl) is, for example, benzyl. Aryl($C_{1-4}$ alkoxy) is, for example, phenylmethoxy. Aryl($C_{1-4}$ alkylthio) is, for example, phenyl$CH_2S$.

Heteroaryl is, for example, an aromatic 5- or 6-membered ring, optionally fused to one or more other rings (which may be carbocyclic or heterocyclic, and aromatic or non-aromatic), comprising at least one heteroatom selected from the group comprising nitrogen, oxygen and sulphur; or an N-oxide thereof, or an S-oxide or S-dioxide thereof. Heteroaryl is, for example, furyl, thienyl (also known as thiophenyl), pyrrolyl, thiazolyl, isothiazolyl, pyrazolyl, oxazolyl, isoxazolyl, imidazolyl, [1,2,3]-thiadiazolyl, [1,2,4]-triazolyl, [1,2,3]-triazolyl, pyridinyl, pyrimidinyl, pyrazinyl, pyridazinyl, indolyl, benzo[b]furyl (also known as benzfuryl), 4,5,6,7-tetrahydrobenzfuryl, benz[b]thienyl (also known as benzthienyl or benzthiophenyl), indazolyl, benzimidazolyl, 1,2,3-benztriazolyl, benzoxazolyl, 1,3-benzthiazolyl, 1,2,3-benzothiadiazolyl, thieno[3,2-b]pyridin-6-yl, 1,2,3-benzoxadiazolyl, benzo[1,2,3]thiadiazolyl, 2,1,3-benzothiadiazolyl, benzofurazan (also known as 2,1,3-benzoxadiazolyl), quinoxalinyl, a pyrazolopyridine (for example 1H-pyrazolo[3,4-b]pyridinyl or pyrazolo[1,5-a]pyridinyl), an imidazopyridine (for example imidazo[1,2-a]pyridinyl or imidazo[1,2-a]-5,6,7,8-tetrahydropyridinyl), a dihydropyrido[2,3-d]pyrimidine (for example 1,4-dihydropyrido[2,3-d]pyrimidinyl), quinolinyl, isoquinolinyl, a naphthyridinyl (for example [1,6]naphthyridinyl, [1,7]naphthyridinyl or [1,8]naphthyridinyl), 1,2,3-thiadiazolyl, 1H-pyrrolo[2,3-b]pyridinyl, thieno[2,3-b]pyridinyl, thieno[2,3-b]pyrazinyl, [1,2,4]triazolo[1,5-a]pyrimidinyl, 6,7-dihydro-5H-[1,3]thiazolo[3,2-a]pyrimidinyl or 4,5,6,7-tetrahydrobenzfuryl; or an N-oxide thereof, or an S-oxide or S-dioxide thereof.

In one aspect of the invention heteroaryl is, for example, pyrrolyl, thiazolyl, pyrazolyl, imidazolyl, [1,2,4]-triazolyl, pyridinyl, pyrimidinyl, pyrazinyl, pyridazinyl, indolyl, indazolyl, benzimidazolyl, quinoxalinyl, a pyrazolopyridine (for example 1H-pyrazolo[3,4-b]pyridinyl or pyrazolo[1,5-a]pyridinyl), an imidazopyridine (for example imidazo[1,2-a]pyridinyl or imidazo[1,2-a]-5,6,7,8-tetrahydropyridinyl), a dihydropyrido[2,3-d]pyrimidine (for example 1,4-dihydropyrido[2,3-d]pyrimidinyl), quinolinyl, isoquinolinyl, a naphthyridinyl (for example [1,6]naphthyridinyl, [1,7]naphthyridinyl or [1,8]naphthyridinyl), 1H-pyrrolo[2,3-b]pyridinyl or [1,2,4]triazolo[1,5-a]pyrimidinyl; or an N-oxide thereof.

NHC(O)Heteroaryl is, for example, NHC(O)pyridinyl. Heteroaryl($C_{1-4}$ alkyl) is, for example, pyridinyl$CH_2$.

Optionally substituted is, for example, an unsubstituted moiety or a moiety carrying 1, 2 or 3 substituents.

In one particular aspect the present invention provides a compound of formula (I) wherein $R^1$ is $NR^7C(O)R^8$.

In another aspect the present invention provides a compound of formula (I) wherein $R^1$ is $NR^9R^{10}$.

In yet another aspect the present invention provides a compound of formula (I) wherein $R^7$ is hydrogen.

In a further aspect the present invention provides a compound of formula (I) wherein $R^9$ is hydrogen.

In a still further aspect the present invention provides a compound of formula (I) wherein $R^8$ is aryl or heteroaryl (optionally substituted as recited above), or $C_{3-6}$ cycloalkyl substituted by $NR^{24}R^{25}$.

In another aspect the present invention provides a compound of formula (I) wherein $R^{10}$ is $C_{1-6}$ alkyl (for example $C_1$ alkyl) substituted by aryl or heteroaryl (either of which is optionally substituted as recited above).

In yet another aspect of the present invention aryl is, for example, phenyl.

In a further aspect of the present invention heteroaryl is, for example, pyrazolyl, imidazo[1,2-a]pyridinyl or 5,6,7,8-tetrahydroimidazo[1,2-a]pyridinyl.

In a still further aspect aryl and heteroaryl are optionally substituted by, for example, halogen, cyano, nitro, hydroxy, $NR^{29}R^{30}$, $C_{1-6}$ alkyl, $C_{1-6}$ hydroxyalkyl, $C_{1-6}$ haloalkyl, $C_{1-6}$ alkoxy($C_{1-6}$)alkyl, amino($C_{1-4}$ alkyl), di($C_{1-6}$)alkylamino ($C_{1-6}$)alkyl, $C_{1-6}$ alkoxy, $C_{1-6}$ haloalkoxy, hydroxyl ($C_{1-6}$ alkoxy), heterocyclyl($C_{1-6}$ alkoxy), $C_{1-6}$ alkoxy($C_{1-6}$)alkoxy, amino($C_{1-4}$ alkoxy), $C_{1-4}$ alkylamino($C_{1-4}$ alkoxy) (itself optionally substituted by phenyl) or di($C_{1-4}$ alkyl)amino($C_{1-4}$ alkoxy); wherein $R^{29}$ and $R^{30}$ are, independently, hydrogen or $C_{1-6}$ alkyl.

In another aspect the present invention provides a compound of formula (I) wherein $R^2$ is hydrogen.

In yet another aspect the present invention provides a compound of formula (I) wherein $R^3$ is halogen (for example fluoro).

In a further aspect the present invention provides a compound of formula (I) wherein $R^4$ is hydrogen.

In a still further aspect the present invention provides a compound of formula (I) wherein $R^5$ is $C_{1-6}$ alkyl (for example $C_1$ alkyl) substituted by $NR^{11}R^{12}$ or heterocyclyl (itself optionally substituted as recited above); wherein $R^{29}$ and $R^{30}$ are, independently, hydrogen or $C_{1-6}$ alkyl In another aspect of the present invention heterocyclyl is piperidinyl, piperazinyl, morpholinyl, homomorpholinyl or homopiperazinyl.

In a still further aspect the present invention provides a compound of formula (I) wherein $R^5$ is methyl, ethyl or propyl substituted by piperidinyl, piperazinyl, morpholinyl, homomorpholinyl or homopiperazinyl.

In a still further aspect the present invention provides a compound of formula (I) wherein $R^5$ is propyl substituted by piperidinyl, piperazinyl, morpholinyl, homomorpholinyl or homopiperazinyl.

In a still further aspect the present invention provides a compound of formula (I) wherein $R^5$ is 3-(piperazin-1-yl) propyl.

In yet another aspect of the present invention heterocyclyl is optionally substituted by $C_{1-6}$ alkyl or $NR^{46}R^{47}$; wherein $R^{46}$ and $R^{47}$ are, independently, hydrogen or $C_{1-6}$ alkyl.

In a further aspect the present invention provides a compound of formula (I) wherein $R^6$ is hydrogen, hydroxyl or $C_{1-4}$ alkoxy (such as methoxy).

In a further aspect the present invention provides a compound of formula (I) wherein $R^6$ is hydrogen, hydroxyl or $C_{1-4}$ alkoxy (such as methoxy) or $C_{1-6}$ alkyl optionally substituted by heterocyclyl.

In a further aspect the present invention provides a compound of formula (I) wherein $R^6$ is hydroxy or $C_{1-6}$ alkyl optionally substituted by piperidinyl, piperazinyl, morpholinyl, homomorpholinyl or homopiperazinyl.

In a further aspect the present invention provides a compound of formula (I) wherein $R^6$ is or $C_{1-6}$ alkyl optionally substituted by morpholinyl or homomorpholinyl.

In a still further aspect the present invention provides a compound of formula (I) wherein the phenyl ring carrying the $R^5$ and $R^6$ groups is on the meta position of the phenyl carrying the $R^4$ group, that is it is as shown immediately below:

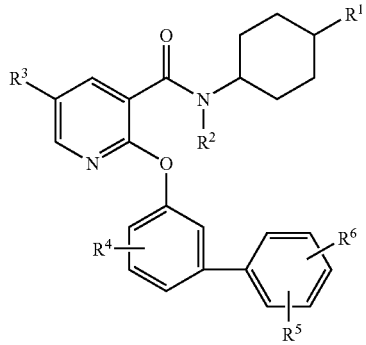

In another aspect the present invention provides a compound of formula (I) wherein $R^6$ is as defined above (for example hydroxyl or methoxy; such as hydroxyl) and is on the para position, and $R^5$ is on an ortho position, that is as shown immediately below:

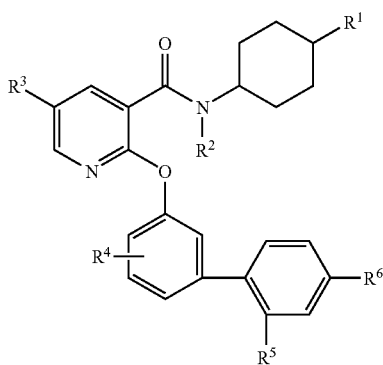

In another aspect the present invention provides a compound of formula (I) wherein $R^6$ is as defined above and is on the ortho position, and $R^5$ is on an para position, that is as shown immediately below:

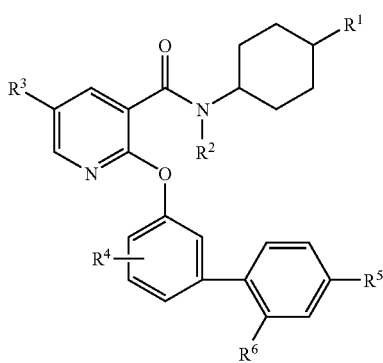

In yet another aspect the present invention provides a compound of formula (I) wherein the substituents are cis-disposed on the cyclohexyl ring of formula (I), that is as shown immediately below:

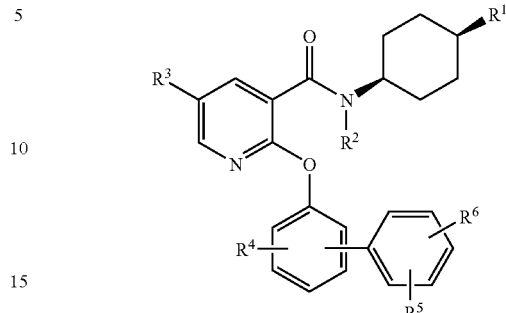

In a further aspect the present invention provides a compound of formula (I) wherein the substituents are disposed as shown immediately below:

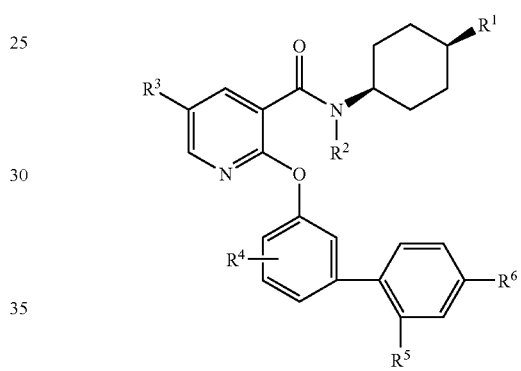

Compounds of the invention are described in the Examples. Each of the compounds of the Examples is a further aspect of the present invention. In another aspect the present invention provides each individual compound of an Example or a pharmaceutically acceptable salt thereof. Further, where the individual compound of an Example is a salt of a compound of formula (I) the invention further provides each parent compound of formula (I), or a different pharmaceutically acceptable salt thereof.

The compounds of the present invention can be prepared as described below, by adapting methods known in the art, or by using or adapting the preparative methods described in the Examples.

In a further aspect of the invention provides a process for the preparation of the compound of formula (I) wherein $R^1$, $R^2$, $R^3$, $R^4$, $R^5$ and $R^6$ are as defined in formula (I) by any of the methods A, B, C, D or E outlined below.

Method A

Compounds of formula (I), wherein $R^1$, $R^2$, $R^3$, $R^4$ and $R^6$ are as defined in formula (I) and wherein $R^5$ is $C_1$ alkyl further substituted by $NR^{11}R^{12}$ or heterocyclyl as defined in formula (I), can be prepared by the reaction of compounds of formula (II), wherein $R^1$, $R^2$, $R^3$, $R^4$ and $R^6$ are as defined in formula (I),

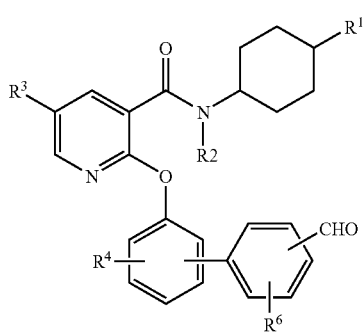

with suitable amines under reductive amination conditions using for example a suitable reducing agent in the presence of a suitable acid catalyst and in a suitable solvent in the presence or absence of a suitable drying agent and at a suitable temperature. Examples of suitable reducing agents include sodium triacetoxy borohydride or sodium cyanoborohydride. Preferably sodium triacetoxy borohydride is used. Examples of a suitable acid catalyst include carboxylic acids such those of acetic, ethanoic or propanoic acids. Preferably acetic acid is used. Examples of suitable solvents include chlorinated solvents such DCM, chloroform, or 1,2-dichloroethane, or ethers such as tetrahydrofuran, 2-methyltetrahydrofuran, diethylether, 1,4-dioxane, glyme or diglyme. Preferably DCM is used. Examples of suitable drying agents include molecular sieves, sodium sulphate or magnesium sulphate. Preferably sodium sulphate is used. The reactions may be carried out at ambient to reflux temperatures. Preferably ambient temperature is used.

Compounds of formula (II), wherein $R^1$, $R^2$, $R^3$, $R^4$ and $R^6$ are as defined in formula (I), can be prepared by reaction of compounds of formula (IX), wherein $R^1$, $R^2$, $R^3$, $R^4$ are as defined in formula (I) and X is a bromide, iodide or a boronic acid/ester derivative,

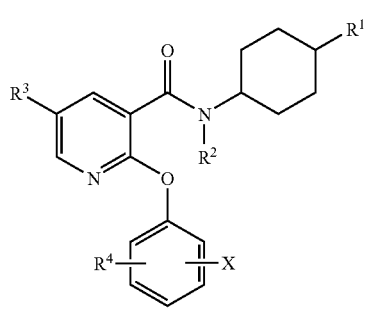

with compounds of formula (X), wherein $R^6$ is as defined in formula (I), using cross coupling chemistry.

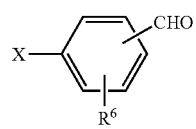

Examples of cross coupling reaction conditions include palladium mediated cross coupling conditions wherein one partner is a chloride, bromide or iodide with a boronic acid or ester derivative as the other partner or Ullman type coupling conditions wherein both partners are either chloride, bromide or iodide derivatives using copper catalysis. Examples of suitable palladium mediated catalysts, ligands, salts, bases and solvents include palladium di-acetate or bis(diphenylphosphino)ferrocene-palladium(II)dichloride DCM complex or palladium tetrakistriphenyl phosphine; with ligands tri-cyclohexylphosphine, or 2,2'bis-dicyclohexyl-phosphino-1,1'-biphenyl or di-t-butyl-phosphino-1,1'-biphenyl or tri-t-butylphosphine; with salts potassium phosphate ($K_3PO_4$) or potassium fluoride in solvents such as tetrahydrofuran, 1,4-dioxane, water or acetonitrile.

Compounds of formula (IX), wherein $R^1$, $R^2$, $R^3$ and $R^4$ are as defined in formula (I) and X is a chloride, bromide or iodide, can be prepared from compounds of formula (XI) wherein $R^1$, $R^2$ and $R^3$ are as defined in formula (I) and Y is a suitable leaving group such as a halogen, by reaction

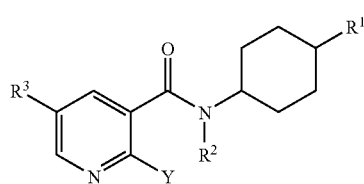

with compounds of formula (XII), wherein $R^4$ is as defined in formula (I) and X is a chloride, bromide or iodide, in a suitable solvent with a base and suitable temperature. Examples of suitable solvents include N,N-dimethylformamide (DMF), N-methylpyrrolidinone, dimethylsulphoxide, acetonitrile, alcohols such as ethanol, propanol or butanol. Examples of suitable bases include cesium carbonate, potassium carbonate, sodium carbonate or trialkylamines such as triethylamine or N,N-diisopropylethylamine. Temperatures ranging from ambient to reflux. Preferably DMF as solvent with cesium carbonate as base at 60-70° C. is used.

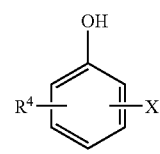

Compounds of formula (XI), wherein $R^1$ and $R^2$ and $R^3$ are as defined in formula (I) and Y is a suitable leaving group such as a halogen, can be prepared from compounds of formula (XIII) wherein $R^3$ is as defined in formula (I) and Y is a leaving group such as a halogen,

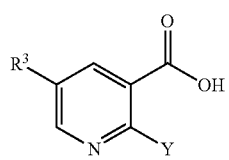

by reaction with compounds of formula (XIV), wherein $R^1$ and $R^2$ are as defined in formula (I) using a suitable coupling agent in a suitable solvent at a suitable temperature.

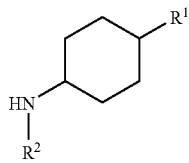

Examples of suitable coupling agents include HATU, PYBOP®, PyBrOP®, DCCI, CDI, optionally in the presence of an excess amine such as triethylamine or N,N-diisopropylethylamine. Examples of suitable solvents include chlorinated solvents such DCM, chloroform, or 1,2-dichloroethane, or ethers such as tetrahydrofuran, 2-methyltetrahydrofuran, diethylether, 1,4-dioxane, glyme or diglyme or alkylnitriles such as acetonitrile or butyronitrile. Preferably HATU is used in acetonitrile using excess N-ethyldiisopropylamine as base at ambient temperature.

Method B

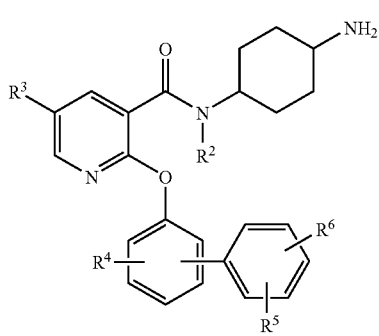

Compounds of formula (I), wherein $R^1$, $R^2$, $R^3$, $R^4$, $R^5$ and $R^6$ are as defined in formula (I), by reaction of compounds of formula (III) wherein $R^2$, $R^3$, $R^4$, $R^5$ and $R^6$ are as defined in formula (I), with suitable acylating agents such as acid chlorides or with suitable carboxylic acids using suitable coupling agents to give compounds wherein $R^1$ is $NR^7C(O)R^8$ or by reaction with suitable sulphonyl chlorides to give compounds wherein $R^1$ is $NR^7S(O)_2R^8$ or by reaction with suitable aldehydes under suitable reductive amination conditions to give compounds wherein $R^1$ is $NR^9R^{10}R^{11}$.

Examples of suitable coupling agents include HATU, PYBOP®, PyBrOP®, DCCI, CDI, optionally in the presence of an excess amine such as triethylamine or N,N-diisopropylethylamine. Examples of suitable solvents include chlorinated solvents such DCM, chloroform, or 1,2-dichloroethane, or ethers such as tetrahydrofuran, 2-methyltetrahydrofuran, diethylether, 1,4-dioxane, glyme or diglyme or alkylnitriles such as acetonitrile or butyronitrile. Preferably HATU is used in acetonitrile using excess N-ethyldiisopropylamine as base at ambient temperature.

Examples of suitable reductive amination conditions include using a suitable reducing agent in the presence of a suitable acid catalyst and in a suitable solvent in the presence or absence of a suitable drying agent and at a suitable temperature. Examples of suitable reducing agents include sodium triacetoxy borohydride or sodium cyanoborohydride. Preferably sodium triacetoxy borohydride is used. Examples of a suitable acid catalyst include carboxylic acids such those of acetic, ethanoic or propanoic acids. Preferably acetic acid is used. Examples of suitable solvents include chlorinated solvents such DCM, chloroform, or 1,2-dichloroethane, or ethers such as tetrahydrofuran, 2-methyltetrahydrofuran, diethylether, 1,4-dioxane, glyme or diglyme or alcohols such as ethanol, propanol or butanol. Preferably DCM is used. Examples of suitable drying agents include molecular sieves, sodium sulphate or magnesium sulphate. Preferably sodium sulphate is used. The reactions may be carried out at ambient to reflux temperatures. Preferably ambient temperature is used.

Compounds of formula (III) wherein $R^2$, $R^3$, $R^4$, $R^5$ and $R^6$ are as defined in formula (I), can be prepared from compounds of formula (XV) wherein $R^2$, $R^3$, $R^4$, $R^5$ and $R^6$ are as defined in formula (I), and PG is a suitable protecting group. Examples of suitable protecting groups include tert-butoxycarbonyl, trifluoroacetamide or benzyloxycarbonyl. Preferably tert-butoxycarbonyl is used.

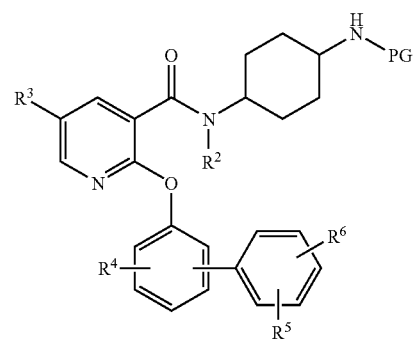

Suitable deprotection conditions are employed. For example for the tert-butoxycarbonyl protecting group, suitable acidic deprotection reaction conditions are employed such as hydrochloric acid or TFA either in the presence or absence of a solvent such as DCM or tetrahydrofuran.

Compounds of formula (XV), wherein $R^2$, $R^3$, $R^4$, $R^5$ and $R^6$ are as defined in formula (I), can be prepared from compounds of formula (XVII), wherein R2, R3, R4 are as defined in formula (I) and X is a chloride, bromide, iodide or boronic acid/ester derivative by reaction

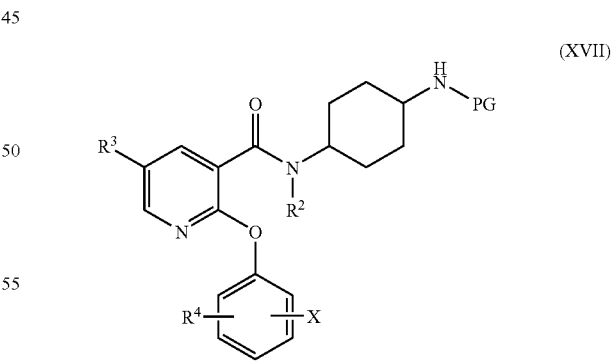

with compounds of formula (V) wherein R5 and R6 are as defined in formula (I) and X is a chloride, bromide, iodide or boronic acid/ester derivative using cross coupling chemistry. Examples of cross coupling reaction conditions include palladium mediated cross coupling conditions wherein one partner is a chloride, bromide or iodide with a boronic acid or ester derivative as the other partner or Ullman type coupling conditions wherein both partners are chloride, bromide or iodide derivatives using copper catalysis. Examples of suitable palladium mediated catalysts, ligands, salts, bases and solvents include palladium di-acetate or bis(diphenylphosphino)ferrocene-palladium(II)dichloride DCM complex or palladium tetrakistriphenyl phosphine; with ligands tri-cyclohexylphosphine, or 2,2'bis-dicyclohexyl-phosphino-1,1'-biphenyl or di-t-butyl-phosphino-1,1'-biphenyl or tri-t-butylphosphine; with salts potassium phosphate ($K_3PO_4$) or potassium fluoride in solvents such as tetrahydrofuran, 1,4-dioxane, water or acetonitrile.

Alternatively, compounds of formula (XV), wherein $R^2$, $R^3$, $R^4$, $R^5$ and $R^6$ are as defined in formula (I), can be prepared from compounds of formula (XVI), wherein $R^2$ and $R^3$ are as defined in formula (I) and Y is a leaving group such as a halogen by reaction with compounds of formula (VI) wherein $R^4$, $R^5$ and $R^6$ are as defined in formula (I), in a suitable solvent with a base and suitable temperature. Examples of suitable solvents include N,N-dimethylformamide (DMF), N-methylpyrrolidinone, dimethylsulphoxide, acetonitrile, alcohols such as ethanol, propanol or butanol. Examples of suitable bases include cesium carbonate, potassium carbonate, sodium carbonate or trialkylamines such as triethylamine or N,N-diisopropylethylamine. Temperatures ranging from ambient to reflux.

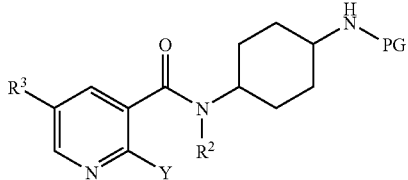

(XVI)

Compounds of formula (XVII), wherein $R^2$, $R^3$, $R^4$ are as defined in formula (I) and X is a chloride, bromide or iodide can be prepared from compounds of formula (XVIII), wherein $R^3$ and $R^4$ are as defined in formula (I) and X is chloride, bromide or iodide by reaction

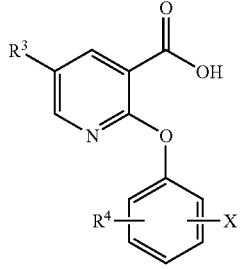

(XVIII)

with compounds of formula (XIX),

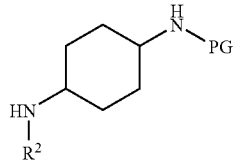

(XIX)

wherein $R^2$ is as defined in formula (I) and PG is a suitable protecting group using a suitable coupling agent in a suitable solvent at a suitable temperature.

Examples of suitable coupling agents include HATU, PYBOP®, PyBrOP®, DCCI, CDI, optionally in the presence of an excess amine such as triethylamine or N,N-diisopropylethylamine. Examples of suitable solvents include chlorinated solvents such DCM, chloroform, or 1,2-dichloroethane, or ethers such as tetrahydrofuran, 2-methyltetrahydrofuran, diethylether, 1,4-dioxane, glyme or diglyme or alkylnitriles such as acetonitrile or butyronitrile. Preferably HATU is used in acetonitrile using excess N-ethyldiisopropylamine as base at ambient temperature.

Examples of suitable protecting groups include tert-butoxycarbonyl, trifluoroacetamide or benzyloxycarbonyl. Preferably tert-butoxycarbonyl is used.

Compounds of formula (XVIII), wherein $R^3$ and $R^4$ are as defined in formula (I) and X is a chloride, bromide or iodide or boronic acid/ester derivative can be prepared from compounds of formula (XIII), wherein $R^3$ is as defined in formula (I) and Y is a leaving group such as a halogen by reaction with compounds of formula (XIII) in a suitable solvent with a base and suitable temperature. Examples of suitable solvents include N,N-dimethylformamide (DMF), N-methylpyrrolidinone, dimethylsulphoxide, acetonitrile, alcohols such as ethanol, propanol or butanol. Examples of suitable bases include cesium carbonate, potassium carbonate, sodium carbonate or trialkylamines such as triethylamine or N,N-diisopropylethylamine. Temperatures ranging from ambient to reflux. Preferably DMF as solvent with cesium carbonate as base at 60-70° C. is used.

Method C

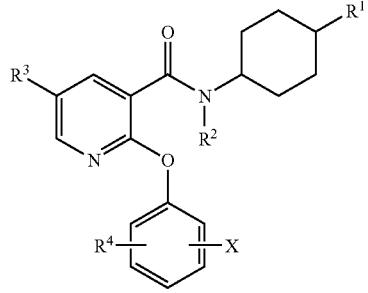

(IV)

Compounds of formula (I), wherein $R^1$, $R^2$, $R^3$, $R^4$, $R^5$ and $R^6$ are as defined in formula (I) can be prepared from compounds of formula (IV), wherein $R^1$, $R^2$, $R^3$, $R^4$ are as defined in formula (I) and X is chloride, bromide, iodide or boronic acid/ester derivative by reaction with compounds of formula (V), wherein $R^4$ and $R^5$ are as defined in formula (I) and X is either a chloride, bromide, iodide, or a boronic acid/ester derivative under suitable cross coupling reaction conditions.

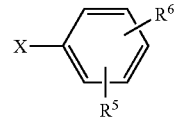

(V)

Examples of cross coupling reaction conditions include palladium mediated cross coupling conditions wherein one partner is a chloride, bromide or iodide with a boronic acid or ester derivative as the other partner or Ullman type coupling conditions wherein both partners are chloride, bromide, or iodide derivatives using copper catalysis. Examples of suitable palladium mediated catalysts, ligands, salts, bases and solvents include palladium di-acetate or bis(diphenylphosphino)ferrocene-palladium(II)dichloride DCM complex or palladium tetrakistriphenyl phosphine; with ligands tri-cyclohexylphosphine, or 2,2'bis-dicyclohexyl-phosphino-1,1'-biphenyl or di-t-butyl-phosphino-1,1'-biphenyl or tri-t-butylphosphine; with salts potassium phosphate ($K_3PO_4$) or potassium fluoride in solvents such as tetrahydrofuran, 1,4-dioxane, water or acetonitrile.

Compounds of formula (IV) wherein $R^1$, $R^2$, $R^3$ and $R^4$ are as defined in formula (I) and X is a chloride, bromide or iodide can be prepared from compounds of formula (VI), wherein $R^1$, $R^2$ and $R^3$ are as defined in formula (I) and Y is a leaving group such as a halogen by reaction with compounds of formula (XII) wherein $R^4$ is as defined in formula (I) and X is a chloride, bromide, iodide in a suitable solvent with a base and suitable temperature. Examples of suitable solvents include N,N-dimethylformamide (DMF), N-methylpyrrolidinone, dimethylsulphoxide, acetonitrile, alcohols such as ethanol, propanol or butanol. Examples of suitable bases include cesium carbonate, potassium carbonate, sodium carbonate or trialkylamines such as triethylamine or N,N-diisopropylethylamine. Temperatures ranging from ambient to reflux.

Method D

Compounds of formula (I), wherein $R^1$, $R^2$, $R^3$, $R^4$, $R^5$ and $R^6$ are as defined in formula (I) from compounds of formula (VI), wherein $R^1$, $R^2$, and $R^3$ and Y is suitable leaving group such as a halogen

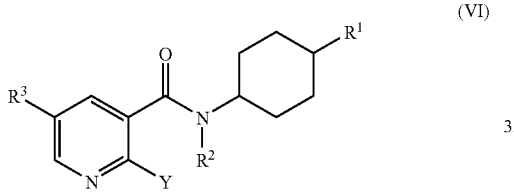

(VI)

by reaction with compounds of formula (VI) wherein $R^4$, $R^5$ and $R^6$ are as defined in formula (I) in a suitable solvent with a base and suitable temperature. Examples of suitable solvents include N,N-dimethylformamide (DMF), N-methylpyrrolidinone, dimethylsulphoxide, acetonitrile, alcohols such as ethanol, propanol or butanol. Examples of suitable bases include cesium carbonate, potassium carbonate, sodium carbonate or trialkylamines such as triethylamine or N,N-diisopropylethylamine. Temperatures ranging from ambient to reflux using a suitable base and solvent.

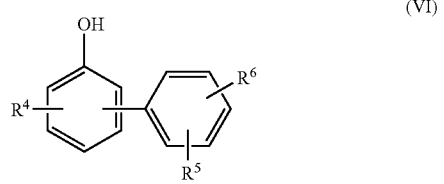

(VI)

Compounds of formula (VI), wherein $R^4$, $R^5$ and $R^6$ are as defined in formula (I) can be prepared from compounds of formula (XII), wherein $R^4$ is as defined in formula (I) and X is a chloride, bromide, iodide or boronic acid/ester derivative by reaction with compounds of formula (X) wherein $R^5$ and $R^6$ are as defined in formula (I), and X is a bromide, iodide or boronic acid/ester derivative under suitable cross coupling reaction conditions.

Examples of cross coupling reaction conditions include palladium mediated cross coupling conditions wherein one partner is a chloride, bromide or iodide with a boronic acid or ester derivative as the other partner or Ullman type coupling conditions wherein both partners are chloride, bromide or iodide derivatives using copper catalysis. Examples of suitable palladium mediated catalysts, ligands, salts, bases and solvents include palladium di-acetate or bis(diphenylphosphino)ferrocene-palladium(II)dichloride DCM complex or palladium tetrakistriphenyl phosphine; with ligands tri-cyclohexylphosphine, or 2,2'bis-dicyclohexyl-phosphino-1,1'-biphenyl or di-t-butyl-phosphino-1,1'-biphenyl or tri-t-butylphosphine; with salts potassium phosphate ($K_3PO_4$) or potassium fluoride in solvents such as tetrahydrofuran, 1,4-dioxane, water or acetonitrile.

Method E

Compounds of formula (I) wherein $R^1$, $R^2$, $R^3$, $R^4$, $R^1$ and $R^6$ are as defined in formula (I) can be prepared from compounds of formula (VII), wherein $R^3$, $R^4$, $R^5$ and $R^6$ are as defined in formula (I)

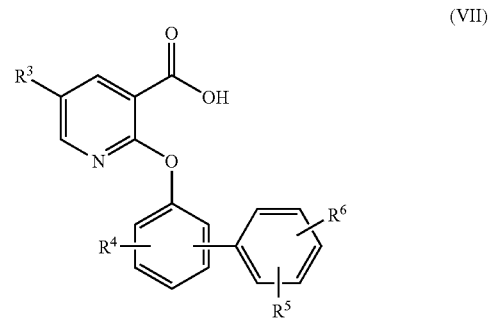

(VII)

by reaction with compounds of formula (VIII) wherein $R^1$ and $R^2$ are as defined in formula (I)

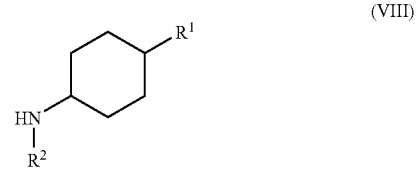

(VIII)

using a suitable coupling agent and solvent and temperature.

Examples of suitable coupling agents include HATU, PYBOP®, PyBrOP®, DCCI, CDI, optionally in the presence of an excess amine such as triethylamine or N,N-diisopropylethylamine. Examples of suitable solvents include chlorinated solvents such DCM, chloroform, or 1,2-dichloroethane, or ethers such as tetrahydrofuran, 2-methyltetrahydrofuran, diethylether, 1,4-dioxane, glyme or diglyme or alkylnitriles such as acetonitrile or butyronitrile. Preferably HATU is used in acetonitrile using excess N-ethyldiisopropylamine as base at ambient temperature.

It should be noted that in any of the above methods A-E conversion of aromatic halides such as chlorides, bromides or iodides can be easily converted to boronic acid/ester derivatives either using halogen-lithium exchanges using n-butyllithium, or sec-butyllithium or tert-butyllithium in an inert solvent such as diethyl ether or tetrahydrofuran at low temperatures and quenching with a tri-alkyl-borate such as trimethylborate. Alternatively, conversion of aromatic halides such as chlorides, bromides or iodides to boronic acid/ester derivatives are preferably carried out using a palladium catalyst and a dioxaborolane such as 4,4,4',4',5,5,5',5'-octamethyl-2,2'-bi(1,3,2-dioxaborolane. For example using 1,1'-Bis(diphenylphosphino)ferrocene and 1,1'-bis (diphenylphosphino)ferrocene-palladium(II) dichloride DCM complex as the palladium catalyst and 4,4,4',4',5,5,5', 5'-octamethyl-2,2'-bi(1,3,2-dioxaborolane) as the dioxaborolane is used in dimethylsulphoxide as solvent in the presence of potassium carbonate at 80° C. is used.

Boronic ester derivatives can be converted into boronic acid derivatives using standard acid or base hydrolysis conditions at ambient to reflux temperatures with or without organic solvents under aqueous conditions.

The Preparation of various intermediates and in particular compounds of formula (V), (VIII), (X), (XII), (XIII) (XIV) or (XIX) wherein $R^1$, $R^2$, $R^3$, $R^4$, $R^5$ and $R^6$ are as defined in formula, PG is a suitable protecting group, and X and Y are halogens are either commercially available, well known in the literature or can be prepared using known literature methods or by routine adaptation of methods described in the literature.

In the above processes it may be desirable or necessary to protect an acid group or a hydroxy or other potentially reactive group. Suitable protecting groups and details of processes for adding and removing such groups may be found in "Protective Groups in Organic Synthesis", 3rd Edition (1999) by Greene and Wuts.

In another aspect the present invention provides processes for the preparation of compounds of formula (I).

In yet another aspect the present invention provides intermediates useful in the preparation of compounds of the invention.

The compounds of formula (I) have activity as pharmaceuticals, in particular as modulators of PDE 4 receptor activity, and may be used in the treatment of inflammatory diseases, asthma or COPD.

Examples of disease states that can be treated with a compound of the invention are:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other demeaning disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortifis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; or, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

According to a further feature of the present invention there is provided a method for treating a PDE 4 mediated disease state in a mammal, such as man, suffering from, or at risk of, said disease state, which comprises administering to a mammal in need of such treatment a therapeutically effective amount of a compound of the formula (I) or a pharmaceutically acceptable salt thereof.

The invention also provides a compound of the formula (I), or a pharmaceutically acceptable salt thereof, for use in therapy.

In another aspect the invention provides the use of a compound of formula (I), or a pharmaceutically acceptable salt thereof, in the manufacture of a medicament for use in therapy (for example modulating PDE 4 enzymatic activity).

The invention further provides the use of a compound of formula (I), or a pharmaceutically acceptable salt thereof, in the manufacture of a medicament for use in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibemian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other demeaning disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; or, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema; in a mammal (for example man).

In a further aspect the invention provides a compound of formula (I), or a pharmaceutically acceptable salt thereof, for use in the treatment of asthma {such as bronchial, allergic, intrinsic, extrinsic or dust asthma, particularly chronic or inveterate asthma (for example late asthma or airways hyper-responsiveness)}; or COPD.

In a still further aspect a compound of formula (I), or a pharmaceutically acceptable salt thereof, is useful in the treatment of COPD.

The present invention also provides the use of a compound of formula (I), or a pharmaceutically acceptable salt thereof, in the manufacture of a medicament for use in the treatment of asthma {such as bronchial, allergic, intrinsic, extrinsic or dust asthma, particularly chronic or inveterate asthma (for example late asthma or airways hyper-responsiveness)}; or COPD.

In order to use a compound of the invention, or a pharmaceutically acceptable salt thereof, for the therapeutic treatment of a mammal, such as man, said ingredient is normally formulated in accordance with standard pharmaceutical practice as a pharmaceutical composition. Therefore in another aspect the present invention provides a pharmaceutical composition which comprises a compound of the formula (I), or a pharmaceutically acceptable salt thereof (active ingredient), and a pharmaceutically acceptable adjuvant, diluent or carrier.

In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), inhalation, oral, rectal or parenteral administration. For these purposes the compounds of this invention may be formulated by means known in the art. A suitable pharmaceutical composition of this invention is one suitable for oral administration in unit dosage form, for example a tablet or capsule which contains between 0.1 mg and 1 g of active ingredient.

Each patient may receive, for example, a dose of 0.001 $mgkg^{-1}$ to 100 $mgkg^{-1}$, for example in the range of 0.1 $mgkg^{-1}$ to 20 $mgkg^{-1}$, of the active ingredient administered, for example, 1 to 4 times per day.

The invention further relates to a combination therapy wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-$\alpha$) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; for example collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-yls such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MIK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agent including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, indacaterol, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agents, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B$_1$.- or B$_2$.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK$_1$. or NK$_3$. receptor antagonist such as NKP-608C, SB-233412 (talnetant) or D4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of p38; (xxv) agent modulating the function of Toll-like receptors (TLR), (xxvi) agent modulating the activity of puringergic receptors such as P2x7; (xxvii) inhibitor of transcription factor activation such as NFkB, API, or STATS; or (xxviii) a non-steroidal glucocorticoid receptor (GR-receptor) agonist.

In a further embodiment the present invention provides a pharmaceutical product comprising, in combination, a first active ingredient which is a compound of formula (I), or a pharmaceutically acceptable salt thereof, as hereinbefore described, and at least one further active ingredient selected from:— a β2. adrenoceptor agonist,
a modulator of chemokine receptor function,
an inhibitor of kinase function,
a protease inhibitor,
a steroidal glucocorticoid receptor agonist,
an anticholinergic agent, and a
a non-steroidal glucocorticoid receptor agonist.

The pharmaceutical product according to this embodiment may, for example, be a pharmaceutical composition comprising the first and further active ingredients in admixture. Alternatively, the pharmaceutical product may, for example, comprise the first and further active ingredients in separate pharmaceutical preparations suitable for simultaneous, sequential or separate administration to a patient in need thereof. The pharmaceutical product of this embodiment is of particular use in treating respiratory diseases such as asthma, COPD or rhinitis.

Examples of a $β_2$-adrenoceptor agonist that may be used in the pharmaceutical product according to this embodiment include metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol or indacaterol. The $\beta_2$-adrenoceptor agonist of this embodiment may be a long-acting $\beta_2$-agonists, for example salmeterol (e.g. as xinafoate), formoterol (e.g. as fumarate), bambuterol (e.g. as hydrochloride), carmoterol (TA 2005, chemically identified as 2(1H)-Quinolone, 8-hydroxy-5-[1-hydroxy-2-[[2-(4-methoxy-phenyl)-1-methylethyl]-amino]ethyl]-monohydrochloride, [R-(R*,R*)] also identified by Chemical Abstract Service Registry Number 137888-11-0 and disclosed in U.S. Pat. No. 4,579,854), indacaterol (CAS no 312753-06-3; QAB-149), formanilide derivatives e.g. 3-(4-{[6-({(2R)-2-[3-(formylamino)-4-hydroxyphenyl]-2-hydroxyethyl}-amino)hexyl]oxy}-butyl)-benzenesulfonamide as disclosed in WO 2002/76933, benzenesulfonamide derivatives e.g. 3-(4-{[6-({(2R)-2-hydroxy-2-[4-hydroxy-3-(hydroxy-methyl)phenyl]ethyl}amino)-hexyl]oxy}butyl)benzenesulfonamide as disclosed in WO 2002/88167, aryl aniline receptor agonists as disclosed in WO 2003/042164 and WO 2005/025555, indole derivatives as disclosed in WO 2004/032921 and US 2005/222144, and compounds GSK 159797, GSK 159802, GSK 597901, GSK 642444 and GSK 678007.

Examples of a modulator of chemokine receptor function that may be used in the pharmaceutical product according to this embodiment include a CCR1 receptor antagonist.

Examples of an inhibitor of kinase function that may be used in the pharmaceutical product according to this embodiment include a p38 kinase inhibitor and an IKK inhibitor.

Examples of a protease inhibitor that may be used in the pharmaceutical product according to this embodiment include an inhibitor of neutrophil elastase or an inhibitor of MMP12.

Examples of a steroidal glucocorticoid receptor agonist that may be used in the pharmaceutical product according to this embodiment include budesonide, fluticasone (e.g. as propionate ester), mometasone (e.g. as furoate ester), beclomethasone (e.g. as 17-propionate or 17,21-dipropionate esters), ciclesonide, loteprednol (as e.g. etabonate), etiprednol (as e.g. dicloacetate), triamcinolone (e.g. as acetonide), flunisolide, zoticasone, flumoxonide, rofleponide, butixocort (e.g. as propionate ester), prednisolone, prednisone, tipredane, steroid esters e.g. 6α,9α-difluoro-17α-[(2-furanylcarbonyl)oxy]-1,0-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, steroid esters according to DE 4129535, steroids according to WO 2002/00679, WO 2005/041980, or steroids GSK 870086, GSK 685698 and GSK 799943.

Examples of an anticholinergic agent that may be used in the pharmaceutical product according to this embodiment include for example a muscarinic receptor antagonist (for example a M1, M2 or M3 antagonist, such as a M3 antagonist) for example ipratropium (e.g. as bromide), tiotropium (e.g. as bromide), oxitropium (e.g. as bromide), tolterodine, pirenzepine, telenzepine, glycopyrronium bromide (such as R,R-glycopyrronium bromide or a mixture of R,S- and S,R-glycopyrronium bromide); mepensolate (e.g. as bromide), a quinuclidine derivative such as 3(R)-(2-hydroxy-2,2-dithien-2-ylacetoxy)-1-(3-phenoxypropyl)-1-azonia-bicyclo[2.2.2]octane bromide as disclosed in US 2003/0055080, quinuclidine derivatives as disclosed in WO 2003/087096 and WO 2005/115467 and DE 10050995; or GSK 656398 or GSK 961081.

Examples of a modulator of a non-steroidal glucocorticoid receptor agonist that may be used in the pharmaceutical product according to this embodiment include those described in WO2006/046916.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropynimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erb b2 antibody trastuzumab, or the anti-erb b 1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostafin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or, (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be illustrated by the following non-limiting Examples in which, unless stated otherwise:

(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-$D_6$ ($CD_3SOCD_3$) or CDCL3 as the solvent unless otherwise stated;

(ii) mass spectra (MS) were run with an electron energy of 70 electron volts in the chemical ionisation (CI) mode using a direct exposure probe. Where indicated ionisation was effected by electrospray ionisation (ES), or atmospheric pressure chemical ionisation (APCI), or multimode ionisation, a combination of ES ionisation and APCI. Where values for m/z are given, generally only ions which indicate the parent mass are reported, and the mass ions quoted are the positive or negative mass ions: [M]+, [M+H]+ or [M−H]−;

(iii) The title and sub-title compounds of the examples and methods were named using Struct=Name 9.0.7 from CambridgeSoft Corporation.

(iv) Unless stated otherwise, reverse phase HPLC was conducted using a Symmetry, or Xterra™, Sunfire™, X-bridge™ reverse phase silica column, all available from Waters Corp.

(v) All title examples were isolated as either mono- or bis-trifluoracetic acid salts after HPLC unless otherwise stated (v) the following abbreviations are used:

| | |
|---|---|
| DMF | N,N-Dimethylformamide |
| DIPEA | N,N-Diisopropylethylamine |
| HATU | O-(7-Azabenzotriazol-1-yl)-N,N,N',N'-tetramethyluronium hexafluorophosphate |
| DCM | Dichloromethane |
| RT | Room temperature |
| THF | Tetrahydrofuran |
| TFA | Trifluoroacetic acid |
| BOC | tert-butoxycarbonyl |
| HPLC | High pressure liquid chromatography |
| D | Day(s) |
| H | Hour(s) |
| Min | Minutes(s) |
| DMSO | Dimethylsulfoxide |
| EtOAc | Ethyl acetate |
| EDCI | N-(3-Dimethylaminopropyl)-N'-ethylcarbodiimide hydrochloride |
| HOBt | 1-hydroxybenzotriazole hydrate |

(vi) Gemini columns are available from Phenomenex (http://www.phenomenex.com)

The starting materials for the Examples below are either commercially available or readily prepared by standard methods from known starting materials

EXAMPLE 1

N-((1s,4s)-4-(5-fluoro-2-(4'-(piperazin-1-ylmethyl)biphenyl-3-yloxy)nicotinamido)cyclohexyl)-5,6,7,8-tetrahydroimidazo[1,2-a]pyridine-2-carboxamide

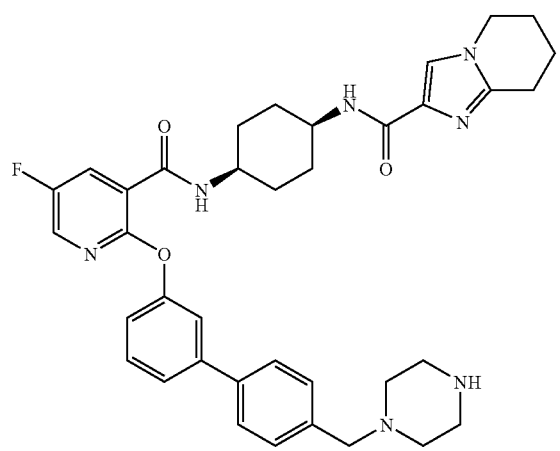

Step (a) tert-butyl (1s,4s)-4-(5-fluoro-2-(3-iodophenoxy)nicotinamido)cyclohexylcarbamate A mixture of 2-chloro-5-fluoronicotinic acid (4.5 g, 25.63 mmol), cesium carbonate (16.70 g, 51.27 mmol) and 3-iodophenol (5.64 g, 25.63 mmol) in a solvent of DMF (50 mL) was heated at 60° C. for 48 h. The mixture was poured into water (200 mL) and the product extracted into EtOAc. The organic layer was dried over sodium sulfate. Filtration and evaporation gave a brown foam (7.5 g). This solid was dissolved in DMF (50 mL) and to the solution was added DIPEA (13.43 mL, 76.90 mmol) followed by HATU (9.75 g, 25.63 mmol) and the mixture stirred at RT for 10 min. To this solution was added tert-butyl (1s,4s)-4-aminocyclohexylcarbamate (5.49 g, 25.63 mmol) and the mixture stirred overnight. The reaction mixture was poured onto water and the product collected by filtration and dried in vacuo to give the sub-title compound as a pale buff solid. Yield: 4.1 g $^1$H NMR (300 MHz, CDCl$_3$) δ 8.35 (dd, J=8.2, 3.2 Hz, 1H), 8.06 (d, J=3.3 Hz, 1H), 7.84 (d, J=7.1 Hz, 1H), 7.65 (dt, J=7.6, 1.4 Hz, 1H), 7.53 (t, J=1.7 Hz, 1H), 7.23-7.11 (m, 2H), 4.41 (s, 1H), 4.21-4.10 (m, 1H), 3.63 (s, 1H), 1.87-1.75 (m, 6H), 1.75-1.62 (m, 2H), 1.44 (s, 9H).

[M+H]+−tBu=500 (MultiMode+)

Step (b) N-((1s,4s)-4-aminocyclohexyl)-5-fluoro-2-(3-iodophenoxy)nicotinamide

To a solution of tert-butyl (1s,4s)-4-(5-fluoro-2-(3-iodophenoxy)nicotinamido)cyclohexylcarbamate (2 g, 3.60 mmol) in DCM (10 mL) was added TFA (5.55 mL, 72.02 mmol) and the mixture stirred at RT for 1 h. The mixture was evaporated to dryness and the residue taken up into water and the pH adjusted to 10 by the addition of 0.88 aqueous ammonia. The resultant solid was collected by filtration and dried in vacuo to give the sub-title compound. Yield: 1.3 g

[M+H]+=456 (MultiMode+)

Step (c) N-((1s,4s)-4-(5-fluoro-2-(3-iodophenoxy) nicotinamido)cyclohexyl)-5,6,7,8-tetrahydroimidazo [1,2-a]pyridine-2-carboxamide To a solution of 5,6,7,8-tetrahydroimidazo[1,2-a]pyridine-2-carboxylic acid (0.183 g, 1.10 mmol) in dry DMF (10 mL) was added DIPEA (0.575 mL, 3.29 mmol) followed by HATU (0.418 g, 1.10 mmol). The mixture was allowed to stir for 10 min at RT. To this mixture was added the N-((1s,4s)-4-aminocyclohexyl)-5-fluoro-2-(3-iodophenoxy)nicotinamide (0.5 g, 1.10 mmol) and the mixture stirred overnight, poured onto water and the crude product collected by filtration, dried in vacuo to give the sub-title compound. Yield: 0.354 g ¹H NMR (300 MHz, CDCl₃) δ 8.36 (dd, J=8.0, 3.0 Hz, 1H), 8.06 (d, J=3.1 Hz, 1H), 7.86 (d, J=7.3 Hz, 1H), 7.64 (dt, J=7.2, 1.3 Hz, 1H), 7.55 (t, J=1.8 Hz, 1H), 7.40 (s, 1H), 7.23-7.12 (m, 2H), 6.94 (d, J=7.3 Hz, 1H), 4.20 (s, 1H), 4.08 (d, J=3.5 Hz, 1H), 3.98 (t, J=8.6 Hz, 3H), 2.85 (q, J=6.2 Hz, 2H), 2.05-1.73 (m, 1H).

[M+H]+=604 (MultiMode+)

Step (d) N-((1s,4s)-4-(5-fluoro-2-(4'-(piperazin-1-ylmethyl)biphenyl-3-yloxy)nicotinamido)cyclohexyl)-5,6,7,8-tetrahydroimidazo[1,2-a]pyridine-2-carboxamide A mixture of diacetoxypalladium (8 mg, 0.04 mmol) and dicyclohexyl(2',6'-dimethoxybiphenyl-2-yl)phosphine (30 mg, 0.07 mmol) was stirred for 10 min in a solvent of dry acetonitrile (7 mL), to this mixture was added consecutively:—a solution of potassium carbonate (151 mg, 1.09 mmol) in water (15 mL), followed by N-((1s,4s)-4-(5-fluoro-2-(3-iodophenoxy)nicotinamido)cyclohexyl)-5,6,7,8-tetrahydroimidazo[1,2-a]pyridine-2-carboxamide (220 mg, 0.36 mmol) and finally 4-((4-(tert-butoxycarbonyl)piperazin-1-yl)methyl)phenylboronic acid (122 mg, 0.36 mmol). The resultant mixture was stirred and heated at 70° C. for 1 h. The mixture was allowed to cool to RT. The organic layer was extracted with EtOAc and washed well with water. The organics were separated and evaporated to dryness. The residue was taken up into TFA (7 mL) and allowed to stand for 1 h. The mixture was evaporated to dryness and the crude product was purified by preparative HPLC on a Waters X-Terra column using a 95-50% gradient of aqueous 0.1% TFA in acetonitrile as eluent. The fractions containing the desired compound were lyophilised to give the title compound as a colorless solid. Yield: 130 mg ¹H NMR (300 MHz, DMSO) δ 8.90 (s, 1H), 8.39 (d, J=6.9 Hz, 1H), 8.25 (d, J=3.1 Hz, 2H), 8.06-7.94 (m, 2H), 7.70 (d, J=8.3 Hz, 2H), 7.56-7.43 (m, 4H), 7.23-7.17 (m, 1H), 4.06 (t, J=10.6 Hz, 2H), 3.91 (d, J=17.5 Hz, 4H), 3.23 (s, 4H), 2.88 (t, J=6.1 Hz, 6H), 1.99-1.83 (m, 6H), 1.79-1.63 (m, 1H).

[M+H]+=652 (MultiMode+)

EXAMPLE 2

N-((1s,4s)-4-(1,5-dimethyl-1H-pyrazole-3-carboxamido)cyclohexyl)-5-fluoro-2-(4'-hydroxy-2'-(morpholinomethyl)biphenyl-3-yloxy)nicotinamide

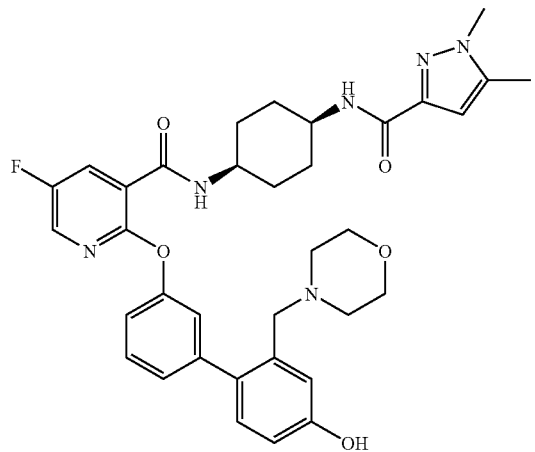

Step (a) N-((1s,4s)-4-(1,5-dimethyl-1H-pyrazole-3-carboxamido)cyclohexyl)-5-fluoro-2-(3-iodophenoxy)nicotinamide To a solution of 1,5-dimethyl-1H-pyrazole-3-carboxylic acid (0.123 g, 0.88 mmol) in dry DMF (10 mL) was added DIPEA (0.460 mL, 2.64 mmol) followed by HATU (0.334 g, 0.88 mmol). The mixture was allowed to stir for 10 min at RT. To this mixture was added N-((1s,4s)-4-aminocyclohexyl)-5-fluoro-2-(3-iodophenoxy)nicotinamide (0.400 g, 0.88 mmol) and the mixture stirred overnight, poured onto water and the crude product collected by filtration, dried and used in step (c) without purification.

[M+H]+=577 (MultiMode+)

Step (b) 4-Hydroxy-2-(morpholinomethyl)phenylboronic acid

Morpholine (1.19 mL, 13.7 mmol) was added to a solution of 2-bromo-5-hydroxybenzaldehyde (2.5 g, 12.4 mmol) in DCM (20 mL) and stirred for 20 min. Sodium triacetoxyborohydride (2.90 g, 13.7 mmol) was added and stirred for 2 h. The reaction was quenched with methanol and stirred for 1 h. The solution was concentrated in vacuo, dissolved in methanol and loaded onto a SCX (50 g) column, flushing with methanol. Eluting with methanolic ammonia and concentration of the eluant gave the 4-bromo-3-(morpholinomethyl)phenol (3 g, 11.02 mmol), which was dissolved in THF (60 mL) cooled to −78° C. and tert-butyllithium (19.45 mL, 33.07 mmol) (1.7M) was added dropwise. The reaction mixture stirred for 10 min then warmed to 0° C. for 15 min. The reaction was then cooled to −78° C. and triisopropyl borate (7.63 mL, 33.07 mmol) was added. The reaction was warmed to RT and stirred for 1 hr. Saturated aqueous ammonium hydroxide was added and the reaction stirred at RT for 2 h. The reaction mixture was diluted with EtOAc (200 mL), the phases were separated, the aqueous was further extracted with EtOAc. The combined organic extracts were washed with saturated brine (200 mL). The organic was dried over magnesium sulfate, filtered and evaporated to give the sub-title compound. Yield: 2.45 g MS: [M+H]+=238 (MultiMode+)

Step (c) N-((1s,4s)-4-(1,5-dimethyl-1H-pyrazole-3-carboxamido)cyclohexyl)-5-fluoro-2-(4'-hydroxy-2'-(morpholinomethyl)biphenyl-3-yloxy)nicotinamide To a solution of dicyclohexyl(2',6'-dimethoxybiphenyl-2-yl)phosphine (28 mg, 0.07 mmol) in acetonitrile (15.00 mL) was added palladium (II) acetate (8 mg, 0.03 mmol) and the mixture stirred for 10 min at RT. To this solution was added as solution of potassium carbonate (144 mg, 1.04 mmol) in water (5 mL) followed by N-((1s,4s)-4-(1,5-dimethyl-1H-pyrazole-3-carboxamido)cyclohexyl)-5-fluoro-2-(3-iodophenoxy)nicotinamide (200 mg, 0.35 mmol) and 4-hydroxy-2-(morpholinomethyl)phenylboronic acid (82 mg, 0.35 mmol). The mixture was then heated at 70° C. for 3 h. The mixture was poured into water, extracted into EtOAc, and the crude product was purified by preparative HPLC on a Waters X-Terra column using a 95-5% gradient of aqueous 0.2% ammonia in acetonitrile as eluent. The fractions containing the desired compound were evaporated to dryness to afford the title compound as a brown solid. Yield: 21 mg $^1$H NMR (300 MHz, DMSO) δ 8.33-8.23 (m, 2H), 8.07-8.00 (m, 1H), 7.43 (t, J=7.9 Hz, 1H), 7.27 (s, 1H), 7.22-7.12 (m, 4H), 7.06 (d, J=8.3 Hz, 1H), 6.88 (s, 1H), 6.69 (d, J=8.3 Hz, 1H), 6.38 (s, 1H), 3.99 (s, 1H), 3.83 (s, 1H), 3.72 (d, J=1.2 Hz, 4H), 3.49-3.22 (m, 4H), 2.24 (d, J=12.9 Hz, 8H), 1.78-1.56 (m, 8H).

MS: [M+H]+=643 (MultiMode+)

EXAMPLE 3

N-((1s,4s)-4-((1,5-dimethyl-1H-pyrazol-3-yl)methylamino)cyclohexyl)-5-fluoro-2-(4'-hydroxy-2'-(morpholinomethyl)biphenyl-3-yloxy)nicotinamide trifluoroacetate

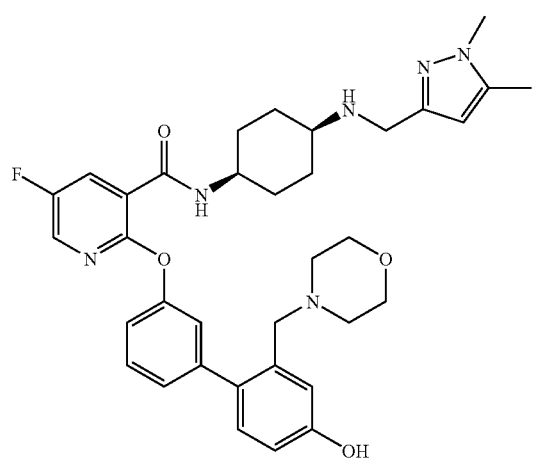

Step (a) tert-butyl (1s,4s)-4-(5-fluoro-2-(4'-hydroxy-2'-(morpholinomethyl)biphenyl-3-yloxy)nicotinamido)cyclohexylcarbamate To a solution of dicyclohexyl(2',6'-dimethoxybiphenyl-2-yl)phosphine (0.177 g, 0.43 mmol) in acetonitrile (60.0 mL) was added palladium (II) acetate (0.049 g, 0.22 mmol) and the mixture stirred for 10 mins at RT. To this solution was added a solution of potassium carbonate (0.896 g, 6.48 mmol) in water (20 mL) followed by tert-butyl (1s,4s)-4-(5-fluoro-2-(3-iodophenoxy)nicotinamido)cyclohexylcarbamate (1.2 g) (from example 1 step a) and 4-hydroxy-2-(morpholinomethyl)phenylboronic acid (0.512 g, 2.16 mmol) (from example 2 step b). The mixture was then heated at 70° C. for 3 h. The mixture was poured into water, extracted into EtOAc and the crude product was purified by preparative HPLC on a Waters X-Terra column using a 95-5% gradient of aqueous 0.2% ammonia in acetonitrile as eluent. The fractions containing the desired compound were evaporated to dryness to afford the sub-title compound as a brown solid. Yield: 490 mg MS: [M+H]+=621 (MultiMode+)

Step (b) N-((1s,4s)-4-aminocyclohexyl)-5-fluoro-2-(4'-hydroxy-2'-(morpholinomethyl)biphenyl-3-yloxy)nicotinamide dihydrochloride To a solution of tert-butyl (1s,4s)-4-(5-fluoro-2-(4'-hydroxy-2'-(morpholinomethyl)biphenyl-3-yloxy)nicotinamido)cyclohexylcarbamate (478 mg, 0.77 mmol) in DCM (3 mL) was added TFA (3 mL, 38.94 mmol). The mixture was stirred at RT for 2 h. The mixture was evaporated to dryness and ethereal HCl added. The mixture was evaporated to dryness and then the process repeated twice more to convert the compound to the HCl salt. This gave a beige powder and used without further purification in step (c). Yield: 550 mg MS: [M+H]+=521 (MultiMode+)

Step (c) N-((1s,4s)-4-((1,5-dimethyl-1H-pyrazol-3-yl)methylamino)cyclohexyl)-5-fluoro-2-(4'-hydroxy-2'-(morpholinomethyl)biphenyl-3-yloxy)nicotinamide trifluoracetate To a solution of N-((1s,4s)-4-aminocyclohexyl)-5-fluoro-2-(4'-hydroxy-2'-(morpholinomethyl)biphenyl-3-yloxy) nicotinamide, 2HCl (100 mg, 0.17 mmol) in DCM (3 mL) was added triethylamine (0.047 mL, 0.34 mmol), 1,5-dimethyl-1H-pyrazole-3-carbaldehyde (21 mg, 0.17 mmol) and then acetic acid (9.65 µL, 0.17 mmol). The mixture was stirred at RT for 50 min. Sodium triacetoxyborohydride (71.4 mg, 0.34 mmol) was then added and the mixture stirred for 3 h. The mixture was added to methanol/water and then purified using reverse phase preparative HPLC (eluent=TFA(aq)/MeCN, Xbridge column), the appropriate fractions were combined and concentrated in vacuo to give an oil. On trituration with ether this gave a white solid which was filtered and dried overnight at 40° C. to give title compound as a white solid. Yield: 52 mg $^1$H NMR (400 MHz, CDCl$_3$) δ 8.17 (dd, J=7.9, 3.1 Hz, 1H), 8.08 (d, J=7.4 Hz, 1H), 8.01 (d, J=3.1 Hz, 1H), 7.46 (t, J=7.8 Hz, 1H), 7.18-7.12 (m, 4H), 7.07 (d, J=7.7 Hz, 1H), 6.90 (dd, J=8.5, 1.8 Hz, 1H), 6.08 (s, 1H), 4.29 (s, 3H), 4.04 (s, 2H), 3.77-3.73 (m, 4H), 3.68 (s, 3H), 3.16-3.07 (m, 3H), 2.68-2.59 (m, 2H), 2.20 (s, 3H), 2.05-1.89 (m, 6H), 1.75-1.66 (m, 2H).
MS: [M+H]+=629 (multimode+).

EXAMPLE 4

N-((1s,4s)-4-(bis((1,5-dimethyl-1H-pyrazol-3-yl)methyl)amino)cyclohexyl)-5-fluoro-2-(4'-hydroxy-2'-(morpholinomethyl)biphenyl-3-yloxy)nicotinamide trifluoroacetate

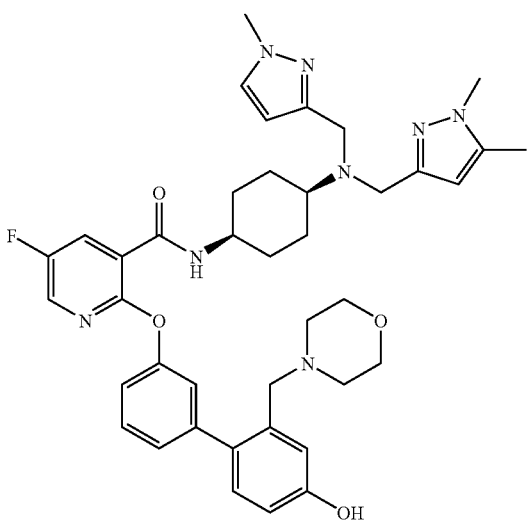

To a solution/suspension of N-((1s,4s)-4-aminocyclohexyl)-5-fluoro-2-(4'-hydroxy-2'-(morpholinomethyl)biphenyl-3-yloxy)nicotinamide, 2HCl (250 mg, 0.42 mmol) in DCM (10 mL) was added 1,5-dimethyl-1H-pyrazole-3-carbaldehyde (105 mg, 0.84 mmol), triethylamine (0.059 mL, 0.42 mmol) and then acetic acid (0.024 mL, 0.42 mmol). The mixture was allowed to stir at RT for 10 min before sodium triacetoxyborohydride (89 mg, 0.42 mmol) was added and the mixture allowed to stir at RT for 2 h. The mixture was concentrated in vacuo and then dissolved in ethylacetate and washed with saturated NaHCO₃ (aq), dried (MgSO₄) and evaporated to give a residue. This was dissolved in methanol and purified by reverse phase preparative HPLC (eluent=TFA (aq)/MeCN) the appropriate fractions were combined and evaporated to give an oil which on trituration with ether was filtered and dried overnight at 40° C. under vacuum to give the title compound as a white solid. Yield: 120 mg ¹H NMR (400 MHz, CDCl₃) δ 8.33 (d, J=7.7 Hz, 1H), 8.08-8.02 (m, 2H), 7.45 (t, J=7.9 Hz, 1H), 7.37 (d, J=1.5 Hz, 1H), 7.23 (dd, J=8.2, 1.8 Hz, 1H), 7.17 (t, J=1.8 Hz, 1H), 7.13 (d, J=8.5 Hz, 1H), 7.04 (d, J=7.4 Hz, 1H), 6.91 (dd, J=8.5, 2.1 Hz, 1H), 6.32 (s, 2H), 4.38-4.34 (m, 1H), 4.27 (s, 2H), 4.10 (s, 4H), 3.81 (s, 4H), 3.72 (s, 6H), 3.16-3.06 (m, 3H), 2.72-2.63 (m, 2H), 2.27-2.20 (m, 8H), 2.15-2.06 (m, 5H), 1.64-1.55 (m, 2H).

[M+H]+=737 (multimode+) (calc=737.3173)

EXAMPLE 5

5-fluoro-2-(4'-hydroxy-2'-(morpholinomethyl)biphenyl-3-yloxy)-N-((1s,4s)-4-((2-methylthiazol-4-yl)methylamino)cyclohexyl)nicotinamide

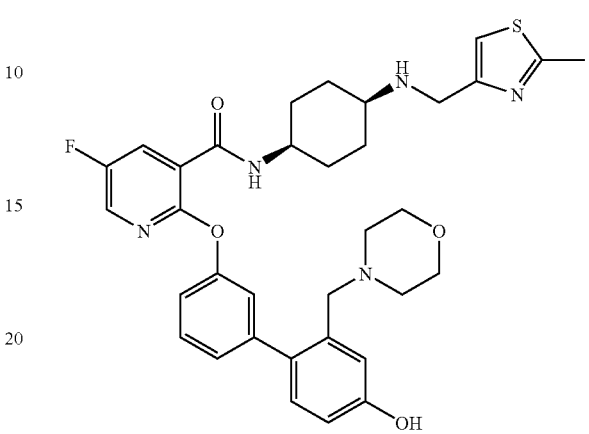

To a solution of N-((1s,4s)-4-aminocyclohexyl)-5-fluoro-2-(4'-hydroxy-2'-(morpholinomethyl)biphenyl-3-yloxy)nicotinamide, bis-trifluoroacetate (150 mg, 0.20 mmol) in DCM (5 mL) was added triethylamine (0.056 mL, 0.40 mmol). After 5 min 2-methyl-1,3-thiazole-4-carbaldehyde (25.5 mg, 0.20 mmol) and acetic acid (0.011 mL, 0.20 mmol) were added. The mixture was stirred at RT for 30 min before sodium triacetoxyborohydride (85 mg, 0.40 mmol) was added and the mixture stirred at RT overnight. The mixture was evaporated and the residue dissolved in methanol and purified by reverse phase prep HPLC (eluent=NH₃(aq)/MeCN). The appropriate fractions were combined and evaporated to give an oil. This was dissolved in the minimum of acetonitrile and then precipitated using water. This suspension was then evaporated and the solid dried overnight at 40° C. under vacuum to give the title compound as a white solid. Yield: 32 mg MS: [M+H]+=632.2 (calc=632.2707) (MultiMode+)

EXAMPLE 6

5-fluoro-2-(4'-hydroxy-2'-(morpholinomethyl)biphenyl-3-yloxy)-N-((1s,4s)-4-((6-methylpyridin-2-yl)methylamino)cyclohexyl)nicotinamide

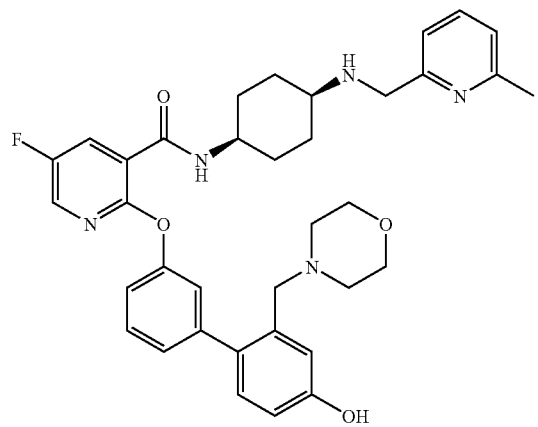

To a solution of N-((1s,4s)-4-aminocyclohexyl)-5-fluoro-2-(4'-hydroxy-2'-(morpholinomethyl)biphenyl-3-yloxy)nicotinamide, bis-trifluoroacetate (150 mg, 0.20 mmol) in DCM (5 mL) was added triethylamine (0.056 mL, 0.40 mmol). After 5 mins 6-methylpyridine-2-carboxaldehyde (24.27 mg, 0.20 mmol) and acetic acid (0.011 mL, 0.20 mmol) were added. The mixture was stirred at RT for 30 min before sodium triacetoxyborohydride (85 mg, 0.40 mmol) was added and the mixture stirred at RT overnight. The mixture was evaporated and the residue dissolved in methanol and purified by reverse phase prep HPLC (eluent=NH$_3$(aq)/MeCN). The appropriate fractions were combined and evaporated to give an oil. This was dissolved in the minimum of acetonitrile and then precipitated using water. The suspension was then evaporated and the solid dried overnight at 40° C. under vacuum to give the title compound as a white solid. Yield: 31 mg $^1$H NMR (400 MHz, CDCl$_3$) δ 8.34 (d, J=5.1 Hz, 1H), 8.11-8.03 (m, 2H), 7.46 (dt, J=33.3, 7.6 Hz, 2H), 7.25 (d, J=11.5 Hz, 2H), 7.11 (d, J=7.7 Hz, 1H), 7.06-7.00 (m, 2H), 6.91 (s, 1H), 6.63 (d, J=6.2 Hz, 1H), 4.20 (s, 1H), 3.88 (s, 2H), 3.54 (s, 4H), 3.32 (s, 2H), 2.75 (s, 1H), 2.50 (s, 3H), 2.31 (s, 4H), 1.91-1.55 (m, 8H)

MS: [M+H]+=626.2 (calc=626.3142) (MultiMode+)

EXAMPLE 7

5-fluoro-2-(4'-hydroxy-2'-(morpholinomethyl)biphenyl-3-yloxy)-N-((1s,4s)-4-(2-hydroxy-5-methylbenzylamino)cyclohexyl)nicotinamide

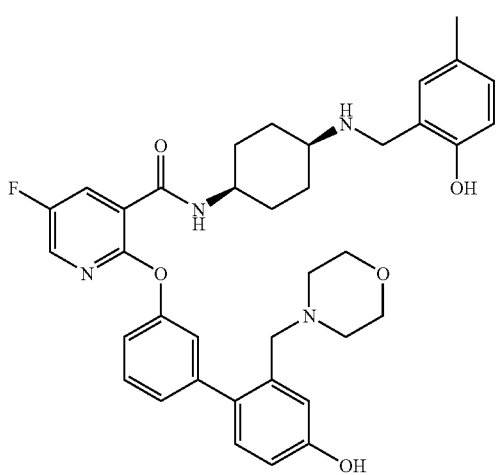

To a solution of N-((1s,4s)-4-aminocyclohexyl)-5-fluoro-2-(4'-hydroxy-2'-(morpholinomethyl)biphenyl-3-yloxy)nicofinamide, bis-trifluoroacetate (150 mg, 0.20 mmol) in DCM (5 mL) was added triethylamine (0.056 mL, 0.40 mmol). After 5 min 2-hydroxy-5-methylbenzaldehyde (27.3 mg, 0.20 mmol) and acetic acid (0.011 mL, 0.20 mmol) were added. The mixture was stirred at RT for 30 min before sodium triacetoxyborohydride (85 mg, 0.40 mmol) was added and the mixture stirred at RT overnight. The mixture was evaporated and the residue dissolved in methanol and purified by reverse phase prep HPLC (eluent=NH$_3$(aq)/MeCN). The appropriate fractions were combined and evaporated to give an oil. This was dissolved in the minimum of acetonirile and then precipitated by the addition of water. The suspension was evaporated and the solid dried overnight at 40° C. under vacuum to give the title compound as a white solid. Yield: 22 mg $^1$H NMR (400 MHz, CDCl$_3$) δ 8.35 (dd, J=8.2, 3.1 Hz, 1H), 8.11-8.06 (m, 2H), 7.47 (t, J=7.9 Hz, 1H), 7.27 (d, J=6.9 Hz, 1H), 7.22 (s, 1H), 7.16-7.11 (m, 2H), 7.00 (d, J=2.3 Hz, 1H), 6.94 (d, J=7.9 Hz, 1H), 6.78-6.73 (m, 2H), 6.67 (d, J=8.2 Hz, 1H), 4.23-4.17 (m, 1H), 3.89 (s, 2H), 3.57 (t, J=4.2 Hz, 4H), 3.37 (s, 2H), 2.72 (d, J=3.1 Hz, 1H), 2.34 (s, 4H), 2.22 (s, 3H), 1.86-1.74 (m, 6H), 1.53-1.44 (m, 2H)

MS: [M+H]+=641.2 (calc=641.3139) (MultiMode+)

EXAMPLE 8

5-fluoro-2-(4'-hydroxy-2'-(morpholinomethyl)biphenyl-3-yloxy)-N-((1s,4s)-4-((5-methylimidazo[1,2-a]pyridin-2-yl)methylamino)cyclohexyl)nicotinamide

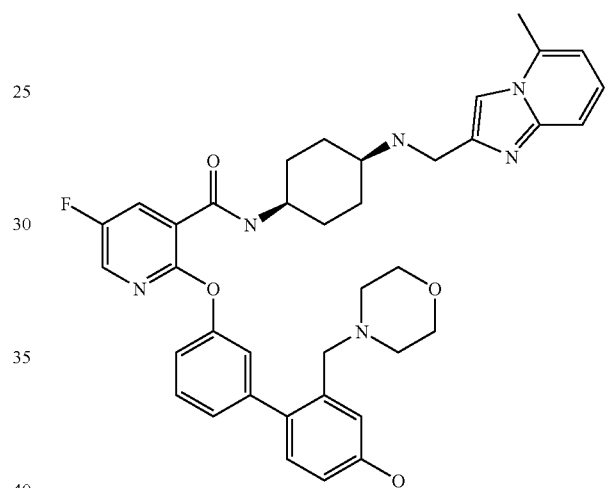

To a solution of N-((1s,4s)-4-aminocyclohexyl)-5-fluoro-2-(4'-hydroxy-2'-(morpholinomethyl)biphenyl-3-yloxy)nicotinamide, bis-trifluoroacetate (150 mg, 0.20 mmol) in DCM (5 mL) was added triethylamine (0.056 mL, 0.40 mmol). After 5 min 5-methylimidazo[1,2-a]pyridine-2-carbaldehyde (32.1 mg, 0.20 mmol) and acetic acid (0.011 mL, 0.20 mmol) were added. The mixture was stirred at RT for 30 min before sodium triacetoxyborohydride (85 mg, 0.40 mmol) was added and the mixture stirred at RT overnight. The mixture was evaporated and the residue dissolved in methanol and purified by reverse phase prep HPLC (eluent=NH$_3$ (aq)/MeCN). The appropriate fractions were combined and evaporated to give an oil. This was dissolved in the minimum of acetonitrile and then precipitated using water. This suspension was then evaporated and the solid dried overnight at 40° C. under vacuum to give the title compound as a white solid. Yield: 62 mg $^1$H NMR (400 MHz, CDCl$_3$) δ 8.35 (dd, J=8.2, 3.1 Hz, 1H), 8.08-8.02 (m, 2H), 7.47-7.35 (m, 3H), 7.24-7.21 (m, 2H), 7.14 (dd, J=8.8, 7.0 Hz, 1H), 7.09 (d, J=8.2 Hz, 1H), 7.00 (d, J=8.5 Hz, 1H), 6.91 (d, J=2.1 Hz, 1H), 6.66-6.59 (m, 2H), 4.18 (s, 1H), 3.97 (s, 2H), 3.54-3.46 (m, 4H), 3.27 (s, 2H), 2.80 (s, 1H), 2.52 (s, 3H), 2.32-2.24 (m, 4H), 1.88-1.69 (m, 6H), 1.62-1.52 (m, 2H)

MS: [M+H]+=665.3 (calc=665.3251) (MultiMode+)

EXAMPLE 9

N-((1s,4s)-4-(2-(2'-((dimethylamino)methyl)-4'-hydroxybiphenyl-3-yloxy)-5-fluoronicotinamido)cyclohexyl)-2-methylthiazole-4-carboxamide

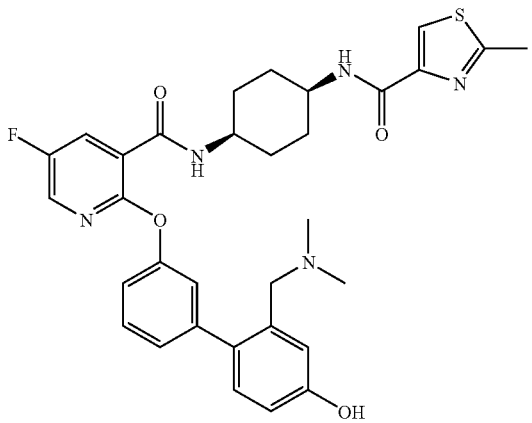

Step (a) tert-butyl (1s,4s)-4-(5-fluoro-2-(3-(4,4,5,5-tetramethyl-1,3,2-dioxaborolan-2-yl)phenoxy)nicotinamido)cyclohexylcarbamate 1,1'-Bis(diphenylphosphino)ferrocene (0.202 g, 0.36 mmol) and 1,1'-bis(diphenylphosphino)ferrocene-palladium(II)dichloride DCM complex (0.294 g, 0.36 mmol) were stirred together in dry dimethylsulfoxide (12 mL) for 10 min, then potassium acetate (2.121 g, 21.61 mmol), a solution of tert-butyl (1s,4s)-4-(5-fluoro-2-(3-iodophenoxy)nicotinamido)cyclohexylcarbamate (4.00 g, 7.20 mmol) in dimethylsulfoxide (24 mL) and bis(pinacolato)diboron (2.432 g, 9.58 mmol) were added and the reaction mixture heated at 80° C. for 16 h. The reaction mixture was allowed to stand for ~4 h then water (~20 mL) was added and the mixture stirred for 1 h. The solid was removed by filtration and washed with water (3×10 mL) then purified by flash silica chromatography (Combi-Flash Companion, 100 g SNAP), elution gradient 50 to 60% EtOAc in isohexane. Pure fractions were evaporated to dryness to the sub-title compound as a cream coloured foam. Yield: 3.51 g $^1$H NMR (400 MHz, CDCl$_3$) δ 8.35 (dd, J=8.2, 3.1 Hz, 1H), 8.06-8.03 (m, 2H), 7.76 (d, J=7.4 Hz, 1H), 7.56 (d, J=2.6 Hz, 1H), 7.49 (t, J=7.7 Hz, 1H), 7.28-7.25 (m, 1H), 4.44-4.38 (m, 1H), 4.19-4.14 (m, 1H), 3.65-3.59 (m, 1H), 1.85-1.67 (m, 8H), 1.42 (s, 9H), 1.35 (s, 12H).

MS: [M+H]+=556 (MultiMode+)

Step (b) tert-butyl (1s,4s)-4-(5-fluoro-2-(2'-formyl-4'-hydroxybiphenyl-3-yloxy)nicotinamido)cyclohexylcarbamate Palladium(II) acetate (0.092 g, 0.41 mmol) and 2-dicyclohexylphosphino-2',6'-dimethoxy-1,1'-biphenyl (S-Phos) (0.336 g, 0.82 mmol) were stirred in acetonitrile (20 mL) for 15 min, then a solution of potassium carbonate (4.24 g, 30.68 mmol) in water (40 mL) added, followed by 2-bromo-5-hydroxybenzaldehyde (2.467 g, 12.27 mmol) and a solution of tert-butyl (1s,4s)-4-(5-fluoro-2-(3-(4,4,5,5-tetramethyl-1,3,2-dioxaborolan-2-yl)phenoxy)nicotinamido)cyclohexylcarbamate (5.68 g, 10.23 mmol) in acetonitrile (27 mL). The reaction mixture was heated at 70° C. for 8 h then allowed to stand overnight. The acetonitrile was evaporated and EtOAc added to the aqueous residue. The layers were separated and the aqueous material extracted with EtOAc (×8). The combined organic extracts were washed with water and saturated brine. The organic was dried over sodium sulfate and filtered to remove the drying agent, leaving a fine suspension. The volatiles were evaporated and the resulting gum partially dissolved in acetone. The suspension was filtered to afford a sample of sub-title compound (3.646 g) as an off-white powder. The filtrate was adsorbed onto 22 g of silica and purified by flash silica chromatography (Combi-Flash Companion, Biotage SNAP 100 g column), elution gradient 20 to 60% EtOAc in isohexane. Pure fractions were evaporated to dryness to afford a further sample of sub-title compound as a pale yellow solid (0.797 g). Yield: 4.443 g $^1$H NMR (400 MHz, DMSO) δ 10.07 (br s, 1H), 9.88 (s, 1H), 8.26-8.25 (m, 2H), 8.02 (dd, J=7.9, 3.1 Hz, 1H), 7.54-7.50 (m, 1H), 7.38 (d, J=8.5 Hz, 1H), 7.28 (d, J=2.6 Hz, 1H), 7.27-7.23 (m, 3H), 7.15 (dd, J=8.5, 2.8 Hz, 1H), 6.61-6.59 (m, 1H), 3.89-3.85 (m, 1H), 3.38-3.34 (m, 1H), 1.74-1.53 (m, 8H), 1.36 (s, 9H).

MS: [M−H]−=548 (MultiMode+)

Step (c) tert-butyl (1s,4s)-4-(2-(2'-((dimethylamino)methyl)-4'-hydroxybiphenyl-3-yloxy)-5-fluoronicotinamido)cyclohexylcarbamate To a solution of tert-butyl (1s,4s)-4-(5-fluoro-2-(2'-formyl-4'-hydroxybiphenyl-3-yloxy)nicotinamido)cyclohexylcarbamate (1.2 g, 2.18 mmol) in DCM (10 mL) was added 2M dimethylamine solution in THF (5.46 mL, 10.92 mmol) and acetic acid (0.125 mL, 2.18 mmol). The mixture was stirred at RT for 10 min before sodium triacetoxyborohydride (0.926 g, 4.37 mmol) was added and the mixture stirred for 1 h. The mixture was diluted with DCM and washed with saturated NaHCO$_3$ (aq) solution (×2), dried (MgSO$_4$) and evaporated to give the sub-title compound as a foam. Yield: 1.2 g MS: [M+H]+=579 (MultiMode+)

Step (d) N-((1s,4s)-4-aminocyclohexyl)-2-(2'-((dimethylamino)methyl)-4'-hydroxybiphenyl-3-yloxy)-5-fluoronicotinamide bis hydrochloride To a solution of tert-butyl (1s,4s)-4-(2-(2'-((dimethylamino)methyl)-4'-hydroxybiphenyl-3-yloxy)-5-fluoronicotinamido)cyclohexylcarbamate (1.2 g, 2.07 mmol) in DCM (10 mL) was added TFA (10 mL, 129.80 mmol). The mixture was stirred at RT overnight. The mixture was evaporated to dryness to give a foam. The foam was then dissolved in DCM and ethereal HCl added (10 mL of 2M HCl in ether). The resulting suspension was evaporated to dryness and the process repeated twice more to give a solid which was triturated with ether, isolated by filtration and dried overnight at 40° C. under vacuum to give the sub-title compound. Yield: 850 mg MS: [M+H]+=479 (MultiMode+)

Step (e) N-((1s,4s)-4-(2-(2'-((dimethylamino)methyl)-4'-hydroxybiphenyl-3-yloxy)-5-fluoronicotinamido)cyclohexyl)-2-methylthiazole-4-carboxamide trifluoroacetate To a solution of 2-methyl-1,3-thiazole-4-carboxylic acid (38.9 mg, 0.27 mmol) in acetonitrile (5 mL) was added DIPEA (0.095 mL, 0.54 mmol) and HATU (103 mg, 0.27 mmol). The mixture was allowed to stir at RT for 10 min before a solution of N-((1s,4s)-4-aminocyclohexyl)-2-(2'-((dimethylamino)methyl)-4'-hydroxybiphenyl-3-yloxy)-5-fluoronicotinamide, 2HCl (150 mg, 0.27 mmol) in MeCN (5 mL) with 2 eq of DIPEA was added and the mixture stirred at RT overnight. The mixture was purified using reverse phase prep HPLC (eluent=TFA (aq)(MeCN), the appropriate fractions were combined and evaporated to give an oil. On trituration with ether the oil gave the title compound as a colourless solid which was dried. Yield: 105 mg $^1$H NMR (400 MHz, CDCl$_3$) δ 8.36 (dd, J=8.2, 3.1 Hz, 1H), 8.02 (d, J=3.3 Hz, 1H), 7.97 (d, J=7.2 Hz, 1H), 7.92 (s, 1H), 7.54 (t, J=7.9 Hz, 1H), 7.33 (s, 1H), 7.25-7.19 (m, 3H), 7.13 (d, J=7.7 Hz, 1H), 7.07 (t, J=1.9 Hz, 1H), 6.95 (d, J=8.5 Hz, 1H), 4.27-4.21 (m, 3H), 4.08-4.01 (m, 1H), 2.66 (s, 3H), 2.58 (s, 6H), 1.97-1.83 (m, 6H), 1.71-1.62 (m, 2H).

MS: [M+H]+=604.2 (calc=604.2394) (MultiMode+)

EXAMPLE 10

N-((1s,4s)-4-(2-(2'-((dimethylamino)methyl)-4'-hydroxybiphenyl-3-yloxy)-5-fluoronicotinamido)cyclohexyl)-6-methylpicolinamide

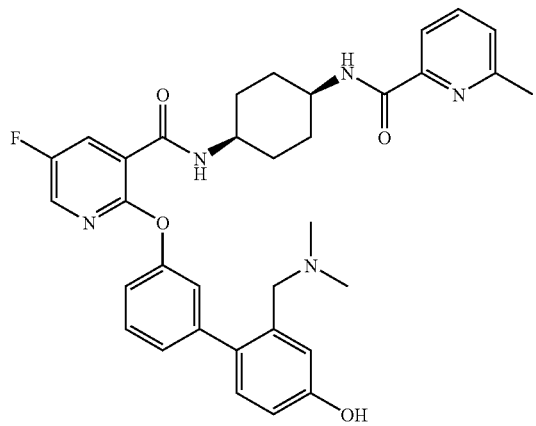

To a solution of 6-methylpicolinic acid (37.3 mg, 0.27 mmol) in acetonitrile (5 mL) was added DIPEA (0.095 mL, 0.54 mmol) and HATU (103 mg, 0.27 mmol). The mixture was allowed to stir at RT for 10 min before a solution of N-((1s,4s)-4-aminocyclohexyl)-2-(2'-((dimethylamino)methyl)-4'-hydroxybiphenyl-3-yloxy)-5-fluoronicotinamide, 2HCl (150 mg, 0.27 mmol) in MeCN (5 mL) with 2 eq of DIPEA was added and the mixture stirred at RT overnight. The mixture was purified using reverse phase prep HPLC (eluent=TFA (aq)/MeCN), the appropriate fractions were combined and evaporated to give an oil. On trituration with ether the oil gave the title compound as a colourless solid which was dried. Yield: 83 mg $^1$H NMR (400 MHz, CDCl$_3$) δ 8.36 (dd, J=8.2, 3.1 Hz, 1H), 8.08 (d, J=7.4 Hz, 1H), 8.03-7.99 (m, 2H), 7.95 (d, J=7.7 Hz, 1H), 7.73 (t, J=7.7 Hz, 1H), 7.52 (t, J=7.8 Hz, 1H), 7.30-7.26 (m, 2H), 7.21 (dd, J=8.2, 1.8 Hz, 1H), 7.18 (d, J=8.5 Hz, 1H), 7.12 (d, J=7.7 Hz, 1H), 7.08 (d, J=1.5 Hz, 1H), 6.92 (d, J=8.2 Hz, 1H), 4.28-4.25 (m, 1H), 4.21 (s, 2H), 4.07-4.02 (m, 1H), 2.56 (s, 6H), 2.49 (s, 3H), 1.99-1.86 (m, 6H), 1.75-1.66 (m, 2H).

MS: [M+H]+=598.2 (calc=598.2829) (MultiMode+)

EXAMPLE 11

N-((1s,4s)-4-(2-(2'-((dimethylamino)methyl)-4'-hydroxybiphenyl-3-yloxy)-5-fluoronicotinamido)cyclohexyl)-5-methylimidazo[1,2-a]pyridine-2-carboxamide

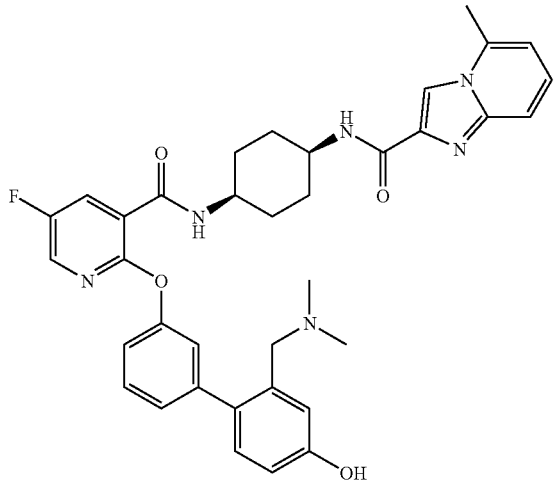

To a solution of 5-methyl-imidazo[1,2-a]pyridine-2-carboxylic acid (47.9 mg, 0.27 mmol) in acetonitrile (5 mL) was added DIPEA (0.095 mL, 0.54 mmol) and HATU (103 mg, 0.27 mmol). The mixture was allowed to stir at RT for 10 min before a solution of N-((1s,4s)-4-aminocyclohexyl)-2-(2'-((dimethylamino)methyl)-4'-hydroxybiphenyl-3-yloxy)-5-fluoronicotinamide, 2HCl (150 mg, 0.27 mmol) in MeCN (5 mL) with 2 eq of DIPEA was added and the mixture stirred at RT overnight. The mixture was purified using reverse phase prep HPLC (eluent=TFA (aq)/MeCN), the appropriate fractions were combined and evaporated to give an oil. On trituration with ether the oil gave the title compound as a colourless solid which was dried overnight under vacuum at 40° C. Yield: 32 mg $^1$H NMR (400 MHz, CDCl$_3$) δ 8.35 (s, 1H), 8.25 (dd, J=7.9, 3.1 Hz, 1H), 8.04 (d, J=3.1 Hz, 1H), 7.62-7.50 (m, 3H), 7.24-7.09 (m, 5H), 7.01 (d, J=6.2 Hz, 1H), 6.86 (dd, J=8.5, 2.3 Hz, 1H), 4.28-4.18 (m, 4H), 2.74 (s, 3H), 2.62 (s, 6H), 1.94-1.79 (m, 8H)

MS: [M+H]+=651.2 (calc=637.2938) (MultiMode+)

EXAMPLE 12

N-((1s,4s)-4-(2-(2'-((dimethylamino)methyl)-4'-hydroxybiphenyl-3-yloxy)-5-fluoronicotinamido)cyclohexyl)-6-fluoroimidazo[1,2-a]pyridine-2-carboxamide

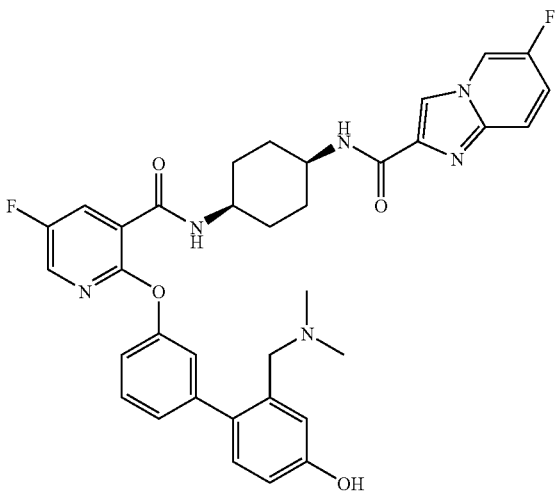

To a solution of 6-fluoroimidazo[1,2-a]pyridine-2-carboxylic acid, HCl (58.9 mg, 0.27 mmol) in acetonitrile (5 mL) was added DIPEA (0.142 mL, 0.82 mmol) and HATU (103 mg, 0.27 mmol). The mixture was allowed to stir at RT for 10 min before a solution of N-((1s,4s)-4-aminocyclohexyl)-2-(2'-((dimethylamino)methyl)-4'-hydroxybiphenyl-3-yloxy)-5-fluoronicotinamide, 2HCl (150 mg, 0.27 mmol) in MeCN (5 mL) with 2 eq of DIPEA was added and the mixture stirred at RT overnight. The mixture was purified using reverse phase prep HPLC (eluent=TFA (aq)/MeCN), the appropriate fractions were combined and evaporated to give an oil. On trituration with ether the oil gave the title compound as a colourless solid which was dried overnight under vacuum at 40° C. Yield: 102 mg $^1$H NMR (400 MHz, CDCl$_3$) δ 8.34 (dd, J=7.9, 3.1 Hz, 1H), 8.25 (t, J=2.7 Hz, 1H), 8.23 (s, 1H), 8.03 (d, J=3.3 Hz, 1H), 7.58 (dd, J=10.0, 4.9 Hz, 1H), 7.52 (t, J=7.8 Hz, 1H), 7.36 (ddd, J=9.9, 7.8, 2.2 Hz, 1H), 7.23-7.18 (m, 2H), 7.14-7.09 (m, 3H), 6.86 (dd, J=8.5, 2.3 Hz, 1H), 4.25-4.20 (m, 3H), 4.14-4.10 (m, 1H), 2.61 (s, 6H), 1.95-1.84 (m, 6H), 1.81-1.70 (m, 2H).

MS: [M+H]+=641.2 (calc=641.2688) (MultiMode+)

EXAMPLE 13

N-((1s,4s)-4-(2-(2'-((1,4-oxazepan-4-yl)methyl)-4'-hydroxybiphenyl-3-yloxy)-5-fluoronicotinamido)cyclohexyl)-6-fluoroimidazo[1,2-a]pyridine-2-carboxamide

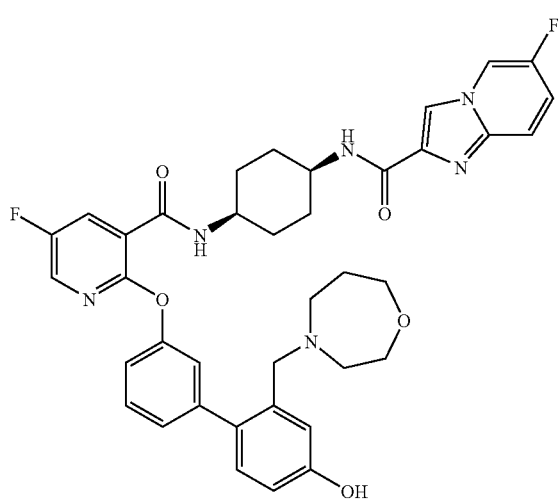

Step (a) tert-butyl (1s,4s)-4-(2-(2'-((1,4-oxazepan-4-yl)methyl)-4'-hydroxybiphenyl-3-yloxy)-5-fluoronicotinamido)cyclohexylcarbamate Homomorpholine hydrochloride (0.445 g, 3.23 mmol), anhydrous sodium sulfate (3.32 g, 23.35 mmol) and tert-butyl (1s,4s)-4-(5-fluoro-2-(2'-formyl-4'-hydroxybiphenyl-3-yloxy)nicotinamido)cyclohexylcarbamate (1.281 g, 2.33 mmol) were suspended in DCM (15 mL). Acetic acid (0.14 mL, 2.45 mmol) was added and the reaction mixture stirred at RT for 1 h before sodium triacetoxyborohydride (0.988 g, 4.66 mmol) was added. The mixture was stirred for 1.5 h then diluted with DCM and washed with water, saturated sodium hydrogen carbonate, water and saturated brine. The organic was dried over sodium sulfate, filtered and evaporated to afford crude product. The crude material was dissolved in methanol and loaded on to a pre-washed 10 g SCX cartridge. The neutral material was washed through with methanol (100 mL). The product was eluted with 1N methanolic ammonia (50 mL) and the solvent evaporated in vacuo to give the sub-title compound as a colourless oil. Yield: 0.92 g MS: [M+H]+=635 (MultiMode+)

Step (b) 2-(2'-((1,4-oxazepan-4-yl)methyl)-4'-hydroxybiphenyl-3-yloxy)-N-((1s,4s)-4-aminocyclohexyl)-5-fluoronicotinamide tert-Butyl (1s,4s)-4-(2-(2'-((1,4-oxazepan-4-yl)methyl)-4'-hydroxybiphenyl-3-yloxy)-5-fluoronicotinamido)cyclohexylcarbamate (0.92 g, 1.45 mmol) was dissolved in DCM (3.5 mL) and cooled in ice. TFA (3.5 mL, 45.43 mmol) was added slowly then the reaction mixture was stirred at RT for 3 h. The volatiles were evaporated and the residue partitioned between saturated sodium hydrogen carbonate and DCM. The organic layer was washed with water and saturated brine. The organic was dried over sodium sulfate, filtered and evaporated to afford crude sub-title compound (0.500 g) as a white foam, which was used without further purification. The aqueous material was exhaustively re-extracted to yield a further 0.232 g. Yield: 0.732 g MS: [M+H]+=535 (MultiMode+)

Step (c) N-((1s,4s)-4-(2-(2'-((1,4-oxazepan-4-yl)methyl)-4'-hydroxybiphenyl-3-yloxy)-5-fluoronicotinamido)cyclohexyl)-6-fluoroimidazo[1,2-a]pyridine-2-carboxamide trifluoroacetate HATU (0.089 g, 0.23 mmol) and N-ethyldiisopropylamine (0.121 mL, 0.70 mmol) were added to a solution of 6-fluoroimidazo[1,2-a]pyridine-2-carboxylic acid hydrochloride (0.051 g, 0.23 mmol) in acetonitrile (4 mL). The mixture was stirred for 10 min then a solution of 2-(2'-((1,4-oxazepan-4-yl)methyl)-4'-hydroxybiphenyl-3-yloxy)-N-((1s,4s)-4-aminocyclohexyl)-5-fluoronicotinamide (0.125 g, 0.23 mmol) in acetonitrile (4 mL) was added and the reaction stirred at RT overnight. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a cream solid. Yield: 82 mg $^1$H NMR (400 MHz, DMSO) δ 9.57 (br s, 1H), 8.83-8.81 (m, 1H), 8.38-8.35 (m, 2H), 8.26-8.24 (m, 1H), 8.05 (dd, J=7.8, 2.9 Hz, 1H), 7.77 (d, J=7.9 Hz, 1H), 7.67-7.63 (m, 1H), 7.54-7.46 (m, 2H), 7.26-7.23 (m, 1H), 7.19-7.09 (m, 4H), 6.92 (d, J=8.5 Hz, 1H), 4.33-4.29 (m, 2H), 3.01-2.80 (m, 2H), 1.95-1.66 (m, 10H). Remaining protons obscured by solvent peak.

MS: [M+H]+=697.2 (calc=697.295) (MultiMode+)

EXAMPLE 14

N-((1s,4s)-4-(2-(2'-((1,4-oxazepan-4-yl)methyl)-4'-hydroxybiphenyl-3-yloxy)-5-fluoronicotinamido)cyclohexyl)-6-methylpicolinamide

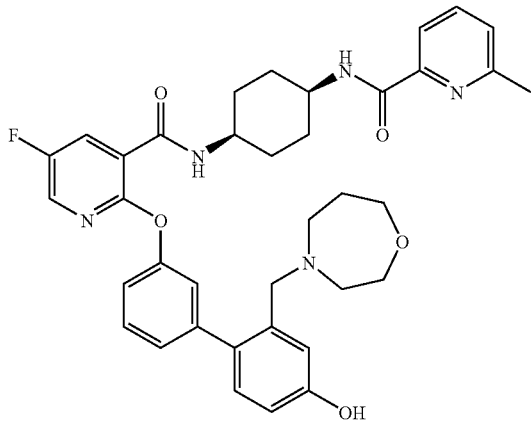

HATU (0.089 g, 0.23 mmol) and DIPEA (0.081 mL, 0.47 mmol) were added to a solution of 6-methylpicolinic acid (0.032 g, 0.23 mmol) in acetonitrile (4 mL). The mixture was stirred for 10 min then a solution of 2-(2'-((1,4-oxazepan-4-yl)methyl)-4'-hydroxybiphenyl-3-yloxy)-N-((1s,4s)-4-aminocyclohexyl)-5-fluoronicotinamide (0.125 g, 0.23 mmol) in acetonitrile (4 mL) was added and the reaction stirred at RT for two days. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a pale yellow foam. Yield: 109 mg $^1$H NMR (400 MHz, DMSO) δ 9.90 (br s, 1H), 8.40 (d, J=7.4 Hz, 1H), 8.25 (d, J=3.1 Hz, 1H), 8.09 (d, J=8.5 Hz, 1H), 8.04 (dd, J=7.9, 3.1 Hz, 1H), 7.90-7.83 (m, 2H), 7.52-7.46 (m, 2H), 7.25-7.22 (m, 1H), 7.17-7.10 (m, 4H), 6.90 (dd, J=8.3, 2.4 Hz, 1H), 4.35-4.27 (m, 2H), 4.04-3.99 (m, 1H), 3.93-3.88 (m, 1H), 3.64-3.46 (m, 4H), 3.02-2.80 (m, 2H), 1.94-1.68 (m, 10H). Remaining protons obscured by solvent peaks.

MS: [M+H]+=654.2 (calc=654.3091) (MultiMode+)

EXAMPLE 15

N-((1s,4s)-4-(2-(2'-((1,4-oxazepan-4-yl)methyl)-4'-hydroxybiphenyl-3-yloxy)-5-fluoronicotinamido)cyclohexyl)-2-methylthiazole-4-carboxamide

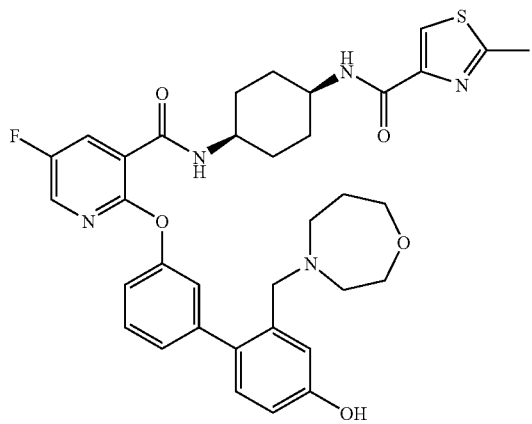

HATU (0.089 g, 0.23 mmol) and DIPEA (0.081 mL, 0.47 mmol) were added to a solution of 2-methylthiazole-4-carboxylic acid (0.033 g, 0.23 mmol) in acetonitrile (4 mL). The mixture was stirred for 10 min then a solution of 2-(2'-((1,4-oxazepan-4-yl)methyl)-4'-hydroxybiphenyl-3-yloxy)-N-((1s,4s)-4-aminocyclohexyl)-5-fluoronicotinamide (0.125 g, 0.23 mmol) in acetonitrile (4 mL) was added and the reaction stirred at RT for 2 days. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as an off-white solid. Yield: 0.134 g $^1$H NMR (400 MHz, DMSO) δ 9.94 (br s, 1H), 8.35 (d, J=7.2 Hz, 1H), 8.25 (d, J=2.8 Hz, 1H), 8.08 (s, 1H), 8.04 (dd, J=7.9, 3.1 Hz, 1H), 7.60 (d, J=7.7 Hz, 1H), 7.51 (t, J=7.8 Hz, 1H), 7.24-7.22 (m, 1H), 7.18-7.10 (m, 4H), 6.92 (d, J=8.3 Hz, 1H), 4.33-4.28 (m, 2H), 4.02-3.97 (m, 1H), 3.90-3.85 (m, 1H), 3.64-3.53 (m, 4H), 3.02-2.80 (m, 2H), 2.68 (s, 3H), 1.96-1.64 (m, 10H). Remaining protons obscured by water peak.

MS: [M+H]+=660.2 (calc=660.2656) (MultiMode+)

EXAMPLE 16

2-(2'-((1,4-oxazepan-4-yl)methyl)-4'-hydroxybiphenyl-3-yloxy)-5-fluoro-N-((1s,4s)-4-(2-hydroxy-5-methylbenzamido)cyclohexyl)nicotinamide HATU (0.089 g, 0.23 mmol) and DIPEA (0.081 mL, 0.47 mmol) were added to a solution of 2-hydroxy-5-methylbenzoic acid (0.036 g, 0.23 mmol) in acetonitrile (4 mL). The mixture was stirred for 10 min then a solution of 2-(2'-((1,4-oxazepan-4-yl)methyl)-4'-hydroxybiphenyl-3-yloxy)-N-((1s,4s)-4-aminocyclohexyl)-5-fluoronicotinamide (0.125 g, 0.23 mmol) in acetonitrile (4 mL) was added and the reaction stirred at RT overnight. Further acid (18 mg), DIPEA (0.04 mL) and HATU (45 mg) were added and the reaction stirred overnight again. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white solid. Yield: 16 mg $^1$H NMR (400 MHz, DMSO) δ 12.03 (s, 1H), 11.42 (br s, 1H), 8.45-8.39 (m, 2H), 8.24 (d, J=2.8 Hz, 1H), 8.01 (dd, J=7.8, 3.0 Hz, 1H), 7.69 (s, 1H), 7.50 (t, J=38.0 Hz, 1H), 7.24-7.09 (m, 6H), 6.92 (d, J=8.0 Hz, 1H), 6.81 (d, J=8.2 Hz, 1H), 4.34-4.25 (m, 2H), 3.98-3.87 (m, 2H), 3.62-3.55 (m, 2H), 3.02-2.78 (m, 2H), 2.23 (s, 3H), 1.94-1.68 (m, 10H). Remaining protons obscured by solvent peaks.

MS: [M+H]+=669.2 (calc=669.3088) (MultiMode+)

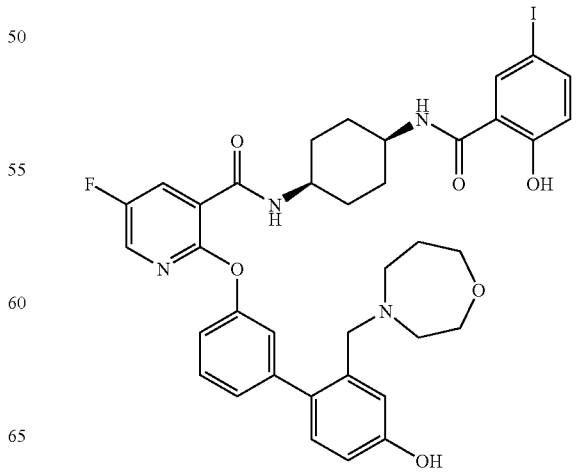

EXAMPLE 17

N-((1s,4s)-4-(1-(dimethylamino)cyclopropanecarboxamido)cyclohexyl)-5-fluoro-2-(4'-hydroxy-2'-(morpholinomethyl)biphenyl-3-yloxy)nicotinamide

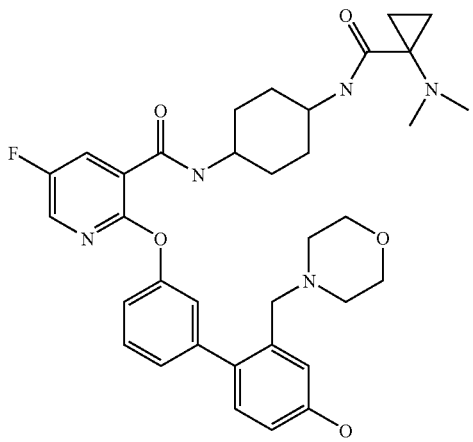

N-((1s,4s)-4-Aminocyclohexyl)-5-fluoro-2-(4'-hydroxy-2'-(morpholinomethyl)biphenyl-3-yloxy)nicotinamide trifluoroacetate (250 mg, 0.33 mmol) was dissolved in methanol (1 mL) and passed through a Stratosphere PL-HCO3 MP SPE cartridge (preconditioned with methanol, eluting with more methanol 2 mL). The solvent was evaporated and the residue was taken in acetonitrile (2 mL), and treated with 1-(dimethylamino)cyclopropanecarboxylic acid (52 mg, 0.40 mmol) and 2,4,6-tripropyl-1,3,5,2,4,6-trioxatriphosphorinane-2,4,6-trioxide (T3P, 1.57M in THF) (0.277 mL, 0.43 mmol) with stirring at RT. Triethylamine (0.279 mL, 2.00 mmol) was added and stirring was continued for 2 h. The solvent was evaporated and the residue was taken up in EtOAc, washed with 2M aqueous sodium bicarbonate solution, dried and evaporated. The residue was taken up in acetonitrile, filtered and purified by RPHPLC (ACE 5C8 column, 0.2% aq TFA-acetonitrile, 80%-40% gradient). Product containing fractions were combined, the acetonitrile evaporated and the residual water removed by freeze drying affording the title compound as a hygroscopic gum. Yield: 9 mg $^1$H NMR (400 MHz, CDCl$_3$+d6-DMSO) δ 8.30 (dd, J=8.2, 3.1 Hz, 1H), 8.07 (d, J=3.1 Hz, 1H), 8.01 (d, J=7.2 Hz, 1H), 7.52 (t, J=7.8 Hz, 1H), 7.39 (d, J=7.4 Hz, 1H), 7.23-7.12 (m, 6H), 6.98 (dd, J=8.5, 2.3 Hz, 1H), 4.32-4.26 (m, 2H), 4.25-4.15 (m, 1H), 3.89-3.78 (m, 6H), 2.61-2.57 (m, 4H), 1.87-1.72 (m, 4H), 1.64-1.47 (m, 2H), 1.33-1.16 (m, 4H). Other resonances obscured by DMSO and water signals.

MS: [M+H]+=632.3 (calc=632.3248) (MultiMode+)

EXAMPLE 18

N-((1s,4s)-4-(5-fluoro-2-(4'-hydroxy-2'-(morpholinomethyl)biphenyl-3-yloxy)nicotinamido)cyclohexyl)-5-methylimidazo[1,2-a]pyridine-2-carboxamide

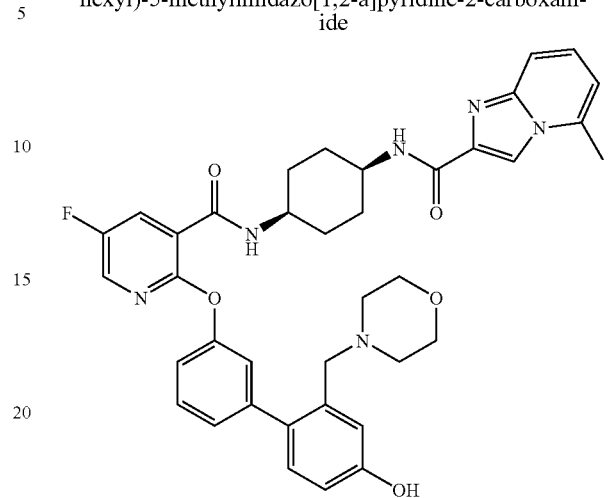

To a solution of 5-methylimidazo[1,2-a]pyridine-2-carboxylic acid (84 mg, 0.48 mmol) in acetonitrile (5 mL) was added DIPEA (0.166 mL, 0.95 mmol) and HATU (181 mg, 0.48 mmol). The mixture was allowed to stir at RT for 10 min before a solution of N-((1s,4s)-4-aminocyclohexyl)-5-fluoro-2-(4'-hydroxy-2'-(morpholinomethyl)biphenyl-3-yloxy)nicotinamide (283 mg, 0.48 mmol) in MeCN (5 mL) with 2 eq of DIPEA was added and the mixture stirred at RT overnight. The mixture was purified using reverse phase prep HPLC (eluent=TFA (aq)/MeCN), the appropriate fractions were combined and evaporated to give an oil. On trituration with ether the oil gave the title compound as colourless solid which was dried overnight under vacuum at 40° C. Yield: 156 mg $^1$H NMR (400 MHz, DMSO) δ 8.25 (s, 1H), 8.22 (dd, J=2.9, 1.2 Hz, 1H), 8.14 (d, J=6.9 Hz, 1H), 7.99 (dd, J=8.1, 2.9 Hz, 1H), 7.66 (d, J=7.2 Hz, 1H), 7.51-7.45 (m, 2H), 7.37 (t, J=7.9 Hz, 1H), 7.23-7.20 (m, 1H), 7.16-7.10 (m, 3H), 7.04 (d, J=2.3 Hz, 1H), 6.91-6.87 (m, 2H), 4.12 (s, 2H), 4.02-3.96 (m, 2H), 3.64 (t, J=4.2 Hz, 4H), 2.86-2.81 (m, 4H), 2.65 (s, 3H), 1.82-1.73 (m, 8H).

MS: [M+H]+=679.2 (calc=679.3044) (MultiMode+)

EXAMPLE 19

2-(2'-((1,4-oxazepan-4-yl)methyl)-4'-hydroxybiphenyl-3-yloxy)-N-((1s,4s)-4-(1,5-dimethyl-1H-pyrazole-3-carboxamido)cyclohexyl)-5-fluoronicotinamide

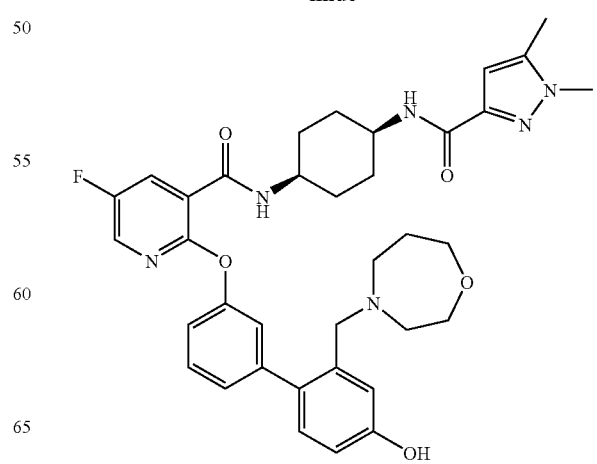

HATU (0.083 g, 0.22 mmol) and DIPEA (0.075 mL, 0.43 mmol) were added to a solution of 1,5-dimethyl-1H-pyrazole-3-carboxylic acid (0.030 g, 0.22 mmol) in acetonitrile (4 mL). The mixture was stirred for 10 min then a solution of 2-(2'-((1,4-oxazepan-4-yl)methyl)-4'-hydroxybiphenyl-3-yloxy)-N-((1s,4s)-4-aminocyclohexyl)-5-fluoronicotinamide (0.116 g, 0.22 mmol) in acetonitrile (4 mL) was added and the reaction stirred at RT for 2 days. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a cream-coloured foam. Yield: 120 mg $^1$H NMR (400 MHz, DMSO) δ 9.93 (br s, 1H), 9.47 (br s, 1H), 8.33 (d, J=6.9 Hz, 1H), 8.25 (d, J=3.1 Hz, 1H), 8.04 (dd, J=7.8, 2.9 Hz, 1H), 7.51 (t, J=7.9 Hz, 1H), 7.24 (d, J=7.9 Hz, 2H), 7.19-7.10 (m, 3H), 6.93-6.91 (m, 1H), 6.39 (s, 1H), 4.35-4.26 (m, 2H), 4.00-3.95 (m, 1H), 3.85-3.80 (m, 1H), 3.74 (s, 3H), 3.01-2.80 (m, 2H), 2.26 (s, 3H), 1.95-1.61 (m, 10H). Remaining protons obscured by solvent peak.

MS: [M+H]+=657.3 (calc=657.32) (MultiMode+)

EXAMPLE 20

N-((1s,4s)-4-(2-(2'-((1,4-oxazepan-4-yl)methyl)-4'-hydroxybiphenyl-3-yloxy)-5-fluoronicotinamido)cyclohexyl)-5-methylimidazo[1,2-a]pyridine-2-carboxamide

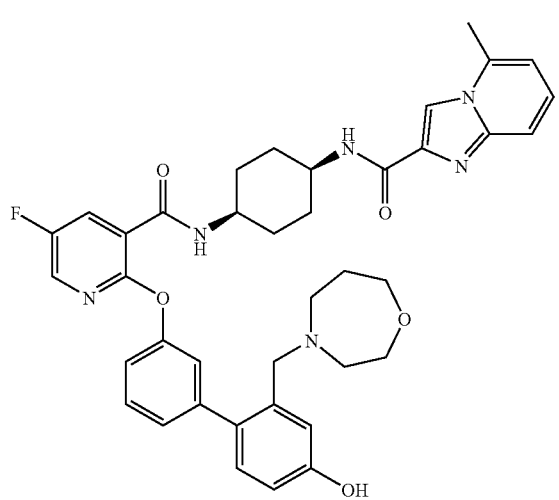

HATU (0.083 g, 0.22 mmol) and DIPEA (0.075 mL, 0.43 mmol) were added to a solution of 5-methylimidazo[1,2-a]pyridine-2-carboxylic acid (0.038 g, 0.22 mmol) in acetonitrile (4 mL). The mixture was stirred for 10 min then a solution of 2-(2'-((1,4-oxazepan-4-yl)methyl)-4'-hydroxybiphenyl-3-yloxy)-N-((1s,4s)-4-aminocyclohexyl)-5-fluoronicotinamide (0.116 g, 0.22 mmol) in acetonitrile (4 mL) was added and the reaction stirred at RT overnight. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white solid. Yield: 21 mg $^1$H NMR (400 MHz, DMSO) δ 9.94 (br s, 1H), 9.45 (br s, 1H), 8.40-8.36 (m, 2H), 8.25 (d, J=3.1 Hz, 1H), 8.05 (dd, J=7.9, 3.1 Hz, 1H), 7.94 (s, 1H), 7.53-7.49 (m, 2H), 7.47-7.42 (m, 1H), 7.24 (dd, J=7.9, 1.8 Hz, 1H), 7.19-7.10 (m, 3H), 7.00-6.96 (m, 1H), 6.92 (dd, J=8.5, 2.6 Hz, 1H), 4.33-4.29 (m, 2H), 4.01-3.93 (m, 2H), 3.01-2.80 (m, 2H), 2.66 (s, 3H), 1.93-1.67 (m, 10H). Remaining protons obscured by solvent peak.

MS: [M+H]+=693.3 (calc=693.32) (MultiMode+)

EXAMPLE 21

6-fluoro-N-((1s,4s)-4-(5-fluoro-2-(4'-hydroxy-2'-(thiomorpholinomethyl)biphenyl-3-yloxy)nicotinamido)cyclohexyl)imidazo[1,2-a]pyridine-2-carboxamide

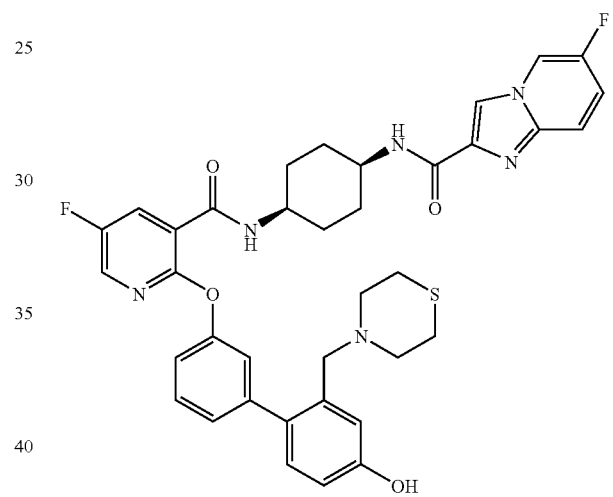

Step (a) tert-butyl (1s,4s)-4-(5-fluoro-2-(4'-hydroxy-2'-(thiomorpholinomethyl)biphenyl-3-yloxy)nicotinamido)cyclohexylcarbamate To a solution of tert-butyl (1s,4s)-4-(5-fluoro-2-(2'-formyl-4'-hydroxybiphenyl-3-yloxy)nicotinamido)cyclohexylcarbamate (0.52 g, 0.95 mmol) in DCM (10 mL) were added thiomorpholine (0.190 mL, 1.89 mmol) and acetic acid (0.054 mL, 0.95 mmol). The mixture was stirred at RT for 10 min before sodium triacetoxyborohydride (0.401 g, 1.89 mmol) was added and the mixture stirred for 1 h. The mixture was diluted with DCM and washed with saturated NaHCO$_3$ (aq) solution (×2), dried (MgSO$_4$) and evaporated to give the sub-title compound as a foam. Yield: 0.5 g MS: [M+H]+=637.2 (calc=637.286) (MultiMode+)

$^1$H NMR (400 MHz, CDCl$_3$) δ 8.36 (dd, J=8.2, 3.3 Hz, 1H), 8.09 (d, J=3.1 Hz, 1H), 8.04 (d, J=7.2 Hz, 1H), 7.47 (t, J=7.8 Hz, 1H), 7.27-7.24 (m, 1H), 7.18-7.15 (m, 2H), 7.12 (dd, J=8.1, 1.9 Hz, 1H), 6.99 (d, J=2.8 Hz, 1H), 6.79 (dd, J=8.3, 2.7 Hz, 1H), 4.47-4.44 (m, 1H), 4.20-4.14 (m, 1H), 3.65-3.59 (m, 1H), 3.40 (s, 2H), 2.62-2.58 (m, 4H), 2.55-2.51 (m, 4H), 1.86-1.66 (m, 6H), 1.54-1.47 (m, 2H), 1.43 (s, 9H)

Step (b) N-((1s,4s)-4-aminocyclohexyl)-5-fluoro-2-(4'-hydroxy-2'-(thiomorpholinomethyl)biphenyl-3-yloxy)nicotinamide (0.130 g, 0.21 mmol) dihydrochloride To a solution of tert-butyl (1s,4s)-4-(5-fluoro-2-(4'-hydroxy-2'-(thiomorpholinomethyl)biphenyl-3-yloxy)nicotinamido)cyclohexylcarbamate (450 mg, 0.71 mmol) in DCM (10 mL) was added hydrogen chloride, 2.0M solution in ether (5 mL, 10.00 mmol). DCM (5 mL) was added and the reaction left to stir at RT overnight. The mixture was evaporated to dryness to give the sub-title compound as a yellow solid. Yield: 470 mg
MS: [M+H]+=537.3 (MultiMode+)

Step (c) 6-fluoro-N-((1s,4s)-4-(5-fluoro-2-(4'-hydroxy-2'-(thiomorpholinomethyl)biphenyl-3-yloxy)nicotinamido)cyclohexyl)imidazo[1,2-a]pyridine-2-carboxamide HATU (0.081 g, 0.21 mmol) and DIPEA (0.184 mL, 1.07 mmol) were added to a suspension of 6-fluoroimidazo[1,2-a]pyridine-2-carboxylic acid (0.046 g, 0.21 mmol) hydrochloride in acetonitrile (4 mL). The mixture was stirred for 10 min then N-((1s,4s)-4-aminocyclohexyl)-5-fluoro-2-(4'-hydroxy-2'-(thiomorpholinomethyl)biphenyl-3-yloxy)nicotinamide (0.130 g, 0.21 mmol) dihydrochloride was added, followed by acetonitrile (6 mL) and the reaction stirred at RT overnight. 880 aqueous ammonia (~3 mL) was added, followed by enough methanol to bring the precipitated solids into solution (~2 mL). The mixture was stirred for a further 4 h then diluted with DCM and washed with water and saturated brine. The organics was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a pale pink solid. Yield: 73 mg
¹H NMR (400 MHz, DMSO) δ 9.90 (br s, 1H), 8.80 (s, 1H), 8.37-8.27 (m, 3H), 8.05 (dd, J=8.1, 2.9 Hz, 1H), 7.75-7.70 (m, 1H), 7.66-7.62 (m, 1H), 7.53-7.45 (m, 2H), 7.24 (d, J=8.5 Hz, 1H), 7.18-7.04 (m, 4H), 6.91 (d, J=9.0 Hz, 1H), 4.27-4.23 (m, 1H), 4.02-3.90 (m, 1H), 2.87-2.61 (m, 4H), 1.80-1.66 (m, 8H). Remaining protons obscured by solvent peaks.
MS: [M+H]+=699.2 (calc=699.2565) (MultiMode+)

EXAMPLE 22

N-((1s,4s)-4-(1,5-dimethyl-1H-pyrazole-3-carboxamido)cyclohexyl)-5-fluoro-2-(4'-hydroxy-2'-(thiomorpholinomethyl)biphenyl-3-yloxy)nicotinamide

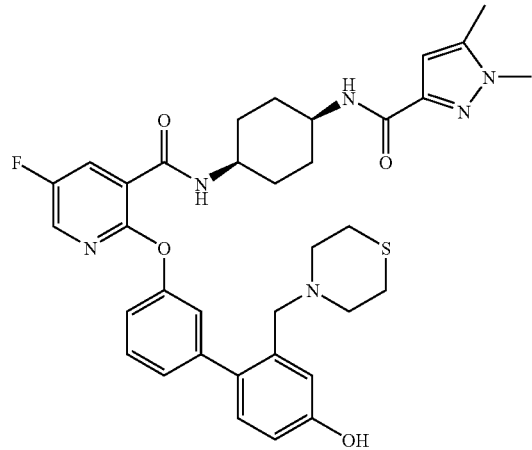

HATU (0.062 g, 0.16 mmol) and DIPEA (0.114 mL, 0.66 mmol) were added to a solution of 1,5-dimethyl-1H-pyrazole-3-carboxylic acid (0.023 g, 0.16 mmol) in acetonitrile (4 mL). The mixture was stirred for 10 min then a solution of N-((1s,4s)-4-aminocyclohexyl)-5-fluoro-2-(4'-hydroxy-2'-(thiomorpholinomethyl)biphenyl-3-yloxy)nicotinamide (0.100 g, 0.16 mmol) dihydrochloride in acetonitrile (4 mL) was added and the reaction stirred at RT for 2 days. 880 aqueous ammonia (~2 mL) was added, followed by enough methanol to bring the precipitated solids into solution (~2 mL). The mixture was stirred for a further 4 h then diluted with DCM and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a cream-coloured foam. Yield: 63 mg.
¹H NMR (400 MHz, DMSO) δ 9.93 (br s, 1H), 8.33 (d, J=6.9 Hz, 1H), 8.27 (d, J=3.1 Hz, 1H), 8.04 (dd, J=7.8, 3.2 Hz, 1H), 7.51 (t, J=8.0 Hz, 1H), 7.23 (d, J=7.9 Hz, 2H), 7.18-7.11 (m, 3H), 7.05-7.04 (m, 1H), 6.92 (d, J=7.6 Hz, 1H), 6.39 (s, 1H), 4.28-4.23 (m, 2H), 3.99-3.95 (m, 1H), 3.85-3.80 (m, 1H), 3.74 (s, 3H), 2.87-2.61 (m, 4H), 2.26 (s, 3H), 1.75-1.62 (m, 8H). Remaining protons obscured by solvent peak.
MS: [M+H]+=659.2 (calc=659.2816) (MultiMode+)

EXAMPLE 23

N-((1s,4s)-4-(2-(2'-(azepan-1-ylmethyl)-4'-hydroxybiphenyl-3-yloxy)-5-fluoronicotinamido)cyclohexyl)-2-methylthiazole-4-carboxamide

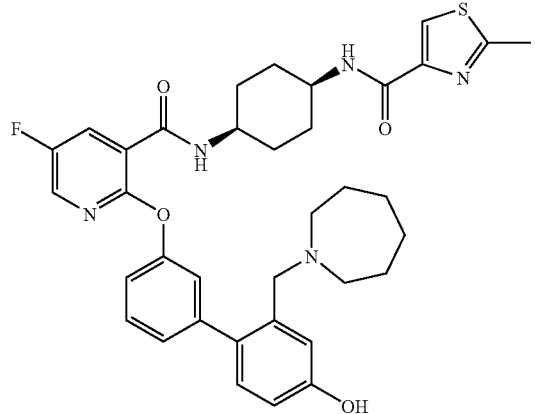

Step (a) N-((1s,4s)-4-(5-fluoro-2-(3-iodophenoxy)nicotinamido)cyclohexyl)-2-methylthiazole-4-carboxamide Triethylamine (4 mL, 28.78 mmol) was added to a stirred suspension of N-((1s,4s)-4-aminocyclohexyl)-5-fluoro-2-(3-iodophenoxy)nicotinamide (1.655 g, 3.64 mmol) and 2-methylthiazole-4-carboxylic acid (0.625 g, 4.36 mmol), whereupon the reaction mixture became homogeneous. It was stirred for 40 min, during which time a precipitate formed, then 1-propanephosphonic acid cyclic anhydride (T3P, 1.57M in THF) (3.01 mL, 4.73 mmol) was added slowly. The reaction mixture became homogeneous once more and the mixture was stirred overnight. The reaction mixture was evaporated to dryness and redissolved in EtOAc, then washed with saturated sodium hydrogen carbonate, 2M hydrochloric acid, water and saturated brine. The organic was dried over sodium sulfate, filtered and evaporated to afford the sub-title compound as a white foam. Yield: 2.16 g
¹H NMR (400 MHz, CDCl₃) δ 8.36 (dd, J=8.2, 3.1 Hz, 1H), 8.07 (d, J=3.1 Hz, 1H), 7.93 (s, 1H), 7.90 (d, J=6.9 Hz, 1H), 7.63 (dt, J=7.2, 1.7 Hz, 1H), 7.55 (t, J=1.9 Hz, 1H), 7.24-7.15 (m, 3H), 4.25-4.20 (m, 1H), 4.12-4.06 (m, 1H), 2.71 (s, 3H), 1.96-1.77 (m, 6H), 1.67-1.61 (m, 2H).
MS: [M+H]+=581 (MultiMode+)

Step (b) N-((1s,4s)-4-(5-fluoro-2-(3-(4,4,5,5-tetramethyl-1,3,2-dioxaborolan-2-yl)phenoxy)nicotinamido)cyclohexyl)-2-methylthiazole-4-carboxamide 1,1'-Bis(diphenylphosphino)ferrocene (0.105 g, 0.19 mmol) and 1,1'-bis(diphenylphosphino)ferrocene-palladium (II)dichloride DCM complex (0.152 g, 0.19 mmol) were stirred together in dry dimethylsulfoxide (5 mL) for 10 min, then potassium acetate (1.099 g, 11.20 mmol), a solution of N-((1s,4s)-4-(5-fluoro-2-(3-iodophenoxy)nicotinamido)cyclohexyl)-2-methylthiazole-4-carboxamide (2.166 g, 3.73 mmol) in dimethylsulfoxide (10.00 mL) and bis(pinacolato)diboron (1.260 g, 4.96 mmol) were added and the reaction mixture heated at 80° C. for 17 h. The reaction mixture was left at RT for 3 days then water added and the mixture extracted with EtOAc (×5). The combined organic extracts were washed with water and saturated brine. The organic was dried over sodium sulfate, filtered and evaporated to afford crude product. The crude product was purified by flash silica chromatography (Combi-Flash Companion, 100 g Biotage SNAP cartridge), elution gradient 50 to 100% EtOAc in isohexane. Pure fractions were evaporated to dryness to afford the sub-title compound as a white foam. Yield: 1.09 g $^1$H NMR (400 MHz, CDCl$_3$) δ 8.36 (dd, J=8.2, 3.1 Hz, 1H), 8.08 (d, J=7.4 Hz, 1H), 8.06 (d, J=3.3 Hz, 1H), 7.90 (s, 1H), 7.74 (d, J=7.4 Hz, 1H), 7.57 (d, J=2.3 Hz, 1H), 7.49 (t, J=7.7 Hz, 1H), 7.29 (ddd, J=7.9, 2.6, 0.8 Hz, 1H), 7.19 (d, J=7.7 Hz, 1H), 4.25-4.21 (m, 1H), 4.12-4.06 (m, 1H), 2.69 (s, 3H), 1.94-1.76 (m, 6H), 1.67-1.60 (m, 2H), 1.32 (s, 12H).

Step (c) N-((1s,4s)-4-(5-fluoro-2-(2'-formyl-4'-hydroxybiphenyl-3-yloxy)nicotinamido)cyclohexyl)-2-methylthiazole-4-carboxamide Palladium(II) acetate (0.017 g, 0.08 mmol) and 2-dicyclohexylphosphino-2',6'-dimethoxy-1,1'-biphenyl (S-Phos) (0.062 g, 0.15 mmol) were stirred in acetonitrile (4 mL) for 15 min, then a solution of potassium carbonate (0.781 g, 5.65 mmol) in water (8 mL) added, followed by 2-bromo-5-hydroxybenzaldehyde (0.454 g, 2.26 mmol) and a solution of N-((1s,4s)-4-(5-fluoro-2-(3-(4,4,5,5-tetramethyl-1,3,2-dioxaborolan-2-yl)phenoxy)nicotinamido)cyclohexyl)-2-methylthiazole-4-carboxamide (1.093 g, 1.88 mmol) in acetonitrile (8 mL). The reaction mixture was heated at 70° C. for 10 h then allowed to stand for 2 days. The acetonitrile was evaporated and EtOAc added to the aqueous residue. The layers were separated and the aqueous material extracted with EtOAc. The combined organic extracts were washed with water and saturated brine. The organic was dried over sodium sulfate, filtered and evaporated to afford crude product. This was purified by flash silica chromatography (Combi-Flash Companion, 100 g column), elution gradient 20 to 90% EtOAc in isohexane. Pure fractions were evaporated to dryness and azeotroped with DCM to afford the sub-title compound as a pale brown foam. Yield: 0.75 g $^1$H NMR (400 MHz, CDCl$_3$) δ 9.98 (s, 1H), 8.37 (dd, J=8.2, 3.1 Hz, 1H), 8.09 (d, J=3.1 Hz, 1H), 8.04 (d, J=7.2 Hz, 1H), 7.93 (s, 1H), 7.55 (t, J=7.8 Hz, 1H), 7.44 (d, J=2.8 Hz, 1H), 7.33 (d, J=8.2 Hz, 1H), 7.29-7.23 (m, 2H), 7.19-7.18 (m, 1H), 7.11 (dd, J=8.2, 2.8 Hz, 1H), 6.86-6.78 (m, 1H), 4.27-4.22 (m, 1H), 4.11-4.06 (m, 1H), 2.63 (s, 3H), 1.97-1.83 (m, 6H), 1.69-1.61 (m, 2H).

MS: [M+H]+=575 (MultiMode+)

Step (d) N-((1s,4s)-4-(2-(2'-(azepan-1-ylmethyl)-4'-hydroxybiphenyl-3-yloxy)-5-fluoronicotinamido)cyclohexyl)-2-methylthiazole-4-carboxamide N-((1s,4s)-4-(5-Fluoro-2-(2'-formyl-4'-hydroxybiphenyl-3-yloxy)nicotinamido)cyclohexyl)-2-methylthiazole-4-carboxamide (0.130 g, 0.23 mmol) and anhydrous sodium sulfate (0.321 g, 2.26 mmol) were stirred in DCM (5 mL) for 20 min then hexamethyleneimine (homopiperidine) (0.031 mL, 0.27 mmol) was added and the reaction mixture stirred for a further 2 h. Sodium triacetoxyborohydride (0.072 g, 0.34 mmol) was added and the reaction mixture was stirred at RT overnight. Methanol (2 mL) was added, followed by DCM and the organics were washed with saturated sodium hydrogen carbonate and saturated brine. The solvent was evaporated and the crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white foam. Yield: 122 mg $^1$H NMR (400 MHz, DMSO) δ 9.93 (s, 1H), 9.25 (s, 1H), 8.35 (d, J=7.4 Hz, 1H), 8.25 (d, J=2.8 Hz, 1H), 8.09 (s, 1H), 8.05 (dd, J=7.9, 2.8 Hz, 1H), 7.59 (d, J=7.9 Hz, 1H), 7.51 (t, J=7.8 Hz, 1H), 7.24 (d, J=6.4 Hz, 1H), 7.18-7.09 (m, 4H), 6.91 (dd, J=8.3, 2.2 Hz, 1H), 4.23 (d, J=4.9 Hz, 2H), 4.02-3.97 (m, 1H), 3.90-3.85 (m, 1H), 3.19-3.12 (m, 2H), 2.82-2.75 (m, 2H), 2.68 (s, 3H), 1.76-1.64 (m, 8H), 1.49-1.44 (m, 4H). Remaining protons obscured by solvent peaks.

MS: [M+H]+=658.2 (calc=658.2863) (MultiMode+)

EXAMPLE 24

N-((1s,4s)-4-(2-(2'-(((2S,6R)-2,6-dimethylmorpholino)methyl)-4'-hydroxybiphenyl-3-yloxy)-5-fluoronicotinamido)cyclohexyl)-2-methylthiazole-4-carboxamide

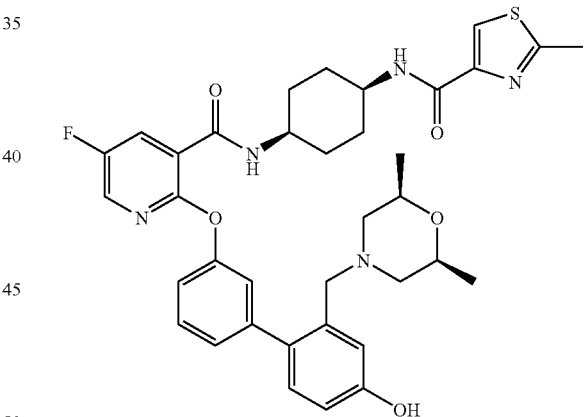

N-((1s,4s)-4-(5-Fluoro-2-(2'-formyl-4'-hydroxybiphenyl-3-yloxy)nicotinamido)cyclohexyl)-2-methylthiazole-4-carboxamide (0.130 g, 0.23 mmol) and anhydrous sodium sulfate (0.321 g, 2.26 mmol) were stirred in DCM (5 mL) for 20 min then cis-2,6-dimethylmorpholine (0.034 mL, 0.27 mmol) was added and the reaction mixture stirred for a further 2 h. Sodium triacetoxyborohydride (0.072 g, 0.34 mmol) was added. The reaction mixture was stirred at RT overnight then methanol (2 mL) added and the mixture diluted with DCM. The organics were washed with saturated sodium hydrogen carbonate, water and saturated brine. The solvent was evaporated and the crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white foam. Yield: 54 mg ¹H NMR (400 MHz, DMSO) δ 8.34 (d, J=7.2 Hz, 1H), 8.26 (d, J=2.8 Hz, 1H), 8.09 (s, 1H), 8.04 (dd, J=7.8, 2.9 Hz, 1H), 7.60 (d, J=7.7 Hz, 1H), 7.50 (t, J=7.7 Hz, 1H), 7.22-7.11 (m, 4H), 7.05-7.02 (m, 1H), 6.94-6.89 (m, 1H), 4.28-4.20 (m, 1H), 4.01-3.96 (m, 1H), 3.90-3.85 (m, 1H), 3.73-3.64 (m, 1H), 3.17-3.06 (m, 2H), 2.68 (s, 3H), 2.28-2.16 (m, 2H), 1.78-1.63 (m, 8H), 1.01-0.96 (m, 6H). Remaining protons obscured by solvent peak.

MS: [M+H]+=674.2 (calc=674.2812) (MultiMode+)

EXAMPLE 25

N-((1s,4s)-4-(5-fluoro-2-(4'-hydroxy-2'-((4-isopropylpiperazin-1-yl)methyl)biphenyl-3-yloxy)nicotinamido)cyclohexyl)-2-methylthiazole-4-carboxamide

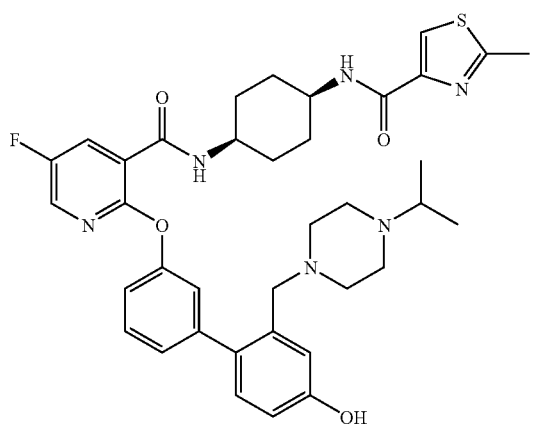

N-((1s,4s)-4-(5-Fluoro-2-(2'-formyl-4'-hydroxybiphenyl-3-yloxy)nicotinamido)cyclohexyl)-2-methylthiazole-4-carboxamide (0.130 g, 0.23 mmol) and anhydrous sodium sulfate (0.321 g, 2.26 mmol) were stirred in DCM (5 mL) for 20 min then 1-isopropylpiperazine (0.035 g, 0.27 mmol) was added and the reaction mixture stirred for a further 2 h. Sodium triacetoxyborohydride (0.072 g, 0.34 mmol) was added and the reaction mixture was stirred at RT overnight. Methanol (~2 mL) and DCM were added and the organics were washed with saturated sodium hydrogen carbonate, water and saturated brine. The solvent was evaporated and the crude product was purified by preparative HPLC on a Waters X-Bridge column using a 95-5% gradient of aqueous 0.2% TFA in acetonitrile as eluent. The fractions containing the desired compound were evaporated to dryness to afford the title as a white foam. Yield: 161 mg ¹H NMR (400 MHz, DMSO) δ 8.34 (d, J=7.2 Hz, 1H), 8.26 (d, J=3.1 Hz, 1H), 8.09 (s, 1H), 8.04 (dd, J=7.9, 3.1 Hz, 1H), 7.61 (d, J=7.9 Hz, 1H), 7.45 (t, J=7.9 Hz, 1H), 7.19-7.14 (m, 3H), 7.09 (d, J=8.2 Hz, 1H), 6.88-6.86 (m, 1H), 6.76 (d, J=8.5 Hz, 1H), 4.03-3.98 (m, 1H), 3.52-3.25 (m, 6H), 2.90-2.80 (m, 4H), 2.67 (s, 3H), 2.31-2.21 (m, 2H), 1.78-1.63 (m, 8H), 1.19 (d, J=6.7 Hz, 6H). Remaining proton obscured by solvent peak.

MS: [M+H]+=687.3 (calc=687.3129) (MultiMode+)

EXAMPLE 26

N-((1s,4s)-4-(2-(2'-((tert-butyl(methyl)amino)methyl)-4'-hydroxybiphenyl-3-yloxy)-5-fluoronicotinamido)cyclohexyl)-2-methylthiazole-4-carboxamide

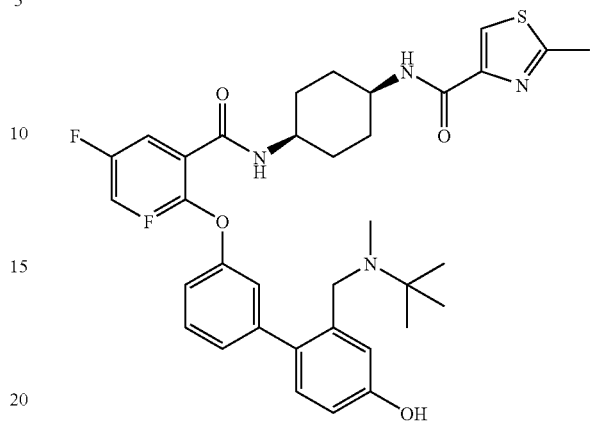

N-((1s,4s)-4-(5-Fluoro-2-(2'-formyl-4'-hydroxybiphenyl-3-yloxy)nicotinamido)cyclohexyl)-2-methylthiazole-4-carboxamide (0.130 g, 0.23 mmol) and anhydrous sodium sulfate (0.321 g, 2.26 mmol) were stirred in DCM (5 mL) for 20 min then N-methyl-tert-butylamine (0.033 mL, 0.27 mmol) was added and the reaction mixture stirred for a further 2 h. Sodium triacetoxyborohydride (0.072 g, 0.34 mmol) was added and the reaction mixture was stirred at RT overnight. Further N-methyl-tert-butylamine (0.033 mL, 0.27 mmol) and anhydrous sodium sulfate (0.321 g, 2.26 mmol) were added, followed after 2 h by further sodium triacetoxyborohydride (0.072 g, 0.34 mmol) and the mixture stirred overnight. Methanol (2 mL) and DCM were added and the organics were washed with saturated sodium hydrogen carbonate, water and saturated brine. The solvent was evaporated and the crude product was purified by preparative HPLC on a Waters X-Bridge column using a 75-25% gradient of aqueous 0.2% TFA in acetonitrile as eluent. The fractions containing the desired compound were evaporated to dryness to afford the title compound as a white solid. Yield: 53 mg ¹H NMR (400 MHz, DMSO) δ 9.96 (s, 1H), 8.59 (s, 1H), 8.33 (d, J=7.0, 1H), 8.23 (d, J=3.0, 1H), 8.09 (s, 1H), 8.05 (dd, J=3.0, 8.0, 1H), 7.59 (d, J=8.2, 1H), 7.52 (t, J=7.9, 1H), 7.24 (dd, J=1.7, 8.0, 1H), 7.21-7.09 (m, 3H), 6.99 (s, 1H), 6.93 (dd, J=2.4, 8.4, 1H), 4.51 (d, J=12.6, 1H), 4.00 (s, 1H), 3.92-3.78 (m, 2H), 2.71 (s, 3H), 2.32 (d, J=4.9, 3H), 1.78-1.61 (m, 8H), 1.19 (s, 9H).

MS: [M+H]+=646.2 (calc=646.2863) (MultiMode+)

EXAMPLE 27

N-((1s,4s)-4-(5-fluoro-2-(4'-hydroxy-2'-((4-methyl-1,4-diazepan-1-yl)methyl)biphenyl-3-yloxy)nicotinamido)cyclohexyl)quinoline-2-carboxamide

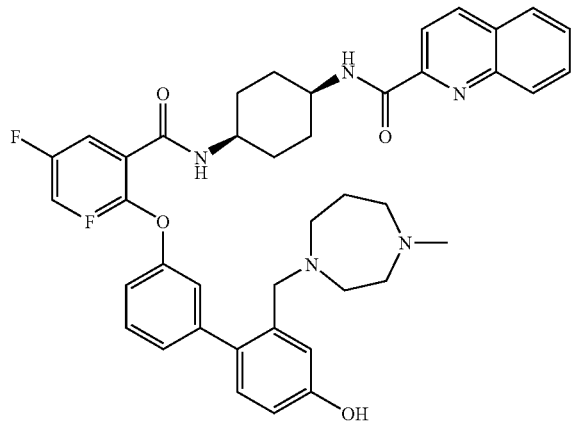

Step (a) tert-butyl (1s,4s)-4-(5-fluoro-2-(4'-hydroxy-2'-((4-methyl-1,4-diazepan-1-yl)methyl)biphenyl-3-yloxy)nicotinamido)cyclohexylcarbamate Tert-Butyl (1s,4s)-4-(5-fluoro-2-(2'-formyl-4'-hydroxybiphenyl-3-yloxy)nicotinamido)cyclohexylcarbamate (750 mg, 1.36 mmol) and 1-methyl-1,4-diazepane (0.255 mL, 2.05 mmol) were stirred together in dichloromethane (20 mL) at RT for 15 min. Sodium triacetoxyborohydride (868 mg, 4.09 mmol) and one drop of glacial acetic acid were added and the reaction was stirred overnight. Water (10 ml) and saturated aqueous sodium bicarbonate solution (10 ml) were added and the mixture was stirred for 1 hour. The organic phase was separated and evaporated affording the sub-title compound as a tan foam which was used without further purification. Yield: 760 mg $^1$H NMR (400 MHz, CDCl$_3$) δ 8.36 (dd, J=8.2, 3.1 Hz, 1H), 8.07 (d, J=3.1 Hz, 1H), 8.04 (d, J=7.4 Hz, 1H), 7.48 (t, J=7.8 Hz, 1H), 7.27 (d, J=9.2 Hz, 1H), 7.22 (t, J=1.9 Hz, 1H), 7.15 (d, J=8.2 Hz, 1H), 7.13-7.09 (m, 1H), 7.06 (d, J=2.6 Hz, 1H), 6.78 (dd, J=8.2, 2.6 Hz, 1H), 4.52-4.40 (m, 1H), 4.21-4.12 (m, 1H), 3.68-3.56 (m, 1H), 3.51 (s, 2H), 2.76-2.56 (m, 9H), 2.34 (s, 3H), 1.88-1.64 (m, 9H), 1.53-1.45 (m, 1H), 1.42 (s, 9H).

Step (b) N-((1s,4s)-4-aminocyclohexyl)-5-fluoro-2-(4'-hydroxy-2'-((4-methyl-1,4-diazepan-1-yl)methyl) biphenyl-3-yloxy)nicotinamide dihydrochloride A solution of 10% TFA in DCM (10 mL) was added to tert-butyl (1s,4s)-4-(5-fluoro-2-(4'-hydroxy-2'-((4-methyl-1,4-diazepan-1-yl)methyl)biphenyl-3-yloxy)nicotinamido)cyclohexylcarbamate (750 mg, 1.16 mmol) at 25° C. The resulting solution was stirred at 25° C. for 2 hours. More TFA (2 ml) was added and stirring was continued overnight. All volatiles were removed in vacuo and the residue was redissolved in DCM; the solution was washed with saturated aqueous sodium bicarbonate solution and brine, and then dried. The combined aqueous solutions were extracted into EtOAc, and then the aqueous solution was evaporated to dryness. The solid residue was thoroughly triturated with warm acetonitrile which was filtered and evaporated. The tacky foam residue was dissolved in warm isopropanol and acidified with c HCl. The resulting precipitate was removed and the filtrate was evaporated to dryness. More conc. HCl was added and the resulting solution was again evaporated thoroughly to dryness affording the sub-title compound as a foam. Yield: 550 mg $^1$H NMR (400 MHz, DMSO) δ 11.85-11.03 (m, 2H), 8.48-8.23 (m, 5H), 8.12-8.01 (m, 1H), 7.56-7.44 (m, 1H), 7.42-7.31 (m, 1H), 7.25 (d, J=9.5 Hz, 1H), 7.22-7.13 (m, 3H), 6.98 (dd, J=8.5, 2.6 Hz, 1H), 3.79-2.94 (m, 10H), 2.76-2.60 (m, 2H), 2.08-1.58 (m, 10H). Other resonances obscured by large water signal.

Step (c) N-((1s,4s)-4-(5-fluoro-2-(4'-hydroxy-2'-((4-methyl-1,4-diazepan-1-yl)methyl)biphenyl-3-yloxy) nicotinamido)cyclohexyl)quinoline-2-carboxamide To a suspension of N-((1s,4s)-4-aminocyclohexyl)-5-fluoro-2-(4'-hydroxy-2'-((4-methyl-1,4-diazepan-1-yl)methyl)biphenyl-3-yloxy)nicotinamide dihydrochloride (110 mg, 0.18 mmol) in acetonitrile (1 mL) at RT was added quinoline-2-carboxylic acid (33.8 mg, 0.19 mmol) and 1-propanephosphonic acid cyclic anhydride (T3P, 1.57M in THF) (0.141 mL, 0.22 mmol) with stirring. After 20 min triethylamine (0.247 mL, 1.77 mmol) was added and the reaction was stirred at RT overnight. The reaction was diluted with EtOAc (5 mL) and saturated aqueous sodium bicarbonate solution (2 mL) was added. After stirring for 15 min the homogeneous solution was concentrated to remove the organic solvents and the aqueous residue was extracted thoroughly into DCM. Evaporation of the organic solvent left a foam which was redissolved in acetonitrile, filtered and purified (RPHPLC ACE 5C8 column, 80-40% 0.2% aqueous TFA-acetonitrile). The product containing fractions were combined, and evaporated to dryness. The residue was triturated with ether to afford the title compound as a white powder. Yield: 11 mg $^1$H NMR (400 MHz, DMSO) δ 8.56 (d, J=8.5 Hz, 1H), 8.40 (d, J=7.2 Hz, 1H), 8.33 (d, J=7.9 Hz, 1H), 8.26 (d, J=3.1 Hz, 1H), 8.16 (d, J=8.5 Hz, 1H), 8.10-8.00 (m, 3H), 7.88-7.83 (m, 1H), 7.74-7.69 (m, 1H), 7.45 (t, J=7.8 Hz, 1H), 7.21-7.08 (m, 3H), 7.08-7.00 (m, 1H), 6.95-6.85 (m, 1H), 6.78-6.62 (m, 1H), 4.12-3.93 (m, 2H), 2.71 (s, 3H), 1.92-1.69 (m, 8H). Other resonances obscured by DMSO and water signals MS: [M+H]+=703.3 (calc=703.3408) (MultiMode+)

EXAMPLE 28

5-fluoro-2-(4'-hydroxy-2'-(morpholinomethyl)biphenyl-3-yloxy)-N-((1s,4s)-4-(2-hydroxy-5-methylbenzamido)cyclohexyl)nicotinamide

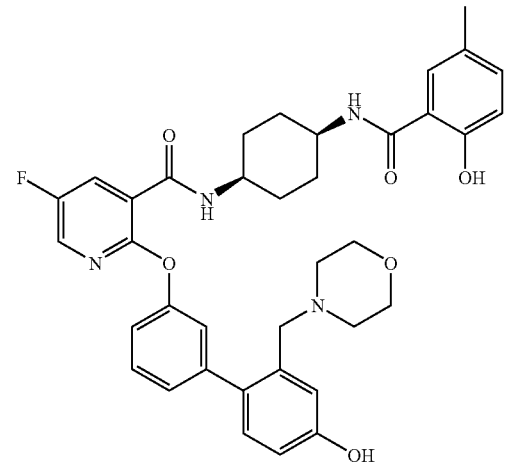

To a solution of 2-hydroxy-5-methylbenzoic acid (61.5 mg, 0.40 mmol) in THF (1 mL) was added HOBt (61.9 mg, 0.40 mmol) and 1-(3-dimethylaminopropyl)-3-ethylcarbodiimide hydrochloride (64.6 mg, 0.34 mmol) the mixture was stirred for 10 min at RT. This mixture was then added to a solution of N-((1s,4s)-4-aminocyclohexyl)-5-fluoro-2-(4'-hydroxy-2'-(morpholinomethyl)biphenyl-3-yloxy)nicotinamide, dihydrochloride (200 mg, 0.34 mmol) and triethylamine (0.188 mL, 1.35 mmol) in THF (1 mL) and N-methyl-2-pyrrolidinone (1 mL). The reaction mixture was stirred at RT overnight. The mixture was diluted with acetonitrile and purified using reverse phase prep HPLC (eluent=TFA(aq)/MeCN), the appropriate fractions were combined and evaporated to give an oil which on trituration with ether afforded the title compound. Yield: 84 mg $^1$H NMR (400 MHz, CDCl$_3$) δ 8.35 (dd, J=8.2, 3.1 Hz, 1H), 8.04 (d, J=3.1 Hz, 1H), 8.00 (d, J=7.2 Hz, 1H), 7.54 (t, J=7.8 Hz, 1H), 7.29 (s, 1H), 7.22-7.13 (m, 4H), 7.08-7.04 (m, 2H), 6.92 (d, J=8.2 Hz, 1H), 6.85 (d, J=8.5 Hz, 1H), 6.36 (d, J=7.2 Hz, 1H), 4.28-4.22 (m, 3H), 4.06-4.01 (m, 1H), 3.80-3.76 (m, 4H), 3.14-2.48 (m, 4H), 2.24 (s, 3H), 1.98-1.86 (m, 6H), 1.75-1.66 (m, 2H)

MS: [M+H]+=655.2 (calc=655.2932) (MultiMode+)

EXAMPLE 29

N-((1s,4s)-4-(2-(2'-((4-acetylpiperazin-1-yl)methyl)-4'-hydroxybiphenyl-3-yloxy)-5-fluoronicotinamido)cyclohexyl)-2-methylthiazole-4-carboxamide

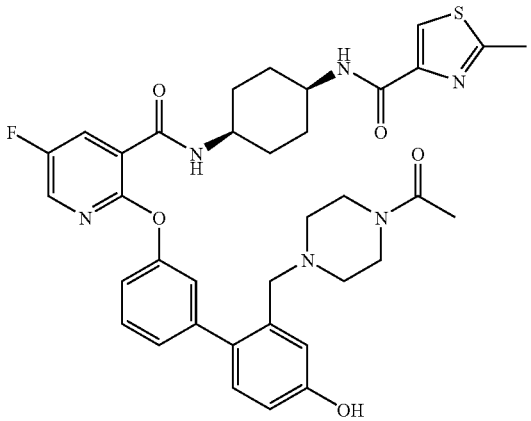

N-((1s,4s)-4-(5-Fluoro-2-(2'-formyl-4'-hydroxybiphenyl-3-yloxy)nicotinamido)cyclohexyl)-2-methylthiazole-4-carboxamide (0.109 g, 0.19 mmol) and anhydrous sodium sulfate (0.269 g, 1.90 mmol) were stirred in DCM (5 mL) for 20 min then 1-acetylpiperazine (0.039 g, 0.30 mmol) was added and the reaction mixture stirred for a further 2 h. Sodium triacetoxyborohydride (0.060 g, 0.28 mmol) was added. The reaction mixture was stirred at RT for 3 days then methanol (2 mL) added and the mixture diluted with EtOAc. The organics were washed with saturated sodium hydrogen carbonate, water and saturated brine. The solvent was evaporated and the crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white foam. Yield: 111 mg $^1$H NMR (400 MHz, DMSO) δ 9.92 (br s, 1H), 9.67 (s, 1H), 8.34 (d, J=7.1 Hz, 1H), 8.27 (d, J=3.0 Hz, 1H), 8.09 (s, 1H), 8.03 (dd, J=3.0, 7.9 Hz, 1H), 7.61 (d, J=8.4 Hz, 1H), 7.49 (t, J=7.8 Hz, 1H), 7.26-7.01 (m, 6H), 6.90 (d, J=6.6 Hz, 1H), 4.39-4.08 (m, 2H), 4.02-3.96 (m, 1H), 3.90-3.74 (m, 2H), 2.93-2.80 (m, 2H), 2.62 (s, 3H), 1.91 (s, 3H), 1.83-1.58 (m, 8H). Remaining protons obscured by solvent peak.

MS: [M+H]+=687.2 (calc=687.2765) (MultiMode+)

EXAMPLE 30

N-((1s,4s)-4-(2-(2'-(((2-(dimethylamino)-2-oxoethyl)(methyl)amino)methyl)-4'-hydroxybiphenyl-3-yloxy)-5-fluoronicotinamido)cyclohexyl)-2-methylthiazole-4-carboxamide

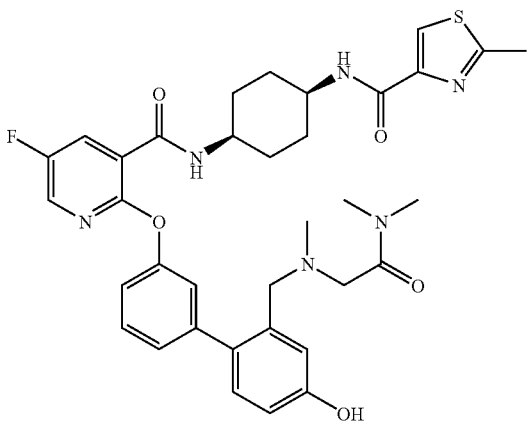

N-((1s,4s)-4-(5-Fluoro-2-(2'-formyl-4'-hydroxybiphenyl-3-yloxy)nicotinamido)cyclohexyl)-2-methylthiazole-4-carboxamide (0.109 g, 0.19 mmol) and anhydrous sodium sulfate (0.269 g, 1.90 mmol) were stirred in 1,2-dichloroethane (5 mL) for 20 min then N,N-dimethyl-2-(methylamino)acetamide (0.026 g, 0.23 mmol) was added and the reaction mixture stirred for a further 2 h. Sodium triacetoxyborohydride (0.060 g, 0.28 mmol) was added. The reaction mixture was stirred at RT for 3 days then methanol (2 mL) added and the mixture diluted with EtOAc. The organics were washed with saturated sodium hydrogen carbonate, water and saturated brine. The solvent was evaporated and the crude product was purified by preparative HPLC on a Waters X-Bridge column using a 95-5% gradient of aqueous 0.2% TFA in acetonitrile as eluent. The fractions containing the desired compound were evaporated to dryness to afford the title as a white foam. Yield 103 mg $^1$H NMR (400 MHz, DMSO) δ 9.92 (s, 1H), 9.38 (s, 1H), 8.34 (d, J=7.2, 1H), 8.25 (d, J=3.1, 1H), 8.09 (s, 1H), 8.03 (dd, J=3.1, 7.9, 1H), 7.63 (d, J=8.1, 1H), 7.49 (t, J=8.1, 1H), 7.22-7.11 (m, 5H), 6.91 (dd, J=2.4, 8.4, 1H), 4.37-4.27 (m, 1H), 4.22-4.13 (m, 1H), 4.05-3.97 (m, 3H), 3.91-3.83 (m, 1H), 2.84 (s, 3H), 2.81 (s, 3H), 2.69 (s, 3H), 2.47 (s, 3H), 1.80-1.64 (m, 8H).

MS: [M+H]+=675.2 (calc=675.2765) (MultiMode+)

EXAMPLE 31

5-fluoro-2-(4'-hydroxy-2'-(morpholinomethyl)biphenyl-3-yloxy)-N-((1s,4s)-4-(4-hydroxybenzamido)cyclohexyl)nicotinamide

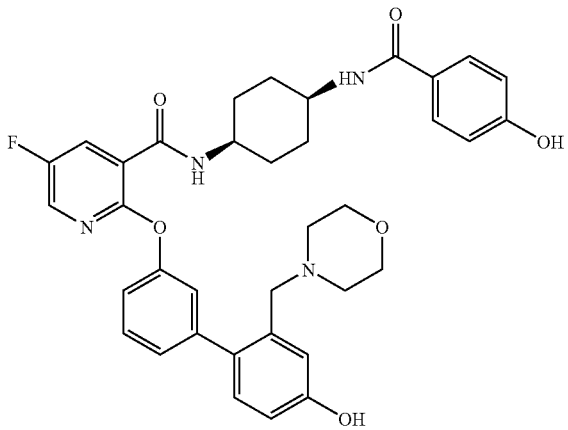

N-((1s,4s)-4-Aminocyclohexyl)-5-fluoro-2-(4'-hydroxy-2'-(morpholinomethyl)biphenyl-3-yloxy)nicotinamide dihydrochloride (150 mg, 0.25 mmol), 4-hydroxybenzoic acid (41.9 mg, 0.30 mmol), N1-((ethylimino)methylene)-N3,N3-dimethylpropane-1,3-diamine hydrochloride (53.3 mg, 0.28 mmol) and 1H-benzo[d][1,2,3]triazol-1-ol hydrate (46.4 mg, 0.30 mmol) were combined in acetonitrile (2.5 mL) and stirred, and then triethylamine (0.176 mL, 1.26 mmol) was added. The solution was stirred at RT overnight. The reaction was evaporated to dryness, and the residue was partitioned between DCM and saturated aqueous sodium bicarbonate solution. The organic phase was separated and evaporated. The residue was redissolved in acetonitrile, filtered and purified (RPHPLC ACE 5C8 column, 95-25% 0.2% aqueous TFA-acetonitrile). The product containing fractions were combined, (transferred by washing with methanol) and evaporated to dryness, affording the title compound as a solid. Yield: 64 mg ¹H NMR (400 MHz, DMSO) δ 10.02-9.86 (m, 2H), 9.82-9.65 (m, 1H), 8.34 (d, J=6.7 Hz, 1H), 8.26 (d, J=3.1 Hz, 1H), 8.03 (dd, J=7.9, 3.1 Hz, 1H), 7.77 (d, J=6.7 Hz, 1H), 7.67 (d, J=9.2 Hz, 2H), 7.49 (t, J=7.7 Hz, 1H), 7.24 (d, J=7.9 Hz, 1H), 7.20-7.02 (m, 4H), 6.97-6.84 (m, 1H), 6.77 (d, J=8.7 Hz, 2H), 4.39-4.19 (m, 2H), 4.01-3.87 (m, 1H), 3.87-3.66 (m, 4H), 2.81-2.61 (m, 2H), 1.87-1.57 (m, 8H). Other resonances obscured by DMSO and water signals. NMR indicated presence of 1 mole methanol.

MS: [M+H]+=641.2 (calc=641.2775) (MultiMode+)

EXAMPLE 32

5-fluoro-2-(4'-hydroxy-2'-(morpholinomethyl)biphenyl-3-yloxy)-N-((1s,4s)-4-(3-hydroxybenzamido)cyclohexyl)nicotinamide

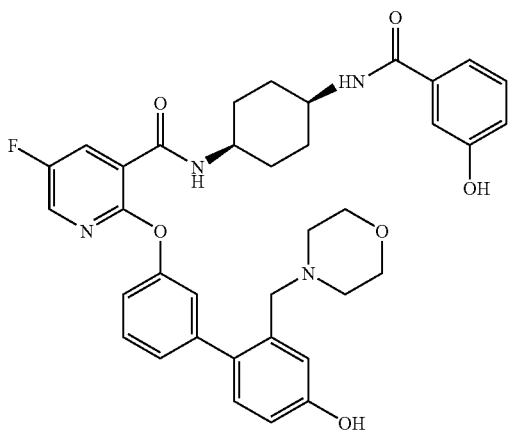

N-((1s,4s)-4-Aminocyclohexyl)-5-fluoro-2-(4'-hydroxy-2'-(morpholinomethyl)biphenyl-3-yloxy)nicotinamide dihydrochloride (150 mg, 0.25 mmol), 3-hydroxybenzoic acid (41.9 mg, 0.30 mmol), HOBt (46.4 mg, 0.30 mmol) and EDCI (53.3 mg, 0.28 mmol) were combined in acetonitrile (2.5 mL) and stirred. Triethylamine (0.176 mL, 1.26 mmol) was added and the solution was stirred at RT overnight. More HOBt (46 mg) and EDCI (53 mg) were added and stirring was continued overnight. Water (1 mL) was added and the reaction was stirred 1 h then evaporated to dryness. The residue was redissolved in acetonitrile, filtered and purified (RPHPLC ACE 5C8 column, 95-25% 0.2% aqueous TFA-acetonitrile). The product containing fractions were combined, (transferred by washing with methanol) and evaporated to dryness affording the title compound as a glass. Yield: 37 mg ¹H NMR (400 MHz, DMSO) δ 10.02-9.80 (m, 1H), 9.67-9.57 (m, 1H), 8.33 (d, J=6.7 Hz, 1H), 8.27 (d, J=2.8 Hz, 1H), 8.03 (dd, J=7.9, 3.1 Hz, 1H), 7.96 (d, J=6.7 Hz, 1H), 7.55-7.43 (m, 1H), 7.27-7.09 (m, 8H), 6.95-6.84 (m, 2H), 4.34-4.18 (m, 1H), 4.01-3.88 (m, 1H), 3.85-3.57 (m, 5H), 2.78-2.57 (m, 1H), 1.90-1.57 (m, 10H). Other resonances obscured by DMSO and water signals. NMR indicates presence of 1 mole methanol MS: [M+H]+=641.2 (calc=641.2775) (MultiMode+)

EXAMPLE 33

N-((1s,4s)-4-(5-fluoro-2-(4'-hydroxy-2'-(morpholinomethyl)biphenyl-3-yloxy)nicotinamido)cyclohexyl)-4-methylthiazole-5-carboxamide

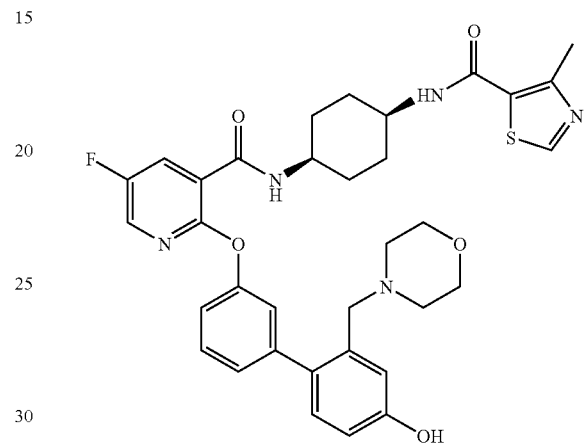

N-((1s,4s)-4-Aminocyclohexyl)-5-fluoro-2-(4'-hydroxy-2'-(morpholinomethyl)biphenyl-3-yloxy)nicotinamide dihydrochloride (150 mg, 0.25 mmol) was suspended in acetonitrile (2 mL) and treated with 4-methylthiazole-5-carboxylic acid (43.4 mg, 0.30 mmol). After stirring for a few moments 1-propanephosphonic acid cyclic anhydride (T3P, 1.57M in THF) (0.241 mL, 0.38 mmol) was added and then triethylamine (0.281 mL, 2.02 mmol) and the reaction was stirred overnight. Further T3P (0.24 mL) and triethylamine (0.28 mL) were added and stirring was continued overnight. Further 4-methylthiazole-5-carboxylic acid (43.4 mg, 0.30 mmol) was added and stirring was continued over a weekend. Further 4-methylthiazole-5-carboxylic acid (43.4 mg, 0.30 mmol), T3P (0.24 mL) and triethylamine (0.28 mL) were added, and stirring was continued overnight. More thiazole acid (215 mg), T3P (1.2 mL) and triethylamine (2 mL) were added and the mixture was stirred at RT overnight. All volatile matter was evaporated and the oily residue was taken up in acetonitrile, filtered and purified (RPHPLC ACE 5C8 column, 95-25% 0.2% aqueous TFA-acetonitrile). The product containing fractions were combined, (transferred by washing with methanol) and evaporated to dryness affording the title compound as a glass. Yield: 26 mg ¹H NMR (400 MHz, DMSO) δ 9.03 (s, 1H), 8.38 (d, J=6.9 Hz, 1H), 8.25 (d, J=3.1 Hz, 1H), 8.05-7.98 (m, 2H), 7.50 (t, J=7.8 Hz, 1H), 7.28-7.04 (m, 5H), 6.93 (d, J=6.9 Hz, 1H), 3.66-3.43 (m, 2H), 3.26-3.04 (m, 2H), 2.85-2.61 (m, 2H), 1.85-1.58 (m, 8H). Other resonances obscured by DMSO and water signals MS: [M+H]+=646.2 (calc=646.2499) (MultiMode+)

EXAMPLE 34

N-((1s,4s)-4-(5-fluoro-2-(4'-hydroxy-2'-(morpholinomethyl)biphenyl-3-yloxy)nicotinamido)cyclohexyl)-2-methylthiazole-4-carboxamide

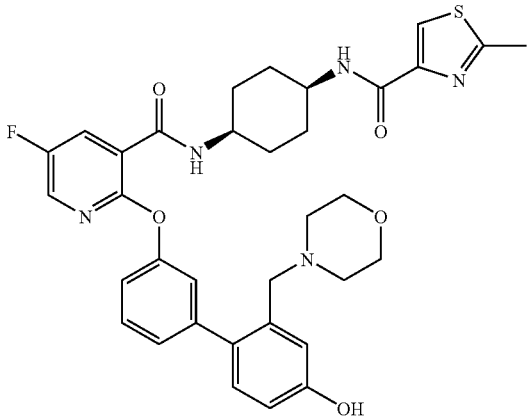

HATU (0.064 g, 0.17 mmol) and DIPEA (0.06 mL, 0.34 mmol) were added to a solution of 2-methylthiazole-4-carboxylic acid (0.024 g, 0.17 mmol) in acetonitrile (4 mL). The mixture was stirred for 10 min then a solution of N-((1s,4s)-4-aminocyclohexyl)-5-fluoro-2-(4'-hydroxy-2'-(morpholinomethyl)biphenyl-3-yloxy)nicotinamide dihydrochloride (0.100 g, 0.17 mmol) and DIPEA (0.09 mL, 0.52 mmol) in acetonitrile (4 mL) was added and the reaction stirred at RT for 2 days. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white solid. Yield: 87 mg.

$^1$H NMR (500 MHz, DMSO) δ 9.92 (br s, 1H), 9.67 (br s, 1H), 8.35 (d, J=7.2 Hz, 1H), 8.26 (d, J=3.0 Hz, 1H), 8.08 (s, 1H), 8.04 (dd, J=3.0, 7.9 Hz, 1H), 7.61 (d, J=8.0 Hz, 1H), 7.50 (t, J=7.9 Hz, 1H), 7.22 (d, J=7.9 Hz, 1H), 7.19-7.09 (m, 3H), 7.05 (s, 1H), 6.91 (d, J=6.7 Hz, 1H), 4.32-4.18 (m, 2H), 4.01-3.96 (m, 1H), 3.91-3.84 (m, 1H), 3.78-3.66 (m, 2H), 3.62-3.51 (m, 2H), 3.20-3.07 (m, 2H), 2.77-2.62 (m, 5H), 1.78-1.63 (m, 8H).

MS: [M+H]+=646.2 (calc=646.2499) (MultiMode+)

EXAMPLE 35

N-((1s,4s)-4-(5-fluoro-2-(4'-hydroxy-2'-(morpholinomethyl)biphenyl-3-yloxy)nicotinamido)cyclohexyl)-3-hydroxypicolinamide

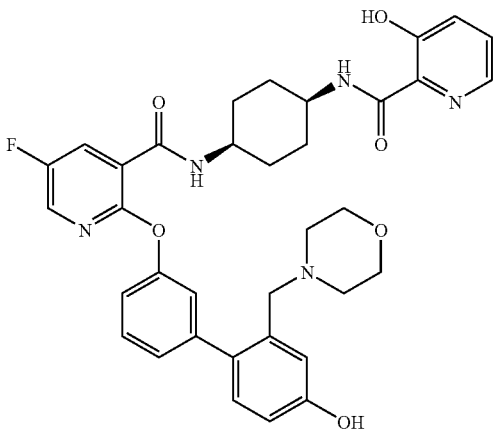

EDCI (0.043 g, 0.22 mmol) and HOBt (0.037 g, 0.24 mmol) were added to a stirred suspension of N-((1s,4s)-4-aminocyclohexyl)-5-fluoro-2-(4'-hydroxy-2'-(morpholinomethyl)biphenyl-3-yloxy)nicotinamide dihydrochloride (0.120 g, 0.20 mmol) and 3-hydroxypicolinic acid (0.034 g, 0.24 mmol) in acetonitrile (4 mL). Triethylamine (0.15 mL, 1.08 mmol) was added slowly, followed by further acetonitrile (4 mL) to give a yellow solution. The reaction was stirred at RT for 5 days then diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white solid. Yield: 38 mg $^1$H NMR (500 MHz, DMSO) δ 12.45 (br s, 1H), 9.93 (br s, 1H), 9.65 (br s, 1H), 8.49 (d, J=7.8 Hz, 1H), 8.36 (d, J=7.0 Hz, 1H), 8.26 (d, J=3.0 Hz, 1H), 8.13 (dd, J=1.0, 4.3 Hz, 1H), 8.05 (dd, J=2.9, 7.9 Hz, 1H), 7.56-7.48 (m, 2H), 7.43 (d, J=8.2 Hz, 1H), 7.24 (dd, J=1.7, 8.2 Hz, 1H), 7.18-7.10 (m, 3H), 7.06 (d, J=1.8 Hz, 1H), 6.92 (dd, J=1.4, 8.4 Hz, 1H), 4.32-4.20 (m, 2H), 4.03-3.88 (m, 2H), 3.79-3.65 (m, 2H), 3.19-3.06 (m, 2H), 2.76-2.61 (m, 2H), 1.86-1.66 (m, 8H). Remaining protons obscured by solvent peaks.

MS: [M+H]+=642.2 (calc=642.2728) (MultiMode+)

EXAMPLE 36

N-((1s,4s)-4-(5-fluoro-2-(4'-hydroxy-2'-(morpholinomethyl)biphenyl-3-yloxy)nicotinamido)cyclohexyl)-2-(trifluoromethyl)thiazole-4-carboxamide

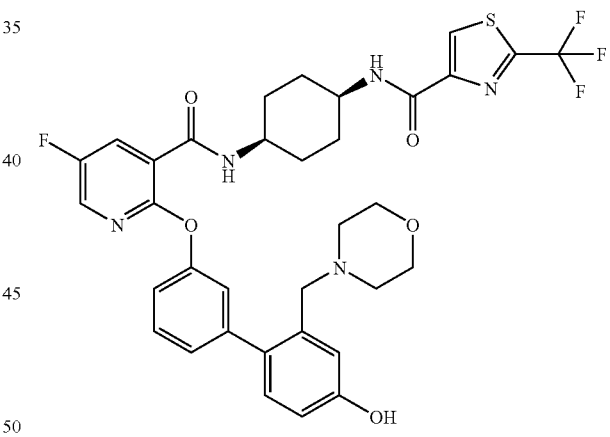

EDCI (0.036 g, 0.19 mmol) and HOBt (0.031 g, 0.20 mmol) were added to a stirred suspension of N-((1s,4s)-4-aminocyclohexyl)-5-fluoro-2-(4'-hydroxy-2'-(morpholinomethyl)biphenyl-3-yloxy)nicotinamide dihydrochloride (0.100 g, 0.17 mmol) and 2-(trifluoromethyl)thiazole-4-carboxylic acid (Atlantic Research Chemicals Ltd) (0.040 g, 0.20 mmol) in acetonitrile (8 mL). Triethylamine (0.141 mL, 1.01 mmol) was added slowly. The reaction stirred at RT overnight then diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a pale orange solid. Yield: 41 mg ¹H NMR (500 MHz, DMSO) δ 9.92 (br s, 1H), 9.79 (br s, 1H), 8.68 (s, 1H), 8.34 (d, J=7.0 Hz, 1H), 8.26 (d, J=3.0 Hz, 1H), 8.04 (dd, J=3.0, 7.9 Hz, 1H), 7.89 (d, J=7.7 Hz, 1H), 7.49 (t, J=7.9 Hz, 1H), 7.22 (d, J=7.8 Hz, 1H), 7.18-7.02 (m, 4H), 6.90 (d, J=7.3 Hz, 1H), 4.32-4.16 (m, 2H), 4.02-3.96 (m, 1H), 3.93-3.85 (m, 1H), 3.20-3.05 (m, 2H), 2.80-2.62 (m, 2H), 1.83-1.62 (m, 8H). Remaining protons obscured by solvent peaks.

MS: [M+H]+=700.2 (calc=700.2217) (MultiMode+)

EXAMPLE 37

N-((1s,4s)-4-(5-fluoro-2-(4'-hydroxy-2'-(morpholinomethyl)biphenyl-3-yloxy)nicotinamido)cyclohexyl)-2-isopropylthiazole-5-carboxamide

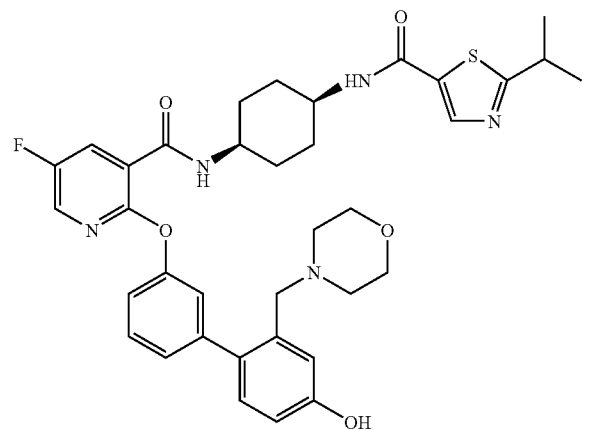

To a stirred solution of N-((1s,4s)-4-aminocyclohexyl)-5-fluoro-2-(4'-hydroxy-2'-(morpholinomethyl)biphenyl-3-yloxy)nicotinamide dihydrochloride (100 mg, 0.17 mmol) and 2-isopropylthiazole-5-carboxylic acid (37.5 mg, 0.22 mmol) in acetonitrile (2 mL) was added 2,4,6-tripropyl-1,3,5,2,4,6-trioxatriphosphorinane-2,4,6-trioxide (T3P, 1.57M in THF) (0.215 mL, 0.34 mmol) and then triethylamine (0.234 mL, 1.68 mmol) was introduced. The reaction was stirred at RT overnight. Further 2-isopropylthiazole-5-carboxylic acid (37 mg), T3P (0.215 mL) and triethylamine (0.5 mL) were added and stirring was continued overnight. A second extra addition of 2-isopropylthiazole-5-carboxylic acid (37 mg), T3P (0.215 mL) and triethylamine (0.5 mL) was made, and the reaction was stirred overnight. All volatile components were evaporated and the residue was taken in DCM and washed with saturated aqueous sodium bicarbonate solution, dried and evaporated. The gummy material remaining was dissolved in acetonitrile, filtered and purified by RPHPLC (ACE 5C8 column, 95-25% 0.2% aqueous TFA-acetonitrile). Product containing fractions were combined (washing together with methanol) and evaporated affording the title compound as a gum. Yield: 26 mg ¹H NMR (400 MHz, DMSO) δ 8.37 (d, J=6.4 Hz, 1H), 8.28-8.25 (m, 2H), 8.23 (d, J=6.4 Hz, 1H), 8.02 (dd, J=7.9, 3.1 Hz, 1H), 7.49 (t, J=7.8 Hz, 1H), 7.26-7.03 (m, 5H), 6.97-6.86 (m, 1H), 4.36-4.22 (m, 2H), 4.01-3.89 (m, 2H), 3.84-3.65 (m, 4H), 2.80-2.62 (m, 2H), 1.87-1.58 (m, 8H), 1.32 (d, J=6.9 Hz, 6H). Other resonances obscured by DMSO and water signals. NMR indicates material contains 1 mole of methanol MS: [M+H]+=674.2 (calc=674.2812) (MultiMode+)

EXAMPLE 38

5-fluoro-2-(4'-hydroxy-2'-(morpholinomethyl)biphenyl-3-yloxy)-N-((1s,4s)-4-(2-hydroxybenzamido)cyclohexyl)nicotinamide

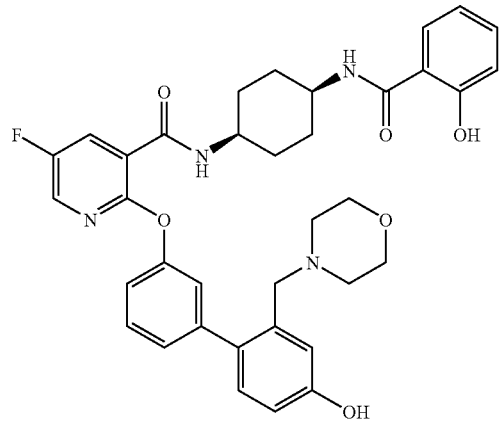

To a solution of 2-hydroxybenzoic acid (27.9 mg, 0.20 mmol) in THF (1 mL) was added HOBt (37.2 mg, 0.24 mmol) and EDCI (38.8 mg, 0.20 mmol) and the mixture was stirred for 10 min at RT. This mixture was then added to a solution of N-((1s,4s)-4-aminocyclohexyl)-5-fluoro-2-(4'-hydroxy-2'-(morpholinomethyl)biphenyl-3-yloxy)nicotinamide dihydrochloride (120 mg, 0.20 mmol) and triethylamine (0.113 mL, 0.81 mmol) in THF (1 mL) and N-methyl-2-pyrrolidinone (3 mL). The reaction mixture was stirred at RT overnight. The mixture was diluted with 1 mL water and purified using reverse phase prep HPLC (eluent=TFA(aq)/MeCN), the appropriate fractions were combined and evaporated to give an oil which on trituration with ether afforded the title compound. Yield: 58 mg ¹H NMR (400 MHz, DMSO) δ 12.29 (s, 1H), 8.43 (dd, J=19.5, 6.7 Hz, 2H), 8.26 (d, J=2.8 Hz, 1H), 8.02 (dd, J=7.9, 3.1 Hz, 1H), 7.89 (d, J=7.2 Hz, 1H), 7.48 (t, J=7.9 Hz, 1H), 7.38 (t, J=7.4 Hz, 1H), 7.21 (d, J=7.7 Hz, 1H), 7.17-7.10 (m, 3H), 7.03 (d, J=15.9 Hz, 1H), 6.95-6.86 (m, 4H), 4.17-4.07 (m, 1H), 3.98-3.88 (m, 2H), 3.66-3.56 (m, 3H), 3.49-3.33 (m, 6H), 1.83-1.65 (m, 8H).

MS: [M+H]+=641.2 (calc=641.2775) (MultiMode+)

EXAMPLE 39

N-((1s,4s)-4-(5-fluoro-2-(4'-hydroxy-2'-(morpholinomethyl)biphenyl-3-yloxy)nicotinamido)cyclohexyl)-2-isopropylthiazole-4-carboxamide

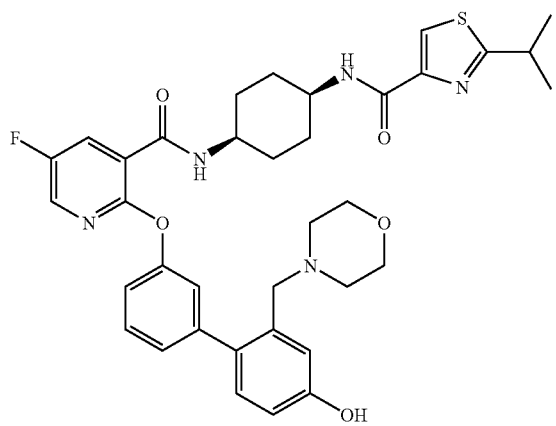

HATU (0.064 g, 0.17 mmol) and DIPEA (0.06 mL, 0.34 mmol) were added to a solution of 2-isopropylthiazole-4-carboxylic acid (ChemBridge Corporation) (0.029 g, 0.17 mmol) in acetonitrile (4 mL). The mixture was stirred for 10 min then a solution of N-((1s,4s)-4-aminocyclohexyl)-5-fluoro-2-(4'-hydroxy-2'-(morpholinomethyl)biphenyl-3-yloxy)nicotinamide dihydrochloride (0.100 g, 0.17 mmol) and DIPEA (0.09 mL, 0.52 mmol) in acetonitrile (4 mL) was added and the reaction stirred at RT for 2 days. The reaction mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white solid. Yield: 59 mg $^1$H NMR (400 MHz, DMSO) δ 10.00-9.61 (m, 2H), 8.38 (d, J=7.4 Hz, 1H), 8.28-8.24 (m, 1H), 8.15-8.11 (m, 1H), 8.04 (dd, J=1.9, 7.8 Hz, 1H), 7.56 (d, J=8.2 Hz, 1H), 7.49 (t, J=7.6 Hz, 1H), 7.25-7.03 (m, 5H), 6.93-6.88 (m, 1H), 4.31-4.15 (m, 1H), 4.03-3.98 (m, 1H), 3.90-3.83 (m, 1H), 2.85-2.64 (m, 2H), 1.82-1.65 (m, 8H), 1.34 (d, J=6.8 Hz, 6H). Remaining protons obscured by solvent peaks.

MS: [M+H]+=674.2 (calc=674.2812) (MultiMode+)

EXAMPLE 40

N-((1s,4s)-4-(5-fluoro-2-(4'-hydroxy-2'-(morpholinomethyl)biphenyl-3-yloxy)nicotinamido)cyclohexyl)-6-hydroxypicolinamide

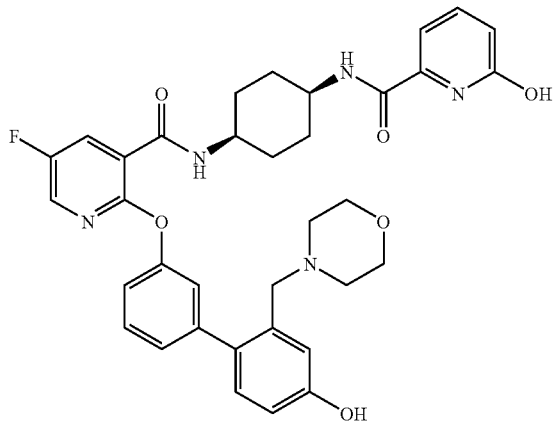

EDCI (0.039 g, 0.20 mmol) and HOBt (0.034 g, 0.22 mmol) were added to a stirred suspension of N-((1s,4s)-4-aminocyclohexyl)-5-fluoro-2-(4'-hydroxy-2'-(morpholinomethyl)biphenyl-3-yloxy)nicotinamide dihydrochloride (0.110 g, 0.19 mmol) and 6-hydroxypicolinic acid (0.031 g, 0.22 mmol) in acetonitrile (4 mL). Triethylamine (0.129 mL, 0.93 mmol) was added, followed by further acetonitrile (4 mL). The reaction was stirred at RT for 2 days then further EDCI (40 mg) was added. The reaction mixture was stirred overnight then HATU (0.070 g, 0.19 mmol) was added and the mixture stirred overnight. 880 ammonia was added and the mixture stirred for a further night then the mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a white solid. Yield: 13 mg $^1$H NMR (400 MHz, CD$_3$OD) δ 8.43 (d, J=7.1 Hz, 1H), 8.13 (d, J=3.0 Hz, 1H), 8.06 (dd, J=3.1, 7.9 Hz, 1H), 7.67 (dd, J=7.4, 8.4 Hz, 1H), 7.54 (t, J=7.9 Hz, 1H), 7.27-7.11 (m, 5H), 7.06-7.04 (m, 1H), 6.92 (dd, J=2.5, 8.4 Hz, 1H), 6.74 (d, J=8.8 Hz, 1H), 4.34 (s, 2H), 4.14-4.08 (m, 1H), 3.97-3.51 (m, 5H), 2.91-2.74 (m, 2H), 1.93-1.71 (m, 8H). Remaining protons obscured by solvent peaks.

MS: [M+H]+=642.2 (calc=642.2728) (MultiMode+)

EXAMPLE 41

N-((1s,4s)-4-(5-fluoro-2-(4'-hydroxy-2'-(morpholinomethyl)biphenyl-3-yloxy)nicotinamido)cyclohexyl)-4-hydroxyquinoline-2-carboxamide

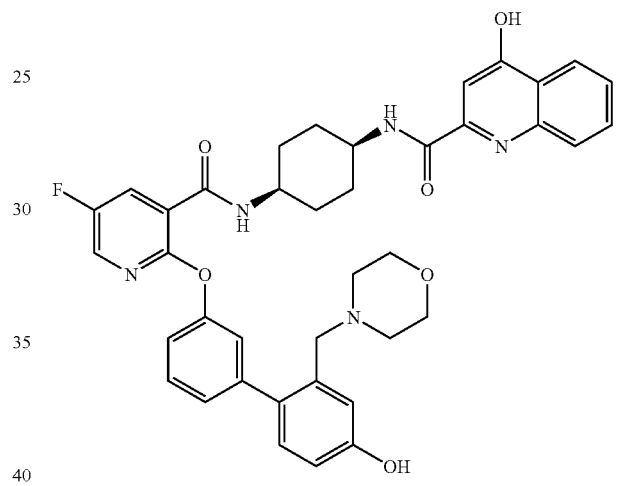

To a solution of 4-hydroxyquinoline-2-carboxylic acid hydrate (38.2 mg, 0.20 mmol) in N-methyl-2-pyrrolidinone (2 mL) was added HOBt (37.2 mg, 0.24 mmol) and EDCI (38.8 mg, 0.20 mmol) the mixture was stirred for 10 min at RT. This mixture was then added to a solution of N-((1s,4s)-4-aminocyclohexyl)-5-fluoro-2-(4'-hydroxy-2'-(morpholinomethyl)biphenyl-3-yloxy)nicotinamide, dihydrochloride (120 mg, 0.20 mmol) and triethylamine (0.113 mL, 0.81 mmol) in N-methyl-2-pyrrolidinone (2 mL). The reaction mixture was stirred at RT overnight. A further aliquot of 0.5 eq of the acid, EDCI and HOBt was preformed and then added the reaction mixture. The mixture was diluted with ~1 mL water and purified using reverse phase prep HPLC (eluent=TFA(aq)/MeCN), the appropriate fractions were combined and evaporated to give an oil which on trituration with ether afforded the title compound. Yield: 23 mg.

$^1$H NMR (600 MHz, CD$_3$OD) δ 8.48 (d, J=7.0 Hz, 1H), 8.23 (dd, J=8.2 Hz, 0.9 Hz, 1H), 8.15 (d, J=3.1 Hz, 1H), 8.11-8.07 (m, 1H), 7.82 (d, J=8.4 Hz, 1H), 7.77-7.73 (m, 1H), 7.57 (t, J=7.9 Hz, 1H), 7.46 (t, J=7.6 Hz, 1H), 7.28 (dd, J=8.1 Hz, 2.2 Hz, 1H), 7.23-7.16 (m, 3H), 7.04 (d, J=2.5 Hz, 1H), 6.92 (dd, J=8.4 Hz, 2.4 Hz, 1H), 6.73 (s, 1H), 4.33 (s, 2H), 4.16 (s, 1H), 4.06-3.98 (m, 1H), 3.87-3.57 (m, 4H), 3.22-2.78 (m, 4H), 1.99-1.76 (m, 8H).

MS: [M+H]+=692.2 (calc=692.2884) (MultiMode+)

EXAMPLE 42

N-((1s,4s)-4-(5-fluoro-2-(4'-hydroxy-2'-(morpholinomethyl)biphenyl-3-yloxy)nicotinamido)cyclohexyl)-2-hydroxyquinoline-3-carboxamide

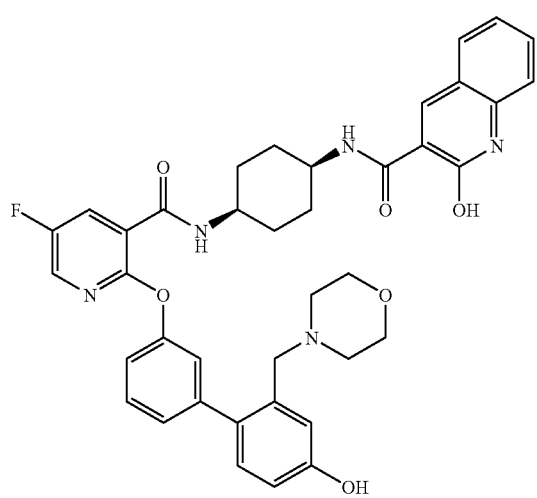

EDCI (0.039 g, 0.20 mmol) and HOBt (0.034 g, 0.22 mmol) were added to a stirred suspension of N-((1s,4s)-4-aminocyclohexyl)-5-fluoro-2-(4'-hydroxy-2'-(morpholinomethyl)biphenyl-3-yloxy)nicotinamide dihydrochloride (0.110 g, 0.19 mmol) and 2-hydroxyquinoline-3-carboxylic acid (Maybridge Chemical Company) (0.042 g, 0.22 mmol) in acetonitrile (4 mL). Triethylamine (0.129 mL, 0.93 mmol) was added, followed by further acetonitrile (4 mL). The reaction was stirred at RT for 2 days then further EDCI (40 mg) was added. The reaction mixture was stirred overnight then HATU (0.070 g, 0.19 mmol) was added and the mixture stirred overnight. 880 ammonia was added and the mixture stirred for a further night then the mixture was diluted with EtOAc and washed with water and saturated brine. The organic was evaporated to afford crude product. The crude product was purified by preparative HPLC on a Waters X-Bridge column using a 95-5% gradient of aqueous 0.2% TFA in acetonitrile as eluent. The fractions containing the desired compound were evaporated to dryness to afford the title compound as a pale yellow solid. Yield: 59 mg $^1$H NMR (400 MHz, DMSO) δ 12.38 (s, 1H), 9.99-9.86 (m, 2H), 9.69-9.56 (m, 1H), 8.85 (s, 1H), 8.53 (d, J=7.4 Hz, 1H), 8.24 (d, J=3.1 Hz, 1H), 8.00 (dd, J=3.1, 7.9 Hz, 1H), 7.95 (d, J=7.4 Hz, 1H), 7.67 (t, J=7.9 Hz, 1H), 7.52-7.43 (m, 2H), 7.30 (t, J=7.5 Hz, 1H), 7.23-7.01 (m, 5H), 6.95-6.87 (m, 1H), 4.33-4.21 (m, 1H), 4.03-3.92 (m, 2H), 3.80-3.67 (m, 2H), 2.79-2.65 (m, 2H), 1.80 (s, 8H). Remaining protons obscured by solvent peaks.

MS: [M+H]+=692.2 (calc=692.2884) (MultiMode+)

EXAMPLE 43

2-tert-butyl-N-((1s,4s)-4-(2-(2'-((dimethylamino)methyl)-4'-hydroxybiphenyl-3-yloxy)-5-fluoronicotinamido)cyclohexyl)thiazole-4-carboxamide

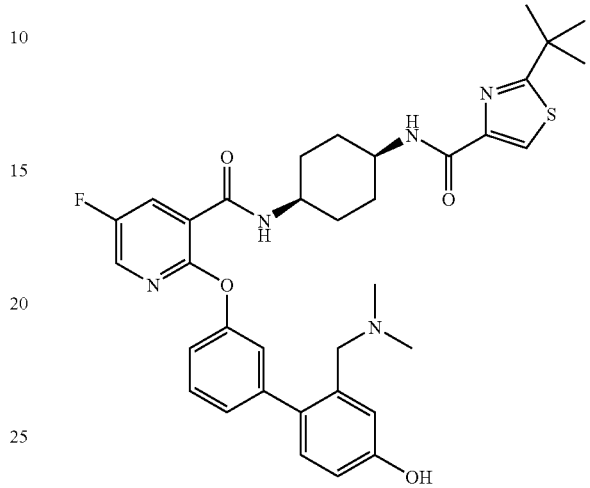

Step (a) 2,2-dimethylpropanethioamide

Phosphorus (V) sulfide (1.330 mL, 12.51 mmol) was added to a stirred suspension of pivalamide (5 g, 49.43 mmol) in methyl t-butyl ether (100 mL) and the reaction stirred over the weekend at RT. The mixture was filtered through celite and evaporated in vacuo to give the sub-title compound as a yellow gummy solid. Yield: 9.27 g $^1$H NMR (300 MHz, CDCl$_3$) δ 7.86 (s, 1H), 7.16 (s, 1H), 1.32 (s, 9H).

MS: [M+H]+=118 (MultiMode+)

Step (b) ethyl 2-tert-butylthiazole-4-carboxylate

Ethyl 3-bromo-2-oxopropanoate (6.20 mL, 49.40 mmol) was added very carefully to a stirred solution of 2,2-dimethylpropanethioamide (5.79 g, 49.40 mmol) in ethanol (60 mL). The solution was then heated under reflux for 16 h. After cooling, the reaction mixture was diluted with EtOAc, washed with saturated aqueous sodium bicarbonate solution and evaporated in vacuo. Purification by silica gel chromatography (Biotage, 100 g) eluting with EtOAc: iso-hexane, 1:10 gave the sub-title compound as a yellow oil. Yield: 6.56 g $^1$H NMR (300 MHz, CDCl$_3$) δ 8.03 (s, 1H), 4.40 (q, J=7.1 Hz, 2H), 1.48 (s, 9H), 1.39 (t, J=6.3 Hz, 3H).

MS: [M+H]+=214 (MultiMode+)

Step (c) 2-tert-butylthiazole-4-carboxylic acid

Lithium hydroxide (2.8 g, 120.25 mmol) was added to a stirred mixture of ethyl 2-tert-butylthiazole-4-carboxylate (6.56 g, 30.76 mmol) in THF (100 mL) and water (40 mL). After 16 h, HCl (62.5 mL, 125 mmol) was added and the solution concentrated to ~40 mL. The reaction mixture was partitioned between EtOAc and brine. The aqueous layer was extracted with EtOAc (×3). The combined organic layers were dried over magnesium sulphate, filtered and evaporated in vacuo to give the sub-title compound as an off white/yellow solid. Yield: 5.41 g $^1$H NMR (300 MHz, CDCl$_3$) δ 8.16 (s, 1H), 1.46 (s, 9H).
MS: [M+H]+=186 (MultiMode+)

Step (d) 2-tert-butyl-N-((1s,4s)-4-(2-(2'-((dimethylamino)methyl)-4'-hydroxybiphenyl-3-yloxy)-5-fluoronicotinamido)cyclohexyl)thiazole-4-carboxamide To a solution of 2-tert-butylthiazole-4-carboxylic acid (0.074 g, 0.40 mmol) in acetonitrile (5 mL) was added DIPEA (0.138 mL, 0.79 mmol) and HATU (0.151 g, 0.40 mmol). The mixture was allowed to stir at RT for 10 min before a solution of N-((1s,4s)-4-aminocyclohexyl)-2-(2'-((dimethylamino)methyl)-4'-hydroxybiphenyl-3-yloxy)-5-fluoronicotinamide (0.19 g, 0.40 mmol) in MeCN (5 mL) with 2 eq of DIPEA (0.139 mL, 0.79 mmol) was added and the mixture stirred at RT overnight. Ammonia (1 mL) was added and after stirring for 1 h. Water (1 mL) was added then the crude reaction purified by preparative HPLC on a Waters X-Bridge column using a 95-5% gradient of aqueous 0.2% TFA in acetonitrile as eluent. The fractions containing the desired compound were freeze-dried to afford the title compound as a white fluffy solid. Yield 174 mg $^1$H NMR (300 MHz, DMSO) δ 9.44 (s, 1H), 8.40 (d, J=7.3 Hz, 1H), 8.26 (d, J=3.1 Hz, 1H), 8.13 (s, 1H), 8.03 (dd, J=7.9, 3.1 Hz, 1H), 7.51-7.45 (m, 2H), 7.23-7.03 (m, 6H), 6.90 (dd, J=8.4, 2.4 Hz, 1H), 4.20 (d, J=4.8 Hz, 2H), 4.00 (s, 1H), 3.90 (s, 1H), 2.50 (s, 6H), 1.71 (s, 8H), 1.39 (s, 9H).
MS: [M+H]+=646 (calc=646) (MultiMode+)

EXAMPLE 44

N-((1s,4s)-4-(2-(2'-((dimethylamino)methyl)-4'-hydroxybiphenyl-3-yloxy)-5-fluoronicotinamido)cyclohexyl)benzo[d]thiazole-2-carboxamide

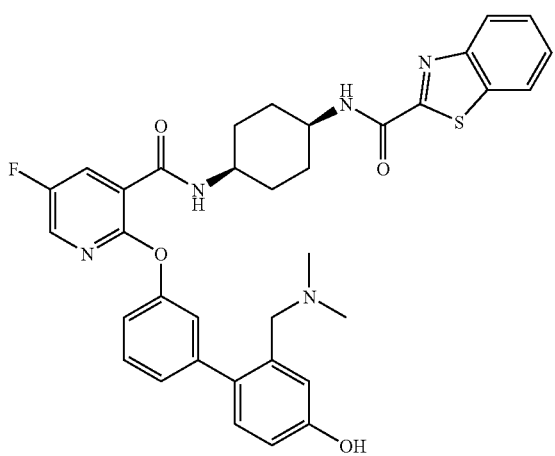

To a solution of benzo[d]thiazole-2-carboxylic acid (0.071 g, 0.40 mmol) in acetonitrile (5 mL) was added DIPEA (0.138 mL, 0.79 mmol) and HATU (0.151 g, 0.40 mmol). The mixture was allowed to stir at RT for 10 min before a solution of N-((1s,4s)-4-aminocyclohexyl)-2-(2'-((dimethylamino)methyl)-4'-hydroxybiphenyl-3-yloxy)-5-fluoronicotinamide (0.19 g, 0.40 mmol) in MeCN (5 mL) with 2 eq of DIPEA (0.139 mL, 0.79 mmol) was added and the mixture stirred at RT for 2 h. A further 1 eq HATU (0.151 g, 0.40 mmol) was added and the reaction stirred for a further 1 h. Water (1 mL) was added then the crude reaction was purified by preparative HPLC on a Waters X-Bridge column using a 95-5% gradient of aqueous 0.1% ammonia in acetonitrile as eluent. The fractions containing the desired compound were freeze dried to afford the title compound as a yellow fluffy solid. Yield: 33 mg $^1$H NMR (300 MHz, DMSO) δ 9.41 (s, 1H), 8.51 (d, J=7.5 Hz, 1H), 8.33-8.21 (m, 3H), 8.11-8.04 (m, 2H), 7.61 (t, J=7.8 Hz, 2H), 7.44 (t, J=7.9 Hz, 1H), 7.18 (t, J=8.8 Hz, 3H), 7.05 (d, J=8.3 Hz, 1H), 6.89 (s, 1H), 6.68 (dd, J=8.5, 2.3 Hz, 1H), 4.00 (s, 1H), 3.92 (s, 1H), 3.21 (s, 2H), 2.00 (s, 6H), 1.89-1.78 (m, 4H), 1.74-1.65 (m, 4H).

MS: [M+H]+=640.1 (calc=640.2394) (MultiMode+)

EXAMPLE 45

N-((1s,4s)-4-(5-fluoro-2-(4'-hydroxy-2'-(morpholinomethyl)biphenyl-3-yloxy)nicotinamido)cyclohexyl)-4-methylthiazole-2-carboxamide

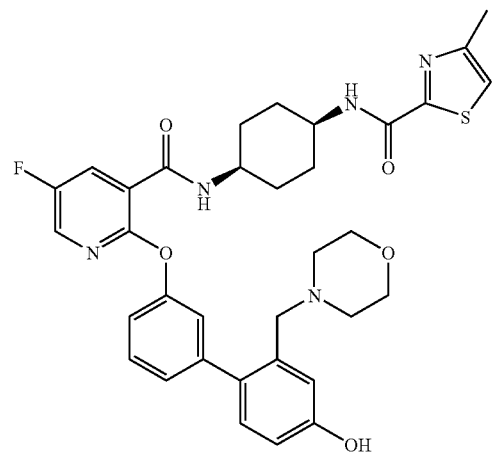

A solution of N-((1s,4s)-4-aminocyclohexyl)-5-fluoro-2-(4'-hydroxy-2'-(morpholinomethyl)biphenyl-3-yloxy)nicotinamide (200 mg, 0.34 mmol), ethyl 4-methylthiazole-2-carboxylate (57.7 mg, 0.34 mmol) and triethylamine (0.094 mL, 0.67 mmol) in ethanol (1 mL) was heated to 100° C. in a sealed tube in the microwave for 24 h. The mixture was purified using reverse phase preparative HPLC (eluent=MeCN/NH$_3$(aq)), the appropriate fractions were combined, evaporated to give a white solid which was dried overnight at 40° C. under vacuum and afforded the title compound. Yield: 23 mg $^1$H NMR (500 MHz, CD$_3$OD) δ 8.04 (d, J=3.1 Hz, 1H), 8.00 (dd, J=8.0 Hz, 3.0 Hz, 1H), 7.35 (t, J=7.9 Hz, 1H), 7.30 (s, 1H), 7.18-7.15 (m, 1H), 7.11 (d, J=7.7 Hz, 1H), 7.06 (dd, J=8.0 Hz, 1.7 Hz, 1H), 6.97 (d, J=8.3 Hz, 1H), 6.81 (d, J=2.5 Hz, 1H), 6.60 (dd, J=8.3 Hz, 2.5 Hz, 1H), 4.08-4.04 (m, 1H), 3.92-3.87 (m, 1H), 3.44-3.41 (m, 4H), 3.25 (s, 2H), 2.33 (s, 3H), 2.17 (s, 4H), 1.86-1.72 (m, 6H), 1.69-1.62 (m, 2H).

MS: [M+H]+=646.2 (calc=646.2499) (MultiMode+)

EXAMPLE 46

N-((1s,4s)-4-(2-(4'-((1,4-oxazepan-4-yl)methyl)biphenyl-3-yloxy)-5-fluoronicotinamido)cyclohexyl)-5-methylimidazo[1,2-a]pyridine-2-carboxamide

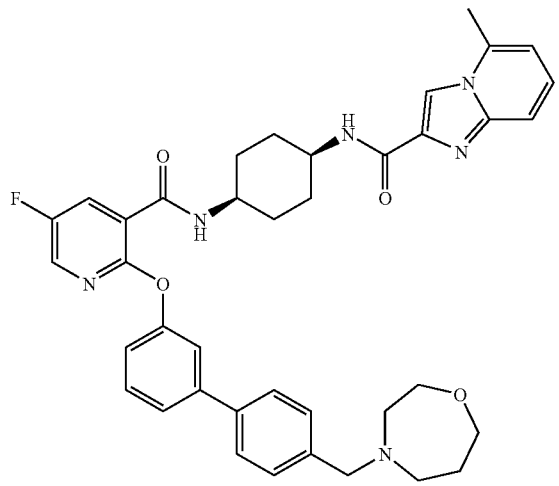

Step (a) N-((1s,4s)-4-(5-fluoro-2-(3-iodophenoxy)nicotinamido)cyclohexyl)-5-methylimidazo[1,2-a]pyridine-2-carboxamide To a suspension of N-((1s,4s)-4-aminocyclohexyl)-5-fluoro-2-(3-iodophenoxy)nicotinamide, hydrochloride (1.8 g, 3.66 mmol) in acetonitrile (100 mL) was added 5-methylimidazo[1,2-a]pyridine-2-carboxylic acid (0.645 g, 3.66 mmol) and triethylamine (5.10 mL, 36.61 mmol). On addition of triethylamine the reaction mixture became a homogeneous solution. 1-Propanephosphonic acid cyclic anhydride, 1.57M solution in THF (2.448 mL, 3.84 mmol) was then added and the mixture stirred at RT overnight. The mixture was evaporated to dryness and the residue dissolved in EtOAc (750 mL) and washed with saturated NaHCO₃ (aq), brine, dried (MgSO₄) and evaporated to give the sub-title compound as a foam. Yield: 1.8 g $^1$H NMR (400 MHz, CDCl₃) δ 8.37 (dd, J=8.2, 3.1 Hz, 1H), 8.08-8.06 (m, 2H), 7.90 (d, J=7.2 Hz, 1H), 7.63 (dt, J=7.1, 1.6 Hz, 1H), 7.56-7.55 (m, 1H), 7.47 (d, J=9.2 Hz, 1H), 7.34 (d, J=7.9 Hz, 1H), 7.25-7.16 (m, 3H), 6.69 (d, J=6.7 Hz, 1H), 4.27-4.15 (m, 2H), 2.61 (s, 3H), 1.99-1.80 (m, 6H), 1.73-1.67 (m, 2H).

Step (b) N-((1s,4s)-4-(5-fluoro-2-(4'-formylbiphenyl-3-yloxy)nicotinamido)cyclohexyl)-5-methylimidazo[1,2-a]pyridine-2-carboxamide Palladium acetate (0.033 g, 0.15 mmol) and 2-dicyclohexylphosphino-2',6'-dimethoxybiphenyl (0.120 g, 0.29 mmol) was added to acetonitrile (22.92 mL) under nitrogen. The resulting solution was stirred for 10 min. To this solution was added potassium carbonate (1.217 g, 8.80 mmol) dissolved in water (22.92 mL), followed by 4-formylphenylboronic acid (0.660 g, 4.40 mmol) and N-((1s,4s)-4-(5-fluoro-2-(3-iodophenoxy)nicotinamido)cyclohexyl)-5-methylimidazo[1,2-a]pyridine-2-carboxamide (1.8 g, 2.93 mmol) and the mixture heated at 80° C. for 24 h. The mixture was poured onto water and extracted into EtOAc (x2). The extractions were combined, washed with brine, dried (MgSO₄) and evaporated to a yellow foam. This was purified using column chromatography (eluent=EtOAc) to give the sub-title compound as a white foam. Yield: 1.5 g $^1$H NMR (400 MHz, CDCl₃) δ 9.99 (s, 1H), 8.39 (ddd, J=8.0, 3.3, 0.2 Hz, 1H), 8.10-8.04 (m, 3H), 7.86 (d, J=8.2 Hz, 1H), 7.73 (d, J=8.2 Hz, 2H), 7.48 (d, J=1.8 Hz, 1H), 7.36-7.17 (m, 5H), 6.68 (dd, J=6.9, 0.8 Hz, 1H), 4.31-4.24 (m, 1H), 4.19-4.12 (m, 1H), 2.59 (s, 3H), 2.01-1.85 (m, 6H), 1.75-1.67 (m, 2H).

Step (c) N-((1s,4s)-4-(2-(4'-((1,4-oxazepan-4-yl)methyl)biphenyl-3-yloxy)-5-fluoronicotinamido)cyclohexyl)-5-methylimidazo[1,2-a]pyridine-2-carboxamide To a solution of homomorpholine hydrochloride (52.3 mg, 0.38 mmol) in DCM (3 mL) was added triethylamine (0.035 mL, 0.25 mmol). The mixture was allowed to stir at RT for 10 min before N-((1s,4s)-4-(5-fluoro-2-(4'-formylbiphenyl-3-yloxy)nicotinamido)cyclohexyl)-5-methylimidazo[1,2-a]pyridine-2-carboxamide (150 mg, 0.25 mmol) was added. After 40 min sodium triacetoxyborohydride (81 mg, 0.38 mmol) was added and the reaction was stirred at RT for 2 h. The mixture was diluted with DCM and washed with sat. NaHCO₃ (aq), dried (MgSO₄) and evaporated to give a foam. This was purified using reverse phase prep HLPC (eluent=TFA(aq)/MeCN), the appropriate fractions were combined, evaporated and the residue triturated with ether to give a solid. The solid was dried overnight at 40° C. under vacuum to afford the title compound. Yield: 93 mg $^1$H NMR (400 MHz, CDCl₃) δ 8.41 (d, J=7.7 Hz, 1H), 8.32 (dd, J=8.2, 3.1 Hz, 1H), 8.19 (s, 1H), 8.06 (d, J=3.1 Hz, 1H), 8.03 (d, J=9.2 Hz, 1H), 7.99 (d, J=7.7 Hz, 1H), 7.71-7.63 (m, 3H), 7.52 (t, J=7.8 Hz, 1H), 7.48-7.45 (m, 3H), 7.41 (t, J=1.9 Hz, 1H), 7.22-7.18 (m, 1H), 7.09 (d, J=6.9 Hz, 1H), 4.36-3.19 (m, 14H), 2.75 (s, 3H), 1.96-1.83 (m, 8H).

MS: [M+H]+=677.2 (calc=677.3251) (MultiMode+)

EXAMPLE 47

N-((1s,4s)-4-(2-(4'-((dimethylamino)methyl)biphenyl-3-yloxy)-5-fluoronicotinamido)cyclohexyl)-5-methylimidazo[1,2-a]pyridine-2-carboxamide

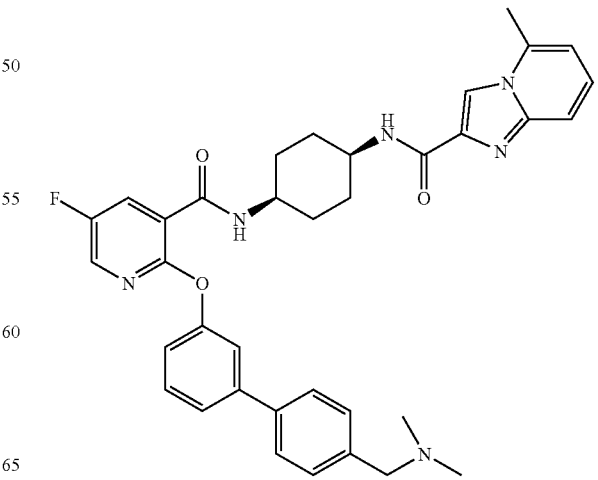

To a solution of N-((1s,4s)-4-(5-fluoro-2-(4'-formylbiphenyl-3-yloxy)nicotinamido)cyclohexyl)-5-methylimidazo[1,2-a]pyridine-2-carboxamide (150 mg, 0.25 mmol) in DCM (3 mL) was added dimethylamine, 2M solution in MTBE (0.190 mL, 0.38 mmol). The mixture was allowed to stir at RT for 40 min before sodium triacetoxyborohydride (81 mg, 0.38 mmol) was added. The reaction was stirred at RT for 2 h. The mixture was diluted with DCM and washed with sat. NaHCO$_3$ (aq), dried (MgSO$_4$) and evaporated to give a foam. This foam was then purified using reverse phase preparative HPLC (eluent=TFA(aq)/MeCN). The appropriate fractions were combined, evaporated and the residue triturated with ether to afford the title compound as a solid. Yield: 89 mg $^1$H NMR (400 MHz, CDCl$_3$) δ 8.33 (dd, J=8.1, 3.2 Hz, 1H), 8.29 (s, 1H), 8.18 (s, 1H), 8.06 (d, J=3.1 Hz, 1H), 8.00-7.95 (m, 2H), 7.68-7.64 (m, 2H), 7.64-7.60 (m, 1H), 7.53 (t, J=7.9 Hz, 1H), 7.49-7.45 (m, 3H), 7.42 (t, J=1.9 Hz, 1H), 7.22-7.18 (m, 1H), 7.04 (d, J=6.9 Hz, 1H), 4.28 (s, 1H), 4.19 (s, 2H), 4.06-3.92 (m, 1H), 2.78 (s, 6H), 2.74 (s, 3H), 1.96-1.82 (m, 8H).

MS: [M+H]+=621.1 (calc=621.2989) (MultiMode+)

EXAMPLE 48

N-((1s,4s)-4-(2-(4'-(((3S,5R)-3,5-dimethylpiperazin-1-yl)methyl)biphenyl-3-yloxy)-5-fluoronicotinamido)cyclohexyl)-5-methylimidazo[1,2-a]pyridine-2-carboxamide

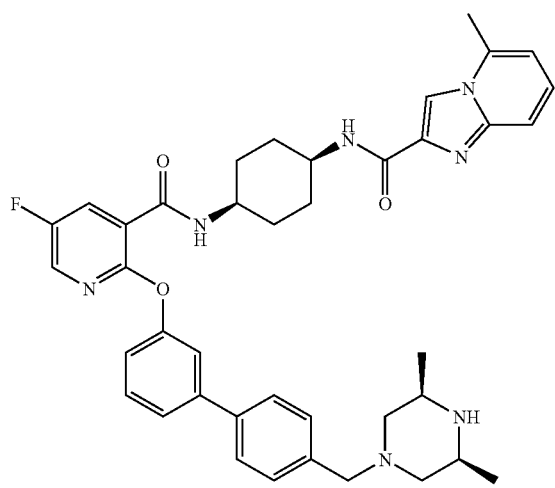

To a solution of N-((1s,4s)-4-(5-fluoro-2-(4'-formylbiphenyl-3-yloxy)nicotinamido)cyclohexyl)-5-methylimidazo[1,2-a]pyridine-2-carboxamide (150 mg, 0.25 mmol) in DCM (3 mL) was added (2S,6R)-2,6-dimethylpiperazine (43.4 mg, 0.38 mmol). The mixture was allowed to stir at RT for 40 min before sodium triacetoxyborohydride (81 mg, 0.38 mmol) was added. The reaction was stirred at RT for 2 h. The mixture was diluted with DCM and washed with sat. NaHCO$_3$ (aq), dried (MgSO$_4$) and evaporated to give a foam. This foam was purified using revere phase prep HPLC (eluent=TFA(aq)/MeCN). The appropriate fractions were combined, evaporated and the residue triturated with ether to give a solid. The solid was dried overnight at 40° C. to afford the title compound. Yield: 131 mg $^1$H NMR (400 MHz, CDCl$_3$) δ 8.47 (d, J=7.4 Hz, 1H), 8.31 (dd, J=8.2, 3.1 Hz, 1H), 8.24 (s, 1H), 8.08-8.04 (m, 2H), 7.98 (d, J=7.4 Hz, 1H), 7.79-7.73 (m, 1H), 7.65 (d, J=8.2 Hz, 2H), 7.53-7.45 (m, 3H), 7.41 (t, J=1.8 Hz, 1H), 7.19-7.16 (m, 1H), 7.14 (d, J=7.2 Hz, 1H), 4.30-4.27 (m, 1H), 4.22-4.15 (m, 3H), 3.84-3.77 (m, 2H), 3.41 (d, J=10.5 Hz, 2H), 3.26 (d, J=12.3 Hz, 2H), 2.77 (s, 4H), 1.95-1.84 (m, 8H), 1.34 (d, J=6.4 Hz, 6H).

MS: [M+H]+=690.2 (calc=690.3568) (MultiMode+)

EXAMPLE 49

5-fluoro-2-(4'-hydroxy-2'-(morpholinomethyl)biphenyl-3-yloxy)-N-((1s,4s)-4-(1-methyl-1H-pyrazole-3-carboxamido)cyclohexyl)nicotinamide

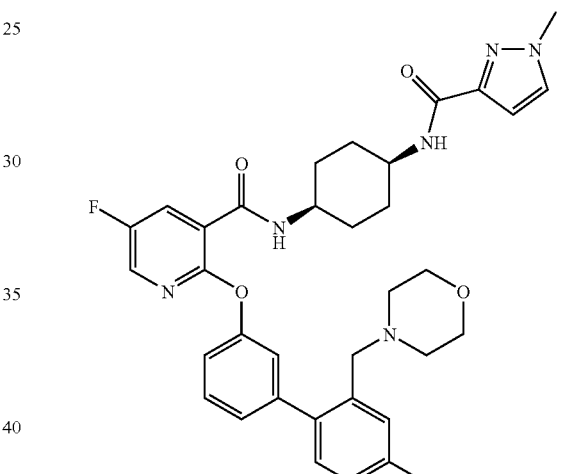

HATU (0.141 g, 0.37 mmol) was added to a solution of 1-methyl-1H-pyrazole-3-carboxylic acid (0.042 g, 0.34 mmol), N-((1s,4s)-4-aminocyclohexyl)-5-fluoro-2-(4'-hydroxy-2'-(morpholinomethyl)biphenyl-3-yloxy)nicotinamide 2HCl (0.2 g, 0.34 mmol) and DIPEA (0.235 mL, 1.35 mmol) in DMF (5 mL) and the solution stirred at RT for 20 h. The reaction was treated with 7M NH$_3$/MeOH (1 mL) and stirred for 1 h and evaporated in vacuo and the remaining DMF solution purified by reverse phase HPLC with aqTFA/MeCN as eluant to afford the title compound as a white solid. Yield: 169 mg $^1$H NMR (300 MHz, DMSO) δ 8.34 (m, 1H), 8.26 (m, 1H), 8.04 (m, 1H), 7.77 (m, 1H), 7.51 (m, 1H), 7.35 (m, 1H), 7.24 (m, 1H), 7.19-7.10 (m, 3H), 7.07 (m, 1H), 6.92 (m, 1H), 6.60 (m, 1H), 4.44-3.46 (m, 6H), 4.24 (s, 2H), 3.87 (s, 3H), 3.28-2.48 (m, 4H), 1.87-1.56 (m, 8H).

MS: APCI (+ve): 629 (M+1)

EXAMPLE 50

N-((1s,4s)-4-(5-fluoro-2-(4'-(pyrrolidin-1-ylmethyl)biphenyl-3-yloxy)nicotinamido)cyclohexyl)-5-methylimidazo[1,2-a]pyridine-2-carboxamide

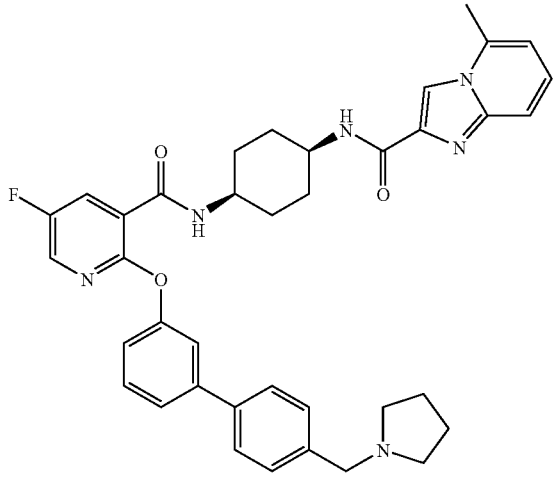

To a solution of N-((1s,4s)-4-(5-fluoro-2-(4'-formylbiphenyl-3-yloxy)nicotinamido)cyclohexyl)-5-methylimidazo[1,2-a]pyridine-2-carboxamide (150 mg, 0.25 mmol) in DCM (3 mL) was added pyrrolidine (0.032 mL, 0.38 mmol). The mixture was allowed to stir at RT for 40 min before sodium triacetoxyborohydride (81 mg, 0.38 mmol) was added. The reaction was stirred at RT for 2 h. The mixture was diluted with DCM and washed with sat. NaHCO$_3$ (aq), dried (MgSO$_4$) and evaporated to afford the title compound as a foam. Yield: 97 mg $^1$H NMR (400 MHz, CDCl$_3$) δ 13.08 (s, 1H), 8.33 (dd, J=8.2, 3.1 Hz, 1H), 8.26 (s, 1H), 8.17 (s, 1H), 8.06 (d, J=3.1 Hz, 1H), 8.00 (d, J=7.4 Hz, 1H), 7.94 (d, J=9.0 Hz, 1H), 7.65-7.58 (m, 3H), 7.54-7.45 (m, 4H), 7.40 (t, J=1.9 Hz, 1H), 7.20 (ddd, J=7.9, 2.3, 1.0 Hz, 1H), 7.02 (d, J=7.2 Hz, 1H), 4.30-3.95 (m, 4H), 3.72-3.65 (m, 2H), 2.91-2.83 (m, 2H), 2.73 (s, 3H), 2.19-2.11 (m, 2H), 2.08-1.99 (m, 2H), 1.95-1.82 (m, 8H).

MS: [M+H]+=647.1 (calc=647.3146) (MultiMode+)

EXAMPLE 51

N-((1s,4s)-4-(5-fluoro-2-(4'-(((2-hydroxyethyl)(methyl)amino)methyl)biphenyl-3-yloxy)nicotinamido)cyclohexyl)-5-methylimidazo[1,2-a]pyridine-2-carboxamide

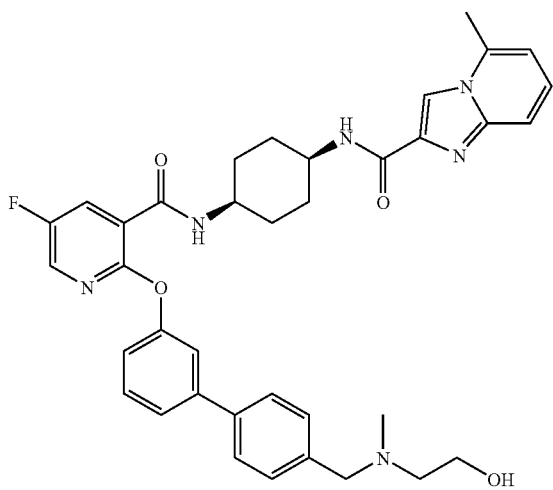

To a solution of N-((1s,4s)-4-(5-fluoro-2-(4'-formylbiphenyl-3-yloxy)nicotinamido)cyclohexyl)-5-methylimidazo[1,2-a]pyridine-2-carboxamide (150 mg, 0.25 mmol) in DCM (3 mL) was added 2-(methylamino)ethanol (0.030 mL, 0.38 mmol). The mixture was allowed to stir at RT for 40 min before sodium triacetoxyborohydride (81 mg, 0.38 mmol) was added. The reaction was stirred at RT for 2 h. The mixture was diluted with DCM and washed with sat. NaHCO$_3$ (aq), dried (MgSO$_4$) and evaporated to afford the title compound as a foam. Yield: 36 mg $^1$H NMR (400 MHz, CDCl$_3$) δ 8.43 (d, J=7.4 Hz, 1H), 8.32 (dd, J=8.2, 3.1 Hz, 1H), 8.20 (s, 1H), 8.07-8.02 (m, 2H), 7.99 (d, J=7.4 Hz, 1H), 7.72-7.65 (m, 3H), 7.54-7.46 (m, 4H), 7.43 (d, J=1.8 Hz, 1H), 7.20 (d, J=8.1 Hz, 1H), 7.10 (d, J=7.2 Hz, 1H), 4.31-4.15 (m, 6H), 3.97 (t, J=4.6 Hz, 2H), 2.86 (s, 3H), 2.75 (s, 3H), 1.96-1.84 (m, 8H).

MS: [M+H]+=651.1 (calc=651.3095) (MultiMode+)

EXAMPLE 52

N-((1s,4s)-4-(2-(2'-((dimethylamino)methyl)-4'-hydroxybiphenyl-3-yloxy)-5-fluoronicotinamido)cyclohexyl)-1H-benzo[d]imidazole-4-carboxamide

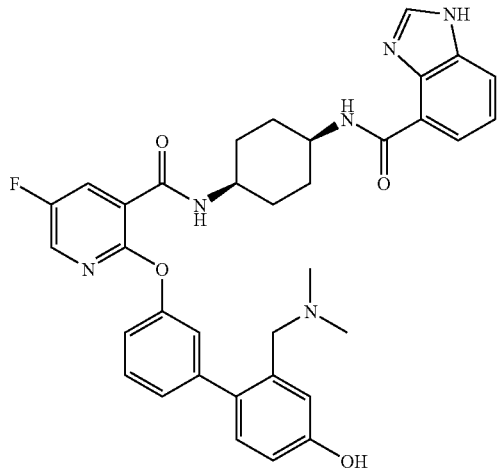

DIPEA (0.081 mL, 0.46 mmol) and HATU (0.176 g, 0.46 mmol) were added to TH-benzo[d]imidazole-4-carboxylic acid (Apollo Scientific Limited) (0.075 g, 0.46 mmol) in acetonitrile (1 mL). The mixture was stirred for 10 min then a solution of DIPEA (0.081 mL, 0.46 mmol) and N-((1s,4s)-4-aminocyclohexyl)-2-(2'-((dimethylamino)methyl)-4'-hydroxybiphenyl-3-yloxy)-5-fluoronicotinamide dihydrochloride (0.085 g, 0.15 mmol) in acetonitrile (1 mL) was added. After 6 h further acid (30 mg) was activated with HATU (60 mg) and DIPEA (0.05 mL) in acetonitrile (1.000 mL) and added to the reaction mixture. It was stirred overnight then 880 ammonia (2 mL) was added and the reaction stirred for 4 h. The reaction mixture was diluted with EtOAc and washed with water and saturated brine. The organic was evaporated to afford crude product. The crude product was purified by preparative HPLC on a Phenomenex Gemini column using a 95-5% gradient of aqueous 0.2% TFA in acetonitrile as eluent. The fractions containing the desired compound were evaporated to dryness to afford the title compound as a white foam. Yield: 61 mg $^1$H NMR (400 MHz, DMSO) δ 9.96-9.67 (m, 2H), 9.45-9.31 (m, 1H), 8.56-8.48 (m, 2H), 8.25 (d, J=3.0 Hz, 1H), 8.01 (dd, J=7.9, 3.0 Hz, 1H), 7.91 (d, J=7.2 Hz, 1H), 7.80 (d, J=7.8 Hz, 1H), 7.46 (t, J=7.8 Hz, 1H), 7.40 (t, J=7.7 Hz, 1H), 7.25-7.19 (m, 1H), 7.16-7.06 (m, 3H), 7.02-7.00 (m, 1H), 6.89 (dd, J=8.4, 2.4 Hz, 1H), 4.22-4.13 (m, 2H), 4.07-3.95 (m, 2H), 1.86-1.70 (m, 8H). Remaining protons obscured by solvent peaks.

MS: [M+H]+=623.2 (calc=623.2782) (MultiMode+)

EXAMPLE 53

N-((1s,4s)-4-(2-(4'-((dimethylamino)methyl)biphenyl-3-yloxy)-5-fluoronicotinamido)cyclohexyl)-2-methylthiazole-4-carboxamide

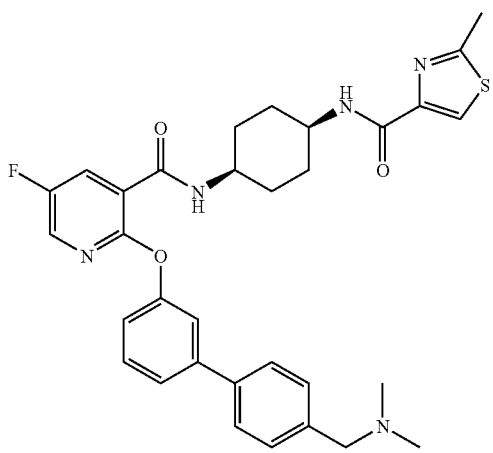

Step (a) N-((1s,4s)-4-(5-fluoro-2-(4'-formylbiphenyl-3-yloxy)nicotinamido)cyclohexyl)-2-methylthiazole-4-carboxamide Palladium acetate (0.050 g, 0.22 mmol), and 2-dicyclohexylphosphino-2',6'-dimethoxybiphenyl (0.184 g, 0.45 mmol) were added to acetonitrile (35.0 mL) under nitrogen. The resulting solution was stirred for 10 min. To this solution was added potassium carbonate (1.857 g, 13.44 mmol) dissolved in water (35.0 mL), followed by 4-formylphenylboronic acid (1.007 g, 6.72 mmol) and N-((1s,4s)-4-(5-fluoro-2-(3-iodophenoxy)nicotinamido)cyclohexyl)-2-methylthiazole-4-carboxamide (2.6 g, 4.48 mmol) and the mixture heated at 80° C. for 2 h. The mixture was poured onto water and extracted into EtOAc (×2). The extractions were combined, washed with brine, dried (MgSO$_4$) and evaporated to give a light brown foam. This was purified using column chromatography (eluent=80% EtOAc:hexane going to neat EtOAc) to give the sub-title compound as a white foam. Yield 2.13 g $^1$H NMR (400 MHz, CDCl$_3$) δ 10.05 (s, 1H), 8.39 (dd, J=8.2, 3.1 Hz, 1H), 8.08 (d, J=3.1 Hz, 1H), 8.04 (d, J=6.9 Hz, 1H), 7.94-7.90 (m, 3H), 7.74 (d, J=8.2 Hz, 2H), 7.60-7.57 (m, 2H), 7.46 (t, J=1.3 Hz, 1H), 7.25-7.23 (m, 1H), 7.21-7.16 (m, 1H), 4.30-4.22 (m, 1H), 4.10-4.03 (m, 1H), 2.60 (s, 3H), 1.99-1.78 (m, 6H), 1.73-1.59 (m, 2H).

MS: [M+H]+=559 (MultiMode+).

Step (b) N-((1s,4s)-4-(2-(4'-((dimethylamino)methyl)biphenyl-3-yloxy)-5-fluoronicotinamido)cyclohexyl)-2-methylthiazole-4-carboxamide trifluoroacetate To a solution of N-((1s,4s)-4-(5-fluoro-2-(4'-formylbiphenyl-3-yloxy)nicotinamido)cyclohexyl)-2-methylthiazole-4-carboxamide (150 mg, 0.27 mmol) in DCM (3 mL) was added dimethylamine, 2M solution in MTBE (0.201 mL, 0.40 mmol). The mixture was allowed to stir at RT for 40 min before sodium triacetoxyborohydride (85 mg, 0.40 mmol) was added. The reaction was stirred at RT for 2 h. The mixture was diluted with DCM and washed with sat. NaHCO$_3$ (aq), dried (MgSO$_4$) and evaporated to give a colourless glass. This was purified by HPLC to afford the title compound as a white solid. Yield: 109 mg $^1$H NMR (400 MHz, CDCl$_3$) δ 8.38 (dd, J=8.2, 3.1 Hz, 1H), 8.08 (d, J=3.1 Hz, 1H), 8.03 (d, J=7.2 Hz, 1H), 7.91 (s, 1H), 7.67-7.62 (m, 2H), 7.57 (t, J=7.8 Hz, 1H), 7.53-7.47 (m, 3H), 7.39 (t, J=1.9 Hz, 1H), 7.23-7.19 (m, 2H), 4.29-4.21 (m, 1H), 4.20 (s, 2H), 4.13-4.04 (m, 1H), 2.80 (s, 6H), 2.64 (s, 3H), 1.98-1.75 (m, 6H), 1.73-1.57 (m, 2H).

MS: [M+H]+=588.3 (calc=588.2444) (MultiMode+)

EXAMPLE 54

N-((1s,4s)-4-(2-(4'-(((3S,5R)-3,5-dimethylpiperazin-1-yl)methyl)biphenyl-3-yloxy)-5-fluoronicotinamido)cyclohexyl)-2-methylthiazole-4-carboxamide

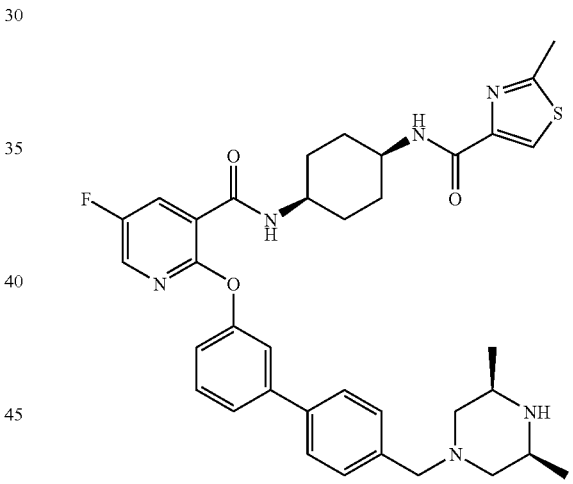

To a solution of N-((1s,4s)-4-(5-fluoro-2-(4'-formylbiphenyl-3-yloxy)nicotinamido)cyclohexyl)-2-methylthiazole-4-carboxamide (150 mg, 0.27 mmol) in DCM (3 mL) was added (2R,6S)-2,6-dimethylpiperazine (46.0 mg, 0.40 mmol). The mixture was allowed to stir at RT for 40 min before sodium triacetoxyborohydride (85 mg, 0.40 mmol) was added. The reaction was stirred at RT for 2 h. The mixture was diluted with DCM and washed with sat. NaHCO$_3$ (aq), dried (MgSO$_4$) and evaporated to give a yellow glass. This was purified by HPLC to give the title compound as a white solid. Yield: 88 mg $^1$H NMR (400 MHz, CDCl$_3$) δ 8.38 (dd, J=8.2, 3.1 Hz, 1H), 8.08 (d, J=3.1 Hz, 1H), 8.03 (d, J=6.9 Hz, 1H), 7.91 (s, 1H), 7.65-7.48 (m, 3H), 7.44 (d, J=8.2 Hz, 2H), 7.37 (s, 1H), 7.24-7.17 (m, 2H), 4.24 (br s, 1H), 4.14-3.97 (m, 3H), 3.67 (br s, 2H), 3.35-3.17 (m, 2H), 3.01 (t, J=12.0 Hz, 2H), 2.64 (s, 3H), 2.00-1.74 (m, 6H), 1.73-1.56 (m, 2H), 1.38-1.23 (m, 8H).

MS: [M+H]+=657.3 (calc=657.3023) (MultiMode+)

EXAMPLE 55

N-((1s,4s)-4-(2-(4'-((1,4-oxazepan-4-yl)methyl)biphenyl-3-yloxy)-5-fluoronicotinamido)cyclohexyl)-2-methylthiazole-4-carboxamide

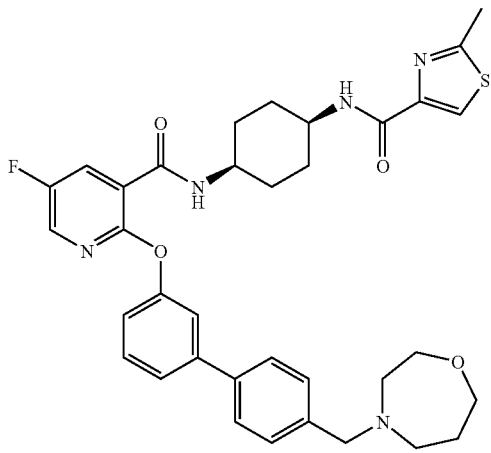

To a solution of N-((1s,4s)-4-(5-fluoro-2-(4'-formylbiphenyl-3-yloxy)nicotinamido)cyclohexyl)-2-methylthiazole-4-carboxamide (150 mg, 0.27 mmol) in DCM (3 mL) was added 1,4-oxazepane hydrochloride (55.4 mg, 0.40 mmol). The mixture was allowed to stir at RT for 40 min before sodium triacetoxyborohydride (85 mg, 0.40 mmol) was added. The reaction was stirred at RT for 2 h. The mixture was diluted with DCM and washed with sat. NaHCO$_3$ (aq), dried (MgSO$_4$) and evaporated to give a white foam. This was purified by HPLC to give the title compound. Yield: 75 mg $^1$H NMR (400 MHz, DMSO) δ 8.35 (d, J=7.2 Hz, 1H), 8.26 (d, J=3.1 Hz, 1H), 8.08 (s, 1H), 8.06 (dd, J=8.1, 3.2 Hz, 1H), 7.77 (d, J=8.2 Hz, 2H), 7.64-7.51 (m, 6H), 7.26-7.22 (m, 1H), 4.41 (d, J=4.1 Hz, 2H), 4.01 (br s, 1H), 3.92-3.81 (m, 2H), 3.81-3.64 (m, 3H), 3.55-3.43 (m, 1H), 3.43-3.33 (m, 1H), 3.31-3.19 (m, 2H), 2.65 (s, 3H), 2.16-1.98 (m, 2H), 1.83-1.58 (m, 8H).

MS: [M+H]+=644.3 (calc=644.2707) (MultiMode+)

EXAMPLE 56

N-((1s,4s)-4-(5-fluoro-2-(2'-hydroxy-4'-(morpholinomethyl)biphenyl-3-yloxy)nicotinamido)cyclohexyl)-2-methylthiazole-4-carboxamide

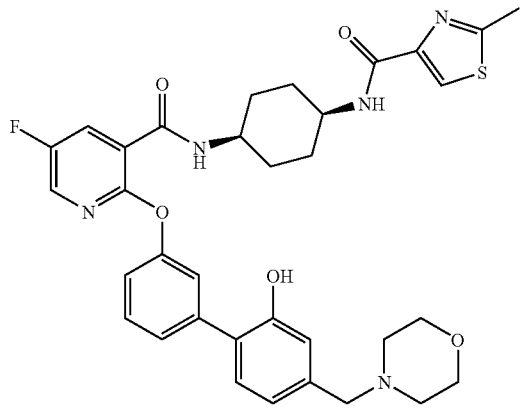

Step (a) N-((1s,4s)-4-(5-fluoro-2-(4'-formyl-2'-hydroxybiphenyl-3-yloxy)nicotinamido)cyclohexyl)-2-methylthiazole-4-carboxamide A solution of potassium carbonate (0.643 g, 4.65 mmol) in water (4.5 mL), 3-hydroxy-4-iodobenzaldehyde (0.385 g, 1.55 mmol) and N-((1s,4s)-4-(5-fluoro-2-(3-(4,4,5,5-tetramethyl-1,3,2-dioxaborolan-2-yl)phenoxy)nicotinamido)cyclohexyl)-2-methylthiazole-4-carboxamide (0.9 g, 1.55 mmol) were added sequentially to a stirred solution of palladium(II) acetate (0.035 g, 0.16 mmol) and dicyclohexyl(2',6'-dimethoxybiphenyl-2-yl)phosphine (0.127 g, 0.31 mmol) in acetonitrile (6.0 mL) and heated at 70° C. for 1 h. The mixture was cooled to RT, extracted with EtOAc, washed with water and brine, dried (MgSO$_4$), filtered and evaporated in vacuo. The residue was purified by chromatography on silica with 50% EtOAc/isohexane as eluent to afford the sub-title compound as a light brown solid. Yield: 139 mg $^1$H NMR (400 MHz, DMSO) δ 10.22 (s, 1H), 9.91 (s, 1H), 8.34 (d, J=7.7 Hz, 1H), 8.26 (d, J=3.2 Hz, 1H), 8.07 (s, 1H), 8.03 (m, 1H), 7.58 (d, J=8.3 Hz, 1H), 7.51-7.44 (m, 4H), 7.41-7.37 (m, 2H), 7.19 (m, 1H), 4.01 (m, 1H), 3.86 (m, 1H), 2.62 (s, 3H), 1.81-1.62 (m, 8H).

MS: APCI (+ve) 575 (M+1)

Step (b) N-((1s,4s)-4-(5-fluoro-2-(2'-hydroxy-4'-(morpholinomethyl)biphenyl-3-yloxy)nicotinamido)cyclohexyl)-2-methylthiazole-4-carboxamide trifluoroacetate N-((1s,4s)-4-(5-fluoro-2-(4'-formyl-2'-hydroxybiphenyl-3-yloxy)nicotinamido)cyclohexyl)-2-methylthiazole-4-carboxamide (65 mg, 0.11 mmol), morpholine (0.020 mL, 0.23 mmol) and acetic acid (0.013 mL, 0.23 mmol) were dissolved in DCM (5 mL) and stirred for 10 min. Sodium triacetoxyborohydride (47.9 mg, 0.23 mmol) was added and the mixture stirred for a further 1 h. The reaction was diluted with DCM (50 mL), washed with saturated NaHCO$_3$ (aq) and brine, dried (MgSO$_4$), filtered and evaporated in vacuo. The residue was purified by reverse phase HPLC with MeCN/aqTFA as eluent to afford the title compound as a white solid. Yield: 27 mg $^1$H NMR (400 MHz, DMSO) δ 10.01 (s, 1H), 9.90 (s, 1H), 8.34 (d, J=7.2 Hz, 1H), 8.26 (d, J=3.3 Hz, 1H), 8.08 (s, 1H), 8.03 (m, 1H), 7.59 (d, J=8.0 Hz, 1H), 7.44 (m, 2H), 7.36 (m, 2H), 7.15 (m, 1H), 7.03-6.95 (m, 2H), 4.34-4.22 (m, 2H), 4.05-3.82 (m, 4H), 3.69-3.56 (m, 2H), 3.35-3.04 (m, 4H), 2.66 (s, 3H), 1.80-1.62 (m, 8H).

MS: APCI (+ve):646 (M+1).

EXAMPLE 57

N-((1s,4s)-4-(5-fluoro-2-(2'-hydroxy-4'-(piperazin-1-ylmethyl)biphenyl-3-yloxy)nicotinamido)cyclohexyl)-2-methylthiazole-4-carboxamide

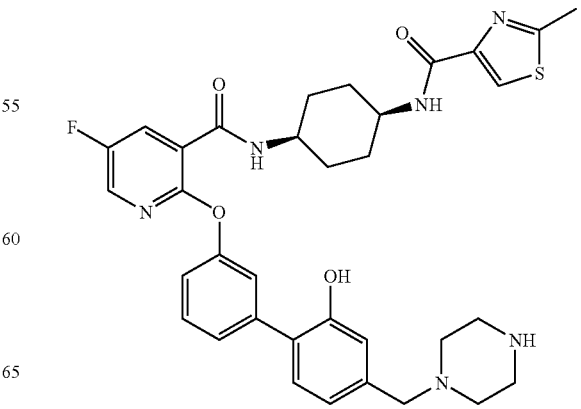

N-((1s,4s)-4-(5-fluoro-2-(4'-formyl-2'-hydroxybiphenyl-3-yloxy)nicotinamido)cyclohexyl)-2-methylthiazole-4-carboxamide (65 mg, 0.11 mmol), piperazine (48.7 mg, 0.57 mmol) and acetic acid (0.032 mL, 0.57 mmol) were dissolved in DCM (5 mL) and stirred for 10 min. Sodium triacetoxyborohydride (47.9 mg, 0.23 mmol) was added and the mixture stirred for a further 1 h. The reaction was diluted with DCM (50 mL), washed with saturated NaHCO₃ (aq) and brine, dried (MgSO₄), filtered and evaporated in vacuo. The residue was purified by reverse phase HPLC with MeCN/aqTFA as eluent to afford the title compound as a white solid. Yield: 22 mg ¹H NMR (400 MHz, DMSO) δ 9.72 (s, 1H), 8.34 (d, J=7.2 Hz, 1H), 8.25 (d, J=3.1 Hz, 1H), 8.08 (s, 1H), 8.03 (m, 1H), 7.59 (d, J=8.2 Hz, 1H), 7.46-7.38 (m, 2H), 7.34 (m, 1H), 7.26 (d, J=8.0 Hz, 1H), 7.13 (m, 1H), 6.92 (m, 1H), 6.84 (d, J=8.0 Hz, 1H), 4.00 (m, 1H), 3.87 (m, 1H), 3.79-3.55 (m, 2H), 3.16 (m, 4H), 2.85-2.68 (m, 4H), 2.65 (s, 3H), 1.79-1.61 (m, 8H).

MS: APCI (+ve) 645 (M+1)

EXAMPLE 58

N-((1s,4s)-4-(5-fluoro-2-(4'-hydroxy-2'-(morpholinomethyl)biphenyl-3-yloxy)nicotinamido)cyclohexyl)-2-(hydroxymethyl)thiazole-4-carboxamide

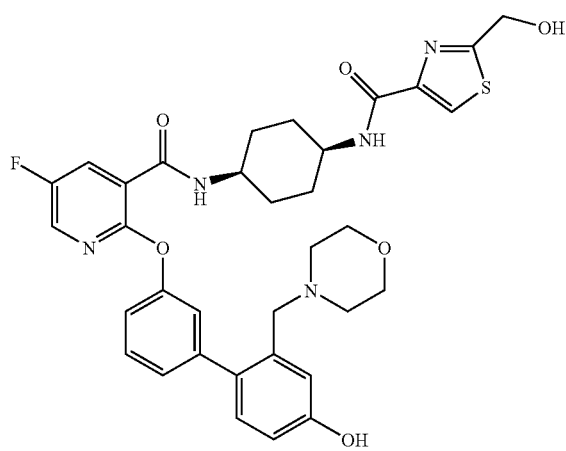

Step (a) Ethyl 2-(pivaloyloxymethyl)thiazole-4-carboxylate

2-Amino-2-thioxoethyl pivalate (3.0 g, 17.12 mmol) and 3-bromo-2-oxopropanoic acid (3.14 g, 18.83 mmol) were dissolved in EtOH (20 mL), 4 Å molecular sieves added and the reaction mixture heated at reflux for 20 h then cooled to RT, filtered, washed with EtOH and evaporated in vacuo. The residual semi solid was treated with 50% EtOAc/DCM and the resulting light brown solid filtered off. The filtrate was evaporated in vacuo and the residue purified by chromatography on silica with 20% EtOAc/isohexane as eluent to afford the sub-title compound as a pale yellow oil. Yield: 2.47 g ¹H NMR (400 MHz, DMSO) δ 8.55 (s, 1H), 5.40 (s, 2H), 4.30 (q, J=7.1 Hz, 2H), 1.30 (t, J=7.3 Hz, 3H), 1.20 (s, 9H).
MS: APCI (+ve) 272 (M+1).

Step (b) 2-(hydroxymethyl)thiazole-4-carboxylic acid

A solution of NaOH (1.769 g, 44.23 mmol) in water (20.0 mL) was added to a stirred solution of ethyl 2-(pivaloyloxymethyl)thiazole-4-carboxylate (2.4 g, 8.85 mmol) in a mixture of THF (20 mL) and MeOH (10.0 mL), and the reaction stirred for 72 h. Acidified with 2M HCl (10 mL) and evaporated in vacuo to afford crude 2-(hydroxymethyl)thiazole-4-carboxylic acid as a white solid. Purified by reverse phase chromatography with MeCN/aqTFA as eluent to afford the sub-title compound as a white solid. Yield: 1.4 g ¹H NMR (400 MHz, DMSO) δ 8.37 (s, 1H), 4.73 (s, 2H).

Step (c) N-((1s,4s)-4-(5-fluoro-2-(4'-hydroxy-2'-(morpholinomethyl)biphenyl-3-yloxy)nicotinamido)cyclohexyl)-2-(hydroxymethyl)thiazole-4-carboxamide trifluoroacetate DCC (0.063 g, 0.30 mmol) was added to a solution of 2-(hydroxymethyl)thiazole-4-carboxylic acid (0.044 g, 0.28 mmol) and HOBt (0.048 g, 0.30 mmol) in DMF (3 mL) and the stirred for 10 min. A solution of N-((1s,4s)-4-aminocyclohexyl)-5-fluoro-2-(4'-hydroxy-2'-(morpholinomethyl)biphenyl-3-yloxy)nicotinamide (0.15 g, 0.25 mmol) and DIPEA (0.088 mL, 0.51 mmol) in DMF (2 mL) was then added and the reaction stirred for 20 h. The mixture was evaporated in vacuo and the remaining DMF solution purified by reverse phase HPLC with aqTFA/MeCN as eluant to afford the title compound as a white solid. Yield: 82 mg ¹H NMR (400 MHz, DMSO) δ 10.18-9.91 (m, 1H), 8.35 (d, J=7.2 Hz, 1H), 8.27 (d, J=3.0 Hz, 1H), 8.18 (s, 1H), 8.04 (m, 1H), 7.60 (d, J=8.2 Hz, 1H), 7.50 (t, J=7.9 Hz, 1H), 7.23 (d, J=8.6 Hz, 1H), 7.19-7.08 (m, 4H), 6.92 (d, J=8.2 Hz, 1H), 4.74 (s, 2H), 4.38-3.47 (m, 9H), 3.23-3.02 (m, 2H), 2.78-2.58 (m, 2H), 1.81-1.57 (m, 8H).

MS: APCI (+ve) 662 (M−1).

EXAMPLE 59

3'-(5-fluoro-3-((1s,4s)-4-(5-methylimidazo[1,2-a]pyridine-2-carboxamido)cyclohexylcarbamoyl)pyridin-2-yloxy)-2-(morpholinomethyl)biphenyl-4-carboxylic acid

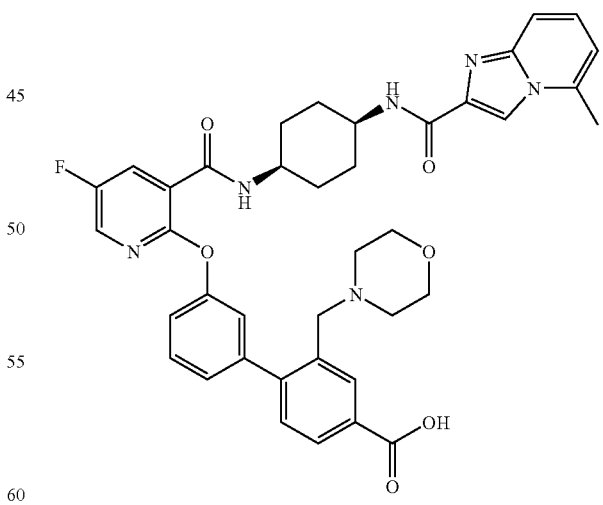

Step (a) methyl 3-(morpholinomethyl)-4-(trifluoromethylsulfonyloxy)benzoate

To a suspension of methyl 4-hydroxy-3-(morpholinomethyl)benzoate, hydrochloride (4 g, 13.90 mmol) in DMF (25 mL) was added triethylamine (6.78 mL, 48.66 mmol). The mixture turned beige in colour and the suspension changed form but did not clear and become a homogenous solution. To this suspension, cooled to 5° C., was then added 1,1,1-trifluoro-N-phenyl-N-(trifluoromethylsulfonyl)methanesulfonamide (10.93 g, 30.58 mmol). The ice bath was removed and the mixture was stirred at RT overnight. The mixture was poured into water (400 mL) and basified using saturated NaHCO$_3$ (aq). The organics were extracted into ether (×3), combined, washed with brine, dried (MgSO$_4$) and evaporated to give a white solid. The crude product was purified using column chromatography (eluent=20% EtOAc in hexane) to give the sub-title compound as a white solid. Yield: 3.9 g $^1$H NMR (400 MHz, CDCl$_3$) δ 8.12 (d, J=2.1 Hz, 1H), 8.05 (dd, J=8.6, 2.2 Hz, 1H), 7.32 (d, J=8.7 Hz, 1H), 3.95 (s, 3H), 3.70 (t, J=4.6 Hz, 4H), 3.58 (s, 2H), 2.46 (t, J=4.6 Hz, 4H).

Step (b) methyl 3'-(3-((1s,4s)-4-(tert-butoxycarbonylamino)cyclohexylcarbamoyl)-5-fluoropyridin-2-yloxy)-2-(morpholinomethyl)biphenyl-4-carboxylate To a microwave tube was charged acetonitrile (2 mL) followed by tert-butyl (1s,4s)-4-(5-fluoro-2-(3-(4,4,5,5-tetramethyl-1,3,2-dioxaborolan-2-yl)phenoxy)nicotinamido)cyclohexylcarbamate (1 g, 1.80 mmol), methyl 3-(morpholinomethyl)-4-(trifluoromethylsulfonyloxy)benzoate (0.690 g, 1.80 mmol), potassium carbonate (0.746 g, 5.40 mmol), water (2 mL), 2-dicyclohexylphosphino-2',6'-dimethoxybiphenyl (0.074 g, 0.18 mmol) and finally palladium acetate (0.020 g, 0.09 mmol). The mixture was heated in the microwave at 80° C. for 1 h. The mixture was diluted with EtOAc and then washed with NaHCO$_3$ (aq), brine, dried (MgSO$_4$) and evaporated to give an oil. This was purified using column chromatography (eluent=1:1 hexane:EtOAc) to give the sub-title compound as an oil. Yield: 650 mg MS: [M+H]+=663 (MultiMode+)

Step (c) methyl 3'-(3-((1s,4s)-4-aminocyclohexylcarbamoyl)-5-fluoropyridin-2-yloxy)-2-(morpholinomethyl)biphenyl-4-carboxylate, dihydrochloride To a solution of methyl 3'-(3-((1s,4s)-4-(tert-butoxycarbonylamino)cyclohexylcarbamoyl)-5-fluoropyridin-2-yloxy)-2-(morpholinomethyl)biphenyl-4-carboxylate (0.6 g, 0.91 mmol) in DCM (5 mL) was added hydrogen chloride, 4.0M solution in dioxane (3.39 mL, 13.58 mmol). The mixture was stirred at RT for 3 days. The mixture was concentrated in vacuo and the residue tritutrated with ether. The ether was removed under vacuum and this gave the sub-title compound as a pale yellow solid. Yield: 0.52 g MS: [M+H]+=563 (MultiMode+)

Step (d) 3'-(5-fluoro-3-((1s,4s)-4-(5-methylimidazo[1,2-a]pyridine-2-carboxamido)cyclohexylcarbamoyl)pyridin-2-yloxy)-2-(morpholinomethyl)biphenyl-4-carboxylic acid To a suspension of methyl 3'-(3-((1s,4s)-4-aminocyclohexylcarbamoyl)-5-fluoropyridin-2-yloxy)-2-(morpholinomethyl)biphenyl-4-carboxylate, hydrochloride (150 mg, 0.25 mmol) and 5-methylimidazo[1,2-a]pyridine-2-carboxylic acid (44.1 mg, 0.25 mmol) in acetonitrile (4 mL) was added triethylamine (0.349 mL, 2.50 mmol). The mixture was stirred at RT until it became homogenous. To this solution was then added 1-propanephosphonic acid cyclic anhydride, 1.57M solution in THF (0.167 mL, 0.26 mmol). The mixture was stirred at room temperature for an hour. To this mixture was then added lithium hydroxide (0.024 mL, 2.50 mmol), water (1 mL) and methanol (1 mL). The mixture was placed into a microwave tube and heated to 80° C. for 30 min. The mixture was purified using reverse phase prep HPLC (eluent=TFA(aq)/MeCN), the appropriate fractions were combined, evaporated and the residue triturated with ether to give a white solid which was dried overnight under vacuum to afford the title compound. Yield: 105 mg $^1$H NMR (400 MHz, CD$_3$OD) δ 8.47 (s, 1H), 8.33 (d, J=1.8 Hz, 1H), 8.14 (d, J=3.1 Hz, 1H), 8.08-8.04 (m, 2H), 7.67-7.56 (m, 3H), 7.49 (d, J=8.2 Hz, 1H), 7.33 (ddd, J=7.8, 2.1, 0.3 Hz, 1H), 7.27-7.23 (m, 2H), 7.11 (d, J=6.9 Hz, 1H), 4.48 (s, 2H), 4.12 (s, 1H), 4.06 (s, 1H), 3.78-3.63 (m, 4H), 3.13-2.90 (m, 4H), 2.72 (s, 3H), 1.96-1.79 (m, 8H).

MS: [M+H]+=707.2 (calc=707.2993) (MultiMode+)

EXAMPLE 60

N-((1s,4s)-4-(5-fluoro-2-(4'-((4-methyl-1,4-diazepan-1-yl)methyl)biphenyl-3-yloxy)nicotinamido)cyclohexyl)-2-methylthiazole-4-carboxamide

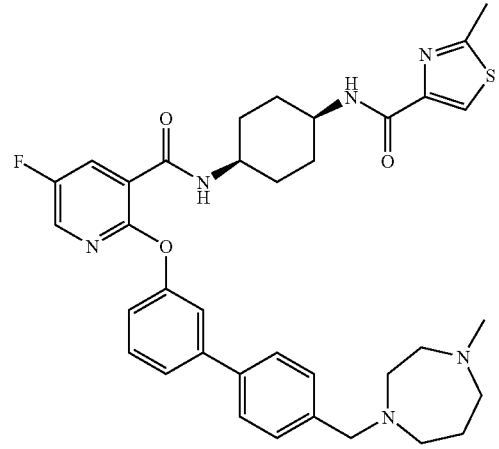

To a solution of N-((1s,4s)-4-(5-fluoro-2-(4'-formylbiphenyl-3-yloxy)nicotinamido)cyclohexyl)-2-methylthiazole-4-carboxamide (150 mg, 0.27 mmol) in DCM (3 mL) was added 1-methyl-1,4-diazepane (0.050 mL, 0.40 mmol). The mixture was allowed to stir at RT for 40 min before sodium triacetoxyborohydride (85 mg, 0.40 mmol) was added. The reaction was stirred at RT for 2 h. The mixture was diluted with DCM and washed with sat. NaHCO$_3$ (aq), dried (MgSO$_4$) and evaporated to give a colourless glass. This was purified by HPLC to afford the title compound. Yield: 20 mg $^1$H NMR (400 MHz, CDCl$_3$) δ 8.38 (dd, J=8.1, 3.2 Hz, 1H), 8.08 (d, J=3.1 Hz, 1H), 8.03 (d, J=7.4 Hz, 1H), 7.91 (s, 1H), 7.65-7.44 (m, 6H), 7.40-7.34 (m, 1H), 7.20 (d, J=7.9 Hz, 2H), 4.24 (br s, 1H), 4.18-4.03 (m, 3H), 3.83-3.20 (m, 8H), 2.87 (s, 3H), 2.64 (s, 3H), 2.48 (br s, 2H), 1.98-1.75 (m, 6H), 1.73-1.57 (m, 2H).

MS: [M+H]+=657.3 (calc=657.3023) (MultiMode+)

EXAMPLE 61

N-((1s,4s)-4-(1,5-dimethyl-1H-pyrazole-3-carboxamido)cyclohexyl)-2-(3'-(((3S,5R)-3,5-dimethylpiperazin-1-yl)methyl)-4'-hydroxybiphenyl-3-yloxy)-5-fluoronicotinamide

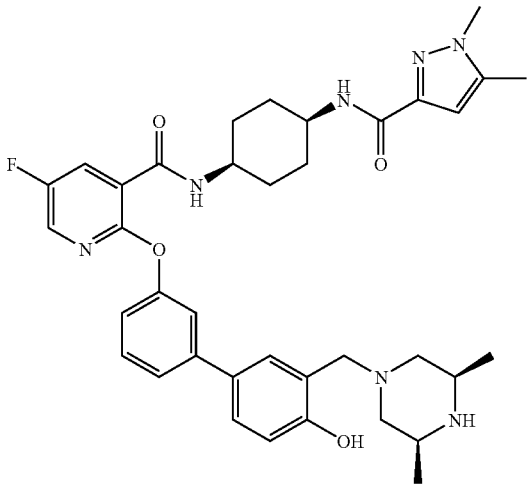

Step (a) N-((1s,4s)-4-aminocyclohexyl)-5-fluoro-2-(3-iodophenoxy)nicotinamide hydrochloride To a solution of tert-butyl (1s,4s)-4-(5-fluoro-2-(3-iodophenoxy)nicotinamido)cyclohexylcarbamate (5.29 g, 9.52 mmol) in DCM (35 mL) was added 4.0 M hydrogen chloride in dioxane (23.81 mL, 95.25 mmol). The mixture was stirred at RT for 24 h. The mixture was evaporated to dryness to give the sub-title compound as a white solid. Yield: 4.56 g MS: [M+H]+=456 (MultiMode+)

Step (b) N-((1s,4s)-4-(1,5-dimethyl-1H-pyrazole-3-carboxamido)cyclohexyl)-5-fluoro-2-(3-iodophenoxy)nicotinamide To a suspension of N-((1s,4s)-4-aminocyclohexyl)-5-fluoro-2-(3-iodophenoxy)nicotinamide hydrochloride (1.5 g, 3.05 mmol) in acetonitrile (100 mL) was added 1,5-dimethyl-1H-pyrazole-3-carboxylic acid (1.069 g, 7.63 mmol) and triethylamine (4.25 mL, 30.50 mmol). 1-Propanephosphonic acid cyclic anhydride, 1.57M solution in THF (T3P) (5.83 mL, 9.15 mmol) was then added and the mixture stirred at RT for 2 h. The mixture was evaporated to dryness and the residue dissolved in DCM (150 mL) and washed with saturated NaHCO$_3$ (aq), brine, dried (MgSO$_4$) and evaporated to give a foam. The product was purified using column chromatography (eluent=neat EtOAc) to give the sub-title compound as a white foam. Yield: 1.04 g $^1$H NMR (400 MHz, CDCl$_3$) δ 8.36 (dd, J=8.2, 3.1 Hz, 1H), 8.07 (d, J=3.1 Hz, 1H), 7.87 (d, J=6.7 Hz, 1H), 7.64 (dt, J=7.5, 1.5 Hz, 1H), 7.55 (t, J=1.8 Hz, 1H), 7.22-7.14 (m, 2H), 6.69 (d, J=7.7 Hz, 1H), 6.53 (s, 1H), 4.26-4.17 (m, 1H), 4.12-4.03 (m, 1H), 3.78 (s, 3H), 2.28 (s, 3H), 1.95-1.73 (m, 6H), 1.67-1.58 (m, 2H)

MS: [M+H]+=578 (MultiMode+).

Step (c) N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide 1,1'-Bis(diphenylphosphino)ferrocene (0.050 g, 0.09 mmol) and 1,1'-bis(diphenylphosphino)ferrocene-palladium(II)dichloride DCM complex (0.074 g, 0.09 mmol) were stirred in dry dimethylsulfoxide (5 mL) under nitrogen for 10 min. Potassium acetate (0.530 g, 5.40 mmol), N-((1s,4s)-4-(1,5-dimethyl-1H-pyrazole-3-carboxamido)cyclohexyl)-5-fluoro-2-(3-iodophenoxy)nicotinamide (1.04 g, 1.80 mmol) and 4,4,4',4',5,5,5',5'-octamethyl-2,2'-bi(1,3,2-dioxaborolane) (0.608 g, 2.40 mmol) were added and the reaction was heated at 80° C. overnight. The reaction was cooled and diluted with water (100 mL). The suspension was stirred at RT for 30 mins, then the precipitate was filtered off. The precipitate was dissolved in DCM, dried (MgSO$_4$) and the solvent removed to give a brown oil. The crude material was purified by Biotage (eluant=neat EtOAc) to give the sub-title compound as an orange foam after evaporation. Yield: 0.81 g $^1$H NMR (400 MHz, CDCl$_3$) δ 8.36 (dd, J=8.3, 3.2 Hz, 1H), 8.10-8.04 (m, 2H), 7.74 (dd, J=6.4, 1.0 Hz, 1H), 7.56 (d, J=2.3 Hz, 1H), 7.49 (t, J=7.8 Hz, 1H), 7.29 (ddd, J=8.1, 2.5, 1.1 Hz, 1H), 6.65 (d, J=7.4 Hz, 1H), 6.51 (s, 1H), 4.26-4.17 (m, 1H), 4.11-4.03 (m, 1H), 3.75 (s, 3H), 2.27 (s, 3H), 1.94-1.73 (m, 6H), 1.67-1.56 (m, 2H), 1.32 (s, 12H).

MS: [M+H]+=578 (MultiMode+)

Step (d) 4-bromo-2-(((3S,5R)-3,5-dimethylpiperazin-1-yl)methyl)phenol

To a solution of 5-bromo-2-hydroxybenzaldehyde (1 g, 4.97 mmol) in DCM (50 mL) was added (2R,6S)-2,6-dimethylpiperazine (0.852 g, 7.46 mmol). The mixture was allowed to stir at RT for 40 min before sodium triacetoxyborohydride (1.582 g, 7.46 mmol) was added. The reaction was stirred at RT for 24 h. The mixture was diluted with DCM and washed with sat. NaHCO$_3$ (aq), dried (MgSO$_4$) and evaporated to give a white foam. This was purified by Biotage (eluent=2.5% 7M ammonia in methanol/DCM) to give the sub-title compound as a white solid. Yield: 1.32 g $^1$H NMR (400 MHz, CDCl$_3$) δ 7.26 (dd, J=8.7, 2.3 Hz, 1H), 7.09 (d, J=2.3 Hz, 1H), 6.70 (d, J=8.5 Hz, 1H), 3.64 (s, 2H), 3.00-2.90 (m, 2H), 2.87-2.80 (m, 2H), 1.74 (t, J=10.9 Hz, 2H), 1.05 (d, J=6.4 Hz, 6H).

MS: [M+H]+=300 (MultiMode+).

Step (e) N-((1s,4s)-4-(1,5-dimethyl-1H-pyrazole-3-carboxamido)cyclohexyl)-2-(3'-(((3S,5R)-3,5-dimethylpiperazin-1-yl)methyl)-4'-hydroxybiphenyl-3-yloxy)-5-fluoronicotinamide To a microwave tube was charged acetonitrile (2 mL) followed by N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide (100 mg, 0.17 mmol), 4-bromo-2-(((3S,5R)-3,5-dimethylpiperazin-1-yl)methyl)phenol (51.8 mg, 0.17 mmol), potassium carbonate (71.8 mg, 0.52 mmol), water (2 mL), 2-dicyclohexylphosphino-2',6'-dimethoxybiphenyl (7 mg, 0.02 mmol) and finally palladium acetate (2 mg, 8.66 µmol). The mixture was heated in the microwave at 80° C. for 1 h. The mixture was diluted with EtOAc and then washed with NaHCO$_3$ (aq), brine, dried (MgSO$_4$) and evaporated to give a yellow oil. This was purified by HPLC to afford the title compound as a white solid. Yield: 7.5 mg ¹H NMR (500 MHz, CDCl₃) δ 8.47 (d, J=7.4 Hz, 1H), 8.13 (d, J=3.1 Hz, 1H), 8.08 (dd, J=7.9, 2.9 Hz, 1H), 7.49-7.41 (m, 5H), 7.37-7.34 (m, 1H), 7.12 (d, J=7.6 Hz, 1H), 6.86 (d, J=8.8 Hz, 1H), 6.42 (s, 1H), 4.16-4.10 (m, 1H), 3.98-3.91 (m, 1H), 3.86 (s, 2H), 3.72 (s, 3H), 3.51-3.40 (m, 3H), 2.34-2.25 (m, 6H), 1.92-1.77 (m, 6H), 1.74-1.63 (m, 2H), 1.29 (d, J=6.6 Hz, 8H).

MS: [M+H]+=670.3 (calc=670.3517) (MultiMode+)

EXAMPLE 62

N-((1s,4s)-4-(1,5-dimethyl-1H-pyrazole-3-carboxamido)cyclohexyl)-2-(4'-(((3S,5R)-3,5-dimethylpiperazin-1-yl)methyl)biphenyl-3-yloxy)-5-fluoronicotinamide

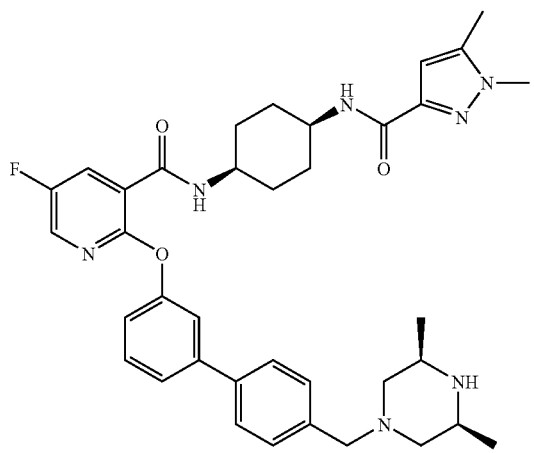

Step (a) N-((1s,4s)-4-(1,5-dimethyl-1H-pyrazole-3-carboxamido)cyclohexyl)-5-fluoro-2-(4'-formylbiphenyl-3-yloxy)nicotinamide Palladium acetate (4.86 mg, 0.02 mmol), and 2-dicyclohexylphosphino-2',6'-dimethoxybiphenyl (17.78 mg, 0.04 mmol) were added to acetonitrile (3.38 mL) under nitrogen. The resulting solution was stirred for 10 min. To this solution was added potassium carbonate (180 mg, 1.30 mmol) dissolved in water (3.38 mL), followed by 4-formylphenylboronic acid (97 mg, 0.65 mmol) and N-((1s,4s)-4-(1,5-dimethyl-1H-pyrazole-3-carboxamido)cyclohexyl)-5-fluoro-2-(3-iodophenoxy)nicotinamide (250 mg, 0.43 mmol) and the mixture heated at 80° C. for 2 h. The mixture was poured onto water and extracted into EtOAc (×2). The extractions were combined, washed with brine, dried (MgSO₄) and evaporated to give a yellow oil. This was purified using column chromatography (eluent=neat EtOAc) to give the sub-title compound as a white foam. Yield: 187 mg ¹H NMR (400 MHz, CDCl₃) δ 10.05 (s, 1H), 8.39 (dd, J=8.2, 3.1 Hz, 1H), 8.08 (d, J=3.1 Hz, 1H), 8.04 (d, J=6.9 Hz, 1H), 7.92-7.88 (m, 2H), 7.76-7.72 (m 2H), 7.62-7.55 (m, 2H), 7.47-7.45 (m, 1H), 7.25-7.20 (m, 1H), 6.67 (d, J=7.4 Hz, 1H), 6.51 (s, 1H), 4.30-4.27 (m, 1H), 4.10-4.01 (m, 1H), 3.66 (s, 3H), 2.26 (s, 3H), 1.98-1.76 (m, 6H), 1.70-1.56 (m, 2H).

MS: [M+H]+=556 (MultiMode+)

Step (b) N-((1s,4s)-4-(1,5-dimethyl-1H-pyrazole-3-carboxamido)cyclohexyl)-2-(4'-(((3S,5R)-3,5-dimethylpiperazin-1-yl)methyl)biphenyl-3-yloxy)-5-fluoronicotinamide To a solution of N-((1s,4s)-4-(1,5-dimethyl-1H-pyrazole-3-carboxamido)cyclohexyl)-5-fluoro-2-(4'-formylbiphenyl-3-yloxy)nicotinamide (150 mg, 0.27 mmol) in DCM (3 mL) was added (2R,6S)-2,6-dimethylpiperazine (46.2 mg, 0.40 mmol). The mixture was allowed to stir at RT for 40 min before sodium triacetoxyborohydride (86 mg, 0.40 mmol) was added. The reaction was stirred at RT overnight. The mixture was diluted with DCM and washed with sat. NaHCO₃ (aq), dried (MgSO₄) and evaporated to give a yellow glass. This was purified by HPLC to afford the title compound as a white solid. Yield: 107 mg ¹H NMR (400 MHz, CDCl₃) δ 8.37 (dd, J=8.2, 3.1 Hz, 1H), 8.07 (d, J=3.1 Hz, 1H), 8.00 (d, J=6.9 Hz, 1H), 7.63 (d, J=8.2 Hz, 2H), 7.59-7.43 (m, 4H), 7.39-7.35 (m, 1H), 7.22-7.17 (m, 1H), 6.70 (d, J=7.7 Hz, 1H), 6.49 (s, 1H), 4.25-4.17 (m, 1H), 4.11 (s, 1H), 4.09-4.01 (m, 1H), 3.76-3.66 (m, 4H), 3.31 (d, J=10.8 Hz, 2H), 3.15 (t, J=12.0 Hz, 2H), 2.26 (s, 3H), 1.95-1.74 (m, 6H), 1.69-1.57 (m, 2H), 1.33 (d, J=6.4 Hz, 6H).

MS: [M+H]+=654.4 (calc=654.3568) (MultiMode+)

EXAMPLE 63

N-((1s,4s)-4-(5-fluoro-2-(4'-hydroxy-2'-(morpholinomethyl)biphenyl-3-yloxy)nicotinamido)cyclohexyl)-2-(methoxymethyl)thiazole-4-carboxamide

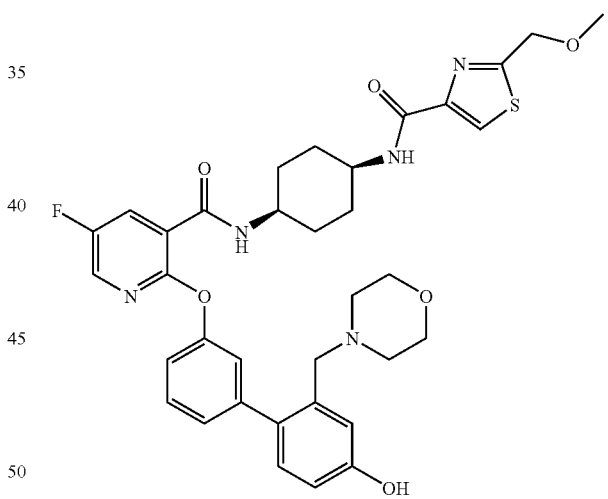

Step (a) 2-(methoxymethyl)thiazole-4-carboxylic acid

Sodium hydride (0.151 g, 3.77 mmol) was added to a solution of 2-(hydroxymethyl)thiazole-4-carboxylic acid (0.2 g, 1.26 mmol) in DMF (2 mL) and stirred for 20 min. Methyl iodide (0.236 mL, 3.77 mmol) was added and the reaction stirred for a further 2 h. Water (2 mL) was added, followed by NaOH (0.251 g, 6.28 mmol) and stirred for 20 h. The reaction mixture was heated at 60° C. for 5 h then cooled to RT, acidified with 2M HCl and purified by reverse phase HPLC with MeCN/aqTFA as eluent to afford the sub-title compound as a white solid. Yield: 31 mg MS: APCI (+ve) 174 (M+1)

Step (b) N-((1s,4s)-4-(5-fluoro-2-(4'-hydroxy-2'-(morpholinomethyl)biphenyl-3-yloxy)nicotinamido)cyclohexyl)-2-(methoxymethyl)thiazole-4-carboxamide DCC (0.042 g, 0.20 mmol) was added to a solution of 2-(methoxymethyl)thiazole-4-carboxylic acid (0.029 g, 0.17 mmol) and HOBt (0.032 g, 0.20 mmol) in DMF (2 mL) and the stirred for 10 min. A solution of N-((1s,4s)-4-aminocyclohexyl)-5-fluoro-2-(4'-hydroxy-2'-(morpholinomethyl)biphenyl-3-yloxy)nicotinamide (0.1 g, 0.17 mmol) and DIPEA (0.059 mL, 0.34 mmol) in DMF (1 mL) was then added and the reaction stirred for 20 h. The mixture was evaporated in vacuo and the remaining DMF solution purified by reverse phase HPLC with aqTFA/MeCN as eluant to afford the title compound as a white solid. Yield: 17 mg $^1$H NMR (400 MHz, DMSO) δ 8.33 (d, J=7.3 Hz, 1H), 8.26 (d, J=3.1 Hz, 1H), 8.25 (s, 1H), 8.04 (m, 1H), 7.63 (d, J=8.0 Hz, 1H), 7.49 (m, 1H), 7.26-6.85 (m, 6H), 4.70 (s, 2H), 4.38-4.17 (m, 1H), 3.99 (m, 1H), 3.87 (m, 1H), 3.82-3.03 (m, 7H), 3.41 (s, 3H), 2.81-2.48 (m, 2H), 1.81-1.60 (m, 8H).

MS: APCI (+ve) 676 (M+1)

EXAMPLE 64

N-((1s,4s)-4-(5-fluoro-2-(4'-((4-methyl-1,4-diazepan-1-yl)methyl)biphenyl-3-yloxy)nicotinamido)cyclohexyl)-5-methylimidazo[1,2-a]pyridine-2-carboxamide

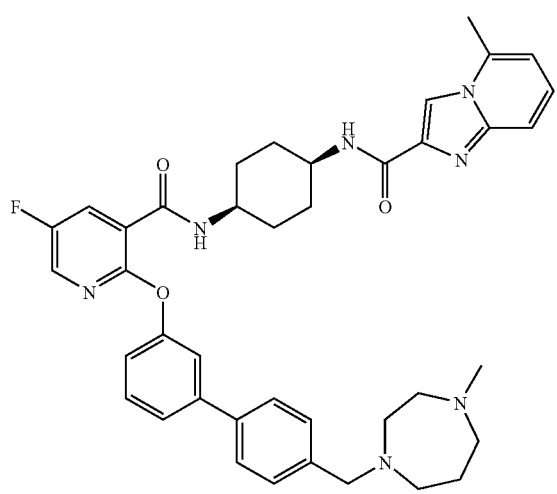

To a solution of N-((1s,4s)-4-(5-fluoro-2-(4'-formylbiphenyl-3-yloxy)nicotinamido)cyclohexyl)-5-methylimidazo[1,2-a]pyridine-2-carboxamide (150 mg, 0.25 mmol) in DCM (3 mL) was added 1-methyl-1,4-diazepane (0.047 mL, 0.38 mmol). The mixture was allowed to stir at RT for 40 min before sodium triacetoxyborohydride (81 mg, 0.38 mmol) was added. The reaction was stirred at RT for 2 h. The mixture was diluted with DCM and washed with sat. NaHCO$_3$ (aq), dried (MgSO$_4$) and evaporated to give a foam. This foam was purified using revere phase prep HPLC (eluent=TFA(aq)/MeCN). The appropriate fractions were combined, evaporated and the residue triturated with ether to give solid. The compound was then purified by reverse phase prep HPLC (eluent=NH$_3$(aq)/MeCN). The appropriate fractions were combined and the residue triturated with ether to give a solid. The solid was dried overnight at 40° C. to afford the title compound. Yield: 31 mg $^1$H NMR (400 MHz, CDCl$_3$) δ 8.38 (dd, J=8.2, 3.1 Hz, 1H), 8.11-8.05 (m, 3H), 7.56-7.50 (m, 4H), 7.41-7.32 (m, 5H), 7.22-7.14 (m, 2H), 6.67 (d, J=6.9 Hz, 1H), 4.28-4.21 (m, 1H), 4.20-4.14 (m, 1H), 2.75-2.69 (m, 6H), 2.66-2.63 (m, 2H), 2.60 (s, 3H), 2.39 (s, 3H), 1.98-1.64 (m, 12H).

MS: [M+H]+=690.3 (calc=690.3568) (MultiMode+)

EXAMPLE 65

N-((1s,4s)-4-(2-(3'-(((3R,5S)-3,5-dimethylpiperazin-1-yl)methyl)-5'-hydroxybiphenyl-3-yloxy)-5-fluoronicotinamido)cyclohexyl)-2-methylthiazole-4-carboxamide

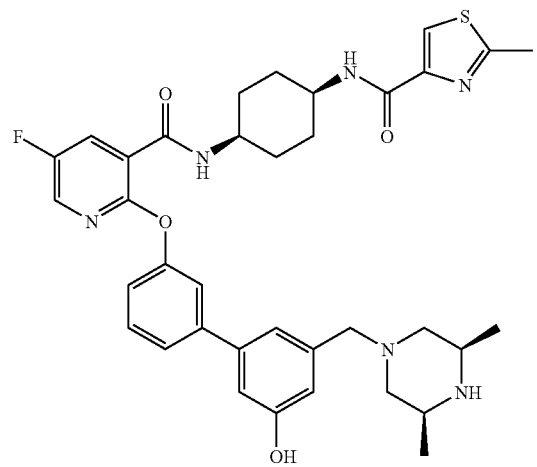

Step (a) N-((1s,4s)-4-(5-fluoro-2-(3'-formyl-5'-hydroxybiphenyl-3-yloxy)nicotinamido)cyclohexyl)-2-methylthiazole-4-carboxamide Palladium acetate (3.87 mg, 0.02 mmol) and 2-dicyclohexylphosphino-2',6'-dimethoxybiphenyl (14.14 mg, 0.03 mmol) were added to acetonitrile (4 mL) under nitrogen. The resulting solution was stirred for 10 min. To this solution was added potassium carbonate (143 mg, 1.03 mmol) dissolved in water (4 mL), followed by N-((1s,4s)-4-(5-fluoro-2-(3-(4,4,5,5-tetramethyl-1,3,2-dioxaborolan-2-yl)phenoxy)nicotinamido)cyclohexyl)-2-methylthiazole-4-carboxamide (200 mg, 0.34 mmol) and 3-bromo-5-hydroxybenzaldehyde (69.3 mg, 0.34 mmol) and the mixture heated at 80° C. for 2 h. The mixture was poured onto water and extracted into EtOAc (×2). The extractions were combined, washed with brine, dried (MgSO$_4$) and evaporated to give a brown oil. The crude material was purified by Biotage (eluant=neat EtOAc) to give the sub-title compound as a white foam after evaporation. Yield: 102 mg MS: [M+H]+=575 (MultiMode+)

Step (b) N-((1s,4s)-4-(2-(3'-(((3R,5S)-3,5-dimethylpiperazin-1-yl)methyl)-5'-hydroxybiphenyl-3-yloxy)-5-fluoronicotinamido)cyclohexyl)-2-methylthiazole-4-carboxamide To a solution of N-((1s,4s)-4-(5-fluoro-2-(3'-formyl-5'-hydroxybiphenyl-3-yloxy)nicotinamido)cyclohexyl)-2-methylthiazole-4-carboxamide (104 mg, 0.18 mmol) in DCM (3 mL) was added (2R,6S)-2,6-dimethylpiperazine (31.0 mg, 0.27 mmol). The mixture was allowed to stir at RT for 40 min before sodium triacetoxyborohydride (57.5 mg, 0.27 mmol) was added. The reaction was stirred at RT for 2 h. The mixture was diluted with DCM and washed with sat. NaHCO$_3$ (aq), dried (MgSO$_4$) and evaporated to give a yellow glass. This was purified by HPLC to afford the title compound. Yield: 29 mg $^1$H NMR (400 MHz, CD$_3$OD) δ 8.47 (d, J=7.3 Hz, 1H), 8.12 (d, J=3.1 Hz, 1H), 8.06 (dd, J=8.0, 3.1 Hz, 1H), 7.96 (s, 1H), 7.80-7.75 (m, 1H), 7.51-7.42 (m, 2H), 7.37-7.35 (m, 1H), 7.18-7.15 (m, 1H), 7.03 (s, 1H), 6.94 (t, J=2.0 Hz, 1H), 6.76 (s, 1H), 4.16-4.10 (m, 1H), 3.98-3.91 (m, 1H), 3.61 (s, 2H), 3.42-3.32 (m, 2H), 3.12-3.07 (m, 3H), 2.62 (s, 3H), 2.12 (t, J=11.8 Hz, 2H), 1.91-1.78 (m, 6H), 1.76-1.64 (m, 2H), 1.25 (d, J=6.7 Hz, 6H)

MS: [M+H]+=673.3 (calc=673.2972) (MultiMode+)

EXAMPLE 66

N-((1s,4s)-4-(1,5-dimethyl-1H-pyrazole-3-carboxamido)cyclohexyl)-2-(3'-(((3R,5S)-3,5-dimethylpiperazin-1-yl)methyl)-5'-hydroxybiphenyl-3-yloxy)-5-fluoronicotinamide

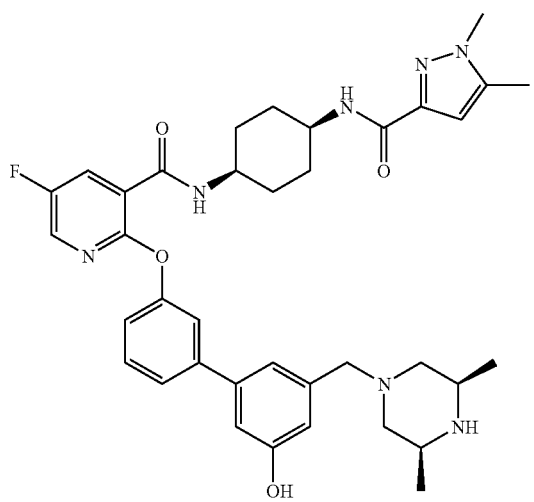

Step (a) N-((1s,4s)-4-(1,5-dimethyl-1H-pyrazole-3-carboxamido)cyclohexyl)-5-fluoro-2-(3'-formyl-5'-hydroxybiphenyl-3-yloxy)nicotinamide Palladium acetate (3.89 mg, 0.02 mmol) and 2-dicyclohexylphosphino-2',6'-dimethoxybiphenyl (14.22 mg, 0.03 mmol) were added to acetonitrile (4 mL) under nitrogen. The resulting solution was stirred for 10 min. To this solution was added potassium carbonate (144 mg, 1.04 mmol) dissolved in water (4 mL), followed by N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide (200 mg, 0.35 mmol) and 3-bromo-5-hydroxybenzaldehyde (69.6 mg, 0.35 mmol) and the mixture heated at 80° C. for 2 h. The mixture was poured onto water and extracted into EtOAc (×2). The extractions were combined, washed with brine, dried (MgSO$_4$) and evaporated to give a light brown foam. The crude material was purified by Biotage (eluant=neat EtOAc) to give the sub-title compound as a white foam after evaporation. Yield: 144 mg MS: [M+H]+=572 (MultiMode+)

Step (b) N-((1s,4s)-4-(1,5-dimethyl-1H-pyrazole-3-carboxamido)cyclohexyl)-2-(3'-(((3R,5S)-3,5-dimethylpiperazin-1-yl)methyl)-5'-hydroxybiphenyl-3-yloxy)-5-fluoronicotinamide To a solution of N-((1s,4s)-4-(1,5-dimethyl-1H-pyrazole-3-carboxamido)cyclohexyl)-5-fluoro-2-(3'-formyl-5'-hydroxybiphenyl-3-yloxy)nicotinamide (159 mg, 0.28 mmol) in DCM (3 mL) was added (2R,6S)-2,6-dimethylpiperazine (47.6 mg, 0.42 mmol). The mixture was allowed to stir at RT for 40 min before sodium triacetoxyborohydride (88 mg, 0.42 mmol) was added. The reaction was stirred at RT for 2 h. The mixture was diluted with DCM and washed with sat. NaHCO$_3$ (aq), dried (MgSO$_4$) and evaporated to give a yellow glass. This was purified by HPLC to give the title compound as a white solid. Yield: 65 mg $^1$H NMR (400 MHz, CD$_3$OD) δ 8.45 (d, J=7.2 Hz, 1H), 8.12 (d, J=3.1 Hz, 1H), 8.06 (dd, J=7.9, 3.1 Hz, 1H), 7.51-7.42 (m, 3H), 7.38-7.36 (m, 1H), 7.16 (dt, J=7.5, 1.9 Hz, 1H), 7.05 (s, 1H), 6.97 (t, J=1.8 Hz, 1H), 6.78 (s, 1H), 6.40 (s, 1H), 4.17-4.07 (m, 1H), 3.97-3.88 (m, 1H), 3.71 (s, 3H), 3.70-3.67 (m, 2H), 3.47-3.35 (m, 2H), 3.16 (dd, J=12.9, 2.2 Hz, 2H), 2.26 (s, 3H), 2.22 (s, 1H), 2.19 (s, 1H), 1.91-1.76 (m, 6H), 1.74-1.62 (m, 2H), 1.27 (d, J=6.7 Hz, 6H).

MS: [M+H]+=670.4 (calc=670.3517) (MultiMode+)

EXAMPLE 67

N-((1s,4s)-4-(2-(4'-(((3S,5R)-3,5-dimethylpiperazin-1-yl)methyl)biphenyl-3-yloxy)-5-fluoronicotinamido)cyclohexyl)-6-fluoroimidazo[1,2-a]pyridine-2-carboxamide

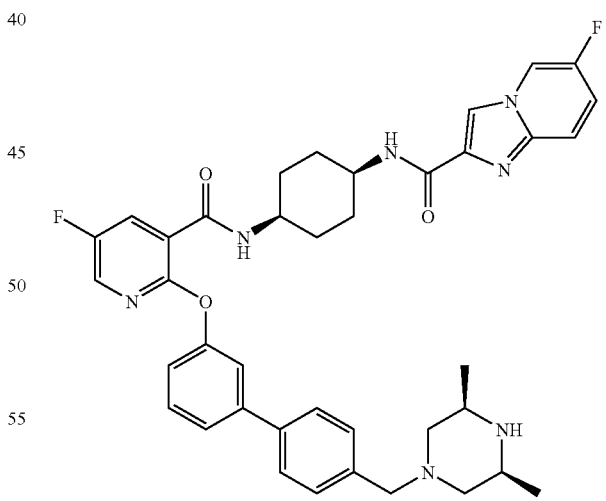

Step (a) tert-butyl (1s,4s)-4-(5-fluoro-2-(4'-formylbiphenyl-3-yloxy)nicotinamido)cyclohexylcarbamate Pd-118 (0.117 g, 0.18 mmol) was stirred in acetonitrile (15 mL) for 15 min, then potassium carbonate (0.747 g, 5.40 mmol), 4-formylphenylboronic acid (0.270 g, 1.80 mmol) and tert-butyl (1s,4s)-4-(5-fluoro-2-(3-iodophenoxy)nicotinamido)cyclohexylcarbamate (1 g, 1.80 mmol) added. The reaction mixture was heated at 80° C. for 8 h then allowed to stand overnight. The acetonitrile was evaporated and EtOAc added to the aqueous residue. The layers were separated and the aqueous material extracted with EtOAc (×3). The combined organic extracts were washed with water and saturated brine. The organic was dried over sodium sulfate and filtered. The filtrate was evaporated and the resulting oil dissolved in DCM. Crude product was purified on Biotage (silica, 50 g) eluting with 50% EtOAc in isohexane. Pure fractions were evaporated to dryness to afford the sub-title compound as an off-white solid. Yield: 0.78 g MS: [M−H]+=532 (MultiMode+)

Step (b) tert-butyl (1s,4s)-4-(2-(4'-(((3S,5R)-3,5-dimethylpiperazin-1-yl)methyl)biphenyl-3-yloxy)-5-fluoronicotinamido)cyclohexylcarbamate To a solution of tert-butyl (1s,4s)-4-(5-fluoro-2-(4'-formylbiphenyl-3-yloxy)nicotinamido)cyclohexylcarbamate (0.78 g, 1.46 mmol) in DCM (5 mL) was added (2S,6R)-2,6-dimethylpiperazine (0.250 g, 2.19 mmol). The mixture was allowed to stir at RT for 2 h. Sodium triacetoxyborohydride (0.465 g, 2.19 mmol) was then added. After stirring for 1 h, reaction was complete. The mixture was diluted with DCM and washed with sat. NaHCO₃ (aq), dried (MgSO₄) and evaporated to give the sub-title compound as a pale foam. Yield: 0.88 g ¹H NMR (300 MHz, CDCl₃) δ 8.37 (dd, J=3.1, 7.8 Hz, 1H), 8.08-8.03 (m, 2H), 7.56-7.53 (m, 4H), 7.42-7.35 (m, 3H), 7.15-7.10 (m, 1H), 4.38-4.31 (m, 1H), 4.22-4.14 (m, 1H), 3.65-3.57 (m, 1H), 3.54 (s, 2H), 3.00-2.93 (m, 2H), 2.79 (d, J=16.3 Hz, 2H), 1.85-1.61 (m, 11H), 1.41 (s, 9H), 1.04 (d, J=6.4 Hz, 6H).

MS: [M+H]+=632 (MultiMode+)

Step (c) N-((1s,4s)-4-aminocyclohexyl)-2-(4'-(((3S,5R)-3,5-dimethylpiperazin-1-yl)methyl)biphenyl-3-yloxy)-5-fluoronicotinamide hydrochloride To a solution of tert-butyl (1s,4s)-4-(2-(4'-(((3S,5R)-3,5-dimethylpiperazin-1-yl)methyl)biphenyl-3-yloxy)-5-fluoronicotinamido)cyclohexylcarbamate (0.88 g, 1.39 mmol) in DCM (3 mL) was added 4M HCl (in dioxane) (3.48 mL, 13.93 mmol). After a min, a solid had begun to precipitate. Methanol (3 mL) was added to make the solution homogeneous. The reaction was stirred at RT overnight. The solution was concentrated in vacuo then triturated with ether. The pale solid was filtered to give the sub-title compound. Yield: 0.71 g MS: [M−H]+=532 (MultiMode+)

Step (d) N-((1s,4s)-4-(2-(4'-(((3S,5R)-3,5-dimethylpiperazin-1-yl)methyl)biphenyl-3-yloxy)-5-fluoronicotinamido)cyclohexyl)-6-fluoroimidazo[1,2-a]pyridine-2-carboxamide To a suspension of N-((1s,4s)-4-aminocyclohexyl)-2-(4'-(((3S,5R)-3,5-dimethylpiperazin-1-yl)methyl)biphenyl-3-yloxy)-5-fluoronicotinamide hydrochloride (0.1 g, 0.19 mmol) in acetonitrile (1 mL) was added 6-fluoroimidazo[1,2-a]pyridine-2-carboxylic acid (0.041 g, 0.19 mmol) and triethylamine (0.262 mL, 1.88 mmol). On addition of triethylamine the reaction mixture became a homogenous solution. 1-Propanephosphonic acid cyclic anhydride, 1.57M solution in THF (T3P) (0.126 mL, 0.20 mmol) was then added and the mixture stirred at RT for 10 min. The mixture was evaporated to dryness and the residue dissolved in EtOAc and washed with saturated NaHCO₃ (aq), brine, dried (MgSO₄) and evaporated to give an oil. The crude product was purified by preparative HPLC on a Waters X-Bridge column using a 95-5% gradient of aqueous 0.1% TFA in acetonitrile as eluent. The fractions containing the desired compound were evaporated to dryness to afford the title compound as a white solid. Yield: 69 mg ¹H NMR (400 MHz, DMSO) δ 8.82-8.80 (m, 1H), 8.37-8.35 (m, 2H), 8.26 (d, J=3.1 Hz, 1H), 8.06 (dd, J=3.1, 7.8 Hz, 1H), 7.74 (d, J=7.9 Hz, 1H), 7.68-7.61 (m, 4H), 7.54-7.45 (m, 4H), 7.40 (d, J=7.9 Hz, 2H), 7.23-7.20 (m, 1H), 3.40-3.32 (m, 2H), 3.15-3.08 (m, 2H), 2.52-2.47 (m, 3H), 2.33-2.32 (m, 2H), 1.79-1.69 (m, 9H), 1.18 (d, J=6.7 Hz, 6H).

MS: [M+H]+=694.3 (calc=694.3317) (MultiMode+)

EXAMPLE 68

N-((1s,4s)-4-(2-(3'-(((3R,5S)-3,5-dimethylpiperazin-1-yl)methyl)-4'-hydroxybiphenyl-3-yloxy)-5-fluoronicotinamido)cyclohexyl)-2-methylthiazole-4-carboxamide

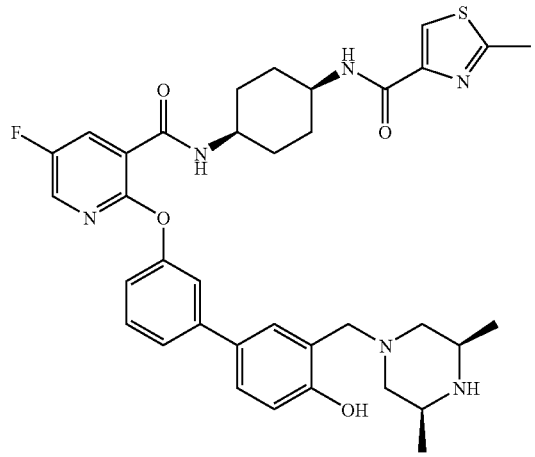

Step (a) N-((1s,4s)-4-(5-fluoro-2-(3'-formyl-4'-hydroxybiphenyl-3-yloxy)nicotinamido)cyclohexyl)-2-methylthiazole-4-carboxamide N-((1s,4s)-4-(5-fluoro-2-(3-(4,4,5,5-tetramethyl-1,3,2-dioxaborolan-2-yl)phenoxy)nicotinamido)cyclohexyl)-2-methylthiazole-4-carboxamide (100 mg, 0.17 mmol), 5-bromo-2-hydroxybenzaldehyde (34.6 mg, 0.17 mmol) and sodium carbonate (148 mg, 0.52 mmol) were added to THF (2.000 mL) and degassed water (1 mL) under nitrogen. Tetrakis(triphenylphosphine)palladium(0) (4 mg, 3.45 μmol) was then added and the reaction mixture was heated at reflux overnight. The mixture was poured onto water and extracted into EtOAc (×2). The extractions were combined, washed with brine, dried (MgSO₄) and evaporated to give a yellow oil. The crude material was purified by Biotage (eluant=neat EtOAc) to give the sub-title compound as a white solid after evaporation. Yield: 95 mg MS: [M+H]+=575 (MultiMode+)

Step (b) N-((1s,4s)-4-(2-(3'-(((3R,5S)-3,5-dimethylpiperazin-1-yl)methyl)-4'-hydroxybiphenyl-3-yloxy)-5-fluoronicotinamido)cyclohexyl)-2-methylthiazole-4-carboxamide To a solution of N-((1s,4s)-4-(5-fluoro-2-(3'-formyl-4'-hydroxybiphenyl-3-yloxy)nicotinamido)cyclohexyl)-2-methylthiazole-4-carboxamide (88.2 mg, 0.15 mmol) in DCM (3 mL) was added (2R,6S)-2,6-dimethylpiperazine (26.3 mg, 0.23 mmol). The mixture was allowed to stir at RT for 40 min before sodium triacetoxyborohydride (48.8 mg, 0.23 mmol) was added. The reaction was stirred at RT for 2 h. The mixture was diluted with DCM and washed with sat. NaHCO$_3$ (aq), dried (MgSO$_4$) and evaporated to give a yellow glass. This was purified by HPLC to afford the title compound as a white solid. Yield: 27.4 mg $^1$H NMR (400 MHz, CD$_3$OD) δ 8.47 (d, J=7.2 Hz, 1H), 8.11 (d, J=3.1 Hz, 1H), 8.06 (dd, J=7.9, 3.1 Hz, 1H), 7.95 (s, 1H), 7.81-7.75 (m, 1H), 7.51-7.40 (m, 4H), 7.37-7.34 (m, 1H), 7.13-7.10 (m, 1H), 6.88 (d, J=8.2 Hz, 1H), 4.17-4.09 (m, 1H), 4.02 (s, 2H), 3.99-3.92 (m, 1H), 3.58-3.47 (m, 2H), 3.40-3.32 (m, 2H), 2.62 (s, 3H), 2.53 (t, J=12.4 Hz, 2H), 1.93-1.78 (m, 6H), 1.77-1.64 (m, 2H), 1.30 (d, J=6.7 Hz, 6H)

MS: [M+H]+=673.3 (calc=673.2972) (MultiMode+)

EXAMPLE 69

N-((1s,4s)-4-(2-(3'-(((3R,5S)-3,5-dimethylpiperazin-1-yl)methyl)-2'-hydroxybiphenyl-3-yloxy)-5-fluoronicotinamido)cyclohexyl)-2-methylthiazole-4-carboxamide

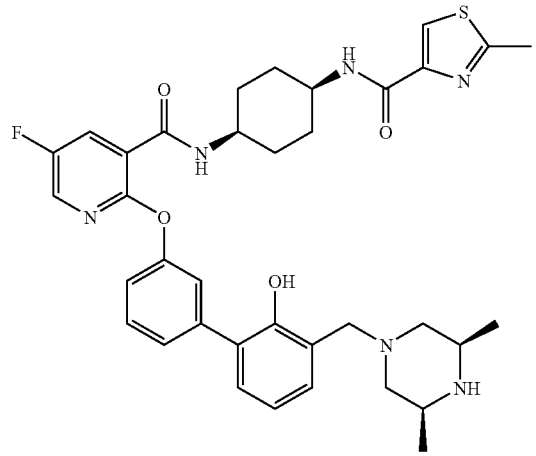

Step (a) N-((1s,4s)-4-(5-fluoro-2-(3'-formyl-2'-hydroxybiphenyl-3-yloxy)nicotinamido)cyclohexyl)-2-methylthiazole-4-carboxamide N-((1s,4s)-4-(5-Fluoro-2-(3-(4,4,5,5-tetramethyl-1,3,2-dioxaborolan-2-yl)phenoxy)nicotinamido)cyclohexyl)-2-methylthiazole-4-carboxamide (100 mg, 0.17 mmol), 3-bromo-2-hydroxybenzaldehyde (34.6 mg, 0.17 mmol) and sodium carbonate (148 mg, 0.52 mmol) were added to THF (2 ml) and degassed water (1 ml) under nitrogen. Tetrakis(triphenylphosphine)palladium(0) (4 mg, 3.45 μmol) was then added and the reaction mixture was heated at reflux overnight. The mixture was poured onto water and extracted into EtOAc (×2). The extractions were combined, washed with brine, dried (MgSO$_4$) and evaporated to give a yellow oil. The crude material was purified by Biotage (eluant=neat EtOAc) to give the sub-title compound as a white solid after evaporation. Yield: 0.74 g MS: [M+H]+=575 (MultiMode+)

Step (b) N-((1s,4s)-4-(2-(3'-(((3R,5S)-3,5-dimethylpiperazin-1-yl)methyl)-2'-hydroxybiphenyl-3-yloxy)-5-fluoronicotinamido)cyclohexyl)-2-methylthiazole-4-carboxamide To a solution of N-((1s,4s)-4-(5-fluoro-2-(3'-formyl-2'-hydroxybiphenyl-3-yloxy)nicotinamido)cyclohexyl)-2-methylthiazole-4-carboxamide (86.2 mg, 0.15 mmol) in dichloromethane (3 mL) was added (2R,6S)-2,6-dimethylpiperazine (25.7 mg, 0.23 mmol). The mixture was allowed to stir at RT for 40 minutes before sodium triacetoxyborohydride (47.7 mg, 0.23 mmol) was added. The reaction was stirred at RT for 2 hours. The mixture was diluted with dichloromethane and washed with sat. NaHCO$_3$(aq), dried (MgSO$_4$) and evaporated to give a yellow glass. This was purified by HPLC to afford the title compound as a white solid. Yield: 14.7 mg $^1$H NMR (400 MHz, CD$_3$OD) δ 8.50 (d, J=7.1 Hz, 1H), 8.13 (d, J=3.1 Hz, 1H), 8.08 (dd, J=7.9, 3.1 Hz, 1H), 7.96 (s, 1H), 7.46-7.38 (m, 4H), 7.27 (dd, J=7.7, 1.5 Hz, 1H), 7.14 (dt, J=7.9, 2.0 Hz, 1H), 7.06 (dd, J=7.4, 1.4 Hz, 1H), 6.86 (t, J=9.3 Hz, 1H), 4.18-4.17 (m, 1H), 3.99-3.91 (m, 1H), 3.79 (s, 2H), 3.47-3.45 (m, 2H), 3.38-3.32 (m, 2H), 3.14-3.08 (m, 2H), 2.54 (s, 3H), 2.12 (t, J=12.3 Hz, 2H), 1.94-1.77 (m, 6H), 1.73-1.60 (m, 2H), 1.23 (d, J=6.7 Hz, 6H)

MS: [M+H]+=673.2 (calc=673.2972) (MultiMode+)

EXAMPLE 70

N-((1s,4s)-4-(2-(4'-(((3S,5R)-3,5-dimethylpiperazin-1-yl)methyl)biphenyl-3-yloxy)-5-fluoronicotinamido)cyclohexyl)-2-(hydroxymethyl)thiazole-4-carboxamide

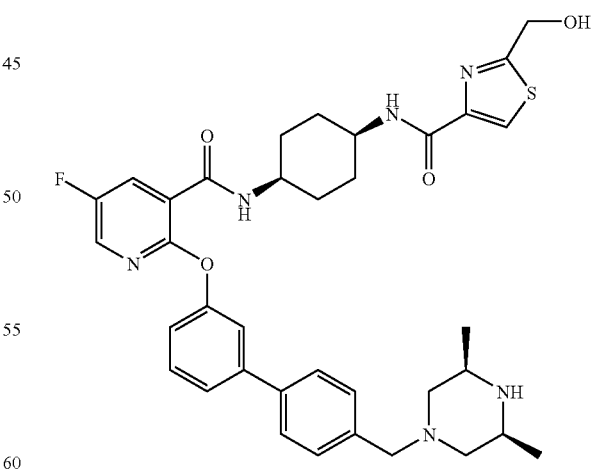

DCC (0.035 g, 0.17 mmol) was added to a solution of 2-(hydroxymethyl)thiazole-4-carboxylic acid (0.027 g, 0.17 mmol) and HOBt (0.026 g, 0.17 mmol) in DMF (1 mL) and stirred for 10 min. A solution of crude N-((1s,4s)-4-aminocyclohexyl)-2-(4'-(((3S,5R)-3,5-dimethylpiperazin-1-yl)methyl)biphenyl-3-yloxy)-5-fluoronicotinamide (0.08 g, 0.14 mmol) and DIPEA (0.098 mL, 0.56 mmol) in DMF (1 mL) was then added and the reaction stirred for 20 h. The solution was concentrated in vacuo, then water/methanol/DMSO was added to the residue. The crude product was purified by preparative HPLC on a Phenomenex Gemini column using a 95-5% gradient of aqueous 0.1% TFA in methanol as eluent. The fractions containing the desired compound were freeze-dried to afford the title compound as a white solid. Yield: 28 mg $^1$H NMR (400 MHz, DMSO) δ 8.33 (d, J=6.9 Hz, 1H), 8.26 (d, J=3.1 Hz, 1H), 8.18 (s, TH), 8.05 (dd, J=7.3, 3.1 Hz, 1H), 7.64 (d, J=8.2 Hz, 2H), 7.58 (d, J=7.9 Hz, 1H), 7.52-7.48 (m, 3H), 7.37 (d, J=7.9 Hz, 2H), 7.21-7.18 (m, 1H), 4.70 (s, 2H), 3.36-3.27 (m, 2H), 3.05-2.97 (m, 2H), 2.53-2.47 (m, 6H), 2.15-2.03 (m, 2H), 1.80-1.63 (m, 8H), 1.17 (d, J=8.9 Hz, 6H).

MS: [M+H]+=673.2 (calc=673.2) (MultiMode+)

EXAMPLE 71

N-((1s,4s)-4-(2-(4'-(((3S,5R)-3,5-dimethylpiperazin-1-yl)methyl)biphenyl-3-yloxy)-5-fluoronicotinamido)cyclohexyl)pyrazolo[1,5-a]pyridine-2-carboxamide

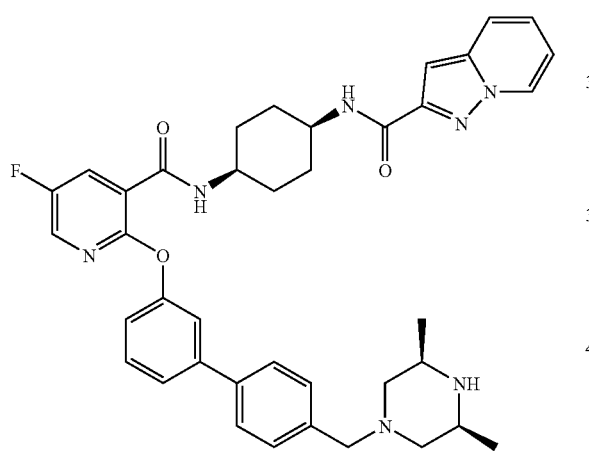

HATU (0.069 g, 0.18 mmol) was added in one portion to N-((1s,4s)-4-aminocyclohexyl)-2-(4'-(((3S,5R)-3,5-dimethylpiperazin-1-yl)methyl)biphenyl-3-yloxy)-5-fluoronicotinamide (0.08 g, 0.15 mmol), pyrazolo[1,5-a]pyridine-2-carboxylic acid (0.024 g, 0.15 mmol) and DIPEA (0.079 mL, 0.45 mmol) in acetonitrile (1 mL) at 25° C. under nitrogen. The resulting solution was stirred at 25° C. for 10 min. The reaction mixture was concentrated and diluted with EtOAc, and washed sequentially with saturated NaHCO$_3$, saturated brine and water. The organic layer was dried over MgSO$_4$, filtered and evaporated to afford crude product. The crude product was purified by preparative HPLC on a Waters X-Bridge column using a 95-5% gradient of aqueous 0.1% TFA in acetonitrile as eluent. The fractions containing the desired compound were evaporated to dryness to afford the title compound as a white solid. Yield: 70 mg $^1$H NMR (400 MHz, DMSO) δ 8.61 (d, J=11.5 Hz, 1H), 8.35 (d, J=6.9 Hz, 1H), 8.26 (d, J=2.8 Hz, 1H), 8.07 (dd, J=3.1, 7.3 Hz, 1H), 7.78-7.65 (m, 4H), 7.53-7.50 (m, 3H), 7.36 (d, J=7.7 Hz, 2H), 7.30 (t, J=7.7 Hz, 1H), 7.23-7.21 (m, 1H), 7.02 (t, J=6.9 Hz, 1H), 6.98 (s, 1H), 3.38-3.28 (m, 2H), 3.10-3.04 (m, 2H), 2.56-2.44 (m, 4H), 2.23-2.14 (m, 2H), 1.84-1.67 (m, 9H), 1.17 (d, J=10.4 Hz, 6H).

MS: [M+H]+=676.3 (calc=676.3411) (MultiMode+)

EXAMPLE 72

N-((1s,4s)-4-(1,5-dimethyl-1H-pyrazole-3-carboxamido)cyclohexyl)-2-(3'-(((3S,5R)-3,5-dimethylpiperazin-1-yl)methyl)biphenyl-3-yloxy)-5-fluoronicotinamide

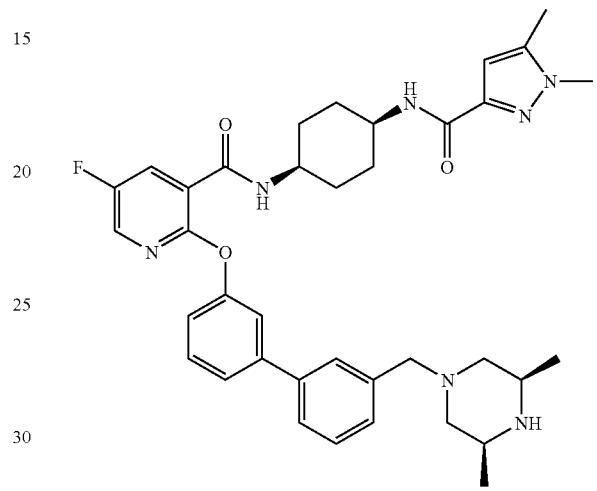

Step (a) N-((1s,4s)-4-(1,5-dimethyl-1H-pyrazole-3-carboxamido)cyclohexyl)-5-fluoro-2-(3'-formylbiphenyl-3-yloxy)nicotinamide Palladium acetate (3.89 mg, 0.02 mmol), and 2-dicyclohexylphosphino-2',6'-dimethoxybiphenyl (14.22 mg, 0.03 mmol) were added to acetonitrile (3.38 mL) under nitrogen. The resulting solution was stirred for 10 min. To this solution was added potassium carbonate (144 mg, 1.04 mmol) dissolved in water (3.38 mL), followed by 3-formylphenylboronic acid (51.9 mg, 0.35 mmol) and N-((1s,4s)-4-(1,5-dimethyl-1H-pyrazole-3-carboxamido)cyclohexyl)-5-fluoro-2-(3-iodophenoxy)nicotinamide (200 mg, 0.35 mmol) and the mixture heated at 80° C. for 2 h. The mixture was poured onto water and extracted into EtOAc (×2). The extractions were combined, washed with brine, dried (MgSO$_4$) and evaporated to give a brown oil. This was purified using column chromatography (eluent=neat EtOAc) to give a light brown foam. Yield: 123 mg MS: [M+H]+=556 (MultiMode+).

Step (b) N-((1s,4s)-4-(1,5-dimethyl-1H-pyrazole-3-carboxamido)cyclohexyl)-2-(3'-(((3S,5R)-3,5-dimethylpiperazin-1-yl)methyl)biphenyl-3-yloxy)-5-fluoronicotinamide To a solution of N-((1s,4s)-4-(1,5-dimethyl-1H-pyrazole-3-carboxamido)cyclohexyl)-5-fluoro-2-(3'-formylbiphenyl-3-yloxy)nicotinamide (121 mg, 0.22 mmol) in DCM (3 mL) was added (2R,6S)-2,6-dimethylpiperazine (37.3 mg, 0.33 mmol). The mixture was allowed to stir at RT for 40 min before sodium triacetoxyborohydride (69.2 mg, 0.33 mmol) was added. The reaction was stirred at RT for 2 h. The mixture was diluted with DCM and washed with sat. NaHCO$_3$ (aq), dried (MgSO$_4$) and evaporated to give a yellow glass. This was purified by HPLC to afford the title compound as a white solid. Yield: 21 mg $^1$H NMR (400 MHz, CDCl$_3$) δ 8.11 (d, J=3.1 Hz, 1H), 8.06 (dd, J=7.9, 3.1 Hz, 1H), 7.61 (s, 1H), 7.58 (d, J=7.7 Hz, 1H), 7.51-7.49 (m, 2H), 7.44-7.34 (m, 3H), 7.21-7.15 (m, 1H), 6.40 (s, 1H), 4.15-4.07 (m, 1H), 3.98-3.09 (m, 1H), 3.85 (s, 2H), 3.70 (s, 3H), 3.51-3.39 (m, 2H), 3.22 (dd, J=12.9, 2.2 Hz, 2H), 2.36 (t, J=12.2 Hz, 2H), 2.25 (s, 3H), 1.89-1.75 (m, 6H), 1.74-1.62 (m, 2H), 1.27 (d, J=6.7 Hz, 6H).

MS: [M+H]+=654.3 (calc=654.3568) (MultiMode+)

EXAMPLE 73

N-((1s,4s)-4-(5-fluoro-2-(4'-(3-(pyrrolidin-1-yl)propyl)biphenyl-3-yloxy)nicotinamido)cyclohexyl)-2-methylthiazole-4-carboxamide

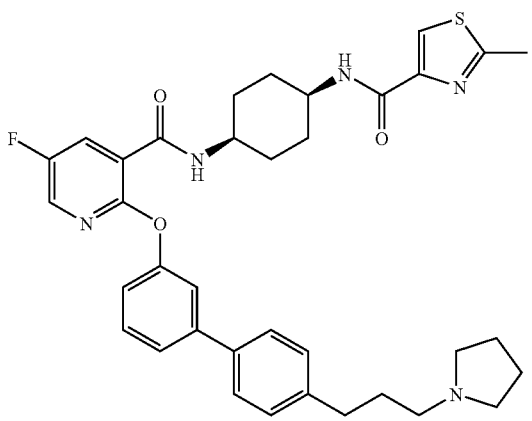

Step (a) N-((1s,4s)-4-(5-fluoro-2-(4'-(3-hydroxypropyl)biphenyl-3-yloxy)nicotinamido)cyclohexyl)-2-methylthiazole-4-carboxamide N-((1s,4s)-4-(5-Fluoro-2-(3-iodophenoxy)nicotinamido)cyclohexyl)-2-methylthiazole-4-carboxamide (1.2 g, 2.07 mmol), 4-(3-hydroxypropyl)phenylboronic acid (0.372 g, 2.07 mmol), Potassium carbonate (0.857 g, 6.20 mmol) and Pd-118 (0.135 g, 0.21 mmol) were stirred in DMF (15 mL). The resultant mixture was stirred and heated at 70° C. overnight. The reaction mixture was poured into water and the organics extracted into EtOAc (×2). The EtOAc extractions were combined, dried (MgSO$_4$) and evaporated to give an oil. The residue was purified using column chromatography (eluent=EtOAc) the appropriate fractions were combined and evaporated to give sub-title compound as a foam. Yield: 0.65 g $^1$H NMR (400 MHz, CDCl$_3$) δ 8.38 (dd, J=8.2, 3.1 Hz, 1H), 8.12-8.08 (m, 2H), 7.90 (s, 1H), 7.55-7.47 (m, 4H), 7.38-7.36 (m, 1H), 7.25-7.20 (m, 3H), 7.16-7.13 (m, 1H), 4.28-4.22 (m, 1H), 4.10-4.06 (m, 1H), 3.73-3.67 (m, 2H), 2.74 (t, J=7.7 Hz, 2H), 2.60 (s, 3H), 1.96-1.79 (m, 8H), 1.69-1.61 (m, 2H).

Step (b) 3-(3'-(5-fluoro-3-((1s,4s)-4-(2-methylthiazole-4-carboxamido)cyclohexylcarbamoyl)pyridin-2-yloxy)biphenyl-4-yl)propyl methanesulfonate To solution of N-((1s,4s)-4-(5-fluoro-2-(4'-(3-hydroxypropyl)biphenyl-3-yloxy)nicotinamido)cyclohexyl)-2-methylthiazole-4-carboxamide (0.65 g, 1.10 mmol) and pyridine (0.107 mL, 1.32 mmol) in DCM (7 mL), was added methanesulfonyl chloride (0.112 mL, 1.44 mmol) and the reaction stirred at RT overnight. Pyridine (0.107 mL, 1.32 mmol) and methanesulfonyl chloride (0.111 mL, 1.44 mmol) were then added to the reaction which was stirred for a further 3 h at RT. The reaction was evaporated to give a residue which was partitioned between EtOAc and 2M HCl(aq). The EtOAc layer was then washed with another aliquot of 2M HCl(aq), 2× sat NaHCO$_3$ (aq), brine, dried (MgSO$_4$) and evaporated to give a brown oil. This was triturated with ether overnight to give the sub-title compound as a white solid. Yield: 0.6 g $^1$H NMR (400 MHz, CDCl$_3$) δ 8.38 (dd, J=8.2, 3.1 Hz, 1H), 8.11-8.07 (m, 2H), 7.90 (s, 1H), 7.56-7.49 (m, 4H), 7.37 (d, J=2.1 Hz, 1H), 7.24-7.19 (m, 3H), 7.15 (dt, J=7.4, 2.1 Hz, 1H), 4.27-4.22 (m, 3H), 4.12-4.04 (m, 1H), 3.01 (s, 3H), 2.78 (t, J=7.6 Hz, 2H), 2.61 (s, 3H), 2.15-2.05 (m, 2H), 1.96-1.80 (m, 6H), 1.69-1.63 (m, 2H).

Step (c) N-((1s,4s)-4-(5-fluoro-2-(4'-(3-(pyrrolidin-1-yl)propyl)biphenyl-3-yloxy)nicotinamido)cyclohexyl)-2-methylthiazole-4-carboxamide To a microwave tube was charged 3-(3'-(5-fluoro-3-((1s,4s)-4-(2-methylthiazole-4-carboxamido)cyclohexylcarbamoyl)pyridin-2-yloxy)biphenyl-4-yl)propyl methanesulfonate (120 mg, 0.18 mmol), pyrrolidine (0.045 mL, 0.54 mmol) and acetonitrile (1 mL). The reaction was heated to 80° C. for 5 mins. The mixture was purified using reverse phase HPLC (eluent=TFA(aq)/MeCN), the appropriate fractions were combined, evaporated and the residue triturated with ether to give a white solid which was dried overnight at 40° C. under vacuum to afford the title compound. Yield: 86 mg $^1$H NMR (400 MHz, CDCl$_3$) δ 13.09 (s, 1H), 8.38 (dd, J=8.2, 3.1 Hz, 1H), 8.09-8.07 (m, 2H), 7.90 (s, 1H), 7.56-7.48 (m, 4H), 7.36 (t, J=1.9 Hz, 1H), 7.21-7.18 (m, 3H), 7.16 (dtd, J=7.5, 1.8, 0.2 Hz, 1H), 4.28-4.22 (m, 1H), 4.11-4.05 (m, 1H), 3.87-3.81 (m, 2H), 3.08-3.01 (m, 2H), 2.76-2.70 (m, 4H), 2.61 (s, 3H), 2.18-2.10 (m, 4H), 2.07-2.01 (m, 2H), 1.95-1.79 (m, 6H), 1.67-1.62 (m, 2H).

MS: [M+H]+=642.2 (calc=642.2914) (MultiMode+)

EXAMPLE 74

N-((1s,4s)-4-(5-fluoro-2-(4'-(3-(piperazin-1-yl)propyl)biphenyl-3-yloxy)nicotinamido)cyclohexyl)-2-methylthiazole-4-carboxamide

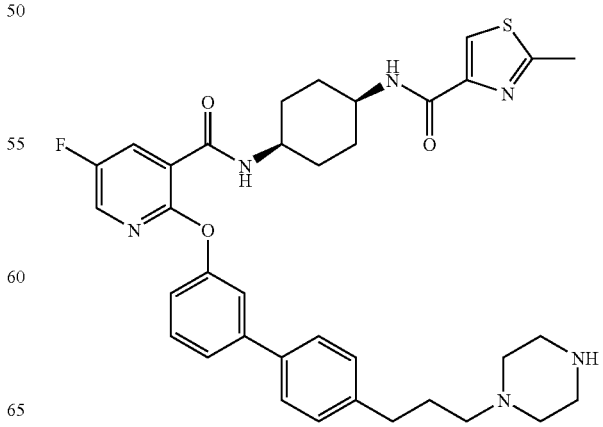

To a microwave tube was charged 3-(3'-(5-fluoro-3-((1s, 4s)-4-(2-methylthiazole-4-carboxamido)cyclohexylcarbamoyl)pyridin-2-yloxy)biphenyl-4-yl)propyl methanesulfonate (120 mg, 0.18 mmol), tert-butyl 1-piperazinecarboxylate (101 mg, 0.54 mmol) and acetonitrile (1 mL). The mixture was heated to 80° C. for 30 min. The mixture was evaporated to dryness and the residue suspended in DCM (2 mL) and TFA (2 mL). After 20 min the reaction was evaporated to dryness. The residue was dissolved in acetonitrile and purified using reverse phase prep chromatography (eluent=TFA (aq)/MeCN). The appropriate fractions were combined, evaporated and the residue triturated with ether to give a white solid which was dried overnight at 40° C. under vacuum to give the title compound. Yield: 85 mg $^1$H NMR (400 MHz, CDCl$_3$) δ 8.35 (dd, J=8.1, 3.2 Hz, 1H), 8.09-8.06 (m, 2H), 7.89 (s, 1H), 7.55-7.47 (m, 4H), 7.35-7.34 (m, 1H), 7.21 (d, J=7.9 Hz, 1H), 7.19-7.14 (m, 3H), 4.25-4.20 (m, 1H), 4.08-4.01 (m, 1H), 3.60-3.54 (m, 4H), 3.47-3.42 (m, 4H), 3.02-2.97 (m, 2H), 2.70 (t, J=7.3 Hz, 2H), 2.60 (s, 3H), 2.09-2.01 (m, 2H), 1.93-1.77 (m, 6H), 1.68-1.58 (m, 2H).

MS: [M+H]+=657.2 (calc=657.3023) (MultiMode+)

EXAMPLE 75

N-((1s,4s)-4-(2-(4'-(3-((3S,5R)-3,5-dimethylpiperazin-1-yl)propyl)biphenyl-3-yloxy)-5-fluoronicotinamido)cyclohexyl)-2-methylthiazole-4-carboxamide

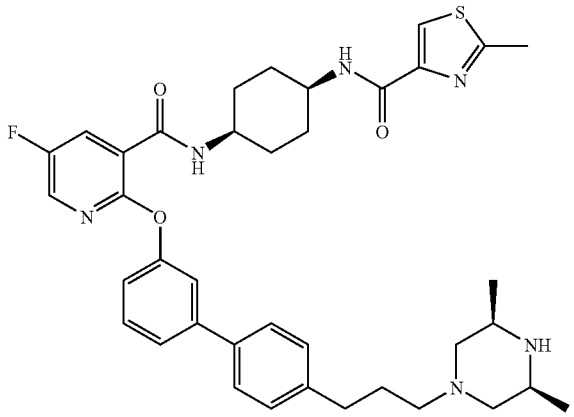

To a microwave tube was charged 3-(3'-(5-fluoro-3-((1s, 4s)-4-(2-methylthiazole-4-carboxamido)cyclohexylcarbamoyl)pyridin-2-yloxy)biphenyl-4-yl)propyl methanesulfonate (110 mg, 0.16 mmol), (2R,6S)-2,6-dimethylpiperazine (56.5 mg, 0.49 mmol) and acetonitrile (1 mL). The mixture was heated to 80° C. for 30 min. The mixture was purified using reverse phase HPLC (eluent=TFA(aq)/MeCN), the appropriate fractions were combined and evaporated to give a residue which was triturated with ether to give a white solid. The solid was dried overnight at 40° C. under vacuum to give the title compound. Yield: 99 mg $^1$H NMR (400 MHz, CDCl$_3$) δ 8.37 (dd, J=8.2, 3.1 Hz, 1H), 8.11-8.07 (m, 2H), 7.91 (s, 1H), 7.56-7.48 (m, 4H), 7.36 (s, 1H), 7.25-7.15 (m, 4H), 4.24 (s, 1H), 4.11-4.04 (m, 1H), 3.85-3.78 (m, 2H), 3.46 (d, J=10.0 Hz, 2H), 3.27 (t, J=12.0 Hz, 2H), 3.08-3.02 (m, 2H), 2.75-2.69 (m, 2H), 2.62 (s, 3H), 2.14-2.07 (m, 2H), 1.95-1.79 (m, 6H), 1.69-1.60 (m, 2H), 1.36 (d, J=5.1 Hz, 6H).

MS: [M+H]+=685.3 (calc=685.3336) (MultiMode+)

EXAMPLE 76

N-((1s,4s)-4-(2-(4'-(((3S,5R)-3,5-dimethylpiperazin-1-yl)methyl)biphenyl-3-yloxy)-5-fluoronicotinamido)cyclohexyl)-2-ethylthiazole-4-carboxamide

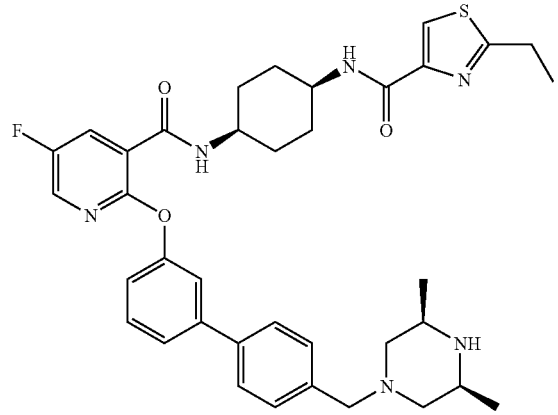

Step (a) Ethyl 2-ethylthiazole-4-carboxylate

Ethyl 3-bromo-2-oxopropanoate (4.10 mL, 32.67 mmol) was added dropwise over 10 min to a stirred solution of propanethioamide (3 g, 33.65 mmol) in ethanol (40 mL) cooled in an ice bath. After 16 h the reaction mixture was evaporated in vacuo. Purification was by silica gel chromatography eluting with EtOAc:iso-hexanes, 1:3 to give the sub-title compound as a yellow oil. Yield: 2.78 g $^1$H NMR (300 MHz, CDCl$_3$) δ 8.06 (s, 1H), 4.46-4.33 (m, 6H), 3.11 (q, J=7.6 Hz, 4H).

Step (b) 2-ethylthiazole-4-carboxylic acid

Lithium hydroxide (1.405 g, 58.68 mmol) in water (13.75 mL) was sonicated for 10 min before being added to a stirred mixture of ethyl 2-ethylthiazole-4-carboxylate (2.78 g, 15.01 mmol) in THF (55 mL). The reaction was stirred art RT overnight. The solution was diluted with water and extracted with EtOAc (×3). The organic extracts were discarded. The aqueous was acidified with 2M HCl and extracted with EtOAc (×3). The combined organic layers were washed with brine, dried over magnesium sulphate, filtered and evaporated in vacuo to give the sub-title compound as a brown oil which solidified on standing to give a waxy solid. Yield: 1.02 g $^1$H NMR (400 MHz, CDCl$_3$) δ 8.17 (s, 1H), 5.65-5.55 (m, 1H), 3.11 (q, J=7.5 Hz, 2H), 1.43 (t, J=7.6 Hz, 3H).

Step (c) N-((1s,4s)-4-(2-(4'-(((3S,5R)-3,5-dimethylpiperazin-1-yl)methyl)biphenyl-3-yloxy)-5-fluoronicotinamido)cyclohexyl)-2-ethylthiazole-4-carboxamide HATU (0.060 g, 0.16 mmol) was added in one portion to N-((1s,4s)-4-aminocyclohexyl)-2-(4'-(((3S,5R)-3,5-dimethylpiperazin-1-yl)methyl)biphenyl-3-yloxy)-5-fluoronicotinamide (0.08 g, 0.15 mmol), 2-ethylthiazole-4-carboxylic acid (0.021 g, 0.13 mmol) and DIPEA (0.069 mL, 0.40 mmol) in acetonitrile (1 mL) at 25° C. under nitrogen. The resulting solution was stirred at 25° C. for 10 min. The reaction mixture was concentrated and diluted with EtOAc, and washed sequentially with saturated NaHCO$_3$, saturated brine and water. The organic layer was dried over MgSO$_4$, filtered and evaporated to afford crude product. The crude product was purified by preparative HPLC on a Waters X-Bridge column using a 95-5% gradient of aqueous 0.1% TFA in acetonitrile as eluent. The fractions containing the desired compound were freeze-dried to afford the title compound as a white fluffy solid. Yield: 59 mg $^1$H NMR (400 MHz, DMSO) δ 8.36 (d, J=7.4 Hz, 1H), 8.26 (d, J=3.1 Hz, 1H), 8.11 (s, 1H), 8.05 (dd, J=7.8, 3.1 Hz, 2H), 7.67 (d, J=8.2 Hz, 2H), 7.57-7.49 (m, 4H), 7.44 (d, J=7.9 Hz, 2H), 7.24-7.19 (m, 1H), 3.43-3.39 (m, 2H), 3.17-3.15 (m, 2H), 2.98 (q, J=7.5 Hz, 2H), 2.52-2.49 (m, 4H), 2.34-2.31 (m, 2H), 1.77-1.67 (m, 8H), 1.29 (t, J=7.6 Hz, 3H), 1.20 (d, J=6.4 Hz, 6H).

MS: [M+H]+=671.2 (calc=671.3179) (MultiMode+)

EXAMPLE 77

N-((1s,4s)-4-(1,5-dimethyl-1H-pyrazole-3-carboxamido)cyclohexyl)-5-fluoro-2-(4'-hydroxy-3'-((4-isopropylpiperazin-1-yl)methyl)biphenyl-3-yloxy)nicotinamide

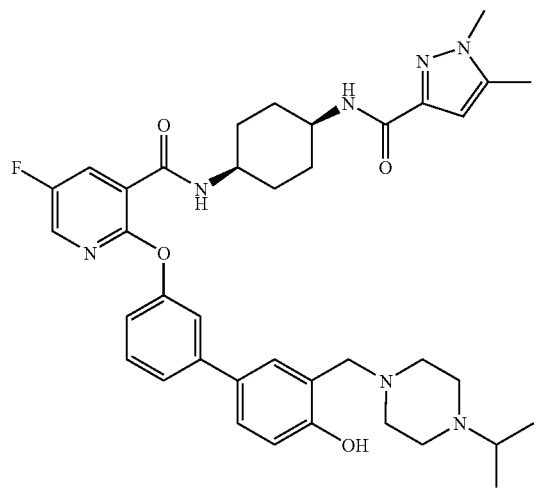

Step (a) N-((1s,4s)-4-(1,5-dimethyl-1H-pyrazole-3-carboxamido)cyclohexyl)-5-fluoro-2-(3'-formyl-4'-hydroxybiphenyl-3-yloxy)nicotinamide N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide (450 mg, 0.78 mmol), 5-bromo-2-hydroxybenzaldehyde (157 mg, 0.78 mmol) and sodium carbonate (669 mg, 2.34 mmol) were added to THF (6.00 mL) and degassed water (3 mL) under nitrogen. Tetrakis(triphenylphosphine)palladium(0) (18 mg, 0.02 mmol) was then added and the reaction mixture was heated at reflux overnight. The mixture was poured onto water and extracted into EtOAc (×2). The extractions were combined, washed with brine, dried (MgSO$_4$) and evaporated to give a yellow oil. The crude material was purified by Biotage (eluant=neat EtOAc) to give the sub-title compound as an off-white solid after evaporation. Yield: 275 mg MS: [M+H]+=572 (MultiMode+)

Step (b) N-((1s,4s)-4-(1,5-dimethyl-1H-pyrazole-3-carboxamido)cyclohexyl)-5-fluoro-2-(4'-hydroxy-3'-((4-isopropylpiperazin-1-yl)methyl)biphenyl-3-yloxy)nicotinamide To a solution of N-((1s,4s)-4-(1,5-dimethyl-1H-pyrazole-3-carboxamido)cyclohexyl)-5-fluoro-2-(3'-formyl-4'-hydroxybiphenyl-3-yloxy)nicotinamide (140 mg, 0.24 mmol) in DCM (3 mL) was added 1-isopropylpiperazine (0.053 mL, 0.37 mmol). The mixture was allowed to stir at RT for 40 min before sodium triacetoxyborohydride (78 mg, 0.37 mmol) was added. The reaction was stirred at RT for 2 h. The mixture was diluted with DCM and washed with sat. NaHCO$_3$ (aq), dried (MgSO$_4$) and evaporated to give a yellow glass. This was purified by HPLC to afford the title compound as a white solid. Yield: 110 mg $^1$H NMR (400 MHz, CD$_3$OD) δ 8.12 (d, J=3.1 Hz, 1H), 8.07 (dd, J=7.9, 3.1 Hz, 1H), 7.52-7.38 (m, 5H), 7.13-7.09 (m, 1H), 6.91 (d, J=9.2 Hz, 1H), 6.38 (s, 1H), 4.16 (s, 2H), 4.14-4.09 (m, 1H), 3.94-3.86 (m, 1H), 3.70 (s, 3H), 3.57-3.32 (m, 8H), 2.25 (s, 3H), 1.92-1.72 (m, 6H), 1.72-1.59 (m, 2H), 1.33 (d, J=6.4 Hz, 6H).

MS: [M+H]+=684.3 (calc=684.3673) (MultiMode+)

EXAMPLE 78

N-((1s,4s)-4-(1,5-dimethyl-1H-pyrazole-3-carboxamido)cyclohexyl)-2-(3'-(((3R,5S)-3,5-dimethylpiperazin-1-yl)methyl)-2'-hydroxybiphenyl-3-yloxy)-5-fluoronicotinamide

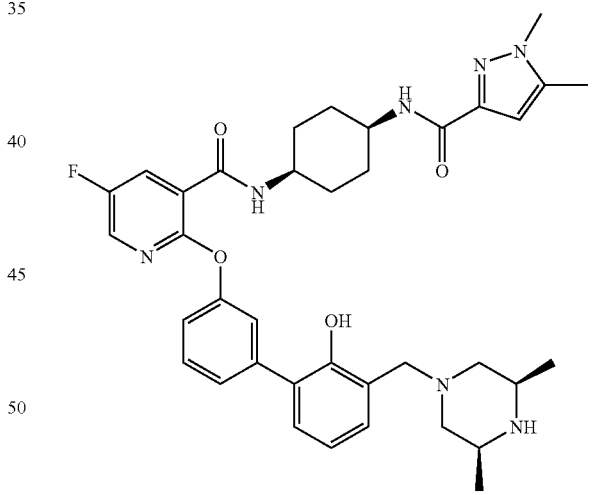

Step (a) N-((1s,4s)-4-(1,5-dimethyl-1H-pyrazole-3-carboxamido)cyclohexyl)-5-fluoro-2-(3'-formyl-2'-hydroxybiphenyl-3-yloxy)nicotinamide N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide (150 mg, 0.26 mmol), 3-bromo-2-hydroxybenzaldehyde (52.2 mg, 0.26 mmol) and sodium carbonate (223 mg, 0.78 mmol) were added to THF (2.000 mL) and degassed water (1 mL) under nitrogen. Tetrakis(triphenylphosphine)palladium(0) (6 mg, 5.20 μmol)

was then added and the reaction mixture was heated at reflux overnight. The mixture was poured onto water and extracted into EtOAc (×2). The extractions were combined, washed with brine, dried (MgSO$_4$) and evaporated to give a yellow oil. The crude material was purified by Biotage (eluant=neat EtOAc) to give the sub-title compound as a white solid after evaporation. Yield: 108.4 mg MS: [M+H]+=572 (MultiMode+)

Step (b) N-((1s,4s)-4-(1,5-dimethyl-1H-pyrazole-3-carboxamido)cyclohexyl)-2-(3'-(((3R,5S)-3,5-dimethylpiperazin-1-yl)methyl)-2'-hydroxybiphenyl-3-yloxy)-5-fluoronicotinamide To a solution of N-((1s,4s)-4-(1,5-dimethyl-1H-pyrazole-3-carboxamido)cyclohexyl)-5-fluoro-2-(3'-formyl-2'-hydroxybiphenyl-3-yloxy)nicotinamide (150 mg, 0.26 mmol) in DCM (3 mL) was added (2R,6S)-2,6-dimethylpiperazine (45 mg, 0.39 mmol). The mixture was allowed to stir at RT for 40 min before sodium triacetoxyborohydride (83 mg, 0.39 mmol) was added. The reaction was stirred at RT for 2 h. The mixture was diluted with DCM and washed with sat. NaHCO$_3$ (aq), dried (MgSO$_4$) and evaporated to give a yellow glass. This was purified by HPLC to give the title compound as a white solid. Yield: 95.5 mg $^1$H NMR (400 MHz, CD$_3$OD) δ 8.11 (d, J=3.1 Hz, 1H), 8.08 (dd, J=7.9, 3.1 Hz, 1H), 7.47 (t, J=7.8 Hz, 1H), 7.41-7.35 (m, 2H), 7.30 (dd, J=7.7, 1.5 Hz, 1H), 7.21-7.14 (m, 2H), 6.92 (t, J=7.6 Hz, 1H), 6.48-6.35 (m, 1H), 4.15-4.08 (m, 1H), 4.04 (s, 2H), 3.97-3.87 (m, 1H), 3.64 (s, 3H), 3.52-3.42 (m, 2H), 3.37-3.30 (m, 2H), 2.52 (t, J=12.4 Hz, 2H), 2.24 (s, 3H), 1.94-1.74 (m, 6H), 1.72-1.59 (m, 2H), 1.27 (d, J=6.4 Hz, 6H).

MS: [M+H]+=670.3 (calc=670.3517) (MultiMode+)

EXAMPLE 79

N-((1s,4s)-4-(1,5-dimethyl-1H-pyrazole-3-carboxamido)cyclohexyl)-5-fluoro-2-(4'-(3-(pyrrolidin-1-yl)propyl)biphenyl-3-yloxy)nicotinamide

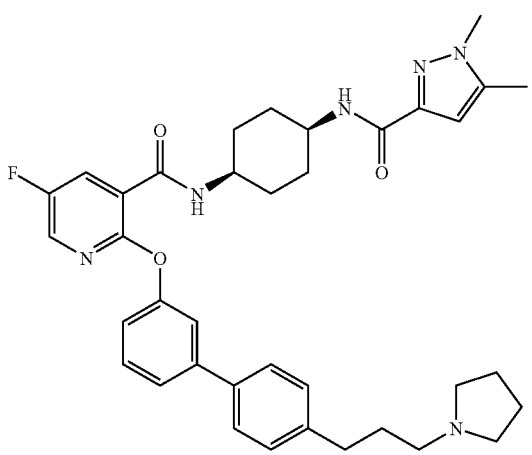

Step (a) N-((1s,4s)-4-(1,5-dimethyl-1H-pyrazole-3-carboxamido)cyclohexyl)-5-fluoro-2-(4'-(3-hydroxypropyl)biphenyl-3-yloxy)nicotinamide Palladium acetate (0.019 g, 0.09 mmol) and 2-dicyclohexylphosphino-2',6'-dimethoxybiphenyl (0.071 g, 0.17 mmol) were added to acetonitrile (10 mL) under nitrogen. The resulting solution was stirred for 10 min. To this solution was added potassium carbonate (0.718 g, 5.20 mmol) dissolved in water (10.00 mL), followed by 4-(3-hydroxypropyl)phenylboronic acid (0.312 g, 1.73 mmol) and N-((1s,4s)-4-(1,5-dimethyl-1H-pyrazole-3-carboxamido)cyclohexyl)-5-fluoro-2-(3-iodophenoxy)nicotinamide (1 g, 1.73 mmol) and the mixture heated at 80° C. for 2 h. The mixture was poured onto water and extracted into EtOAc (×2). The extractions were combined, washed with brine, dried (MgSO$_4$) and evaporated to give a light yellow foam. This was purified using column chromatography (eluent=3% methanol/DCM) to give the sub-title compound as a white foam. Yield: 0.61 g $^1$H NMR (400 MHz, CD$_3$OD) δ 8.37 (dd, J=8.2, 3.1 Hz, 1H), 8.11-8.05 (m, 2H), 7.55-7.47 (m, 4H), 7.37-7.35 (m, 1H), 7.25-7.22 (m, 2H), 7.16-7.12 (m, 1H), 6.67 (d, J=7.7 Hz, 1H), 6.50 (s, 1H), 4.27-4.19 (m, 1H), 4.12-4.01 (m, 1H), 3.70 (t, J=6.3 Hz, 2H), 3.66 (s, 3H), 2.74 (t, J=7.8 Hz, 2H), 2.25 (s, 3H) 1.95-1.75 (m, 6H), 1.67-1.54 (m, 4H).

MS: [M+H]+=586 (MultiMode+)

Step (b) 3-(3'-(3-((1s,4s)-4-(1,5-dimethyl-1H-pyrazole-3-carboxamido)cyclohexylcarbamoyl)-5-fluoropyridin-2-yloxy)biphenyl-4-yl)propyl methanesulfonate To solution of N-((1s,4s)-4-(1,5-dimethyl-1H-pyrazole-3-carboxamido)cyclohexyl)-5-fluoro-2-(4'-(3-hydroxypropyl)biphenyl-3-yloxy)nicotinamide (0.61 g, 1.04 mmol) and pyridine (0.295 mL, 3.65 mmol) in DCM (7 mL), was added methanesulfonyl chloride (0.284 mL, 3.65 mmol) and the reaction stirred at RT overnight. The reaction was evaporated to give a residue which was partitioned between EtOAc and 2M HCl(aq). The EtOAc layer was then washed with another aliquot of 2M HCl(aq), 2× sat NaHCO$_3$ (aq), brine, dried (MgSO$_4$) and evaporated to give a light yellow oil. This was triturated with ether overnight to give the sub-title compound as a white solid. Yield: 665 mg $^1$H NMR (400 MHz, CD$_3$OD) δ 8.45 (d, J=7.6 Hz, 1H), 8.11 (d, J=3.1 Hz, 1H), 8.07 (dd, J=7.9, 3.1 Hz, 1H), 7.54-7.47 (m, 4H), 7.23 (d, J=8.2 Hz, 2H), 7.15-7.11 (m, 1H), 6.41 (s, 1H), 4.22 (t, J=6.3 Hz, 2H), 4.16-4.08 (m, 1H), 3.97-3.90 (m, 1H), 3.69 (s, 3H), 3.03 (s, 3H), 2.75 (t, J=7.6 Hz, 2H), 2.25 (s, 3H) 2.08-2.00 (m, 2H), 1.90-1.76 (m, 6H), 1.73-1.62 (m, 2H).

MS: [M+H]+=664 (MultiMode+)

Step (c) N-((1s,4s)-4-(1,5-dimethyl-1H-pyrazole-3-carboxamido)cyclohexyl)-5-fluoro-2-(4'-(3-(pyrrolidin-1-yl)propyl)biphenyl-3-yloxy)nicotinamide To a microwave tube was charged 3-(3'-(3-((1s,4s)-4-(1,5-dimethyl-1H-pyrazole-3-carboxamido)cyclohexylcarbamoyl)-5-fluoropyridin-2-yloxy)biphenyl-4-yl)propyl methanesulfonate (150 mg, 0.23 mmol), Pyrrolidine (0.057 mL, 0.68 mmol) and acetonitrile (1 mL). The reaction was heated to 80° C. for 5 mins and the mixture purified by HPLC to give the title compound as a white solid. Yield: 99.5 mg $^1$H NMR (400 MHz, CD$_3$OD) δ 8.10 (d, J=3.1 Hz, 1H), 8.05 (dd, J=8.1, 3.2 Hz, 1H), 7.55-7.51 (m, 2H), 7.48-7.46 (m, 2H), 7.41-7.39 (m, 1H), 7.26 (d, J=8.2 Hz, 2H), 7.17-7.11 (m, 1H), 6.51-6.36 (m, 1H), 4.15-4.06 (m, 1H), 3.98-3.87 (m, 1H), 3.70 (s, 3H), 3.67-3.58 (m, 2H), 3.21-3.13 (m, 2H), 3.07-2.98 (m, 2H), 2.72 (t, J=7.6 Hz, 2H), 2.17-1.92 (m, 6H) 1.90-1.75 (m, 6H), 1.73-1.62 (m, 2H).

MS: [M+H]+=639.3 (calc=639.3459) (MultiMode+)

EXAMPLE 80

N-((1s,4s)-4-(1,5-dimethyl-1H-pyrazole-3-carboxamido)cyclohexyl)-5-fluoro-2-(4'-(3-(4-methylpiperazin-1-yl)propyl)biphenyl-3-yloxy)nicotinamide

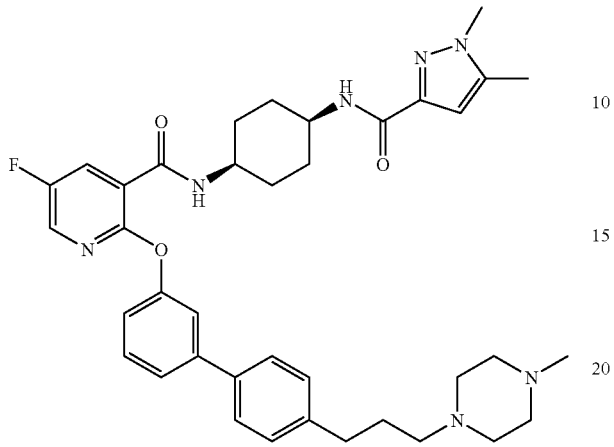

To a microwave tube was charged 3-(3'-(3-((1s,4s)-4-(1,5-dimethyl-1H-pyrazole-3-carboxamido)cyclohexylcarbamoyl)-5-fluoropyridin-2-yloxy)biphenyl-4-yl)propyl methanesulfonate (150 mg, 0.23 mmol), 1-methylpiperazine (0.075 mL, 0.68 mmol) and acetonitrile (1 mL). The reaction was heated to 80° C. for 20 mins and the mixture purified by HPLC to give the title compound as a white solid. Yield: 76 mg $^1$H NMR (400 MHz, CD$_3$OD) δ 8.10 (d, J=3.1 Hz, 1H), 8.05 (dd, J=7.9, 3.1 Hz, 1H), 7.51 (d, J=8.2, 2H), 7.46 (d, J=4.9, 2H), 7.40 (s, 1H), 7.24 (d, J=8.2 Hz, 2H), 7.16-7.10 (m, 1H), 6.48-6.39 (m, 1H), 4.13-4.06 (m, 1H), 3.97-3.89 (m, 1H), 3.70 (s, 3H), 3.53-3.36 (m, 8H), 3.10-3.03 (m, 2H), 2.89 (s, 3H), 2.71 (t, J=7.4 Hz, 2H), 2.25 (s, 3H), 2.07-1.98 (m, 2H), 1.89-1.73 (m, 6H), 1.73-1.61 (m, 2H).

MS: [M+H]+=668.3 (calc=668.3724) (MultiMode+)

EXAMPLE 81

N-((1s,4s)-4-(1,5-dimethyl-1H-pyrazole-3-carboxamido)cyclohexyl)-2-(4'-(3-((3S,5R)-3,5-dimethylpiperazin-1-yl)propyl)biphenyl-3-yloxy)-5-fluoronicotinamide

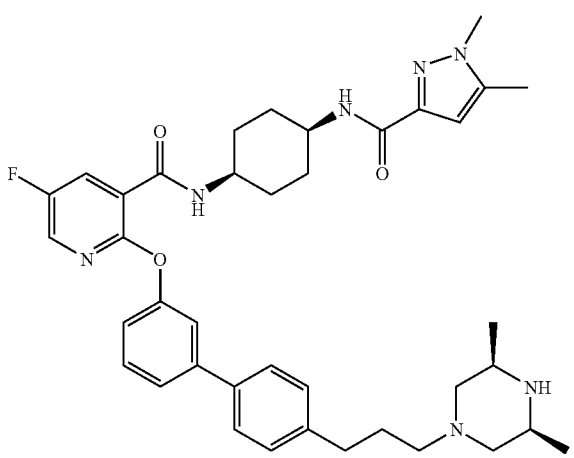

To a microwave tube was charged 3-(3'-(3-((1s,4s)-4-(1,5-dimethyl-1H-pyrazole-3-carboxamido)cyclohexylcarbamoyl)-5-fluoropyridin-2-yloxy)biphenyl-4-yl)propyl methanesulfonate (145 mg, 0.22 mmol), (2R,6S)-2,6-dimethylpiperazine (74.8 mg, 0.66 mmol) and acetonitrile (1 mL). The reaction was heated to 80° C. for 30 mins and the mixture was purified by HPLC to afford the title compound as a white solid. Yield: 86 mg $^1$H NMR (400 MHz, CDCl$_3$) δ 8.11-8.07 (m, 1H), 8.07-8.02 (m, 1H), 7.51 (d, J=6.9 Hz, 2H), 7.46 (d, J=3.8 Hz, 2H), 7.39 (s, 1H), 7.24 (d, J=7.2 Hz, 2H), 7.16-7.09 (m, 1H), 6.43 (s, 1H), 4.15-4.04 (m, 1H), 3.98-3.86 (m, 1H), 3.73-3.56 (m, 6H), 3.04 (t, J=7.6 Hz, 2H), 2.82 (t, J=12.8 Hz, 2H), 2.71 (t, J=7.2 Hz, 2H), 2.24 (s, 3H), 2.09-1.99 (m, 2H), 1.90-1.72 (m, 6H), 1.72-1.61 (m, 2H), 1.35 (d, J=6.2 Hz, 6H).

MS: [M+H]+=682.3 (calc=682.3881) (MultiMode+)

EXAMPLE 82

N-((1s,4s)-4-(1,5-dimethyl-1H-pyrazole-3-carboxamido)cyclohexyl)-2-(4'-(2-((3S,5R)-3,5-dimethylpiperazin-1-yl)ethyl)biphenyl-3-yloxy)-5-fluoronicotinamide

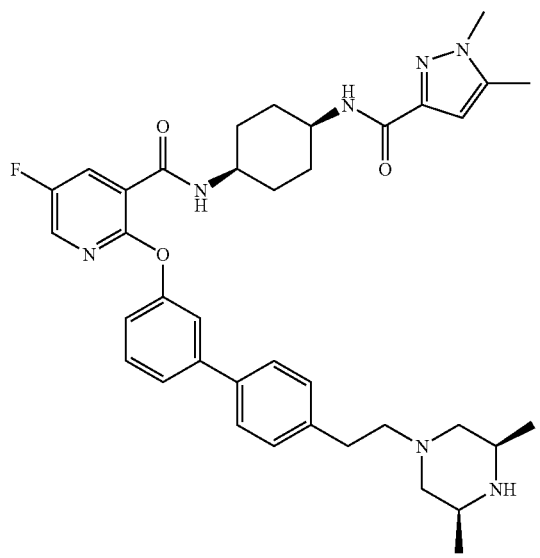

Step (a) N-((1s,4s)-4-(1,5-dimethyl-1H-pyrazole-3-carboxamido)cyclohexyl)-5-fluoro-2-(4'-(2-hydroxyethyl)biphenyl-3-yloxy)nicotinamide N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide (450 mg, 0.78 mmol), 2-(4-bromophenyl)ethanol (0.109 mL, 0.78 mmol) and sodium carbonate (669 mg, 2.34 mmol) were added to THF (6.00 mL) and degassed water (3 mL) under nitrogen. Tetrakis(triphenylphosphine)palladium(0) (18 mg, 0.02 mmol) was then added and the reaction mixture was heated at reflux for 2 h. The mixture was poured onto water and extracted into EtOAc (×2). The extractions were combined, washed with brine, dried (MgSO$_4$) and evaporated to give a yellow oil. The crude material was purified by Biotage (eluent=3% methanol/DCM) to give the sub-title compound as a white foam after evaporation. Yield: 310 mg $^1$H NMR (400 MHz, CD$_3$OD) δ 8.38 (dd, J=8.2, 3.1 Hz, 1H), 8.08 (d, J=3.3 Hz, 1H), 8.06 (s, 1H), 7.56-7.48 (m, 3H), 7.38-7.35 (m, 1H), 7.29 (s, 1H), 7.15 (dt, J=7.4, 2.1 Hz, 1H), 6.67 (d, J=7.4 Hz, 1H), 6.51 (d, J=0.8 Hz, 1H), 4.27-4.19 (m, 1H), 3.93-3.86 (m, 1H), 3.67 (s, 3H), 2.90 (t, J=6.5 Hz, 2H), 2.25 (s, 3H) 1.95-1.75 (m, 6H), 1.67-1.59 (m, 2H).

MS: [M+H]+=572 (MultiMode+)

Step (b) 2-(3'-(3-((1s,4s)-4-(1,5-dimethyl-1H-pyrazole-3-carboxamido)cyclohexylcarbamoyl)-5-fluoropyridin-2-yloxy)biphenyl-4-yl)ethyl methanesulfonate To solution of N-((1s,4s)-4-(1,5-dimethyl-1H-pyrazole-3-carboxamido)cyclohexyl)-5-fluoro-2-(4'-(2-hydroxyethyl)biphenyl-3-yloxy)nicotinamide (0.315 g, 0.55 mmol) and pyridine (0.134 mL, 1.65 mmol) in DCM (7 mL), was added methanesulfonyl chloride (0.129 mL, 1.65 mmol) and the reaction stirred at RT overnight. The reaction was evaporated to give a residue which was partitioned between EtOAc and 2M HCl(aq). The EtOAc layer was then washed with another aliquot of 2M HCl(aq), 2× sat NaHCO₃ (aq), brine, dried (MgSO₄) and evaporated to give a yellow oil. This was triturated with ether to give the sub-title compound as a white solid. Yield: 310 mg
MS: [M+H]+=650 (MultiMode+)

Step (b) N-((1s,4s)-4-(1,5-dimethyl-1H-pyrazole-3-carboxamido)cyclohexyl)-2-(4'-(2-((3S,5R)-3,5-dimethylpiperazin-1-yl)ethyl)biphenyl-3-yloxy)-5-fluoronicotinamide To a microwave tube was charged 2-(3'-(3-((1s,4s)-4-(1,5-dimethyl-1H-pyrazole-3-carboxamido)cyclohexylcarbamoyl)-5-fluoropyridin-2-yloxy)biphenyl-4-yl)ethyl methanesulfonate (150 mg, 0.23 mmol), (2R,6S)-2,6-dimethylpiperazine (79 mg, 0.69 mmol) and acetonitrile (1 mL). The reaction was heated to 80° C. for 30 mins and the mixture was purified by HPLC to afford the title compound as a white solid. Yield: 72 mg
¹H NMR (400 MHz, CDCl₃) δ 8.08 (d, J=2.8 Hz, 1H), 8.04 (dd, J=7.9, 3.1 Hz, 1H), 7.54 (d, J=7.9 Hz, 2H), 7.46 (d, J=4.6 Hz, 2H), 7.41 (s, 1H), 7.29 (d, J=8.2 Hz, 2H), 7.15-7.10 (m, 1H), 6.42 (s, 1H), 4.13-4.05 (m, 1H), 3.96-3.87 (m, 1H), 3.67 (s, 3H), 3.34-3.19 (m, 4H), 3.07-3.00 (m, 2H), 2.88 (t, J=12.3 Hz, 2H), 2.24 (s, 3H), 1.90-1.73 (m, 6H), 1.72-1.60 (m, 2H), 1.38 (d, J=6.4 Hz, 6H).
MS: [M+H]+=668.3 (calc=668.3724) (MultiMode+)

EXAMPLE 83

N-((1s,4s)-4-(1,5-dimethyl-1H-pyrazole-3-carboxamido)cyclohexyl)-5-fluoro-2-(4'-(2-(4-isopropylpiperazin-1-yl)ethyl)biphenyl-3-yloxy)nicotinamide

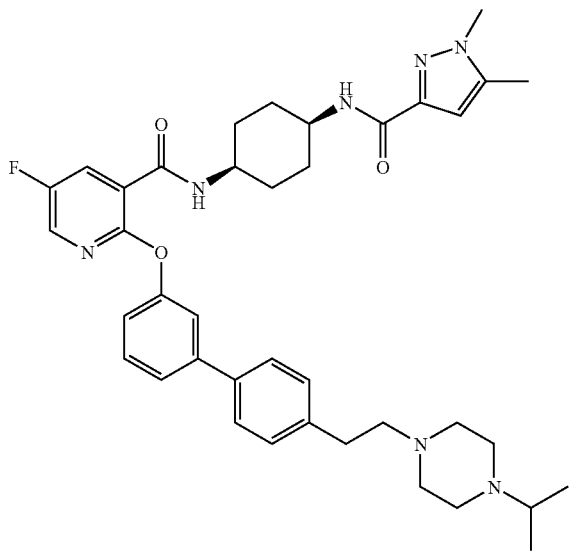

To a microwave tube was charged 2-(3'-(3-((1s,4s)-4-(1,5-dimethyl-1H-pyrazole-3-carboxamido)cyclohexylcarbamoyl)-5-fluoropyridin-2-yloxy)biphenyl-4-yl)ethyl methanesulfonate (150 mg, 0.23 mmol), 1-isopropylpiperazine (0.099 mL, 0.69 mmol) and acetonitrile (1 mL). The reaction was heated to 80° C. for 30 mins and the reaction mixture was purified by HPLC to afford the title compound as a white solid. Yield: 110 mg
¹H NMR (400 MHz, CDCl₃) δ 8.11 (d, J=3.1 Hz, 1H), 8.06 (dd, J=7.9, 3.1 Hz, 1H), 7.54 (d, J=8.2 Hz, 2H), 7.47 (d, J=4.9 Hz, 2H), 7.42-7.39 (m, 1H), 7.30 (d, J=8.2 Hz, 2H), 7.18-7.12 (m, 1H), 6.42 (s, 1H), 4.14-4.06 (m, 1H), 3.97-3.90 (m, 1H), 3.71 (s, 3H), 3.59-3.31 (m, 9H), 3.22-3.15 (m, 2H), 3.03-2.96 (m, 2H), 2.25 (s, 3H), 1.91-1.74 (m, 6H), 1.73-1.61 (m, 2H), 1.35 (d, J=6.7 Hz, 6H).
MS: [M+H]+=682.3 (calc=682.3881) (MultiMode+)

EXAMPLE 84

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-6-fluoroimidazo[1,2-a]pyridine-2-carboxamide

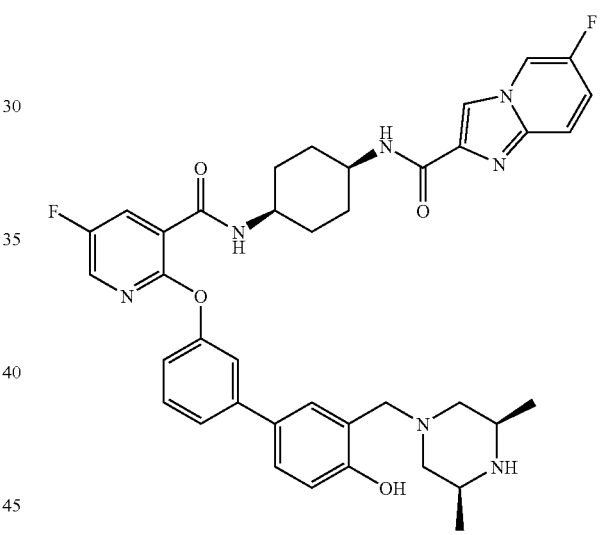

Step (a) tert-butyl (1s,4s)-4-(5-fluoro-2-(3'-formyl-4'-hydroxybiphenyl-3-yloxy)nicotinamido)cyclohexylcarbamate Tert-butyl (1s,4s)-4-(5-fluoro-2-(3-(4,4,5,5-tetramethyl-1,3,2-dioxaborolan-2-yl)phenoxy)nicotinamido)cyclohexylcarbamate (1 g, 1.80 mmol), 5-bromo-2-hydroxybenzaldehyde (0.362 g, 1.80 mmol) and sodium carbonate (0.572 g, 5.40 mmol) were added to THF (6 mL) and degassed water (3 mL) under nitrogen. Tetrakis(triphenylphosphine)palladium (0) (0.042 g, 0.04 mmol) was then added and the reaction mixture was heated at reflux for 28 h then left to cool over the weekend. Further tert-butyl (1s,4s)-4-(5-fluoro-2-(3-(4,4,5,5-tetramethyl-1,3,2-dioxaborolan-2-yl)phenoxy)nicotinamido)cyclohexylcarbamate (0.3 g), sodium carbonate (0.1 g) and tetrakis(triphenylphosphine)palladium(0) (0.01 g) were added and stirred at 80° C. for a further 3 h. The mixture was poured onto water and extracted into EtOAc (×2). The extractions were combined, washed with brine, dried (MgSO₄) and evaporated to give a yellow oil. The crude material was purified by Biotage (silica, 50 g) eluting with 100% DCM to remove an impurity then 20% DCM in ether to elute product. Product containing fractions were combined and concentrated to give the sub-title compound as an off-white solid. Yield: 1.0 g MS: [M−H]−=548 (MultiMode+)

Step (b) tert-Butyl (1s,4s)-4-(2-(3'-(((3S,5R)-3,5-dimethylpiperazin-1-yl)methyl)-4'-hydroxybiphenyl-3-yloxy)-5-fluoronicotinamido)cyclohexylcarbamate Tert-butyl (1s,4s)-4-(5-fluoro-2-(3'-formyl-4'-hydroxybiphenyl-3-yloxy)nicotinamido)cyclohexylcarbamate (1.2 g, 2.18 mmol) and (2S,6R)-2,6-dimethylpiperazine (1.247 g, 10.92 mmol) were stirred in DCM (10 mL) at RT. Acetic acid (0.625 mL, 10.92 mmol) was added and the reaction stirred for 30 min. Sodium triacetoxyborohydride (2.314 g, 10.92 mmol) was then added and the reaction left to stir under nitrogen overnight. The mixture was diluted with DCM and washed with saturated NaHCO$_3$ (aq) solution (×2), dried (MgSO$_4$) and evaporated to give a pale foam. Purification on SCX cartridge eluting with 100% methanol to remove the impurities then flushed with 20% ammonia in methanol to elute the product. Product containing fractions were combined and concentrated in vacuo to leave the sub-title compound as a white solid. Yield: 0.38 g MS: [M+H]+=648 (MultiMode+)

Step (c) N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide hydrochloride To tert-butyl (1s,4s)-4-(2-(3'-(((3S,5R)-3,5-dimethylpiperazin-1-yl)methyl)-4'-hydroxybiphenyl-3-yloxy)-5-fluoronicotinamido)cyclohexylcarbamate (0.35 g, 0.54 mmol) in DCM (1 mL) was added HCl (4 Molar in dioxane) (1.351 mL, 5.40 mmol). After 1 min, a cloudy precipitate began to form so methanol (0.5 mL) was added to make the solution homogenous. The reaction was stirred at RT for 2 h. The reaction was concentrated in vacuo and triturated with ether to deliver the sub-title compound as a white solid. Yield: 0.35 g MS: [M+H]+=548 (MultiMode+)

Step (d) N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-6-fluoroimidazo[1,2-a]pyridine-2-carboxamide To a suspension of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide hydrochloride (0.08 g, 0.15 mmol) in acetonitrile (1 mL) was added 6-fluoroimidazo[1,2-a]pyridine-2-carboxylic acid (0.047 g, 0.22 mmol) and DIPEA (0.077 mL, 0.44 mmol). HATU (0.167 g, 0.44 mmol) was then added and the mixture stirred at RT for 1 h. Water (0.5 mL) and conc. HCl (1 mL) was added and the crude product was purified by preparative HPLC on a Phenomenex column using a 95-50% gradient of aqueous 0.1% TFA in acetonitrile as eluent. The fractions containing the desired compound were freeze dried overnight to afford the title compound as a fluffy white solid. Yield: 25 mg $^1$H NMR (400 MHz, DMSO) δ 8.98-8.86 (m, 1H), 8.81-8.79 (m, 1H), 8.38-8.34 (m, 2H), 8.26 (d, J=4.6 Hz, 1H), 8.07 (dd, J=6.6, 6.6 Hz, 1H), 7.80 (d, J=4.9 Hz, 1H), 7.74-7.43 (m, 5H), 7.26-7.20 (m, 2H), 4.13-3.88 (m, 4H), 3.67 (s, 2H), 2.52-2.47 (m, 7H), 1.81-1.66 (m, 8H), 1.16 (d, J=18.2 Hz, 6H).

MS: [M+H]+=717.3 (calc=710.3266) (MultiMode+)

EXAMPLE 85

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-5-methylimidazo[1,2-a]pyridine-2-carboxamide

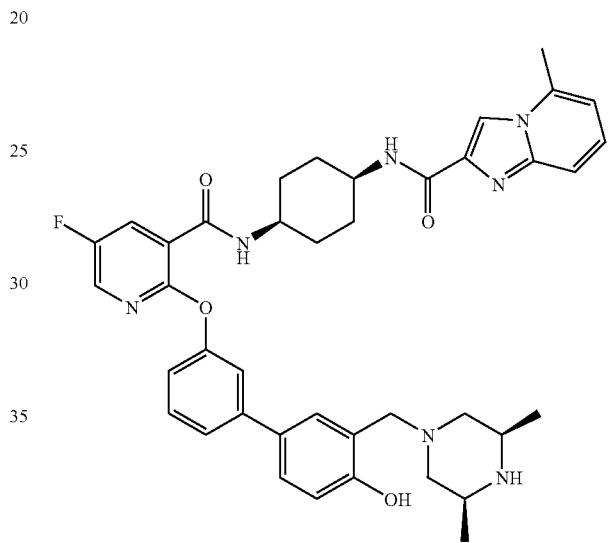

To a suspension of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (0.08 g, 0.13 mmol) in acetonitrile (1 mL) was added 5-methylimidazo[1,2-a]pyridine-2-carboxylic acid (0.034 g, 0.19 mmol) and DIPEA (0.068 mL, 0.39 mmol). HATU (0.147 g, 0.39 mmol) was then added and the mixture stirred at RT for 1 h. 880 ammonia (2 mL) was added and the reaction stirred for 5 days. Water (0.5 mL) was added and the crude product was purified by preparative HPLC on a Waters X-Bridge column using a 95-5% gradient of aqueous 0.1% TFA in acetonitrile as eluent. The fractions containing the desired compound were freeze dried to afford the title compound as a white fluffy solid. Yield: 40 mg $^1$H NMR (400 MHz, DMSO) δ 8.39-8.37 (m, 2H), 8.25 (d, J=3.1 Hz, 1H), 8.05 (dd, J=7.9, 3.1 Hz, 1H), 7.95-7.93 (m, 1H), 7.61 (s, 1H), 7.54-7.42 (m, 5H), 7.38 (s, 1H), 7.16-7.11 (m, 2H), 6.99-6.94 (m, 3H), 3.50-3.43 (m, 2H), 3.36-3.33 (m, 2H), 2.66 (s, 3H), 2.50-2.49 (m, 6H), 1.81-1.71 (m, 8H), 1.20 (d, J=6.7 Hz, 6H).

MS: [M+H]+=706.3 (calc=706.3517) (MultiMode+)

EXAMPLE 86

N-((1s,4s)-4-(2-(4'-(2-((3S,5R)-3,5-dimethylpiperazin-1-yl)ethyl)biphenyl-3-yloxy)-5-fluoronicotinamido)cyclohexyl)-2-methylthiazole-4-carboxamide

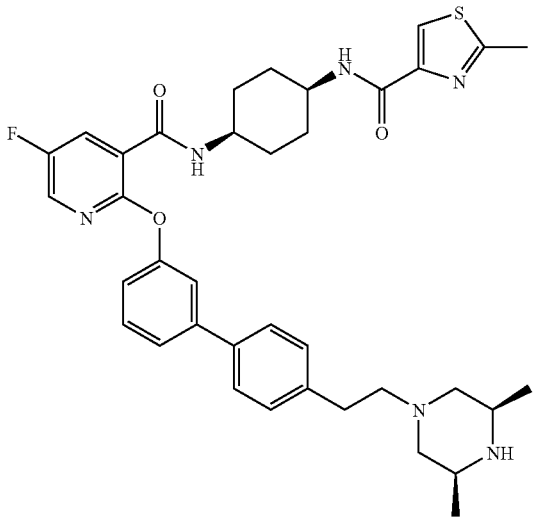

Step (a) N-((1s,4s)-4-(5-fluoro-2-(4'-(2-hydroxyethyl)biphenyl-3-yloxy)nicotinamido)cyclohexyl)-2-methylthiazole-4-carboxamide To a solution of N-((1s,4s)-4-(5-fluoro-2-(3-iodophenoxy) nicotinamido)cyclohexyl)-2-methylthiazole-4-carboxamide (1.2 g, 2.07 mmol), 4-(2-hydroxyethyl)phenylboronic acid (0.446 g, 2.69 mmol) and sodium carbonate (0.260 mL, 6.20 mmol) in THF (10 mL) and water (5.00 mL) was added tetrakis(triphenylphosphine)palladium(0) (0.048 g, 0.04 mmol). The mixture was heated to 80° C. overnight. A further 4-(2-hydroxyethyl)phenylboronic acid (0.446 g, 2.69 mmol) was added and the reaction heated for a further 24 h. The mixture was evaporated and the residue partitioned between water and EtOAc. The aqueous layer was extracted again with EtOAc and the extractions combined. The mixture was purified using normal phase chromatography (eluent=EtOAc), the appropriate fractions were combined and evaporated to give a foam. This was triturated with ether overnight to give a fine solid which was isolated by filtration to give the sub-title compound. Yield: 0.9 g $^1$H NMR (400 MHz, CDCl$_3$) δ 8.38 (dd, J=8.2, 3.1 Hz, 1H), 8.11-8.07 (m, 2H), 7.90 (s, 1H), 7.55-7.49 (m, 4H), 7.37 (t, J=1.8 Hz, 1H), 7.28 (s, 1H), 7.20 (d, J=7.7 Hz, 1H), 7.15 (dt, J=7.4, 2.1 Hz, 1H), 4.27-4.22 (m, 1H), 4.12-4.04 (m, 1H), 3.92-3.87 (m, 2H), 2.90 (t, J=6.5 Hz, 2H), 2.61 (s, 3H), 1.96-1.79 (m, 6H), 1.69-1.62 (m, 2H).

MS: [M+H]+=575 (MultiMode+)

Step (b) 2-(3'-(5-fluoro-3-((1s,4s)-4-(2-methylthiazole-4-carboxamido)cyclohexylcarbamoyl)pyridin-2-yloxy)biphenyl-4-yl)ethyl methanesulfonate To a solution of N-((1s,4s)-4-(5-fluoro-2-(4'-(2-hydroxyethyl)biphenyl-3-yloxy)nicotinamido)cyclohexyl)-2-methylthiazole-4-carboxamide (0.8 g, 1.39 mmol) and pyridine (0.225 mL, 2.78 mmol) in DCM (10 mL), was added methanesulfonyl chloride (0.226 mL, 2.92 mmol) and the reaction stirred at RT overnight. A further 2 eq of methanesulfonyl chloride (0.226 mL, 2.92 mmol) and pyridine (0.225 mL, 2.78 mmol) were added and the reaction left to stir for another 24 h. The reaction had proceeded to completion after this time. The mixture was diluted with DCM (50 mL) and washed with 2×2M HCl(aq), NaHCO$_3$ (aq), dried (MgSO$_4$) and evaporated to give an oil. This was triturated with ether to give the sub-title compound as a solid. Yield: 0.81 g $^1$H NMR (300 MHz, CDCl$_3$) δ 8.38 (dd, J=8.3, 3.1 Hz, 1H), 8.10-8.06 (m, 2H), 7.90 (s, 1H), 7.57-7.49 (m, 4H), 7.38 (d, J=1.7 Hz, 1H), 7.30-7.25 (m, 2H), 7.23-7.14 (m, 2H), 4.44 (t, J=6.8 Hz, 2H), 4.28-4.21 (m, 1H), 4.13-4.03 (m, 1H), 3.09 (t, J=6.8 Hz, 2H), 2.91 (s, 3H), 2.61 (s, 3H), 1.98-1.78 (m, 6H), 1.71-1.62 (m, 2H).

Step (c) N-((1s,4s)-4-(2-(4'-(2-((3S,5R)-3,5-dimethylpiperazin-1-yl)ethyl)biphenyl-3-yloxy)-5-fluoronicotinamido)cyclohexyl)-2-methylthiazole-4-carboxamide To a suspension of 2-(3'-(5-fluoro-3-((1s,4s)-4-(2-methylthiazole-4-carboxamido)cyclohexylcarbamoyl)pyridin-2-yloxy)biphenyl-4-yl)ethyl methanesulfonate (120 mg, 0.18 mmol) in acetonitrile (1 mL) was added (2R,6S)-2,6-dimethylpiperazine (63.0 mg, 0.55 mmol). The mixture was heated to 80° C. in the microwave for 30 mins. The mixture was purified using reverse phase prep HPLC (eluent=TFA(aq)/MeCN), the appropriate fractions were combined, evaporated to give a residue which was triturated with ether to give a solid which was isolated by filtration and dried overnight under vacuum at 40° C. to give the title compound. Yield: 102 mg $^1$H NMR (400 MHz, CDCl$_3$) δ 8.37-8.33 (m, 1H), 8.13 (d, J=7.4 Hz, 1H), 8.09 (q, J=1.6 Hz, 1H), 7.94 (s, 1H), 7.57-7.49 (m, 4H), 7.39-7.35 (m, 2H), 7.27 (d, J=8.2 Hz, 2H), 7.17 (dd, J=7.7, 1.8 Hz, 1H), 4.25-4.21 (m, 1H), 4.10-4.06 (m, 1H), 3.70-3.63 (m, 2H), 3.48-3.38 (m, 2H), 3.25-2.95 (m, 6H), 2.63 (s, 3H), 1.97-1.88 (m, 4H), 1.87-1.79 (m, 2H), 1.71-1.63 (m, 2H), 1.39 (dd, J=6.7, 1.8 Hz, 6H).

MS: [M+H]+=671.3 (calc=671.3179) (MultiMode+)

EXAMPLE 87

N-((1s,4s)-4-(5-fluoro-2-(4'-(2-(4-methyl-1,4-diazepan-1-yl)ethyl)biphenyl-3-yloxy)nicotinamido) cyclohexyl)-2-methylthiazole-4-carboxamide

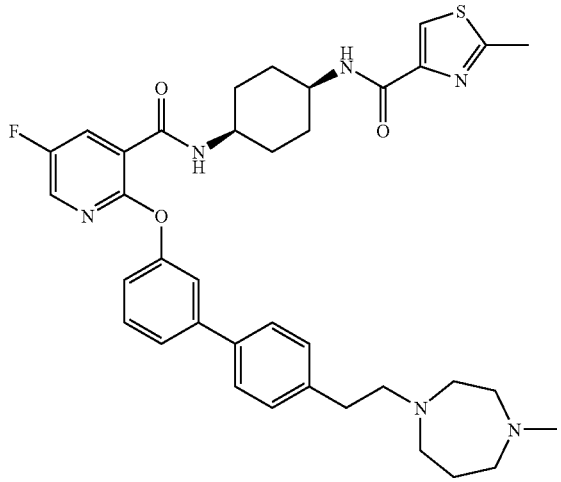

To a microwave tube was charged 2-(3'-(5-fluoro-3-(((1s,4s)-4-(2-methylthiazole-4-carboxamido)cyclohexylcarbamoyl)pyridin-2-yloxy)biphenyl-4-yl)ethyl methanesulfonate (100 mg, 0.15 mmol), 1-methyl-1,4-diazepane (0.057 mL, 0.46 mmol) and acetonitrile (1 mL). The reaction was heated to 80° C. for 1 h and the reaction mixture was purified by HPLC to afford the title compound as a white solid. Yield: 18 mg $^1$H NMR (400 MHz, CDCl$_3$) δ 8.47 (d, J=7.2 Hz, 1H), 8.11 (d, J=3.1 Hz, 1H), 8.06 (d, J=7.9 Hz, 1H), 7.96 (s, 1H), 7.79 (d, J=7.91 Hz, 1H), 7.57 (d, J=8.2 Hz, 2H), 7.50-7.46 (m, 2H), 7.43-7.40 (m, 1H), 7.31 (d, J=8.2 Hz, 2H), 7.19-7.13 (m, 1H), 4.17-4.09 (m, 1H), 4.01-3.93 (m, 1H), 3.71 (s, 3H), 3.57-3.43 (m, 4H), 3.42-3.34 (m, 2H), 3.09-3.00 (m, 2H), 2.95 (s, 3H), 2.33-2.23 (m, 2H), 2.61 (s, 3H), 1.92-1.78 (m, 6H), 1.77-1.65 (m, 2H).

MS: [M+H]+=671.3 (calc=671.3179) (MultiMode+)

EXAMPLE 88

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-4-methylthiazole-2-carboxamide

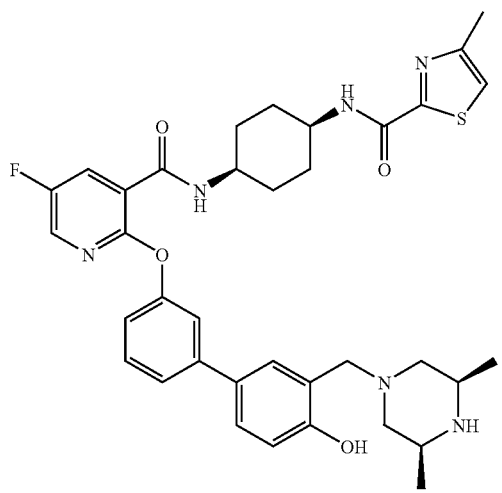

Under an atmosphere of nitrogen and at RT, to a solution of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (0.07 g, 0.13 mmol) in dry DCE (1 mL) was slowly added trimethylaluminum (0.192 mL, 0.38 mmol) (2M in heptane). After being stirred at RT for 15 min (Caution! methane gas is produced), ethyl 4-methylthiazole-2-carboxylate (0.022 g, 0.13 mmol) was added. The mixture was then stirred in a microwave (CEM Discover) at 80° C. for 1 h. The reaction was then carefully quenched by the addition of aqueous HCl (1M, 10 mL) followed by dilution with DCM (20 mL). The organic phase was then dried over MgSO$_4$ and then concentrated to give the crude amide. The crude amide was redissolved in methanol and purified by preparative HPLC on a Phenomenex Gemini column using a 95-5% gradient of aqueous 0.1% TFA in acetonitrile as eluent. The fractions containing the desired compound were freeze dried to afford the title compound as a white solid. Yield: 10 mg $^1$H NMR (500 MHz, DMSO) δ 8.31 (d, J=7.1 Hz, 1H), 8.26 (d, J=3.1 Hz, 1H), 8.07-8.03 (m, 2H), 7.59 (s, 2H), 7.49-7.44 (m, 2H), 7.37 (s, 1H), 7.14 (d, J=13.9 Hz, 1H), 4.01-3.98 (m, 1H), 3.88-3.84 (m, 1H), 3.37 (s, 2H), 2.66-2.62 (m, 2H), 2.50-2.50 (m, 7H), 2.41 (s, 3H), 2.38-2.35 (m, 1H), 1.83-1.79 (m, 4H), 1.69-1.66 (m, 4H), 1.18 (d, J=6.4 Hz, 6H).

MS: [M+H]+=673.2 (calc=673.2972) (MultiMode+)

EXAMPLE 89

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-6-methylpicolinamide

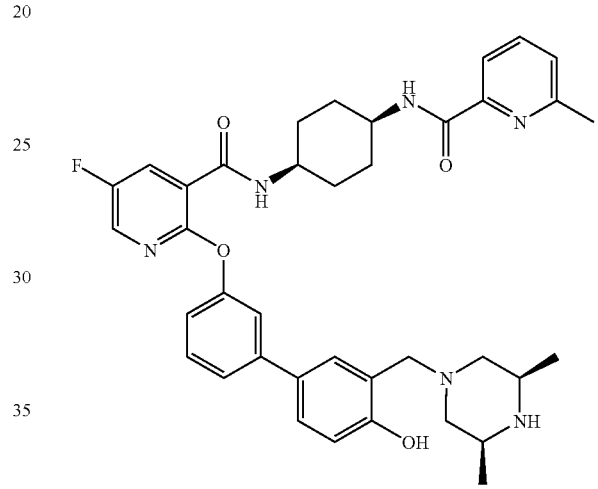

To a suspension of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (147 mg, 0.25 mmol) in acetonitrile (4 mL) was added 6-methylpicolinic acid (34.5 mg, 0.25 mmol) and triethylamine (0.351 mL, 2.52 mmol). On addition of triethylamine the reaction mixture became a homogeneous solution. 1-Propanephosphonic acid cyclic anhydride, 1.57M solution in THF (0.168 mL, 0.26 mmol) was then added and the mixture stirred at RT for 2 h. The mixture was evaporated to dryness and the residue dissolved in DCM (15 mL) and washed with saturated NaHCO$_3$ (aq), brine, dried (MgSO$_4$) and evaporated to give a foam. This was purified by preparative HPLC to afford the title compound. Yield: 43 mg $^1$H NMR (400 MHz, CD$_3$OD) δ 8.10 (d, J=3.1 Hz, 1H), 8.06 (dd, J=7.9, 3.1 Hz, 1H), 7.86-7.76 (m, 2H), 7.58-7.48 (m, 2H), 7.46-7.42 (m, 2H), 7.39-7.34 (m, 2H), 7.15-7.10 (m, 1H), 6.90 (d, J=8.5 Hz, 1H), 4.19 (s, 2H), 4.17-4.11 (m, 1H), 4.03-3.94 (m, 1H), 3.67-3.56 (m, 2H), 3.51 (d, J=12.8 Hz, 2H), 2.78 (t, J=12.3 Hz, 2H), 2.47 (s, 3H), 1.91-1.82 (m, 6H), 1.79-1.68 (m, 2H), 1.33 (d, J=6.4 Hz, 6H).

MS: [M+H]+=667 (calc=667.3408) (MultiMode+)

EXAMPLE 90

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-2-isopropylthiazole-4-carboxamide

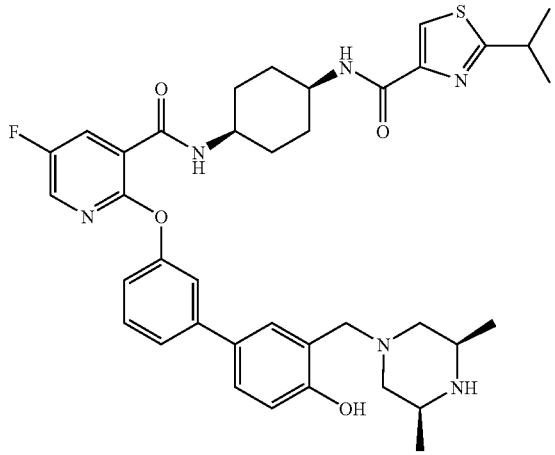

To a suspension of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (150 mg, 0.26 mmol) in acetonitrile (4 mL) was added 2-isopropylthiazole-4-carboxylic acid (44.0 mg, 0.26 mmol) and triethylamine (0.358 mL, 2.57 mmol). On addition of triethylamine, the reaction mixture became a homogeneous solution. 1-Propanephosphonic acid cyclic anhydride, 1.57M solution in THF (0.172 mL, 0.27 mmol) was then added and the mixture stirred at RT for 2 h. The mixture was evaporated to dryness and the residue dissolved in DCM (15 mL) and washed with saturated $NaHCO_3$ (aq), brine, dried ($MgSO_4$) and evaporated to give a foam. This was purified by preparative HPLC to afford the title compound. Yield: 15 mg $^1$H NMR (400 MHz, $CD_3OD$) δ 8.48 (d, J=7.4 Hz, 1H), 8.12-7.97 (m, 3H), 7.52-7.40 (m, 4H), 7.36 (s, 1H), 7.14-7.09 (m, 1H), 6.89 (d, J=8.2 Hz, 1H), 4.17-4.10 (m, 1H), 4.03 (s, 2H), 4.00-3.92 (m, 1H), 3.56-3.47 (m, 2H), 3.37 (d, J=13.1 Hz, 2H), 2.56 (t, J=12.3 Hz, 2H), 1.91-1.78 (m, 6H), 1.78-1.65 (m, 2H), 1.38-1.25 (m, 12H).

MS: [M+H]+=701.2 (calc=701.3285) (MultiMode+)

EXAMPLE 91

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-5,6,7,8-tetrahydroimidazo[1,2-a]pyridine-2-carboxamide

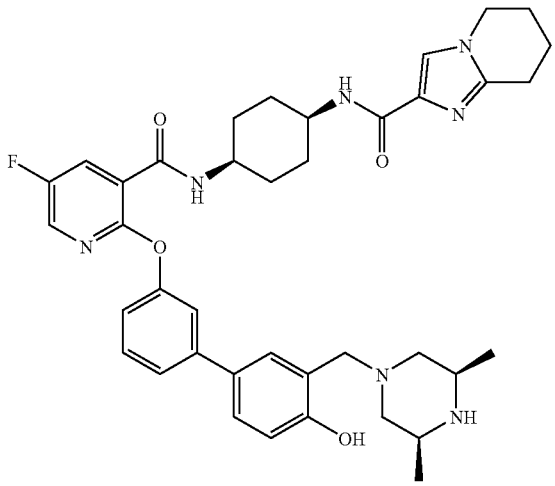

To a solution of 5,6,7,8-tetrahydroimidazo[1,2-a]pyridine-2-carboxylic acid (28.4 mg, 0.17 mmol) in acetonitrile (5 mL) was added DIPEA (0.057 mL, 0.34 mmol) and HATU (65.1 mg, 0.17 mmol). The mixture was allowed to stir at RT for 10 min before a solution of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (100 mg, 0.17 mmol) in acetonitrile (5 mL) with DIPEA (0.057 mL, 0.34 mmol) was added and the mixture stirred at RT for 30 mins. The reaction mixture was diluted in EtOAc (10 mL), washed with water, brine, dried ($MgSO_4$) and evaporated to give a foam. This was purified by preparative HPLC to afford the title compound as a white solid. Yield: 31 mg $^1$H NMR (400 MHz, $CD_3OD$) δ 8.42 (d, J=6.9 Hz, 1H), 8.11-8.06 (m, 2H), 7.75 (s, 1H), 7.57-7.42 (m, 4H), 7.38 (s, 1H), 7.15-7.08 (m, 1H), 6.92 (d, J=8.5 Hz, 1H), 4.16-4.07 (m, 5H), 3.98-3.89 (m, 1H), 3.62-3.52 (m, 2H), 3.44 (d, J=12.8 Hz, 2H), 2.95 (t, J=6.2 Hz, 2H), 2.67 (t, J=12.6 Hz, 2H), 2.10-1.64 (m, 12H), 1.32 (d, J=6.7 Hz, 6H).

MS: [M+H]+=696.4 (calc=696.3673) (MultiMode+)

EXAMPLE 92

2-(3'-(((3S,5R)-3,5-dimethylpiperazin-1-yl)methyl)-4'-hydroxybiphenyl-3-yloxy)-5-fluoro-N-((1s,4s)-4-(1-methyl-5-(trifluoromethyl)-1H-pyrazole-3-carboxamido)cyclohexyl)nicotinamide

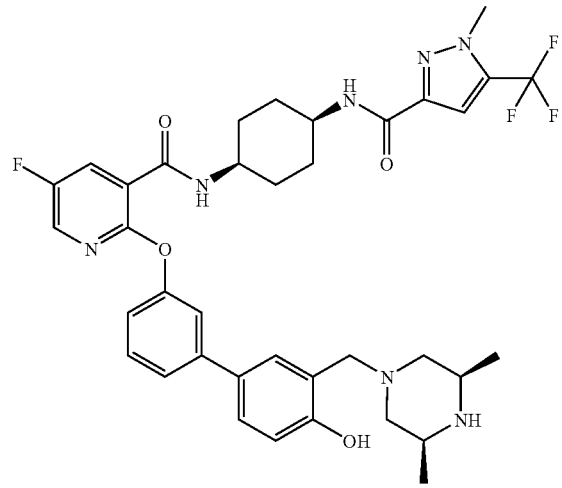

To a solution of 1-methyl-5-(trifluoromethyl)-1H-pyrazole-3-carboxylic acid (33.2 mg, 0.17 mmol) in acetonitrile (5 mL) was added DIPEA (0.057 mL, 0.34 mmol) and HATU (65.1 mg, 0.17 mmol). The mixture was allowed to stir at RT for 10 min before a solution of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (100 mg, 0.17 mmol) in acetonitrile (5 mL) with DIPEA (0.057 mL, 0.34 mmol) was added and the mixture stirred at RT for 30 mins. The reaction mixture was diluted in EtOAc (25 mL), washed with water, brine, dried ($MgSO_4$) and evaporated to give a yellow oil. This was purified by preparative HPLC to afford the title compound as a white solid. Yield: 55 mg ¹H NMR (400 MHz, CD₃OD) δ 8.14-8.04 (m, 2H), 7.58-7.47 (m, 4H), 7.38 (s, 1H), 7.15-7.11 (m, 1H), 7.06 (s, 1H), 6.92 (d, J=8.2 Hz, 1H), 4.18 (s, 2H), 4.17-4.11 (m, 1H), 3.98-3.90 (m, 4H), 3.66-3.56 (m, 2H), 3.52 (d, J=13.3 Hz, 2H), 2.79 (t, J=12.6 Hz, 2H), 1.96-1.76 (m, 6H), 1.75-1.63 (m, 2H), 1.33 (d, J=6.4 Hz, 6H).

MS: [M+H]+=724.3 (calc=724.3234) (MultiMode+)

EXAMPLE 93

N-((1s,4s)-4-(5-fluoro-2-(4'-(3-(piperazin-1-yl)propyl)biphenyl-3-yloxy)nicotinamido)cyclohexyl)-5-methylimidazo[1,2-a]pyridine-2-carboxamide

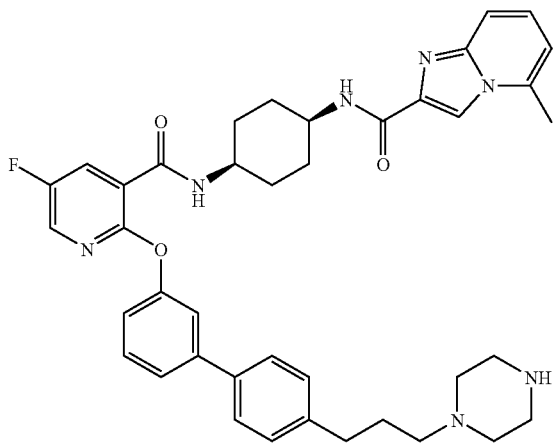

Step (a) N-((1s,4s)-4-(5-fluoro-2-(4'-(3-hydroxypropyl)biphenyl-3-yloxy)nicotinamido)cyclohexyl)-5-methylimidazo[1,2-a]pyridine-2-carboxamide Palladium(II) acetate (5.49 mg, 0.02 mmol) and 2-dicyclohexylphosphino-2',6'-dimethoxy-1,1'-biphenyl (S-Phos) (0.020 g, 0.05 mmol) were stirred in acetonitrile (1.5 mL) for 15 min, then a solution of potassium carbonate (0.203 g, 1.47 mmol) in water (3.00 mL) added, followed by 4-(3-hydroxypropyl)phenylboronic acid (0.106 g, 0.59 mmol) and a solution of N-((1s,4s)-4-(5-fluoro-2-(3-iodophenoxy)nicotinamido)cyclohexyl)-5-methylimidazo[1,2-a]pyridine-2-carboxamide (0.300 g, 0.49 mmol) in acetonitrile (2.000 mL). The reaction mixture was heated at 70° C. for 18 h then stood at RT for 3 days. The reaction mixture was diluted with EtOAc and washed with water and saturated brine. The organic was dried over sodium sulfate, filtered and evaporated to afford crude product. This was purified by flash silica chromatography (Combi-Flash Companion, Biotage SNAP 100 g column), elution gradient 0 to 10% EtOAc in isohexane. Pure fractions were evaporated to dryness to afford the sub-title compound as a pale yellow foam. Yield: 0.219 g ¹H NMR (400 MHz, CDCl₃) δ 8.38 (dd, J=8.2, 3.1 Hz, 1H), 8.12-8.04 (m, 3H), 7.56-7.46 (m, 4H), 7.41-7.36 (m, 2H), 7.33 (d, J=7.9 Hz, 1H), 7.23-7.12 (m, 4H), 6.67 (d, J=6.8 Hz, 1H), 4.30-4.12 (m, 2H), 3.68 (dd, J=11.7, 6.3 Hz, 2H), 2.74-2.67 (m, 2H), 2.60 (s, 3H), 1.99-1.82 (m, 8H), 1.76-1.67 (m, 2H).

MS: [M+H]+=622.2 (calc=622.2829) (MultiMode+)

Step (b) 3-(3'-(5-fluoro-3-((1s,4s)-4-(5-methylimidazo[1,2-a]pyridine-2-carboxamido)cyclohexylcarbamoyl)pyridin-2-yloxy)biphenyl-4-yl)propyl methanesulfonate Methanesulfonyl chloride (0.048 mL, 0.62 mmol) and pyridine (0.050 mL, 0.62 mmol) were added to a stirred solution of N-((1s,4s)-4-(5-fluoro-2-(4'-(3-hydroxypropyl)biphenyl-3-yloxy)nicotinamido)cyclohexyl)-5-methylimidazo[1,2-a]pyridine-2-carboxamide (0.192 g, 0.31 mmol) in DCM (5 mL). The reaction mixture was stirred at RT overnight then diluted with DCM and washed with water and saturated brine. The organic was dried over sodium sulfate, filtered and evaporated to afford the crude sub-title compound as a pale yellow oil which was used in the next step without further purification. Yield: 0.25 g

[M+H]+=700 (MultiMode+)

Step (c) N-((1s,4s)-4-(5-fluoro-2-(4'-(3-(piperazin-1-yl)propyl)biphenyl-3-yloxy)nicotinamido)cyclohexyl)-5-methylimidazo[1,2-a]pyridine-2-carboxamide A mixture of 3-(3'-(5-fluoro-3-((1s,4s)-4-(5-methylimidazo[1,2-a]pyridine-2-carboxamido)cyclohexylcarbamoyl)pyridin-2-yloxy)biphenyl-4-yl)propyl methanesulfonate (0.108 g, 0.15 mmol) and tert-butyl piperazine-1-carboxylate (0.086 g, 0.46 mmol) in acetonitrile (1.2 mL) was heated to 80° C. in a microwave for 30 min. Further amine (60 mg) was added and the reaction mixture was subjected to the same conditions for a further 2 h. The volatiles were evaporated and the residue dissolved in DCM (0.5 mL). TFA (0.5 mL, 6.49 mmol) was added and the reaction mixture stirred overnight. The volatiles were evaporated and the crude product was purified by preparative HPLC on a Phenomenex Gemini column using a 95-5% gradient of aqueous 0.2% TFA in acetonitrile as eluent. The fractions containing the desired compound were evaporated to dryness to afford the title compound as a white solid. Yield: 101 mg ¹H NMR (400 MHz, CD₃OD) δ 8.49-8.36 (m, 2H), 8.13-8.05 (m, 2H), 7.73-7.56 (m, 2H), 7.54-7.44 (m, 4H), 7.42-7.39 (m, 1H), 7.23 (d, J=8.2 Hz, 2H), 7.18-7.11 (m, 2H), 4.19-4.01 (m, 2H), 3.50-2.89 (m, 10H), 2.74-2.64 (m, 5H), 2.06-1.72 (m, 10H).

MS: [M+H]+=690.3 (calc=690.3568) (MultiMode+)

EXAMPLE 94

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)-1H-benzo[d]imidazole-4-carboxamide

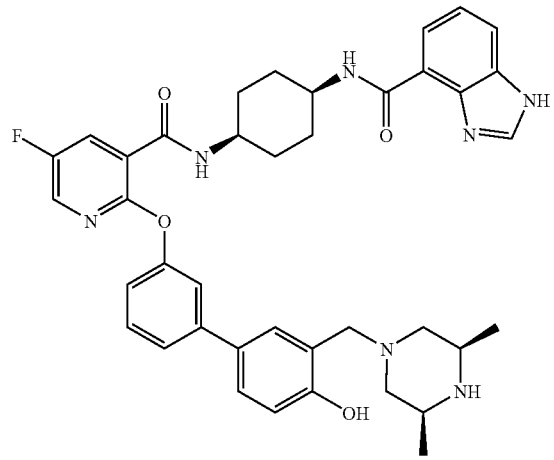

To a solution of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (100 mg, 0.17 mmol) in dry DMF (5 mL) under nitrogen was added DIPEA (0.057 mL, 0.34 mmol) at RT. The solution was stirred until homogeneous. To this solution was added dropwise a solution of 1H-benzo[d]imidazole-4-carboxylic acid (27.8 mg, 0.17 mmol) and 1,1'-carbonyldiimidazole (27.8 mg, 0.17 mmol) in dry DMF (5 mL) under nitrogen which had been allowed to stir at 40° C. for 1 h. The reaction mixture was allowed to stir at 50° C. overnight. The mixture was evaporated to dryness and the residue dissolved in chloroform (15 mL) and washed with saturated NaHCO$_3$ (aq), water, dried (MgSO$_4$) and evaporated to give a yellow oil. This was purified by preparative HPLC to afford the title compound. Yield: 36.5 mg $^1$H NMR (400 MHz, CD$_3$OD) δ 8.69 (s, 1H), 8.49 (d, J=6.9 Hz, 1H), 8.12-8.07 (m, 2H), 7.91 (d, J=7.7 Hz, 1H), 7.84 (d, J=8.2 Hz, 1H), 7.52-7.41 (m, 6H), 7.38 (s, 1H), 7.16-7.10 (m, 1H), 6.87 (d, J=8.5 Hz, 1H), 4.21-4.09 (m, 2H), 4.07 (s, 2H), 3.62-3.49 (m, 2H), 3.41 (d, J=12.8 Hz, 2H), 2.65 (t, J=12.4 Hz, 2H), 1.99-1.74 (m, 8H), 1.30 (d, J=6.7 Hz, 6H).

MS: [M+H]+=692.3 (calc=692.336) (MultiMode+)

EXAMPLE 95

2-(3'-(((3S,5R)-3,5-dimethylpiperazin-1-yl)methyl)-4'-hydroxybiphenyl-3-yloxy)-5-fluoro-N-((1s,4s)-4-(2-hydroxy-5-methylbenzamido)cyclohexyl)nicotinamide

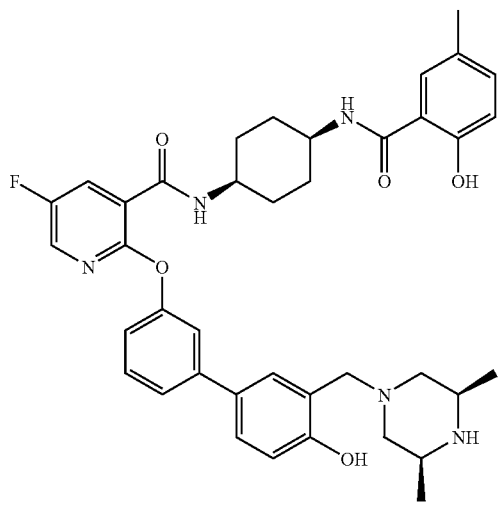

To a solution of 2-hydroxy-5-methylbenzoic acid (29.4 mg, 0.19 mmol) in THF (1 mL) was added HOBt (29.6 mg, 0.19 mmol) and EDCI (30.9 mg, 0.16 mmol) the mixture was stirred for 10 min at RT. This mixture was then added to a solution of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide (100 mg, 0.16 mmol) and triethylamine (0.090 mL, 0.64 mmol) in THF (1 mL) and N-methyl-2-pyrrolidinone (1 mL). The reaction mixture was stirred at RT overnight. A further aliquot of 0.5 eq of the phenol, EDCI and HOBt was preformed and then added the reaction mixture. The reaction mixture was evaporated to dryness and the residue dissolved in DCM (15 mL) and washed with saturated NaHCO$_3$ (aq), water, dried (MgSO$_4$) and evaporated to give a yellow oil. This was purified by preparative HPLC to afford the title compound. Yield: 33.5 mg $^1$H NMR (400 MHz, CD$_3$OD) δ 8.46 (d, J=7.0 Hz, 1H), 8.11 (d, J=3.1 Hz, 1H), 8.07 (dd, J=7.9, 3.1 Hz, 1H), 7.54-7.52 (m, 1H), 7.51-7.40 (m, 4H), 7.36-7.34 (m, 1H), 7.16-7.08 (m, 2H), 6.88 (d, J=8.2 Hz, 1H), 6.74 (d, J=8.2 Hz, 1H), 4.16-4.09 (m, 1H), 4.04 (s, 2H), 4.01-3.93 (m, 1H), 3.58-3.48 (m, 2H), 3.39 (d, J=11.3 Hz, 2H), 2.59 (t, J=12.4 Hz, 2H), 2.22 (s, 3H), 1.90-1.80 (m, 6H), 1.79-1.67 (m, 2H), 1.30 (d, J=6.4 Hz, 6H).

MS: [M+H]+=682.3 (calc=682.3404) (MultiMode+)

EXAMPLE 96

N-((1s,4s)-4-(2-(4'-(((3S,5R)-3,5-dimethylpiperazin-1-yl)methyl)-3'-hydroxybiphenyl-3-yloxy)-5-fluoronicotinamido)cyclohexyl)-5-methylimidazo[1,2-a]pyridine-2-carboxamide

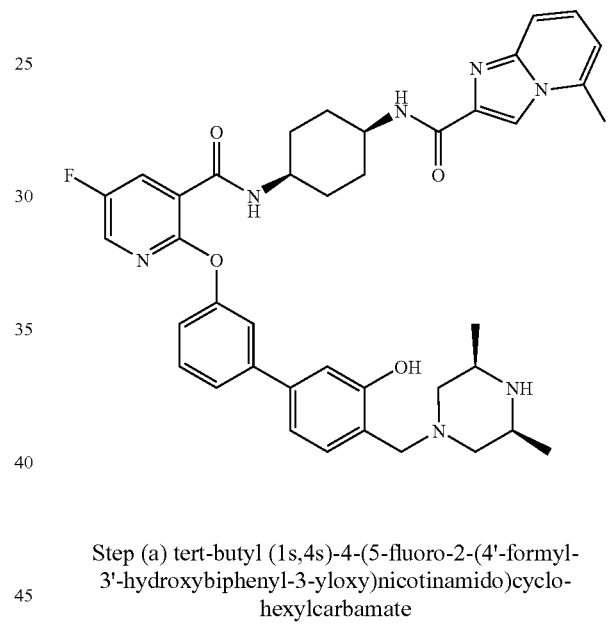

Step (a) tert-butyl (1s,4s)-4-(5-fluoro-2-(4'-formyl-3'-hydroxybiphenyl-3-yloxy)nicotinamido)cyclohexylcarbamate To a solution of tert-butyl (1s,4s)-4-(5-fluoro-2-(3-(4,4,5,5-tetramethyl-1,3,2-dioxaborolan-2-yl)phenoxy)nicotinamido)cyclohexylcarbamate (700 mg, 1.26 mmol) in THF (11.900 mL) was added 4-bromo-2-hydroxybenzaldehyde (500 mg, 2.49 mmol), sodium carbonate (0.158 mL, 3.78 mmol) and water (5.95 mL). Tetrakis(triphenylphosphine)palladium(0) (29 mg, 0.03 mmol) was then added and the mixture was heated to 80° C. for 24 h. The reaction was diluted with EtOAc, washed with brine, dried (MgSO$_4$) and evaporated to give a crude material. This was purified using column chromatography to give the sub-title compound as a foam. Yield: 0.5 g $^1$H NMR (400 MHz, CDCl$_3$) δ 11.11 (s, 1H), 9.94 (s, 1H), 8.38 (dd, J=8.2, 3.1 Hz, 1H), 8.07 (d, J=3.1 Hz, 1H), 7.96 (d, J=7.2 Hz, 1H), 7.64 (d, J=8.2 Hz, 1H), 7.61-7.56 (m, 2H), 7.42 (t, J=1.4 Hz, 1H), 7.28-7.19 (m, 3H), 4.42-4.34 (m, 1H), 4.21-4.15 (m, 1H), 3.65-3.59 (m, 1H), 1.88-1.67 (m, 6H), 1.54-1.46 (m, 2H), 1.41 (s, 9H).

MS: [M−H]−=548 (MultiMode−)

Step (b) tert-butyl (1s,4s)-4-(2-(4'-(((3S,5R)-3,5-dimethylpiperazin-1-yl)methyl)-3'-hydroxybiphenyl-3-yloxy)-5-fluoronicotinamido)cyclohexylcarbamate To a solution of tert-butyl (1s,4s)-4-(5-fluoro-2-(4'-formyl-3'-hydroxybiphenyl-3-yloxy)nicotinamido)cyclohexylcarbamate (500 mg, 0.91 mmol) in DCM (10 mL) was added cis-2,6-dimethylpiperazine (156 mg, 1.36 mmol). The mixture was stirred at RT for 20 min before sodium triacetoxyborohydride (289 mg, 1.36 mmol) was added. The mixture was stirred at RT overnight. The reaction mixture was evaporated and the residue dissolved in EtOAc. The EtOAc layer was washed with water, brine, dried (MgSO$_4$) and evaporated to give a solid. This was purified by column chromatography (eluent=5% 7N NH$_3$ in methanol/DCM) to give the sub-title compound as a foam. Yield: 430 mg $^1$H NMR (400 MHz, CDCl$_3$) δ 8.37 (dd, J=8.2, 3.1 Hz, 1H), 8.07 (d, J=3.1 Hz, 1H), 8.04 (d, J=7.4 Hz, 1H), 7.54-7.50 (m, 2H), 7.36-7.34 (m, 1H), 7.13-7.10 (m, 1H), 7.06-7.00 (m, 3H), 4.39-4.33 (m, 1H), 4.20-4.14 (m, 1H), 3.73 (s, 2H), 3.63-3.58 (m, 1H), 3.02-2.94 (m, 2H), 2.91-2.87 (m, 2H), 1.86-1.67 (m, 8H), 1.50-1.44 (m, 2H), 1.41 (s, 9H), 1.07 (d, J=6.4 Hz, 6H).

MS: [M+H]+=648 (MultiMode+)

Step (c) N-((1s,4s)-4-aminocyclohexyl)-2-(4'-(((3S,5R)-3,5-dimethylpiperazin-1-yl)methyl)-3'-hydroxybiphenyl-3-yloxy)-5-fluoronicotinamide hydrochloride To a solution of tert-butyl (1s,4s)-4-(2-(4'-(((3S,5R)-3,5-dimethylpiperazin-1-yl)methyl)-3'-hydroxybiphenyl-3-yloxy)-5-fluoronicotinamido)cyclohexylcarbamate (0.4 g, 0.62 mmol) in DCM (6 mL) was added hydrogen chloride, 4.0M solution in dioxane (1.544 mL, 6.17 mmol). The mixture was stirred at RT overnight. The mixture was evaporated to dryness and the residue triturated with ether to give a solid which was isolated by filtration to give the sub-title compound as a white solid. Yield: 478 mg MS: [M+H]+=548 (MultiMode+)

Step (d) N-((1s,4s)-4-(2-(4'-(((3S,5R)-3,5-dimethylpiperazin-1-yl)methyl)-3'-hydroxybiphenyl-3-yloxy)-5-fluoronicotinamido)cyclohexyl)-5-methylimidazo[1,2-a]pyridine-2-carboxamide To a solution of 5-methylimidazo[1,2-a]pyridine-2-carboxylic acid (40.2 mg, 0.23 mmol) in acetonitrile (3 mL) was added DIPEA (0.040 mL, 0.23 mmol) To this mixture was then added HATU (87 mg, 0.23 mmol). The mixture was stirred at RT for 10 min before it was added to a solution of N-((1s,4s)-4-aminocyclohexyl)-2-(4'-(((3S,5R)-3,5-dimethylpiperazin-1-yl)methyl)-3'-hydroxybiphenyl-3-yloxy)-5-fluoronicotinamide hydrochloride (150 mg, 0.23 mmol) and DIPEA (0.040 mL, 0.23 mmol) in acetonitrile (3 mL). The mixture was stirred at RT overnight. 1 mL water and 1 mL acetic acid was then added to the mixture and this was then purified using reverse phase prep HPLC (eluent=TFA(aq)/MeCN), the appropriate fractions were combined and evaporated to give a residue. This was triturated with ether to afford the title compound as a solid which was isolated by filtration and dried overnight under vacuum at 40° C. Yield: 103 mg $^1$H NMR (400 MHz, CDCl$_3$) δ 8.31 (dd, J=8.2, 3.1 Hz, 1H), 8.25 (s, 1H), 8.11-8.05 (m, 2H), 7.75 (d, J=9.2 Hz, 1H), 7.60-7.56 (m, 1H), 7.52-7.45 (m, 2H), 7.37 (t, J=3.7 Hz, 1H), 7.27 (d, J=8.2 Hz, 1H), 7.17-7.11 (m, 3H), 6.98 (d, J=6.9 Hz, 1H), 4.24-4.17 (m, 4H), 3.74-3.67 (m, 2H), 3.41-3.33 (m, 2H), 3.23-3.15 (m, 2H), 2.72 (s, 3H), 1.96-1.78 (m, 8H), 1.36 (d, J=6.7 Hz, 6H).

MS: [M+H]+=706.3 (calc=706.3517) (MultiMode+)

EXAMPLE 97

N-((1s,4s)-4-(2-(4'-(((3S,5R)-3,5-dimethylpiperazin-1-yl)methyl)-3'-hydroxybiphenyl-3-yloxy)-5-fluoronicotinamido)cyclohexyl)pyrazolo[1,5-a]pyridine-2-carboxamide

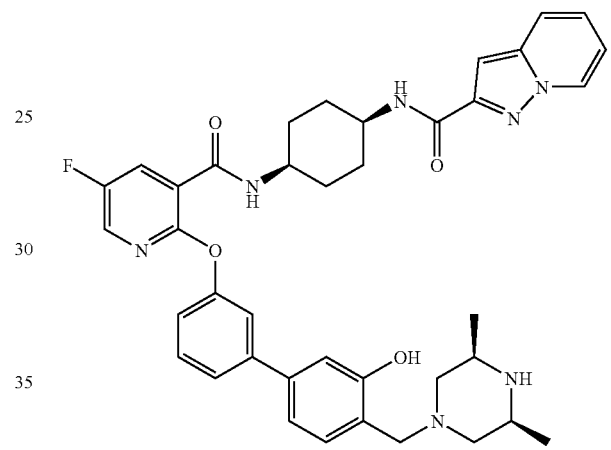

To a solution of pyrazolo[1,5-a]pyridine-2-carboxylic acid (30.8 mg, 0.19 mmol) in acetonitrile (3 mL) was added DIPEA (0.066 mL, 0.38 mmol). To this mixture was then added HATU (72.3 mg, 0.19 mmol). The mixture was stirred at RT for 10 min before it was added to a solution of N-((1s,4s)-4-aminocyclohexyl)-2-(4'-(((3S,5R)-3,5-dimethylpiperazin-1-yl)methyl)-3'-hydroxybiphenyl-3-yloxy)-5-fluoronicotinamide, hydrochloride (125 mg, 0.19 mmol) and DIPEA (0.066 mL, 0.38 mmol) in acetonitrile (3 mL). The mixture was stirred at RT overnight. 1 mL water and 1 mL acetic acid was then added to the mixture before being purified using reverse phase preparative HPLC (eluent=TFA(aq)/MeCN). The appropriate fractions were combined and evaporated to give a residue. This was triturated with ether to give the title compound as a solid which was isolated by filtration and dried overnight under vacuum at 40° C. Yield: 96 mg $^1$H NMR (400 MHz, CD$_3$OD) δ 8.48 (d, J=7.4 Hz, 1H), 8.43 (d, J=7.2 Hz, 1H), 8.12 (d, J=3.1 Hz, 1H), 8.06 (dd, J=7.9, 3.1 Hz, 1H), 7.66 (d, J=9.0 Hz, 1H), 7.51-7.43 (m, 2H), 7.40-7.37 (m, 1H), 7.25-7.17 (m, 3H), 7.10-7.07 (m, 2H), 6.97-6.93 (m, 2H), 4.17-4.11 (m, 1H), 4.07 (s, 1H), 4.04-3.99 (m, 1H), 3.58-3.51 (m, 2H), 3.45-3.40 (m, 2H), 2.64 (t, J=12.6 Hz, 2H), 1.92-1.70 (m, 8H), 1.31 (d, J=6.4 Hz, 6H).

MS: [M+H]+=692.2 (calc=692.336) (MultiMode+)

EXAMPLE 98

N-((1s,4s)-4-(2-(4'-(((3S,5R)-3,5-dimethylpiperazin-1-yl)methyl)-3'-hydroxybiphenyl-3-yloxy)-5-fluoronicotinamido)cyclohexyl)-2-methylthiazole-4-carboxamide

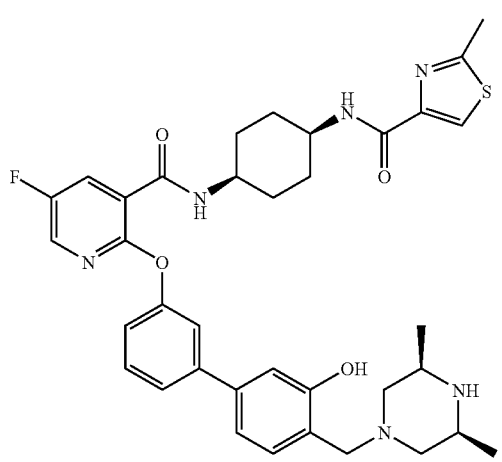

To a solution of 2-methylthiazole-4-carboxylic acid (27.2 mg, 0.19 mmol) in acetonitrile (3.00 mL) was added DIPEA (0.066 mL, 0.38 mmol). To this mixture was then added HATU (72.3 mg, 0.19 mmol). The mixture was stirred at RT for 10 min before it was added to a solution of N-((1s,4s)-4-aminocyclohexyl)-2-(4'-(((3S,5R)-3,5-dimethylpiperazin-1-yl)methyl)-3'-hydroxybiphenyl-3-yloxy)-5-fluoronicotinamide, hydrochloride (125 mg, 0.19 mmol) and DIPEA (0.066 mL, 0.38 mmol) in acetonitrile (3 mL). The mixture was stirred at RT overnight. 1 mL of 7N $NH_3$ in methanol was added to the reaction and then left to stir for 2 h. 1 mL water and 1 mL acetic acid was then added to the mixture and this was then purified using reverse phase prep HPLC (eluent=TFA(aq)/MeCN), the appropriate fractions were combined and evaporated to give a residue. This was triturated with ether to afford the title compound as a solid which was isolated by filtration and dried overnight under vacuum at 40° C. Yield: 84 mg $^1$H NMR (400 MHz, $CD_3OD$) δ 8.47 (d, J=7.2 Hz, 1H), 8.11 (d, J=3.1 Hz, 1H), 8.05 (dd, J=7.9, 3.1 Hz, 1H), 7.96 (s, 1H), 7.80 (d, J=9.0 Hz, 1H), 7.51-7.43 (m, 2H), 7.37 (t, J=1.8 Hz, 1H), 7.28 (d, J=7.7 Hz, 1H), 7.18 (dt, J=7.9, 1.8 Hz, 1H), 7.11-7.08 (m, 2H), 4.14-4.11 (m, 1H), 4.09 (s, 2H), 4.00-3.94 (m, 1H), 3.58-3.51 (m, 2H), 3.43 (d, J=13.3 Hz, 2H), 2.67-2.60 (m, 5H), 1.88-1.67 (m, 8H), 1.32 (d, J=6.7 Hz, 6H).

MS: [M+H]+=673.2 (calc=673.2972) (MultiMode+)

EXAMPLE 99

N-((1s,4s)-4-(2-(4'-(2-((3S,5R)-3,5-dimethylpiperazin-1-yl)ethyl)biphenyl-3-yloxy)-5-fluoronicotinamido)cyclohexyl)quinoxaline-2-carboxamide

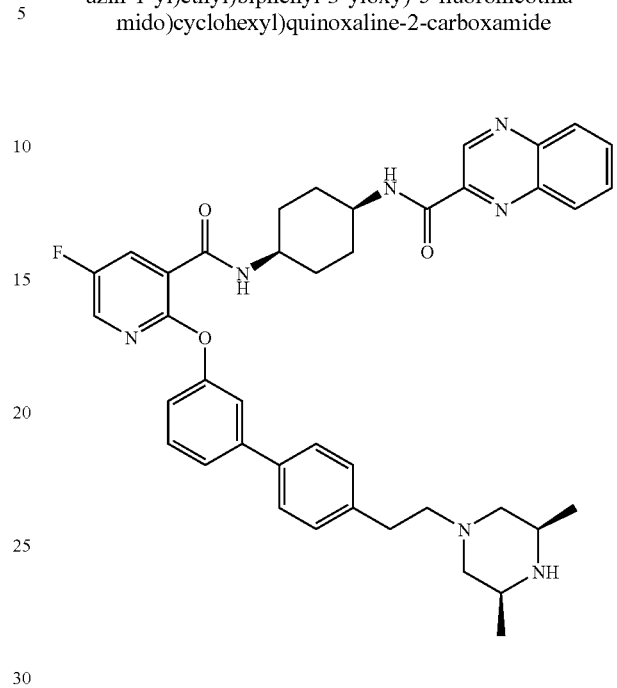

Step (a) N-((1s,4s)-4-(5-fluoro-2-(3-iodophenoxy)nicotinamido)cyclohexyl)quinoxaline-2-carboxamide To a suspension of N-((1s,4s)-4-aminocyclohexyl)-5-fluoro-2-(3-iodophenoxy)nicotinamide (2.56 g, 5.21 mmol) in acetonitrile (100 mL) was added quinoxaline-2-carboxylic acid (0.907 g, 5.21 mmol) and triethylamine (7.26 mL, 52.06 mmol). On addition of triethylamine the reaction mixture became a homogeneous solution. 1-Propanephosphonic acid cyclic anhydride, 1.57M solution in THF (3.48 mL, 5.47 mmol) was then added and the mixture stirred at RT for 2 h. The mixture was evaporated to dryness and the residue dissolved in DCM (150 mL) and washed with saturated $NaHCO_3$ (aq), brine, dried ($MgSO_4$) and evaporated to give the sub-title compound as a light brown foam. Yield: 3.08 g $^1$H NMR (400 MHz, $CDCl_3$) δ 9.67 (s, 1H), 8.37 (dd, J=8.1, 3.2 Hz, 1H), 8.22-8.18 (m, 1H), 8.11-8.07 (m, 2H), 7.95 (d, J=6.9 Hz, 1H), 7.91-7.85 (m, 3H), 7.64-7.59 (m, 1H), 7.59-7.56 (m, 1H), 7.20-7.14 (m, 2H), 4.33-4.24 (m, 1H), 4.24-4.13 (m, 1H), 2.07-1.82 (m, 6H), 1.80-1.67 (m, 2H).

MS: [M+H]+=612 (MultiMode+).

Step (b) N-((1s,4s)-4-(5-fluoro-2-(3-(4,4,5,5-tetramethyl-1,3,2-dioxaborolan-2-yl)phenoxy)nicotinamido)cyclohexyl)quinoxaline-2-carboxamide 1,1'-Bis(diphenylphosphino)ferrocene (0.046 g, 0.08 mmol) and 1,1'-bis(diphenylphosphino)ferrocene-palladium(II)dichloride DCM complex (0.067 g, 0.08 mmol) were stirred in dry dimethylsulfoxide (10 mL) under nitrogen for 10 min. Potassium acetate (0.482 g, 4.91 mmol), N-((1s,4s)-4-(5-fluoro-2-(3-iodophenoxy)nicotinamido)cyclohexyl)quinoxaline-2-carboxamide (1 g, 1.64 mmol) and 4,4,4',4',5,5,5',5'-octamethyl-2,2'-bi(1,3,2-dioxaborolane) (0.552 g, 2.18 mmol) were added and the reaction was heated at 80° C. overnight. The reaction was cooled and diluted with water (100 mL). The suspension was stirred at RT for 30 mins, then the precipitate was filtered off. The precipitate was dissolved in DCM, dried (MgSO$_4$) and the solvent removed to give a brown oil. The crude material was purified by Biotage (eluant=neat EtOAc) to give the sub-title compound as a brown oil after evaporation. Yield: 0.492 g Step (c) N-((1s,4s)-4-(5-fluoro-2-(4'-(2-hydroxyethyl)biphenyl-3-yloxy)nicotinamido)cyclohexyl)quinoxaline-2-carboxamide N-((1s,4s)-4-(5-fluoro-2-(3-(4,4,5,5-tetramethyl-1,3,2-dioxaborolan-2-yl)phenoxy)nicotinamido)cyclohexyl)quinoxaline-2-carboxamide (485 mg, 0.79 mmol), 2-(4-bromophenyl)ethanol (0.111 mL, 0.79 mmol) and sodium carbonate (681 mg, 2.38 mmol) were added to THF (6 mL) and degassed water (3 mL) under nitrogen. Tetrakis(triphenylphosphine)palladium(0) (18 mg, 0.02 mmol) was then added and the reaction mixture was heated at reflux for 2 h. The mixture was poured onto water and extracted into EtOAc (×2). The extractions were combined, washed with brine, dried (MgSO$_4$) and evaporated to give a yellow oil. The crude material was purified by Biotage (eluent=3% methanol/DCM) to give the sub-title compound as a white foam after evaporation. Yield: 223 mg
$^1$H NMR (400 MHz, CDCl$_3$) δ 9.51 (s, 1H), 8.39 (dd, J=8.2, 3.3 Hz, 1H), 8.23-8.19 (m, 1H), 8.16-8.13 (m, 1H), 8.10 (d, J=3.1 Hz, 1H), 7.96 (dd, J=8.2, 1.5 Hz, 1H), 7.89-7.76 (m, 2H), 7.70 (d, J=7.8 Hz, 1H), 7.51 (t, J=7.8 Hz, 1H), 7.42-7.34 (m, 4H), 7.17-7.11 (m, 3H), 4.36-4.27 (m, 1H), 4.14-4.05 (m, 1H), 3.88 (t, J=6.3 Hz, 2H), 2.83 (t, J=6.3 Hz, 2H), 2.09-1.85 (m, 8H).
MS: [M+H]+=606 (MultiMode+)

Step (d) 2-(3'-(5-fluoro-3-((1s,4s)-4-(quinoxaline-2-carboxamido)cyclohexylcarbamoyl)pyridin-2-yloxy)biphenyl-4-yl)ethyl methanesulfonate To solution of N-((1s,4s)-4-(5-fluoro-2-(4'-(2-hydroxyethyl)biphenyl-3-yloxy)nicotinamido)cyclohexyl)quinoxaline-2-carboxamide (0.265 g, 0.44 mmol) and pyridine (0.124 mL, 1.53 mmol) in DCM (10 mL), was added methanesulfonyl chloride (0.119 mL, 1.53 mmol) and the reaction stirred at RT for 48 h. The reaction was evaporated to give a residue which was partitioned between EtOAc and 2M HCl(aq). The EtOAc layer was then washed with another aliquot of 2M HCl(aq), 2× sat NaHCO$_3$ (aq), brine, dried (MgSO$_4$) and evaporated to give a light yellow oil. This was triturated with ether to afford the sub-title compound as an off-white solid. Yield: 248 mg
$^1$H NMR (400 MHz, CD$_3$OD) δ 9.41 (s, 1H), 8.15-8.07 (m, 3H), 8.02-7.99 (m, 1H), 7.95-7.84 (m, 2H), 7.50-7.42 (m, 5H), 7.21-7.17 (m, 3H), 4.35 (t, J=6.8 Hz, 2H), 4.22-4.15 (m, 1H), 4.08-4.00 (m, 1H), 2.93 (s, 3H), 2.01-1.73 (m, 10H).
MS: [M+H]+=684 (MultiMode+)

Step (e) N-((1s,4s)-4-(2-(4'-(2-((3S,5R)-3,5-dimethylpiperazin-1-yl)ethyl)biphenyl-3-yloxy)-5-fluoronicotinamido)cyclohexyl)quinoxaline-2-carboxamide To a microwave tube was charged 2-(3'-(5-fluoro-3-((1s,4s)-4-(quinoxaline-2-carboxamido)cyclohexylcarbamoyl)pyridin-2-yloxy)biphenyl-4-yl)ethyl methanesulfonate (100 mg, 0.15 mmol), (2R,6S)-2,6-dimethylpiperazine (50.1 mg, 0.44 mmol) and acetonitrile (1 mL). The reaction was heated to 80° C. for 30 mins. The reaction mixture was purified by HPLC to give the title compound as a white solid. Yield: 52 mg
$^1$H NMR (400 MHz, CDCl$_3$) δ 9.40 (s, 1H), 8.51 (d, J=6.9 Hz, 1H), 8.29 (d, J=7.4 Hz, 1H), 8.15-8.05 (m, 3H), 8.01 (d, J=8.5 Hz, 1H), 7.95-7.83 (m, 2H), 7.51-7.39 (m, 5H), 7.19-7.11 (m, 3H), 4.23-4.14 (m, 1H), 4.07-3.98 (m, 1H), 3.67-3.55 (m, 4H), 3.15-3.07 (m, 2H), 2.96-2.88 (m, 2H), 2.75 (t, J=12.9 Hz, 2H), 2.02-1.71 (m, 8H), 1.37 (d, J=6.4 Hz, 6H).
MS: [M+H]+=702.5 (calc=702.3568) (MultiMode+)

EXAMPLE 100

N-((1s,4s)-4-(5-fluoro-2-(3'-(piperazin-1-ylmethyl)biphenyl-3-yloxy)nicotinamido)cyclohexyl)-5-methylimidazo[1,2-a]pyridine-2-carboxamide

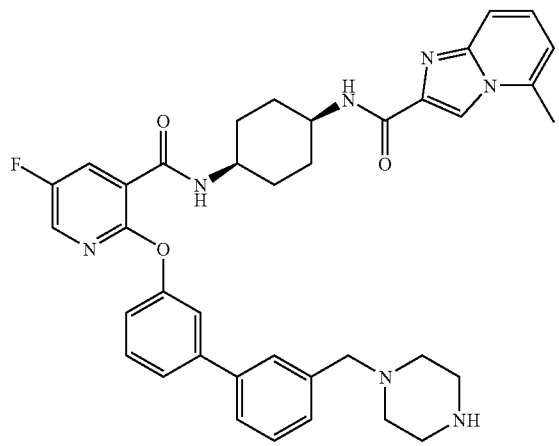

Step (a) N-((1s,4s)-4-(5-fluoro-2-(3'-formylbiphenyl-3-yloxy)nicotinamido)cyclohexyl)-5-methylimidazo[1,2-a]pyridine-2-carboxamide Palladium(II) acetate (7.32 mg, 0.03 mmol) was added to a suspension of 2-dicyclohexylphosphino-2',6'-dimethoxy-1,1'-biphenyl (S-Phos) (0.027 g, 0.07 mmol) in acetonitrile (6 mL). The mixture was stirred at RT under nitrogen for 1 h. A solution of potassium carbonate (0.270 g, 1.96 mmol) in water (3.00 mL) was added, followed by a mixture of N-((1s,4s)-4-(5-fluoro-2-(3-iodophenoxy)nicotinamido)cyclohexyl)-5-methylimidazo[1,2-a]pyridine-2-carboxamide (0.400 g, 0.65 mmol) and 3-formylphenylboronic acid (0.147 g, 0.98 mmol). The mixture was heated at 80° C. overnight then concentrated, diluted with EtOAc and water and filtered to remove palladium residues. The layers were separated and the organic layer washed with water and saturated brine. The organic was dried over sodium sulfate, filtered and evaporated. The crude product was purified by flash silica chromatography (Combi-Flash Companion, 50 g Biotage SNAP), elution gradient 0 to 5% methanol in EtOAc. Pure fractions were evaporated to dryness to afford the sub-title compound as a cream-coloured foam. Yield: 0.341 g
MS: [M+H]+=592 (MultiMode+)

Step (b) N-((1s,4s)-4-(5-fluoro-2-(3'-formylbiphenyl-3-yloxy)nicotinamido)cyclohexyl)-5-methylimidazo[1,2-a]pyridine-2-carboxamide Tert-Butyl piperazine-1-carboxylate (0.071 g, 0.38 mmol) was added to a solution of N-((1s,4s)-4-(5-fluoro-2-(3'- formylbiphenyl-3-yloxy)nicotinamido)cyclohexyl)-5-methylimidazo[1,2-a]pyridine-2-carboxamide (0.113 g, 0.19 mmol) in DCM (2 mL). After 40 min sodium triacetoxyborohydride (0.061 g, 0.29 mmol) was added and the mixture stirred overnight. Methanol (1 mL) was added, then the mixture partitioned between EtOAc and water. The organic layer was washed with saturated brine and dried over sodium sulfate then concentrated. DCM (1 mL) was added, followed slowly by TFA (1 mL, 12.98 mmol). The mixture was stirred for 4 h then concentrated and the crude product was purified by preparative HPLC on a Phenomenex Gemini column using a 95-5% gradient of aqueous 0.1% TFA in methanol as eluent. The fractions containing the desired compound were evaporated to dryness to afford the title compound as a white solid. Yield: 120 mg $^1$H NMR (400 MHz, CD$_3$OD) δ 8.48-8.44 (m, 2H), 8.11-8.07 (m, 2H), 7.75-7.70 (m, 1H), 7.63-7.60 (m, 2H), 7.56 (d, J=8.3 Hz, 1H), 7.50 (d, J=5.3 Hz, 2H), 7.45-7.44 (m, 1H), 7.39-7.32 (m, 2H), 7.21-7.17 (m, 2H), 4.17-4.11 (m, 1H), 4.07-4.02 (m, 1H), 3.90-3.85 (m, 2H), 2.97-2.91 (m, 4H), 2.73-2.72 (m, 3H), 1.97-1.75 (m, 8H).

MS: [M+H]+=662.5 (calc=662.3255) (MultiMode+)

EXAMPLE 101

N-((1s,4s)-4-(2-(3'-(((3R,5S)-3,5-dimethylpiperazin-1-yl)methyl)-4'-hydroxybiphenyl-3-yloxy)-5-fluoronicotinamido)cyclohexyl)-4,5,6,7-tetrahydropyrazolo[1,5-a]pyridine-2-carboxamide

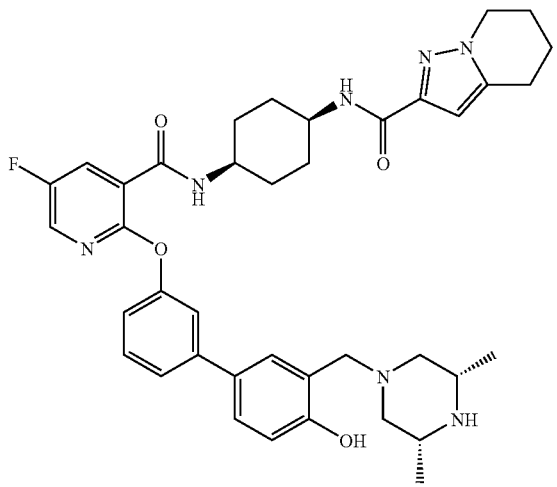

EDCI (0.046 g, 0.24 mmol) was added to a solution of 4,5,6,7-tetrahydropyrazolo[1,5-a]pyridine-2-carboxylic acid (0.040 g, 0.24 mmol) and HOBt (0.037 g, 0.24 mmol) in DMF (2 mL) and stirred for 15 min. A solution of N-((1s,4s)-4-aminocyclohexyl)-2-(3'-(((3R,5S)-3,5-dimethylpiperazin-1-yl)methyl)-4'-hydroxybiphenyl-3-yloxy)-5-fluoronicotinamide (0.12 g, 0.22 mmol) and triethylamine (0.061 mL, 0.44 mmol) in DMF (2 mL) was added and the reaction stirred for a further 20 h. 7M NH$_3$/MeOH (1 mL) added and stirred for 2 h. Acidified with 2M HCl and purified by reverse phase HPLC with aqTFA/MeCN as eluent to afford the title compound as a white solid. Yield: 143 mg $^1$H NMR (400 MHz, DMSO) δ 8.33 (d, J=7.2 Hz, 1H), 8.25 (d, J=3.4 Hz, 1H), 8.05 (m, 1H), 7.68 (m, 1H), 7.58 (m, 1H), 7.48 (m, 2H), 7.40 (m, 1H), 7.27 (d, J=8.1 Hz, 1H), 7.14 (m, 1H), 7.00 (d, J=8.5 Hz, 1H), 6.34 (s, 1H), 4.18 (m, 2H), 4.01 (m, 4H), 3.84 (m, 2H), 3.62-3.45 (m, 5H), 2.89-2.76 (m, 2H), 2.74 (t, J=7.1 Hz, 2H), 1.96 (m, 2H), 1.81-1.60 (m, 8H), 1.24 (d, J=6.6 Hz, 6H).

MS: APCI (+ve):696 (M+1)

EXAMPLE 102

N-((1s,4s)-4-(1,5-dimethyl-1H-pyrazole-3-carboxamido)cyclohexyl)-5-fluoro-2-(3'-(2-(piperazin-1-yl)ethyl)biphenyl-3-yloxy)nicotinamide

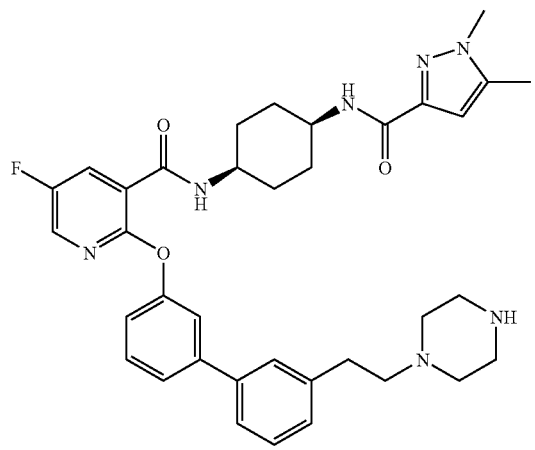

Step (a) N-((1s,4s)-4-(1,5-dimethyl-1H-pyrazole-3-carboxamido)cyclohexyl)-5-fluoro-2-(3'-(2-hydroxyethyl)biphenyl-3-yloxy)nicotinamide To a solution of N-((1s,4s)-4-(1,5-dimethyl-1H-pyrazole-3-carboxamido)cyclohexyl)-5-fluoro-2-(3-iodophenoxy)nicotinamide (0.5 g, 0.87 mmol), 3-(2-hydroxyethyl)phenylboronic acid (0.144 g, 0.87 mmol) and sodium carbonate (0.109 mL, 2.60 mmol) in THF (4 mL) and water (2 mL) was added tetrakis(triphenylphosphine)palladium(0) (0.020 g, 0.02 mmol). The mixture was heated to 80° C. overnight. The reaction mixture was cooled, diluted with EtOAc and washed with water. The organic layer was dried (MgSO$_4$), filtered and evaporated to give a residue. The crude material was purified using column chromatography (eluent=5% MeOH/DCM) to give the sub-title compound as a white foam. Yield: 320 mg $^1$H NMR (400 MHz, CD$_3$OD) δ 8.11 (d, J=3.1 Hz, 1H), 8.07 (dd, J=7.9, 3.1 Hz, 1H), 7.50-7.47 (m, 2H), 7.45-7.43 (m, 2H), 7.41 (d, J=7.9 Hz, 1H), 7.29 (t, J=7.6 Hz, 1H), 7.19 (d, J=7.7 Hz, 1H), 7.16-7.13 (m, 1H), 6.40 (s, 1H), 4.14-4.10 (m, 1H), 3.96-3.92 (m, 1H), 3.75 (t, J=6.9 Hz, 2H), 3.68 (s, 3H), 2.83 (t, J=6.9 Hz, 2H), 2.25 (s, 3H), 1.90-1.78 (m, 6H), 1.72-1.64 (m, 2H).

MS: [M+H]+=572 (MultiMode+)

Step (b) 2-(3'-(3-((1s,4s)-4-(1,5-dimethyl-1H-pyrazole-3-carboxamido)cyclohexylcarbamoyl)-5-fluoropyridin-2-yloxy)biphenyl-3-yl)ethyl methanesulfonate To a solution of N-((1s,4s)-4-(1,5-dimethyl-1H-pyrazole-3-carboxamido)cyclohexyl)-5-fluoro-2-(3'-(2-hydroxyethyl)biphenyl-3-yloxy)nicotinamide (0.32 g, 0.56 mmol) in DCM (5 mL) was added pyridine (0.091 mL, 1.12 mmol) and then methanesulfonyl chloride (0.091 mL, 1.18 mmol). The mixture was stirred at RT for 18 h. The mixture was diluted with DCM and washed with 2M HCl(aq), sat. NaHCO$_3$ (aq), brine, dried (MgSO$_4$) and evaporated to give the sub-title compound as a white foam. Yield: 312 mg $^1$H NMR (400 MHz, CDCl$_3$) δ 8.38 (dd, J=8.2, 3.1 Hz, 1H), 8.08-8.04 (m, 2H), 7.57-7.46 (m, 3H), 7.44-7.43 (m, 1H), 7.39-7.34 (m, 2H), 7.23 (d, J=7.7 Hz, 1H), 7.17 (dt, J=7.6, 1.9 Hz, 1H), 6.67 (d, J=7.4 Hz, 1H), 6.50 (s, 1H), 4.44 (t, J=6.9 Hz, 2H), 4.26-4.20 (m, 1H), 4.10-4.04 (m, 1H), 3.67 (s, 3H), 3.10 (t, J=6.9 Hz, 2H), 2.88 (s, 3H), 2.25 (s, 3H), 1.94-1.78 (m, 6H), 1.67-1.58 (m, 2H).
MS: [M−H]−=647.6 (MultiMode−)

Step (c) N-((1s,4s)-4-(1,5-dimethyl-1H-pyrazole-3-carboxamido)cyclohexyl)-5-fluoro-2-(3'-(2-(piperazin-1-yl)ethyl)biphenyl-3-yloxy)nicotinamide To a microwave vial was charged 2-(3'-(3-((1s,4s)-4-(1,5-dimethyl-1H-pyrazole-3-carboxamido)cyclohexylcarbamoyl)-5-fluoropyridin-2-yloxy)biphenyl-3-yl)ethyl methanesulfonate (100 mg, 0.15 mmol), tert-butyl piperazine-1-carboxylate (86 mg, 0.46 mmol) and acetonitrile (1 mL). The mixture was heated at 80° C. for 45 min. The mixture was evaporated and dissolved in DCM (2 mL) and then TFA (2 mL) was added. The mixture was evaporated and the residue dissolved in methanol and purified using reverse phase preparative HPLC (eluent=TFA(aq)/MeCN), the appropriate fractions were combined, evaporated to give a residue that was dissolved in the minimum amount of DCM and then precipitated using isohexane. The solvents were removed in vacuo to give the title compound which was dried overnight at 40° C. under vacuum. Yield: 73 mg $^1$H NMR (400 MHz, CD$_3$OD) δ 8.46 (d, J=6.9 Hz, 1H), 8.12 (d, J=3.1 Hz, 1H), 8.06 (dd, J=7.9, 3.1 Hz, 1H), 7.51-7.45 (m, 4H), 7.43 (s, 1H), 7.34 (t, J=7.9 Hz, 1H), 7.25-7.21 (m, 1H), 7.19-7.15 (m, 1H), 6.41 (s, 1H), 4.16-4.09 (m, 1H), 3.97-3.90 (m, 1H), 3.69 (s, 3H), 3.45-3.40 (m, 4H), 3.30-3.24 (m, 4H), 3.17-3.10 (m, 2H), 3.02-2.95 (m, 2H), 2.25 (s, 3H), 1.88-1.78 (m, 6H), 1.74-1.64 (m, 2H).
MS: [M+H]+=640 (calc=640) (MultiMode+)

EXAMPLE 103

N-((1s,4s)-4-(1,5-dimethyl-1H-pyrazole-3-carboxamido)cyclohexyl)-2-(3'-(2-((3S,5R)-3,5-dimethylpiperazin-1-yl)ethyl)biphenyl-3-yloxy)-5-fluoronicotinamide

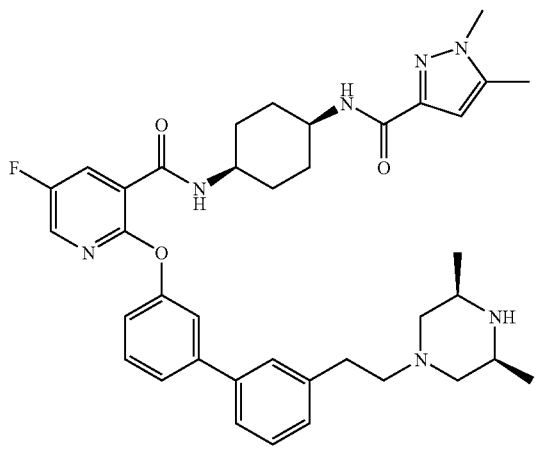

To a microwave vial was charged 2-(3'-(3-((1s,4s)-4-(1,5-dimethyl-1H-pyrazole-3-carboxamido)cyclohexylcarbamoyl)-5-fluoropyridin-2-yloxy)biphenyl-3-yl)ethyl methanesulfonate (100 mg, 0.15 mmol), (2S,6R)-2,6-dimethylpiperazine (52.7 mg, 0.46 mmol) and acetonitrile (1 mL). The mixture was heated to 80° C. for 20 min. The mixture was purified using reverse phase prep HPLC (eluent=TFA/MeCN), the appropriate fractions were combined, evaporated and the residue triturated with ether to give the title compound as a colourless solid which was dried overnight at 40° C. under vacuum. Yield: 78 mg $^1$H NMR (400 MHz, CD$_3$OD) δ 8.46 (d, J=8.2 Hz, 1H), 8.11 (d, J=3.1 Hz, 1H), 8.06 (dd, J=7.9, 3.1 Hz, 1H), 7.51-7.46 (m, 4H), 7.43-7.42 (m, 1H), 7.36-7.31 (m, 1H), 7.23 (d, J=7.7 Hz, 1H), 7.19-7.15 (m, 1H), 6.40 (s, 1H), 4.15-4.08 (m, 1H), 3.91 (s, 1H), 3.69 (s, 3H), 3.58-3.53 (m, 4H), 3.14-3.07 (m, 2H), 3.01-2.94 (m, 2H), 2.64 (t, J=12.9 Hz, 2H), 2.25 (s, 3H), 1.87-1.77 (m, 6H), 1.73-1.64 (m, 2H), 1.35 (d, J=6.4 Hz, 6H).
MS: [M+H]+=668.3 (calc=668.3724) (MultiMode+)

EXAMPLE 104

N-((1s,4s)-4-(2-(4'-(3-((3S,5R)-3,5-dimethylpiperazin-1-yl)propyl)biphenyl-3-yloxy)-5-fluoronicotinamido)cyclohexyl)-5,6,7,8-tetrahydroimidazo[1,2-a]pyridine-2-carboxamide

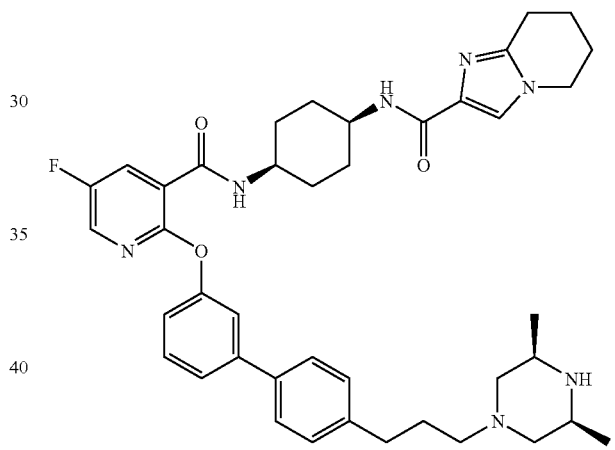

Step (a) N-((1s,4s)-4-(5-fluoro-2-(4'-(3-hydroxypropyl)biphenyl-3-yloxy)nicotinamido)cyclohexyl)-4,5,6,7-tetrahydropyrazolo[1,5-a]pyridine-2-carboxamide A stirred mixture of 4-(3-hydroxypropyl)phenylboronic acid (345 mg, 1.91 mmol), N-((1s,4s)-4-(5-fluoro-2-(3-iodophenoxy)nicotinamido)cyclohexyl)-5,6,7,8-tetrahydroimidazo[1,2-a]pyridine-2-carboxamide (825 mg, 1.37 mmol) and sodium carbonate (435 mg, 4.10 mmol) in THF (16 mL) and water (8 mL) was degassed for 5 min, treated with tetrakis(triphenylphosphine)palladium(0) (32 mg, 0.03 mmol) and heated under reflux overnight. The solution was diluted with water and extracted with EtOAc (2×). The extracts were washed with brine, dried (Na$_2$SO$_4$) and evaporated. The residue was purified on 25 g silica cartridge using a gradient of acetone in isohexane as eluent to give the sub-title compound as a white foam. Yield: 351 mg $^1$H NMR (300 MHz, CDCl$_3$) δ 8.40-8.35 (m, 1H), 8.09-8.04 (m, 2H), 7.70-7.59 (m, 2H), 7.54-7.49 (m, 4H), 7.39-7.35 (m, 2H), 7.26-7.24 (m, 1H), 7.17-7.12 (m, 1H), 6.95-6.90 (m, 1H), 4.27-4.17 (m, 1H), 4.13-4.03 (m, 1H), 3.98-

3.94 (m, 1H), 3.76-3.66 (m, 3H), 2.81-2.71 (m, 4H), 2.02-1.78 (m, 12H), 1.70-1.61 (m, 2H).

Step (b) 3-(3'-(5-fluoro-3-((1s,4s)-4-(5,6,7,8-tetrahydroimidazo[1,2-a]pyridine-2-carboxamido)cyclohexylcarbamoyl)pyridin-2-yloxy)biphenyl-4-yl)propyl methanesulfonate A stirred solution of N-((1s,4s)-4-(5-fluoro-2-(4'-(3-hydroxypropyl)biphenyl-3-yloxy)nicotinamido)cyclohexyl)-5,6,7,8-tetrahydroimidazo[1,2-a]pyridine-2-carboxamide (351 mg, 0.57 mmol), pyridine (0.139 mL, 1.72 mmol) and DMAP (7.01 mg, 0.06 mmol) in DCM (20 mL) was treated with methanesulfonyl chloride (0.134 mL, 1.72 mmol) and stirred overnight. The mixture was treated with more DMAP (7.01 mg, 0.06 mmol), followed by pyridine (0.139 mL, 1.72 mmol) followed by methanesulfonyl chloride (0.134 mL, 1.72 mmol) and stirred for 3 h. The mixture was treated with more DMAP (7.01 mg, 0.06 mmol), followed by pyridine (0.139 mL, 1.72 mmol) followed by methanesulfonyl chloride (0.134 mL, 1.72 mmol) and stirred and heated under reflux 2 h. The mixture was diluted with DCM, washed successively with 0.1M aqueous potassium hydrogen sulphate solution followed by 1M aqueous sodium bicarbonate solution followed by brine, was dried ($Na_2SO_4$) and evaporated. The residue was stirred under ether for 3 h and filtered. The solid was washed with ether and dried to give the sub-title compound as a yellow powder. Yield: 283 mg $^1$H NMR (300 MHz, $CDCl_3$) δ 8.59-8.51 (m, 1H), 8.26 (dd, J=8.3, 3.1 Hz, 1H), 8.08-8.03 (m, 2H), 7.68 (d, J=8.1 Hz, 1H), 7.59 (d, J=8.3 Hz, 2H), 7.52-7.44 (m, 3H), 7.25-7.22 (m, 1H), 6.94-6.91 (m, 1H), 4.26-4.09 (m, 6H), 3.20 (t, J=6.2 Hz, 2H), 2.99 (s, 3H), 2.78 (t, J=7.5 Hz, 3H), 2.16-1.80 (m, 14H).

Step (c) N-((1s,4s)-4-(2-(4'-(3-((3S,5R)-3,5-dimethylpiperazin-1-yl)propyl)biphenyl-3-yloxy)-5-fluoronicotinamido)cyclohexyl)-5,6,7,8-tetrahydroimidazo[1,2-a]pyridine-2-carboxamide A stirred solution of 3-(3'-(5-fluoro-3-((1s,4s)-4-(5,6,7,8-tetrahydroimidazo[1,2-a]pyridine-2-carboxamido)cyclohexylcarbamoyl)pyridin-2-yloxy)biphenyl-4-yl)propyl methanesulfonate (282 mg, 0.38 mmol) and (2S,6R)-2,6-dimethylpiperazine (217 mg, 1.90 mmol) in acetonitrile (3 mL) was heated at 80° C. in a microwave for 20 min. The solution was concentrated to a low volume and purified by reversed phase preparative HPLC on Gemini-NX C18 5 micron 110 A 30×100 mm Axia column, using a gradient of methanol in 0.1% aqueous TFA at 30 mL/min as eluent to give the title compound as a white powder. Yield: 240 mg $^1$H NMR (400 MHz, DMSO) δ 8.38 (d, J=6.7 Hz, 1H), 8.25 (d, J=3.1 Hz, 1H), 8.22-8.15 (m, 1H), 8.02 (dd, J=7.9, 3.1 Hz, 1H), 7.97-7.93 (m, 1H), 7.60 (d, J=8.2 Hz, 2H), 7.53-7.50 (m, 2H), 7.44-7.43 (m, 1H), 7.31 (d, J=8.5 Hz, 2H), 7.19-7.16 (m, 1H), 4.08-4.05 (m, 2H), 3.97-3.84 (m, 2H), 3.53-3.39 (m, 4H), 2.87 (t, J=6.2 Hz, 2H), 2.68-2.63 (m, 2H), 2.54-2.46 (m, 5H), 1.95-1.70 (m, 14H), 1.22 (d, J=6.4 Hz, 6H).

MS: [M+H]+=708.5 (calc=708.4037) (MultiMode+)

EXAMPLE 105

N-((1s,4s)-4-(2-(4'-(((2-(dimethylamino)ethyl)(methyl)amino)methyl)biphenyl-3-yloxy) 5-fluoronicotinamido)cyclohexyl)-5,6,7,8-tetrahydroimidazo[1,2-a]pyridine-2-carboxamide

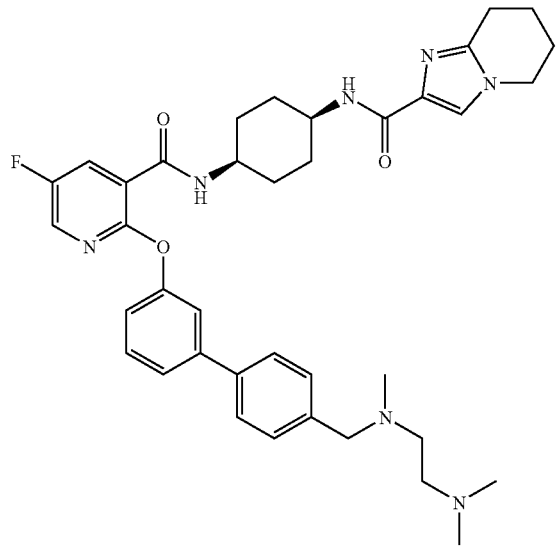

Step (a) N-((1s,4s)-4-(5-fluoro-2-(4'-formylbiphenyl-3-yloxy)nicotinamido)cyclohexyl)-5,6,7,8-tetrahydroimidazo[1,2-a]pyridine-2-carboxamide Palladium(II) acetate (3.72 mg, 0.02 mmol) was added to a suspension of 2-dicyclohexylphosphino-2',6'-dimethoxy-1,1'-biphenyl (S-Phos) (0.014 g, 0.03 mmol) in acetonitrile (2.210 mL). The mixture was stirred at RT under nitrogen for 1 h. A solution of potassium carbonate (0.137 g, 0.99 mmol) in water (1.105 mL) was added, followed by a mixture of N-((1s,4s)-4-(5-fluoro-2-(3-iodophenoxy)nicotinamido)cyclohexyl)-5,6,7,8-tetrahydroimidazo[1,2-a]pyridine-2-carboxamide (0.2 g, 0.33 mmol) and 4-formylphenylboronic acid (0.075 g, 0.50 mmol). The mixture was heated at 80° C. overnight. The solution was concentrated, diluted with EtOAc and water. The layers were separated and the organic layer washed with water and saturated brine. The organic was dried ($MgSO_4$), filtered and concentrated. The resulting solid was purified on silica (Biotage, 50 g) eluting with 7% methanol in EtOAc. Product containing fractions were combined and concentrated to leave the sub-title compound as a pale brown foam. Yield: 0.11 g MS: [M–H]-=580 (MultiMode+)

Step (b) N-((1s,4s)-4-(2-(4'-(((2-(dimethylamino)ethyl)(methyl)amino)methyl)biphenyl-3-yloxy)-5-fluoronicotinamido)cyclohexyl)-5,6,7,8-tetrahydroimidazo[1,2-a]pyridine-2-carboxamide N-((1s,4s)$_{1-4}$-(5-fluoro-2-(4'-formylbiphenyl-3-yloxy)nicotinamido)cyclohexyl)-5,6,7,8-tetrahydroimidazo[1,2-a]pyridine-2-carboxamide (0.11 g, 0.19 mmol) and N1,N1,N2-trimethylethane-1,2-diamine (0.024 mL, 0.19 mmol) were stirred in methanol (2 mL) at RT. Acetic acid (0.016 mL, 0.28 mmol) was added and the reaction stirred for 30 min. Sodium triacetoxyborohydride (0.200 g, 0.95 mmol) was then added and the reaction left to stir under nitrogen for 3 h. The mixture was diluted with EtOAc and washed with saturated NaHCO$_3$ (aq) solution (×2), dried (MgSO$_4$) and evaporated to give a yellow solid (0.12 g). The crude product was purified by preparative HPLC on a Waters X-Bridge column using a 95-5% gradient of aqueous 0.2% TFA in acetonitrile as eluent. The fractions containing the desired compound were freeze dried to afford the title compound as a white solid. Yield: 36 mg $^1$H NMR (400 MHz, DMSO) δ 8.21 (d, J=4.0 Hz, 1H), 8.12 (d, J=12.8 Hz, 1H), 8.00-7.96 (m, 1H), 7.70 (s, 1H), 7.64 (d, J=9.2 Hz, 2H), 7.61-7.57 (m, 1H), 7.50-7.44 (m, 6H), 7.21-7.16 (m, 1H), 4.02 (t, J=5.8 Hz, 4H), 3.84 (s, 3H), 3.32-3.28 (m, 4H), 2.95 (t, J=6.1 Hz, 2H), 2.81-2.76 (m, 3H), 2.64 (s, 1H), 2.37 (s, 3H), 1.97-1.84 (m, 5H), 1.79-1.67 (m, 8H).

MS: [M+H]+=668.5 (calc=668.3724) (MultiMode+)

EXAMPLE 106

N-((1s,4s)-4-(1,5-dimethyl-1H-pyrazole-3-carboxamido)cyclohexyl)-2-(3'-(((3S,5R)-3,5-dimethylpiperazin-1-yl)methyl)-2'-methoxybiphenyl-3-yloxy)-5-fluoronicotinamide

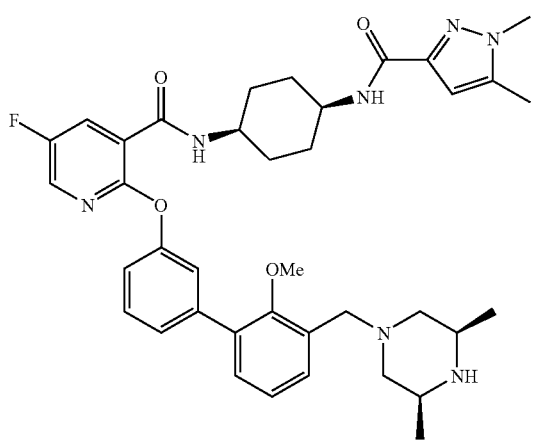

Step (a) N-((1s,4s)-4-(1,5-dimethyl-1H-pyrazole-3-carboxamido)cyclohexyl)-5-fluoro-2-(3'-formyl-2'-methoxybiphenyl-3-yloxy)nicotinamide A solution of potassium carbonate (0.215 g, 1.56 mmol) in water (5 mL), N-((1s,4s)-4-(1,5-dimethyl-1H-pyrazole-3-carboxamido)cyclohexyl)-5-fluoro-2-(3-iodophenoxy)nicotinamide (0.3 g, 0.52 mmol) and 3-formyl-2-methoxyphenylboronic acid (0.112 g, 0.62 mmol) were added sequentially to a stirred solution of palladium(II) acetate (0.012 g, 0.05 mmol) and S-Phos (0.042 g, 0.10 mmol) in acetonitrile (7 mL) and heated at 70° C. for 1 h. The mixture was cooled to RT, extracted with EtOAc, washed with water and brine, dried (MgSO$_4$), filtered and evaporated in vacuo. The residue was purified by chromatography on silica with 40% EtOAc/isohexane as eluent to give the sub-title compound as a brown foam. Yield: 290 mg $^1$H NMR (300 MHz, CDCl$_3$) δ 10.36 (s, 1H), 8.38 (m, 1H), 8.08 (m, 2H), 7.84 (m, 2H), 7.63 (m, 1H), 7.58 (t, J=8.0 Hz, 1H), 7.49 (m, 2H), 7.24 (m, 1H), 6.66 (d, J=8.3 Hz, 1H), 6.51 (s, 1H), 4.24 (m, 1H), 4.04 (m, 1H), 3.69 (s, 3H), 3.55 (s, 3H), 2.27 (s, 3H), 1.98-1.81 (m, 8H).

MS: APCI (+ve):586 (M+1).

Step (b) N-((1s,4s)-4-(1,5-dimethyl-1H-pyrazole-3-carboxamido)cyclohexyl)-2-(3'-(((3S,5R)-3,5-dimethylpiperazin-1-yl)methyl)-2'-methoxybiphenyl-3-yloxy)-5-fluoronicotinamide N-((1s,4s)-4-(1,5-dimethyl-1H-pyrazole-3-carboxamido)cyclohexyl)-5-fluoro-2-(3'-formyl-2'-methoxybiphenyl-3-yloxy)nicotinamide (0.28 g, 0.48 mmol) and (2S,6R)-2,6-dimethylpiperazine (0.109 g, 0.96 mmol) were stirred in DCM (50 mL) for 30 min. Acetic acid (0.055 mL, 0.96 mmol) and MeOH (10 mL) were added, followed by sodium triacetoxyborohydride (0.203 g, 0.96 mmol) and the reaction stirred for a further 20 h. The reaction was quenched with 2M HCl (30 mL), extracted with EtOAc, washed with water and brine, dried (Na2SO4) and evaporated in vacuo. The residue was purified by chromatography on silica with 5% MeOH/DCM as eluent to give the title compound as a white solid. Yield: 234 mg $^1$H NMR (400 MHz, DMSO) δ 9.81-9.54 (m, 1H), 9.03-8.77 (m, 1H), 8.34 (d, J=7.4 Hz, 1H), 8.24 (d, J=3.3 Hz, 1H), 8.01 (m, 1H), 7.51 (t, J=7.8 Hz, 1H), 7.46 (d, J=8.1 Hz, 1H), 7.38 (m, 3H), 7.20 (m, 3H), 6.36 (s, 1H), 4.04 (s, 2H), 3.97 (m, 1H), 3.80 (m, 1H), 3.70 (s, 3H), 3.59-3.30 (m, 4H), 3.33 (s, 3H), 2.65 (m, 2H), 2.23 (s, 3H), 1.77-1.57 (m, 8H), 1.21 (d, J=6.5 Hz, 6H).

MS: APCI (+ve):684 (M+1).

EXAMPLE 107

2-(2'-chloro-3'-(((3S,5R)-3,5-dimethylpiperazin-1-yl)methyl)biphenyl-3-yloxy)-N-((1s,4s)-4-(1,5-dimethyl-1H-pyrazole-3-carboxamido)cyclohexyl)-5-fluoronicotinamide

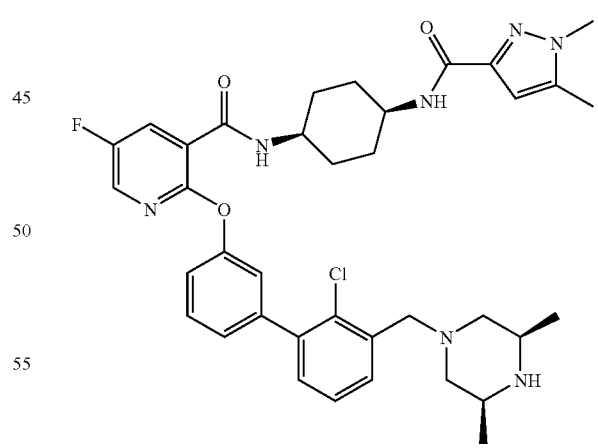

Step (a) 2-(2'-chloro-3'-formylbiphenyl-3-yloxy)-N-((1s,4s)-4-(1,5-dimethyl-1H-pyrazole-3-carboxamido)cyclohexyl)-5-fluoronicotinamide A solution of potassium carbonate (0.215 g, 1.56 mmol) in water (5 mL), 3-bromo-2-chlorobenzaldehyde (0.137 g, 0.62 mmol) and N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide (0.3 g, 0.52 mmol) were added sequentially to a stirred solution of palladium(II) acetate (0.012 g, 0.05 mmol) and S-Phos (0.043 g, 0.10 mmol) in acetonitrile (7 mL) and heated at 70° C. for 2 h. The mixture was cooled to RT, extracted with EtOAc, washed with water and brine, dried (MgSO$_4$), filtered and evaporated in vacuo. The residue was purified by chromatography on silica with 40% EtOAc/isohexane as eluent to give the sub-title compound as a brown foam. Yield: 170 mg Step (b) 2-(2'-chloro-3'-(((3S,5R)-3,5-dimethylpiperazin-1-yl)methyl)biphenyl-3-yloxy)-N-((1s,4s)-4-(1,5-dimethyl-1H-pyrazole-3-carboxamido)cyclohexyl)-5-fluoronicotinamide 2-(2'-Chloro-3'-formylbiphenyl-3-yloxy)-N-((1s,4s)-4-(1,5-dimethyl-1H-pyrazole-3-carboxamido)cyclohexyl)-5-fluoronicotinamide (0.17 g, 0.29 mmol) and (2S,6R)-2,6-dimethylpiperazine (0.066 g, 0.58 mmol) were stirred in DCM (50 mL) for 30 min. Acetic acid (0.033 mL, 0.58 mmol) and MeOH (10 mL) were added, followed by sodium triacetoxyborohydride (0.122 g, 0.58 mmol) and the reaction stirred for a further 20 h. The reaction was quenched with 2M HCl (30 mL), extracted with EtOAc, washed with water and brine, dried (Na$_2$SO$_4$) and evaporated in vacuo. The residue was purified by chromatography on silica with 5% MeOH/DCM as eluent to give the title compound as a white solid. Yield: 145 mg $^1$H NMR (400 MHz, DMSO) δ 9.07-8.93 (m, 1H), 8.34-8.18 (m, 1H), 8.30 (d, J=7.4 Hz, 1H), 8.25 (d, J=3.2 Hz, 1H), 8.00 (m, 1H), 7.49 (m, 2H), 7.37 (t, J=7.6 Hz, 1H), 7.31 (m, 1H), 7.19 (m, 3H), 6.37 (s, 1H), 3.95 (m, 1H), 3.87-3.58 (m, 2H), 3.70 (s, 2H), 3.54 (s, 2H), 3.31 (m, 2H), 2.99 (m, 2H), 2.23 (s, 3H), 2.16 (m, 2H), 1.75-1.56 (m, 8H), 1.16 (d, J=6.5 Hz, 6H).

MS: APCI (+ve):688 (M+1).

EXAMPLE 108

N-((1s,4s)-4-(1,5-dimethyl-1H-pyrazole-3-carboxamido)cyclohexyl)-5-fluoro-2-(3'-(3-(piperazin-1-yl)propyl)biphenyl-3-yloxy)nicotinamide

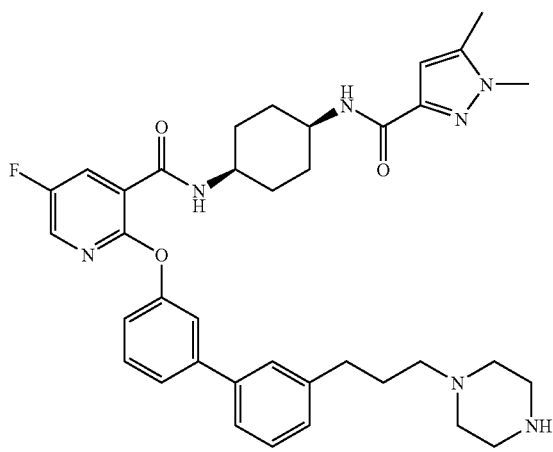

Step (a) tert-butyl (1s,4s)-4-(5-fluoro-2-(3'-(3-hydroxypropyl)biphenyl-3-yloxy)nicotinamido)cyclohexylcarbamate Tetrakis(triphenylphosphine)palladium(0) (0.033 g, 0.03 mmol) was added to a mixture of tert-butyl (1s,4s)-4-(5-fluoro-2-(3-iodophenoxy)nicotinamido)cyclohexylcarbamate (0.8 g, 1.44 mmol), 3-(3-hydroxypropyl)phenylboronic acid (0.285 g, 1.58 mmol) and sodium carbonate (0.458 g, 4.32 mmol) in water (5.00 mL) and THF (10 mL). The mixture was heated at 70° C. for 17 h. The reaction mixture was diluted with EtOAc and washed with water and saturated brine. The organic was dried over sodium sulfate, filtered and evaporated to afford crude product. The crude product was purified by flash silica chromatography (Biotage, 100 g) eluting with 1:1 isohexane/EtOAc. Pure fractions were combined and evaporated to dryness to afford the sub-title compound as a white solid. Yield: 0.55 g MS: [M+H]+=564 (MultiMode+)

Step (b) 3-(3'-(3-((1s,4s)-4-(tert-butoxycarbonylamino)cyclohexylcarbamoyl)-5-fluoropyridin-2-yloxy)biphenyl-3-yl)propyl methanesulfonate To solution of tert-butyl (1s,4s)-4-(5-fluoro-2-(3'-(3-hydroxypropyl)biphenyl-3-yloxy)nicotinamido)cyclohexylcarbamate (0.5 g, 0.89 mmol) and pyridine (0.143 mL, 1.77 mmol) in DCM (5 mL), was added methanesulfonyl chloride (0.145 mL, 1.86 mmol) and the reaction stirred at RT for 2 h. The reaction mixture was diluted with aqueous aqueous 2M HCl and extracted with DCM (X3) and EtOAc (×3). Organics were combined and dried (MgSO$_4$) and concentrated to give the sub-title compound as an off-white foam. Yield: 0.56 g MS: [M−H]−=640 (MultiMode+)

Step (c) benzyl 4-(3-(3'-(3-((1s,4s)-4-(tert-butoxycarbonylamino)cyclohexylcarbamoyl)-5-fluoropyridin-2-yloxy)biphenyl-3-yl)propyl)piperazine-1-carboxylate To a solution of 3-(3'-(3-((1s,4s)-4-(tert-butoxycarbonylamino)cyclohexylcarbamoyl)-5-fluoropyridin-2-yloxy)biphenyl-3-yl)propyl methanesulfonate (0.278 g, 0.43 mmol) in acetonitrile (2.5 mL) was added benzyl piperazine-1-carboxylate (0.167 mL, 0.87 mmol). The mixture was heated to 80° C. in the microwave for 45 mins. The solution was diluted with ethyl actetate and washed with water. Organics were separated (×3), dried (MgSO$_4$) and concentrated to leave a yellow oil. The oil was redissolved in DCM then purified on silica (Biotage, 25 g) eluting with 100% EtOAc. The organics were combined and concentrated to leave the sub-title compound as a white foam. Yield: 0.26 g MS: [M+H]+=766 (MultiMode+)

Step (d) benzyl 4-(3-(3'-(3-((1s,4s)-4-aminocyclohexylcarbamoyl)-5-fluoropyridin-2-yloxy)biphenyl-3-yl)propyl)piperazine-1-carboxylate hydrochloride To benzyl 4-(3-(3'-(3-((1s,4s)-4-(tert-butoxycarbonylamino)cyclohexylcarbamoyl)-5-fluoropyridin-2-yloxy)biphenyl-3-yl)propyl)piperazine-1-carboxylate (0.26 g, 0.34 mmol) in DCM (2 mL) was added HCl (4 Molar in dioxane) (1.5 mL, 6.00 mmol). The reaction was stirred at RT for 2 h. The reaction was concentrated in vacuo and triturated with ether to leave the sub-title compound as a white solid as the mono HCl salt. Yield: 0.17 g MS: [M+H]+=666 (MultiMode+)

Step (e) benzyl 4-(3-(3'-(3-((1s,4s)-4-(1,5-dimethyl-1H-pyrazole-3-carboxamido)cyclohexylcarbamoyl)-5-fluoropyridin-2-yloxy)biphenyl-3-yl)propyl)piperazine-1-carboxylate To a solution of benzyl 4-(3-(3'-(3-((1s,4s)-4-aminocyclohexylcarbamoyl)-5-fluoropyridin-2-yloxy)biphenyl-3-yl)propyl)piperazine-1-carboxylate (0.17 g, 0.26 mmol) and 1,5-dimethyl-1H-pyrazole-3-carboxylic acid (0.036 g, 0.26 mmol) in acetonitrile (2 mL) was added triethylamine (0.356 mL, 2.55 mmol). The initial suspension was left for 10 min to become a solution. 1.57M T3P in THF (0.171 mL, 0.27 mmol) was then added and the mixture stirred for 2 h. The solution was diluted with water and extracted with EtOAc. The organics were combined, dried (MgSO$_4$) and concentrated in vacuo to give the sub-title compound as a white fluffy foam. Yield: 0.18 g
MS: [M+H]+=788 (MultiMode+)

Step (f) N-((1s,4s)-4-(1,5-dimethyl-1H-pyrazole-3-carboxamido)cyclohexyl)-5-fluoro-2-(3'-(3-(piperazin-1-yl)propyl)biphenyl-3-yloxy)nicotinamide Benzyl 4-(3-(3'-(3-((1s,4s)-4-(1,5-dimethyl-1H-pyrazole-3-carboxamido)cyclohexylcarbamoyl)-5-fluoropyridin-2-yloxy)biphenyl-3-yl)propyl)piperazine-1-carboxylate (0.15 g, 0.19 mmol) in HCl (aqueous 5M) (10.74 mL, 53.69 mmol) was heated at 80° C. for 1 h. The crude concentrated product was purified by preparative HPLC on a Waters X-Bridge column using a 95-5% gradient of aqueous 0.2% TFA in acetonitrile as eluent. The fractions containing the desired compound were freeze dried to afford the title compound as a white solid. Yield: 161 mg
$^1$H NMR (400 MHz, DMSO) δ 8.21 (d, J=3.4 Hz, 1H), 8.10 (d, J=11.7 Hz, 1H), 7.99 (dd, J=5.4, 5.4 Hz, 1H), 7.49-7.42 (m, 5H), 7.33 (t, J=7.3 Hz, 1H), 7.21-7.16 (m, 2H), 6.97 (d, J=7.8 Hz, 1H), 6.35 (s, 1H), 4.04-3.98 (m, 1H), 3.89-3.82 (m, 1H), 3.69 (s, 3H), 2.72-2.63 (m, 6H), 2.53-2.46 (m, 6H), 2.25 (s, 3H), 1.84-1.66 (m, 10H).
MS: [M+H]+=654 (calc=654) (MultiMode+)

EXAMPLE 109

N-((1s,4s)-4-(5-fluoro-2-(4'-((4-(pyrrolidin-1-yl)piperidin-1-yl)methyl)biphenyl-3-yloxy)nicotinamido)cyclohexyl)-5-methylimidazo[1,2-a]pyridine-2-carboxamide

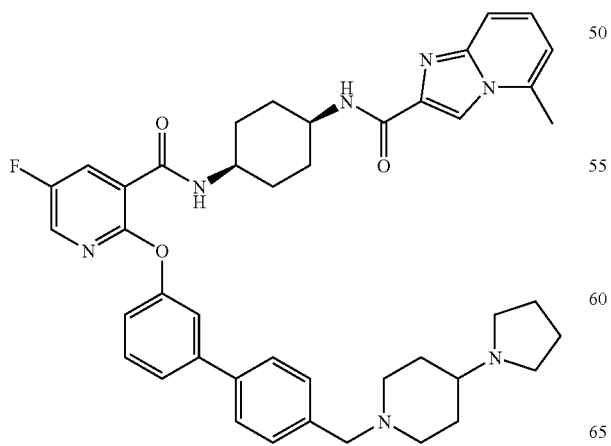

4-(Pyrrolidin-1-yl)piperidine (0.044 g, 0.29 mmol) was added to a solution of N-((1s,4s)-4-(5-fluoro-2-(4'-formylbiphenyl-3-yloxy)nicotinamido)cyclohexyl)-5-methylimidazo[1,2-a]pyridine-2-carboxamide (0.085 g, 0.14 mmol) in DCM (2 mL). After 40 min sodium triacetoxyborohydride (0.046 g, 0.22 mmol) was added and the mixture stirred overnight. Methanol (1 mL) was added, then the mixture partitioned between EtOAc and water. The organic layer was washed with saturated brine and concentrated, then the crude product was purified by preparative HPLC on a Phenomenex Gemini column using a 95-5% gradient of aqueous 0.1% TFA in methanol as eluent. The fractions containing the desired compound were evaporated to dryness to afford the title compound as a white foam. Yield: 107 mg
$^1$H NMR (400 MHz, CD$_3$OD) δ 8.54-8.43 (m, 2H), 8.10 (d, J=3.1 Hz, 1H), 8.06 (dd, J=7.9, 3.1 Hz, 1H), 7.77-7.68 (m, 3H), 7.66-7.60 (m, 1H), 7.56-7.51 (m, 4H), 7.47-7.45 (m, 1H), 7.24-7.14 (m, 2H), 4.35 (s, 2H), 4.16-4.03 (m, 2H), 3.68-3.59 (m, 3H), 3.44-3.37 (m, 1H), 3.17-3.04 (m, 4H), 2.73 (d, J=2.8 Hz, 3H), 2.44-2.36 (m, 2H), 2.18-1.74 (m, 14H). Remaining proton obscured by solvent.
MS: [M+H]+=730 (calc=730) (MultiMode+)

EXAMPLE 110

N-((1s,4s)-4-(2-(4'-(((2-(dimethylamino)ethyl)(methyl)amino)methyl)biphenyl-3-yloxy)-5-fluoronicotinamido)cyclohexyl)-4,5,6,7-tetrahydropyrazolo[1,5-a]pyridine-2-carboxamide hydrochloride

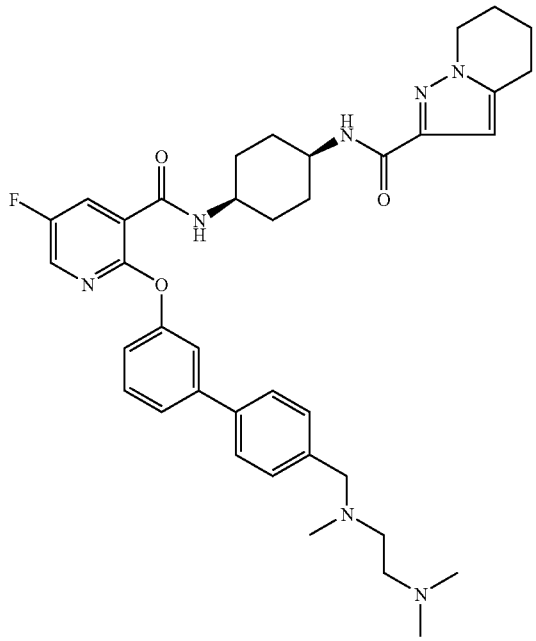

Step (a) 4,5,6,7-tetrahydropyrazolo[1,5-a]pyridine-2-carboxylic acid

A solution of pyrazolo[1,5-a]pyridine-2-carboxylic acid (1 g, 6.17 mmol) in methanol (100 mL) was hydrogenated at 3½ bar over 5% rhodium on carbon (100 mg) overnight. The mixture was filtered through Celite and the pad was washed with methanol. The filtrates were evaporated to give the sub-title compound as a cream powder. Yield: 0.953 g
$^1$H NMR (300 MHz, DMSO) δ 6.41 (s, 1H), 4.10 (t, J=6.2 Hz, 2H), 2.75 (t, J=6.3 Hz, 2H), 2.01-1.94 (m, 2H), 1.83-1.74 (m, 2H).

Step (b) N-((1s,4s)-4-(5-fluoro-2-(3-iodophenoxy) nicotinamido)cyclohexyl)-4,5,6,7-tetrahydropyrazolo [1,5-a]pyridine-2-carboxamide A stirred solution of N-((1s,4s)-4-aminocyclohexyl)-5-fluoro-2-(3-iodophenoxy)nicotinamide hydrochloride (2 g, 4.07 mmol), 4,5,6,7-tetrahydropyrazolo[1,5-a]pyridine-2-carboxylic acid (0.676 g, 4.07 mmol) and DIPEA (3.55 mL, 20.34 mmol) in DMF (20 mL) was treated with HATU (1.624 g, 4.27 mmol) and stirred overnight. The mixture was evaporated to remove most of the DMF and the residue was taken up in DCM, washed with water (3×), dried ($Na_2SO_4$) and evaporated. The residue was purified on a 50 g silica cartridge, eluting with a gradient of methanol in DCM to give a yellow glass. A few milligrams of the yellow glass was triturated with a drop of acetonitrile to give a solid. The bulk material was dissolved in a little warm acetonitrile and seeded with the solid. The solution was then evaporated with no heat on the rotavapour at 50 mbar to give the sub-title compound as a cream powder. Yield 2.27 g $^1$H NMR (400 MHz, DMSO) δ 8.29-8.26 (m, 2H), 8.03 (dd, J=7.9, 3.1 Hz, 1H), 7.60-7.57 (m, 2H), 7.24-7.20 (m, 3H), 6.34 (s, 1H), 4.08 (t, J=6.2 Hz, 2H), 3.99-3.93 (m, 1H), 3.87-3.81 (m, 1H), 2.75 (t, J=6.8 Hz, 2H), 2.00-1.94 (m, 2H), 1.81-1.62 (m, 10H). Also a singlet at 2.689, possibly tetramethyl urea from the HATU.

Step (c) N-((1s,4s)-4-(5-fluoro-2-(4'-formylbiphenyl-3-yloxy)nicotinamido)cyclohexyl)-4,5,6,7-tetrahydropyrazolo[1,5-a]pyridine-2-carboxamide A stirred solution of diacetoxypalladium (15 mg, 0.07 mmol) and dicyclohexyl(2',6'-dimethoxybiphenyl-2-yl)phosphine (54 mg, 0.13 mmol) in acetonitrile (2.5 mL) was treated sequentially with a solution of potassium carbonate (275 mg, 1.99 mmol) in water (2 mL), then N-((1s,4s)-4-(5-fluoro-2-(3-iodophenoxy)nicotinamido)cyclohexyl)-4,5,6,7-tetrahydropyrazolo[1,5-a]pyridine-2-carboxamide (400 mg, 0.66 mmol), then 4-formylphenylboronic acid (139 mg, 0.93 mmol) and heated at 70° C. for 6 h. The mixture was diluted with EtOAc, washed with water and then brine, dried ($MgSO_4$) and evaporated. The residue was purified on a 50 g silica cartridge, using EtOAc as eluent to give the sub-title compound as a brown glass. Yield: 349 mg $^1H$ NMR (400 MHz, DMSO) δ 10.03 (s, 1H), 8.32 (d, J=7.41 Hz, 1H), 8.26 (d, J=3.1 Hz, 1H), 8.06 (dd, J=7.9, 3.1 Hz, 1H), 7.91 (dd, J=15.5, 8.3 Hz, 4H), 7.66-7.64 (m, 2H), 7.57 (t, J=8.2 Hz, 1H), 7.30-7.27 (m, 1H), 7.24 (d, J=7.9 Hz, 1H), 6.33 (s, 1H), 4.00 (mult, obscured by EtOAc), 3.86-3.79 (m, 1H), 2.74 (t, J=6.3 Hz, 2H), 1.97-1.91 (m, 2H), 1.79-1.62 (m, 10H)+0.65 mol % EtOAc.

Step (d) N-((1s,4s)-4-(2-(4'-(((2-(dimethylamino) ethyl)(methyl)amino)methyl)biphenyl-3-yloxy)-5-fluoronicotinamido)cyclohexyl)-4,5,6,7-tetrahydropyrazolo[1,5-a]pyridine-2-carboxamide hydrochloride A stirred solution of N-((1s,4s)-4-(5-fluoro-2-(4'-formylbiphenyl-3-yloxy)nicotinamido)cyclohexyl)-4,5,6,7-tetrahydropyrazolo[1,5-a]pyridine-2-carboxamide (100 mg, 0.17 mmol) and N1,N1,N2-trimethylethane-1,2-diamine (17.57 mg, 0.17 mmol) in DCM (10 mL) was treated with acetic acid (9.84 μL, 0.17 mmol) followed by sodium triacetoxyborohydride (54.7 mg, 0.26 mmol) and stirred overnight. The mixture was washed with 1M aqueous sodium bicarbonate solution followed by brine, was dried ($Na_2SO_4$) and evaporated. The residue was purified on a 25 g silica cartridge, using a gradient of 0.7M methanolic ammonia solution in DCM as eluent to give a glassy oil. The glass was taken up in a little DCM, treated with a few drops of 4M hydrogen chloride in dioxane and evaporated. The residue was triturated to give the title compound as cream powder. Yield: 81 mg $^1$H NMR (400 MHz, DMSO) δ 11.40 (br s, 1H), 11.06 (br s, 1H), 8.33 (d, J=7.2 Hz, 1H), 8.23 (d, J=3.1 Hz, 1H), 8.02 (dd, J=7.9, 3.1 Hz, 1H), 7.72 (dd, J=14.9, 8.5 Hz, 4H), 7.57-7.49 (m, 3H), 7.21 (d, J=7.9 Hz, 2H), 6.31 (s, 1H), 4.57-4.54 (m, 1H), 4.29-4.25 (m, 1H), 4.02 (t, J=6.2 Hz, 2H), 3.98-3.93 (m, 1H), 3.83-3.79 (m, 1H), 3.69-3.62 (m, 4H), 2.81 (s, 6H), 2.71 (t, j=6.3 Hz, 2H), 2.66 (s, 3H), 1.96-1.90 (m, 2H), 1.77-1.60 (m, 10H). Also showed the presence of 0.5 mol % dioxane MS: [M+H]+=668 (calc=668) (MultiMode+)

EXAMPLE 111

N-((1s,4s)-4-(2-(4'-(((3S,5R)-3,5-dimethylpiperazin-1-yl)methyl)biphenyl-3-yloxy)-5-fluoronicotinamido)cyclohexyl)-5-methylisoxazole-3-carboxamide

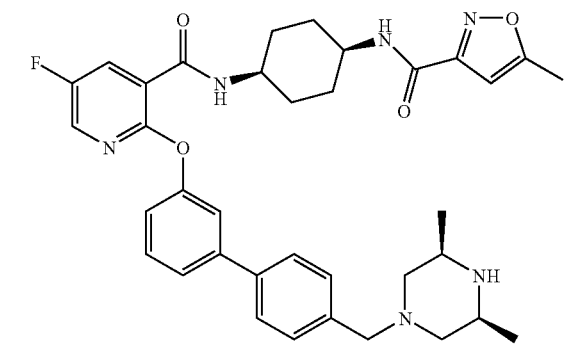

HATU (0.104 g, 0.27 mmol) was added to a solution of 5-methylisoxazole-3-carboxylic acid (0.035 g, 0.27 mmol), N-((1s,4s)-4-aminocyclohexyl)-2-(4'-(((3S,5R)-3,5-dimethylpiperazin-1-yl)methyl)biphenyl-3-yloxy)-5-fluoronicotinamide (0.15 g, 0.25 mmol) and DIPEA (0.173 mL, 0.99 mmol) in DMF (5 mL) and the solution stirred at RT for 20 h. The mixture was purified by reverse phase HPLC with aqTFA/MeCN as eluent to the title compound as a white solid. Yield: 47 mg $^1$H NMR (400 MHz, $CD_3OD$) δ 8.45 (d, J=7.9 Hz, 1H), 8.11 (d, J=3.4 Hz, 1H), 8.07 (m, 1H), 7.61 (d, J=8.2 Hz, 2H), 7.49 (d, J=5.3 Hz, 2H), 7.42 (m, 3H), 7.16 (m, 1H), 6.38 (s, 1H), 4.13 (m, 1H), 3.94 (m, 1H), 3.79 (s, 2H), 3.43 (m, 2H), 3.17 (m, 2H), 2.44 (s, 3H), 2.25 (m, 4H), 1.92-1.66 (m, 8H), 1.28 (d, J=6.9 Hz, 6H).

MS: APCI (+ve):641 (M+1).

EXAMPLE 112

N-((1s,4s)-4-(5-fluoro-2-(4'-(2-(4-(pyrrolidin-1-yl)piperidin-1-yl)ethyl)biphenyl-3-yloxy)nicotinamido)cyclohexyl)-2-methylthiazole-4-carboxamide

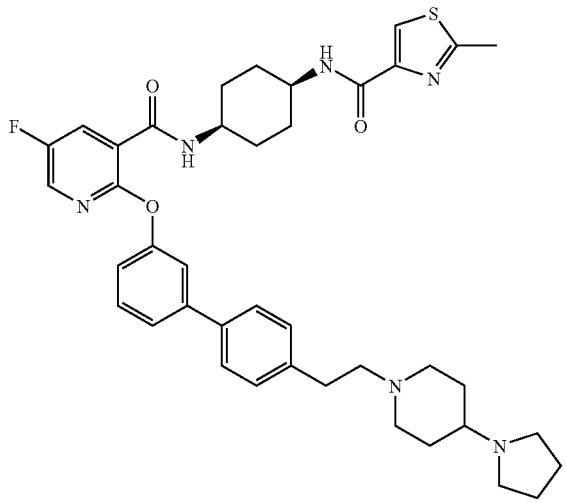

Step (a) tert-butyl (1s,4s)-4-(5-fluoro-2-(4'-(2-hydroxyethyl)biphenyl-3-yloxy)nicotinamido)cyclohexylcarbamate Tetrakis(triphenylphosphine)palladium(0) (0.062 g, 0.05 mmol) was added to a mixture of tert-butyl (1s,4s)-4-(5-fluoro-2-(3-(4,4,5,5-tetramethyl-1,3,2-dioxaborolan-2-yl)phenoxy)nicotinamido)cyclohexylcarbamate (1.500 g, 2.70 mmol), 2-(4-bromophenyl)ethanol (0.416 ml, 2.97 mmol) and sodium carbonate (0.859 g, 8.10 mmol) in water (10.00 ml) and THF (20 ml). The mixture was heated at 70° C. for 17 h then the reaction mixture was diluted with EtOAc and washed with water and saturated brine. The organic was dried over sodium sulfate, filtered and evaporated to afford crude product. The crude product was purified by flash silica chromatography (Combi-Flash Companion, 10 g Biotage SNAP) elution gradient 20 to 100% EtOAc in isohexane. Pure fractions were evaporated to dryness to afford the sub-title compound as a colourless gum. Yield: 1.036 g MS: [M−H]−=548 (MultiMode+)

Step (b) N-((1s,4s)-4-aminocyclohexyl)-5-fluoro-2-(4'-(2-hydroxyethyl)biphenyl-3-yloxy)nicotinamide hydrochloride To tert-butyl (1s,4s)-4-(5-fluoro-2-(4'-(2-hydroxyethyl)biphenyl-3-yloxy)nicotinamido)cyclohexylcarbamate (1.1 g, 2.00 mmol) in DCM (10 mL) was added HCl (4 Molar in dioxane) (10 mL, 40.00 mmol). The reaction was stirred at RT for 2 h. The reaction was concentrated in vacuo and triturated with ether to leave the sub-title compound as an off white solid as the mono HCl salt. Yield: 0.8 g MS: [M+H]+=450 (MultiMode+)

Step (c) N-((1s,4s)-4-(5-fluoro-2-(4'-(2-hydroxyethyl)biphenyl-3-yloxy)nicotinamido)cyclohexyl)-2-methylthiazole-4-carboxamide To a solution of N-((1s,4s)-4-aminocyclohexyl)-5-fluoro-2-(4'-(2-hydroxyethyl)biphenyl-3-yloxy)nicotinamide (0.3 g, 0.67 mmol) and 2-methylthiazole-4-carboxylic acid (0.105 g, 0.73 mmol) in acetonitrile (2 mL) was added triethylamine (0.930 mL, 6.67 mmol). The initial suspension was left for 10 min to become a solution. 1-Propanephosphonic acid cyclic anhydride, 1.57M in THF (T3P) (0.446 mL, 0.70 mmol) was then added and the mixture stirred for 30 min. The solution was diluted with water and extracted with EtOAc. The organics were combined, dried (MgSO$_4$) and concentrated in vacuo to give the sub-title compound as a white fluffy foam. Yield: 0.33 g MS: [M+H]+=575 (MultiMode+)

Step (d) 2-(3'-(5-fluoro-3-((1s,4s)-4-(2-methylthiazole-4-carboxamido)cyclohexylcarbamoyl)pyridin-2-yloxy)biphenyl-4-yl)ethyl methanesulfonate To a solution of N-((1s,4s)-4-(5-fluoro-2-(4'-(2-hydroxyethyl)biphenyl-3-yloxy)nicotinamido)cyclohexyl)-2-methylthiazole-4-carboxamide (0.33 g, 0.57 mmol) and pyridine (0.093 mL, 1.15 mmol) in DCM (3 mL), was added methanesulfonyl chloride (0.094 mL, 1.21 mmol) and the reaction stirred at RT for 2 h. The reaction mixture was diluted with aqueous 2M HCl and extracted with DCM (×3) and EtOAc (×3). The organics were combined and dried (MgSO$_4$) and concentrated to give an oil. The oil was dissolved in DCM then isohexane added until a solid crashed out. The suspension was concentrated in vacuo to give the sub-title compound as an off-white foam. Yield: 0.38 g MS: [M+H]+=653 (MultiMode+)

Step (e) N-((1s,4s)-4-(5-fluoro-2-(4'-(2-(4-(pyrrolidin-1-yl)piperidin-1-yl)ethyl)biphenyl-3-yloxy)nicotinamido)cyclohexyl)-2-methylthiazole-4-carboxamide To a solution of 2-(3'-(5-fluoro-3-((1s,4s)-4-(2-methylthiazole-4-carboxamido)cyclohexylcarbamoyl)pyridin-2-yloxy)biphenyl-4-yl)ethyl methanesulfonate (0.19 g, 0.29 mmol) in acetonitrile (2 mL) was added 4-(pyrrolidin-1-yl)piperidine (0.112 g, 0.73 mmol). The mixture was heated to 80° C. in the microwave for 30 min. Further 4-(pyrrolidin-1-yl)piperidine (0.112 g, 0.73 mmol) was added and the reaction stirred for a further hour at 80° C. Crude product was purified by preparative HPLC on a Waters X-Bridge column using a 95-5% gradient of aqueous 0.2% TFA in acetonitrile as eluent. The fractions containing the desired compound were freeze dried to afford the title compound as a white solid. Yield: 86 mg $^1$H NMR (300 MHz, DMSO) δ 10.29-10.21 (m, 1H), 10.03-9.96 (m, 1H), 8.35 (d, J=7.2 Hz, 1H), 8.26 (d, J=3.4 Hz, 1H), 8.08-8.03 (m, 2H), 7.64 (d, J=8.4 Hz, 2H), 7.59-7.47 (m, 3H), 7.34 (s, 1H), 7.31 (s, 1H), 7.22-7.17 (m, 1H), 4.05-3.97 (m, 1H), 3.91-3.83 (m, 1H), 3.78-3.68 (m, 2H), 3.13-2.95 (m, 3H), 2.67 (s, 3H), 2.53-2.48 (m, 9H), 2.37-2.30 (m, 2H), 2.07-1.83 (m, 5H), 1.78-1.65 (m, 8H).

MS: [M+H]+=711 (calc=711) (MultiMode+)

EXAMPLE 113

N-((1s,4s)-4-(2-(4'-(((3S,5R)-3,5-dimethylpiperazin-1-yl)methyl)biphenyl-3-yloxy)-5-fluoronicotinamido)cyclohexyl)-4,5,6,7-tetrahydropyrazolo[1,5-a]pyridine-2-carboxamide

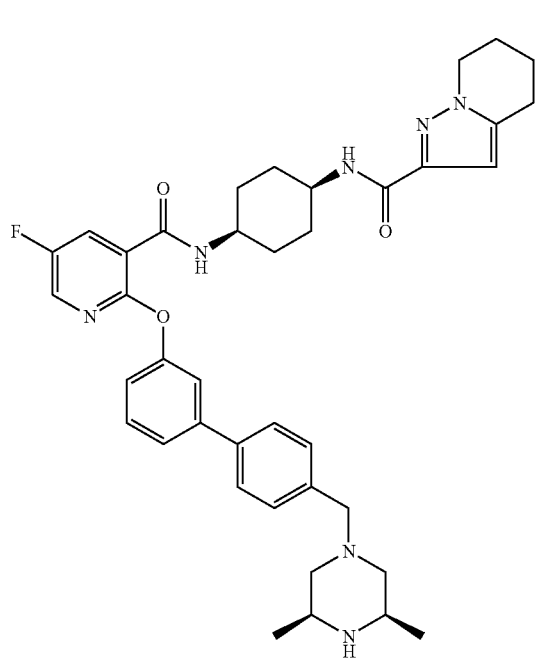

A stirred solution of N-((1s,4s)-4-(5-fluoro-2-(4'-formyl-biphenyl-3-yloxy)nicotinamido)cyclohexyl)-4,5,6,7-tetrahydropyrazolo[1,5-a]pyridine-2-carboxamide (100 mg, 0.17 mmol) and (2R,6S)-2,6-dimethylpiperazine (29.4 mg, 0.26 mmol) in DCM (10 mL) was treated with acetic acid (9.84 µL, 0.17 mmol) followed by sodium triacetoxyborohydride (54.7 mg, 0.26 mmol) and stirred overnight. The mixture was treated with more (2R,6S)-2,6-dimethylpiperazine (15 mg) and sodium triacetoxyborohydride (22 mg) and stirred for 6 h. The mixture was washed with 1M aqueous sodium bicarbonate solution followed by brine, was dried (Na$_2$SO$_4$) and evaporated. The residue was purified by reversed phase preparative HPLC on Gemini-NX C18 5 micron 110 A 30×100 mm Axia column, using a gradient of methanol in 0.1% aqueous TFA at 30 mL/min as eluent to give the title compound as a white powder. Yield: 94 mg $^1$H NMR (400 MHz, DMSO) δ 8.97-8.88 (m, 1H), 8.32 (d, J=7.2 Hz, 1H), 8.26 (d, J=3.1 Hz, 1H), 8.23-8.14 (m, 1H), 8.05 (dd, J=7.9, 3.1 Hz, 1H), 7.66 (d, J=7.9 Hz, 2H), 7.54-7.51 (m, 2H), 7.48-7.46 (m, 1H), 7.39 (d, J=7.9 Hz, 2H), 7.26-7.19 (m, 2H), 6.34 (s, 1H), 4.04 (t, J=6.2 Hz, 2H), 4.00-3.96 (m, 1H), 3.86-3.82 (m, 1H), 3.72-3.68 (m, 1H), 3.35-3.31 (m, 2H), 3.05-3.01 (m, 2H), 2.75 (t, J=6.3 Hz, 2H), 2.54-2.52 (m, 2H obscured by DMSO), 2.16-2.07 (m, 1H), 1.99-1.93 (m, 2H), 1.80-1.61 (m, 10H), 1.17 (d, J=6.7 Hz, 6H).

MS: [M+H]+=680 (calc=680) (MultiMode+)

EXAMPLE 114

N-((1s,4s)-4-(5-fluoro-2-(4'-(piperazin-1-ylmethyl)biphenyl-3-yloxy)nicotinamido)cyclohexyl)-4,5,6,7-tetrahydropyrazolo[1,5-a]pyridine-2-carboxamide

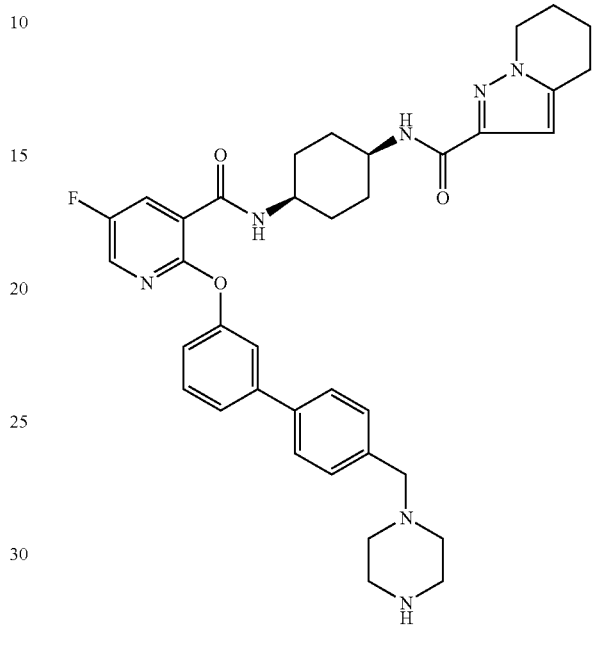

A stirred solution of N-((1s,4s)-4-(5-fluoro-2-(4'-formyl-biphenyl-3-yloxy)nicotinamido)cyclohexyl)-4,5,6,7-tetrahydropyrazolo[1,5-a]pyridine-2-carboxamide (100 mg, 0.17 mmol) and tert-butyl piperazine-1-carboxylate (48.0 mg, 0.26 mmol) in DCM (10 mL) was treated with acetic acid (9.84 µL, 0.17 mmol) followed by sodium triacetoxyborohydride (54.7 mg, 0.26 mmol) and stirred overnight. The mixture was treated with more tert-butyl piperazine-1-carboxylate (24 mg, 0.26 mmol) and sodium triacetoxyborohydride (22 mg) and stirred for 6 h. The mixture was washed with 1M aqueous sodium bicarbonate solution followed by brine, was dried (Na$_2$SO$_4$) and evaporated. The residue was taken up in DCM (20 mL) was treated with TFA (10 mL, 129.80 mmol) and stirred for 1 h. The mixture was evaporated and the residue was purified by reversed phase preparative HPLC on Gemini-NX C18 5 micron 110 A 30×100 mm Axia column, using a gradient of methanol in 0.1% aqueous TFA at 30 mL/min as eluent to give the title compound as a white powder. Yield: 88 mg $^1$H NMR (400 MHz, DMSO) δ 8.80-8.66 (m, 2H), 8.33 (d, J=7.2 Hz, 1H), 8.26 (d, J=3.1 Hz, 1H), 8.05 (dd, J=7.9, 3.1 Hz, 1H), 7.69 (d, J=7.9 Hz, 2H), 7.55-7.50 (m, 3H), 7.44 (d, J=7.7 Hz, 2H), 7.26-7.20 (m, 2H), 6.34 (s, 1H), 4.04 (t, J=6.2 Hz, 2H), 4.01-3.95 (m, 2H), 3.89-3.81 (m, 2H), 3.25-3.14 (m, 4H), 2.91-2.81 (m, 2H), 2.75 (t, J=6.3 Hz, 2H), 2.54-2.52 (m, 2H), 1.99-1.93 (m, 2H), 1.80-1.61 (m, 10H).

MS: [M+H]+=652.2 (calc=652.3411) (MultiMode+)

EXAMPLE 115

6-fluoro-N-((1s,4s)-4-(5-fluoro-2-(4'-((3-morpholinopropylamino)methyl)biphenyl-3-yloxy)nicotinamido)cyclohexyl)imidazo[1,2-a]pyridine-2-carboxamide

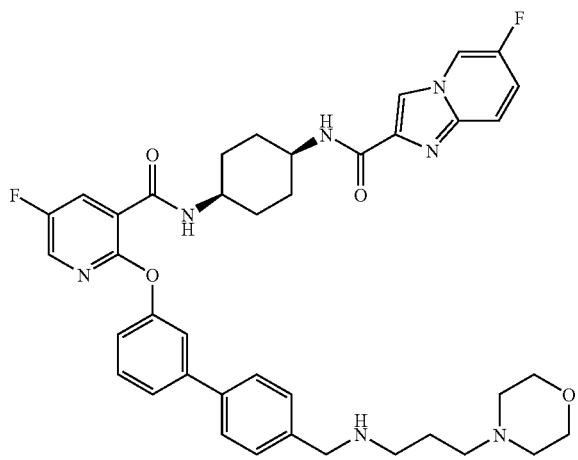

Step (a) 6-fluoro-N-((1s,4s)-4-(5-fluoro-2-(4'-formylbiphenyl-3-yloxy)nicotinamido)cyclohexyl)imidazo[1,2-a]pyridine-2-carboxamide A solution of palladium(II) acetate (0.013 g, 0.06 mmol) and 2-dicyclohexylphosphino-2',6'-dimethoxy-1,1'-biphenyl (0.047 g, 0.11 mmol) in acetonitrile (9.45 ml) was stirred at RT under nitrogen for 15 min. Potassium carbonate (0.470 g, 3.40 mmol) in water (4.72 ml) was added followed by 4-formylphenylboronic acid (0.255 g, 1.70 mmol) and 6-fluoro-N-((1s,4s)-4-(5-fluoro-2-(3-iodophenoxy)nicotinamido)cyclohexyl)imidazo[1,2-a]pyridine-2-carboxamide (0.7 g, 1.13 mmol). The reaction mixture was heated to 80° C. for 1 h. The reaction mixture was diluted with EtOAc, and washed with water. The organic was dried over magnesium sulfate, filtered and evaporated to afford crude product. The crude product was purified by flash silica chromatography using Isco Companion, 100 g silica column, elution gradient 3 to 7% methanol in dichloromethane. Pure fractions were evaporated to dryness to afford the sub-title compound as a yellow solid. Yield: 0.500 g $^1$H NMR (400 MHz, CDCl$_3$) δ 10.03 (s, 1H), 8.40 (dd, J=8.3, 3.9 Hz, 1H), 8.10 (s, 1H), 8.09-8.02 (m, 3H), 7.90 (s, 1H), 7.88 (s, 1H), 7.75 (s, 1H), 7.73 (s, 1H), 7.58 (s, 1H), 7.47-7.46 (m, 1H), 7.44-7.40 (m, 1H), 7.25-7.12 (m, 3H), 4.30-4.23 (m, 1H), 2.00-1.81 (m, 6H), 1.76-1.65 (m, 2H).

MS: [M+H]+=596.2 (Multimode+)

Step (b) 6-fluoro-N-((1s,4s)-4-(5-fluoro-2-(4'-((3-morpholinopropylamino)methyl)biphenyl-3-yloxy)nicotinamido)cyclohexyl)imidazo[1,2-a]pyridine-2-carboxamide To a stirred solution of 6-fluoro-N-((1s,4s)-4-(5-fluoro-2-(4'-formylbiphenyl-3-yloxy)nicotinamido)cyclohexyl)imidazo[1,2-a]pyridine-2-carboxamide (0.200 g, 0.34 mmol) in DCM (5 mL) was added acetic acid (0.038 mL, 0.67 mmol). The reaction mixture was stirred at RT for 15 min. Sodium triacetoxyborohydride (0.142 g, 0.67 mmol) was added and the reaction mixture stirred at RT for 3 days. The reaction mixture was diluted with DCM, and washed with saturated sodium hydrogen carbonate. The organic was dried over magnesium sulfate, filtered and evaporated to afford crude product. The crude product was purified by preparative HPLC on a Phenomenex Gemini column using a 95-15% gradient of aqueous 0.2% TFA in acetonitrile as eluent. The fractions containing the desired compound were evaporated to dryness to afford the title compound as a white solid. Yield: 35 mg $^1$H NMR (400 MHz, CD$_3$OD) δ 8.61-8.58 (m, 1H), 8.47 (d, J=7.5 Hz, 1H), 8.30 (s, 1H), 8.11 (d, J=3.1 Hz, 1H), 8.06 (dd, J=7.5, 3.8 Hz, 1H), 7.70 (s, 1H), 7.68 (s, 1H), 7.60-7.55 (m, 1H), 7.52-7.49 (m, 3H), 7.45-7.43 (m, 2H), 7.23-7.19 (m, 1H), 4.24 (s, 2H), 4.15-4.08 (m, 1H), 4.08-4.00 (m, 1H), 3.98-3.77 (m, 2H), 3.32-3.29 (m, 2H), 3.23 (t, J=8.4 Hz, 4H), 3.15 (t, J=8.4 Hz, 4H), 2.22-2.12 (m, 2H), 1.90-1.71 (m, 8H).

MS: [M+H]+=724.2 (Multimode+)

EXAMPLE 116

N-((1s,4s)-4-(5-fluoro-2-(4'-(3-(isopropylamino)propyl)biphenyl-3-yloxy)nicotinamido)cyclohexyl)-5-methylimidazo[1,2-a]pyridine-2-carboxamide

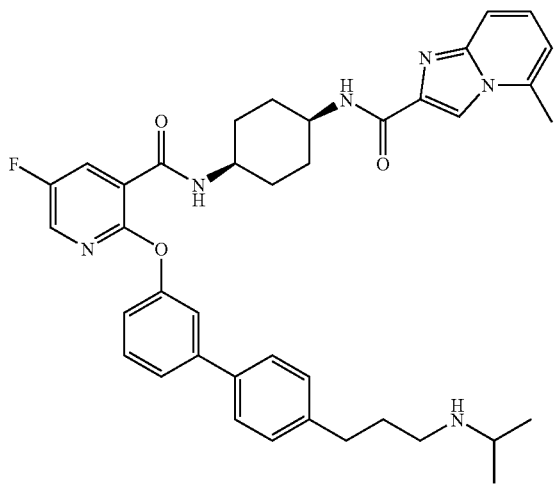

To a microwave tube was charged 3-(3'-(5-fluoro-3-((1s,4s)-4-(5-methylimidazo[1,2-a]pyridine-2-carboxamido)cyclohexylcarbamoyl)pyridin-2-yloxy)biphenyl-4-yl)propyl methanesulfonate (0.2 g, 0.29 mmol), propan-2-amine (0.122 mL, 1.43 mmol) and acetonitrile (1.5 mL). The reaction was heated in the microwave at 80° C. for 2 h. This was purified by HPLC to give the title compound as a white solid. Yield: 96 mg $^1$H NMR (400 MHz, CD$_3$OD) δ 8.52 (s, 1H), 8.46 (d, J=7.8 Hz, 1H), 8.12-8.04 (m, 2H), 7.75 (dd, J=8.8, 7.3 Hz, 1H), 7.64 (d, J=9.0 Hz, 1H), 7.53 (d, J=8.2 Hz, 2H), 7.47 (d, J=5.1 Hz, 2H), 7.42 (s, 1H), 7.27-7.12 (m, 5H), 4.18-4.09 (m, 1H), 4.09-4.01 (m, 1H), 3.38-3.26 (m, 5H), 2.99 (t, J=8.1 Hz, 2H), 2.72-2.67 (m, 1H), 2.03-1.74 (m, 10H), 1.29 (d, J=6.7 Hz, 6H).

MS: [M+H]+=663 (calc=663) (MultiMode+)

EXAMPLE 117

6-fluoro-N-((1s,4s)-4-(5-fluoro-2-(4'-(2-(piperazin-1-yl)ethyl)biphenyl-3-yloxy)nicotinamido)cyclohexyl)imidazo[1,2-a]pyridine-2-carboxamide

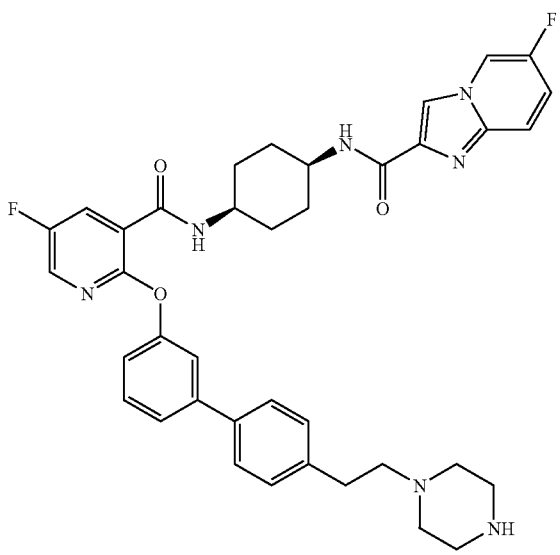

Step (a) 6-fluoro-N-((1s,4s)-4-(5-fluoro-2-(4'-(2-hydroxyethyl)biphenyl-3-yloxy)nicotinamido)cyclohexyl)imidazo[1,2-a]pyridine-2-carboxamide To a stirred solution of 6-fluoro-N-((1s,4s)-4-(5-fluoro-2-(3-iodophenoxy)nicotinamido)cyclohexyl)imidazo[1,2-a]pyridine-2-carboxamide (0.304 g, 0.49 mmol) in THF (3.81 mL) was added 4-(2-hydroxyethyl)phenylboronic acid (0.09 g, 0.54 mmol) and sodium carbonate (0.157 g, 1.48 mmol) in water (1.903 mL). The reaction mixture was stirred at RT under nitrogen for 15 min. Tetrakis(triphenylphosphine)palladium(0) (0.011 g, 9.86 µmol) was added and reaction mixture heated to 70° C. overnight. The reaction mixture was diluted with EtOAc, and washed with water. The organic was dried over magnesium sulfate, filtered and evaporated to afford crude product. The crude product was purified by flash silica chromatography, using Isco Companion, 50 g silica column, elution gradient 3 to 7% methanol in DCM. Pure fractions were evaporated to dryness to afford the sub-title compound as a yellow foam. Yield: 0.295 g $^1$H NMR (400 MHz, CDCl$_3$) δ 8.39 (dd, J=7.7, 3.0 Hz, 1H), 8.10-8.05 (m, 3H), 7.54-7.50 (m, 3H), 7.46-7.41 (m, 2H), 7.38-7.37 (m, 1H), 7.25-7.19 (m, 2H), 7.17-7.12 (m, 2H), 4.29-4.19 (m, 1H), 4.18-4.09 (m, 1H), 3.88 (t, J=6.1 Hz, 2H), 2.88 (t, J=6.1 Hz, 2H), 1.99-1.79 (m, 6H), 1.74-1.64 (m, 2H).

MS: [M+H]+=612.2 (Multimode+)

Step (b) 2-(3'-(5-fluoro-3-((1s,4s)-4-(6-fluoroimidazo[1,2-a]pyridine-2-carboxamido)cyclohexylcarbamoyl)pyridin-2-yloxy)biphenyl-4-yl)ethyl methanesulfonate To a stirred solution of 6-fluoro-N-((1s,4s)-4-(5-fluoro-2-(4'-(2-hydroxyethyl)biphenyl-3-yloxy)nicotinamido)cyclohexyl)imidazo[1,2-a]pyridine-2-carboxamide (0.295 g, 0.48 mmol) in DCM (6.74 mL) was added pyridine (0.078 mL, 0.96 mmol) and methanesulfonyl chloride (0.075 mL, 0.96 mmol). The reaction mixture was stirred at RT under nitrogen overnight. The reaction mixture was diluted with DCM, and washed with 2M hydrochloric acid. The organic was dried over magnesium sulfate, filtered and evaporated to afford crude product. The crude gum was triturated with diethyl ether to give a solid which was collected by filtration and air dried to afford the sub-title compound as a yellow solid. Yield: 0.200 g $^1$H NMR (400 MHz, CDCl$_3$) δ 8.36 (dd, J=8.2, 3.5 Hz, 1H), 8.21 (s, 1H), 8.19-8.16 (m, 1H), 8.08 (s, 1H), 8.06 (d, J=2.9 Hz, 1H), 7.62-7.42 (m, 7H), 7.28 (s, 1H), 7.22 (d, J=8.2 Hz, 2H), 4.44 (t, J=6.8 Hz, 2H), 4.27-4.19 (m, 1H), 3.07 (t, J=6.5 Hz, 2H), 2.87 (s, 3H), 2.04-1.50 (m, 8H).

MS: [M+H]+=690.2 (Multimode+)

Step (c) 6-fluoro-N-((1s,4s)-4-(5-fluoro-2-(4'-(2-(piperazin-1-yl)ethyl)biphenyl-3-yloxy)nicotinamido)cyclohexyl)imidazo[1,2-a]pyridine-2-carboxamide To a microwave vial was added 2-(3'-(5-fluoro-3-((1s,4s)-4-(6-fluoroimidazo[1,2-a]pyridine-2-carboxamido)cyclohexylcarbamoyl)pyridin-2-yloxy)biphenyl-4-yl)ethyl methanesulfonate (0.200 g, 0.29 mmol) and tert-butyl piperazine-1-carboxylate (0.270 g, 1.45 mmol) in acetonitrile (2 mL). The reaction mixture was heated to 100° C. by microwave for 4 h. The reaction mixture was evaporated to dryness and redissolved in DCM (2 mL), and TFA (0.894 mL, 11.60 mmol) added. The reaction mixture was stirred at RT for 1 h then concentrated to give crude product. The crude product was purified by preparative HPLC on a Waters X-Bridge column using a 80-0% gradient of aqueous 0.2% TFA in methanol as eluent. The fractions containing the desired compound were evaporated to dryness to afford the title compound as a white solid. Yield: 100 mg $^1$H NMR (400 MHz, CD$_3$OD) δ8.62 (t, J=3.8 Hz, 1H), 8.31 (s, 1H), 8.12-8.10 (m, 1H), 8.09-8.05 (m, 1H), 7.61-7.52 (m, 3H), 7.50-7.44 (m, 3H), 7.42-7.40 (m, 1H), 7.30 (s, 1H), 7.28 (s, 1H), 7.18-7.15 (m, 1H), 4.16-4.08 (m, 1H), 4.06-4.00 (m, 1H), 3.52-3.48 (m, 4H), 3.43-3.38 (m, 4H), 3.27-3.24 (m, 2H), 3.05-2.98 (m, 2H), 1.92-1.70 (m, 8H).

MS: (M+H)+=680.2

EXAMPLE 118

N-((1s,4s)-4-(5-fluoro-2-(4'-(3-(piperazin-1-yl)propyl)biphenyl-3-yloxy)nicotinamido)cyclohexyl)-4,5,6,7-tetrahydropyrazolo[1,5-a]pyridine-2-carboxamide

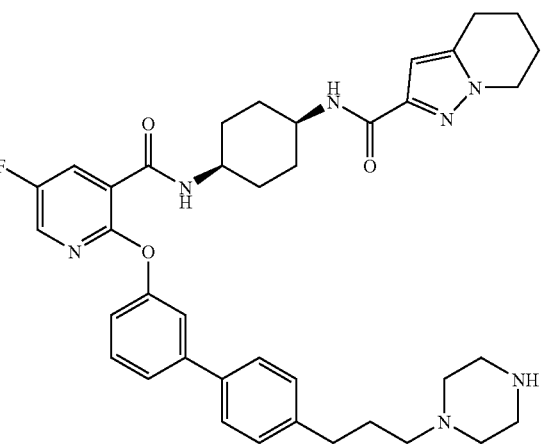

Step (a) N-((1s,4s)-4-(5-fluoro-2-(4'-(3-hydroxypropyl)biphenyl-3-yloxy)nicotinamido)cyclohexyl)-4,5,6,7-tetrahydropyrazolo[1,5-a]pyridine-2-carboxamide A stirred solution of diacetoxypalladium (7 mg, 0.03 mmol) and dicyclohexyl(2',6'-dimethoxybiphenyl-2-yl)phosphine (27 mg, 0.07 mmol) in acetonitrile (2.5 mL) was treated sequentially with a solution of potassium carbonate (137 mg, 0.99 mmol) in water (2 mL), then N-((1s,4s)-4-(5-fluoro-2-(3-iodophenoxy)nicotinamido)cyclohexyl)-4,5,6,7-tetrahydropyrazolo[1,5-a]pyridine-2-carboxamide (200 mg, 0.33 mmol), then 4-(3-hydroxypropyl)phenylboronic acid (84 mg, 0.46 mmol) and heated at 70° C. for 6 h. The mixture was diluted with EtOAc, washed with water and saturated brine, dried ($MgSO_4$) and evaporated. The residue was purified on a 25 g Biotage Snap cartridge, eluting with a gradient of 50 to 100% acetone in isohexane to afford the sub-title compound as a white foam. Yield: 170 mg $^1$H NMR (400 MHz, $CDCl_3$) δ 8.37 (dd, J=8.2, 3.1 Hz, 1H), 8.08 (d, J=3.1 Hz, 2H), 7.55-7.49 (m, 4H), 7.37-7.35 (m, 1H), 7.25-7.23 (m, 4H), 7.14 (dt, J=4.7, 2.4 Hz, 1H), 6.71-6.69 (m, 1H), 6.47 (s, 1H), 4.26-4.20 (m, 1H), 4.11-4.05 (m, 1H), 4.00 (t, J=6.0 Hz, 2H), 3.74-3.68 (m, 2H), 2.79-2.73 (m, 4H), 2.02-1.95 (m, 2H), 1.94-1.80 (m, 10H), 1.66-1.60 (m, 2H).

Step (b) 3-(3'-(5-fluoro-3-((1s,4s)-4-(4,5,6,7-tetrahydropyrazolo[1,5-a]pyridine-2-carboxamido)cyclohexylcarbamoyl)pyridin-2-yloxy)biphenyl-4-yl)propyl methanesulfonate A stirred solution of N-((1s,4s)-4-(5-fluoro-2-(4'-(3-hydroxypropyl)biphenyl-3-yloxy)nicotinamido)cyclohexyl)-4,5,6,7-tetrahydropyrazolo[1,5-a]pyridine-2-carboxamide (170 mg, 0.28 mmol) and pyridine (0.067 mL, 0.83 mmol) in DCM (10 mL) was treated with methanesulfonyl chloride (0.065 mL, 0.83 mmol) and stirred over the weekend. The solution was diluted with DCM and washed with 2M HCl and saturated brine. The organic layer was dried over magnesium sulfate, filtered and evaporated to give the sub-title compound.

$^1$H NMR (400 MHz, $CDCl_3$) δ 8.33 (dd, J=8.7, 2.9 Hz, 1H), 8.07 (s, 1H), 8.06 (d, J=3.6 Hz, 1H), 7.66-7.59 (m, 1H), 7.57-7.48 (m, 5H), 7.43-7.41 (m, 1H), 7.24 (d, J=7.3 Hz, 2H), 6.67 (s, 1H), 4.29-4.14 (m, 2H), 3.00 (s, 3H), 2.87 (t, J=6.7 Hz, 2H), 2.78 (t, J=8.1 Hz, 2H), 2.17-2.03 (m, 4H), 1.95-1.70 (m, 10H).

MS: [M+H]+=690.2 (Multimode+)

Step (c) N-((1s,4s)-4-(5-fluoro-2-(4'-(3-(piperazin-1-yl)propyl)biphenyl-3-yloxy)nicotinamido)cyclohexyl)-4,5,6,7-tetrahydropyrazolo[1,5-a]pyridine-2-carboxamide To a microwave vial was added 3-(3'-(5-fluoro-3-((1s,4s)-4-(4,5,6,7-tetrahydropyrazolo[1,5-a]pyridine-2-carboxamido)cyclohexylcarbamoyl)pyridin-2-yloxy)biphenyl-4-yl)propyl methanesulfonate (0.09 g, 0.13 mmol) and piperazine (0.225 g, 2.61 mmol) in acetonitrile (1 mL). The reaction mixture was heated to 100° C. by microwave for 30 min. The reaction mixture was concentrated to give the crude product which was purified by preparative HPLC on a Phenomenex Gemini column using a 95-15% gradient of aqueous 0.2% TFA in methanol as eluent. The fractions containing the desired compound were evaporated to dryness to afford the title compound as a white solid. Yield: 0.043 g $^1$H NMR (400 MHz, $CD_3OD$) δ 8.12 (d, J=2.4 Hz, 1H), 8.07 (dd, J=9.2, 2.4 Hz, 1H), 7.52-7.46 (m, 5H), 7.39 (s, 1H), 7.23 (d, J=8.6 Hz, 2H), 7.16-7.12 (m, 1H), 6.38 (s, 1H), 4.14-4.09 (m, 1H), 4.01 (t, J=6.1 Hz, 2H), 3.98-3.91 (m, 1H), 2.92-2.64 (m, 9H), 2.03-1.95 (m, 2H), 1.93-1.63 (m, 10H).

MS: [M+H]+=680.3 (Multimode+)

EXAMPLE 119

N-((1s,4s)-4-(2-(4'-((dimethylamino)methyl)-2'-(morpholinomethyl)biphenyl-3-yloxy)-5-fluoronicotinamido)cyclohexyl)-2-methylthiazole-4-carboxamide

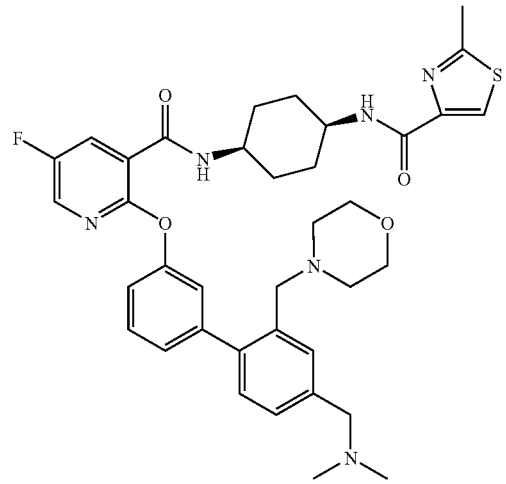

Step (a) 4-hydroxy-N-methoxy-N-methyl-3-(morpholinomethyl)benzamide

EDCI (4.44 g, 23.18 mmol) was added portionwise to a solution of 4-hydroxy-3-(morpholinomethyl)benzoic acid (5 g, 21.07 mmol), N,O-dimethylhydroxylamine (2.67 g, 27.40 mmol), DIPEA (4.05 mL, 23.18 mmol) and HOBt (3.55 g, 23.18 mmol) in DMF (25 mL) whilst maintaining the temperature below 10° C. The mixture was stirred for 48 h, diluted with EtOAc (200 mL), washed with saturated $NaHCO_3$ (200 mL), water (2×100 mL) & brine, dried ($Na_2SO_4$), filtered and evaporated in vacuo. The residue was purified by chromatography on silica with EtOAc as eluent to give the sub-title compound as a colourless oil. Yield: 3.20 g $^1$H NMR (400 MHz, $CDCl_3$) δ 7.63 (d, J=8.8 Hz, 1H), 7.47 (s, 1H), 6.81 (d, J=8.8 Hz, 1H), 3.82-3.71 (m, 4H), 3.75 (s, 2H), 3.57 (s, 3H), 3.34 (s, 3H), 2.67-2.50 (m, 4H).

MS: APCI (+ve):281 (M+1)

Step (b) 4-hydroxy-3-(morpholinomethyl)benzaldehyde

Bis(cyclopentadienyl)zirconium chloride hydride (4.29 g, 16.27 mmol) was added portionwise over 10 min to a solution of 4-hydroxy-N-methoxy-N-methyl-3-(morpholinomethyl)benzamide (3.8 g, 13.56 mmol) in THF (50 mL), under $N_2$ whilst maintaining the temperature below 20° C. Stirred for 2 h, quenched with saturated potassium sodium tartrate, extracted with EtOAc (3×100 mL), washed with more saturated potassium sodium tartrate and brine, dried ($Na_2SO_4$), filtered and evaporated in vacuo. Purified by flash chromatography with EtOAc as eluent to give the sub-title compound as a colourless oil. Yield: 2.1 g $^1$H NMR (400 MHz, CDCl$_3$) δ 9.82 (s, 1H), 7.72 (m, 1H), 7.58 (m, 1H), 6.93 (d, J=8.7 Hz, 1H), 3.85-3.70 (m, 4H), 3.80 (s, 2H), 2.71-2.49 (m, 4H).

MS: APCI (+ve):222 (M+1)

Step (c) 4-formyl-2-(morpholinomethyl)phenyl trifluoromethanesulfonate

N-Phenyltrifluoromethanesulfonimide (5.09 g, 14.24 mmol) was added to a solution of 4-hydroxy-3-(morpholinomethyl)benzaldehyde (2.1 g, 9.49 mmol) and triethylamine (3.97 mL, 28.47 mmol) in DCM (20 mL) cooled to 0° C. The mixture was allowed to attain RT and stirred for a further 16 h. The solution was washed with water and brine, dried (Na$_2$SO$_4$), filtered and evaporated in vacuo. The residue was purified by chromatography with 30% EtOAc/isohexane as eluent to give the sub-title compound as a colourless oil. Yield: 3.17 g $^1$H NMR (400 MHz, CDCl$_3$) δ 10.05 (s, 1H), 8.02 (d, J=2.2 Hz, 1H), 7.90 (dd, J=8.3, 2.2 Hz, 1H), 7.44 (d, J=8.4 Hz, 7H), 3.71 (m, 4H), 3.62 (s, 2H), 2.48 (m, 4H).

MS: APCI (+ve):354 (M+1)

Step (d) tert-butyl (1s,4s)-4-(5-fluoro-2-(4'-formyl-2'-(morpholinomethyl)biphenyl-3-yloxy)nicotinamido)cyclohexylcarbamate A solution of potassium carbonate (2.426 g, 17.55 mmol) in water (30 mL), 4-formyl-2-(morpholinomethyl)phenyl trifluoromethanesulfonate (2.481 g, 7.02 mmol) and tert-butyl (1s,4s)-4-(5-fluoro-2-(3-(4,4,5,5-tetramethyl-1,3,2-dioxaborolan-2-yl)phenoxy)nicotinamido)cyclohexylcarbamate (3.25 g, 5.85 mmol) were added sequentially to a stirred solution of palladium(II) acetate (0.131 g, 0.59 mmol) and S-Phos (0.480 g, 1.17 mmol) in acetonitrile (50 mL) and heated at 70° C. for 2 h. The mixture was cooled to RT, extracted with EtOAc, washed with water and brine, dried (MgSO$_4$), filtered and evaporated in vacuo. The residue was purified by chromatography on silica with 30% EtOAc/isohexane as eluent to give the sub-title compound as a brown foam. Yield: 2.3 g $^1$H NMR (400 MHz, CDCl$_3$) δ 10.07 (s, 1H), 8.37 (m, 1H), 8.06 (d, J=3.1 Hz, 1H), 8.00 (m, 1H), 7.96 (d, J=8.2 Hz, 1H), 7.85 (m, 1H), 7.55 (t, J=8.0 Hz, 1H), 7.50 (d, J=7.8 Hz, 1H), 7.36 (m, 1H), 7.30 (m, 1H), 7.20 (m, 1H), 4.49 (m, 1H), 4.17 (m, 1H), 3.63 (m, 1H), 3.58 (m, 4H), 3.49 (s, 2H), 2.36 (m, 4H), 1.88-1.46 (m, 8H), 1.42 (s, 9H).

MS: APCI (+ve):633 (M+1)

Step (e) N-((1s,4s)-4-aminocyclohexyl)-2-(4'-((dimethylamino)methyl)-2'-(morpholinomethyl)biphenyl-3-yloxy)-5-fluoronicotinamide To a solution of tert-butyl (1s,4s)-4-(5-fluoro-2-(4'-formyl-2'-(morpholinomethyl)biphenyl-3-yloxy)nicotinamido)cyclohexylcarbamate (1.2 g, 1.90 mmol) in DCM (300 mL) was added dimethylamine (1.832 mL, 3.79 mmol) 2.07M in MTBE. The mixture was allowed to stir at RT for 30 min before acetic acid (0.217 mL, 3.79 mmol) was added, followed by sodium triacetoxyborohydride (0.804 g, 3.79 mmol). The reaction was stirred at RT for 20 h. The reaction was quenched with 2M aqueous HCl (300 mL), extracted with EtOAc, washed with water and brine, dried (Na$_2$SO$_4$) and evaporated in vacuo. The acid wash partly removed the BOC group and consequently most of the product was in the aqueous which was subsequently basified with 2M aqueous NaOH and extracted with EtOAc. All the organic extracts were combined, dried (MgSO$_4$) and concentrated in vacuo. The residue was dissolved in DCM (15 mL) and HCl 4M in dioxan (8 mL, 32.00 mmol) was added and the mixture stirred for 30 mins. The solvents were removed in vacuo and the residue triturated with diethyl ether until a solid was obtained. The solid was collected by filtration to give the sub-title compound as a white solid. Yield: 0.952 g $^1$H NMR (300 MHz, DMSO) δ 11.05 (s, 1H), 8.37 (d, J=6.5 Hz, 1H), 8.29 (d, J=3.1 Hz, 1H), 8.15 (m, 3H), 8.05 (dd, J=8.1, 3.1 Hz, 1H), 7.74 (d, J=7.9 Hz, 1H), 7.56 (t, J=7.9 Hz, 1H), 7.47 (d, J=7.9 Hz, 1H), 7.33 (m, 1H), 7.25 (m, 2H), 4.35 (m, 4H), 4.01-3.68 (m, 5H), 3.15 (m, 2H), 2.85 (m, 2H), 2.78 (s, 3H), 2.76 (s, 3H), 1.93-1.56 (m, 8H).

MS: [M+H]+=562 (calc=562) (MultiMode+)

Step (f) N-((1s,4s)-4-(2-(4'-((dimethylamino)methyl)-2'-(morpholinomethyl)biphenyl-3-yloxy)-5-fluoronicotinamido)cyclohexyl)-2-methylthiazole-4-carboxamide HATU (116 mg, 0.30 mmol) was added in one portion to N-((1s,4s)-4-aminocyclohexyl)-2-(4'-((dimethylamino)methyl)-2'-(morpholinomethyl)biphenyl-3-yloxy)-5-fluoronicotinamide (170 mg, 0.25 mmol), 2-methylthiazole-4-carboxylic acid (39.9 mg, 0.28 mmol) and DIPEA (0.221 mL, 1.27 mmol) in DMF (2 mL) at 25° C. under nitrogen. The resulting solution was stirred at 25° C. for 2 h. The reaction was diluted with methanol (2 mL) and acidified with HCl. The crude reaction was then purified on reverse phase HPLC 95/05 MeOH/TFA. The title compound was obtained as a white solid after freeze drying. Yield: 90 mg $^1$H NMR (300 MHz, DMSO) δ 8.37 (d, J=6.9 Hz, 1H), 8.28 (d, J=2.9 Hz, 1H), 8.09 (s, 1H), 8.05 (dd, J=7.9, 2.9 Hz, 1H), 7.78 (s, 1H), 7.66-7.52 (m, 3H), 7.46 (d, J=7.9 Hz, 1H), 7.30 (d, J=7.7 Hz, 1H), 7.22 (m, 2H), 4.33 (s, 6H), 3.99 (s, 1H), 3.88 (s, 1H), 3.65 (s, 4H), 2.79 (s, 8H), 2.68 (s, 3H), 1.69 (m, 8H).

MS: [M+H]+=687 (calc=687) (MultiMode+)

EXAMPLE 120

N-((1s,4s)-4-(1,5-dimethyl-1H-pyrazole-3-carboxamido)cyclohexyl)-2-(4'-((dimethylamino)methyl)-2'-(morpholinomethyl)biphenyl-3-yloxy)-5-fluoronicotinamide

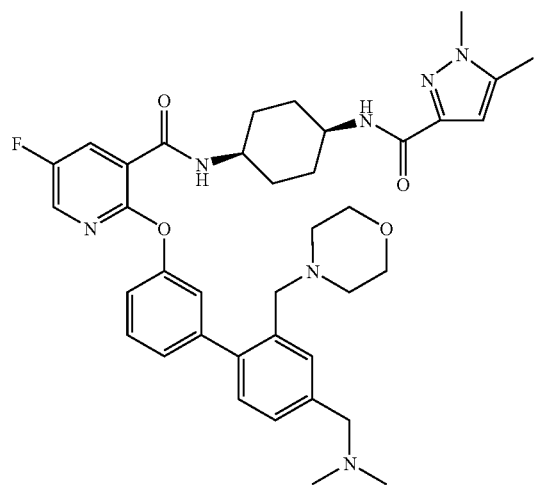

HATU (116 mg, 0.30 mmol) was added in one portion to N-((1s,4s)-4-aminocyclohexyl)-2-(4'-((dimethylamino)methyl)-2'-(morpholinomethyl)biphenyl-3-yloxy)-5-fluoronicotinamide (170 mg, 0.25 mmol), 1,5-dimethyl-1H-pyrazole-3-carboxylic acid (39.1 mg, 0.28 mmol) and DIPEA (0.221 mL, 1.27 mmol) in DMF (2 mL) at 25° C. under nitrogen. The resulting solution was stirred at 25° C. for 2 h. The reaction was diluted with methanol (2 mL) and acidified with HCl. The crude reaction was then purified on reverse phase HPLC 95/05 MeOH/TFA. The title compound was obtained as a white solid after freeze drying. Yield: 132 mg $^1$H NMR (300 MHz, DMSO) δ 8.36 (d, J=7.1 Hz, 1H), 8.28 (d, J=3.1 Hz, 1H), 8.05 (dd, J=8.0, 3.0 Hz, 1H), 7.77 (s, 1H), 7.67-7.52 (m, 3H), 7.48 (d, J=7.9 Hz, 1H), 7.22 (m, 3H), 6.40 (s, 1H), 4.33 (s, 6H), 3.96 (s, 1H), 3.84 (s, 1H), 3.75 (s, 3H), 3.66 (s, 4H), 2.79 (s, 8H), 2.26 (s, 3H), 1.70 (m, 8H).

MS: [M+H]+=684 (calc=684) (MultiMode+)

EXAMPLE 121

6-fluoro-N-((1s,4s)-4-(5-fluoro-2-(4'-(3-(piperazin-1-yl)propyl)biphenyl-3-yloxy)nicotinamido)cyclohexyl)imidazo[1,2-a]pyridine-2-carboxamide

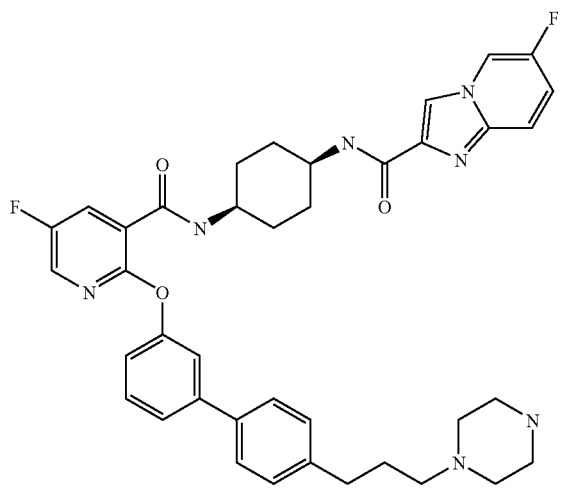

Step (a) 3-(4-bromophenyl)propan-1-ol

To a stirred solution of 3-(4-bromophenyl)propanoic acid (7 g, 30.56 mmol) in THF (50.9 ml) at −10° C. was added borane tetrahydrofuran complex (1M in THF) (153 ml, 152.79 mmol) dropwise over 1 h, keeping the temperature below 0° C. The reaction mixture was allowed to warm to RT overnight then cooled to 5° C. and quenched with MeOH (50 mL). Reaction mixture stirred at RT for 1 h and then concentrated to give an oil. The oil was partitioned between ether (120 mL) and 2M NaOH (60 mL). The organic layer was then washed with water (60 mL) and brine, dried over magnesium sulfate, filtered and evaporated to afford the sub-title compound. Yield: 6.17 g $^1$H NMR (400 MHz, CDCl$_3$) δ 7.40 (d, J=8.5 Hz, 2H), 7.07 (d, J=8.5 Hz, 2H), 3.66 (t, J=6.3 Hz, 2H), 2.67 (t, J=7.5 Hz, 2H), 1.90-1.82 (m, 2H).

Step (b) 3-(4-bromophenyl)propyl methanesulfonate

To a stirred solution of 3-(4-bromophenyl)propan-1-ol (6.17 g, 28.69 mmol) in dichloromethane (40 ml) was added triethylamine (4.80 ml, 34.42 mmol) and methanesulfonyl chloride (2.68 ml, 34.42 mmol). Reaction mixture stirred at RT under nitrogen overnight. The reaction mixture was evaporated to dryness and partitioned between EtOAc (50 mL) and water (25 mL), the aqueous portion was extracted with EtOAc (2×25 mL). Combined organics washed with 2M hydrochloric acid (2×25 mL) and saturated brine (25 mL). The organic was dried over magnesium sulfate, filtered and evaporated to afford the sub-title compound. Yield: 8.60 g $^1$H NMR (400 MHz, CDCl$_3$) δ 7.42 (d, J=9.0 Hz, 2H), 7.07 (d, J=8.0 Hz, 2H), 4.22 (t, J=6.5 Hz, 2H), 3.00 (s, 3H), 2.71 (t, J=8.0 Hz, 2H), 2.09-2.01 (m, 2H).

Step (c) tert-butyl 4-(3-(4-bromophenyl)propyl)piperazine-1-carboxylate

To a stirred solution of 3-(4-bromophenyl)propyl methanesulfonate (4.2 g, 14.33 mmol) in acetonitrile (33.2 ml) was added tert-butyl piperazine-1-carboxylate (3.47 g, 18.62 mmol) and triethylamine (2.60 ml, 18.62 mmol). Reaction mixture heated to 75° C. overnight. The reaction mixture was evaporated to dryness and redissolved in EtOAc (40 mL), and washed with 2:8 saturated brine:water (45 mL). The aqueous was extracted with EtOAc (2×25 mL), organics combined and washed with 2:8 saturated brine:water (2×45 mL) and saturated brine (25 mL). The organic was dried over magnesium sulfate, filtered and evaporated to afford crude product. The crude product was purified by flash silica chromatography using Isco Companion, 50 g silica column, elution gradient 30 to 50% EtOAc in dichloromethane. Pure fractions were evaporated to dryness to afford the sub-title compound as a yellow oil. Yield: 2.4 g $^1$H NMR (400 MHz, CDCl$_3$) δ 7.39 (d, J=10.4 Hz, 2H), 7.05 (d, J=8.3 Hz, 2H), 3.43 (t, J=5.4 Hz, 4H), 2.59 (t, J=7.8 Hz, 2H), 2.38-2.31 (m, 6H), 1.78 (quintet, J=7.4 Hz, 2H), 1.46 (s, 9H).

MS: [M+H]+=383.0 (Multimode+)

Step (d) tert-butyl 4-(3-(4-(4,4,5,5-tetramethyl-1,3,2-dioxaborolan-2-yl)phenyl)propyl)piperazine-1-carboxylate To a stirred solution of tert-butyl 4-(3-(4-bromophenyl)propyl)piperazine-1-carboxylate (2.4 g, 6.26 mmol) in acetonitrile (12 ml) was added triethylamine (2.62 ml, 18.78 mmol) and Pd-118 (0.122 g, 0.19 mmol). Reaction mixture was stirred at RT under nitrogen for 10 min. 4,4,5,5-Tetramethyl-1,3,2-dioxaborolane (1.363 ml, 9.39 mmol) added and reaction mixture heated to 80° C. for 1 h. The reaction mixture was evaporated to dryness and redissolved in EtOAc and washed with water and saturated brine. The organic was dried over magnesium sulfate, filtered and evaporated to afford crude product. The crude product was purified by flash silica chromatography using Isco Companion, 100 g silica column, elution gradient 40 to 100% EtOAc in isohexane. Pure fractions were evaporated to dryness to afford sub-title compound as a brown oil. Yield: 0.9 g $^1$H NMR (400 MHz, CDCl$_3$) δ 7.72 (d, J=7.1 Hz, 2H), 7.21-7.16 (m, 2H), 3.45-3.40 (m, 4H), 2.67-2.61 (m, 2H), 2.39-2.32 (m, 6H), 1.86-1.77 (m, 2H), 1.45 (s, 9H), 1.24 (s, 12H).

MS: [M+H]+=431.2 (Multimode+)

Step (e) tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate To a solution of N-((1s,4s)-4-aminocyclohexyl)-5-fluoro-2-(3-iodophenoxy)nicotinamide (1.587 g, 3.49 mmol) and tert-butyl 4-(3-(4-(4,4,5,5-tetramethyl-1,3,2-dioxaborolan-2-yl)phenyl)propyl)piperazine-1-carboxylate (1.5 g, 3.49 mmol) in THF (22.85 mL) was added sodium carbonate (0.584 mL, 13.94 mmol), water (11.42 mL) and tetrakis (triphenylphosphine)palladium(0) (0.201 g, 0.17 mmol). The mixture was heated to 80° C. for 36 h. The mixture was cooled, poured into water and the organics extracted in EtOAc (×2). The extractions were combined, dried and evaporated to give an oil. This was purified using column chromatography (eluent=4% 7N NH$_3$ in methanol/DCM) to give the sub-title compound as an oil. Yield: 1.5 g MS: [M+H]+=632.43 (MultiMode+)

Step (f) 6-fluoro-N-((1s,4s)-4-(5-fluoro-2-(4'-(3-(piperazin-1-yl)propyl)biphenyl-3-yloxy)nicotinamido)cyclohexyl)imidazo[1,2-a]pyridine-2-carboxamide To a solution of tert-butyl 4-(3-(3'-(3-(((1s,4s)-4-aminocyclohexylcarbamoyl)-5-fluoropyridin-2-yloxy)biphenyl-4-yl)propyl)piperazine-1-carboxylate (150 mg, 0.24 mmol) in acetonitrile (2 mL) was added 6-fluoroimidazo[1,2-a]pyridine-2-carboxylic acid, hydrochloride (51.4 mg, 0.24 mmol) and triethylamine (0.331 mL, 2.37 mmol). 1-Propanephosphonic acid cyclic anhydride, 1.57M solution in THF (0.159 mL, 0.25 mmol) was then added and the mixture stirred at RT for 1 h. The mixture was poured into sat NaHCO$_3$ (aq) and the organics extracted into EtOAc (×2). The extractions were combined, dried (MgSO$_4$) and evaporated to give a residue. This was dissolved in DCM (2 mL) to which TFA (2 mL) was added and the mixture stirred at RT for 20 min. The solvents were removed in vacuo and the residue dissolved in methanol and purified using reverse phase preparative chromatography using eluent=TFA(aq)/MeOH). The appropriate fractions were combined and evaporated to give a residue which on trituration with ether gave a solid. The solid was dried overnight under vacuum at 40° C. to give the title compound. Yield: 64 mg $^1$H NMR (400 MHz, CD$_3$OD) δ 8.57 (t, J=3.1 Hz, 1H), 8.47 (d, J=7.2 Hz, 1H), 8.28 (s, 1H), 8.12-8.05 (m, 2H), 7.59-7.44 (m, 5H), 7.43-7.37 (m, 2H), 7.21 (d, J=8.2 Hz, 2H), 7.18-7.12 (m, 1H), 4.15-4.10 (m, 1H), 4.05-4.00 (m, 1H), 3.48-3.44 (m, 4H), 3.35-3.31 (m, 4H), 3.05-2.99 (m, 2H), 2.69 (t, J=7.4 Hz, 2H), 2.05-1.96 (m, 2H), 1.92-1.70 (m, 8H).

MS: [M+H]+=694 (calc=694) (MultiMode+)

EXAMPLE 122

N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)-6-fluoroimidazo[1,2-a]pyridine-2-carboxamide

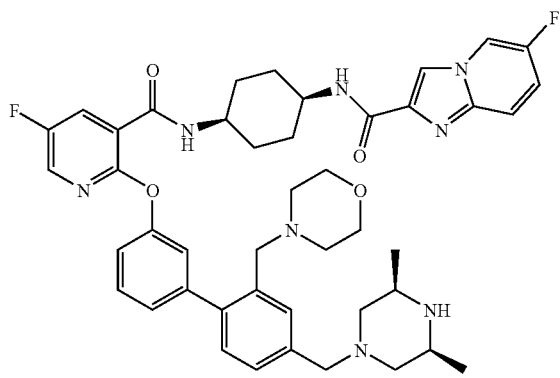

Step (a) tert-butyl (1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexylcarbamate Tert-butyl (1s,4s)-4-(5-fluoro-2-(4'-formyl-2'-(morpholinomethyl)biphenyl-3-yloxy)nicotinamido)cyclohexylcarbamate (1.0 g, 1.58 mmol) and (2S,6R)-2,6-dimethylpiperazine (0.361 g, 3.16 mmol) were stirred in DCM (30 mL) for 15 min. Acetic acid (0.181 mL, 3.16 mmol), followed by sodium triacetoxyborohydride (0.670 g, 3.16 mmol) were added and the reaction stirred for a further 20 h. The reaction was quenched with 2M HCl (30 mL), extracted with EtOAc, washed with water and brine, dried (Na$_2$SO$_4$) and evaporated in vacuo. The residue was purified by chromatography on silica with 5% MeOH/DCM as eluent to give the sub-title compound as a white solid. Yield: 1.05 g $^1$H NMR (300 MHz, CDCl$_3$) δ 8.36 (m, 1H), 8.06 (d, J=3.2 Hz, 1H), 8.02 (d, J=7.7 Hz, 1H), 7.50 (t, J=7.8 Hz, 1H), 7.38 (m, 2H), 7.35 (m, 1H), 7.30 (m, 1H), 7.27 (m, 3H), 7.14 (m, 1H), 4.49 (m, 1H), 4.16 (m, 1H), 3.55 (m, 8H), 3.41 (s, 2H), 3.01 (m, 2H), 2.80 (m, 2H), 2.33 (m, 4H), 1.88-1.43 (m, 8H), 1.42 (s, 9H), 1.10 (d, J=6.6 Hz, 6H).

MS: APCI (+ve):731 (M+1)

Step (b) N-((1s,4s)-4-aminocyclohexyl)-2-(4'-(((3S,5R)-3,5-dimethylpiperazin-1-yl)methyl)-2'-(morpholinomethyl)biphenyl-3-yloxy)-5-fluoronicotinamide hydrochloride HCl/dioxane (10 mL, 329.12 mmol) was added to a solution of tert-butyl (1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexylcarbamate (1.0 g, 1.37 mmol) in DCM (20 mL) and stirred for 2 h. Evaporated in vacuo to give the sub-title compound as a white solid. Yield: 1.1 g $^1$H NMR (300 MHz, DMSO) δ 8.38 (d, J=6.4 Hz, 1H), 8.28 (d, J=3.4 Hz, 1H), 8.22-8.14 (m, 1H), 8.14-8.03 (m, 2H), 8.04 (m, 5H), 7.76-7.65 (m, 1H), 7.56 (t, J=8.1 Hz, 1H), 7.45 (d, J=8.1 Hz, 1H), 7.31 (m, 1H), 7.21 (m, 2H), 4.46-4.07 (m, 3H), 4.00-3.04 (m, 12H), 2.85-2.66 (m, 4H), 1.93-1.56 (m, 8H), 1.30 (d, J=6.8 Hz, 6H).

MS: APCI (+ve):631 (M+1)

Step (c) N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)-2-methylthiazole-4-carboxamide HATU (0.113 g, 0.30 mmol) was added to a solution of N-((1s,4s)-4-aminocyclohexyl)-2-(4'-(((3S,5R)-3,5-dimethylpiperazin-1-yl)methyl)-2'-(morpholinomethyl)biphenyl-3-yloxy)-5-fluoronicotinamide HCl (0.2 g, 0.27 mmol), 6-fluoroimidazo[1,2-a]pyridine-2-carboxylic acid (0.064 g, 0.30 mmol) and DIPEA (0.236 mL, 1.35 mmol) in DMF (5 mL) and the solution stirred at RT for 20 h. The mixture was purified by reverse phase HPLC with aqTFA/MeCN as eluant to give the title compound as a white solid. Yield: 203 mg $^1$H NMR (400 MHz, CD$_3$OD) δ 8.73 (m, 1H), 8.45 (s, 1H), 8.13 (d, J=3.3 Hz, 1H), 8.04 (m, 1H), 7.81 (m, 1H), 7.71 (m, 1H), 7.60 (m, 3H), 7.42 (d, J=7.9 Hz, 1H), 7.32 (m, 1H), 7.21 (m, 1H), 7.18 (m, 1H), 4.43 (s, 2H), 4.15-4.02 (m, 2H), 4.07 (s, 2H), 3.87-3.64 (m, 4H), 3.56 (m, 2H), 3.38 (m, 2H), 3.31-3.09 (m, 2H), 2.98-2.75 (m, 2H), 2.66 (t, J=12.7 Hz, 2H), 1.97-1.75 (m, 8H), 1.32 (d, J=6.3 Hz, 6H).

MS: APCI (+ve):793 (M+1).

EXAMPLE 123

N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)-5-methylimidazo[1,2-a]pyridine-2-carboxamide

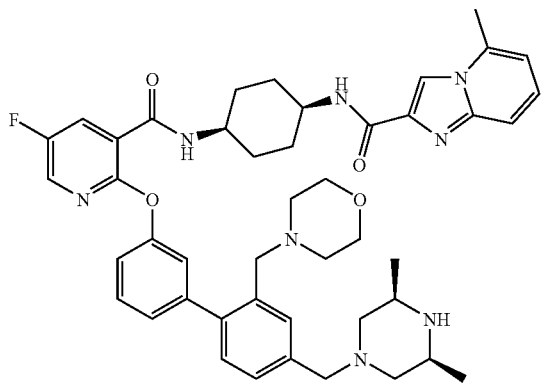

HATU (0.113 g, 0.30 mmol) was added to a solution of N-((1s,4s)-4-aminocyclohexyl)-2-(4'-(((3 S,5R)-3,5-dimethylpiperazin-1-yl)methyl)-2'-(morpholinomethyl)biphenyl-3-yloxy)-5-fluoronicotinamide HCl (0.2 g, 0.27 mmol), 5-methylimidazo[1,2-a]pyridine-2-carboxylic acid (0.052 g, 0.30 mmol) and DIPEA (0.236 mL, 1.35 mmol) in DMF (5 mL) and the solution stirred at RT for 20 h. The mixture was purified by reverse phase HPLC with aqTFA/MeCN as eluant to give the title compound as a white solid. Yield: 253 mg $^1$H NMR (400 MHz, CD$_3$OD) δ 8.73 (s, 1H), 8.12 (d, J=3.3 Hz, 1H), 8.03 (m, 1H), 7.89 (m, 1H), 7.84 (m, 1H), 7.74 (d, J=8.8 Hz, 1H), 7.59 (m, 2H), 7.44 (d, J=8.3 Hz, 1H), 7.32 (m, 2H), 7.20 (m, 2H), 4.44 (s, 2H), 4.17-4.05 (m, 4H), 4.14 (s, 2H), 3.87-3.66 (m, 4H), 3.64-3.55 (m, 2H), 3.44 (m, 2H), 3.31-3.09 (m, 2H), 2.99-2.81 (m, 2H), 2.79 (s, 3H), 2.77 (m, 2H), 2.00-1.80 (m, 8H), 1.33 (d, J=6.9 Hz, 6H).

MS: APCI (+ve):789 (M+1).

EXAMPLE 124

N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)-4,5,6,7-tetrahydropyrazolo[1,5-a]pyridine-2-carboxamide

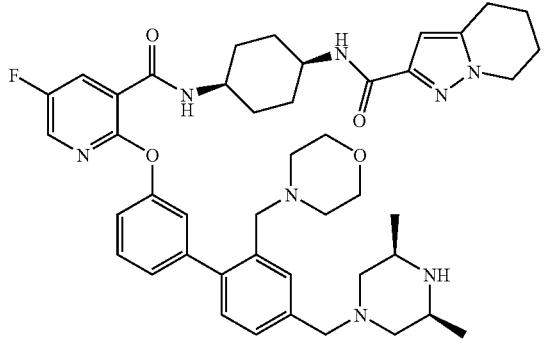

HATU (0.113 g, 0.30 mmol) was added to a solution of N-((1s,4s)-4-aminocyclohexyl)-2-(4'-(((3S,5R)-3,5-dimethylpiperazin-1-yl)methyl)-2'-(morpholinomethyl)biphenyl-3-yloxy)-5-fluoronicotinamide (0.2 g, 0.27 mmol), 4,5,6,7-tetrahydropyrazolo[1,5-a]pyridine-2-carboxylic acid (0.049 g, 0.30 mmol) and DIPEA (0.236 mL, 1.35 mmol) in DMF (5 mL) and the solution stirred at RT for 20 h. The mixture was purified by reverse phase HPLC with aqTFA/MeCN as eluant to afford the title compound as a white solid. Yield: 144 mg $^1$H NMR (400 MHz, CD$_3$OD) δ 8.12 (d, J=3.1 Hz, 1H), 8.06 (m, 1H), 8.03 (m, 1H), 7.68 (m, 1H), 7.60 (t, J=7.8 Hz, 1H), 7.46 (d, J=8.0 Hz, 1H), 7.33 (m, 1H), 7.24 (d, J=7.8 Hz, 1H), 7.21 (m, 1H), 6.41 (s, 1H), 4.47 (s, 2H), 4.46 (s, 2H), 4.09 (t, J=6.3 Hz, 2H), 3.97 (m, 1H), 3.86-3.75 (m, 6H), 3.71 (m, 2H), 3.34-3.18 (m, 4H), 2.97-2.75 (m, 2H), 2.79 (t, J=6.7 Hz, 2H), 2.03 (m, 2H), 1.91-1.67 (m, 12H), 1.40 (d, J=6.4 Hz, 6H).

MS: APCI (+ve):779 (M+1)

EXAMPLE 125

N-((1s,4s)-4-(2-(3'-(((3S,5R)-3,5-dimethylpiperazin-1-yl)methyl)-4'-hydroxybiphenyl-3-yloxy)-5-fluoronicotinamido)cyclohexyl)pyrazolo[1,5-a]pyrimidine-3-carboxamide

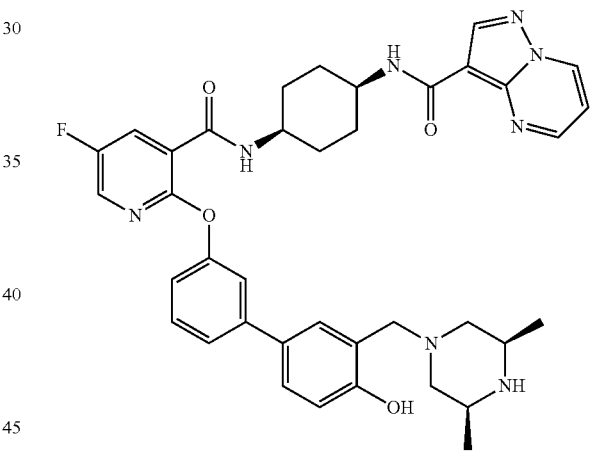

Pyrazolo[1,5-a]pyrimidine-3-carboxylic acid (0.031 g, 0.19 mmol) was dissolved in acetonitrile (5 mL) then DIPEA (0.067 mL, 0.38 mmol) and HATU (0.073 g, 0.19 mmol) added then stirred for 20 min. It was added to a stirred solution of N-((1s,4s)-4-aminocyclohexyl)-2-(3'-(((3S,5R)-3,5-dimethylpiperazin-1-yl)methyl)-4'-hydroxybiphenyl-3-yloxy)-5-fluoronicotinamide hydrochloride (presumed tri-) (0.120 g, 0.18 mmol) in acetonitrile (5 mL) and DIPEA (0.064 mL, 0.37 mmol). The reaction mixture was stirred overnight then 880 aqueous ammonia (2 mL) was added and the reaction mixture was stirred for 4 h. The reaction mixture was diluted with EtOAc and washed with water and saturated brine. The organic was dried over sodium sulfate, filtered and evaporated to afford crude product. The crude product was purified by preparative HPLC on a Sunfire column using a 95-5% gradient of aqueous 0.1% TFA in methanol as eluent. The fractions containing the desired compound were evaporated to dryness to afford the title compound as a white solid. Yield: 100 mg $^1$H NMR (400 MHz, DMSO) δ 9.30 (dd, J=7.0, 1.6 Hz, 1H), 8.58 (dd, J=4.2, 1.5 Hz, 1H), 8.55 (s, 1H), 8.48 (d, J=7.5

Hz, 1H), 8.24 (d, J=3.1 Hz, 1H), 8.03 (dd, J=8.0, 3.1 Hz, 1H), 7.91 (d, J=7.8 Hz, 1H), 7.55-7.50 (m, 1H), 7.49-7.36 (m, 4H), 7.19 (dd, J=7.0, 4.2 Hz, 1H), 7.15-7.11 (m, 1H), 6.89 (d, J=8.5 Hz, 1H), 4.05-3.77 (m, 4H), 3.45-3.30 (m, 2H), 3.28-3.13 (m, 2H), 1.82-1.63 (m, 8H), 1.18 (d, J=6.4 Hz, 6H). Remaining protons obscured by solvent.

MS: [M+H]+=693 (calc=693) (MultiMode+)

EXAMPLE 126

N-((1s,4s)-4-(1,5-dimethyl-1H-pyrazole-3-carboxamido)cyclohexyl)-2-(3'-(3-((3S,5R)-3,5-dimethylpiperazin-1-yl)propyl)biphenyl-3-yloxy)-5-fluoronicotinamide

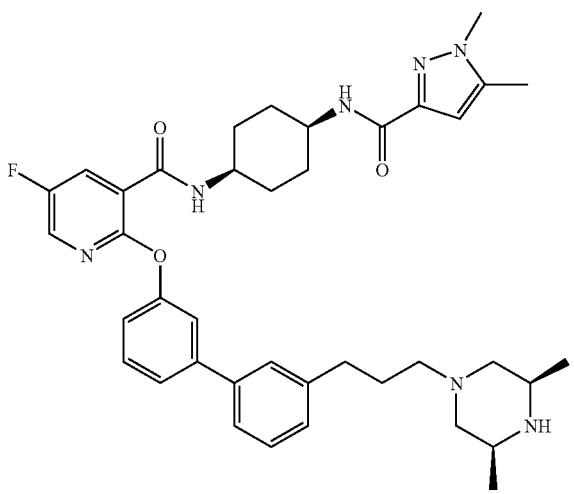

Step (a) N-((1s,4s)-4-(1,5-dimethyl-1H-pyrazole-3-carboxamido)cyclohexyl)-5-fluoro-2-(3'-(3-hydroxypropyl)biphenyl-3-yloxy)nicotinamide To a stirred solution of N-((1s,4s)-4-(1,5-dimethyl-1H-pyrazole-3-carboxamido)cyclohexyl)-5-fluoro-2-(3-iodophenoxy)nicotinamide (0.350 g, 0.61 mmol) in THF (4.04 ml) was added 3-(3-hydroxypropyl)phenylboronic acid (0.120 g, 0.67 mmol) and sodium carbonate (0.193 g, 1.82 mmol) in water (2.021 ml). Tetrakis(triphenylphosphine)palladium(0) (0.035 g, 0.03 mmol) was added and reaction mixture heated to 70° C. overnight. The reaction mixture poured into water and extracted into EtOAc. The organic was dried over magnesium sulfate, filtered and evaporated to afford crude product. The crude product was purified by flash silica chromatography using Isco Companion, 50 g silica column, elution gradient 1 to 5% methanol in dichloromethane. Pure fractions were evaporated to dryness to afford the sub-title compound as a yellow solid. Yield: 0.293 g ¹H NMR (400 MHz, CDCl₃) δ 8.38 (dd, J=8.9, 3.2 Hz, 1H), 8.08 (d, J=3.4 Hz, 2H), 7.54-7.51 (m, 2H), 7.41-7.36 (m, 3H), 7.32 (t, J=7.7 Hz, 1H), 7.20-7.14 (m, 2H), 6.70-6.65 (m, 1H), 6.50 (s, 1H), 4.27-4.20 (m, 1H), 4.10-4.02 (m, 1H), 3.68 (t, J=6.6 Hz, 2H), 3.66 (s, 3H), 2.74 (t, J=7.7 Hz, 2H), 2.24 (s, 3H), 1.96-1.79 (m, 8H), 1.68-1.58 (m, 2H).

MS: [M+H]+=586.2 (Multimode+)

Step (b) 3-(3'-(3-((1s,4s)-4-(1,5-dimethyl-1H-pyrazole-3-carboxamido)cyclohexylcarbamoyl)-5-fluoropyridin-2-yloxy)biphenyl-3-yl)propyl methanesulfonate To a stirred solution of N-((1s,4s)-4-(1,5-dimethyl-1H-pyrazole-3-carboxamido)cyclohexyl)-5-fluoro-2-(3'-(3-hydroxypropyl)biphenyl-3-yloxy)nicotinamide (0.293 g, 0.50 mmol) in dichloromethane (3 ml) was added pyridine (0.162 ml, 2.00 mmol) followed by methanesulfonyl chloride (0.156 ml, 2.00 mmol). The reaction mixture was stirred at RT under nitrogen overnight. The reaction mixture was diluted with dichloromethane, and washed with 2M hydrochloric acid, water and saturated brine. The organic was dried over magnesium sulfate, filtered and evaporated to afford the sub-title compound, which was used without further purification.

¹H NMR (400 MHz, CDCl₃) δ 8.35 (dd, J=8.7, 4.4 Hz, 1H), 8.07 (d, J=2.9 Hz, 2H), 7.55-7.52 (m, 2H), 7.44-7.41 (m, 3H), 7.34 (t, J=7.6 Hz, 1H), 7.21-7.17 (m, 2H), 6.94 (d, J=7.3 Hz, 1H), 6.52 (s, 1H), 4.23 (t, J=6.2 Hz, 2H), 4.25-4.19 (m, 1H), 4.12-4.04 (m, 1H), 3.72 (s, 3H), 2.99 (s, 3H), 2.79 (t, J=7.3 Hz, 2H), 2.27 (s, 3H), 2.10 (quintet, J=6.9 Hz, 2H), 1.92-1.82 (m, 6H), 1.70-1.60 (m, 2H)

MS: [M+H]+=663.9 (Multimode+)

Step (c) N-((1s,4s)-4-(1,5-dimethyl-1H-pyrazole-3-carboxamido)cyclohexyl)-2-(3'-(3-((3S,5R)-3,5-dimethylpiperazin-1-yl)propyl)biphenyl-3-yloxy)-5-fluoronicotinamide To a microwave vial was added 3-(3'-(3-((1s,4s)-4-(1,5-dimethyl-1H-pyrazole-3-carboxamido)cyclohexylcarbamoyl)-5-fluoropyridin-2-yloxy)biphenyl-3-yl)propyl methanesulfonate (0.150 g, 0.23 mmol) and (2S,6R)-2,6-dimethylpiperazine (0.103 g, 0.90 mmol) in acetonitrile (1 mL). Reaction mixture was heated to 80° C. by microwave for 30 min. The reaction mixture concentrated to give the crude product which was purified by preparative HPLC on a Phenomenex Gemini column using a 95-15% gradient of aqueous 0.2% TFA in methanol as eluent. The fractions containing the desired compound were evaporated to dryness to afford the title compound as a white solid. Yield: 21 mg ¹H NMR (400 MHz, CD₃OD) δ 8.10 (d, J=3.3 Hz, 1H), 8.06 (dd, J=7.8, 2.8 Hz, 1H), 7.48 (d, J=5.0 Hz, 2H), 7.45-7.41 (m, 3H), 7.31 (t, J=7.8 Hz, 1H), 7.21-7.13 (m, 2H), 6.38 (s, 1H), 4.15-4.08 (m, 1H), 3.95-3.87 (m, 1H), 3.78 (d, J=13.0 Hz, 4H), 3.69 (s, 3H), 3.23-3.16 (m, 2H), 3.03 (t, J=11.7 Hz, 2H), 2.71 (t, J=7.8 Hz, 2H), 2.23 (s, 3H), 2.14-2.04 (m, 2H), 1.90-1.73 (m, 6H), 1.72-1.61 (m, 2H), 1.37 (d, J=3.9 Hz, 6H).

MS: m/z (APCI+), (M+H)+=682.4

EXAMPLE 127

N-((1s,4s)-4-(2-(4'-(3-(1,4-diazepan-1-yl)propyl)biphenyl-3-yloxy)-5-fluoronicotinamido)cyclohexyl)-4,5,6,7-tetrahydropyrazolo[1,5-a]pyridine-2-carboxamide

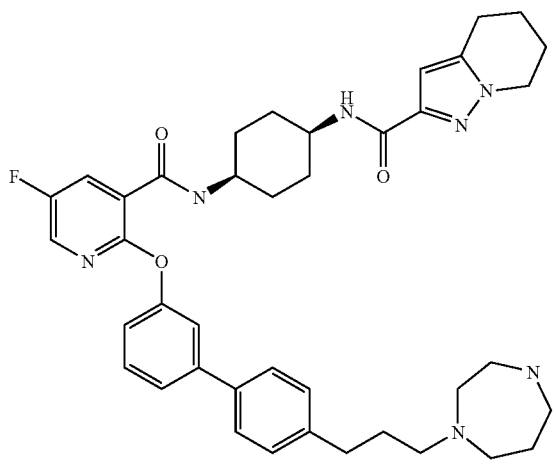

Step (a) N-((1s,4s)-4-(5-fluoro-2-(4'-(3-hydroxypropyl)biphenyl-3-yloxy)nicotinamido)cyclohexyl)-4,5,6,7-tetrahydropyrazolo[1,5-a]pyridine-2-carboxamide Tetrakis(triphenylphosphine)palladium(0) (0.011 g, 9.94 μmol) was added to a mixture of N-((1s,4s)-4-(5-fluoro-2-(3-iodophenoxy)nicotinamido)cyclohexyl)-4,5,6,7-tetrahydropyrazolo[1,5-a]pyridine-2-carboxamide (0.3 g, 0.50 mmol), 4-(3-hydroxypropyl)phenylboronic acid (0.098 g, 0.55 mmol) and sodium carbonate (0.158 g, 1.49 mmol) in water (2.500 mL) and THF (5 mL). The mixture was heated at 70° C. for 18 h. The reaction mixture was diluted with EtOAc and washed with water and saturated brine. The organic was dried over sodium sulfate, filtered and evaporated to afford crude product. The crude product was purified by flash silica chromatography (Biotage, 100 g) eluting with 100% EtOAc then 5% methanol in EtOAc. Pure fractions were combined and evaporated to dryness to afford the title compound as a white solid. Yield: 0.25 g MS: m/z (APCI+), (M+H)+=612

Step (b) 3-(3'-(5-fluoro-3-((1s,4s)-4-(4,5,6,7-tetrahydropyrazolo[1,5-a]pyridine-2-carboxamido)cyclohexylcarbamoyl)pyridin-2-yloxy)biphenyl-4-yl)propyl methanesulfonate To a solution of N-((1s,4s)-4-(5-fluoro-2-(4'-(3-hydroxypropyl)biphenyl-3-yloxy)nicotinamido)cyclohexyl)-4,5,6,7-tetrahydropyrazolo[1,5-a]pyridine-2-carboxamide (0.3 g, 0.49 mmol) and pyridine (0.079 mL, 0.98 mmol) in DCM (2 mL), was added methanesulfonyl chloride (0.080 mL, 1.03 mmol) and the reaction stirred at RT overnight. The reaction mixture was diluted with aqueous 2M HCl and extracted with DCM (×3) and EtOAc (×3). Organics were combined and dried (MgSO4) and concentrated to give an oil. The oil was dissolved in DCM then isohexane added until a solid crashed out. The suspension was concentrated in vacuo to give an oil. The oil was again dissolved in DCM and isohexane added until a solid crashed out (repeated ×4). On concentration, the title compound became an off white foam. Yield: 0.25 g MS: [M+H]+=690 (MultiMode+)

Step (c) N-((1s,4s)-4-(2-(4'-(3-(1,4-diazepan-1-yl)propyl)biphenyl-3-yloxy)-5-fluoronicotinamido)cyclohexyl)-4,5,6,7-tetrahydropyrazolo[1,5-a]pyridine-2-carboxamide To a solution of 3-(3'-(5-fluoro-3-((1s,4s)-4-(4,5,6,7-tetrahydropyrazolo[1,5-a]pyridine-2-carboxamido)cyclohexylcarbamoyl)pyridin-2-yloxy)biphenyl-4-yl)propyl methanesulfonate (0.125 g, 0.18 mmol) in acetonitrile (1 mL) was added 1,4-diazepane (0.363 g, 3.62 mmol). The mixture was heated to 80° C. in the microwave for 30 min. The crude product was purified by preparative HPLC on a Phenomenex Gemini column using a 95-5% gradient of aqueous 0.1% TFA in methanol as eluent. The fractions containing the desired compound were freeze dried to afford the title compound as a white solid. Yield: 43 mg $^1$H NMR (400 MHz, CD$_3$OD) δ 8.45 (d, J=10.8 Hz, 1H), 8.11 (d, J=4.8 Hz, 1H), 8.07-8.03 (m, 1H), 7.53 (d, J=7.8 Hz, 2H), 7.48-7.46 (m, 2H), 7.39-7.37 (m, 1H), 7.26 (d, J=7.8 Hz, 2H), 7.16-7.13 (m, 1H), 6.38 (s, 1H), 4.13-4.07 (m, 1H), 4.03 (t, J=6.4 Hz, 2H), 3.98-3.92 (m, 1H), 3.68-3.59 (m, 3H), 3.52-3.45 (m, 1H), 3.40 (t, J=7.6 Hz, 2H), 3.22-3.18 (m, 2H), 2.80-2.71 (m, 4H), 2.26-2.20 (m, 2H), 2.11-1.97 (m, 4H), 1.87-1.77 (m, 8H), 1.73-1.65 (m, 2H), 0.89-0.82 (m, 2H).

MS: [M+H]+=694 (calc=694) (MultiMode+)

EXAMPLE 128

N-((1s,4s)-4-(5-fluoro-2-(4'-(3-(3-hydroxypropylamino)propyl)biphenyl-3-yloxy)nicotinamido)cyclohexyl)-4,5,6,7-tetrahydropyrazolo[1,5-a]pyridine-2-carboxamide

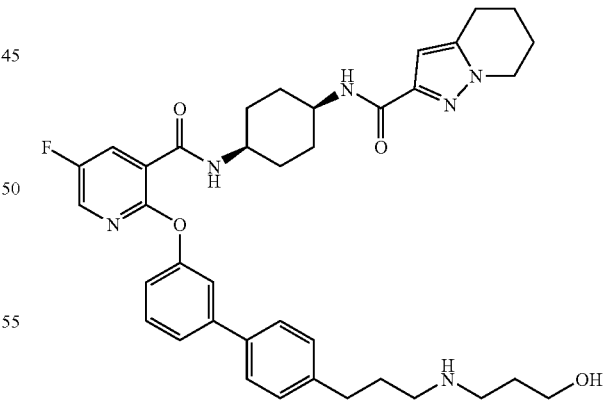

To a solution of 3-(3'-(5-fluoro-3-((1s,4s)-4-(4,5,6,7-tetrahydropyrazolo[1,5-a]pyridine-2-carboxamido)cyclohexylcarbamoyl)pyridin-2-yloxy)biphenyl-4-yl)propyl methanesulfonate (0.125 g, 0.18 mmol) in acetonitrile (1 mL) was added 3-aminopropan-1-ol (0.069 mL, 0.91 mmol). The mixture was heated to 80° C. in the microwave for 20 min. The crude product was purified by preparative HPLC on a Phenomenex Gemini column using a 95-5% gradient of aqueous 0.1% TFA in methanol as eluent. The fractions containing the desired compound were freeze dried to afford the title compound as a white solid. Yield: 59 mg $^1$H NMR (400 MHz, CD$_3$OD) δ 8.44 (d, J=15.0 Hz, 1H), 8.11 (d, J=3.3 Hz, 1H), 8.07-8.04 (m, 1H), 7.53 (d, J=7.4 Hz, 2H), 7.47 (d, J=7.4 Hz, 2H), 7.40-7.38 (m, 1H), 7.25 (d, J=6.2 Hz, 2H), 7.16-7.12 (m, 1H), 6.38 (s, 1H), 4.15-4.08 (m, 1H), 4.01 (t, J=5.9 Hz, 2H), 3.98-3.92 (m, 1H), 3.66 (t, J=7.0 Hz, 2H), 3.10 (t, J=7.9 Hz, 2H), 3.03-2.98 (m, 2H), 2.80-2.71 (m, 4H), 2.03-1.96 (m, 4H), 1.88-1.78 (m, 10H), 1.74-1.64 (m, 2H).

MS: [M+H]+=669 (calc=669) (MultiMode+)

EXAMPLE 129

N-((1s,4s)-4-(1,5-dimethyl-1H-pyrazole-3-carboxamido)cyclohexyl)-2-(4'-(((3S,5R)-3,5-dimethylpiperazin-1-yl)methyl)-3'-hydroxybiphenyl-3-yloxy)-5-fluoronicotinamide

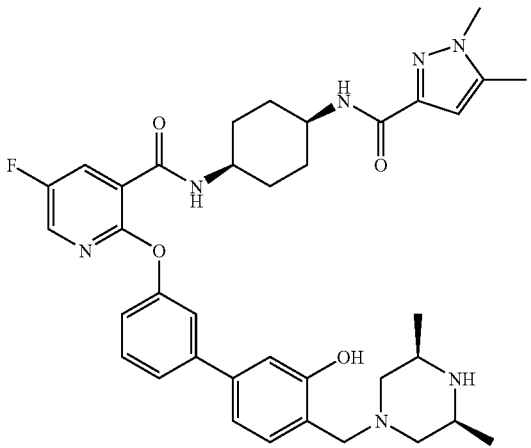

To a solution of 1,5-dimethyl-1H-pyrazole-3-carboxylic acid (32.0 mg, 0.23 mmol) in acetonitrile (3.00 mL) was added DIPEA (0.080 mL, 0.46 mmol) and HATU (87 mg, 0.23 mmol). After stirring for 5 min this solution was then added to a mixture of N-((1s,4s)-4-aminocyclohexyl)-2-(4'-(((3S,5R)-3,5-dimethylpiperazin-1-yl)methyl)-3'-hydroxybiphenyl-3-yloxy)-5-fluoronicotinamide, trihydrochloride (150 mg, 0.23 mmol) and DIPEA (0.080 mL, 0.46 mmol) in acetonitrile (3 mL). The mixture was left to stir at RT for 1 h. To this solution was then added 2 mL of 0.88 NH$_3$(aq) and the mixture was allowed to stir for 1 h. The reaction mixture was evaporated to dryness and the residue was then dissolved in methanol and acidified using 0.2 mL TFA before being purified using reverse phase preparative HPLC (eluent=TFA(aq)/MeCN). The appropriate fractions were combined and evaporated to give a residue that on trituration with ether gave a solid. The solid was dried overnight at 40° C. to give the title compound. Yield: 88 mg $^1$H NMR (400 MHz, CD$_3$OD) δ 8.45 (d, J=7.2 Hz, 1H), 8.11 (d, J=3.1 Hz, 1H), 8.04 (dd, J=7.9, 3.1 Hz, 1H), 7.51-7.43 (m, 2H), 7.36 (t, J=1.9 Hz, 1H), 7.32 (d, J=7.7 Hz, 1H), 7.18 (dt, J=7.8, 1.9 Hz, 1H), 7.13-7.10 (m, 2H), 6.42 (s, 1H), 4.17 (s, 2H), 4.11-4.08 (m, 1H), 3.97-3.91 (m, 1H), 3.73 (s, 3H), 3.63-3.56 (m, 2H), 3.53-3.47 (m, 2H), 2.75 (t, J=12.6 Hz, 2H), 2.26 (s, 3H), 1.86-1.77 (m, 6H), 1.74-1.64 (m, 2H), 1.33 (d, J=6.7 Hz, 6H).

MS: [M+H]+=670 (calc=670) (MultiMode+)

EXAMPLE 130

N-((1s,4s)-4-(1,5-dimethyl-1H-pyrazole-3-carboxamido)cyclohexyl)-5-fluoro-2-(4'-(3-(piperazin-1-yl)propyl)biphenyl-3-yloxy)nicotinamide

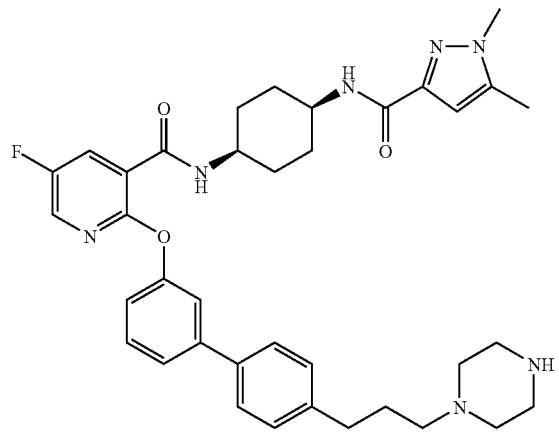

To a microwave tube was charged 3-(3'-(3-((1s,4s)-4-(1,5-dimethyl-1H-pyrazole-3-carboxamido)cyclohexylcarbamoyl)-5-fluoropyridin-2-yloxy)biphenyl-4-yl)propyl methanesulfonate (90 mg, 0.14 mmol), tert-butyl piperazine-1-carboxylate (76 mg, 0.41 mmol) and acetonitrile (1.667 mL). The reaction was heated to 80° C. for 3 h. The reaction mixture was evaporated to dryness before being dissolved in DCM (5 mL). To this was added TFA (5 mL, 65.29 mmol) and the reaction mixture was stirred for overnight. This was purified by HPLC to give the title compound as a white solid. Yield: 57 mg $^1$H NMR (400 MHz, CD$_3$OD) δ 8.45 (d, J=7.4 Hz, 1H), 8.12 (d, J=3.1 Hz, 1H), 8.08-8.04 (m, 1H), 7.52 (d, J=8.2 Hz, 2H), 7.48-7.45 (m, 2H), 7.41-7.38 (m, 1H), 7.25 (d, J=8.2 Hz, 2H), 7.17-7.11 (m, 1H), 6.42 (s, 1H), 4.15-4.07 (m, 1H), 3.98-3.89 (m, 1H), 3.72 (s, 3H), 3.39 (t, J=5.3 Hz, 4H), 3.22-3.11 (m, 4H), 2.92-2.86 (m, 2H), 2.71 (t, J=7.4 Hz, 2H), 2.26 (s, 3H), 2.03-1.93 (m, 2H), 1.89-1.75 (m, 6H), 1.74-1.64 (m, 2H).

MS: [M+H]+=654 (calc=654) (MultiMode+)

EXAMPLE 131

N-((1s,4s)-4-(5-fluoro-2-(3'-(3-(piperazin-1-yl)propyl)biphenyl-3-yloxy)nicotinamido)cyclohexyl)-2-methylthiazole-4-carboxamide

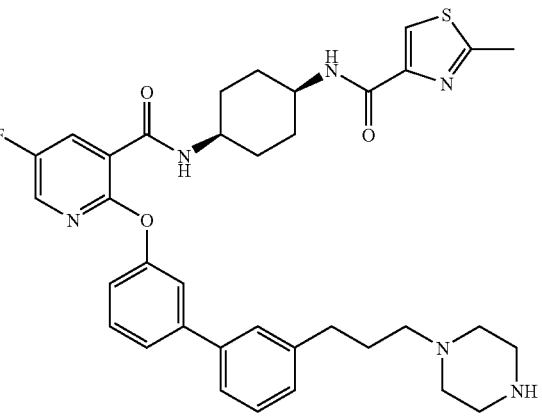

Step (a) N-((1s,4s)-4-(5-fluoro-2-(3'-(3-hydroxypropyl)biphenyl-3-yloxy)nicotinamido)cyclohexyl)-2-methylthiazole-4-carboxamide To a stirred solution of N-((1s,4s)-4-(5-fluoro-2-(3-iodophenoxy)nicotinamido)cyclohexyl)-2-methylthiazole-4-carboxamide (0.300 g, 0.52 mmol) in THF (3.45 ml) was added 3-(3-hydroxypropyl)phenylboronic acid (0.112 g, 0.62 mmol) and sodium carbonate (0.164 g, 1.55 mmol) in water (1.723 ml). Tetrakis(triphenylphosphine)palladium(0) (0.030 g, 0.03 mmol) was added and the reaction mixture heated to 70° C. for 2 days. The reaction was mixture poured into water and extracted into EtOAc. The organic was dried over magnesium sulfate, filtered and evaporated to afford crude product. The crude product was purified by flash silica chromatography using Isco Companion, 50 g silica column, elution gradient 1 to 5% methanol in dichloromethane. Pure fractions were evaporated to dryness to afford the sub-title compound as an off-white solid. Yield: 0.235 g $^1$H NMR (400 MHz, CDCl$_3$) δ 8.38 (dd, J=7.1, 2.1 Hz, 1H), 8.12-8.08 (m, 2H), 7.90 (s, 1H), 7.52 (s, 1H), 7.40-7.36 (m, 3H), 7.32 (t, J=7.6 Hz, 1H), 7.21-7.15 (m, 3H), 4.30-4.22 (m, 1H), 4.12-4.02 (m, 1H), 3.68 (t, J=6.3 Hz, 2H), 2.74 (t, J=7.0 Hz, 2H), 2.60 (s, 3H), 1.99-1.77 (m, 8H), 1.72-1.58 (m, 2H).

MS: [M+H]+=589.2 (Multimode+)

Step (b) 3-(3'-(5-fluoro-3-((1s,4s)-4-(2-methylthiazole-4-carboxamido)cyclohexylcarbamoyl)pyridin-2-yloxy)biphenyl-3-yl)propyl methanesulfonate To a stirred solution of N-((1s,4s)-4-(5-fluoro-2-(3'-(3-hydroxypropyl)biphenyl-3-yloxy)nicotinamido)cyclohexyl)-2-methylthiazole-4-carboxamide (0.235 g, 0.40 mmol) in dichloromethane (1.742 ml) was added pyridine (0.129 ml, 1.60 mmol) and methanesulfonyl chloride (0.124 ml, 1.60 mmol). Reaction mixture stirred at RT under nitrogen overnight. The reaction mixture was diluted with dichloromethane, and washed with 2M hydrochloric acid. The organic was dried over magnesium sulfate, filtered and evaporated to afford the sub-title compound, which was used in the next step without further purification. Yield: 0.260 g $^1$H NMR (400 MHz, CDCl$_3$) δ 8.37-8.33 (m, 1H), 8.12-8.06 (m, 2H), 8.01 (s, 1H), 7.68 (d, J=7.3 Hz, 1H), 7.54-7.49 (m, 2H), 7.42 (s, 2H), 7.34 (t, J=7.9 Hz, 1H), 7.26 (d, J=2.0 Hz, 1H), 7.21-7.16 (m, 2H), 4.24 (t, J=6.2 Hz, 2H), 4.19-4.10 (m, 1H), 2.99 (s, 3H), 2.80 (t, J=8.0 Hz, 2H), 2.76 (s, 3H), 2.10 (quintet, J=6.6 Hz, 2H), 1.96-1.66 (m, 8H).

MS: [M+H]+=667.2 (Multimode+)

Step (c) N-((1s,4s)-4-(5-fluoro-2-(3'-(3-(piperazin-1-yl)propyl)biphenyl-3-yloxy)nicotinamido)cyclohexyl)-2-methylthiazole-4-carboxamide To a microwave vial was added 3-(3'-(5-fluoro-3-((1s,4s)-4-(2-methylthiazole-4-carboxamido)cyclohexylcarbamoyl)pyridin-2-yloxy)biphenyl-3-yl)propyl methanesulfonate (0.260 g, 0.39 mmol) and piperazine (0.672 g, 7.80 mmol) in acetonitrile (2 mL). Reaction mixture heated to 80° C. for 30 min. Reaction mixture concentrated to give crude product. The crude product was purified by preparative HPLC on a Waters X-Bridge column using a 95-15% gradient of aqueous 0.2% TFA in acetonitrile as eluent. The fractions containing the desired compound were evaporated to dryness to afford the title compound as a white solid. Yield: 0.081 g $^1$H NMR (400 MHz, CD$_3$OD) δ 8.48 (d, J=7.6 Hz, 1H), 8.12 (d, J=2.9 Hz, 1H), 8.06 (dd, J=7.6, 2.9 Hz, 1H), 7.95 (s, 1H), 7.50-7.47 (m, 2H), 7.45-7.40 (m, 3H), 7.31 (t, J=7.9 Hz, 1H), 7.21-7.15 (m, 3H), 4.17-4.10 (m, 1H), 3.99-3.92 (m, 1H), 3.48 (m, 4H), 3.42-3.36 (m, 4H), 3.12-3.07 (m, 2H), 2.72 (t, J=7.3 Hz, 2H), 2.61 (s, 3H), 2.08-1.99 (m, 2H), 1.91-1.63 (m, 8H).

MS: [M+H]+=657.2 (MultiMode+)

EXAMPLE 132

N-((1s,4s)-4-(5-fluoro-2-(4'-(3-(piperazin-1-yl)propyl)biphenyl-3-yloxy)nicotinamido)cyclohexyl)pyrazolo[1,5-a]pyridine-2-carboxamide

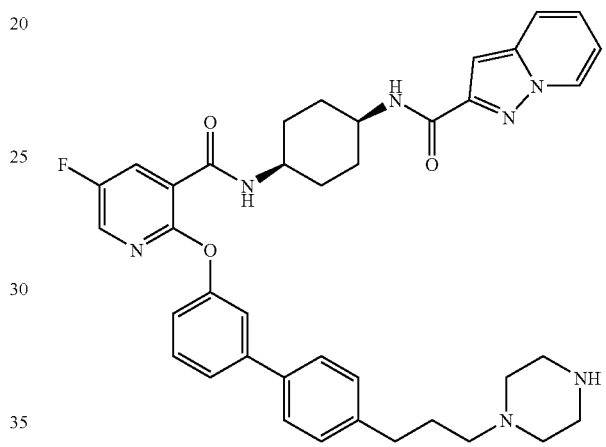

To a solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (150 mg, 0.24 mmol) in acetonitrile (2 mL) was added pyrazolo[1,5-a]pyridine-2-carboxylic acid (38.5 mg, 0.24 mmol) and triethylamine (0.331 mL, 2.37 mmol). 1-Propanephosphonic acid cyclic anhydride, 1.57M solution in THF (0.159 mL, 0.25 mmol) was then added and the mixture stirred at RT for 1 h. The mixture was poured into sat NaHCO$_3$ (aq) and the organics extracted into EtOAc (×2). The extractions were combined, dried (MgSO$_4$) and evaporated to give a residue. This was dissolved in dichlormethane (2 mL) to which TFA (2 mL) was added and the mixture stirred at RT for 20 min. The solvents were removed in vacuo and the residue dissolved in methanol and purified using reverse phase preparative chromatography using eluent=TFA(aq)/MeOH. The appropriate fractions were combined and evaporated to give a residue which on trituration with ether gave a solid. The solid was dried overnight under vacuum at 40° C. to give the title compound. Yield: 58 mg $^1$H NMR (400 MHz, CD$_3$OD) δ 8.49 (d, J=7.2 Hz, 1H), 8.41 (d, J=6.9 Hz, 1H), 8.12 (d, J=3.1 Hz, 1H), 8.07 (dd, J=7.9, 3.1 Hz, 1H), 7.66 (d, J=9.0 Hz, 1H), 7.50-7.45 (m, 4H), 7.42-7.41 (m, 1H), 7.25-7.20 (m, 1H), 7.18-7.13 (m, 3H), 6.96-6.92 (m, 2H), 4.17-4.12 (m, 1H), 4.04-3.98 (m, 1H), 3.41 (t, J=5.4 Hz, 4H), 3.24-3.19 (m, 4H), 2.94-2.89 (m, 2H), 2.64 (t, J=7.6 Hz, 2H), 1.99-1.68 (m, 10H).

MS: [M+H]+=676 (calc=676) (MultiMode+)

EXAMPLE 133

N-((1s,4s)-4-(5-fluoro-2-(4'-(3-(piperazin-1-yl)propyl)biphenyl-3-yloxy)nicotinamido)cyclohexyl)-5,6-dihydro-4H-pyrrolo[1,2-b]pyrazole-2-carboxamide

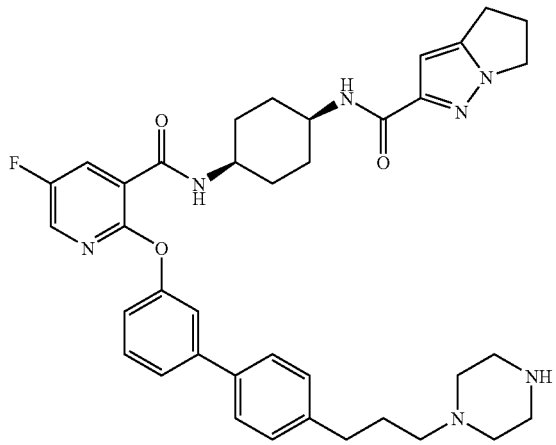

To a solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (150 mg, 0.24 mmol) in acetonitrile (2 mL) was added 5,6-dihydro-4H-pyrrolo[1,2-b]pyrazole-2-carboxylic acid (36.1 mg, 0.24 mmol) and triethylamine (0.331 mL, 2.37 mmol). 1-Propanephosphonic acid cyclic anhydride, 1.57M solution in THF (0.159 mL, 0.25 mmol) was then added and the mixture stirred at RT for 1 h. The mixture was poured into sat NaHCO$_3$ (aq) and the organics extracted into EtOAc (×2). The extractions were combined, dried (MgSO$_4$) and evaporated to give a residue. This was dissolved in DCM (2 mL) to which TFA (2 mL) was added and the mixture stirred at RT for 20 min. The solvents were removed in vacuo and the residue dissolved in methanol and purified using reverse phase preparative chromatography using eluent=TFA(aq)/MeOH. The appropriate fractions were combined and evaporated to give a residue which on trituration with ether gave a solid. The solid was dried overnight under vacuum at 40° C. to give the title compound. Yield: 48 mg $^1$H NMR (400 MHz, CD$_3$OD) δ 8.45 (d, J=7.2 Hz, 1H), 8.11 (d, J=3.1 Hz, 1H), 8.05 (dd, J=7.9, 3.1 Hz, 1H), 7.51 (d, J=8.2 Hz, 2H), 7.47 (d, J=5.1 Hz, 2H), 7.40-7.39 (m, 1H), 7.24 (d, J=8.2 Hz, 2H), 7.15-7.12 (m, 1H), 6.39 (s, 1H), 4.14-4.07 (m, 1H), 4.03 (t, J=7.3 Hz, 2H), 3.99-3.92 (m, 1H), 3.41 (t, J=5.1 Hz, 4H), 3.24-3.19 (m, 4H), 2.95-2.90 (m, 2H), 2.87 (t, J=7.3 Hz, 2H), 2.71 (t, J=7.4 Hz, 2H), 2.61-2.53 (m, 2H), 2.04-1.95 (m, 2H), 1.87-1.77 (m, 6H), 1.73-1.64 (m, 2H).

MS: [M+H]+=666 (calc=666) (MultiMode+)

EXAMPLE 134

N-((1s,4s)-4-(5-fluoro-2-(4'-(3-(4-methyl-1,4-diazepan-1-yl)propyl)biphenyl-3-yloxy)nicotinamido)cyclohexyl)-2-methylthiazole-4-carboxamide

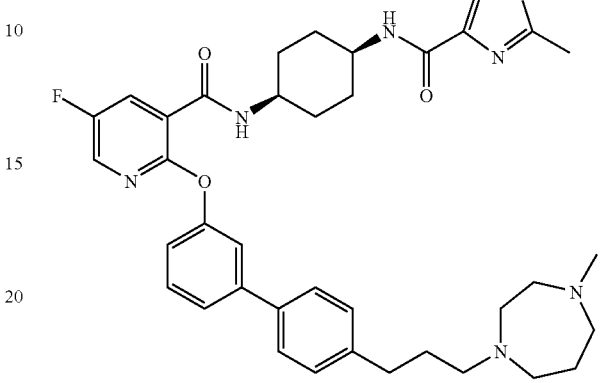

To a solution of 3-(3'-(5-fluoro-3-((1s,4s)-4-(2-methylthiazole-4-carboxamido)cyclohexylcarbamoyl)pyridin-2-yloxy)biphenyl-4-yl)propyl methanesulfonate (0.125 g, 0.19 mmol) in acetonitrile (1 mL) was added 1-methyl-1,4-diazepane (0.117 mL, 0.94 mmol). The mixture was heated to 80° C. in the microwave for 30 min. The crude product was purified by preparative HPLC on a Phenomenex Gemini column using a 95-5% gradient of aqueous 0.1% TFA in methanol as eluent. The fractions containing the desired compound were freeze dried to afford the title compound as a white solid. Yield: 49 mg $^1$H NMR (400 MHz, CD$_3$OD) δ 8.48 (d, J=11.4 Hz, 1H), 8.12 (d, J=6.7 Hz, 1H), 8.06 (dd, J=7.9, 3.1 Hz, 1H), 7.97 (s, 1H), 7.53 (d, J=9.0 Hz, 2H), 7.48-7.46 (m, 2H), 7.40-7.38 (m, 1H), 7.26 (d, J=8.2 Hz, 2H), 7.16-7.13 (m, 1H), 4.15-4.10 (m, 1H), 3.99-3.93 (m, 1H), 3.71 (s, 4H), 3.52-3.45 (m, 4H), 2.94 (s, 3H), 2.72 (t, J=7.5 Hz, 2H), 2.62 (s, 3H), 2.29-2.23 (m, 2H), 2.11-2.03 (m, 2H), 1.88-1.79 (m, 6H), 1.75-1.67 (m, 2H), 0.89-0.82 (m, 2H).

MS: [M+H]+=685 (calc=685) (MultiMode+)

EXAMPLE 135

N-((1s,4s)-4-(2-(4'-(3-(1,4-diazepan-1-yl)propyl)biphenyl-3-yloxy)-5-fluoronicotinamido)cyclohexyl)-2-methylthiazole-4-carboxamide

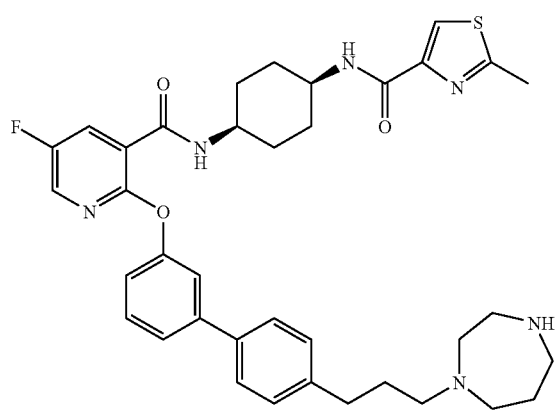

To a solution of 3-(3'-(5-fluoro-3-((1s,4s)-4-(2-methylthiazole-4-carboxamido)cyclohexylcarbamoyl)pyridin-2-yloxy)biphenyl-4-yl)propyl methanesulfonate (0.125 g, 0.19 mmol) in acetonitrile (1 mL) was added 1,4-diazepane (0.376 g, 3.75 mmol). The mixture was heated to 80° C. in the microwave for 30 min. The crude product was purified by preparative HPLC on a Phenomenex Gemini column using a 95-5% gradient of aqueous 0.1% TFA in methanol as eluent. The fractions containing the desired compound were triturated with DCM and isohexane then dried under vacuum at 45° C. overnight to afford the title compound as a white solid. Yield: 48 mg $^1$H NMR (400 MHz, CD$_3$OD) δ 8.48 (d, J=11.0 Hz, 1H), 8.12 (d, J=4.4 Hz, 1H), 8.05 (dd, J=7.9, 3.1 Hz, 1H), 7.96 (s, 1H), 7.53 (d, J=8.1 Hz, 2H), 7.48-7.46 (m, 2H), 7.40-7.38 (m, 1H), 7.26 (d, J=7.3 Hz, 2H), 7.17-7.13 (m, 1H), 4.15-4.10 (m, 1H), 3.99-3.93 (m, 1H), 3.68-3.58 (m, 4H), 3.52-3.45 (m, 2H), 3.40 (t, J=6.0 Hz, 2H), 2.73 (t, J=6.7 Hz, 2H), 2.62 (s, 3H), 2.27-2.21 (m, 2H), 2.11-2.04 (m, 2H), 1.89-1.78 (m, 6H), 1.75-1.65 (m, 2H), 0.88-0.83 (m, 2H).

MS: [M+H]+=671 (calc=671) (MultiMode+)

EXAMPLE 136

N-((1s,4s)-4-(5-fluoro-2-(4'-(3-(3-hydroxypropylamino)propyl)biphenyl-3-yloxy)nicotinamido)cyclohexyl)-2-methylthiazole-4-carboxamide

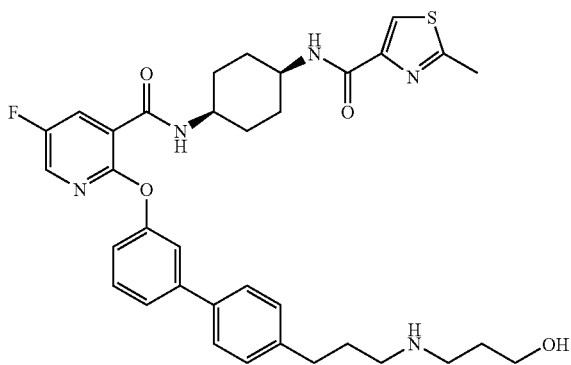

To a solution of 3-(3'-(5-fluoro-3-((1s,4s)-4-(2-methylthiazole-4-carboxamido)cyclohexylcarbamoyl)pyridin-2-yloxy)biphenyl-4-yl)propyl methanesulfonate (0.12 g, 0.18 mmol) in acetonitrile (1 mL) was added 3-aminopropan-1-ol (0.068 mL, 0.90 mmol). The mixture was heated to 80° C. in the microwave for 30 min. The crude product was purified by preparative HPLC on a Phenomenex Gemini column using a 95-5% gradient of aqueous 0.1% TFA in methanol as eluent. The fractions containing the desired compound were freeze dried to afford the title compound as a white solid. Yield: 71 mg $^1$H NMR (400 MHz, CD$_3$OD) δ 8.47 (d, J=7.5 Hz, 1H), 8.11 (d, J=10.3 Hz, 1H), 8.07-8.04 (m, 1H), 7.96 (d, J=4.0 Hz, 1H), 7.53 (d, J=10.9 Hz, 2H), 7.49-7.46 (m, 2H), 7.40-7.39 (m, 1H), 7.24 (d, J=8.9 Hz, 2H), 7.17-7.13 (m, 1H), 4.15-4.09 (m, 1H), 4.00-3.93 (m, 1H), 3.66 (t, J=7.4 Hz, 2H), 3.10 (t, J=8.2 Hz, 2H), 3.01 (t, J=7.9 Hz, 2H), 2.72 (t, J=8.4 Hz, 2H), 2.62 (s, 3H), 2.03-1.95 (m, 2H), 1.91-1.77 (m, 8H), 1.76-1.65 (m, 2H).

MS: [M+H]+=646 (calc=646) (MultiMode+)

EXAMPLE 137

N-((1s,4s)-4-(5-fluoro-2-(4'-(3-(piperazin-1-yl)propyl)biphenyl-3-yloxy)nicotinamido)cyclohexyl)-5,6,7,8-tetrahydroimidazo[1,2-a]pyridine-2-carboxamide

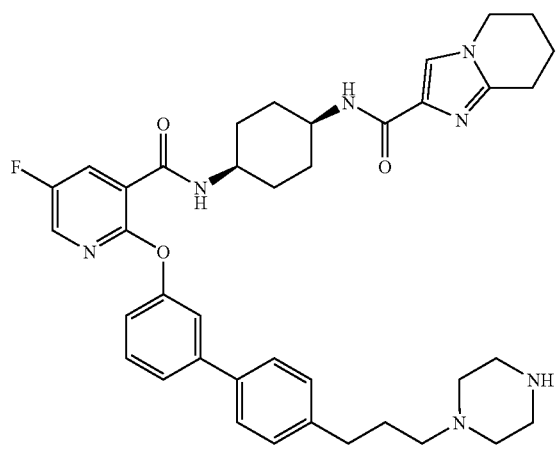

To a solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (150 mg, 0.24 mmol) in acetonitrile (2 mL) was added 5,6,7,8-tetrahydroimidazo[1,2-a]pyridine-2-carboxylic acid (39.5 mg, 0.24 mmol) and triethylamine (0.331 mL, 2.37 mmol). 1-Propanephosphonic acid cyclic anhydride, 1.57M solution in THF (0.159 mL, 0.25 mmol) was then added and the mixture stirred at RT for 1 h. The mixture was poured into sat NaHCO$_3$ (aq) and the organics extracted into EtOAc (×2). The extractions were combined, dried (MgSO$_4$) and evaporated to give a residue. This was dissolved in DCM (2 mL) to which TFA (2 mL) was added and the mixture stirred at RT for 20 min. The solvents were removed in vacuo and the residue dissolved in methanol and purified using reverse phase preparative chromatography using eluent=TFA(aq)/MeOH. The appropriate fractions were combined and evaporated to give a residue which on trituration with ether gave a solid. The solid was dried overnight under vacuum at 40° C. to give the title compound. Yield: 42 mg $^1$H NMR (400 MHz, CD$_3$OD) δ 8.42 (d, J=6.9 Hz, 1H), 8.10-8.06 (m, 2H), 7.74 (s, 1H), 7.53 (d, J=8.2 Hz, 2H), 7.50-7.46 (m, 2H), 7.41-7.39 (m, 1H), 7.28 (d, J=8.2 Hz, 2H), 7.16-7.12 (m, 1H), 4.15-4.08 (m, 3H), 3.98-3.91 (m, 1H), 3.40 (t, J=5.4 Hz, 4H), 3.21-3.16 (m, 4H), 2.97-2.89 (m, 4H), 2.72 (t, J=7.4 Hz, 2H), 2.07-1.96 (m, 6H), 1.92-1.80 (m, 6H), 1.75-1.66 (m, 2H).

MS: [M+H]+=680 (calc=680) (MultiMode+)

EXAMPLE 138

N-((1s,4s)-4-(1,5-dimethyl-1H-pyrazole-3-carboxamido)cyclohexyl)-5-fluoro-2-(2'-(morpholinomethyl)-4'-(thiomorpholinomethyl)biphenyl-3-yloxy)nicotinamide

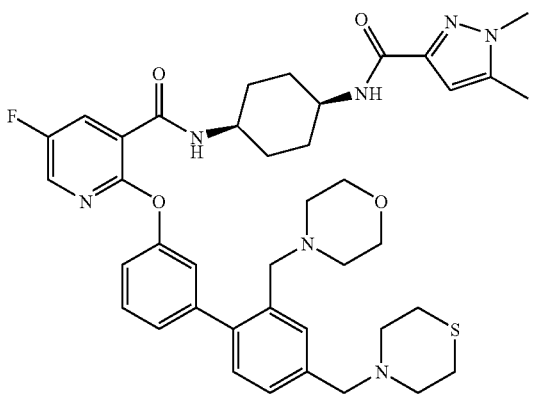

Step (a) N-((1s,4s)-4-(1,5-dimethyl-1H-pyrazole-3-carboxamido)cyclohexyl)-5-fluoro-2-(4'-formyl-2'-(morpholinomethyl)biphenyl-3-yloxy)nicotinamide A solution of potassium carbonate (0.144 g, 1.04 mmol) in water (3 mL), 4-formyl-2-(morpholinomethyl)phenyl trifluoromethanesulfonate (0.147 g, 0.42 mmol) and N-((1s,4s)-4-(1,5-dimethyl-1H-pyrazole-3-carboxamido)cyclohexyl)-5-fluoro-2-(3-(4,4,5,5-tetramethyl-1,3,2-dioxaborolan-2-yl)phenoxy)nicotinamide (0.2 g, 0.35 mmol) were added sequentially to a stirred solution of palladium(II) acetate (7.78 mg, 0.03 mmol) and S-Phos (0.028 g, 0.07 mmol) in acetonitrile (5 mL) and heated at 70° C. for 2 h. The mixture was cooled to RT, extracted with EtOAc, washed with water and brine, dried (MgSO$_4$), filtered and evaporated in vacuo. The residue was purified by chromatography on silica with 5% MeOH/DCM as eluent to give the sub-title compound as a brown foam. Yield: 0.13 g $^1$H NMR (400 MHz, CDCl$_3$) δ 10.05 (s, 1H), 8.37 (m, 1H), 8.07 (d, J=3.4 Hz, 1H), 8.04-7.98 (m, 2H), 7.78 (m, 1H), 7.54 (t, J=7.9 Hz, 1H), 7.46 (d, J=7.9 Hz, 1H), 7.33 (m, 2H), 7.22 (m, 1H), 6.67 (d, J=7.5 Hz, 1H), 6.52 (s, 1H), 4.22 (m, 1H), 4.06 (m, 1H), 3.71 (s, 3H), 3.58 (m, 4H), 3.47 (s, 2H), 2.35 (m, 4H), 2.28 (s, 3H), 1.96-1.53 (m, 8H).

MS: APCI (+ve):655 (M+1).

Step (b) N-((1s,4s)-4-(1,5-dimethyl-1H-pyrazole-3-carboxamido)cyclohexyl)-5-fluoro-2-(2'-(morpholinomethyl)-4'-(thiomorpholinomethyl)biphenyl-3-yloxy)nicotinamide Thiomorpholine (0.041 g, 0.40 mmol) was added to a solution of N-((1s,4s)-4-(1,5-dimethyl-1H-pyrazole-3-carboxamido)cyclohexyl)-5-fluoro-2-(4'-formyl-2'-(morpholinomethyl)biphenyl-3-yloxy)nicotinamide (0.13 g, 0.20 mmol) in DCM (5 mL) and stirred for 15 min. AcOH (0.011 mL, 0.20 mmol), followed by sodium triacetoxyborohydride (0.084 g, 0.40 mmol) were added and the reaction stirred for 20 h. The reaction was quenched with aqueous NaHCO$_3$, extracted with EtOAc, washed with water and brine, dried (Na$_2$SO$_4$), filtered and evaporated in vacuo. The residue was purified by reverse phase HPLC to give the title compound as a white solid. Yield: 0.102 g $^1$H NMR (400 MHz, CD$_3$OD) δ 8.46 (d, J=7.7 Hz, 1H), 8.13 (d, J=3.2 Hz, 1H), 8.03 (m, 1H), 7.91 (d, J=2.1 Hz, 1H), 7.62 (m, 2H), 7.50 (d, J=7.7 Hz, 1H), 7.34 (m, 1H), 7.22 (m, 1H), 7.17 (m, 1H), 6.45 (s, 1H), 4.44 (s, 2H), 4.41 (s, 2H), 4.09 (m, 1H), 3.96 (m, 1H), 3.82-3.71 (m, 4H), 3.77 (s, 3H), 3.20-2.78 (m, 12H), 2.28 (s, 3H), 1.88-1.68 (m, 8H).

MS: APCI (+ve):742 (M+1).

EXAMPLE 139

N-((1s,4s)-4-(1,5-dimethyl-1H-pyrazole-3-carboxamido)cyclohexyl)-5-fluoro-2-(3'-(3-((S)-3-methylpiperazin-1-yl)propyl)biphenyl-3-yloxy)nicotinamide

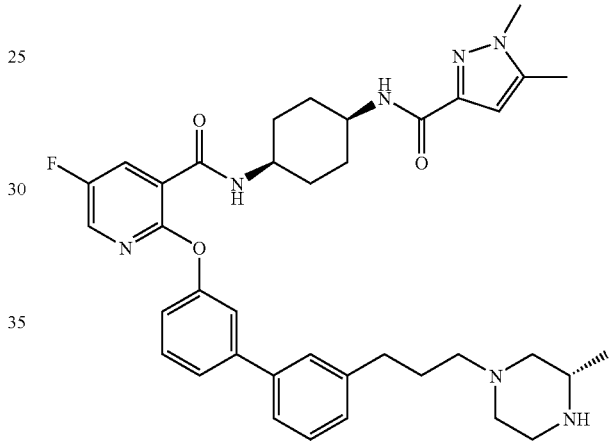

To a microwave vial was added 3-(3'-(3-((1s,4s)-4-(1,5-dimethyl-1H-pyrazole-3-carboxamido)cyclohexylcarbamoyl)-5-fluoropyridin-2-yloxy)biphenyl-3-yl)propyl methanesulfonate (0.120 g, 0.18 mmol), (S)-tert-butyl 2-methylpiperazine-1-carboxylate (0.145 g, 0.72 mmol) and triethylamine (0.076 mL, 0.54 mmol) in acetonitrile (1 mL). The reaction mixture heated to 80° C. by microwave for 3 h. The reaction mixture was evaporated to dryness and redissolved in DCM. 4M HCl/dioxane (0.904 mL, 3.62 mmol) added and reaction mixture stirred at RT for 3 h. The reaction mixture was concentrated to give crude product which was purified by preparative HPLC on a Phenomenex Gemini column using a 95-15% gradient of aqueous 0.2% TFA in methanol as eluent. The fractions containing the desired compound were evaporated to dryness to afford title compound as a white solid. Yield: 56 mg $^1$H NMR (400 MHz, CD$_3$OD) δ 8.46 (d, J=8.9 Hz, 1H), 8.12 (s, 1H), 8.07 (d, J=8.9 Hz, 1H), 7.49-7.46 (m, 2H), 7.45-7.41 (m, 3H), 7.31 (t, J=7.8 Hz, 1H), 7.21-7.14 (m, 2H), 6.38 (s, 1H), 4.16-4.06 (m, 1H), 3.95-3.85 (m, 1H), 3.69 (s, 3H), 3.64 (t, J=13.3 Hz, 4H), 3.43-3.34 (m, 1H), 3.12-3.02 (m, 3H), 2.89 (t, J=13.3 Hz, 1H), 2.70 (t, J=7.8 Hz, 2H), 2.24 (s, 3H), 2.03 (quintet, J=8.0 Hz, 2H), 1.91-1.74 (m, 6H), 1.72-1.61 (m, 2H), 1.35 (d, J=6.7 Hz, 3H).

MS: [M+H]+=668 (MultiMode+)

EXAMPLE 140

N-((1s,4s)-4-(2-(4'-(3-((3S,5R)-3,5-dimethylpiperazin-1-yl)propyl)biphenyl-3-yloxy)-5-fluoronicotinamido)cyclohexyl)-5,6-dihydro-4H-pyrrolo[1,2-b]pyrazole-2-carboxamide

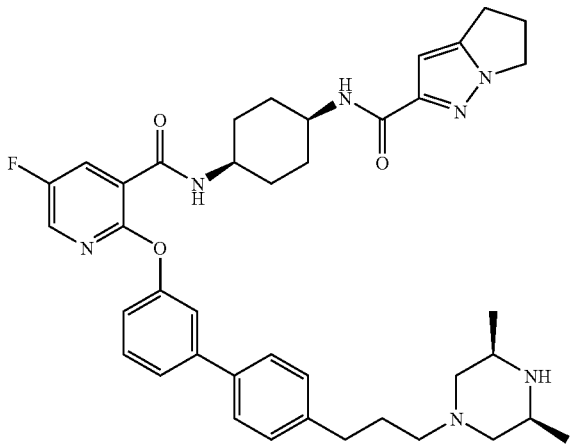

Step (a) tert-butyl (1s,4s)-4-(5-fluoro-2-(4'-(3-hydroxypropyl)biphenyl-3-yloxy)nicotinamido)cyclohexylcarbamate tert-Butyl (1s,4s)-4-(5-fluoro-2-(3-iodophenoxy)nicotinamido)cyclohexylcarbamate (3 g, 5.40 mmol), 4-(3-hydroxypropyl)phenylboronic acid (1.021 g, 5.67 mmol) and sodium carbonate (4.64 g, 16.21 mmol) were added to THF (36.0 ml) and degassed water (18.01 ml) under nitrogen. Tetrakis(triphenylphosphine)palladium(0) (0.125 g, 0.11 mmol) was then added and the reaction mixture was heated at reflux overnight. The mixture was poured onto water and extracted into EtOAc (×2). The extractions were combined, washed with brine, dried (MgSO₄) and evaporated to give a light brown foam. The crude material was purified by Biotage (eluant=neat EtOAc) to give the sub-title compound as a white foam after evaporation. Yield: 2.6 g $^1$H NMR (400 MHz, CDCl$_3$) δ 8.37 (dd, J=8.2, 3.1 Hz, 1H), 8.07 (d, J=3.1 Hz, 1H), 8.04 (d, J=7.5 Hz, 1H), 7.55-7.49 (m, 4H), 7.36-7.34 (m, 1H), 7.29 (d, J=8.2 Hz, 2H), 7.14-7.08 (m, 1H), 4.42-4.29 (m, 1H), 4.22-4.14 (m, 1H), 3.71 (t, J=6.4 Hz, 2H), 3.65-3.55 (m, 1H), 2.76 (t, J=7.7 Hz, 2H), 1.98-1.88 (m, 2H), 1.87-1.66 (m, 6H), 1.63-1.51 (m, 2H), 1.40 (s, 9H).

MS: [M+H]+=564 (MultiMode+)

Step (b) 3-(3'-(3-((1s,4s)-4-(tert-Butoxycarbonylamino)cyclohexylcarbamoyl)-5-fluoropyridin-2-yloxy)biphenyl-4-yl)propyl methanesulfonate To solution of tert-butyl (1s,4s)-4-(5-fluoro-2-(4'-(3-hydroxypropyl)biphenyl-3-yloxy)nicotinamido)cyclohexylcarbamate (1.5 g, 2.66 mmol) and pyridine (0.646 mL, 7.98 mmol) in DCM (12 mL), was added methanesulfonyl chloride (0.622 mL, 7.98 mmol) and the reaction stirred at RT overnight. The reaction was evaporated to give a residue which was partitioned between DCM and 2M HCl(aq). The DCM layer was then washed with another aliquot of 2M HCl(aq), 2× saturated NaHCO₃ (aq), brine, dried (MgSO₄) and evaporated to give the sub-title compound as an off-white solid. Yield: 1.54 g MS: [M+H]+=642 (calc=642) (MultiMode+)

Step (c) tert-butyl (1s,4s)-4-(2-(4'-(3-((3S,5R)-3,5-dimethylpiperazin-1-yl)propyl)biphenyl-3-yloxy)-5-fluoronicotinamido)cyclohexylcarbamate To a solution of 3-(3'-(3-((1s,4s)-4-(tert-butoxycarbonylamino)cyclohexylcarbamoyl)-5-fluoropyridin-2-yloxy)biphenyl-4-yl)propyl methanesulfonate (1.5 g, 2.34 mmol) in acetonitrile (10 ml) was added (2R,6S)-2,6-dimethylpiperazine (0.294 g, 2.57 mmol) and triethylamine (0.358 ml, 2.57 mmol). The reaction was heated at 90° C. overnight. The reaction mixture was cooled before being evaporated to dryness to give an brown foam. The foam was partitioned between sat. NaHCO₃ and EtOAc. The aqueous layer was extracted again with EtOAc. The organic fractions were combined, washed with brine, dried (MgSO₄) and concentrated to give an off-white foam. The product was purified by Biotage (eluent=2. % 7M ammonia in methanol/DCM) to give the sub-title compound as a white foam. Yield: 1.124 g MS: [M+H]+=660 (MultiMode+)

Step (d) N-((1s,4s)-4-Aminocyclohexyl)-2-(4'-(3-((3S,5R)-3,5-dimethylpiperazin-1-yl)propyl)biphenyl-3-yloxy)-5-fluoronicotinamide To a solution of tert-butyl (1s,4s)-4-(2-(4'-(3-((3S,5R)-3,5-dimethylpiperazin-1-yl)propyl)biphenyl-3-yloxy)-5-fluoronicotinamido)cyclohexylcarbamate (1.124 g, 1.70 mmol) in DCM (20 mL) was added 4.0 M hydrogen chloride in dioxane (4.26 mL, 17.03 mmol). The mixture was stirred at RT for 2 hours. The mixture was evaporated to dryness to give the sub-title compound hydrochloride salt as a white solid. Yield: 1.2 g MS: [M+H]+=560 (MultiMode+)

Step (e) ((1s,4s)-4-(2-(4'-(3-((3S,5R)-3,5-dimethylpiperazin-1-yl)propyl)biphenyl-3-yloxy)-5-fluoronicotinamido)cyclohexyl)-5,6-dihydro-4H-pyrrolo[1,2-b]pyrazole-2-carboxamide To a suspension of N-((1s,4s)-4-aminocyclohexyl)-2-(4'-(3-((3S,5R)-3,5-dimethylpiperazin-1-yl)propyl)biphenyl-3-yloxy)-5-fluoronicotinamide (150 mg, 0.24 mmol) in acetonitrile (4 mL) was added 5,6-dihydro-4H-pyrrolo[1,2-b]pyrazole-2-carboxylic acid (36.1 mg, 0.24 mmol) and triethylamine (0.330 mL, 2.37 mmol). 1-Propanephosphonic acid cyclic anhydride, 1.57M solution in THF (0.159 mL, 0.25 mmol) was then added and the mixture stirred at RT for 2 hours. The mixture was evaporated to dryness and the residue dissolved in DCM (100 ml) and washed with saturated NaHCO₃ (aq), brine, dried (MgSO₄) and evaporated to give a foam. This was purified by HPLC to give the title compound as a white solid. Yield: 95 mg $^1$H NMR (400 MHz, CD$_3$OD) δ 8.45 (d, J=7.4 Hz, 1H), 8.12 (d, J=3.1 Hz, 1H), 8.08-8.04 (m, 1H), 7.52 (d, J=8.2 Hz, 2H), 7.48-7.45 (m, 2H), 7.40-7.37 (m, 1H), 7.25 (d, J=8.2 Hz, 2H), 7.17-7.11 (m, 1H), 6.39 (s, 1H), 4.15-4.07 (m, 1H), 4.04 (t, J=7.3 Hz, 2H), 3.98-3.91 (m, 1H), 3.58-3.47 (m, 4H), 2.94-2.83 (m, 4H), 2.71 (t, J=7.1 Hz, 2H), 2.64-2.52 (m, 4H), 2.06-1.93 (m, 2H), 1.89-1.76 (m, 6H), 1.74-1.63 (m, 2H), 1.33 (d, J=6.2 Hz, 6H).

MS: [M+H]+=694 (calc=694) (MultiMode+)

EXAMPLE 141

N-((1s,4s)-4-(5-fluoro-2-(4'-(3-(piperazin-1-yl)propyl)biphenyl-3-yloxy)nicotinamido)cyclohexyl)-2-(hydroxymethyl)thiazole-4-carboxamide

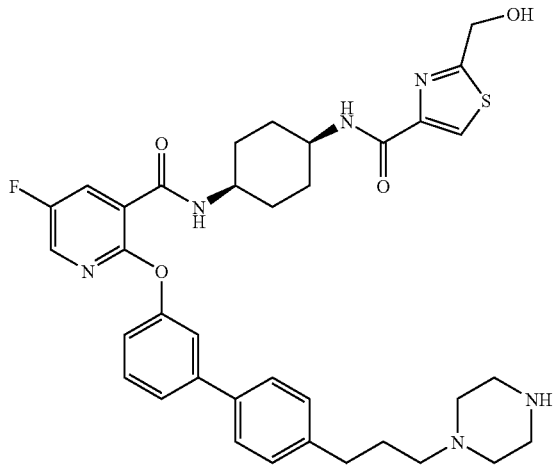

To a suspension of 2-(hydroxymethyl)thiazole-4-carboxylic acid (45.7 mg, 0.29 mmol) in DMF (4 mL) was added tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (145 mg, 0.23 mmol), HOBt (46.5 mg, 0.34 mmol) and EDCI (53.4 mg, 0.34 mmol). The mixture was stirred at RT overnight. The reaction mixture was poured onto water and extracted with EtOAc (×2). The organic extractions were combined, washed with brine, dried (MgSO$_4$) and evaporated to give a yellow oil. The oil was dissolved in DCM (5 mL). To this was added TFA (5 mL, 64.90 mmol) and the reaction mixture was stirred for overnight. This was purified by HPLC to give the title compound as a white solid. Yield: 51 mg $^1$H NMR (400 MHz, CD$_3$OD) δ 8.47 (d, J=6.3 Hz, 1H), 8.12 (d, J=3.1 Hz, 1H), 8.08-8.04 (m, 2H), 7.53-7.49 (m, 2H), 7.48-7.45 (m, 2H), 7.41-7.38 (m, 1H), 7.25-7.22 (m, 2H), 7.17-7.11 (m, 1H), 4.72 (s, 2H), 4.17-4.09 (m, 1H), 4.00-3.92 (m, 1H), 3.36 (t, J=5.3 Hz, 4H), 3.13-3.07 (m, 4H), 2.87-2.81 (m, 2H), 2.71 (t, J=8.1 Hz, 2H), 2.01-1.91 (m, 2H), 1.90-1.77 (m, 6H), 1.76-1.64 (m, 2H).

MS: [M+H]+=673 (calc=673) (MultiMode+)

EXAMPLE 142

N-((1s,4s)-4-(1,5-dimethyl-1H-pyrazole-3-carboxamido)cyclohexyl)-5-fluoro-2-(4'-(3-((R)-2-methylpiperazin-1-yl)propyl)biphenyl-3-yloxy)nicotinamide

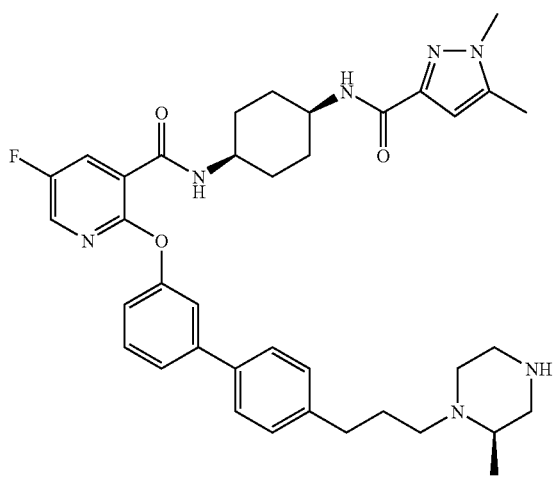

To a microwave tube was charged 3-(3'-(3-((1s,4s)-4-(1,5-dimethyl-1H-pyrazole-3-carboxamido)cyclohexylcarbamoyl)-5-fluoropyridin-2-yloxy)biphenyl-4-yl)propyl methanesulfonate (95 mg, 0.14 mmol), (R)-tert-butyl 2-methylpiperazine-1-carboxylate (102 mg, 0.43 mmol) and acetonitrile (1.667 mL). The reaction was heated to 80° C. for 3 h. Triethylamine (0.060 mL, 0.43 mmol) was added and the reaction was heated at 80° C. overnight. The reaction mixture was evaporated to dryness before being dissolved in DCM (5 mL). To this was added TFA (5 mL, 65.29 mmol) and the reaction mixture was stirred overnight. This was purified by HPLC to give the title compound as a white solid. Yield: 60 mg 1H NMR (400 MHz, CD$_3$OD) δ 8.46 (d, J=7.8 Hz, 1H), 8.12 (d, J=3.1 Hz, 1H), 8.08-8.04 (m, 1H), 7.53-7.49 (m, 2H), 7.49-7.46 (m, 2H), 7.41-7.38 (m, 1H), 7.26-7.22 (m, 2H), 7.17-7.12 (m, 1H), 6.42 (s, 1H), 4.15-4.07 (m, 1H), 3.98-3.90 (m, 1H), 3.71 (s, 3H), 3.56-3.33 (m, 4H), 2.84-2.77 (m, 2H), 2.75-2.65 (m, 3H), 2.51 (t, J=12.3 Hz, 2H), 2.26 (s, 3H), 2.01-1.90 (m, 2H), 1.88-1.76 (m, 6H), 1.74-1.62 (m, 2H), 1.32 (d, J=6.7 Hz, 3H).

MS: [M+H]+=668 (calc=668) (MultiMode+)

EXAMPLE 143

N-((1s,4s)-4-(2-(4'-(3-((3S,5R)-3,5-dimethylpiperazin-1-yl)propyl)biphenyl-3-yloxy)-5-fluoronicotinamido)cyclohexyl)pyrazolo[1,5-a]pyrimidine-2-carboxamide

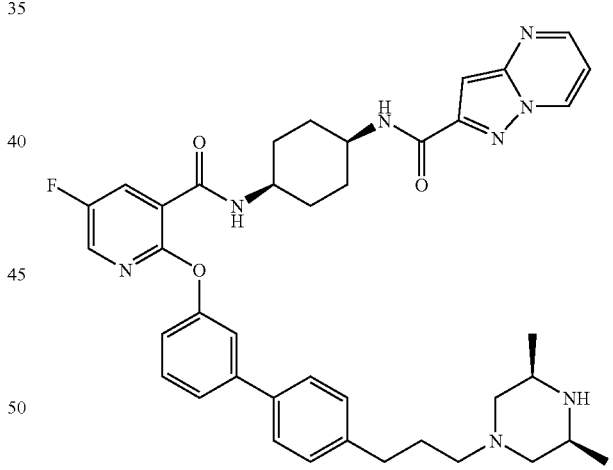

To a suspension of N-((1s,4s)-4-aminocyclohexyl)-2-(4'-(3-((3S,5R)-3,5-dimethylpiperazin-1-yl)propyl)biphenyl-3-yloxy)-5-fluoronicotinamide (150 mg, 0.24 mmol) in acetonitrile (4 mL) was added pyrazolo[1,5-a]pyrimidine-2-carboxylic acid (48.3 mg, 0.30 mmol) and triethylamine (0.330 mL, 2.37 mmol). 1-Propanephosphonic acid cyclic anhydride, 1.57M solution in THF (0.189 mL, 0.30 mmol) was then added and the mixture stirred at RT for 2 h. The mixture was evaporated to dryness and the residue dissolved in DCM (150 mL) and washed with saturated NaHCO$_3$ (aq), brine, dried (MgSO$_4$) and evaporated to give a foam. This was purified by HPLC to give the title compound as a white solid. Yield: 88 mg ¹H NMR (400 MHz, CD₃OD) δ 8.79 (d, J=7.4 Hz, 1H), 8.56-8.54 (m, 1H), 8.48 (d, J=6.9 Hz, 1H), 8.13 (d, J=3.1 Hz, 1H), 8.10-8.07 (m, 1H), 7.49-7.43 (m, 4H), 7.42-7.40 (m, 1H), 7.17-7.10 (m, 3H), 7.08-7.04 (m, 1H), 7.02 (s, 1H), 4.19-4.13 (m, 1H), 4.03-3.97 (m, 1H), 3.56-3.44 (m, 4H), 2.88-2.82 (m, 2H), 2.65-2.59 (m, 2H), 2.52 (t, J=12.2 Hz, 2H), 1.98-1.68 (m, 10H) 1.33 (d, J=6.4 Hz, 6H).

MS: [M+H]+=705 (calc=705) (MultiMode+)

EXAMPLE 144

N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)-4-methylthiazole-2-carboxamide

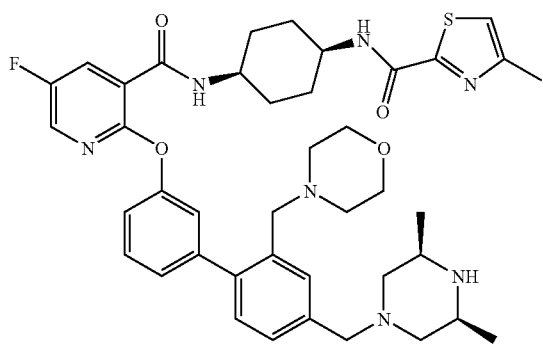

EDCI (0.021 g, 0.11 mmol) was added to a solution of 4-methylthiazole-2-carboxylic acid (0.016 g, 0.11 mmol) and 1H-benzo[d][1,2,3]triazol-1-ol hydrate (0.017 g, 0.11 mmol) in THF (2 mL) and stirred for 10 min. A solution of N-((1s,4s)-4-aminocyclohexyl)-2-(4'-(((3S,5R)-3,5-dimethylpiperazin-1-yl)methyl)-2'-(morpholinomethyl)biphenyl-3-yloxy)-5-fluoronicotinamide (0.075 g, 0.10 mmol) and triethylamine (0.042 mL, 0.30 mmol) in DMF (2 mL) was then added and the reaction stirred for 20 h. The reaction was diluted with 10% 2M HCl/MeCN (1 mL) and purified by reverse phase HPLC with aqTFA/MeOH as eluent to afford the title compound as a white solid. Yield: 70 mg ¹H NMR (400 MHz, CD₃OD) δ 8.14 (d, J=2.9 Hz, 1H), 8.04 (m, 1H), 7.74 (m, 1H), 7.58 (t, J=7.9 Hz, 1H), 7.51 (m, 1H), 7.38 (m, 2H), 7.32 (m, 1H), 7.20 (m, 1H), 7.16 (m, 1H), 4.43 (s, 2H), 4.12 (m, 1H), 3.98 (m, 1H), 3.90-3.66 (m, 4H), 3.79 (s, 2H), 3.43 (m, 2H), 3.29-2.74 (m, 4H), 3.13 (m, 2H), 2.44 (s, 3H), 2.27 (t, J=12.3 Hz, 2H), 1.93-1.74 (m, 8H), 1.29 (d, J=6.6 Hz, 6H).

MS: APCI (+ve):756 (M+1)

EXAMPLE 145

2-(4'-(((3S,5R)-3,5-dimethylpiperazin-1-yl)methyl)-2'-(morpholinomethyl)biphenyl-3-yloxy)-5-fluoro-N-((1s,4s)-4-(2-hydroxy-5-methylbenzamido)cyclohexyl)nicotinamide

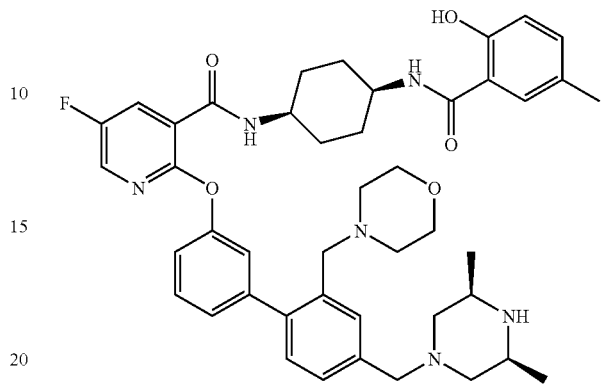

EDCI (0.214 g, 1.11 mmol) was added to a solution of 2-hydroxy-5-methylbenzoic acid (0.017 g, 0.11 mmol) and 1H-benzo[d][1,2,3]triazol-1-ol hydrate (0.171 g, 1.11 mmol) in THF (2 mL) and stirred for 10 min. A solution of N-((1s,4s)-4-aminocyclohexyl)-2-(4'-(((3S,5R)-3,5-dimethylpiperazin-1-yl)methyl)-2'-(morpholinomethyl)biphenyl-3-yloxy)-5-fluoronicotinamide (0.75 g, 1.01 mmol) and triethylamine (0.424 mL, 3.04 mmol) in DMF (2 mL) was then added and the reaction stirred for 20 h. The reaction was diluted with MeCN (1 mL), acidified with 2M HCl (1 mL) and purified by reverse phase HPLC with aqTFA/MeOH as eluent to afford the title compound as a white solid. Yield: 50 mg ¹H NMR (400 MHz, CD₃OD) δ 8.14 (d, J=2.9 Hz, 1H), 8.03 (m, 1H), 7.70 (m, 1H), 7.57 (m, 2H), 7.48 (m, 1H), 7.34 (d, J=8.0 Hz, 1H), 7.30 (m, 1H), 7.17 (m, 3H), 6.77 (d, J=8.6 Hz, 1H), 4.40 (s, 2H), 4.11 (m, 1H), 3.97 (m, 1H), 3.82-3.63 (m, 4H), 3.75 (s, 2H), 3.46-3.36 (m, 2H), 3.27-2.67 (m, 4H), 3.11 (m, 2H), 2.25 (s, 3H), 2.24 (t, J=12.1 Hz, 2H), 1.90-1.74 (m, 8H), 1.28 (d, J=7.0 Hz, 6H).

MS: APCI (+ve):765 (M+1)

EXAMPLE 146

N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)quinoline-8-carboxamide

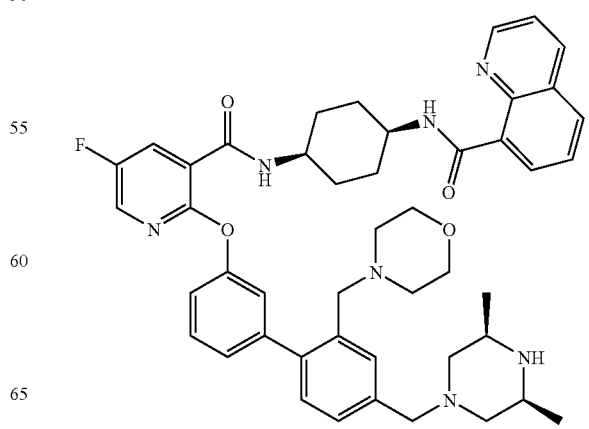

EDCI (0.214 g, 1.11 mmol) was added to a solution of quinoline-8-carboxylic acid (0.019 g, 0.11 mmol) and 1H-benzo[d][1,2,3]triazol-1-ol hydrate (0.171 g, 1.11 mmol) in THF (2 mL) and stirred for 10 min. A solution of N-((1s,4s)-4-aminocyclohexyl)-2-(4'-(((3S,5R)-3,5-dimethylpiperazin-1-yl)methyl)-2'-(morpholinomethyl)biphenyl-3-yloxy)-5-fluoronicotinamide (0.75 g, 1.01 mmol) and triethylamine (0.424 mL, 3.04 mmol) in DMF (2 mL) was then added and the reaction stirred for 20 h. The reaction was diluted with MeCN (1 mL), acidified with 2M HCl (1 mL) and purified by reverse phase HPLC with aqTFA/MeOH as eluent to afford the title compound as a white solid. Yield: 67 mg $^1$H NMR (400 MHz, CD$_3$OD) δ 8.83 (m, 1H), 8.67 (m, 1H), 8.52 (m, 1H), 8.15 (m, 1H), 8.13 (d, J=3.3 Hz, 1H), 8.04 (m, 1H), 7.74 (t, J=7.7 Hz, 1H), 7.71 (m, 1H), 7.55 (d, J=7.9 Hz, 1H), 7.53 (m, 1H), 7.45 (m, 1H), 7.32 (m, 1H), 7.26 (d, J=7.9 Hz, 1H), 7.17 (m, 2H), 4.39 (s, 2H), 4.26 (m, 1H), 4.10 (m, 1H), 3.84 (s, 2H), 3.83-3.59 (m, 4H), 3.45 (m, 2H), 3.26-2.65 (m, 4H), 3.18 (m, 2H), 2.36 (t, J=11.8 Hz, 2H), 2.01-1.82 (m, 8H), 1.29 (d, J=7.0 Hz, 6H).

MS: APCI (+ve):786 (M+1)

EXAMPLE 147

N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)quinoline-2-carboxamide

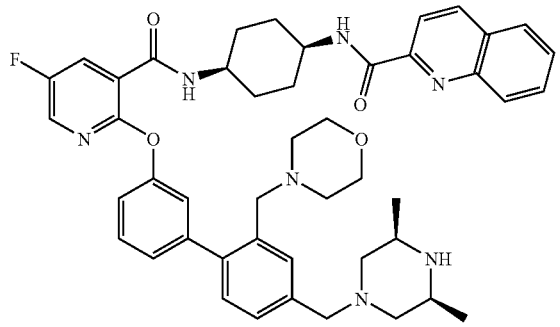

EDCI (0.214 g, 1.11 mmol) was added to a solution of quinoline-2-carboxylic acid (0.019 g, 0.11 mmol) and 1H-benzo[d][1,2,3]triazol-1-ol hydrate (0.171 g, 1.11 mmol) in THF (2 mL) and stirred for 10 min. A solution of N-((1s,4s)-4-aminocyclohexyl)-2-(4'-(((3S,5R)-3,5-dimethylpiperazin-1-yl)methyl)-2'-(morpholinomethyl)biphenyl-3-yloxy)-5-fluoronicotinamide (0.75 g, 1.01 mmol) and triethylamine (0.424 mL, 3.04 mmol) in DMF (2 mL) was then added and the reaction stirred for 20 h. The reaction was diluted with MeCN (1 mL), acidified with 2M HCl (1 mL) and purified by reverse phase HPLC with aqTFA/MeOH as eluent to afford the title compound as a white solid. Yield: 64 mg $^1$H NMR (400 MHz, CD$_3$OD) δ 8.46 (d, J=8.3 Hz, 1H), 8.16 (d, J=8.6 Hz, 1H), 8.14 (d, J=3.3 Hz, 1H), 8.05 (m, 2H), 7.99 (m, 1H), 7.80 (m, 1H), 7.67 (m, 2H), 7.57 (t, J=8.2 Hz, 1H), 7.43 (m, 1H), 7.33 (m, 2H), 7.17 (m, 2H), 4.40 (s, 2H), 4.15 (m, 1H), 4.07 (m, 1H), 3.84-3.59 (m, 4H), 3.74 (s, 2H), 3.41 (m, 2H), 3.28-2.66 (m, 4H), 3.10 (m, 2H), 2.25 (t, J=11.8 Hz, 2H), 1.99-1.79 (m, 8H), 1.27 (d, J=7.2 Hz, 6H).

MS: APCI (+ve):786 (M+1)

EXAMPLE 148

N-((1s,4s)-4-(5-fluoro-2-(4'-(3-(piperazin-1-yl)propyl)biphenyl-3-yloxy)nicotinamido)cyclohexyl)-4-methylthiazole-2-carboxamide

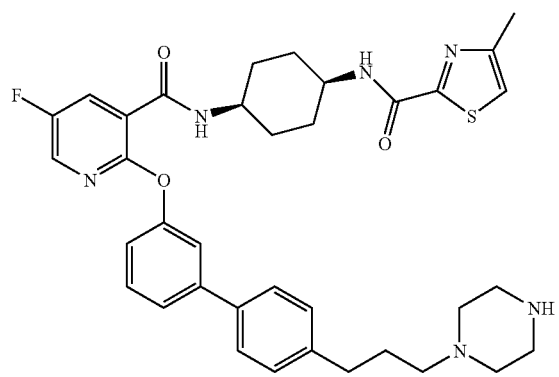

HATU (0.093 g, 0.24 mmol) was added to a solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (0.14 g, 0.22 mmol), 4-methylthiazole-2-carboxylic acid (0.035 g, 0.24 mmol) and DIPEA (0.194 mL, 1.11 mmol) in DMF (5 mL) and the solution stirred at RT for 20 h. The mixture was quenched with water, extracted with EtOAc (50 mL), washed with water and brine, dried (Na$_2$SO$_4$), filtered and evaporated in vacuo. The residue was dissolved in DCM (10 mL), 4M HCl/dioxane (5 mL, 20.00 mmol) added and stirred for 2 h. The mixture was evaporated in vacuo and the residue was purified by reverse phase HPLC with aq TFA/MeCN as eluant to afford the title compound as a white solid. This was stirred in DCM (2 mL) and MeOH (1 mL) with triethylamine (0.031 mL, 0.22 mmol) and PS-benzaldehyde (0.07 g, 0.22 mmol) for 48 h. Filtered and purified by reverse phase HPLC with MeOH/aqTFA as eluent to afford the title compound as a white solid. Yield: 40 mg $^1$H NMR (400 MHz, CD$_3$OD) δ 8.47 (d, J=7.3 Hz, 1H), 8.12 (d, J=3.3 Hz, 1H), 8.06 (m, 1H), 7.98 (m, 1H), 7.52 (d, J=8.7 Hz, 2H), 7.47 (m, 2H), 7.40 (m, 1H), 7.36 (s, 1H), 7.24 (d, J=8.7 Hz, 1H), 7.14 (m, 1H), 4.13 (m, 1H), 3.96 (m, 1H), 3.41 (t, J=5.7 Hz, 4H), 3.20 (m, 4H), 2.92 (m, 2H), 2.71 (t, J=7.5 Hz, 2H), 2.39 (s, 3H), 2.03-1.70 (m, 10H).

MS: APCI (+ve):657 (M+1)

EXAMPLE 149

N-((1s,4s)-4-(2-(4'-(3-((3S,5R)-3,5-dimethylpiperazin-1-yl)propyl)biphenyl-3-yloxy)-5-fluoronicotinamido)cyclohexyl)-2-(hydroxymethyl)thiazole-4-carboxamide

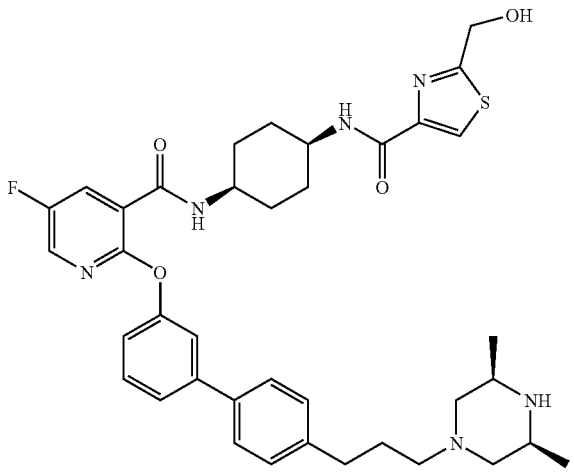

To a suspension of 2-(hydroxymethyl)thiazole-4-carboxylic acid (44.0 mg, 0.28 mmol) in DMF (4 mL) was added N-((1s,4s)-4-aminocyclohexyl)-2-(4'-(3-((3S,5R)-3,5-dimethylpiperazin-1-yl)propyl)biphenyl-3-yloxy)-5-fluoronicotinamide (140 mg, 0.22 mmol), triethylamine (0.123 mL, 0.89 mmol), 1H-benzo[d][1,2,3]triazol-1-ol (44.9 mg, 0.33 mmol) and EDCI (51.5 mg, 0.33 mmol). The mixture was stirred at RT overnight. The reaction mixture was poured onto water and extracted with EtOAc (×2). The organic extractions were combined, washed with brine, dried (MgSO$_4$) and evaporated to give a yellow oil. This was purified by HPLC to give the title compound as a white solid. Yield: 48 mg $^1$H NMR (400 MHz, CD$_3$OD) δ 8.47 (d, J=7.8 Hz, 1H), 8.12 (d, J=3.1 Hz, 1H), 8.09-8.04 (m, 2H), 7.53-7.49 (m, 2H), 7.48-7.45 (m, 2H), 7.41-7.38 (m, 1H), 7.26-7.21 (m, 2H), 7.17-7.10 (m, 1H), 4.71 (s, 2H), 4.18-4.10 (m, 1H), 4.00-3.91 (m, 2H), 3.54-3.41 (m, 4H), 2.88-2.81 (m, 2H), 2.70 (t, J=7.3 Hz, 2H), 2.47 (t, J=11.6 Hz, 2H), 2.03-1.92 (m, 2H), 1.91-1.76 (m, 6H), 1.75-1.64 (m, 2H), 1.32 (d, J=6.7 Hz, 6H).

MS: [M+H]+=701 (calc=701) (MultiMode+)

EXAMPLE 150

N-((1s,4s)-4-(2-(4'-(3-((3S,5R)-3,5-dimethylpiperazin-1-yl)propyl)biphenyl-3-yloxy)-5-fluoronicotinamido)cyclohexyl)-4-(hydroxymethyl)thiazole-2-carboxamide

Step (a) ethyl 4-(acetoxymethyl)thiazole-2-carboxylate

Ethyl 2-amino-2-thioxoacetate (0.5 g, 3.75 mmol) and 3-chloro-2-oxopropyl acetate (0.565 g, 3.75 mmol) were dissolved in toluene (10 mL) and heated in a microwave at 100° C. for 1 h then heated for a further 3 h at 120° C. Cooled to RT, evaporated in vacuo and purified by chromatography on silica with 20% EtOAc/isohexane as eluent to afford the sub-title compound as a pale yellow solid. Yield: 0.7 g $^1$H NMR (400 MHz, CDCl$_3$) δ 7.59 (s, 1H), 5.29 (s, 2H), 4.50 (q, J=7.0 Hz, 2H), 2.13 (s, 3H), 1.45 (t, J=7.3 Hz, 3H).

Step (b) 4-(hydroxymethyl)thiazole-2-carboxylic acid

2M NaOH (4.58 mL, 9.16 mmol) was added to a solution of ethyl 4-(acetoxymethyl)thiazole-2-carboxylate (0.7 g, 3.05 mmol) in MeOH (3 mL) and stirred for 1 h. Acidified with 2M HCl, purified by reverse phase HPLC with aqTFA/MeOH as eluent and freeze dried to afford the sub-title compound as a white solid. Yield: 0.510 g $^1$H NMR (400 MHz, DMSO) δ 7.78 (s, 1H), 4.63 (s, 2H).

Step (c) N-((1s,4s)-4-(2-(4'-(3-((3S,5R)-3,5-dimethylpiperazin-1-yl)propyl)biphenyl-3-yloxy)-5-fluoronicotinamido)cyclohexyl)-4-(hydroxymethyl)thiazole-2-carboxamide To a suspension of 4-(hydroxymethyl)thiazole-2-carboxylic acid (44.0 mg, 0.28 mmol) in DMF (4 mL) was added N-((1s,4s)-4-aminocyclohexyl)-2-(4'-(3-((3S,5R)-3,5-dimethylpiperazin-1-yl)propyl)biphenyl-3-yloxy)-5-fluoronicotinamide (140 mg, 0.22 mmol), triethylamine (0.123 mL, 0.89 mmol), HOBt (44.9 mg, 0.33 mmol) and EDCI (51.5 mg, 0.33 mmol). The mixture was stirred at RT overnight. The reaction mixture was poured onto water and extracted with DCM (×2). The organic extractions were combined, washed with brine, dried (MgSO$_4$) and evaporated to give a yellow oil. This was purified by HPLC to give the title compound as a white solid. Yield: 78 mg $^1$H NMR (400 MHz, CD$_3$OD) δ 8.47 (d, J=7.2 Hz, 1H), 8.12 (d, J=3.1 Hz, 1H), 8.09-8.05 (m, 1H), 7.62-7.60 (m, 1H), 7.53-7.49 (m, 2H), 7.48-7.45 (m, 2H), 7.40-7.38 (m, 1H), 7.26-7.22 (m, 2H), 7.16-7.12 (m, 1H), 4.65-4.63 (m, 2H), 4.17-4.09 (m, 1H), 4.01-3.92 (m, 2H), 3.50-3.35 (m, 4H), 2.81-2.75 (m, 2H), 2.70 (t, J=7.4 Hz, 2H), 2.39 (t, J=12.1 Hz, 2H), 2.00-1.70 (m, 10H), 1.31 (d, J=6.7 Hz, 6H).

MS: [M+H]+=701 (MultiMode+)

EXAMPLE 151

N-((1s,4s)-4-(2-(3'-(((3S,5R)-3,5-dimethylpiperazin-1-yl)methyl)biphenyl-3-yloxy)-5-fluoronicotinamido)cyclohexyl)pyrazolo[1,5-a]pyridine-2-carboxamide

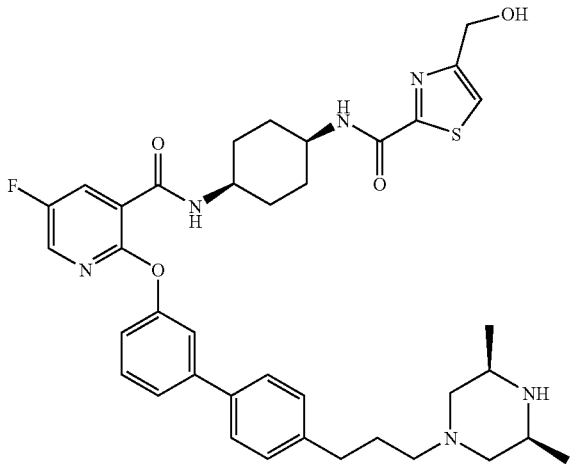

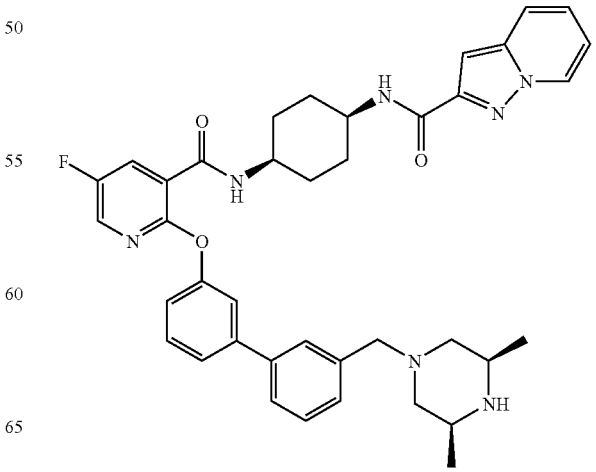

Step (a) tert-butyl (1s,4s)-4-(5-fluoro-2-(3'-formylbiphenyl-3-yloxy)nicotinamido)cyclohexylcarbamate tert-Butyl (1s,4s)-4-(5-fluoro-2-(3-iodophenoxy)nicotinamido)cyclohexylcarbamate (1.5 g, 2.70 mmol), 3-formylphenylboronic acid (0.425 g, 2.84 mmol) and sodium carbonate (2.319 g, 8.10 mmol) were added to THF (18.01 ml) and degassed water (9.00 ml) under nitrogen. Tetrakis(triphenylphosphine)palladium(0) (62 mg, 0.05 mmol) was then added and the reaction mixture was heated at reflux overnight. The mixture was poured onto water and extracted into EtOAc (×2). The extractions were combined, washed with brine, dried (MgSO$_4$) and evaporated to give a yellow foam. The crude material was purified by Biotage (eluant=40% EtOAc:iso-hexane) to give the sub-title compound as an off-white foam after evaporation. Yield: 1.2 g $^1$H NMR (400 MHz, CDCl$_3$) δ 10.09 (s, 1H), 8.38 (dd, J=8.2, 3.3 Hz, 1H), 8.12 (t, J=1.7 Hz, 1H), 8.07 (t, J=3.1 Hz, 1H), 7.99 (d, J=7.4 Hz, 1H), 7.91-7.86 (m, 2H), 7.64 (t, J=7.6 Hz, 1H), 7.59 (d, J=5.1, 2H), 7.45-7.41 (m, 1H), 7.22-7.16 (m, 1H), 4.23-4.13 (m, 1H), 3.70-3.53 (m, 1H), 1.88-1.65 (m, 6H), 1.55-1.45 (m, 2H), 1.40 (s, 9H).

MS: [M+H]+=534 (MultiMode+)

Step (b) tert-butyl (1s,4s)-4-(2-(3'-(((3S,5R)-3,5-dimethylpiperazin-1-yl)methyl)biphenyl-3-yloxy)-5-fluoronicotinamido)cyclohexylcarbamate To a solution of tert-butyl (1s,4s)-4-(5-fluoro-2-(3'-formylbiphenyl-3-yloxy)nicotinamido)cyclohexylcarbamate (250 mg, 0.47 mmol) in dichloromethane (10 mL) was added (2R,6S)-2,6-dimethylpiperazine (80 mg, 0.70 mmol). The mixture was allowed to stir at RT for 40 minutes before sodium triacetoxyborohydride (149 mg, 0.70 mmol) was added. The reaction was stirred at RT overnight. The mixture was diluted with dichloromethane and washed with sat. NaHCO$_3$(aq), dried (MgSO$_4$) and evaporated to give a yellow glass. This was purified by Biotage (eluent=2.5% 7M ammonia in methanol/DCM) to give the sub-title compound as a white foam after evaporation. Yield: 220 mg MS: [M+H]+=632 (MultiMode+)

Step (c) N-((1s,4s)-4-aminocyclohexyl)-2-(3'-(((3S,5R)-3,5-dimethylpiperazin-1-yl)methyl)biphenyl-3-yloxy)-5-fluoronicotinamide To a solution of tert-butyl (1s,4s)-4-(2-(3'-(((3S,5R)-3,5-dimethylpiperazin-1-yl)methyl)biphenyl-3-yloxy)-5-fluoronicotinamido)cyclohexylcarbamate (220 mg, 0.35 mmol) in DCM (4 ml) was added 4.0 M hydrogen chloride in dioxane (0.871 ml, 3.48 mmol). The mixture was stirred at RT for 2 h. The mixture was evaporated to dryness to give the sub-title compound as a white solid. Yield: 210 mg MS: [M+H]+=532 (MultiMode+)

Step (d) N-((1s,4s)-4-(2-(3'-(((3S,5R)-3,5-dimethylpiperazin-1-yl)methyl)biphenyl-3-yloxy)-5-fluoronicotinamido)cyclohexyl)pyrazolo[1,5-a]pyridine-2-carboxamide To a suspension of N-((1s,4s)-4-aminocyclohexyl)-2-(3'-(((3S,5R)-3,5-dimethylpiperazin-1-yl)methyl)biphenyl-3-yloxy)-5-fluoronicotinamide (210 mg, 0.35 mmol) in acetonitrile (4.2 mL) was added pyrazolo[1,5-a]pyridine-2-carboxylic acid (70.4 mg, 0.43 mmol) and triethylamine (484 μl, 3.47 mmol). 1-Propanephosphonic acid cyclic anhydride, 1.57M solution in THF (277 μl, 0.43 mmol) was then added and the mixture stirred at RT for 2 hours. The mixture was evaporated to dryness and the residue dissolved in DCM (100 mL) and washed with saturated NaHCO$_3$ (aq), brine, dried (MgSO$_4$) and evaporated to give a foam. This was purified by HPLC to give the title compound as a white solid. Yield: 197 mg $^1$H NMR (400 MHz, CD$_3$OD) δ 8.48 (d, J=7.2 Hz, 1H), 8.39 (d, J=7.5 Hz, 1H), 8.13 (d, J=3.1 Hz, 1H), 8.10-8.05 (m, 1H), 7.68-7.63 (m, 1H), 7.58-7.55 (m, 1H), 7.54-7.47 (m, 3H), 7.45-7.42 (m, 1H), 7.36-7.17 (m, 4H), 6.96-6.92 (m, 2H), 4.19-4.12 (m, 1H), 4.04-3.97 (m, 1H), 3.72 (s, 2H), 3.44-3.34 (m, 2H), 3.15-3.09 (m, 2H), 2.20 (t, J=12.4 Hz, 2H), 1.98-1.68 (m, 8H), 1.24 (d, J=6.7 Hz, 6H).

MS: [M+H]+=676 (calc=676) (MultiMode+)

EXAMPLE 152

N-((1s,4s)-4-(1,5-dimethyl-1H-pyrazole-3-carboxamido)cyclohexyl)-5-fluoro-2-(4'-(3-(3-hydroxypropylamino)propyl)biphenyl-3-yloxy)nicotinamide

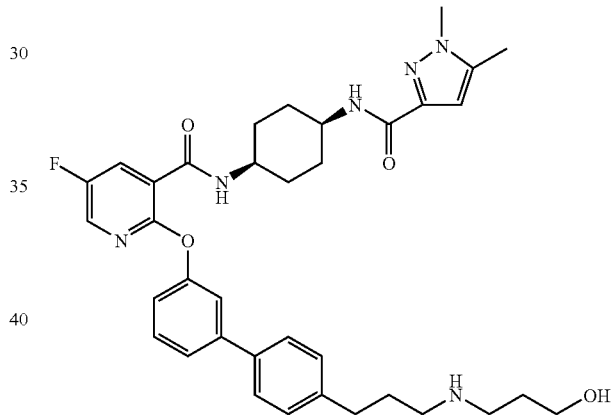

To 3-(3'-(3-((1s,4s)-4-(1,5-dimethyl-1H-pyrazole-3-carboxamido)cyclohexylcarbamoyl)-5-fluoropyridin-2-yloxy)biphenyl-4-yl)propyl methanesulfonate (0.12 g, 0.18 mmol) in acetonitrile (1 mL) was added 3-aminopropan-1-ol (0.069 mL, 0.90 mmol). The mixture was heated to 80° C. in the microwave for 30 min. The crude product was purified by preparative HPLC on a Phenomenex Gemini column using a 95-5% gradient of aqueous 0.1% ammonia in methanol as eluent. The fractions containing the desired compound were freeze dried to afford the title compound as a white solid. Yield: 50 mg $^1$H NMR (400 MHz, CDCl$_3$) δ 8.40-8.34 (m, 1H), 8.11-8.06 (m, 2H), 7.57-7.47 (m, 4H), 7.38-7.36 (m, 1H), 7.28-7.20 (m, 2H), 7.17-7.13 (m, 1H), 6.72-6.68 (m, 1H), 6.52 (s, 1H), 4.28-4.20 (m, 1H), 4.11-4.04 (m, 1H), 3.86-3.78 (m, 2H), 3.69 (s, 3H), 3.20-3.06 (m, 2H), 2.94-2.88 (m, 2H), 2.73-2.66 (m, 4H), 2.25 (s, 3H), 1.95-1.59 (m, 10H).

MS: [M+H]+=643 (calc=643) (MultiMode+)

EXAMPLE 153

N-((1s,4s)-4-(5-fluoro-2-(4'-(3-(piperazin-1-yl)propyl)biphenyl-3-yloxy)nicotinamido)cyclohexyl)-6-methylpicolinamide

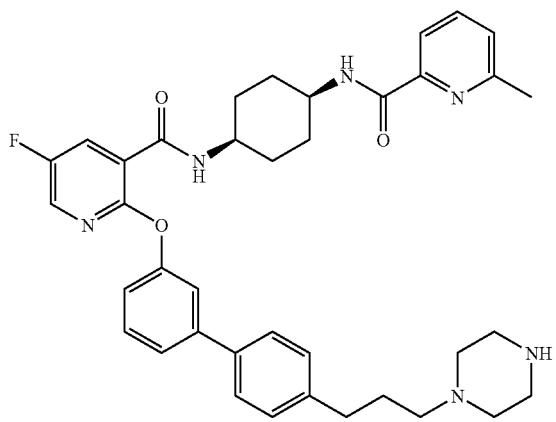

To a stirred solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (0.080 g, 0.13 mmol) in acetonitrile (2 mL) was added 6-methylpicolinic acid (0.035 g, 0.25 mmol) and triethylamine (0.176 mL, 1.27 mmol). The reaction mixture was stirred at RT for 10 min. 1-Propanephosphonic acid cyclic anhydride, 1.57M solution in THF (T3P) (0.169 mL, 0.25 mmol) was added and the reaction mixture stirred at RT overnight. The reaction mixture was evaporated to dryness and redissolved in DCM and washed with saturated sodium hydrogen carbonate. The organic layer was treated with 4M HCl/dioxane (0.633 mL, 2.53 mmol) and allowed to stir at RT for 2 h. The crude product was purified by preparative HPLC on a Waters X-Bridge column using a 75-0% gradient of aqueous 0.2% TFA in methanol as eluent. The fractions containing the desired compound were evaporated to dryness to afford the title compound as a white solid. Yield: 17 mg $^1$H NMR (400 MHz, CD$_3$OD) δ 8.11 (d, J=3.3 Hz, 1H), 8.05 (dd, J=8.2, 3.3 Hz, 1H), 7.86-7.77 (m, 2H), 7.50 (d, J=8.2 Hz, 2H), 7.47-7.44 (m, 2H), 7.41-7.39 (m, 1H), 7.37 (d, J=7.4 Hz, 1H), 7.23 (d, J=8.2 Hz, 2H), 7.16-7.12 (m, 1H), 4.16-4.10 (m, 1H), 4.02-3.95 (m, 1H), 3.56-3.46 (m, 8H), 3.19-3.14 (m, 2H), 2.71 (t, J=7.2 Hz, 2H), 2.45 (s, 3H), 2.06 (quintet, J=8.2 Hz, 2H), 1.90-1.79 (m, 6H), 1.79-1.66 (m, 2H).

MS: m/z (APCI+), (M+H)+=651.2

EXAMPLE 154

N-((1s,4s)-4-(1,5-dimethyl-1H-pyrazole-3-carboxamido)cyclohexyl)-5-fluoro-2-(4'-(2-(4-(pyrrolidin-1-yl)piperidin-1-yl)ethyl)biphenyl-3-yloxy)nicotinamide

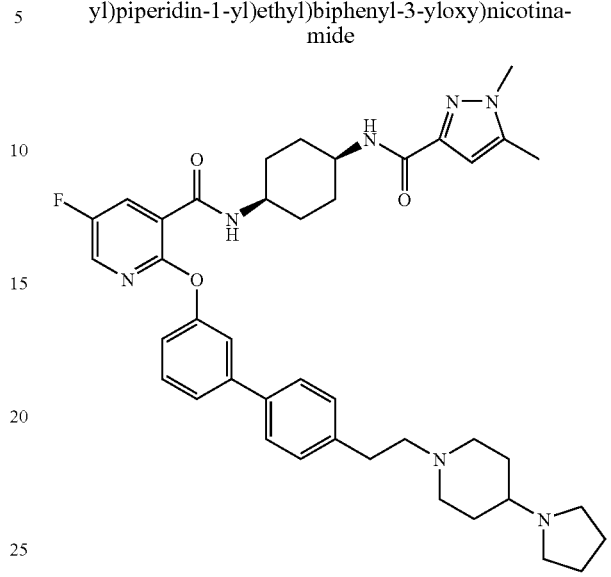

To a microwave tube was charged 2-(3'-(3-((1s,4s)-4-(1,5-dimethyl-1H-pyrazole-3-carboxamido)cyclohexylcarbamoyl)-5-fluoropyridin-2-yloxy)biphenyl-4-yl)ethyl methanesulfonate (120 mg, 0.18 mmol), 4-(pyrrolidin-1-yl)piperidine (85 mg, 0.55 mmol) and acetonitrile (1 mL). The reaction was heated in the microwave at 80° C. for 2 h. This was purified by HPLC to give the title compound as a white solid. Yield: 65 mg $^1$H NMR (400 MHz, CDCl$_3$) δ 8.45 (d, J=7.9 Hz, 1H), 8.11 (d, J=3.3 Hz, 1H), 8.07-8.03 (m, 1H), 7.60-7.56 (m, 2H), 7.51-7.46 (m, 2H), 7.41-7.39 (m, 1H), 7.35-7.31 (m, 2H), 7.19-7.14 (m, 1H), 6.42 (s, 1H), 4.21-4.18 (m, 1H), 4.16-4.07 (m, 1H), 3.98-3.90 (m, 1H), 3.87-3.77 (m, 2H), 3.72 (s, 3H), 3.49-3.34 (m, 4H), 3.23-2.04 (m, 8H), 2.50-2.47 (m, 2H), 2.26 (s, 3H), 2.20-1.98 (m, 6H), 1.89-1.75 (m, 6H), 1.74-1.63 (m, 2H).

MS: [M+H]+=708 (calc=708) (MultiMode+)

EXAMPLE 155

N-((1s,4s)-4-(2-(4'-(3-((3S,5R)-3,5-dimethylpiperazin-1-yl)propyl)biphenyl-3-yloxy)-5-fluoronicotinamido)cyclohexyl)thiazole-4-carboxamide

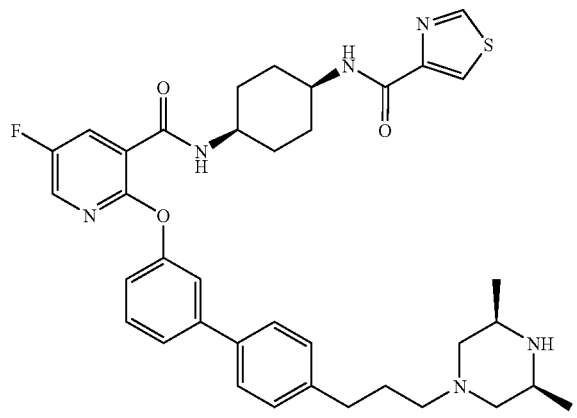

To a suspension of N-((1s,4s)-4-aminocyclohexyl)-2-(4'-(3-((3S,5R)-3,5-dimethylpiperazin-1-yl)propyl)biphenyl-3-yloxy)-5-fluoronicotinamide (150 mg, 0.24 mmol) in acetonitrile (4 mL) was added thiazole-4-carboxylic acid (38.3 mg, 0.30 mmol) and triethylamine (0.330 mL, 2.37 mmol). 1-Propanephosphonic acid cyclic anhydride, 1.57M solution in THF (0.189 mL, 0.30 mmol) was then added and the mixture stirred at RT for 2 h. The mixture was evaporated to dryness and the residue dissolved in DCM (100 mL) and washed with saturated NaHCO₃ (aq), brine, dried (MgSO₄) and evaporated to give a foam. This was purified by HPLC to give the title compound as a white solid. Yield: 68 mg $^1$H NMR (400 MHz, CD₃OD) δ 8.88 (d, J=2.1 Hz, 1H), 8.18 (d, J=2.1 Hz, 1H), 8.12 (d, J=3.1 Hz, 1H), 8.08-8.05 (m, 1H), 7.52-7.45 (m, 5H), 7.43-7.40 (m, 1H), 7.23-7.19 (m, 2H), 7.14-7.09 (m, 1H), 4.17-4.10 (m, 1H), 4.02-3.95 (m, 1H), 2.91-2.78 (m, 4H), 2.63 (t, J=7.9 Hz, 2H), 2.39-2.33 (m, 2H), 1.92-1.66 (m, 9H), 1.60 (t, J=11.4 Hz, 2H), 1.04 (d, J=6.4 Hz, 6H).

MS: [M+H]+=671 (calc=671) (MultiMode+)

EXAMPLE 156

2-(4'-(3-((3S,5R)-3,5-Dimethylpiperazin-1-yl)propyl)biphenyl-3-yloxy)-5-fluoro-N-((1s,4s)-4-(3-methyl-1H-pyrazole-5-carboxamido)cyclohexyl)nicotinamide

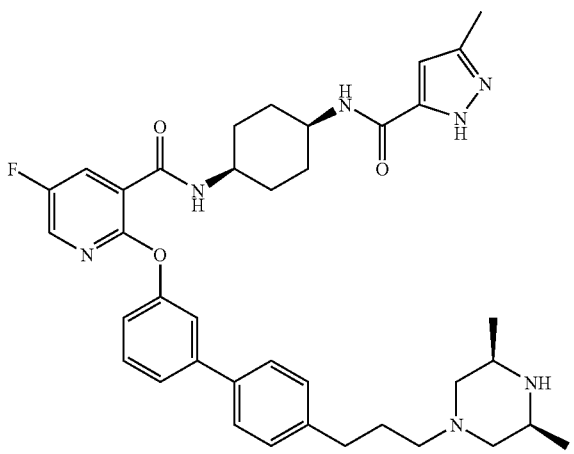

To a suspension of 3-methyl-1H-pyrazole-5-carboxylic acid (34.9 mg, 0.28 mmol) in DMF (4 mL) was added N-((1s,4s)-4-aminocyclohexyl)-2-(4'-(3-((3S,5R)-3,5-dimethylpiperazin-1-yl)propyl)biphenyl-3-yloxy)-5-fluoronicotinamide hydrochloride (140 mg, 0.22 mmol), triethylamine (0.123 mL, 0.89 mmol) HOBt (44.9 mg, 0.33 mmol) and EDCI (51.5 mg, 0.33 mmol). The mixture was stirred at RT overnight. The reaction mixture was poured onto water and extracted with EtOAc (×2). The organic extractions were combined, washed with brine, dried (MgSO₄) and evaporated to give a yellow oil. This was purified by HPLC to give the title compound as a white solid. Yield: 0.110 g $^1$H NMR (400 MHz, CD₃OD) δ 8.45 (d, J=8.0 Hz, 1H), 8.12 (d, J=3.1 Hz, 1H), 8.05 (dd, J=7.9, 3.1 Hz, 1H), 7.54-7.50 (m, 2H), 7.48-7.44 (m, 2H), 7.40-7.37 (m, 1H), 7.26-7.22 (m, 2H), 7.16-7.10 (m, 1H), 6.44 (s, 1H), 4.14-4.06 (m, 1H), 3.99-3.92 (m, 1H), 3.64-3.53 (m, 4H), 3.03-2.96 (m, 2H), 2.75-2.66 (m, 4H), 2.28 (s, 3H), 2.07-1.98 (m, 2H), 1.88-1.64 (m, 6H), 1.35 (d, J=6.4 Hz, 6H).

MS: [M+H]+=668 (calc=668) (MultiMode+)

EXAMPLE 157

5-Fluoro-N-((1s,4s)-4-(5-methyl-1H-pyrazole-3-carboxamido)cyclohexyl)-2-(4'-(3-(piperazin-1-yl)propyl)biphenyl-3-yloxy)nicotinamide

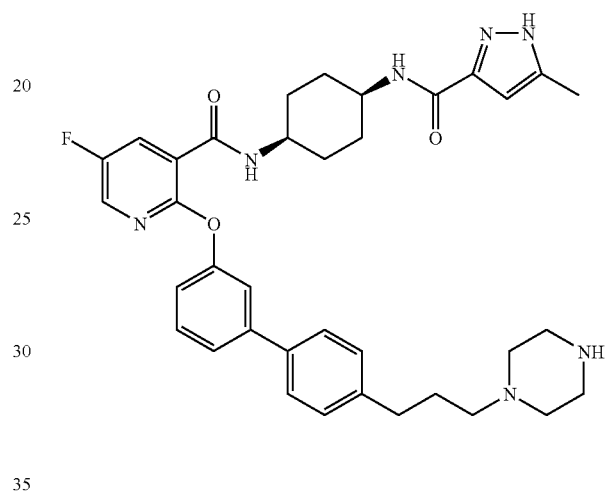

To a solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (150 mg, 0.24 mmol) in acetonitrile (2 mL) was added 5-methyl-1H-pyrazole-3-carboxylic acid (29.9 mg, 0.24 mmol) and triethylamine (0.331 ml, 2.37 mmol). 1-Propanephosphonic acid cyclic anhydride, 1.57M solution in THF (0.159 ml, 0.25 mmol) was then added and the mixture stirred at RT for 1 hour. The mixture was poured into saturated NaHCO₃(aq) and the organics extracted into EtOAc (×2). The extractions were combined, dried (MgSO₄) and evaporated to give a residue. This was dissolved in dichloromethane (2 ml) to which TFA (2 ml) was added and the mixture stirred at RT for 20 minutes. The solvents were removed in vacuo and the residue dissolved in methanol and purified twice using reverse phase preparative chromatography using eluent=TFA(aq)/MeOH and then eluent=NH₃(aq)/MeOH. To the residue left after purification was added water and a few drops of TFA. This was then lyophilized to give the title compound as a white solid. Yield: 19 mg $^1$H NMR (400 MHz, CD₃OD) δ 8.45 (d, J=6.8 Hz, 1H), 8.12 (d, J=3.1 Hz, 1H), 8.07-8.04 (m, 1H), 7.52 (d, J=8.2 Hz, 2H), 7.47-7.45 (m, 2H), 7.39-7.37 (m, 1H), 7.24 (d, J=8.2 Hz, 2H), 7.15-7.12 (m, 1H), 6.44 (s, 1H), 4.11-4.08 (m, 1H), 3.97-3.93 (m, 1H), 3.43 (t, J=5.4 Hz, 4H), 3.29-3.23 (m, 4H), 3.00-2.95 (m, 2H), 2.72 (s, 2H), 2.28 (s, 3H), 2.05-1.97 (m, 2H), 1.86-1.78 (m, 6H), 1.74-1.66 (m, 2H).

MS: [M+H]+=640 (calc=640) (MultiMode+)

EXAMPLE 158

N-((1s,4s)-4-(5-Fluoro-2-(4'-(3-(3-hydroxypropylamino)propyl)biphenyl-3-yloxy)nicotinamido)cyclohexyl)-6-methylpicolinamide

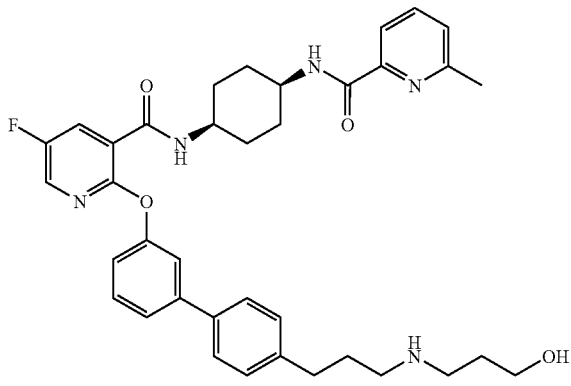

Step (a) N-((1s,4s)-4-Aminocyclohexyl)-5-fluoro-2-(4'-(3-hydroxypropyl)biphenyl-3-yloxy)nicotinamide To tert-butyl (1s,4s)-4-(5-fluoro-2-(4'-(3-hydroxypropyl)biphenyl-3-yloxy)nicotinamido)cyclohexylcarbamate (0.9 g, 1.60 mmol) in dichloromethane (5 mL) was added 4 M HCl in dioxane (4 mL, 16.00 mmol). The reaction was stirred at RT for 2 hours. The reaction was concentrated in vacuo and triturated with ether and filtered to leave the sub-title compound hydrochloride salt as an off white solid. Yield: 0.690 g
MS: [M+H]+=464 (calc=464) (MultiMode+)

Step (b) N-((1s,4s)-4-(5-Fluoro-2-(4'-(3-hydroxypropyl)biphenyl-3-yloxy)nicotinamido)cyclohexyl)-6-methylpicolinamide To a solution of N-((1s,4s)-4-aminocyclohexyl)-5-fluoro-2-(4'-(3-hydroxypropyl)biphenyl-3-yloxy)nicotinamide hydrochloride (0.1 g, 0.22 mmol) and 6-methylpicolinic acid (0.030 g, 0.22 mmol) in acetonitrile (1 mL) under nitrogen was added DIPEA (0.075 mL, 0.43 mmol) at RT. The solution was stirred for 10 minutes. To this solution was added HATU (0.164 g, 0.43 mmol). The reaction was diluted with EtOAc and washed with saturated sodium bicarbonate solution. The organics were extracted (×3), dried (MgSO$_4$) and concentrated to leave a yellow gum. The crude product was purified on silica (Isolute, 10 g) eluting with 100% EtOAc. Pure fractions were combined to afford the sub-title compound as a pale yellow solid. Yield: 0.120 g
MS: [M+H]+=583 (calc=583) (MultiMode+)

Step (c) 3-(3'-(5-Fluoro-3-((1s,4s)-4-(6-methylpicolinamido)cyclohexylcarbamoyl)pyridin-2-yloxy)biphenyl-4-yl)propyl methanesulfonate To solution of N-((1s,4s)-4-(5-Fluoro-2-(4'-(3-hydroxypropyl)biphenyl-3-yloxy)nicotinamido)cyclohexyl)-6-methylpicolinamide (0.12 g, 0.21 mmol) and pyridine (0.033 ml, 0.41 mmol) in DCM (1 ml), was added methanesulfonyl chloride (0.034 ml, 0.43 mmol) and the reaction stirred at RT overnight. The reaction mixture was diluted with aqueous 2M HCl and extracted with DCM (×3) and EtOAc (×3). The organics were combined and dried (MgSO$_4$) and concentrated to give an oil. The oil was dissolved in DCM then isohexane added until a solid crashed out. The suspension was concentrated in vacuo to give an oil. The oil was again dissolved in DCM and isohexane added until a solid crashed out (repeated ×4). On concentration, the sub-title compound became an off white foam. Yield: 0.10 g
MS: [M–H]-659 (calc=659) (MultiMode+)

Step (d) N-((1s,4s)-4-(5-Fluoro-2-(4'-(3-(3-hydroxypropylamino)propyl)biphenyl-3-yloxy)nicotinamido)cyclohexyl)-6-methylpicolinamide To a solution of 3-(3'-(5-fluoro-3-((1s,4s)-4-(6-methylpicolinamido)cyclohexylcarbamoyl)pyridin-2-yloxy)biphenyl-4-yl)propyl methanesulfonate (0.1 g, 0.15 mmol) in acetonitrile (1 mL) was added 3-aminopropan-1-ol (0.058 mL, 0.76 mmol). The mixture was heated to 80° C. in the microwave for 30 minutes. The crude product was purified by preparative HPLC on a Phenomenex Gemini column using a 95-5% gradient of aqueous 0.2% ammonia in methanol as eluent. The fractions containing the desired compound were freeze dried to afford the title compound as a white solid. Yield: 35 mg
$^1$H NMR (400 MHz, CDCl$_3$) δ 8.38 (dd, J=8.2, 3.1 Hz, 1H), 8.14 (d, J=15.6 Hz, 1H), 8.09-8.04 (m, 2H), 7.97 (d, J=6.7 Hz, 1H), 7.70 (t, J=7.3 Hz, 1H), 7.52-7.45 (m, 4H), 7.38-7.37 (m, 1H), 7.24-7.13 (m, 4H), 4.31-4.24 (m, 1H), 4.14-4.06 (m, 1H), 3.82 (t, J=5.3 Hz, 2H), 2.90 (t, J=5.0 Hz, 2H), 2.70-2.65 (m, 4H), 2.44 (s, 3H), 1.98-1.63 (m, 12H).
MS: [M+H]+=640 (calc=640) (MultiMode+)

EXAMPLE 159

N-((1s,4s)-4-(5-Fluoro-2-(4'-(3-(3-hydroxypropylamino)propyl)biphenyl-3-yloxy)nicotinamido)cyclohexyl)pyrazolo[1,5-a]pyridine-2-carboxamide

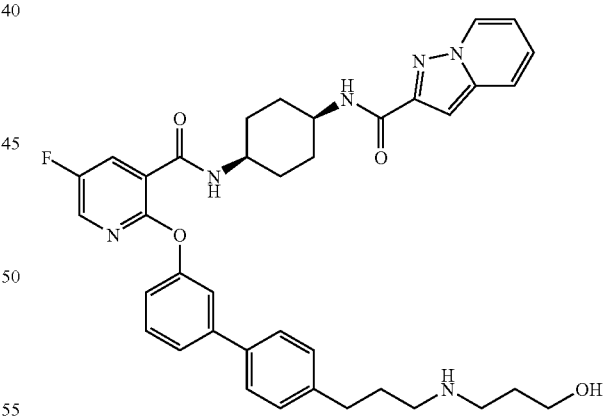

Step (a) N-((1s,4s)-4-(5-Fluoro-2-(3-iodophenoxy)nicotinamido)cyclohexyl)pyrazolo[1,5-a]pyridine-2-carboxamide To a stirred solution of N-((1s,4s)-4-aminocyclohexyl)-5-fluoro-2-(3-iodophenoxy)nicotinamide (0.500 g, 1.10 mmol) in acetonitrile (5 ml) was added pyrazolo[1,5-a]pyridine-2-carboxylic acid (0.196 g, 1.21 mmol) and triethylamine (1.5 ml, 10.98 mmol). The reaction mixture was allowed to stir at RT under nitrogen for 15 min. 1-Propanephosphonic acid cyclic anhydride (T3P, 1.5 M in THF) was added (0.805 ml, 1.21 mmol) and the reaction mixture stirred at RT for 5 h. The reaction mixture was evaporated to dryness and redissolved in dichloromethane, and washed with saturated sodium hydrogen carbonate and saturated brine. The organic was dried over magnesium sulfate, filtered and evaporated to afford crude product. The crude product was purified by flash silica chromatography using Isco Companion, 50 g silica column, elution gradient 70 to 100% EtOAc in isohexane. Pure fractions were evaporated to dryness to afford the sub-title compound as a white solid. Yield: 0.322 g MS: [M+H]+=600 (calc=600) (MultiMode+)

Step (b) N-((1s,4s)-4-(5-Fluoro-2-(4'-(3-hydroxypropyl)biphenyl-3-yloxy)nicotinamido)cyclohexyl)pyrazolo[1,5-a]pyridine-2-carboxamide To a stirred solution of N-((1s,4s)-4-(5-fluoro-2-(3-iodophenoxy)nicotinamido)cyclohexyl)pyrazolo[1,5-a]pyridine-2-carboxamide (0.320 g, 0.53 mmol) in THF (1.780 ml) was added 4-(3-hydroxypropyl)phenylboronic acid (0.144 g, 0.80 mmol) and sodium carbonate (0.170 g, 1.60 mmol) in water (0.890 ml). Tetrakis(triphenylphosphine)palladium(0) (31 mg, 0.03 mmol) was added and the reaction mixture heated to 70° C. for 3 days. The reaction mixture was poured into water and extracted into EtOAc. The organic was dried over magnesium sulfate, filtered and evaporated to afford crude product. The crude product was purified by flash silica chromatography, elution gradient 0 to 5% methanol in dichloromethane. Pure fractions were evaporated to dryness to afford the sub-title compound as a yellow oil. Yield: 0.259 g MS: [M+H]+=608 (calc=608) (MultiMode+)

Step (c) 3-(3'-(5-Fluoro-3-((1s,4s)-4-(pyrazolo[1,5-a]pyridine-2-carboxamido)cyclohexylcarbamoyl)pyridin-2-yloxy)biphenyl-4-yl)propyl methanesulfonate To a stirred solution of N-((1s,4s)-4-(5-fluoro-2-(4'-(3-hydroxypropyl)biphenyl-3-yloxy)nicotinamido)cyclohexyl)pyrazolo[1,5-a]pyridine-2-carboxamide (0.259 g, 0.43 mmol) in dichloromethane (2.5 mL) was added pyridine (0.103 mL, 1.28 mmol) and methanesulfonyl chloride (0.100 mL, 1.28 mmol). The reaction mixture was stirred at RT overnight then diluted with dichloromethane and washed with 2M hydrochloric acid. The organic was dried over magnesium sulfate, filtered and evaporated to afford the subtitle compound. Yield: 0.307 g MS: [M+H]+=686 (calc=686) (MultiMode+)

Step (d) N-((1s,4s)-4-(5-Fluoro-2-(4'-(3-(3-hydroxypropylamino)propyl)biphenyl-3-yloxy)nicotinamido)cyclohexyl)pyrazolo[1,5-a]pyridine-2-carboxamide To a microwave vial was added 3-(3'-(5-fluoro-3-((1s,4s)-4-(pyrazolo[1,5-a]pyridine-2-carboxamido)cyclohexylcarbamoyl)pyridin-2-yloxy)biphenyl-4-yl)propyl methanesulfonate (0.307 g, 0.45 mmol) and 3-aminopropan-1-ol (0.034 mL, 0.45 mmol) in acetonitrile (3 mL). The reaction mixture was heated to 80° C. by microwave for 1 h then concentrated to give crude product. The crude product was purified by preparative HPLC on a Phenomenex Gemini column using a 75-5% gradient of aqueous 0.1% ammonia in methanol as eluent. The fractions containing the desired compound were evaporated to dryness to afford the title compound as a white solid. Yield: 32 mg ¹H NMR (400 MHz, CD₃OD) δ 8.37 (d, J=6.9 Hz, 1H), 8.12-8.06 (m, 2H), 7.64 (d, J=8.2 Hz, 1H), 7.48-7.43 (m, 6H), 7.21 (t, J=7.9 Hz, 1H), 7.14-7.10 (m, 3H), 6.94 (s, 1H), 4.17-4.12 (m, 1H), 4.04-3.96 (m, 1H), 3.59 (t, J=6.3 Hz, 2H), 2.66 (t, J=7.5 Hz, 2H), 2.60-2.55 (m, 4H), 1.97-1.66 (m, 12H).

MS: [M+H]+=665 (calc=665) (MultiMode+)

EXAMPLE 160

5-Fluoro-N-((1s,4s)-4-(1-methyl-5-(trifluoromethyl)-1H-pyrazole-3-carboxamido)cyclohexyl)-2-(4'-(3-(piperazin-1-yl)propyl)biphenyl-3-yloxy)nicotinamide

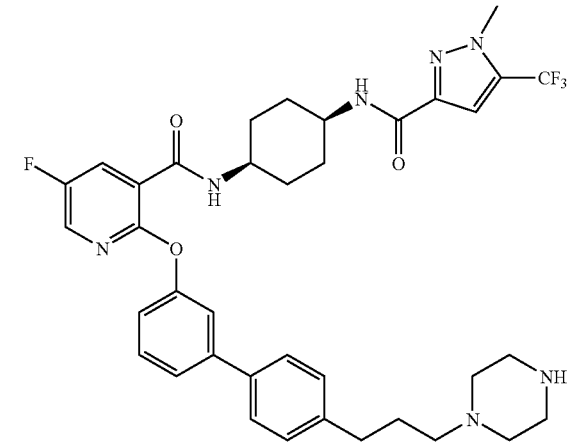

To a stirred solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (0.08 g, 0.13 mmol) in acetonitrile (2 mL) was added 1-methyl-5-(trifluoromethyl)-1H-pyrazole-3-carboxylic acid (0.049 g, 0.25 mmol) and triethylamine (0.176 mL, 1.27 mmol). The reaction mixture was stirred at RT for 10 min. 1-Propanephosphonic acid cyclic anhydride (T3P, 1.5 M in THF) (0.169 mL, 0.25 mmol) was added and reaction mixture stirred at RT overnight. The reaction mixture was evaporated to dryness and redissolved in dichloromethane and washed with saturated sodium hydrogen carbonate. The organic layer was treated with 4M HCl/dioxane (0.633 mL, 2.53 mmol) and allowed to stir at RT for 2 h. The crude product was purified by preparative HPLC on a Waters X-Bridge column using a 75-0% gradient of aqueous 0.2% TFA in methanol as eluent. The fractions containing the desired compound were evaporated to dryness to afford the title compound as a white solid. Yield: 22 mg ¹H NMR (400 MHz, CD₃OD) δ 8.46 (d, J=7.9 Hz, 1H), 8.12 (d, J=3.9 Hz, 1H), 8.08 (dd, J=7.1, 3.9 Hz, 1H), 7.51 (d, J=7.9 Hz, 2H), 7.48 (d, J=4.7 Hz, 2H), 7.41 (s, 1H), 7.24 (d, J=7.9 Hz, 2H), 7.17-7.13 (m, 1H), 7.07 (s, 1H), 4.17-4.09 (m, 1H), 3.98-3.90 (m, 1H), 3.94 (s, 3H), 3.35 (t, J=5.5 Hz, 4H), 3.12-3.04 (m, 4H), 2.82 (t, J=7.9 Hz, 2H), 2.70 (t, J=7.5 Hz, 2H), 1.99-1.62 (m, 10H).

MS: [M+H]+=708 (calc=708) (MultiMode+)

EXAMPLE 161

N-((1s,4s)-4-(5-Fluoro-2-(4'-(3-(3-hydroxypropylamino)propyl)biphenyl-3-yloxy)nicotinamido)cyclohexyl)quinoline-8-carboxamide

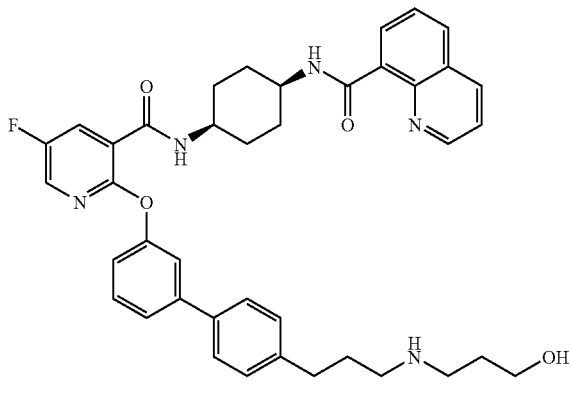

Step (a) N-((1s,4s)-4-(5-Fluoro-2-(4'-(3-hydroxypropyl)biphenyl-3-yloxy)nicotinamido)cyclohexyl)quinoline-8-carboxamide To a solution of N-((1s,4s)-4-aminocyclohexyl)-5-fluoro-2-(4'-(3-hydroxypropyl)biphenyl-3-yloxy)nicotinamide (0.14 g, 0.30 mmol) and quinoline-8-carboxylic acid (0.058 g, 0.33 mmol) in acetonitrile (1 mL) under nitrogen was added triethylamine (0.421 mL, 3.02 mmol) at RT. The solution was stirred for 10 minutes. To this solution was added 1-propanephosphonic acid cyclic anhydride (T3P) (1.57M in THF) (0.212 mL, 0.33 mmol). The reaction was diluted with EtOAc and washed with saturated sodium bicarbonate solution. The organics were extracted (×3), dried (MgSO$_4$) and concentrated to leave the sub-title compound as a white foam. Yield: 0.150 g MS: [M+H]+=619 (calc=619) (MultiMode+)

Step (b) 3-(3'-(5-Fluoro-3-((1s,4s)-4-(quinoline-8-carboxamido)cyclohexylcarbamoyl)pyridin-2-yloxy)biphenyl-4-yl)propyl methanesulfonate To solution of N-((1s,4s)-4-(5-fluoro-2-(4'-(3-hydroxypropyl)biphenyl-3-yloxy)nicotinamido)cyclohexyl)quinoline-8-carboxamide (0.15 g, 0.24 mmol) and pyridine (0.038 ml, 0.47 mmol) in DCM (1 ml), was added methanesulfonyl chloride (0.039 ml, 0.50 mmol) and the reaction stirred at RT overnight. The reaction mixture was diluted with aqueous 2M HCl and extracted with DCM (×3) and EtOAc (×3). The organics were combined and dried (MgSO$_4$) and concentrated to give an oil. The oil was dissolved in DCM then isohexane added until a solid crashed out. The suspension was concentrated in vacuo to give an oil. The oil was again dissolved in DCM and isohexane added until a solid crashed out (repeated ×4). On concentration, the sub-title compound became a white foam. Yield: 0.170 g MS: [M+H]+=697 (calc=697) (MultiMode+)

Step (c) N-((1s,4s)-4-(5-Fluoro-2-(4'-(3-(3-hydroxypropylamino)propyl)biphenyl-3-yloxy)nicotinamido)cyclohexyl)quinoline-8-carboxamide To 3-(3'-(5-fluoro-3-((1s,4s)-4-(quinoline-8-carboxamido)cyclohexylcarbamoyl)pyridin-2-yloxy)biphenyl-4-yl) propyl methanesulfonate in acetonitrile (1 mL) was added 3-aminopropan-1-ol. The mixture was heated to 80° C. in the microwave for 30 minutes. The crude product was purified by preparative HPLC on a Phenomenex Gemini column using a 95-5% gradient of aqueous 0.1% ammonia in methanol as eluent. The fractions containing the desired compound were freeze dried to afford product which was re-purified by preparative HPLC on a Phenomenex Gemini column using a 95-5% gradient of aqueous 0.1% TFA in methanol as eluent. The fractions containing the desired compound were freeze dried to afford the title compound as a white solid. Yield: 65 mg $^1$H NMR (400 MHz, CD$_3$OD) δ 8.64-8.59 (m, 2H), 8.53 (d, J=15.4 Hz, 1H), 8.38 (dd, J=8.3, 1.7 Hz, 1H), 8.11-8.05 (m, 3H), 7.68 (t, J=8.0 Hz, 1H), 7.45-7.41 (m, 5H), 7.34-7.30 (m, 1H), 7.18-7.14 (m, 3H), 4.26-4.21 (m, 1H), 4.16-4.10 (m, 1H), 3.67 (t, J=6.2 Hz, 2H), 3.09 (t, J=7.3 Hz, 2H), 2.99 (t, J=8.2 Hz, 2H), 2.68 (t, J=6.5 Hz, 2H), 2.00-1.81 (m, 12H).

MS: [M+H]+=676 (calc=676) (MultiMode+)

EXAMPLE 162

N-((1s,4s)-4-(2-(4'-(2-((3S,5R)-3,5-Dimethylpiperazin-1-yl)ethyl)biphenyl-3-yloxy)-5-fluoronicotinamido)cyclohexyl)-4,5,6,7-tetrahydropyrazolo[1,5-a]pyridine-2-carboxamide

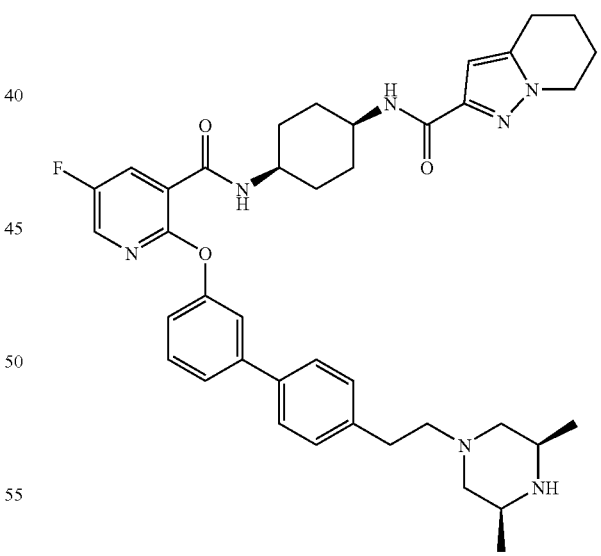

Step (a) 2-(3'-(3-((1s,4s)-4-(tert-Butoxycarbonylamino)cyclohexylcarbamoyl)-5-fluoropyridin-2-yloxy)biphenyl-4-yl)ethyl methanesulfonate Methanesulfonyl chloride (0.338 mL, 4.37 mmol) and pyridine (0.353 mL, 4.37 mmol) were added to a stirred solution of tert-butyl (1s,4s)-4-(5-fluoro-2-(4'-(2-hydroxyethyl)biphenyl-3-yloxy)nicotinamido)cyclohexylcarbamate (1.200 g, 2.18 mmol) in dichloromethane (15 mL). The reaction mixture was stirred at RT overnight then diluted with dichloromethane and washed with saturated sodium hydrogen carbonate (×2), water and saturated brine. The organic was dried over sodium sulfate, filtered and evaporated to afford crude product which was triturated with ether to afford the sub-title compound as a colourless oil. Yield: 1.09 g MS: [M-Boc]+=528 (calc=528) (MultiMode+)

Step (b) tert-Butyl (1s,4s)-4-(2-(4'-(2-((3S,5R)-3,5-dimethylpiperazin-1-yl)ethyl)biphenyl-3-yloxy)-5-fluoronicotinamido)cyclohexylcarbamate To a solution/suspension of 2-(3'-(3-((1s,4s)-4-(tert-butoxycarbonylamino)cyclohexylcarbamoyl)-5-fluoropyridin-2-yloxy)biphenyl-4-yl)ethyl methanesulfonate (0.4 g, 0.64 mmol) in acetonitrile (2 ml) was added cis-2,6-dimethylpiperazine (0.291 g, 2.55 mmol). The mixture was heated in a sealed microwave tube at 100° C. for 2 minutes. The mixture was diluted with EtOAc and washed with saturated NaHCO₃ (aq), brine and evaporated to give a crude product. This was purified using column chromatography (eluent=2% 7N NH₃ in MeOH/DCM) to give the sub-title compound as a yellow foam. Yield: 0.25 g MS: [M+H]+=646 (calc=646) (MultiMode+)

Step (c) N-((1s,4s)-4-Aminocyclohexyl)-2-(4'-(2-((3S,5R)-3,5-dimethylpiperazin-1-yl)ethyl)biphenyl-3-yloxy)-5-fluoronicotinamide To a solution of tert-butyl (1s,4s)-4-(2-(4'-(2-((3S,5R)-3,5-dimethylpiperazin-1-yl)ethyl)biphenyl-3-yloxy)-5-fluoronicotinamido)cyclohexylcarbamate (250 mg, 0.39 mmol) in DCM (2 mL) was added 4.0M solution of hydrogen chloride in dioxane (3 mL, 12.00 mmol). The mixture was stirred at RT for 2 hours. The mixture was evaporated to dryness to give the sub-title compound hydrochloride salt as a cream solid. Yield: 0.295 g MS: [M+H]+=546 (calc=546) (MultiMode+)

Step (d) N-((1s,4s)-4-(2-(4'-(2-((3S,5R)-3,5-Dimethylpiperazin-1-yl)ethyl)biphenyl-3-yloxy)-5-fluoronicotinamido)cyclohexyl)-4,5,6,7-tetrahydropyrazolo[1,5-a]pyridine-2-carboxamide To a solution of N-((1s,4s)-4-aminocyclohexyl)-2-(4'-(2-((3S,5R)-3,5-dimethylpiperazin-1-yl)ethyl)biphenyl-3-yloxy)-5-fluoronicotinamide, trihydrochloride (140 mg, 0.21 mmol) and 4,5,6,7-tetrahydropyrazolo[1,5-a]pyridine-2-carboxylic acid (35.5 mg, 0.21 mmol) in acetonitrile (2 mL) was added triethylamine (0.298 ml, 2.14 mmol). The mixture was allowed to stir until it became a solution. 1.57M solution of 1-propanephosphonic acid cyclic anhydride in THF (T3P) (0.667 ml, 1.05 mmol) was then added and the mixture allowed to stir for 2 hours. A further equivalent of both acid and T3P was added. The mixture was concentrated in vacuo and the residue partitioned between EtOAc and saturated NaHCO₃(aq). The EtOAc was evaporated and the residue purified using reverse phase preparative chromatography (eluent=TFA(aq)/MeCN). The appropriate fractions were combined and evaporated to give a residue which was dissolved in water and lyophilised to give the title compound as a white solid. Yield: 38 mg ¹H NMR (400 MHz, CD₃OD) δ 8.45 (d, J=7.2 Hz, 1H), 8.11 (d, J=3.1 Hz, 1H), 8.06 (dd, J=8.0 Hz, 3.1 Hz, 1H), 7.52 (d, J=8.2 Hz, 2H), 7.48-7.46 (m, 2H), 7.41-7.39 (m, 1H), 7.27 (d, J=8.2 Hz, 2H), 7.18-7.12 (m, 1H), 6.38 (s, 1H), 4.11 (s, 1H), 4.01 (t, J=6.1 Hz, 2H), 3.98-3.92 (m, 1H), 3.48-3.34 (m, 4H), 2.92 (s, 4H), 2.77 (t, J=6.4 Hz, 2H), 2.36 (t, J=12.1 Hz, 2H), 2.04-1.96 (m, 2H), 1.87-1.78 (m, 8H), 1.73-1.65 (m, 2H), 1.32 (d, J=6.5 Hz, 6H).

MS: [M+H]+=694 (calc=694) (MultiMode+)

EXAMPLE 163

2-(4'-(2-((3S,5R)-3,5-Dimethylpiperazin-1-yl)ethyl) biphenyl-3-yloxy)-5-fluoro-N-((1s,4s)-4-(1-methyl-1H-pyrazole-3-carboxamido)cyclohexyl)nicotinamide

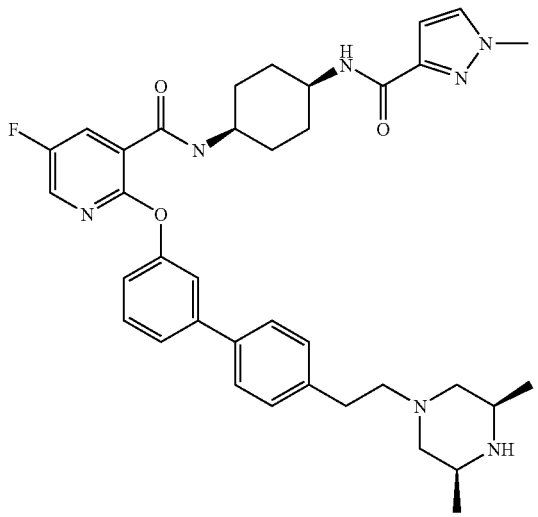

To a solution of N-((1s,4s)-4-aminocyclohexyl)-2-(4'-(2-((3S,5R)-3,5-dimethylpiperazin-1-yl)ethyl)biphenyl-3-yloxy)-5-fluoronicotinamide, trihydrochloride (140 mg, 0.21 mmol) and 1-methyl-1H-pyrazole-3-carboxylic acid (27.0 mg, 0.21 mmol) in acetonitrile (2 mL) was added triethylamine (0.298 ml, 2.14 mmol). The mixture was allowed to stir until it became a solution. 1.57M solution of 1-propanephosphonic acid cyclic anhydride (T3P) in THF (0.667 ml, 1.05 mmol) was then added and the mixture allowed to stir for 2 hours. A further 1 eq of both acid and T3P were added. The mixture was concentrated in vacuo and the residue partitioned between EtOAc and saturated NaHCO₃(aq). The EtOAc was evaporated and the residue purified using reverse phase preparative chromatography (eluent=TFA(aq)/MeOH). The appropriate fractions were combined and evaporated to give a residue which was lyophilised to give the title compound as a white solid. Yield: 35 mg ¹H NMR (400 MHz, CD₃OD) δ 8.46 (d, J=7.0 Hz, 1H), 8.11 (d, J=3.1 Hz, 1H), 8.06 (dd, J=8.0 Hz, 3.1 Hz, 1H), 7.57 (d, J=2.2 Hz, 1H), 7.53 (d, J=8.2 Hz, 2H), 7.47 (dd, J=6.7 Hz, 3.3 Hz, 2H), 7.40 (d, J=1.2 Hz, 1H), 7.28 (d, J=8.2 Hz, 2H), 7.17-7.13 (m, 1H), 6.65 (d, J=2.3 Hz, 1H), 4.12 (s, 1H), 3.96 (s, 1H), 3.84 (s, 3H), 3.51-3.41 (m, 4H), 3.00-2.91 (m, 4H), 2.45 (t, J=12.0 Hz, 2H), 1.89-1.78 (m, 6H), 1.75-1.65 (m, 2H), 1.33 (d, J=6.5 Hz, 6H).

[M+H]+=654 (calc=654) (MultiMode+)

EXAMPLE 164

N-((1s,4s)-4-(5-Fluoro-2-(4'-(3-(3-hydroxypropylamino)propyl)biphenyl-3-yloxy)nicotinamido)cyclohexyl)pyrazolo[1,5-a]pyrimidine-3-carboxamide

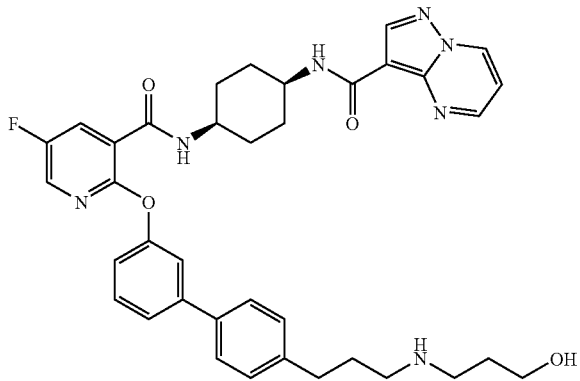

Step (a) N-((1s,4s)-4-(5-Fluoro-2-(4'-(3-hydroxypropyl)biphenyl-3-yloxy)nicotinamido)cyclohexyl)pyrazolo[1,5-a]pyrimidine-3-carboxamide To N-((1s,4s)-4-aminocyclohexyl)-5-fluoro-2-(4'-(3-hydroxypropyl)biphenyl-3-yloxy)nicotinamide (0.1 g, 0.22 mmol) and pyrazolo[1,5-a]pyrimidine-3-carboxylic acid (0.035 g, 0.22 mmol) in acetonitrile (1 mL) was added triethylamine (0.301 mL, 2.16 mmol) and the reaction stirred for 10 minutes. 1-Propanephosphonic acid cyclic anhydride (T3P) (1.57M in THF) (0.151 mL, 0.24 mmol) was added and the reaction stirred overnight. The solution was diluted with EtOAc and washed with water (×3). The organics were combined and washed with brine (×3), dried (MgSO$_4$) and concentrated to leave the sub-title compound as a white foam. Yield: 0.120 g MS: [M+H]+=609 (calc=609) (MultiMode+)

Step (b) 3-(3'-(5-Fluoro-3-((1s,4s)-4-(pyrazolo[1,5-a]pyrimidine-3-carboxamido)cyclohexylcarbamoyl)pyridin-2-yloxy)biphenyl-4-yl)propyl methanesulfonate To a solution of N-((1s,4s)-4-(5-fluoro-2-(4'-(3-hydroxypropyl)biphenyl-3-yloxy)nicotinamido)cyclohexyl)pyrazolo[1,5-a]pyrimidine-3-carboxamide (0.11 g, 0.18 mmol) and pyridine (0.029 ml, 0.36 mmol) in DCM (1 ml), was added methanesulfonyl chloride (0.030 ml, 0.38 mmol) and the reaction stirred at RT overnight. The reaction mixture was diluted with aqueous 2M HCl and extracted with DCM (×3) and EtOAc (×3). The organics were combined and dried (MgSO$_4$) and concentrated to give an oil.

The oil was dissolved in DCM then isohexane added until a solid crashed out. The suspension was concentrated in vacuo to give an oil. The oil was again dissolved in DCM and isohexane added until a solid crashed out (repeated ×4). On concentration, the sub-title compound became a beige foam. Yield: 0.110 g MS: [M+H]+=687 (calc=687) (MultiMode+)

Step (c) N-((1s,4s)-4-(5-Fluoro-2-(4'-(3-(3-hydroxypropylamino)propyl)biphenyl-3-yloxy)nicotinamido)cyclohexyl)pyrazolo[1,5-a]pyrimidine-3-carboxamide To 3-(3'-(5-fluoro-3-((1s,4s)-4-(pyrazolo[1,5-a]pyrimidine-3-carboxamido)cyclohexylcarbamoyl)pyridin-2-yloxy)biphenyl-4-yl)propyl methanesulfonate (0.11 g, 0.16 mmol) in acetonitrile (1 mL) was added 3-aminopropan-1-ol (0.061 mL, 0.80 mmol). The mixture was heated to 80° C. in the microwave for 30 minutes. The crude product was purified by preparative HPLC on a Phenomenex N—X column using a 95-5% gradient of aqueous 0.1% ammonia in methanol as eluent. The fractions containing the desired compound were freeze dried to afford the title compound as a white solid. Yield: 17 mg $^1$H NMR (400 MHz, CD$_3$OD) δ 8.93 (dd, J=5.3, 5.3 Hz, 1H), 8.49 (s, 1H), 8.26 (dd, J=3.2, 3.2 Hz, 1H), 8.12-8.06 (m, 2H), 7.46-7.43 (m, 4H), 7.41-7.38 (m, 2H), 7.13-7.09 (m, 3H), 6.94-6.91 (m, 1H), 4.18-4.07 (m, 2H), 3.60 (t, J=7.3 Hz, 2H), 2.68-2.57 (m, 6H), 1.95-1.66 (m, 12H).

MS: [M+H]+=666 (calc=666) (MultiMode+)

EXAMPLE 164

N-((1s,4s)-4-(5-Fluoro-2-(4'-(3-(3-hydroxypropylamino)propyl)biphenyl-3-yloxy)nicotinamido)cyclohexyl-1H-benzo[d]imidazole-4-carboxamide

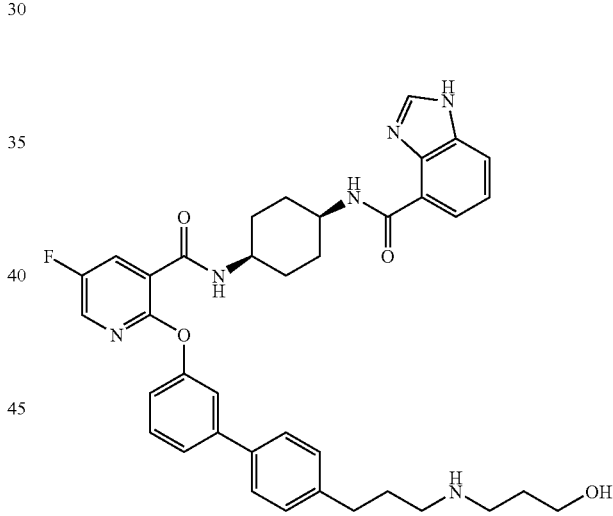

Step (a) N-((1s,4s)-4-(5-Fluoro-2-(4'-(3-hydroxypropyl)biphenyl-3-yloxy)nicotinamido)cyclohexyl)-1H-benzo[d]imidazole-4-carboxamide To a solution of N-((1s,4s)-4-aminocyclohexyl)-5-fluoro-2-(4'-(3-hydroxypropyl)biphenyl-3-yloxy)nicotinamide (0.1 g, 0.22 mmol) and 1H-benzo[d]imidazole-4-carboxylic acid (0.035 g, 0.22 mmol) in acetonitrile under nitrogen was added DIPEA (0.075 ml, 0.43 mmol) at RT. The solution was stirred for 10 minutes. To this solution was added HATU (0.164 g, 0.43 mmol). The reaction was diluted with EtOAc and washed with saturated sodium bicarbonate solution. The organics were extracted (×3), dried (MgSO$_4$) and concentrated to leave the sub-title compound as a yellow solid. Yield: 0.120 g MS: [M+H]+=608 (calc=608) (MultiMode+)

Step (b) 3-(3'-(3-((1s,4s)-4-(1H-Benzo[d]imidazole-4-carboxamido)cyclohexylcarbamoyl)-5-fluoropyridin-2-yloxy)biphenyl-4-yl)propyl methanesulfonate To solution of N-((1s,4s)-4-(5-fluoro-2-(4'-(3-hydroxypropyl)biphenyl-3-yloxy)nicotinamido)cyclohexyl)-1H-benzo[d]imidazole-4-carboxamide (0.12 g, 0.20 mmol) and pyridine (0.032 ml, 0.39 mmol) in DCM (1 ml), was added methanesulfonyl chloride (0.032 ml, 0.41 mmol) and the reaction stirred at RT overnight. The reaction mixture was diluted with aqueous 2M HCl and extracted with DCM (×3) and EtOAc (×3). The organics were combined and dried (MgSO$_4$) and concentrated to give an oil. The oil was dissolved in DCM then isohexane added until a solid crashed out. The suspension was concentrated in vacuo to give an oil. The oil was again dissolved in DCM and isohexane added until a solid crashed out (repeated ×4). On concentration, the sub-title compound became an off white foam. Yield: 0.110 g
MS: [M−H]−=684 (calc=684) (MultiMode+)

Step (c) N-((1s,4s)-4-(5-Fluoro-2-(4'-(3-(3-hydroxypropylamino)propyl)biphenyl-3-yloxy)nicotinamido)cyclohexyl)-1H-benzo[d]imidazole-4-carboxamide To 3-(3'-(3-((1s,4s)-4-(1H-benzo[d]imidazole-4-carboxamido)cyclohexylcarbamoyl)-5-fluoropyridin-2-yloxy)biphenyl-4-yl)propyl methanesulfonate (0.11 g, 0.16 mmol) in acetonitrile (1 mL) was added 3-aminopropan-1-ol (0.061 mL, 0.80 mmol). The mixture was heated to 80° C. in the microwave for 30 minutes. The crude product was purified by preparative HPLC on a Sunfire column using a 95-5% gradient of aqueous 0.1% TFA in methanol as eluent. The fractions containing the desired compound were freeze dried to afford the title compound as a white solid. Yield: 64 mg
$^1$H NMR (400 MHz, CD$_3$OD) δ 8.76 (s, 1H), 8.50 (d, J=13.3 Hz, 1H), 8.11 (d, J=6.8 Hz, 3H), 8.08 (dd, J=7.9, 3.1 Hz, 1H), 7.92 (d, J=11.0 Hz, 1H), 7.85 (d, J=9.4 Hz, 1H), 7.52-7.45 (m, 5H), 7.42-7.40 (m, 1H), 7.22-7.14 (m, 1H), 4.17-4.11 (m, 2H), 3.66 (t, J=4.7 Hz, 2H), 3.10 (t, J=6.5 Hz, 2H), 3.00 (t, J=7.8 Hz, 2H), 2.70 (t, J=7.8 Hz, 2H), 2.01-1.79 (m, 12H).
MS: [M+H]+=665 (calc=665) (MultiMode+)

EXAMPLE 165

2-(4'-(3-((3S,5R)-3,5-Dimethylpiperazin-1-yl)propyl)biphenyl-3-yloxy)-5-fluoro-N-((1s,4s)-4-(1-methyl-1H-pyrazole-3-carboxamido)cyclohexyl)nicotinamide

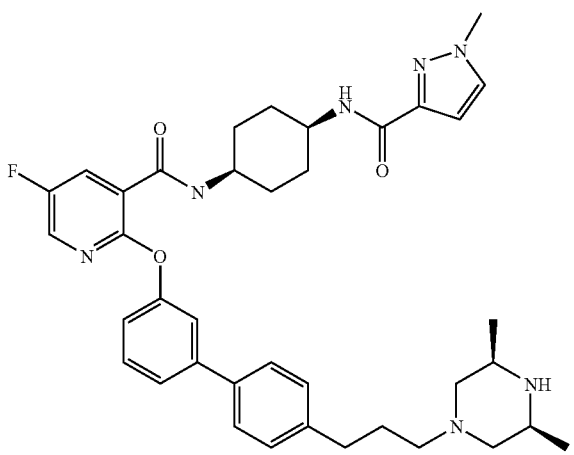

To a suspension of N-((1s,4s)-4-aminocyclohexyl)-2-(4'-(3-((3S,5R)-3,5-dimethylpiperazin-1-yl)propyl)biphenyl-3-yloxy)-5-fluoronicotinamide (150 mg, 0.24 mmol) in acetonitrile (4 mL) was added 1-methyl-1H-pyrazole-3-carboxylic acid (37 mg, 0.30 mmol) and triethylamine (0.330 mL, 2.37 mmol). 1-Propanephosphonic acid cyclic anhydride, 1.57M solution in THF (0.189 mL, 0.30 mmol) was then added and the mixture stirred at RT for 2 hours. The mixture was evaporated to dryness and the residue dissolved in DCM (100 ml) and washed with saturated NaHCO$_3$(aq), brine, dried (MgSO$_4$) and evaporated to give a foam. This was purified by HPLC to give the title compound as a white solid. Yield: 84 mg
$^1$H NMR (400 MHz, CD$_3$OD) δ 8.46 (d, J=7.5 Hz, 1H), 8.12 (d, J=3.1 Hz, 1H), 8.08-8.04 (m, 1H), 7.58-7.56 (m, 1H), 7.54-7.50 (m, 2H), 7.48-7.45 (m, 2H), 7.41-7.38 (m, 1H), 7.26-7.23 (m, 2H), 7.17-7.12 (m, 1H), 6.65 (d, J=2.3 Hz, 1H), 4.16-4.08 (m, 1H), 4.00-3.90 (m, 1H), 3.84 (s, 3H), 3.58-3.46 (m, 4H), 2.95-2.87 (m, 2H), 2.71 (t, J=7.6 Hz, 2H), 2.57 (t, J=12.8 Hz, 2H), 2.05-1.94 (m, 2H), 1.91-1.77 (m, 6H), 1.74-1.62 (m, 2H), 1.33 (d, J=6.7 Hz, 6H).
MS: [M+H]+=668 (calc=668) (MultiMode+)

EXAMPLE 166

N-((1s,4s)-4-(1,5-Dimethyl-1H-pyrazole-3-carboxamido)cyclohexyl)-5-fluoro-2-(4'-(2-(4-methyl-1,4-diazepan-1-yl)ethyl)biphenyl-3-yloxy)nicotinamide

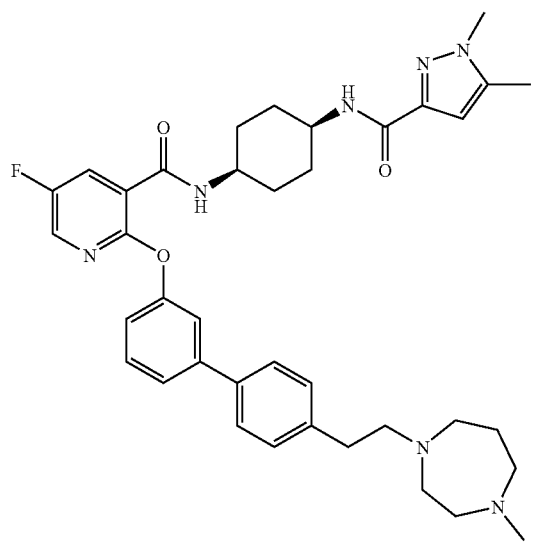

To a solution of 2-(3'-(3-((1s,4s)-4-(1,5-dimethyl-1H-pyrazole-3-carboxamido)cyclohexylcarbamoyl)-5-fluoropyridin-2-yloxy)biphenyl-4-yl)ethyl methanesulfonate (120 mg, 0.18 mmol) in acetonitrile (1 mL) was added 1-methyl-1,4-diazepane (0.069 mL, 0.55 mmol). The reaction mixture was allowed to stir at RT overnight. This was purified by HPLC to give the title compound as a white solid. Yield: 42 mg
$^1$H NMR (400 MHz, CDCl$_3$) δ 8.48-8.42 (m, 1H), 8.12-8.10 (m, 1H), 8.09-8.03 (m, 1H), 7.60-7.56 (m, 2H), 7.51-7.47 (m, 2H), 7.41-7.39 (m, 1H), 7.35-7.30 (m, 2H), 7.19-7.14 (m, 1H), 6.42 (s, 1H), 4.17-4.07 (m, 1H), 3.96-3.84 (m, 1H), 3.77-3.70 (m, 7H), 3.58-3.38 (m, 6H), 3.10-3.03 (m, 2H), 2.96 (s, 3H), 2.33-2.24 (m, 3H), 1.96-1.62 (m, 10H).
MS: [M+H]+=668 (calc=668) (MultiMode+)

EXAMPLE 167

N-((1s,4s)-4-(1,5-Dimethyl-1H-pyrazole-3-carboxamido)cyclohexyl)-5-fluoro-2-(4'-(2-(4-methylpiperazin-1-yl)ethyl)biphenyl-3-yloxy)nicotinamide

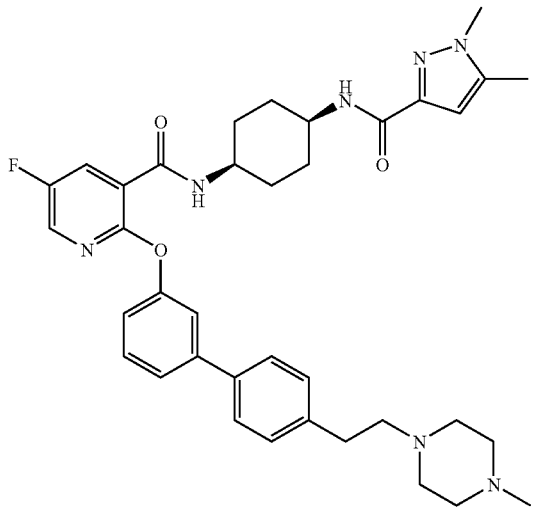

To a solution of 2-(3'-(3-((1s,4s)-4-(1,5-dimethyl-1H-pyrazole-3-carboxamido)cyclohexylcarbamoyl)-5-fluoropyridin-2-yloxy)biphenyl-4-yl)ethyl methanesulfonate (120 mg, 0.18 mmol) in acetonitrile (2 mL) was added 1-methylpiperazine (0.061 mL, 0.55 mmol). The reaction mixture was allowed to stir at RT overnight. This was purified by HPLC to give the title compound as a white solid. Yield: 65 mg $^1$H NMR (400 MHz, CDCl$_3$) δ 8.47-8.42 (m, 1H), 8.12-8.10 (m, 1H), 8.07-8.03 (m, 1H), 7.55-7.51 (m, 2H), 7.50-7.46 (m, 2H), 7.41-7.39 (m, 1H), 7.30-7.26 (m, 2H), 7.17-7.12 (m, 1H), 6.42 (s, 1H), 4.18-4.08 (m, 1H), 3.97-3.91 (m, 1H), 3.92 (s, 3H), 3.72 (s, 3H), 3.23-2.87 (m, 12H), 2.83 (s, 3H), 1.90-1.75 (m, 6H), 1.74-1.62 (m, 2H).

MS: [M+H]+=654 (calc=654) (MultiMode+)

EXAMPLE 168

N-((1s,4s)-4-(2-(4'-(3-((3S,5R)-3,5-Dimethylpiperazin-1-yl)propyl)biphenyl-3-yloxy)-5-fluoronicotinamido)cyclohexyl)-6,7-dihydro-5H-pyrazolo[5,1-b][1,3]oxazine-2-carboxamide

Step (a) 6,7-Dihydro-5H-pyrazolo[5,1-b][1,3]oxazine-2-carboxylic acid

Ethyl 5-hydroxy-1H-pyrazole-3-carboxylate (0.5 g, 3.20 mmol), 1,3-dibromopropane (0.358 mL, 3.52 mmol) and potassium carbonate (1.770 g, 12.81 mmol) were heated at reflux in acetonitrile (20 mL) for 20 h then cooled to RT, filtered and evaporated in vacuo. The residue was dissolved in a mixture of MeOH (10 mL) and water (20 mL), NaOH (0.384 g, 9.61 mmol) added and stirred for 2 h. The reaction mixture was adjusted to pH5 with 2M HCl and purified by reverse phase HPLC with MeCN/aqTFA as eluent. The solvent was evaporated in vacuo to ~15 mL and freeze dried to give the sub-title compound as a white solid. Yield: 440 mg $^1$H NMR (400 MHz, DMSO) δ 5.87 (s, 1H), 4.30 (t, J=5.2 Hz, 2H), 4.14 (t, J=6.3 Hz, 2H), 2.50 (m, 2H).

Step (b) N-((1s,4s)-4-(2-(4'-(3-((3S,5R)-3,5-Dimethylpiperazin-1-yl)propyl)biphenyl-3-yloxy)-5-fluoronicotinamido)cyclohexyl)-6,7-dihydro-5H-pyrazolo[5,1-b][1,3]oxazine-2-carboxamide HATU (0.063 g, 0.16 mmol) was added to a solution of N-((1s,4s)-4-aminocyclohexyl)-2-(4'-(3-((3S,5R)-3,5-dimethylpiperazin-1-yl)propyl)biphenyl-3-yloxy)-5-fluoronicotinamide (0.1 g, 0.15 mmol), 6,7-dihydro-5H-pyrazolo[5,1-b][1,3]oxazine-2-carboxylic acid (0.028 g, 0.16 mmol) and DIPEA (0.131 mL, 0.75 mmol) in DMF (2 mL) and the solution stirred at RT for 20 h. The mixture was purified by reverse phase HPLC with aq TFA/MeCN as eluent to give the title compound as a white solid. Yield: 62 mg $^1$H NMR (400 MHz, CD$_3$OD) δ 8.12 (d, J=3.1 Hz, 1H), 8.06 (m, 1H), 7.52 (m, 2H), 7.47 (m, 2H), 7.40 (m, 1H), 7.25 (m, 2H), 7.14 (m, 1H), 5.83 (s, 1H), 4.27 (m, 2H), 4.11 (m, 1H), 4.05 (t, J=6.2 Hz, 2H), 3.92 (m, 1H), 3.56 (m, 4H), 2.96 (m, 2H), 2.72 (t, J=7.5 Hz, 2H), 2.66 (t, J=13.5 Hz, 2H), 2.20 (m, 2H), 2.02 (m, 2H), 1.89-1.61 (m, 8H), 1.34 (d, J=6.5 Hz, 6H).

MS: [M+H]+=710 (calc=710) (MultiMode+)

EXAMPLE 169

N-((1s,4s)-4-(2-(4'-(((3S,5R)-3,5-Dimethylpiperazin-1-yl)methyl)-2'-(thiomorpholinomethyl)biphenyl-3-yloxy)-5-fluoronicotinamido)cyclohexyl)-6-fluoroimidazo[1,2-a]pyridine-2-carboxamide

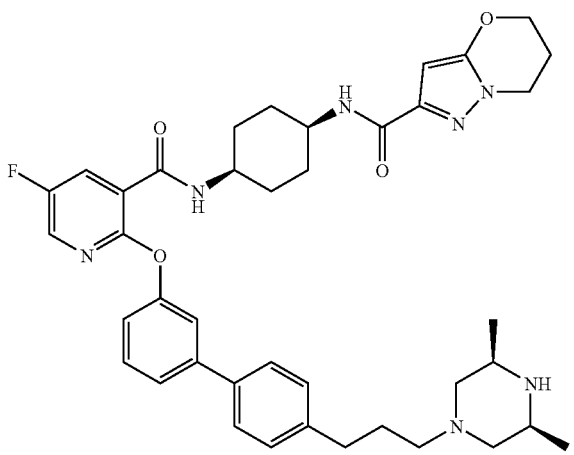

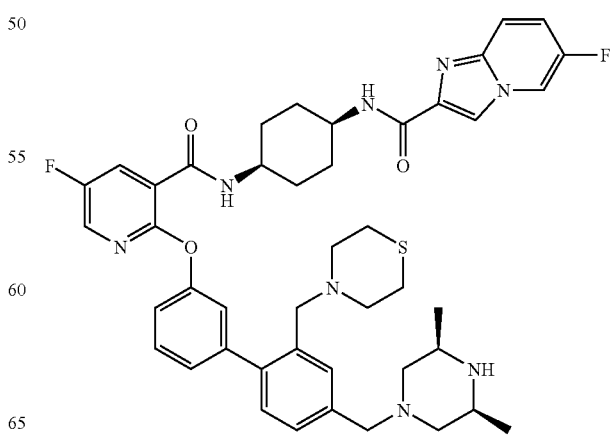

Step (a) 4-Bromo-3-(thiomorpholinomethyl)benzonitrile

To a solution of 4-bromo-3-(bromomethyl)benzonitrile (0.95 g, 3.46 mmol) in DMF (13.40 ml) was added thiomorpholine (0.417 ml, 4.15 mmol) and potassium carbonate (0.573 g, 4.15 mmol). The reaction mixture was allowed to stir at RT overnight. The reaction mixture was poured onto water and extracted with EtOAc (×2). The organic extractions were combined, washed with brine (×3), dried (MgSO$_4$) and evaporated to give a yellow oil. This was purified by flash silica chromatography (Biotage column) (eluent=25% ether/isohexane) to give the sub-title compound as a colourless oil. Yield: 0.951 g $^1$H NMR (400 MHz, CDCl$_3$) δ 7.80 (d, J=2.1 Hz, 1H), 7.65 (d, J=8.2 Hz, 1H), 7.39 (dd, J=8.3, 2.2 Hz, 1H), 3.59 (s, 2H), 2.82-2.67 (m, 8H).

Step (b) 4-Bromo-3-(thiomorpholinomethyl)benzaldehyde

To a solution of 4-bromo-3-(thiomorpholinomethyl)benzonitrile (0.92 g, 3.10 mmol) in DCM (10.67 ml) at 0° C. was added diisobutylaluminum hydride (3.40 ml, 3.40 mmol). The reaction mixture was allowed to stir at 0° C. for 10 minutes. The reaction mixture was poured into a mixture of crushed ice and 6M HCl and stirred for 1 hour. The organic phase was separated, washed with saturated NaHCO$_3$, brine, dried (MgSO$_4$) and evaporated to give the sub-title compound as a pink oil. Yield: 0.735 g MS: [M+H]+=300/302 (calc=300/302) (MultiMode+)

Step (c) 4-(2-Bromo-5-(((3S,5R)-3,5-dimethylpiperazin-1-yl)methyl)benzyl)thiomorpholine To a solution of 4-bromo-3-(thiomorpholinomethyl)benzaldehyde (0.73 g, 2.43 mmol) in dichloromethane (24.32 ml) was added (2R,6S)-2,6-dimethylpiperazine (0.416 g, 3.65 mmol). The mixture was allowed to stir at RT for 40 minutes before sodium triacetoxyborohydride (0.773 g, 3.65 mmol) was added. The reaction was stirred at RT for 2 hours. The mixture was diluted with dichloromethane and washed with saturated NaHCO$_3$(aq), dried (MgSO$_4$) and evaporated to give the sub-title compound as a pale yellow oil. Yield: 0.92 g MS: [M+H]+=398/400 (calc=398/400) (MultiMode+)

Step (d) tert-Butyl (1s,4s)-4-(2-(4'-(((3S,5R)-3,5-dimethylpiperazin-1-yl)methyl)-2'-(thiomorpholinomethyl)biphenyl-3-yloxy)-5-fluoronicotinamido)cyclohexylcarbamate tert-Butyl (1s,4s)-4-(5-fluoro-2-(3-(4,4,5,5-tetramethyl-1,3,2-dioxaborolan-2-yl)phenoxy)nicotinamido)cyclohexylcarbamate (1.283 g, 2.31 mmol), 4-(2-bromo-5-(((3S,5R)-3,5-dimethylpiperazin-1-yl)methyl)benzyl)thiomorpholine (0.92 g, 2.31 mmol) and sodium carbonate (1.983 g, 6.93 mmol) were added to THF (15.39 ml) and degassed water (7.70 ml) under nitrogen. Tetrakis(triphenylphosphine)palladium(0) (0.053 g, 0.05 mmol) was then added and the reaction mixture was heated at reflux overnight. The mixture was poured onto water and extracted into EtOAc (×2). The extractions were combined, washed with brine, dried (MgSO$_4$) and evaporated to give a light brown foam. The crude material was purified by flash silica chromatography (Biotage column) (eluant=4% 7M ammonia in methanol/DCM) to give the sub-title compound as a light brown oil. Yield: 1.25 g MS: [M+H]+=747 (calc=747) (MultiMode+)

Step (e) N-((1s,4s)-4-Aminocyclohexyl)-2-(4'-(((3S,5R)-3,5-dimethylpiperazin-1-yl)methyl)-2'-(thiomorpholinomethyl)biphenyl-3-yloxy)-5-fluoronicotinamide To a solution of tert-butyl (1s,4s)-4-(2-(4'-(((3S,5R)-3,5-dimethylpiperazin-1-yl)methyl)-2'-(thiomorpholinomethyl)biphenyl-3-yloxy)-5-fluoronicotinamido)cyclohexylcarbamate (1.24 g, 1.66 mmol) in DCM (20 mL) was added 4.0 M hydrogen chloride in dioxane (4.15 mL, 16.60 mmol). The mixture was stirred at RT for 2 hours. The mixture was evaporated to dryness to give the sub-title compound hydrochloride as a white solid. Yield: 1.32 g MS: [M+H]+=647 (calc=647) (MultiMode+)

Step (f) N-((1s,4s)-4-(2-(4'-(((3S,5R)-3,5-Dimethylpiperazin-1-yl)methyl)-2'-(thiomorpholinomethyl)biphenyl-3-yloxy)-5-fluoronicotinamido)cyclohexyl)-6-fluoroimidazo[1,2-a]pyridine-2-carboxamide To a suspension of N-((1s,4s)-4-aminocyclohexyl)-2-(4'-(((3S,5R)-3,5-dimethylpiperazin-1-yl)methyl)-2'-(thiomorpholinomethyl)biphenyl-3-yloxy)-5-fluoronicotinamide hydrochloride (150 mg, 0.19 mmol) in acetonitrile (2.29 ml) was added 6-fluoroimidazo[1,2-a]pyridine-2-carboxylic acid (49.2 mg, 0.23 mmol) and triethylamine (0.264 ml, 1.89 mmol). 1-Propanephosphonic acid cyclic anhydride, 1.57M solution in THF (0.151 ml, 0.24 mmol) was then added and the mixture stirred at RT for 2 hours. The mixture was evaporated to dryness and the residue dissolved in DCM (100 ml) and washed with saturated NaHCO$_3$(aq), brine, dried (MgSO$_4$) and evaporated to give a foam. The crude product was purified by preparative HPLC using a 95-5% gradient of aqueous 0.2% TFA in methanol as eluent to give the title compound as a white solid. Yield: 64 mg $^1$H NMR (400 MHz, CDCl$_3$) δ 8.38 (s, 1H), 8.16 (d, J=3.1 Hz, 1H), 8.05 (dd, J=7.7, 3.1 Hz, 1H), 7.76-7.74 (m, 1H), 7.66 (dd, J=10.0, 4.9 Hz, 1H), 7.59 (t, J=7.9 Hz, 1H), 7.55-7.49 (m, 2H), 7.39 (d, J=7.9 Hz, 1H), 7.35-7.30 (m, 1H), 7.22-7.18 (m, 1H), 7.17-7.15 (m, 1H), 4.42 (s, 2H), 4.15-4.02 (m, 2H), 3.88 (s, 2H), 3.53-3.42 (m, 2H), 3.00-2.59 (m, 8H), 2.40 (t, J=12.0 Hz, 2H), 1.94-1.73 (m, 8H), 1.30 (d, J=6.4 Hz, 6H).

MS: [M+H]+=809 (calc=809) (MultiMode+)

EXAMPLE 170

N-((1s,4s)-4-(5-Fluoro-2-(2'-(morpholinomethyl)-4'-(thiomorpholinomethyl)biphenyl-3-yloxy)nicotinamido)cyclohexyl)-2-(hydroxymethyl)thiazole-4-carboxamide

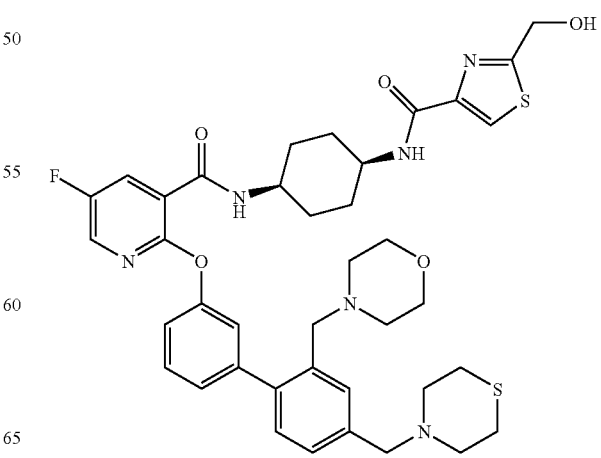

Step (a) tert-Butyl (1s,4s)-4-(5-fluoro-2-(2'-(morpholinomethyl)-4'-(thiomorpholinomethyl)biphenyl-3-yloxy)nicotinamido)cyclohexylcarbamate tert-Butyl (1s,4s)-4-(5-fluoro-2-(4'-formyl-2'-(morpholinomethyl)biphenyl-3-yloxy)nicotinamido)cyclohexylcarbamate (0.28 g, 0.44 mmol) and thiomorpholine (0.091 g, 0.89 mmol) were stirred in DCM (30 mL) for 15 min. Acetic acid (0.051 mL, 0.89 mmol), followed by sodium triacetoxyborohydride (0.188 g, 0.89 mmol) were added and the reaction stirred for a further 20 h. The reaction was quenched with 2M HCl (30 mL), extracted with EtOAc, washed with water and brine, dried (Na$_2$SO$_4$) and evaporated in vacuo to afford the sub-title compound as a white solid. Yield: 0.300 g $^1$H NMR (400 MHz, CDCl$_3$) δ 8.36 (m, 1H), 8.06 (d, J=3.1 Hz, 1H), 8.01 (d, J=7.7 Hz, 1H), 7.50 (t, J=8.0 Hz, 1H), 7.38 (s, 1H), 7.35 (m, 1H), 7.29 (m, 1H), 7.27 (s, 1H), 7.14 (m, 1H), 4.54-4.08 (m, 2H), 3.77-3.47 (m, 2H), 3.56 (m, 4H), 3.41 (s, 2H), 2.70 (m, 8H), 2.33 (m, 2H), 1.87-1.46 (m, 10H), 1.42 (s, 9H).

Step (b) N-((1s,4s)-4-Aminocyclohexyl)-5-fluoro-2-(2'-(morpholinomethyl)-4'-(thiomorpholinomethyl)biphenyl-3-yloxy)nicotinamide 4M HCl in dioxane (5 ml, 20.00 mmol) was added to a solution of tert-butyl (1s,4s)-4-(5-fluoro-2-(2'-(morpholinomethyl)-4'-(thiomorpholinomethyl)biphenyl-3-yloxy)nicotinamido)cyclohexylcarbamate (0.3 g, 0.42 mmol) in DCM (5 mL) and stirred for 2 h. The solvent was evaporated in vacuo to afford the sub-title compound hydrochloride salt as a pale yellow gum. Yield: 0.280 g $^1$H NMR (400 MHz, DMSO) δ 8.37 (d, J=6.8 Hz, 1H), 8.29 (d, J=3.4 Hz, 1H), 8.23-8.09 (m, 4H), 8.05 (m, 1H), 7.79 (d, J=8.1 Hz, 1H), 7.56 (t, J=7.8 Hz, 1H), 7.46 (d, J=7.4 Hz, 1H), 7.33 (m, 1H), 7.27 (m, 1H), 7.24 (m, 1H), 4.38 (s, 2H), 3.97-3.57 (m, 8H), 3.45-3.08 (m, 8H), 2.79 (m, 2H), 1.92-1.59 (m, 10H).

Step (c) N-((1s,4s)-4-(5-Fluoro-2-(2'-(morpholinomethyl)-4'-(thiomorpholinomethyl)biphenyl-3-yloxy)nicotinamido)cyclohexyl)-2-(hydroxymethyl)thiazole-4-carboxamide HATU (0.094 g, 0.25 mmol) was added to a solution of N-((1s,4s)-4-aminocyclohexyl)-5-fluoro-2-(2'-(morpholinomethyl)-4'-(thiomorpholinomethyl)biphenyl-3-yloxy)nicotinamide hydrochloride (0.14 g, 0.23 mmol), 2-(hydroxymethyl)thiazole-4-carboxylic acid (0.040 g, 0.25 mmol) and DIPEA (0.197 mL, 1.13 mmol) in DMF (2 mL) and the solution stirred at RT for 20 h. The mixture was purified by reverse phase HPLC with aq TFA/MeCN as eluant to afford the title compound as a white solid. Yield: 45 mg $^1$H NMR (400 MHz, CD$_3$OD) δ 8.13 (d, J=3.1 Hz, 1H), 8.10 (s, 1H), 8.03 (m, 1H), 7.92 (d, J=1.7 Hz, 1H), 7.61 (m, 2H), 7.48 (d, J=8.0 Hz, 1H), 7.33 (m, 1H), 7.22 (m, 1H), 7.19 (m, 1H), 4.79 (s, 2H), 4.45 (s, 2H), 4.41 (s, 2H), 4.11 (m, 1H), 3.99 (m, 1H), 3.94-3.56 (m, 4H), 3.43-2.69 (m, 12H), 1.93-1.68 (m, 8H).

MS: [M+H]+=761 (calc=761) (MultiMode+)

EXAMPLE 171

N-((1s,4s)-4-(5-Fluoro-2-(4'-(2-(4-methyl-1,4-diazepan-1-yl)ethyl)biphenyl-3-yloxy)nicotinamido)cyclohexyl)-4,5,6,7-tetrahydropyrazolo[1,5-a]pyridine-2-carboxamide

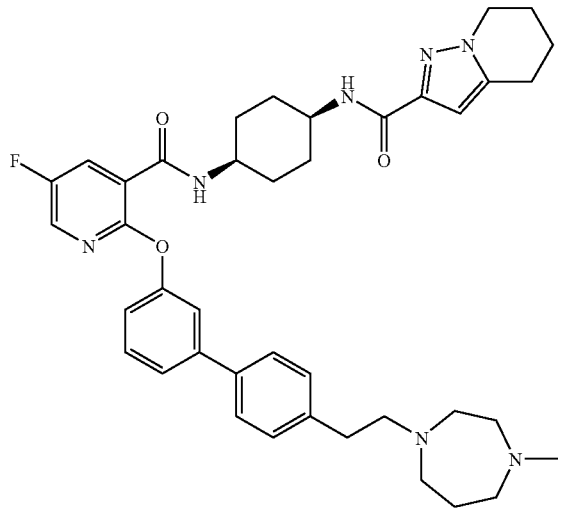

Step (a) N-((1s,4s)-4-(5-Fluoro-2-(3-(4,4,5,5-tetramethyl-1,3,2-dioxaborolan-2-yl)phenoxy)nicotinamido)cyclohexyl)-4,5,6,7-tetrahydropyrazolo[1,5-a]pyridine-2-carboxamide A solution of 1,1'-bis(diphenylphosphino)ferrocene (0.034 g, 0.06 mmol) and 1,1'-bis(diphenylphosphino)ferrocene-palladium(II)dichloride dichloromethane complex (0.049 g, 0.06 mmol) was stirred under nitrogen for 10 min. Potassium acetate (0.356 g, 3.63 mmol), N-((1s,4s)-4-(5-fluoro-2-(3-iodophenoxy)nicotinamido)cyclohexyl)-4,5,6,7-tetrahydropyrazolo[1,5-a]pyridine-2-carboxamide (0.730 g, 1.21 mmol) and bis(pinacolato)diboron (0.399 g, 1.57 mmol) added and reaction mixture heated to 80° C. overnight. The reaction mixture was poured into water and extracted into EtOAc. The organic was dried over magnesium sulfate, filtered and evaporated to afford crude product. The crude product was purified by flash silica chromatography using Isco Companion, 100 g silica column, elution 100% EtOAc. Pure fractions were evaporated to dryness to afford the sub-title compound as a yellow oil. Yield: 0.324 g MS: [M+H]+=604 (calc=604) (MultiMode+)

Step (b) N-((1s,4s)-4-(5-Fluoro-2-(4'-(2-hydroxyethyl)biphenyl-3-yloxy)nicotinamido)cyclohexyl)-4,5,6,7-tetrahydropyrazolo[1,5-a]pyridine-2-carboxamide To a stirred solution of N-((1s,4s)-4-(5-fluoro-2-(3-(4,4,5,5-tetramethyl-1,3,2-dioxaborolan-2-yl)phenoxy)nicotinamido)cyclohexyl)-4,5,6,7-tetrahydropyrazolo[1,5-a]pyridine-2-carboxamide (0.320 g, 0.53 mmol) in THF (3 mL) was added 2-(4-bromophenyl)ethanol (0.111 mL, 0.80 mmol) and sodium carbonate (0.169 g, 1.59 mmol) in water (1.500 mL). Tetrakis(triphenylphosphine)palladium(0) (0.031 g, 0.03 mmol) added and reaction mixture heated to 70° C. for 1 h. The reaction mixture was poured into water and extracted into EtOAc. The organic was dried over magnesium sulfate, filtered and evaporated to afford crude product. The crude product was purified by flash silica chromatography using ISCO Companion, 50 g silica column, elution gradient 90 to 100% EtOAc in isohexane. Pure fractions were evaporated to dryness to afford the sub-title compound as a yellow oil. Yield: 68 mg MS: [M+H]+=598 (calc=598) (MultiMode+)

Step (c) 2-(3'-(5-Fluoro-3-((1s,4s)-4-(4,5,6,7-tetrahydropyrazolo[1,5-a]pyridine-2-carboxamido)cyclohexylcarbamoyl)pyridin-2-yloxy)biphenyl-4-yl)ethyl methanesulfonate To a stirred solution of N-((1s,4s)-4-(5-fluoro-2-(4'-(2-hydroxyethyl)biphenyl-3-yloxy)nicotinamido)cyclohexyl)-4,5,6,7-tetrahydropyrazolo[1,5-a]pyridine-2-carboxamide (0.068 g, 0.11 mmol) in dichloromethane (1 mL) was added pyridine (0.037 mL, 0.46 mmol) and methanesulfonyl chloride (0.035 mL, 0.46 mmol). The reaction mixture was stirred at RT for 3 days then diluted with dichloromethane and washed with 2M hydrochloric acid and saturated brine. The organic was dried over magnesium sulfate, filtered and evaporated to afford crude product. The crude oil was triturated with diethyl ether to give a solid which was collected by filtration and air dried to give the sub-title compound (also contains some N-((1s,4s)-4-(2-(4'-(2-chloroethyl)biphenyl-3-yloxy)-5-fluoronicotinamido)cyclohexyl)-4,5,6,7-tetrahydropyrazolo[1,5-a]pyridine-2-carboxamide) as a yellow solid. Yield: 60 mg MS: [M+H]+=676 (calc=676) (MultiMode+)

Step (d) N-((1s,4s)-4-(5-Fluoro-2-(4'-(2-(4-methyl-1,4-diazepan-1-yl)ethyl)biphenyl-3-yloxy)nicotinamido)cyclohexyl)-4,5,6,7-tetrahydropyrazolo[1,5-a]pyridine-2-carboxamide To a microwave vial was added 2-(3'-(5-fluoro-3-((1s,4s)-4-(4,5,6,7-tetrahydropyrazolo[1,5-a]pyridine-2-carboxamido)cyclohexylcarbamoyl)pyridin-2-yloxy)biphenyl-4-yl)ethyl methanesulfonate (0.060 g, 0.09 mmol) and 1-methyl-1,4-diazepane (0.033 mL, 0.27 mmol) in acetonitrile (0.5 mL). The reaction mixture was heated by microwave to 80° C. for 3 h. The crude product was purified by preparative HPLC on a Waters X-Bridge column using a 65-0% gradient of aqueous 0.2% TFA in methanol as eluent. The fractions containing the desired compound were evaporated to dryness to afford the title compound as a white solid. Yield: 3 mg ¹H NMR (400 MHz, CD₃OD) δ 8.11 (d, J=3.1 Hz, 1H), 8.06 (dd, J=8.2, 3.1 Hz, 1H), 7.56 (d, J=7.8 Hz, 2H), 7.48 (d, J=5.9 Hz, 2H), 7.42-7.40 (m, 1H), 7.33 (d, J=8.2 Hz, 2H), 7.18-7.13 (m, 1H), 6.38 (s, 1H), 4.14-4.07 (m, 1H), 4.02 (t, J=6.6 Hz, 2H), 3.98-3.91 (m, 1H), 3.67 (s, 4H), 3.52-3.41 (m, 4H), 3.35 (t, J=8.4 Hz, 2H), 3.06 (t, J=7.7 Hz, 2H), 2.93 (s, 3H), 2.78 (t, J=6.2 Hz, 2H), 2.30-2.22 (m, 2H), 2.04-1.96 (m, 2H), 1.88-1.76 (m, 8H), 1.74-1.62 (m, 2H).

MS: [M+H]+=694 (calc=694) (MultiMode+)

EXAMPLE 172

N-((1s,4s)-4-(2-(3'-(3-((3S,5R)-3,5-Dimethylpiperazin-1-yl)propyl)biphenyl-3-yloxy)-5-fluoronicotinamido)cyclohexyl)-5,6-dihydro-4H-pyrrolo[1,2-b]pyrazole-2-carboxamide

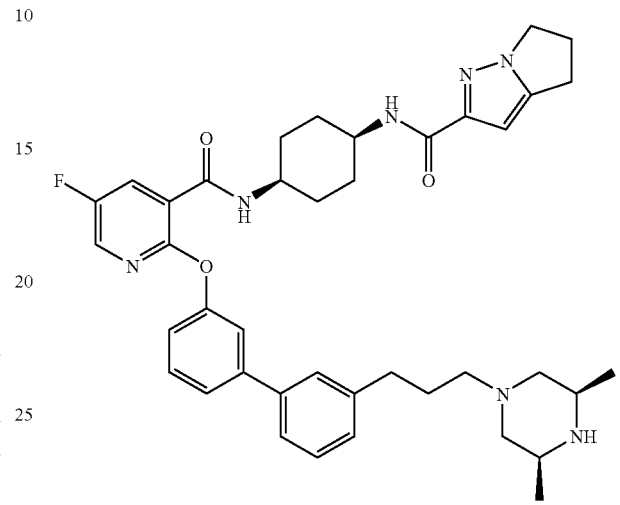

Step (a) tert-Butyl (1s,4s)-4-(2-(3'-(3-((3S,5R)-3,5-dimethylpiperazin-1-yl)propyl)biphenyl-3-yloxy)-5-fluoronicotinamido)cyclohexylcarbamate To a microwave vial was added 3-(3'-(3-((1s,4s)-4-(tert-butoxycarbonylamino)cyclohexylcarbamoyl)-5-fluoropyridin-2-yloxy)biphenyl-3-yl)propyl methanesulfonate (0.150 g, 0.23 mmol) and (2S,6R)-2,6-dimethylpiperazine (0.214 g, 1.87 mmol) in acetonitrile (3 mL). The reaction mixture was heated to 80° C. by microwave for 40 min. The reaction mixture was evaporated to dryness and redissolved in EtOAc and washed with saturated sodium hydrogen carbonate and saturated brine. The organic was dried over magnesium sulfate, filtered and evaporated to afford crude product. The crude product was purified by flash silica chromatography using ISCO Companion, 50 g silica column, elution gradient 2 to 4% 7N methanolic ammonia in dichloromethane. Pure fractions were evaporated to dryness to afford the sub-title compound as a yellow oil. Yield: 0.120 g MS: [M+H]+=660 (calc=660) (MultiMode+)

Step (b) N-((1s,4s)-4-Aminocyclohexyl)-2-(3'-(3-((3S,5R)-3,5-dimethylpiperazin-1-yl)propyl)biphenyl-3-yloxy)-5-fluoronicotinamide To a stirred solution of tert-butyl (1s,4s)-4-(2-(3'-(3-((3S,5R)-3,5-dimethylpiperazin-1-yl)propyl)biphenyl-3-yloxy)-5-fluoronicotinamido)cyclohexylcarbamate (0.175 g, 0.27 mmol) in dichloromethane (1.2 mL) was added 4M HCl/dioxane (0.995 mL, 3.98 mmol). The reaction mixture was stirred at RT under nitrogen overnight then concentrated to give the sub-title compound hydrochloride as a yellow oil which was used without further purification. Yield: 0.180 g MS: [M+H]+=560 (calc=560) (MultiMode+)

Step (c) N-((1s,4s)-4-(2-(3'-(3-((3S,5R)-3,5-Dimethylpiperazin-1-yl)propyl)biphenyl-3-yloxy)-5-fluoronicotinamido)cyclohexyl)-5,6-dihydro-4H-pyrrolo[1,2-b]pyrazole-2-carboxamide To a stirred solution of N-((1s,4s)-4-aminocyclohexyl)-2-(3'-(3-((3S,5R)-3,5-dimethylpiperazin-1-yl)propyl)biphenyl-3-yloxy)-5-fluoronicotinamide hydrochloride (0.180 g, 0.28 mmol) in acetonitrile (2 mL) was added 5,6-dihydro-4H-pyrrolo[1,2-b]pyrazole-2-carboxylic acid (0.052 g, 0.34 mmol) and triethylamine (0.397 mL, 2.85 mmol). The reaction mixture was stirred at RT for 10 min. 1-Propanephosphonic acid cyclic anhydride, 1.57M solution in THF (0.228 mL, 0.34 mmol) was added and the reaction mixture was stirred at RT under nitrogen for 2 h then concentrated to give crude product. The crude product was purified by preparative HPLC on a Waters X-Bridge column using a 70-20% gradient of aqueous 0.2% TFA in methanol as eluent. The fractions containing the desired compound were evaporated to dryness to afford the title compound as a white solid. Yield: 14 mg $^1$H NMR (400 MHz, CD$_3$OD) δ 8.05 (s, 1H), 8.01 (d, J=8.3 Hz, 1H), 7.42 (s, 2H), 7.38-7.32 (m, 3H), 7.27-7.23 (m, 1H), 7.16-7.06 (m, 2H), 6.30 (s, 1H), 4.08-4.02 (m, 1H), 3.95-3.91 (m, 2H), 3.88-3.69 (m, 3H), 3.06-2.94 (m, 2H), 2.80-2.75 (m, 2H), 2.69-2.58 (m, 2H), 2.54-2.44 (m, 2H), 2.10-1.95 (m, 2H), 1.84-1.65 (m, 6H), 1.64-1.52 (m, 4H), 1.40-1.25 (m, 6H), 0.97-0.90 (m, 1H).

[M+H]+=694 (calc=694) (MultiMode+)

EXAMPLE 173

N-((1s,4s)-4-(3-Cyclopropyl-1H-pyrazole-5-carboxamido)cyclohexyl)-5-fluoro-2-(4'-(3-(piperazin-1-yl)propyl)biphenyl-3-yloxy)nicotinamide

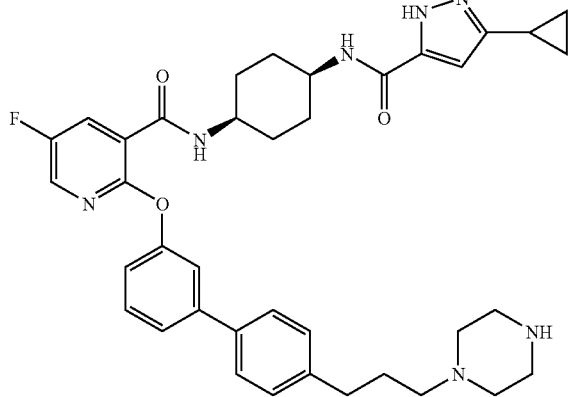

To a stirred solution of tert-butyl 4-(3-(3'-(3-((1s,4s)-4-aminocyclohexylcarbamoyl)-5-fluoropyridin-2-yloxy)biphenyl-4-yl)propyl)piperazine-1-carboxylate (0.080 g, 0.13 mmol) in acetonitrile (2 mL) was added 3-cyclopropyl-1H-pyrazole-5-carboxylic acid (0.039 g, 0.25 mmol) and triethylamine (0.176 mL, 1.27 mmol). The reaction mixture was stirred at RT for 10 min. 1-Propanephosphonic acid cyclic anhydride, 1.57M solution in THF (0.081 g, 0.25 mmol) was added and reaction mixture stirred at RT overnight. The reaction mixture was evaporated to dryness and redissolved in dichloromethane and washed with saturated sodium hydrogen carbonate. The organic layer was treated with 4M HCl/dioxane (0.633 mL, 2.53 mmol) and allowed to stir at RT overnight. The crude product was purified by preparative HPLC on a Waters X-Bridge column using a 75-0% gradient of aqueous 0.2% TFA in methanol as eluent. The fractions containing the desired compound were evaporated to dryness to afford crude product, which was dissolved in DCM/methanol, triethylamine (0.1 mL) and PS-benzaldehyde (0.030 g) added and solution allowed to stir at RT for 3 days. The resin was filtered off and the compound purified by preparative HPLC on a Waters X-Bridge column using a 90-40% gradient of aqueous 0.2% TFA in acetonitrile as eluent. The fractions containing the desired compound were evaporated to dryness to afford the title compound as a white solid. Yield: 8 mg $^1$H NMR (400 MHz, CD$_3$OD) δ 8.45 (d, J=8.1 Hz, 1H), 8.12 (s, 1H), 8.06 (d, J=8.1 Hz, 1H), 7.51 (d, J=9.3 Hz, 2H), 7.47-7.44 (m, 2H), 7.38 (s, 1H), 7.23 (d, J=9.3 Hz, 2H), 7.15-7.11 (m, 1H), 6.32 (s, 1H), 4.13-4.06 (m, 1H), 3.97-3.89 (m, 1H), 3.41-3.36 (m, 4H), 3.19-3.12 (m, 4H), 2.92-2.84 (m, 2H), 2.71 (t, J=7.0 Hz, 2H), 2.02-1.63 (m, 1H), 0.98 (q, J=7.0 Hz, 2H), 0.69 (q, J=4.6 Hz, 2H).

MS: [M+H]+=666 (calc=666) (MultiMode+)

EXAMPLE 174

N-((1s,4s)-4-(2-(3'-(3-((3S,5R)-3,5-Dimethylpiperazin-1-yl)propyl)biphenyl-3-yloxy)-5-fluoronicotinamido)cyclohexyl)-4,5,6,7-tetrahydropyrazolo[1,5-a]pyridine-2-carboxamide

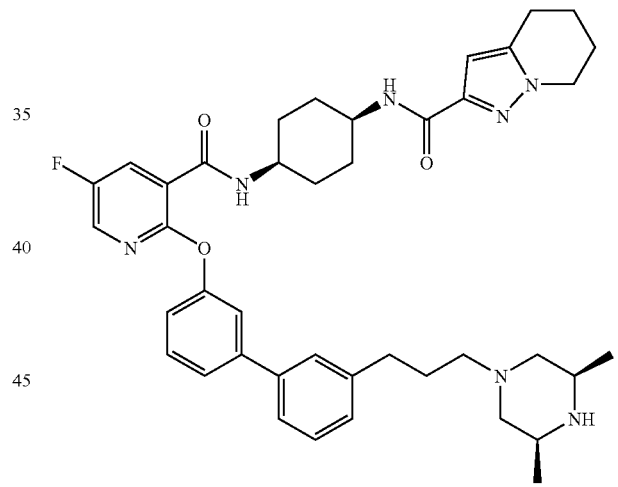

To N-((1s,4s)-4-aminocyclohexyl)-2-(3'-(3-((3S,5R)-3,5-dimethylpiperazin-1-yl)propyl)biphenyl-3-yloxy)-5-fluoronicotinamide (0.1 g, 0.18 mmol) and 4,5,6,7-tetrahydropyrazolo[1,5-a]pyridine-2-carboxylic acid (0.033 g, 0.20 mmol) in acetonitrile (1 mL) was added triethylamine (0.249 mL, 1.79 mmol). The reaction was stirred for 10 minutes before 1-propanephosphonic acid cyclic anhydride, 1.57M solution in THF (T3P) (0.137 mL, 0.21 mmol) was added. The reaction was stirred at RT for 1 hour. The crude product was purified by preparative HPLC on a Phenomenex Gemini column using a 95-5% gradient of aqueous 0.1% TFA in methanol as eluent. The fractions containing the desired compound were freeze dried to afford the title compound as a white solid. Yield: 42 mg $^1$H NMR (300 MHz, CD$_3$OD) δ 8.14-8.06 (m, 2H), 7.53-7.42 (m, 6H), 7.32 (t, J=9.6 Hz, 1H), 7.22-7.15 (m, 2H), 6.36 (s, 1H), 4.19-4.09 (m, 1H), 4.03-3.90 (m, 3H), 3.87-3.67 (m, 4H), 3.22 (t, J=8.6 Hz, 2H), 3.06 (t, J=12.0 Hz, 2H), 2.79-2.70 (m, 4H), 2.16-1.96 (m, 4H), 1.93-1.61 (m, 10H), 1.39 (d, J=17.1 Hz, 6H).

MS: [M+H]+=708 (calc=708) (MultiMode+)

EXAMPLE 175

N-((1s,4s)-4-(2-(4'-(((3S,5R)-3,5-Dimethylpiperazin-1-yl)methyl)-2'-(((S)-3-methylmorpholino)methyl)biphenyl-3-yloxy)-5-fluoronicotinamido)cyclohexyl)-5-methylimidazo[1,2-a]pyridine-2-carboxamide

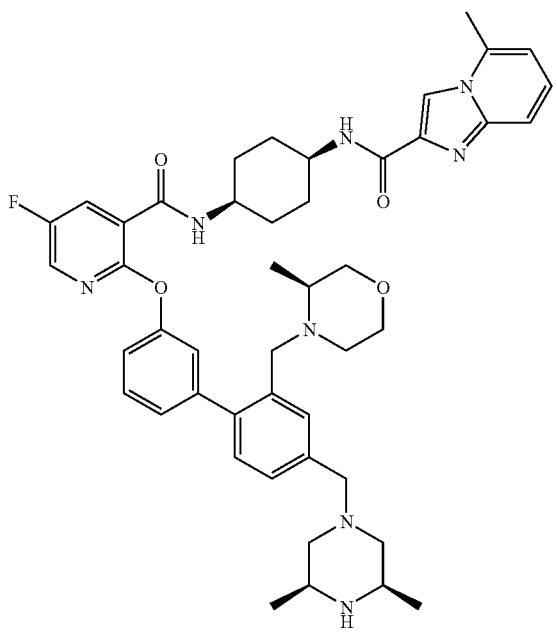

Step (a) (S)-4-Bromo-3-((3-methylmorpholino)methyl)benzonitrile

To a solution of 4-bromo-3-(bromomethyl)benzonitrile (0.9 g, 3.27 mmol) in DMF (13.09 ml) was added (S)-3-methylmorpholine (0.541 g, 3.93 mmol) and potassium carbonate (0.995 g, 7.20 mmol). The reaction mixture was allowed to stir at RT overnight. The reaction mixture was poured onto water and extracted with EtOAc (×2). The organic extractions were combined, washed with brine (×3), dried (MgSO$_4$) and evaporated to give the sub-title compound as a yellow oil. Yield: 0.75 g MS: [M+H]+=295/297 (calc=295/297) (MultiMode+)

Step (b) (S)-4-Bromo-3-((3-methylmorpholino)methyl)benzaldehyde

A solution of (S)-4-bromo-3-((3-methylmorpholino)methyl)benzonitrile (0.750 g, 2.54 mmol) in DCM (10 ml) was cooled in an ice bath to 0° C. and slowly treated with diisobutylaluminum hydride (1M in DCM) (3.04 ml, 3.04 mmol). The ice bath was removed and the reaction mixture stirred at 0° C. for 15 minutes. The reaction mixture was poured into a mixture of ice water (100 ml) and 6M HCl (20 ml) and stirred for 1 hour. 2M NaOH was added to make the solution basic (~pH 10) and diluted with DCM. The organic phase was separated, washed with saturated NaHCO$_3$, dried (MgSO$_4$) and evaporated to give a pale yellow oil. The crude product was purified on Biotage (silica, 50 g) eluting with 30% EtOAc in isohexane. The product containing fractions were combined and concentrated to leave the sub-title compound as a colourless oil. Yield: 0.530 g MS: [M+H]+=298/300 (calc=298/300) (MultiMode+)

Step (c) (S)-4-(2-Bromo-5-(((3S,5R)-3,5-dimethylpiperazin-1-yl)methyl)benzyl)-3-methylmorpholine (2S,6R)-2,6-Dimethylpiperazine (0.304 g, 2.67 mmol) and (S)-4-bromo-3-((3-methylmorpholino)methyl)benzaldehyde (0.530 g, 1.78 mmol) in DCM (10 ml) were stirred at RT under nitrogen for 30 minutes. Sodium triacetoxyborohydride (0.565 g, 2.67 mmol) was then added and the resulting solution was stirred at RT over the weekend. The reaction mixture was quenched with saturated NaHCO$_3$. The reaction mixture was extracted with DCM (×3). The organic layer was dried over MgSO$_4$, filtered and evaporated to afford the sub-title compound as a yellow oil. Yield: 0.620 g MS: [M+H]+=396/398 (calc=396/398) (MultiMode+)

Step (d) tert-Butyl (1s,4s)-4-(2-(4'-(((3S,5R)-3,5-dimethylpiperazin-1-yl)methyl)-2'-(((S)-3-methylmorpholino)methyl)biphenyl-3-yloxy)-5-fluoronicotinamido)cyclohexylcarbamate Tetrakis(triphenylphosphine)palladium(0) (0.033 g, 0.03 mmol) was added to a mixture of tert-butyl (1s,4s)-4-(5-fluoro-2-(3-(4,4,5,5-tetramethyl-1,3,2-dioxaborolan-2-yl)phenoxy)nicotinamido)cyclohexylcarbamate (0.790 g, 1.42 mmol), (S)-4-(2-bromo-5-(((3S,5R)-3,5-dimethylpiperazin-1-yl)methyl)benzyl)-3-methylmorpholine (0.62 g, 1.56 mmol) and sodium carbonate (0.452 g, 4.27 mmol) in water (5 ml) and THF (10 ml). The mixture was heated at 70° C. for 18 h. The reaction mixture was diluted with EtOAc and washed with water and saturated brine. The organic was dried over sodium sulfate, filtered and evaporated to afford crude product as a brown oil. The crude product was purified by flash silica chromatography (Biotage, 100 g) eluting with 50%:50% EtOAc/isohexane then flushed with 10/1/0.1 DCM/methanol/triethylamine. Pure fractions were combined and evaporated to dryness to afford the sub-title compound as a brown solid. Yield: 0.50 g MS: [M–H]–=743 (calc=743) (MultiMode+)

Step (e) N-((1s,4s)-4-Aminocyclohexyl)-2-(4'-(((3S,5R)-3,5-dimethylpiperazin-1-yl)methyl)-2'-(((S)-3-methylmorpholino)methyl)biphenyl-3-yloxy)-5-fluoronicotinamide To tert-butyl (1s,4s)-4-(2-(4'-(((3S,5R)-3,5-dimethylpiperazin-1-yl)methyl)-2'-(((S)-3-methylmorpholino)methyl)biphenyl-3-yloxy)-5-fluoronicotinamido)cyclohexylcarbamate (0.5 g, 0.67 mmol) in dichloromethane (5 mL) was added 4 Molar HCl in dioxane (1.678 mL, 6.71 mmol). The reaction mixture was stirred at RT for 2 hours. The reaction was concentrated in vacuo and triturated with ether and filtered to leave the sub-title compound hydrochloride salt as an off-white solid. Yield: 0.490 g MS: [M+H]+=645 (calc=645) (MultiMode+)

Step (f) N-((1s,4s)-4-(2-(4'-(((3S,5R)-3,5-Dimethylpiperazin-1-yl)methyl)-2'-(((S)-3-methylmorpholino)methyl)biphenyl-3-yloxy) 5-fluoronicotinamido)cyclohexyl)-5-methylimidazo[1,2-a]pyridine-2-carboxamide To N-((1s,4s)-4-aminocyclohexyl)-2-(4'-(((3S,5R)-3,5-dimethylpiperazin-1-yl)methyl)-2'-(((S)-3-methylmorpholino)methyl)biphenyl-3-yloxy)-5-fluoronicotinamide hydrochloride (0.126 g, 0.16 mmol) in acetonitrile (1 mL) was added 5-methylimidazo[1,2-a]pyridine-2-carboxylic acid (0.031 g, 0.18 mmol) and triethylamine (0.222 mL, 1.59 mmol) and the reaction stirred for 5 minutes. 1-Propanephosphonic acid cyclic anhydride (T3P) (1.57M in THF) (0.112 mL, 0.18 mmol) was added and the reaction stirred for 30 minutes. Methanol was added then the crude product was purified by preparative HPLC on a Phenomenex Gemini column using a 95-5% gradient of aqueous 0.1% TFA in methanol as eluent. The fractions containing the desired compound were concentrated then triturated with ether to afford the title compound as a white solid. Yield: 22 mg
$^1$H NMR (400 MHz, CD$_3$OD) δ 8.50-8.43 (m, 2H), 8.13 (d, J=2.6 Hz, 1H), 8.04 (dd, J=7.9, 2.7 Hz, 1H), 7.86-7.81 (m, 1H), 7.66-7.50 (m, 4H), 7.40 (d, J=8.2 Hz, 1H), 7.32 (d, J=8.9 Hz, 1H), 7.21 (d, J=7.5 Hz, 1H), 7.17-7.16 (m, 1H), 7.10 (d, J=6.8 Hz, 1H), 4.20-4.07 (m, 3H), 3.90-3.79 (m, 3H), 3.76-3.59 (m, 2H), 3.56-3.45 (m, 3H), 3.25-3.16 (m, 2H), 3.06-2.97 (m, 2H), 2.73 (s, 3H), 1.95-1.59 (m, 8H), 1.34-1.21 (m, 6H), 1.04-0.99 (m, 3H).
[M+H]+=803 (calc=803) (MultiMode+)

EXAMPLE 176

5-Fluoro-N-((1s,4s)-4-(1-methyl-5-(trifluoromethyl)-1H-pyrazole-3-carboxamido)cyclohexyl)-2-(4'-(2-(piperazin-1-yl)ethyl)biphenyl-3-yloxy)nicotinamide

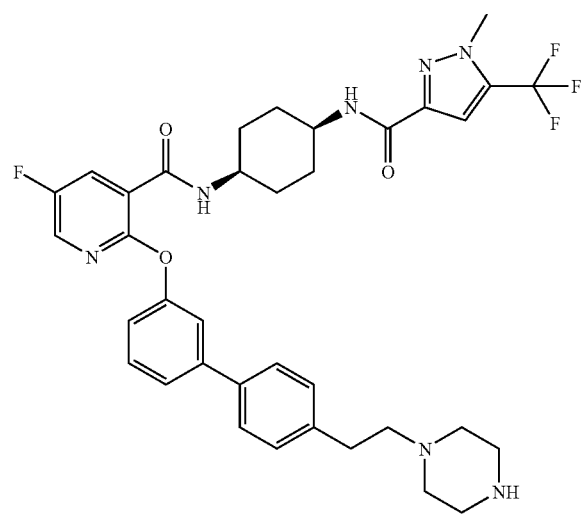

Step (a) Benzyl 4-(2-(3'-(3-((1s,4s)-4-(tert-butoxycarbonylamino)cyclohexylcarbamoyl)-5-fluoropyridin-2-yloxy)biphenyl-4-yl)ethyl)piperazine-1-carboxylate Benzyl 1-piperazinecarboxylate (0.922 mL, 4.78 mmol) and 2-(3'-(3-((1s,4s)-4-(tert-butoxycarbonylamino)cyclohexylcarbamoyl)-5-fluoropyridin-2-yloxy)biphenyl-4-yl) ethyl methanesulfonate (0.600 g, 0.96 mmol) were heated at 100° C. and 50 W in a microwave for 2 h 15 min. The volatiles were evaporated and the residue suspended in a small amount of EtOAc, then filtered to remove the resulting white solid. The filtrate was purified by flash silica chromatography (Combi-Flash Companion, 100 g SNAP cartridge), elution gradient 60 to 100% EtOAc in isohexane. Pure fractions were evaporated to dryness to afford the sub-title compound as a colorless oil. Yield: 0.453 g
[M+H]+=752 (calc=752) (MultiMode+)

Step (b) Benzyl 4-(2-(3'-(3-((1s,4s)-4-aminocyclohexylcarbamoyl)-5-fluoropyridin-2-yloxy)biphenyl-4-yl)ethyl)piperazine-1-carboxylate TFA (2 mL, 25.96 mmol) was added slowly to a solution of benzyl 4-(2-(3'-(3-((1s,4s)-4-(tert-butoxycarbonylamino)cyclohexylcarbamoyl)-5-fluoropyridin-2-yloxy)biphenyl-4-yl)ethyl)piperazine-1-carboxylate (0.453 g, 0.60 mmol) in dichloromethane (2 mL). The reaction mixture was stirred for 5 h at RT then concentrated. The residue was dissolved in dichloromethane and washed with saturated sodium hydrogen carbonate (×2), water and saturated brine. The organic was dried over sodium sulfate, filtered and evaporated to afford the sub-title compound as a colourless gum. Yield: 0.368 g
MS: [M+H]+=652 (calc=652) (MultiMode+)

Step (c) Benzyl 4-(2-(3'-(5-fluoro-3-((1s,4s)-4-(1-methyl-5-(trifluoromethyl)-1H-pyrazole-3-carboxamido)cyclohexylcarbamoyl)pyridin-2-yloxy)biphenyl-4-yl)ethyl)piperazine-1-carboxylate 1-Methyl-5-(trifluoromethyl)-1H-pyrazole-3-carboxylic acid (0.055 g, 0.28 mmol) was dissolved in acetonitrile (1 mL) then DIPEA (0.066 mL, 0.38 mmol) and HATU (HATU) (0.108 g, 0.28 mmol) added and the mixture stirred for 20 minutes. It was then added to a stirred solution of benzyl 4-(2-(3'-(3-((1s,4s)-4-aminocyclohexylcarbamoyl)-5-fluoropyridin-2-yloxy)biphenyl-4-yl)ethyl)piperazine-1-carboxylate (0.123 g, 0.19 mmol) in acetonitrile (1 mL). The reaction mixture was stirred overnight then diluted with EtOAc and washed with water and saturated brine. The organic was dried over sodium sulfate, filtered and evaporated to afford the sub-title compound. Yield: 0.156 g
MS: [M+H]+=828 (calc=828) (MultiMode+)

Step (d) 5-Fluoro-N-((1s,4s)-4-(1-methyl-5-(trifluoromethyl)-1H-pyrazole-3-carboxamido)cyclohexyl)-2-(4'-(2-(piperazin-1-yl)ethyl)biphenyl-3-yloxy)nicotinamide Hydrobromic acid (33% in acetic acid) (1 mL, 5.79 mmol) was added slowly to a solution of benzyl 4-(2-(3'-(5-fluoro-3-((1s,4s)-4-(1-methyl-5-(trifluoromethyl)-1H-pyrazole-3-carboxamido)cyclohexylcarbamoyl)pyridin-2-yloxy)biphenyl-4-yl)ethyl)piperazine-1-carboxylate (0.156 g, 0.19 mmol) in dichloromethane (1 mL). After stirring for 1 h at RT, the reaction mixture was diluted with dichloromethane (10 mL) and neutralised by addition of saturated sodium hydrogen carbonate solution. The layers were separated and aqueous layer extracted with further dichloromethane. The combined organic extracts were washed with water and saturated brine, and evaporated to afford crude product. The crude product was purified by preparative HPLC on a Gemini-NX column using a 95-5% gradient of aqueous 0.1% TFA in methanol as eluent. The fractions containing the desired compound were evaporated to dryness to afford the title compound as a white solid. Yield: 26 mg
$^1$H NMR (400 MHz, CD$_3$OD) δ 8.46 (d, J=7.3 Hz, 1H), 8.12 (d, J=3.1 Hz, 1H), 8.09-8.06 (m, 1H), 7.55-7.52 (m, 2H), 7.49-7.48 (m, 2H), 7.42-7.40 (m, 1H), 7.28 (d, J=8.2 Hz, 2H), 7.18-7.13 (m, 1H), 7.07 (s, 1H), 4.16-4.11 (m, 1H), 3.97-3.91 (m, 4H), 3.38-3.35 (m, 4H), 3.13-3.09 (m, 4H), 3.05-2.99 (m, 2H), 2.96-2.91 (m, 2H), 1.93-1.67 (m, 8H).
MS: [M+H]+=694 (calc=694) (MultiMode+)

EXAMPLE 177

N-((1s,4s)-4-(5-Fluoro-2-(4'-(2-(piperazin-1-yl) ethyl)biphenyl-3-yloxy)nicotinamido)cyclohexyl)-2-methylthiazole-4-carboxamide

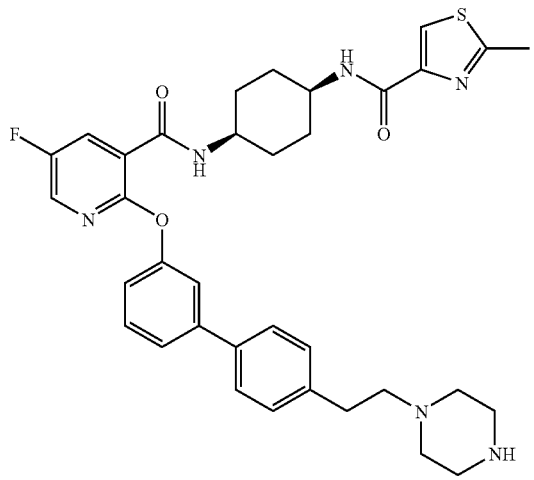

Step (a) Benzyl 4-(2-(3'-(5-fluoro-3-((1s,4s)-4-(2-methylthiazole-4-carboxamido)cyclohexylcarbamoyl)pyridin-2-yloxy)biphenyl-4-yl)ethyl)piperazine-1-carboxylate 2-Methylthiazole-4-carboxylic acid (0.041 g, 0.28 mmol) was dissolved in acetonitrile (1 mL) then DIPEA (0.066 mL, 0.38 mmol) and HATU (HATU) (0.108 g, 0.28 mmol) added and the mixture stirred for 20 minutes. It was then added to a stirred solution of benzyl 4-(2-(3'-(3-((1s,4s)-4-aminocyclohexylcarbamoyl)-5-fluoropyridin-2-yloxy)biphenyl-4-yl) ethyl)piperazine-1-carboxylate (0.123 g, 0.19 mmol) in acetonitrile (1.000 mL). The reaction mixture was stirred overnight then diluted with EtOAc and washed with water and saturated brine. The organic was dried over sodium sulfate, filtered and evaporated to afford the sub-title compound. Yield: 0.147 g
MS: [M+H]+=777 (calc=777) (MultiMode+)

Step (b) N-((1s,4s)-4-(5-fluoro-2-(4'-(2-(piperazin-1-yl)ethyl)biphenyl-3-yloxy)nicotinamido)cyclohexyl)-2-methylthiazole-4-carboxamide Hydrobromic acid (33% in acetic acid) (1 mL, 5.79 mmol) was added slowly to a solution of benzyl 4-(2-(3'-(5-fluoro-3-((1s,4s)-4-(2-methylthiazole-4-carboxamido)cyclohexylcarbamoyl)pyridin-2-yloxy)biphenyl-4-yl)ethyl)piperazine-1-carboxylate (0.147 g, 0.19 mmol) in dichloromethane (1 mL). After stirring for 1 h at RT, the reaction mixture was diluted with dichloromethane (10 mL) and neutralised by addition of saturated sodium hydrogen carbonate solution. The layers were separated and aqueous layer extracted with further dichloromethane. The combined organic extracts were washed with water and saturated brine, and evaporated to afford crude product. The crude product was purified by preparative HPLC on a Gemini-NX column using a 95-5% gradient of aqueous 0.1% TFA in methanol as eluent. The fractions containing the desired compound were evaporated to dryness to afford the title compound as a white solid. Yield: 18 mg
$^1$H NMR (400 MHz, CD$_3$OD) δ 8.47 (d, J=7.1 Hz, 1H), 8.12 (d, J=3.1 Hz, 1H), 8.06 (dd, J=7.9, 3.1 Hz, 1H), 7.96 (s, 1H), 7.55-7.47 (m, 4H), 7.42-7.40 (m, 1H), 7.29 (d, J=8.2 Hz, 2H), 7.17-7.14 (m, 1H), 4.15-4.10 (m, 1H), 3.99-3.94 (m, 1H), 3.43-3.39 (m, 4H), 3.25-3.21 (m, 4H), 3.14-3.10 (m, 2H), 3.00-2.95 (m, 2H), 2.61 (s, 3H), 1.88-1.67 (m, 8H).
MS: [M+H]+=643 (calc=643) (MultiMode+)

EXAMPLE 178

N-((1s,4s)-4-(5-Fluoro-2-(4'-((4-(2-(isopropylamino)-2-oxoethyl)piperazin-1-yl)methyl)-2'-(morpholinomethyl)biphenyl-3-yloxy)nicotinamido)cyclohexyl)-5,7-dimethylpyrazolo[1,5-a]pyrimidine-3-carboxamide

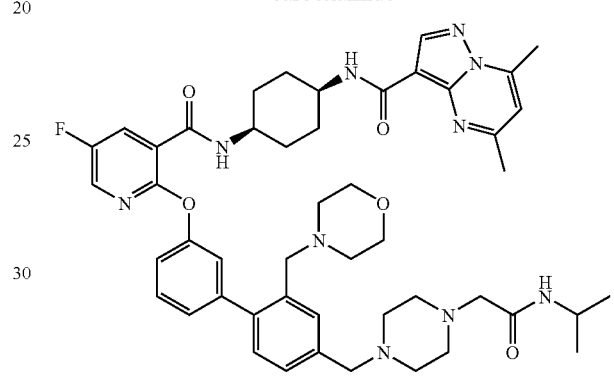

Step (a) tert-Butyl (1s,4s)-4-(5-fluoro-2-(4'-((4-(2-(isopropylamino)-2-oxoethyl)piperazin-1-yl)methyl)-2'-(morpholinomethyl)biphenyl-3-yloxy)nicotinamido)cyclohexylcarbamate To a stirred solution of tert-butyl (1s,4s)-4-(5-fluoro-2-(4'-formyl-2'-(morpholinomethyl)biphenyl-3-yloxy)nicotinamido)cyclohexylcarbamate (0.800 g, 1.26 mmol) in dichloromethane (8 mL) was added N-isopropyl-2-(piperazin-1-yl) acetamide (0.468 g, 2.53 mmol) and acetic acid (0.145 mL, 2.53 mmol). The reaction mixture was stirred at RT for 5 min. Sodium triacetoxyborohydride (0.536 g, 2.53 mmol) was added and the reaction mixture stirred at RT for 1 h. The reaction mixture was diluted with dichloromethane and washed with saturated sodium hydrogen carbonate and saturated brine. The organic was dried over magnesium sulfate, filtered and evaporated to afford the sub-title compound. Yield: 0.781 g
MS: [M+H]+=802 (calc=802) (MultiMode+)

Step (b) N-((1s,4s)-4-Aminocyclohexyl)-5-fluoro-2-(4'-((4-(2-(isopropylamino)-2-oxoethyl)piperazin-1-yl)methyl)-2'-(morpholinomethyl)biphenyl-3-yloxy) nicotinamide To a stirred solution of tert-butyl (1s,4s)-4-(5-fluoro-2-(4'-((4-(2-(isopropylamino)-2-oxoethyl)piperazin-1-yl)methyl)-2'-(morpholinomethyl)biphenyl-3-yloxy)nicotinamido)cyclohexylcarbamate (0.781 g, 0.97 mmol) in dichloromethane (7.5 mL) was added 4M HCl/dioxane (3.65 mL, 14.61 mmol). The reaction mixture was stirred at RT for 1 h then concentrated to give the sub-title compound as the hydrochloride salt. Yield: 0.800 g
MS: [M+H]+=702 (calc=702) (MultiMode+)

Step (c) N-((1s,4s)-4-(5-Fluoro-2-(4'-((4-(2-(isopropylamino)-2-oxoethyl)piperazin-1-yl)methyl)-2'-(morpholinomethyl)biphenyl-3-yloxy)nicotinamido)cyclohexyl)-5,7-dimethylpyrazolo[1,5-a]pyrimidine-3-carboxamide To a stirred solution of N-((1s,4s)-4-aminocyclohexyl)-5-fluoro-2-(4'-((4-(2-(isopropylamino)-2-oxoethyl)piperazin-1-yl)methyl)-2'-(morpholinomethyl)biphenyl-3-yloxy)nicotinamide hydrochloride (0.200 g, 0.19 mmol) in DMF (2 mL) was added 5,7-dimethylpyrazolo[1,5-a]pyrimidine-3-carboxylic acid (0.040 g, 0.21 mmol) and DIPEA (0.234 mL, 1.34 mmol). HATU (0.087 g, 0.23 mmol) was added and the reaction mixture stirred at RT overnight. The reaction mixture was acidified to pH4 using 2M HCl and purified by preparative HPLC on a Waters X-Bridge column using a 95-0% gradient of aqueous 0.2% TFA in acetonitrile as eluent. The fractions containing the desired compound were evaporated to dryness to afford the title compound as a white solid. Yield: 36 mg $^1$H NMR (400 MHz, CD$_3$OD) δ 8.52 (d, J=6.8 Hz, 1H), 8.48 (s, 1H), 8.13 (d, J=3.8 Hz, 1H), 8.02 (dd, J=7.5, 3.0 Hz, 1H), 7.74 (s, 1H), 7.55-7.50 (m, 2H), 7.35 (d, J=8.3 Hz, 1H), 7.29 (dd, J=8.3, 2.3 Hz, 1H), 7.18-7.13 (m, 2H), 6.97 (s, 1H), 4.41 (s, 2H), 4.17-4.11 (m, 1H), 4.10-3.96 (m, 7H), 3.80-3.64 (m, 2H), 3.51 (s, 2H), 3.17-3.01 (m, 8H), 2.77 (s, 3H), 2.53 (s, 3H), 1.99-1.75 (m, 8H), 1.15 (d, J=6.8 Hz, 6H).
MS: [M+H]+=875 (calc=875) (MultiMode+)

EXAMPLE 179

N-((1s,4s)-4-(5-Fluoro-2-(4'-((4-(2-hydroxyethyl)-1,4-diazepan-1-yl)methyl)-2'-(((S)-3-methylmorpholino)methyl)biphenyl-3-yloxy)nicotinamido)cyclohexyl)-5,7-dimethylpyrazolo[1,5-a]pyrimidine-2-carboxamide

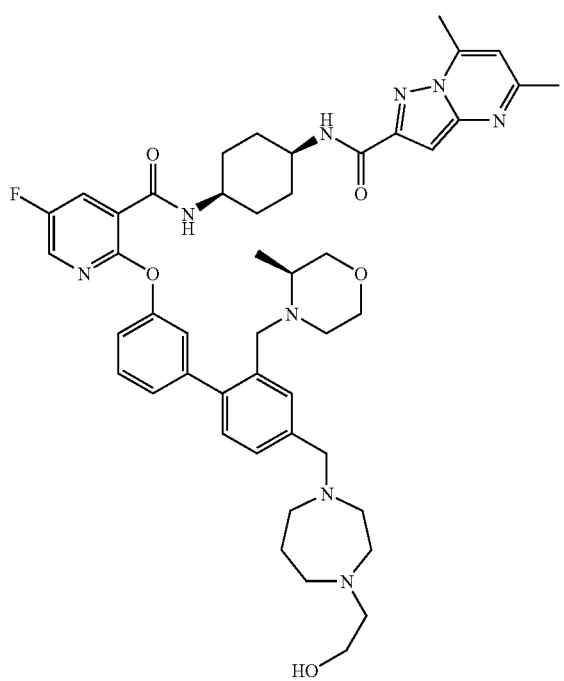

Step (a) tert-Butyl (1s,4s)-4-(5-fluoro-2-(4'-formyl-2'-(((S)-3-methylmorpholino)methyl)biphenyl-3-yloxy)nicotinamido)cyclohexylcarbamate tert-Butyl (1s,4s)-4-(5-fluoro-2-(3-(4,4,5,5-tetramethyl-1,3,2-dioxaborolan-2-yl)phenoxy)nicotinamido)cyclohexylcarbamate (1.526 g, 2.75 mmol), (S)-4-bromo-3-((3-methylmorpholino)methyl)benzaldehyde (0.819 g, 2.75 mmol) and sodium carbonate (2.359 g, 8.24 mmol) were added to THF (18 ml) and degassed water (9 ml) under nitrogen. Tetrakis(triphenylphosphine)palladium(0) (0.063 g, 0.05 mmol) was then added and the reaction mixture was heated at reflux overnight. The mixture was poured onto water and extracted into EtOAc (×2). The extractions were combined, washed with brine, dried (MgSO$_4$) and evaporated to give a light brown oil. The crude material was purified by flash silica chromatography (Biotage column) (eluant=60/40 EtOAc/hexane) to give a light brown oil. Yield: 1.42 g
MS: [M+H]+=647 (calc=647) (MultiMode+)

Step (b) tert-Butyl (1s,4s)-4-(5-fluoro-2-(4'-((4-(2-hydroxyethyl)-1,4-diazepan-1-yl)methyl)-2'-(((S)-3-methylmorpholino)methyl)biphenyl-3-yloxy)nicotinamido)cyclohexylcarbamate To a solution of tert-butyl (1s,4s)-4-(5-fluoro-2-(4'-formyl-2'-(((S)-3-methylmorpholino)methyl)biphenyl-3-yloxy)nicotinamido)cyclohexylcarbamate (0.7 g, 1.08 mmol) in dichloromethane (10.5 ml) was added 2-(1,4-diazepan-1-yl)ethanol (0.283 ml, 2.17 mmol). The mixture was allowed to stir at RT for 40 minutes before sodium triacetoxyborohydride (0.573 g, 2.71 mmol) was added. The reaction was stirred at RT for 2 hours. The mixture was diluted with dichloromethane and washed with saturated NaHCO$_3$(aq), dried (MgSO$_4$) and evaporated to give a pale yellow foam. This was purified by flash silica chromatography (Biotage column) (eluent=4% 7M ammonia in methanol/DCM) to give the sub-title compound as a white solid. Yield: 0.710 g
MS: [M+H]+=775 (calc=775) (MultiMode+)

Step (c) N-((1s,4s)-4-Aminocyclohexyl)-5-fluoro-2-(4'-((4-(2-hydroxyethyl)-1,4-diazepan-1-yl)methyl)-2'-(((S)-3-methylmorpholino)methyl)biphenyl-3-yloxy)nicotinamide To a solution of tert-butyl (1s,4s)-4-(5-fluoro-2-(4'-((4-(2-hydroxyethyl)-1,4-diazepan-1-yl)methyl)-2'-(((S)-3-methylmorpholino)methyl)biphenyl-3-yloxy)nicotinamido)cyclohexylcarbamate (0.65 g, 0.84 mmol) in DCM (6 ml) was added 4.0 M hydrogen chloride in dioxane (2.1 ml, 8.39 mmol). The mixture was stirred at RT for 2 hours. The mixture was evaporated to dryness to give the sub-title compound hydrochloride salt as a white solid. Yield: 0.69 g
MS: [M+H]+=675 (calc=675) (MultiMode+)

Step (d) N-((1s,4s)-4-(5-Fluoro-2-(4'-((4-(2-hydroxyethyl)-1,4-diazepan-1-yl)methyl)-2'-(((S)-3-methylmorpholino)methyl)biphenyl-3-yloxy)nicotinamido)cyclohexyl)-5,7-dimethylpyrazolo[1,5-a]pyrimidine-2-carboxamide To a suspension of N-((1s,4s)-4-aminocyclohexyl)-5-fluoro-2-(4'-((4-(2-hydroxyethyl)-1,4-diazepan-1-yl)methyl)-2'-(((S)-3-methylmorpholino)methyl)biphenyl-3-yloxy)nicotinamide hydrochloride (200 mg, 0.24 mmol) in acetonitrile (2.74 ml) was added 5,7-dimethylpyrazolo[1,5-a]pyrimidine-2-carboxylic acid (48.9 mg, 0.26 mmol) and triethylamine (0.340 ml, 2.44 mmol). 1-Propanephosphonic acid cyclic anhydride, 1.57M solution in THF (0.171 ml, 0.27 mmol) was then added and the mixture stirred at RT for 2 hours. The mixture was evaporated to dryness and the residue dissolved in DCM (150 ml) and washed with saturated NaHCO$_3$(aq), brine, dried (MgSO$_4$) and evaporated to give a foam. The crude product was purified by preparative HPLC using a 95-5% gradient of aqueous 0.2% ammonia in methanol as eluent to give the title compound as a white solid. Yield: 33 mg $^1$H NMR (400 MHz, CDCl$_3$) δ 8.11-8.03 (m, 2H), 7.48-7.37 (m, 2H), 7.22-7.14 (m, 3H), 7.12-7.07 (m, 2H), 6.88 (d, J=6.9 Hz, 2H), 4.20-4.09 (m, 1H), 4.06-3.96 (m, 1H), 3.89 (d, J=13.1 Hz, 1H), 3.63-3.54 (m, 4H), 3.52-3.31 (m, 9H), 3.31-3.26 (m, 2H) 3.09-2.96 (m, 2H), 2.81-2.70 (m, 4H) 2.69-2.59 (m, 4H), 2.53 (s, 3H), 2.44-2.36 (m, 1H), 2.23-2.11 (m, 1H), 1.96-1.68 (m, 10H), 0.75 (d, J=6.2 Hz, 3H).

MS: [M+H]+=848 (calc=848) (MultiMode+)

EXAMPLE 180

N-((1s,4s)-4-(5-Fluoro-2-(4'-((4-(2-hydroxyethyl)-1,4-diazepan-1-yl)methyl)-2'-(((S)-3-methylmorpholino)methyl)biphenyl-3-yloxy)nicotinamido)cyclohexyl)-1H-benzo[d]imidazole-4-carboxamide

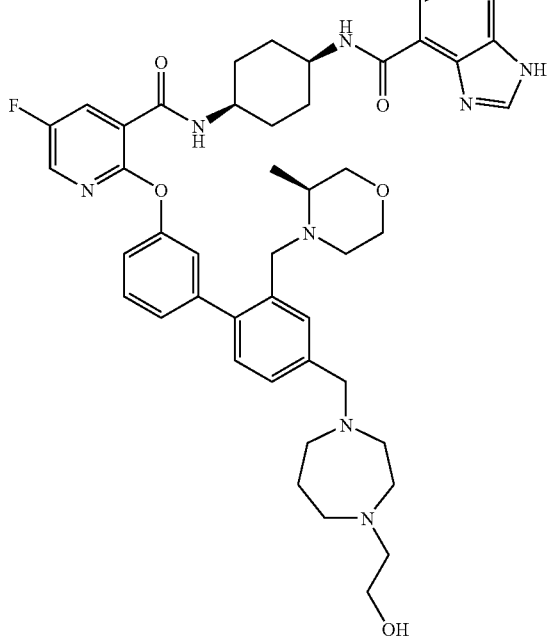

To a solution of N-((1s,4s)-4-aminocyclohexyl)-5-fluoro-2-(4'-((4-(2-hydroxyethyl)-1,4-diazepan-1-yl)methyl)-2'-(((S)-3-methylmorpholino)methyl)biphenyl-3-yloxy)nicotinamide (200 mg, 0.24 mmol) in dry DMF (5 mL) under nitrogen was added DIPEA (0.161 mL, 0.97 mmol) at RT. The solution was stirred until homogeneous. To this solution was added dropwise a solution of 1H-benzo[d]imidazole-4-carboxylic acid (39.5 mg, 0.24 mmol) and 1,1'-carbonyldiimidazole (39.5 mg, 0.24 mmol) in dry DMF (5 mL) under nitrogen which had been allowed to stir at 40° C. for 1 hour. The reaction mixture was allowed to stir at 50° C. overnight. The mixture was evaporated to dryness and the residue dissolved in DCM (100 ml) and washed with saturated NaHCO$_3$ (aq), brine, dried (MgSO$_4$) and evaporated to give a yellow oil. The crude product was purified by preparative HPLC using a 95-5% gradient of aqueous 0.2% ammonia in methanol as eluent to give the title compound as a white solid. Yield: 22 mg $^1$H NMR (400 MHz, CDCl$_3$) δ 8.12-8.06 (m, 2H), 7.94-7.82 (m, 2H), 7.70 (d, J=7.9 Hz, 1H), 7.43 (d, J=7.9 Hz, 1H), 7.38-7.31 (m, 2H), 7.24-7.10 (m, 5H), 7.07 (d, J=7.9 Hz, 1H), 4.25-4.18 (m, 1H), 4.16-4.09 (m, 1H), 3.82 (d, J=13.9 Hz, 1H), 3.64-3.58 (m, 5H), 3.49-3.43 (m, 1H), 3.40-3.31 (m, 1H) 3.03-2.93 (m, 2H), 2.81-2.73 (m, 5H) 2.72-2.62 (m, 7H), 2.39-2.31 (m, 1H), 2.12-2.03 (m, 1H), 1.98-1.74 (m, 10H), 0.66 (d, J=6.2 Hz, 3H).

MS: [M+H]+=819 (calc=819) (MultiMode+)

EXAMPLE 181

N-((1s,4s)-4-(1,5-Dimethyl-1H-pyrazole-3-carboxamido)cyclohexyl)-5-fluoro-2-(2'-(morpholinomethyl)-4'-((4-propylpiperazin-1-yl)methyl)biphenyl-3-yloxy)nicotinamide

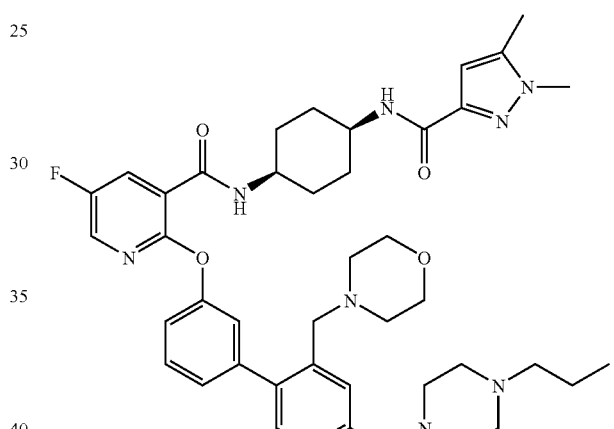

Step (a) tert-Butyl (1s,4s)-4-(5-fluoro-2-(2'-(morpholinomethyl)-4'-((4-propylpiperazin-1-yl)methyl)biphenyl-3-yloxy)nicotinamido)cyclohexylcarbamate A solution of 1-propylpiperazine dihydrobromide (183 mg, 0.63 mmol) in methanol (2 ml) and water (1 ml) was filtered through a PL-HCO3 MP-resin cartridge. The resin was washed with methanol (2×1 ml) and the eluents were evaporated. The residue was treated with a solution of tert-butyl (1s,4s)-4-(5-fluoro-2-(4'-formyl-2'-(morpholinomethyl)biphenyl-3-yloxy)nicotinamido)cyclohexylcarbamate (200 mg, 0.32 mmol) in dichloromethane (6 mL), and acetic acid (0.018 mL, 0.32 mmol) followed by sodium triacetoxyborohydride (134 mg, 0.63 mmol) and stirred overnight. The mixture was treated with more 1-propylpiperazine free base (from 1-propylpiperazine dihydrobromide, prepared as above, 183 mg, 0.63 mmol) followed by sodium triacetoxyborohydride (134 mg, 0.63 mmol) and stirred over the weekend. The mixture was treated with 1-propylpiperazine dihydrobromide (183 mg, 0.63 mmol) followed by DIPEA (0.221 mL, 1.26 mmol), stirred for 1 h, treated with sodium triacetoxyborohydride (134 mg, 0.63 mmol) and stirred for 4 h. The mixture was diluted with dichloromethane, washed with 1M aqueous sodium bicarbonate solution followed by brine, was dried (Na$_2$SO$_4$) and evaporated to give the sub-title compound as a white foam. Yield: 0.200 g

[M+H]+=745 (calc=745) (MultiMode+)

Step (b) N-((1s,4s)-4-Aminocyclohexyl)-5-fluoro-2-(2'-(morpholinomethyl)-4'-((4-propylpiperazin-1-yl)methyl)biphenyl-3-yloxy)nicotinamide A stirred solution of tert-butyl (1s,4s)-4-(5-fluoro-2-(2'-(morpholinomethyl)-4'-((4-propylpiperazin-1-yl)methyl)biphenyl-3-yloxy)nicotinamido)cyclohexylcarbamate (200 mg, 0.27 mmol) in dichloromethane (2 mL) was treated with HCl 4M in dioxane (4 mL, 131.65 mmol) and stirred for 1 h. The mixture was evaporated to give the sub-title compound hydrochloride as a white solid. Yield: 0.247 g MS: [M+H]+=645 (calc=645) (MultiMode+)

Step (c) N-((1s,4s)-4-(1,5-Dimethyl-1H-pyrazole-3-carboxamido)cyclohexyl)-5-fluoro-2-(2'-(morpholinomethyl)-4'-((4-propylpiperazin-1-yl)methyl)biphenyl-3-yloxy)nicotinamide A stirred solution of N-((1s,4s)-4-aminocyclohexyl)-5-fluoro-2-(2'-(morpholinomethyl)-4'-((4-propylpiperazin-1-yl)methyl)biphenyl-3-yloxy)nicotinamide hydrochloride (174 mg, 0.27 mmol), 1,5-dimethyl-1H-pyrazole-3-carboxylic acid (37.8 mg, 0.27 mmol) and DIPEA (0.330 mL, 1.89 mmol) in DMF (10 mL) was treated with HATU (108 mg, 0.28 mmol) and stirred for 2 h. The solution was evaporated to remove most of the DMF and the residue was taken up in dichloromethane, was washed with water (3×), dried ($Na_2SO_4$) and evaporated. The residue was purified by reversed phase preparative HPLC on a Gemini-NX column, using a gradient of methanol in 0.1% aqueous TFA solution as eluent to give a gum. The gum was taken up in a little dichloromethane and methanol and diluted with isohexane to precipitate a semi-solid. The solvents were evaporated and the residue was triturated with ether and filtered. The solid was washed with ether and dried to give the title compound as a white powder. Yield: 46 mg $^1$H NMR (400 MHz, DMSO) δ 10.32-10.16 (m, 1H), 9.63-9.47 (m, 1H), 8.36 (d, J=6.9 Hz, 1H), 8.26 (d, J=3.1 Hz, 1H), 8.04-8.00 (m, 2H), 7.65-7.59 (m, 1H), 7.54 (t, J=7.9 Hz, 1H), 7.48-7.42 (m, 1H), 7.38-7.32 (m, 1H), 7.28 (d, J=7.9 Hz, 1H), 7.19-7.14 (m, 2H), 6.59 (s, 1H), 4.45-4.21 (m, 1H), 3.96-3.89 (m, 1H), 3.92 (s, 3H), 3.82-3.42 (m, 7H), 3.25-2.63 (m, 7H), 2.55-2.35 (m, 8H), 2.14 (s, 3H), 1.84-1.59 (m, 10H), 0.91 (t, J=7.4 Hz, 3H).

MS: [M+H]+=767 (calc=767) (MultiMode+)

EXAMPLE 182

N-((1s,4s)-4-(5-Fluoro-2-(4'-((4-(2-hydroxyethyl)-1,4-diazepan-1-yl)methyl)-2'-(thiomorpholinomethyl)biphenyl-3-yloxy)nicotinamido)cyclohexyl)-5,7-dimethylpyrazolo[1,5-a]pyrimidine-3-carboxamide

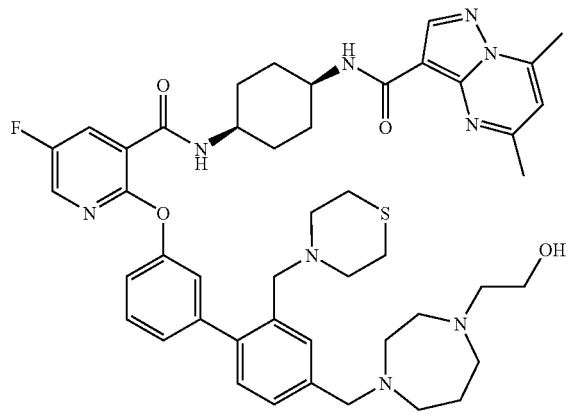

Step (a) tert-butyl (1s,4s)-4-(5-fluoro-2-(4'-formyl-2'-(thiomorpholinomethyl)biphenyl-3-yloxy)nicotinamido)cyclohexylcarbamate To a solution/suspension of tert-butyl (1s,4s)-4-(5-fluoro-2-(3-(4,4,5,5-tetramethyl-1,3,2-dioxaborolan-2-yl)phenoxy)nicotinamido)cyclohexylcarbamate (1 g, 1.80 mmol), 4-bromo-3-(thiomorpholinomethyl)benzaldehyde (0.540 g, 1.80 mmol) and sodium carbonate (0.572 g, 5.40 mmol) in THF (12.00 ml) and water was added tetrakis(triphenylphosphine)palladium(0) (0.104 g, 0.09 mmol). The mixture was heated to 80° C. overnight. The mixture was poured into water and the organics extracted into EtOAc (×3). The extractions were combined, dried ($MgSO_4$) and evaporated to give a crude product. This was purified using column chromatography (eluent=1:1 hexane:EtOAc) to give the sub-title compound as an oil. Yield: 0.745 g MS: [M+H]+=649 (calc=649) (MultiMode+)

Step (b) tert-Butyl (1s,4s)-4-(5-fluoro-2-(4'-((4-(2-hydroxyethyl)-1,4-diazepan-1-yl)methyl)-2'-(thiomorpholinomethyl)biphenyl-3-yloxy)nicotinamido)cyclohexylcarbamate To a solution of tert-butyl (1s,4s)-4-(5-fluoro-2-(4'-formyl-2'-(thiomorpholinomethyl)biphenyl-3-yloxy)nicotinamido)cyclohexylcarbamate (0.740 g, 1.14 mmol) in DCM (10 mL) was added 2-(1,4-diazepan-1-yl)ethanol (0.298 mL, 2.28 mmol). The mixture was stirred at RT for 20 minutes before sodium triacetoxyborohydride (0.604 g, 2.85 mmol) was added. After 40 minutes the mixture was diluted with DCM, washed with saturated $NaHCO_3$(aq), dried ($MgSO_4$) and purified using column chromatography (eluent=3% 7N $NH_3$ in methanol/DCM). The appropriate fractions were combined and evaporated to give the sub-title compound as an oil. Yield: 0.5 g MS: [M+H]+=777 (calc=777) (MultiMode+)

Step (c) N-((1s,4s)-4-Aminocyclohexyl)-5-fluoro-2-(4'-((4-(2-hydroxyethyl)-1,4-diazepan-1-yl)methyl)-2'-(thiomorpholinomethyl)biphenyl-3-yloxy)nicotinamide To a solution of tert-butyl (1s,4s)-4-(5-fluoro-2-(4'-((4-(2-hydroxyethyl)-1,4-diazepan-1-yl)methyl)-2'-(thiomorpholinomethyl)biphenyl-3-yloxy)nicotinamido)cyclohexylcarbamate (0.5 g, 0.64 mmol) in DCM (3 mL) was added TFA (3 ml, 38.94 mmol). The mixture was stirred at RT for 40 minutes. The mixture was poured into saturated $NaHCO_3$(aq) and the organics extracted into DCM (×3). The dichloromethane was dried ($MgSO_4$) and evaporated to give the sub-title compound as a foam. Yield: 0.375 g MS: [M+H]+=677 (calc=677) (MultiMode+)

Step (d) N-((1s,4s)-4-(5-Fluoro-2-(4'-((4-(2-hydroxyethyl)-1,4-diazepan-1-yl)methyl)-2'-(thiomorpholinomethyl)biphenyl-3-yloxy)nicotinamido)cyclohexyl)-5,7-dimethylpyrazolo[1,5-a]pyrimidine-3-carboxamide To a solution of N-((1s,4s)-4-aminocyclohexyl)-5-fluoro-2-(4'-((4-(2-hydroxyethyl)-1,4-diazepan-1-yl)methyl)-2'-(thiomorpholinomethyl)biphenyl-3-yloxy)nicotinamide (150 mg, 0.22 mmol) in acetonitrile (5 mL) was added 5,7-dimethylpyrazolo[1,5-a]pyrimidine-3-carboxylic acid (42.4 mg, 0.22 mmol) and triethylamine (0.309 mL, 2.22 mmol). To this mixture was then added 1-propanephosphonic acid cyclic anhydride, 1.57M solution in THF (0.148 mL, 0.23 mmol) and the reaction left to stir for 10 minutes. The mixture was diluted with DCM and then washed with saturated $NaHCO_3$ (aq), dried ($MgSO_4$) and evaporated to give a crude product.

This was purified using reverse phase preparative chromatography (eluent=NH$_3$(aq)/methanol), the appropriate fractions were combined and evaporated to give an oil. On trituration with DCM/hexane mixtures this gave a solid which was dried overnight at 40° C. under vacuum to afford the title compound. Yield: 43 mg $^1$H NMR (400 MHz, CD$_3$OD) δ 8.13 (d, J=3.1 Hz, 1H), 8.08 (dd, J=7.9, 3.1 Hz, 1H), 7.44 (t, J=7.8 Hz, 1H), 7.34 (s, 1H), 7.26 (t, J=1.9 Hz, 1H), 7.18 (dd, J=7.9, 2.1 Hz, 2H), 7.13 (s, 2H), 6.91-6.87 (m, 2H), 4.18-4.13 (m, 1H), 4.04-3.98 (m, 1H), 3.62-3.56 (m, 4H), 3.37 (s, 2H), 2.79-2.73 (m, 4H), 2.69-2.62 (m, 9H), 2.54 (s, 3H), 2.46-2.43 (m, 4H), 2.41-2.38 (m, 4H), 1.94-1.72 (m, 10H).

MS: [M+H]+=850 (calc=850) (MultiMode+)

EXAMPLE 183

N-((1s,4s)-4-(1,5-Dimethyl-1H-pyrazole-3-carboxamido)cyclohexyl)-5-fluoro-2-(4'-((4-isopropylpiperazin-1-yl)methyl)-2'-(morpholinomethyl)biphenyl-3-yloxy)nicotinamide

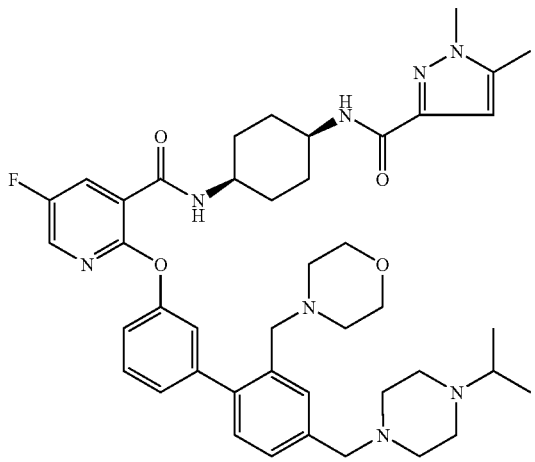

Step (a) tert-Butyl (1s,4s)-4-(5-fluoro-2-(4'-((4-isopropylpiperazin-1-yl)methyl)-2'-(morpholinomethyl)biphenyl-3-yloxy)nicotinamido)cyclohexylcarbamate A stirred solution of tert-butyl (1s,4s)-4-(5-fluoro-2-(4'-formyl-2'-(morpholinomethyl)biphenyl-3-yloxy)nicotinamido)cyclohexylcarbamate (200 mg, 0.32 mmol), 1-isopropylpiperazine (81 mg, 0.63 mmol) and acetic acid (0.018 mL, 0.32 mmol) in dichloromethane (6 mL) was treated with sodium triacetoxyborohydride (134 mg, 0.63 mmol) and stirred overnight. The mixture was diluted with dichloromethane, washed with saturated aqueous sodium bicarbonate solution followed by brine, was dried (Na$_2$SO$_4$) and evaporated to give the sub-title compound as a pale yellow glassy oil. Yield: 0.208 g MS: [M+H]+=745 (calc=745) (APCI)+ve Step (b) N-((1s,4s)-4-Aminocyclohexyl)-5-fluoro-2-(4'-((4-isopropylpiperazin-1-yl)methyl)-2'-(morpholinomethyl)biphenyl-3-yloxy)nicotinamide A stirred solution tert-butyl (1s,4s)-4-(5-fluoro-2-(4'-((4-isopropylpiperazin-1-yl)methyl)-2'-(morpholinomethyl)biphenyl-3-yloxy)nicotinamido)cyclohexylcarbamate (208 mg, 0.28 mmol) in dichloromethane (2 mL) was treated with HCl 4M in dioxane (4 mL, 16.00 mmol) and stirred for 1 h.

The mixture was evaporated to give the sub-title compound hydrochloride as a white solid. Yield: 0.271 g MS: [M+H]+=645 (calc=645) (MultiMode+)

Step (c) N-((1s,4s)-4-(1,5-Dimethyl-1H-pyrazole-3-carboxamido)cyclohexyl)-5-fluoro-2-(4'-((4-isopropylpiperazin-1-yl)methyl)-2'-(morpholinomethyl)biphenyl-3-yloxy)nicotinamide A stirred solution of N-((1s,4s)-4-aminocyclohexyl)-5-fluoro-2-(4'-((4-isopropylpiperazin-1-yl)methyl)-2'-(morpholinomethyl)biphenyl-3-yloxy)nicotinamide hydrochloride (221 mg, 0.28 mmol), 1,5-dimethyl-1H-pyrazole-3-carboxylic acid (39.2 mg, 0.28 mmol) and DIPEA (0.342 mL, 1.96 mmol) in DMF (10 mL) was treated with HATU (112 mg, 0.29 mmol) and stirred overnight. The solution was evaporated to remove most of the DMF and the residue was taken up in dichloromethane, was washed with water (3×), dried (Na$_2$SO$_4$) and evaporated. The residue was purified by reversed phase preparative HPLC on a Sunfire™ column, using a gradient of methanol in 0.1% aqueous TFA solution as eluent to give the title compound as a white solid. Yield: 110 mg $^1$H NMR (400 MHz, DMSO) δ 10.18-9.97 (m, 1H), 9.44-9.23 (m, 1H), 8.36 (d, J=6.4 Hz, 1H), 8.27 (d, J=3.1 Hz, 1H), 8.04-8.00 (m, 2H), 7.65-7.61 (m, 1H), 7.54 (t, J=7.9 Hz, 1H), 7.50-7.45 (m, 1H), 7.36 (d, J=7.9 Hz, 1H), 7.29 (d, J=8.2 Hz, 1H), 7.22-7.14 (m, 2H), 6.59 (s, 1H), 4.36-3.59 (m, 20H), 3.51-3.38 (m, 2H), 3.21-2.94 (m, 4H), 2.82-2.64 (m, 1H), 2.52-2.38 (m, 2H), 2.14 (s, 3H), 1.84-1.60 (m, 8H), 1.25 (d, J=6.4 Hz, 3H).

MS: [M+H]+=767 (calc=767) (MultiMode+)

EXAMPLE 184

N-((1s,4s)-4-(5-Fluoro-2-(4'-(2-(piperazin-1-yl)ethyl)biphenyl-3-yloxy)nicotinamido)cyclohexyl)-4-methylthiazole-2-carboxamide

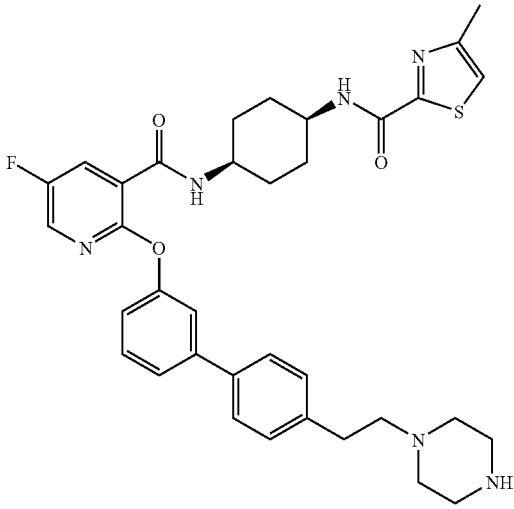

Step (a) Benzyl 4-(2-(3'-(5-fluoro-3-((1s,4s)-4-(4-methylthiazole-2-carboxamido)cyclohexylcarbamoyl)pyridin-2-yloxy)biphenyl-4-yl)ethyl)piperazine-1-carboxylate 4-Methylthiazole-2-carboxylic acid (0.041 g, 0.28 mmol) was dissolved in acetonitrile (1 mL) then DIPEA (0.066 mL, 0.38 mmol) and HATU (HATU) (0.108 g, 0.28 mmol) added and the mixture stirred for 20 minutes. It was then added to a stirred solution of benzyl 4-(2-(3'-(3-((1s,4s)-4-aminocyclohexylcarbamoyl)-5-fluoropyridin-2-yloxy)biphenyl-4-yl)ethyl)piperazine-1-carboxylate (0.123 g, 0.19 mmol) in acetonitrile (1.000 mL). The reaction mixture was stirred overnight then diluted with EtOAc and washed with water and saturated brine. The organic was dried over sodium sulfate, filtered and evaporated to afford the sub-title compound. Yield: 0.147 g MS: [M+H]+=777 (calc=777) (MultiMode+)

Step (b) N-((1s,4s)-4-(5-fluoro-2-(4'-(2-(piperazin-1-yl)ethyl)biphenyl-3-yloxy)nicotinamido)cyclohexyl)-4-methylthiazole-2-carboxamide Hydrobromic acid (33% in acetic acid) (1 mL, 5.79 mmol) was added slowly to a solution of benzyl 4-(2-(3'-(5-fluoro-3-((1s,4s)-4-(4-methylthiazole-2-carboxamido)cyclohexylcarbamoyl)pyridin-2-yloxy)biphenyl-4-yl)ethyl)piperazine-1-carboxylate (0.147 g, 0.19 mmol) in dichloromethane (1 mL). After stirring for 1 h at RT, the reaction mixture was diluted with dichloromethane (10 mL) and neutralised by addition of saturated sodium hydrogen carbonate solution. The layers were separated and the aqueous layer extracted with further dichloromethane. The combined organic extracts were washed with water and saturated brine, and evaporated. To a solution of the residue in acetic acid (1.2 mL) was added Pd/C (0.020 g, 0.19 mmol). The reaction mixture was stirred at RT under 4 bar hydrogen for 24 h then filtered and the filtrate concentrated to give crude product. This was purified by preparative HPLC on a Phenomenex Gemini column using a 75-05% gradient of aqueous 0.2% TFA in methanol as eluent. The fractions containing the desired compound were evaporated to dryness to afford the title compound as a white solid. Yield: 7 mg $^1$H NMR (400 MHz, CD$_3$OD) δ 8.47 (d, J=7.3 Hz, 1H), 8.12 (d, J=4.0 Hz, 1H), 8.07 (dd, J=8.1, 4.0 Hz, 1H), 7.53 (d, J=8.1 Hz, 2H), 7.48-7.46 (m, 2H), 7.42-7.40 (m, 1H), 7.36 (s, 1H), 7.27 (d, J=8.1 Hz, 2H), 7.17-7.13 (m, 1H), 4.17-4.09 (m, 1H), 3.99-3.93 (m, 1H), 3.34 (t, J=5.7 Hz, 4H), 3.09-3.03 (m, 4H), 2.99-2.89 (m, 4H), 2.39 (s, 3H), 1.91-1.68 (m, 8H).

MS: [M+H]+=643 (calc=643) (MultiMode+)

EXAMPLE 185

N-((1s,4s)-4-(5-Fluoro-2-(4'-((4-methyl-1,4-diazepan-1-yl)methyl)-2'-(morpholinomethyl)biphenyl-3-yloxy)nicotinamido)cyclohexyl)-5-methylimidazo[1,2-a]pyridine-2-carboxamide

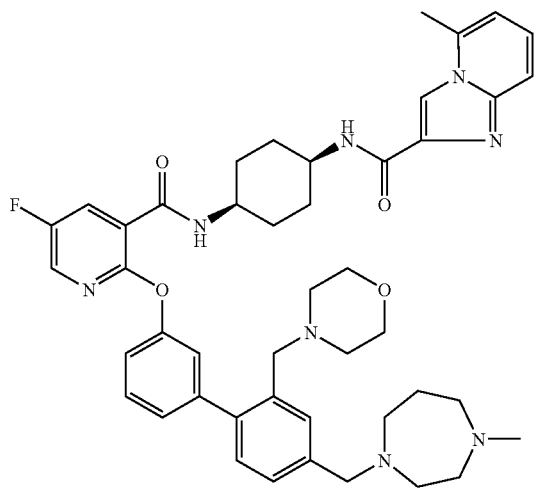

Step (a) tert-Butyl (1s,4s)-4-(5-fluoro-2-(4'-((4-methyl-1,4-diazepan-1-yl)methyl)-2'-(morpholinomethyl)biphenyl-3-yloxy)nicotinamido)cyclohexylcarbamate A stirred solution of tert-butyl (1s,4s)-4-(5-fluoro-2-(4'-formyl-2'-(morpholinomethyl)biphenyl-3-yloxy)nicotinamido)cyclohexylcarbamate (200 mg, 0.32 mmol), 1-methyl-1,4-diazepane (72.2 mg, 0.63 mmol) and acetic acid (0.018 mL, 0.32 mmol) in dichloromethane (6 mL) was treated with sodium triacetoxyborohydride (134 mg, 0.63 mmol) and stirred overnight. The mixture was diluted with dichloromethane, washed with saturated aqueous sodium bicarbonate solution followed by brine, was dried (Na$_2$SO$_4$) and evaporated to give the sub-title compound as a white foam. Yield: 0.228 g MS: [M+H]+=731 (calc=731) (APCI)+ve Step (b) N-((1s,4s)-4-Aminocyclohexyl)-5-fluoro-2-(4'-((4-methyl-1,4-diazepan-1-yl)methyl)-2'-(morpholinomethyl)biphenyl-3-yloxy)nicotinamide A stirred solution of tert-butyl (1s,4s)-4-(5-fluoro-2-(4'-((4-methyl-1,4-diazepan-1-yl)methyl)-2'-(morpholinomethyl)biphenyl-3-yloxy)nicotinamido)cyclohexylcarbamate (228 mg, 0.31 mmol) in dichloromethane (2 mL) was treated with HCl 4M in dioxane (4 mL, 131.65 mmol) and stirred for 1 h. The mixture was evaporated to give the sub-title compound hydrochloride as a white solid. Yield: 0.341 g MS: [M+H]+=631 (calc=631) (APCI)+ve Step (c) N-((1s,4s)-4-(5-Fluoro-2-(4'-((4-methyl-1,4-diazepan-1-yl)methyl)-2'-(morpholinomethyl)biphenyl-3-yloxy)nicotinamido)cyclohexyl)-5-methylimidazo[1,2-a]pyridine-2-carboxamide A stirred solution of N-((1s,4s)-4-aminocyclohexyl)-5-fluoro-2-(4'-((4-methyl-1,4-diazepan-1-yl)methyl)-2'-(morpholinomethyl)biphenyl-3-yloxy)nicotinamide (241 mg, 0.31 mmol), 5-methylimidazo[1,2-a]pyridine-2-carboxylic acid (54.6 mg, 0.31 mmol) and DIPEA (0.379 mL, 2.17 mmol) in DMF (10 mL) was treated with HATU (124 mg, 0.33 mmol) and stirred overnight. The solution was evaporated to remove most of the DMF and the residue was taken up in dichloromethane, was washed with water (3×), dried (Na$_2$SO$_4$) and evaporated. The residue was purified by reversed phase preparative HPLC on a Sunfire™ column, using a gradient of methanol in 0.1% aqueous TFA solution as eluent to give the title compound as a white powder. Yield: 0.150 g $^1$H NMR (400 MHz, DMSO) δ 8.41-8.38 (m, 2H), 8.27 (d, J=3.1 Hz, 1H), 8.05 (dd, J=7.9, 3.1 Hz, 1H), 7.93 (d, J=7.7 Hz, 1H), 7.70-7.66 (m, 1H), 7.58-7.51 (m, 3H), 7.47-7.42 (m, 2H), 7.29 (d, J=7.9 Hz, 1H), 7.21-7.19 (m, 2H), 6.98 (d, J=6.9 Hz, 1H), 4.42-2.70 (m, 22H), 2.84 (s, 3H), 2.66 (s, 3H), 2.12-2.02 (m, 2H), 1.84-1.67 (m, 8H).

MS: [M+H]+=789 (calc=789) (MultiMode+)

EXAMPLE 186

N-((1s,4s)-4-(5-Fluoro-2-(4'-(2-(piperazin-1-yl)ethyl)biphenyl-3-yloxy)nicotinamido)cyclohexyl)quinoxaline-2-carboxamide

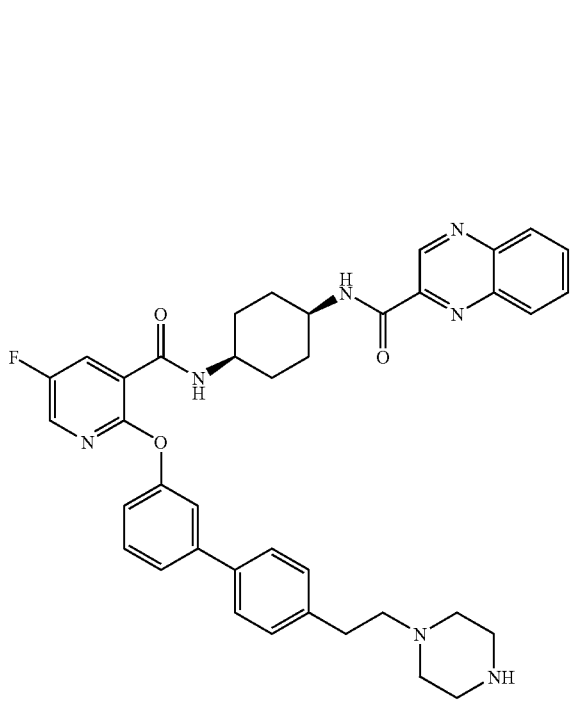

To a microwave tube was charged 2-(3'-(5-fluoro-3-((1s,4s)-4-(quinoxaline-2-carboxamido)cyclohexylcarbamoyl)pyridin-2-yloxy)biphenyl-4-yl)ethyl methanesulfonate (120 mg, 0.18 mmol), tert-butyl 1-piperazinecarboxylate (98 mg, 0.53 mmol) and acetonitrile (1 mL). The reaction was heated to 80° C. for 3 hours. The reaction mixture was evaporated to dryness before being dissolved in DCM (3 mL). To this was added TFA (3.67 mL, 47.91 mmol) and the reaction mixture was stirred overnight. The crude product was purified by HPLC to give the title compound as a white solid. Yield: 56 mg $^1$H NMR (400 MHz, CDCl$_3$) δ 9.37 (s, 1H), 8.16-8.03 (m, 3H), 7.98 (d, J=7.9 Hz, 1H), 7.94-7.80 (m, 2H), 7.51-7.37 (m, 5H), 7.14 (d, J=7.7 Hz, 3H), 4.22-4.10 (m, 1H), 4.08-3.94 (m, 1H), 3.61-3.42 (m, 8H), 3.27-3.20 (m, 2H), 3.01-2.90 (m, 2H), 2.04-1.69 (m, 8H).

MS: [M+H]+=674 (calc=674) (MultiMode+)

EXAMPLE 187

N-((1s,4s)-4-(5-Fluoro-2-(4'-(3-(piperazin-1-yl)propyl)biphenyl-3-yloxy)nicotinamido)cyclohexyl)-4-(hydroxymethyl)thiazole-2-carboxamide

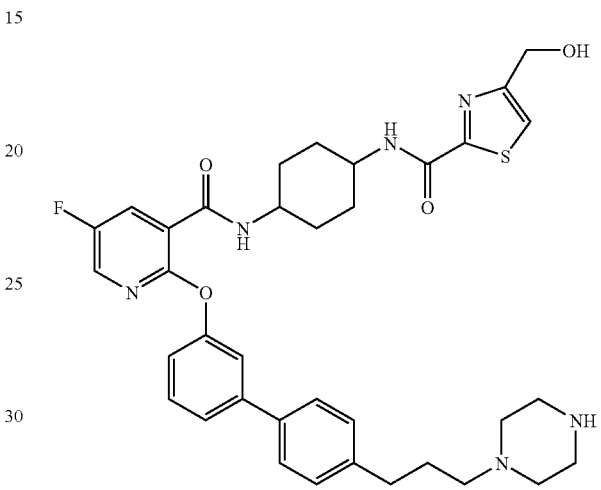

HATU (0.093 g, 0.24 mmol) was added to a solution of tert-butyl 4-(3-(3'-(3-(((1s,4s)-4-aminocyclohexylcarbamoyl)-5-fluoropyridin-2-yloxy)biphenyl-4-yl)propyl)piperazine 1-carboxylate (0.14 g, 0.22 mmol), 4-(hydroxymethyl)thiazole-2-carboxylic acid (0.039 g, 0.24 mmol) and DIPEA (0.194 mL, 1.11 mmol) in DMF (5 mL) and the solution stirred at RT for 20 h. The mixture was quenched with water, extracted with EtOAc (50 mL), washed with water and brine, dried (Na$_2$SO$_4$), filtered and evaporated in vacuo. The residue was dissolved in DCM (10 mL), 4M HCl/dioxane (5 mL, 20.00 mmol) added and stirred for 2 h. The mixture was evaporated in vacuo and the residue purified twice by reverse phase HPLC with aq TFA/MeCN as eluant to afford the title compound as a white solid. Yield: 9 mg $^1$H NMR (400 MHz, CD$_3$OD) δ 8.47 (d, J=7.6 Hz, 1H), 8.11 (d, J=3.1 Hz, 1H), 8.07 (m, 1H), 7.61 (s, 1H), 7.52 (m, 2H), 7.47 (m, 2H), 7.40 (m, 1H), 7.25 (d, J=8.2 Hz, 2H), 7.14 (m, 1H), 4.64 (s, 2H), 4.13 (m, 1H), 3.96 (m, 1H), 3.45 (t, J=5.4 Hz, 4H), 3.30 (m, 4H), 3.01 (m, 2H), 2.72 (t, J=7.8 Hz, 2H), 2.02 (m, 2H), 1.92-1.69 (m, 8H).

MS: [M+H]+=673 (calc=673) (MultiMode+)

Using analogous procedures to those described in Examples 122, 169, 170, 175, 178, 179 and 180, intermediate compounds were reacted with the appropriate carboxylic acid to give the compounds described in Table 1.

TABLE 1

| Ex | Compound name | Structure | ¹H NMR Data | MS M+H+ |
|---|---|---|---|---|
| 188 | N-((1s,4s)-4-(2-(4'-(((3S,5R)-3,5-dimethylpiperazin-1-yl)methyl)-2'-(thiomorpholinomethyl)biphenyl-3-yloxy)-5-fluoronicotinamido)cyclohexyl)-4,5,6,7-tetrahydropyrazolo[1,5-a]pyridine-2-carboxamide | 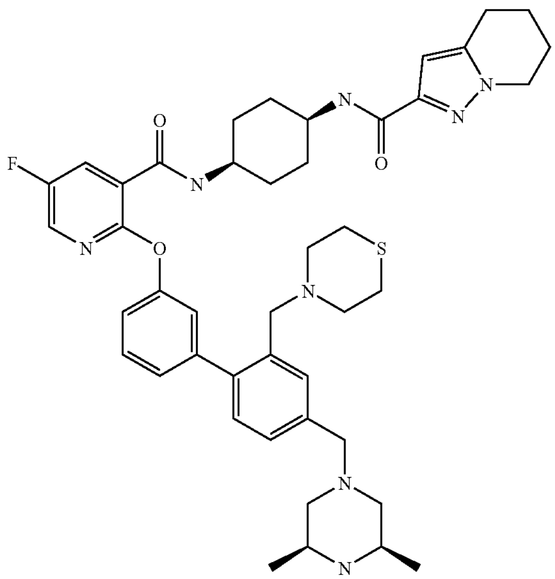 | ¹H NMR (400 MHz, CDCl₃) δ 8.16 (d, J = 3.1 Hz, 1H), 8.05-8.01 (m, 1H), 8.00 (s, 1H), 7.73-7.71 (m, 1H), 7.58 (t, J = 4.0 Hz, 1H), 7.53-7.50 (m, 1H), 7.38 (d, J = 7.9 Hz, 1H), 7.34-7.30 (m, 1H), 7.22-7.18 (m, 1H), 7.16-7.13 (m, 1H), 4.42 (s, 2H), 4.13-4.08 (m, 1H), 4.03-3.96 (m, 1H), 3.79 (s, 2H), 3.49-3.38 (m, 2H), 3.17-3.10 (m, 2H), 2.96-2.75 (m, 12H) 2.68 (s, 4H), 2.27 (t, J = 12.0 Hz, 2H), 1.89-1.70 (m, 8H), 1.29 (d, J = 6.4 Hz, 6H). | 795 |
| 189 | N-((1s,4s)-4-(2-(4'-(((3S,5R)-3,5-dimethylpiperazin-1-yl)methyl)-2'-(thiomorpholinomethyl)biphenyl-3-yloxy)-5-fluoronicotinamido)cyclohexyl)-2-methylthiazole-4-carboxamide | 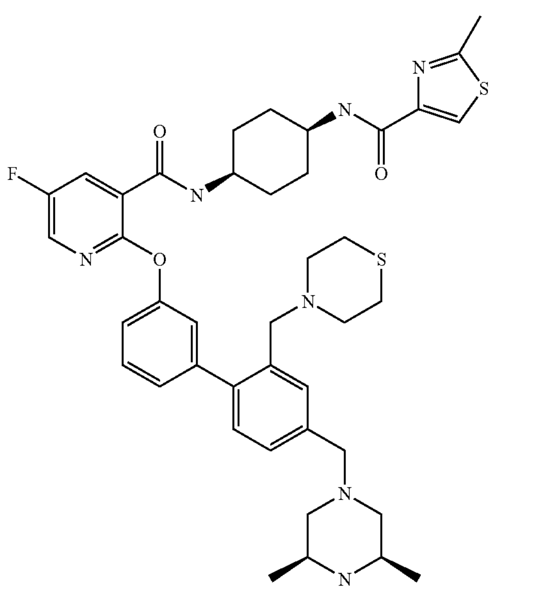 | ¹H NMR (400 MHz, CDCl₃) δ 8.16 (d, J = 3.1 Hz, 1H), 8.05-8.02 (m, 1H), 7.72-7.70 (m, 1H), 7.61-7.56 (m, 1H), 7.54-7.50 (m, 1H), 7.38 (d, J = 7.9 Hz, 1H), 7.34-7.30 (m, 1H), 7.22-7.18 (m, 1H), 7.15-7.13 (m, 1H), 6.40 (s, 1H), 4.41 (s, 2H), 4.09 (t, J = 6.2 Hz, 3H), 4.01-3.93 (m, 1H), 3.77 (s, 2H), 3.48-3.37 (m, 2H), 3.16-3.07 (m, 2H), 2.94-2.57 (m, 7H) 2.23 (t, J = 11.5 Hz, 2H), 2.08-1.99 (m, 2H), 1.90-1.67 (m, 8H), 1.28 (d, J = 6.4 Hz, 6H). | 772 |

TABLE 1-continued

| Ex | Compound name | Structure | ¹H NMR Data | MS M + H+ |
|---|---|---|---|---|
| 190 | N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)-2-isopropylthiazole-4-carboxamide | 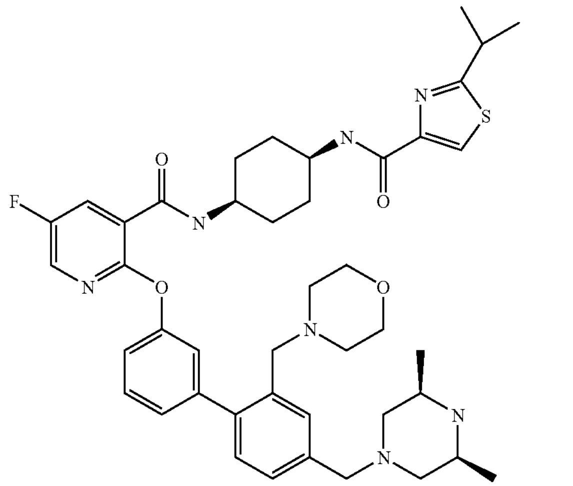 | ¹H NMR (400 MHz, CD₃OD) δ 8.13 (d, J = 3.1 Hz, 1H), 8.04-8.01 (m, 2H), 7.76 (s, 1H), 7.60-7.52 (m, 2H), 7.38 (d, J = 7.9 Hz, 1H), 7.31 (dd, J = 8.3, 3.1 Hz, 1H), 7.19 (d, J = 8.3 Hz, 1H), 7.16-7.14 (m, 1H), 4.42 (s, 2H), 4.14-4.08 (m, 1H), 4.03-3.94 (m, 1H), 3.88 (s, 2H), 3.85-3.61 (m, 4H), 3.52-3.44 (m, 2H), 3.25-3.18 (m, 4H), 2.96-2.78 (m, 2H), 2.39 (t, J = 11.2 Hz, 2H), 1.89-1.74 (m, 8H), 1.54-1.40 (m, 1H), 1.37 (d, J = 6.7 Hz, 6H), 1.30 (d, J = 5.4 Hz, 6H). | 784 |
| 191 | 2-(4'-(((3S,5R)-3,5-dimethylpiperazin-1-yl)methyl)-2'-(thiomorpholinomethyl)biphenyl-3-yloxy)-5-fluoro-N-((1s,4s)-4-(1-methyl-5-(trifluoromethyl)-1H-pyrazole-3-carboxamido)cyclohexyl)nicotinamide | 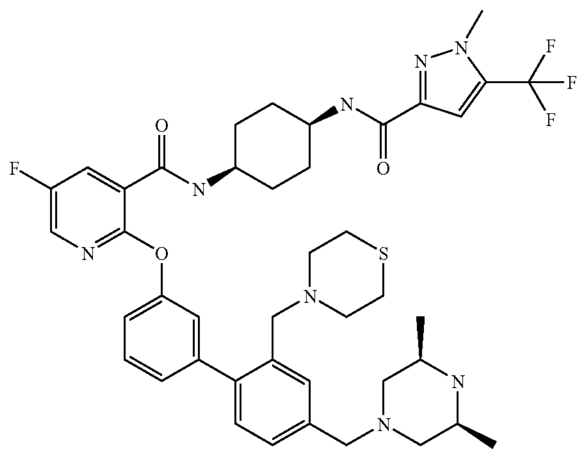 | ¹H NMR (500 MHz, CD₃OD) δ 8.56-8.47 (m, 1H), 8.21 (d, J = 2.9 Hz, 1H), 8.14-8.03 (m, 1H), 7.75 (s, 1H), 7.63 (t, J = 7.8 Hz, 1H), 7.55 (d, J = 7.0 Hz, 1H), 7.39 (dd, J = 26.1, 7.9 Hz, 2H), 7.25 (d, J = 7.2 Hz, 1H), 7.17 (d, J = 18.2 Hz, 2H), 4.46 (s, 2H), 4.16 (s, 1H), 4.09-4.05 (m, 3H), 4.03-3.99 (m, 1H), 3.78 (s, 2H), 3.45 (s, 2H), 3.13 (d, J = 12.2 Hz, 2H), 2.87 (s, 8H), 2.24 (t, J = 11.8 Hz, 2H), 2.00-1.76 (m, 8H), 1.32 (d, J = 6.4 Hz, 6H). | 823 |
| 192 | N-((1s,4s)-4-(2-(4'-(((3S,5R)-3,5-dimethylpiperazin-1-yl)methyl)-2'-(thiomorpholinomethyl)biphenyl-3-yloxy)-5-fluoronicotinamido)cyclohexyl)-4-methylthiazole-2-carboxamide | 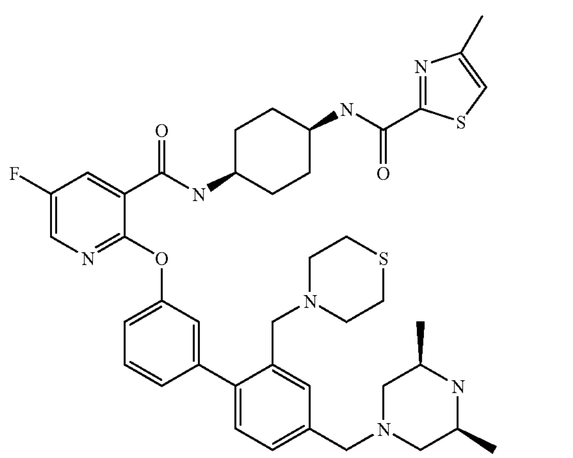 | ¹H NMR (500 MHz, CD₃OD) δ 8.40 (d, J = 7.0 Hz, 1H), 8.09 (d, J = 3.0 Hz, 1H), 7.97 (dd, J = 7.8 Hz, 3.0 Hz, 1H), 7.63 (s, 1H), 7.51 (t, J = 7.9 Hz, 1H), 7.43 (d, J = 7.8 Hz, 1H), 7.32-7.28 (m, 2H), 7.24 (d, J = 8.0 Hz, 1H), 7.12 (d, J = 7.8 Hz, 1H), 7.08 (s, 1H), 4.34 (s, 2H), 4.04 (s, 1H), 3.90 (s, 1H), 3.67 (s, 2H), 3.40-3.32 (m, 2H), 3.43-2.52 (m, 8H), 3.09-2.96 (m, 2H), 2.36 (s, 3H), 2.13 (t, J = 12.0 Hz, 2H), 1.87-1.65 (m, 8H), 1.20 (d, J = 6.5 Hz, 6H). | 772 |

| Ex | Compound name | Structure | ¹H NMR Data | MS M + H+ |
|---|---|---|---|---|
| 193 | N-((1s,4s)-4-(2-(4'-(((3S,5R)-3,5-dimethylpiperazin-1-yl)methyl)-2'-(thiomorpholinomethyl)biphenyl-3-yloxy)-5-fluoronicotinamido)cyclohexyl)-5,7-dimethylpyrazolo[1,5-a]pyrimidine-3-carboxamide | 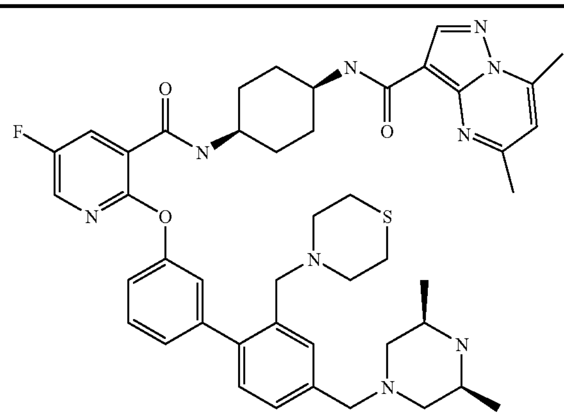 | ¹H NMR (500 MHz, CD₃OD) δ 8.44 (d, J = 7.6 Hz, 1H), 8.39 (s, 1H), 8.08 (d, J = 3.0 Hz, 1H), 7.94 (dd, J = 7.8 Hz, 3.0, 1H), 7.60 (s, 1H), 7.44 (t, J = 7.9 Hz, 1H), 7.37 (d, J = 7.7 Hz, 1H), 7.19 (t, J = 7.2 Hz, 2H), 7.08 (d, J = 7.7 Hz, 1H), 7.05 (s, 1H), 6.89 (s, 1H), 4.31 (s, 2H), 4.06 (s, 1H), 3.99 (s, 1H), 3.65 (s, 2H), 3.40-3.31 (m, 2H), 3.53-2.48 (m, 8H), 3.03 (t, J = 17.6 Hz, 2H), 2.68 (s, 3H), 2.43 (s, 3H), 2.12 (t, J = 12.0 Hz, 2H), 1.90-1.68 (m, 8H), 1.20 (d, J = 6.6 Hz, 6H). | 820 |
| 194 | N-((1s,4s)-4-(2-(4'-(((3S,5R)-3,5-dimethylpiperazin-1-yl)methyl)-2'-(((S)-3-methylmorpholino)methyl)biphenyl-3-yloxy)-5-fluoronicotinamido)cyclohexyl)-4-methylthiazole-2-carboxamide | 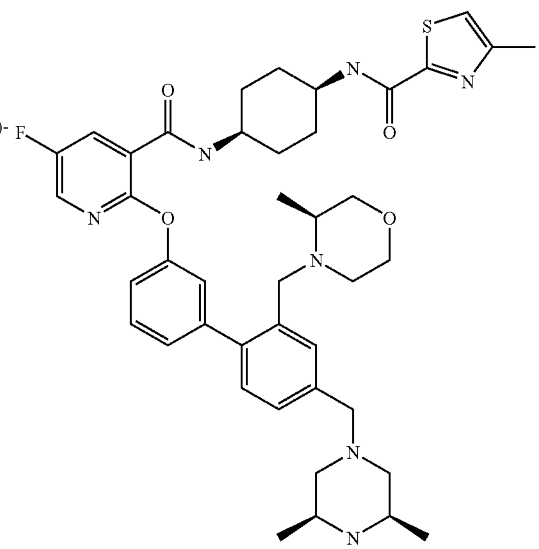 | ¹H NMR (400 MHz, CD₃OD) δ 8.13 (d, J = 2.4 Hz, 1H), 8.04 (dd, J = 7.8, 3.1 Hz, 1H), 7.95-7.92 (m, 1H), 7.61-7.50 (m, 2H), 7.41-7.38 (m, 2H), 7.34-7.31 (m, 1H), 7.20 (d, J = 7.6 Hz, 2H), 7.16-7.14 (m, 2H), 4.19-4.10 (m, 2H), 4.01-3.95 (m, 3H), 3.86-3.81 (m, 1H), 3.75-3.51 (m, 7H), 3.03-2.99 (m, 1H), 2.47-2.39 (m, 5H), 1.89-1.59 (m, 8H), 1.31-1.25 (m, 6H), 1.04-1.00 (m, 3H). | 770 |
| 195 | N-((1s,4s)-4-(2-(4'-(((3S,5R)-3,5-dimethylpiperazin-1-yl)methyl)-2'-(((S)-3-methylmorpholino)methyl)biphenyl-3-yloxy)-5-fluoronicotinamido)cyclohexyl)-1H-benzo[d]imidazole-4-carboxamide | 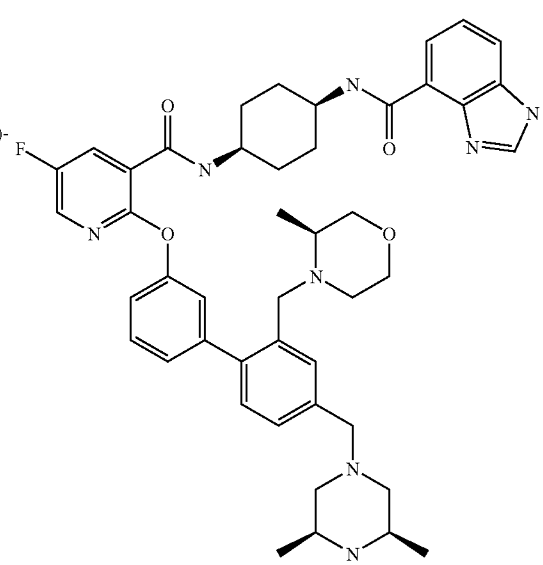 | ¹H NMR (400 MHz, CD₃OD) δ 8.92-8.87 (m, 1H), 8.14 (d, J = 3.0 Hz, 1H), 8.05 (dd, J = 7.7, 3.0 Hz, 1H), 7.99 (d, J = 7.7 Hz, 1H), 7.97-7.93 (m, 1H), 7.90 (d, J = 8.6 Hz, 1H), 7.59-7.49 (m, 3H), 7.37-7.32 (m, 2H), 7.22-7.17 (m, 2H), 4.17-3.99 (m, 4H), 3.83-3.46 (m, 5H), 3.02-2.95 (m, 1H), 2.60-2.50 (m, 2H), 1.97-1.57 (m, 8H), 1.35-1.22 (m, 6H), 1.05-1.00 (m, 3H). | 789 |

TABLE 1-continued

| Ex | Compound name | Structure | $^1$H NMR Data | MS M + H+ |
|---|---|---|---|---|
| 196 | N-((1s,4s)-4-(2-(4'-(((3S,5R)-3,5-dimethylpiperazin-1-yl)methyl)-2'-(((S)-3-methylmorpholino)methyl)biphenyl-3-yloxy)-5-fluoronicotinamido)cyclohexyl)-5,7-dimethylpyrazolo[1,5-a]pyrimidine-3-carboxamide | 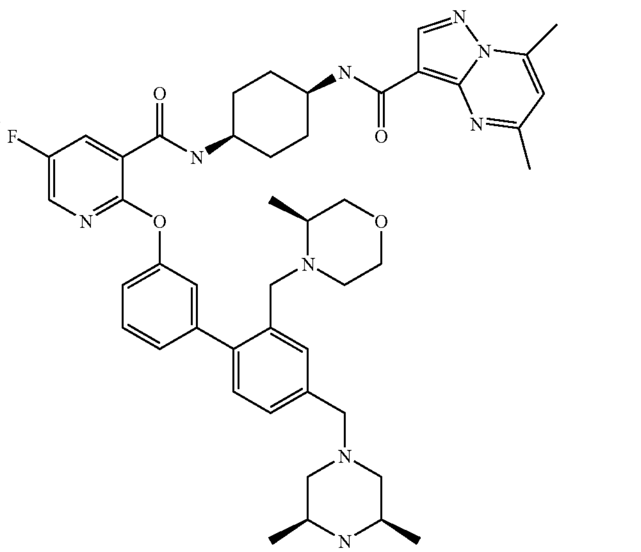 | $^1$H NMR (400 MHz, CD$_3$OD) δ 8.55-8.47 (m, 2H), 8.14 (d, J = 6.1 Hz, 1H), 8.04 (dd, J = 8.9, 4.1 Hz, 1H), 7.78-7.75 (m, 1H), 7.56-7.47 (m, 2H), 7.30 (d, J = 12.7 Hz, 2H), 7.20-7.12 (m, 2H), 6.98 (s, 1H), 4.18-4.05 (m, 3H), 3.87-3.79 (m, 3H), 3.74-3.56 (m, 2H), 3.54-3.44 (m, 3H), 3.22-3.15 (m, 2H), 3.03-2.95 (m, 2H), 2.78 (s, 3H), 2.54 (s, 3H), 2.05-1.60 (m, 8H), 1.38-1.20 (m, 6H), 1.06-1.01 (m, 3H). | 818 |
| 197 | N-((1s,4s)-4-(5-fluoro-2-(2'-(morpholinomethyl)-4'-(thiomorpholinomethyl)biphenyl-3-yloxy)nicotinamido)cyclohexyl)pyrazolo[1,5-a]pyrimidine-3-carboxamide | 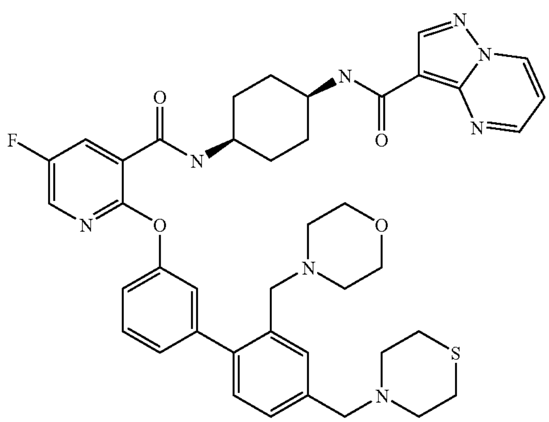 | $^1$H NMR (400 MHz, CD$_3$OD) δ 9.06 (dd, J = 7.4, 1.9 Hz, 1H), 8.62 (dd, J = 4.2, 1.9 Hz, 1H), 8.54 (s, 1H), 8.14 (d, J = 3.3 Hz, 1H), 8.02 (dd, J = 7.9, 2.8 Hz, 1H), 7.87 (d, J = 0.9 Hz, 1H), 7.59-7.53 (m, 2H), 7.40 (d, J = 7.9 Hz, 1H), 7.32 (dd, J = 8.4, 2.8 Hz, 1H), 7.19-7.14 (m, 3H), 4.41 (d, J = 4.8 Hz, 4H), 4.16-4.06 (m, 2H), 3.78-3.70 (m, 5H), 3.05-2.83 (m, 6H), 1.94-1.77 (m, 8H). | 765 |
| 198 | N-((1s,4s)-4-(5-fluoro-2-(4'-((4-(2-(isopropylamino)-2-oxoethyl)piperazin-1-yl)methyl)-2'-(morpholinomethyl)biphenyl-3-yloxy)nicotinamido)cyclohexyl)-4-methylthiazole-2-carboxamide | 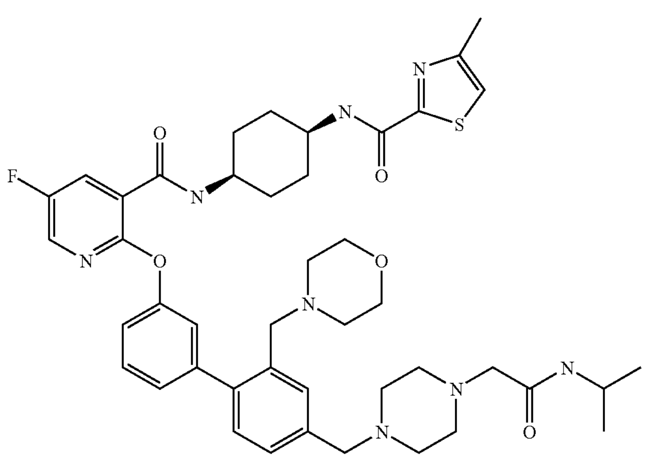 | $^1$H NMR (400 MHz, CD$_3$OD) δ 8.48 (d, J = 8.4 Hz, 1H), 8.14 (d, J = 2.8 Hz, 1H), 8.05 (dd, J = 8.4, 3.7 Hz, 1H), 7.80 (s, 1H), 7.62-7.56 (m, 2H), 7.45 (d, J = 6.5 Hz, 1H), 7.40 (s, 1H), 7.34 (dd, J = 7.7, 2.4 Hz, 1H), 7.21 (d, J = 6.8 Hz, 1H), 7.18-7.16 (m, 1H), 4.44 (s, 2H), 4.14-4.05 (m, 3H), 4.03-3.96 (m, 2H), 3.82-3.68 (m, 2H), 3.47 (s, 2H), 3.16-3.02 (m, 14H), 2.45 (s, 2H), 1.92-1.76 (m, 8H), 1.15 (d, J = 7.1 Hz, 6H). | 827 |

TABLE 1-continued

| Ex | Compound name | Structure | ¹H NMR Data | MS M+H+ |
|---|---|---|---|---|
| 199 | 5-fluoro-N-((1s,4s)-4-(1-methyl-1H-pyrazole-3-carboxamido)cyclohexyl)-2-(2'-(morpholinomethyl)-4'-(thiomorpholinomethyl)biphenyl-3-yloxy)nicotinamide | 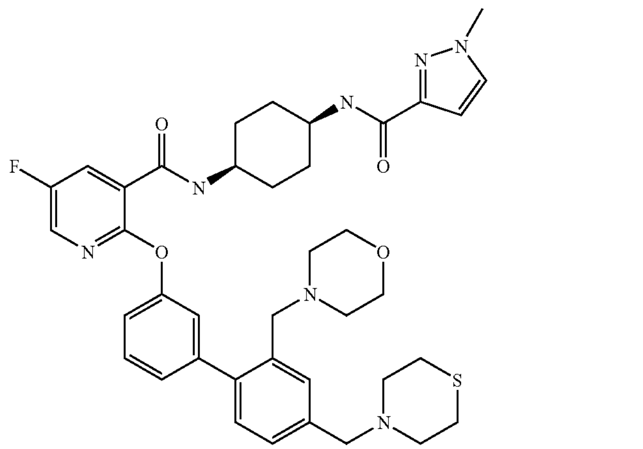 | ¹H NMR (400 MHz, CD₃OD) δ 8.47 (d, J = 5.6 Hz, 1H), 8.14 (d, J = 3.7 Hz, 1H), 8.03 (dd, J = 8.4, 2.8 Hz, 1H), 7.90-7.84 (m, 1H), 7.65-7.58 (m, 3H), 7.51 (d, J = 8.4 Hz, 1H), 7.34 (dd, J = 8.0, 2.3 Hz, 1H), 7.22 (d, J = 6.6 Hz, 1H), 7.16 (s, 1H), 6.67 (d, J = 2.5 Hz, 1H), 4.44-4.41 (m, 4H), 4.14-4.07 (m, 1H), 4.01-3.94 (m, 1H), 3.90 (s, 3H), 3.80-3.70 (m, 5H), 3.05-2.86 (m, 5H), 1.88-1.72 (m, 8H), 1.33-1.26 (m, 1H). | 728 |
| 200 | N-((1s,4s)-4-(5-fluoro-2-(4'-((4-(2-(isopropylamino)-2-oxoethyl)piperazin-1-yl)methyl)-2'-(morpholinomethyl)biphenyl-3-yloxy)nicotinamido)cyclohexyl)-4,5,6,7-tetrahydropyrazolo[1,5-a]pyridine-2-carboxamide | 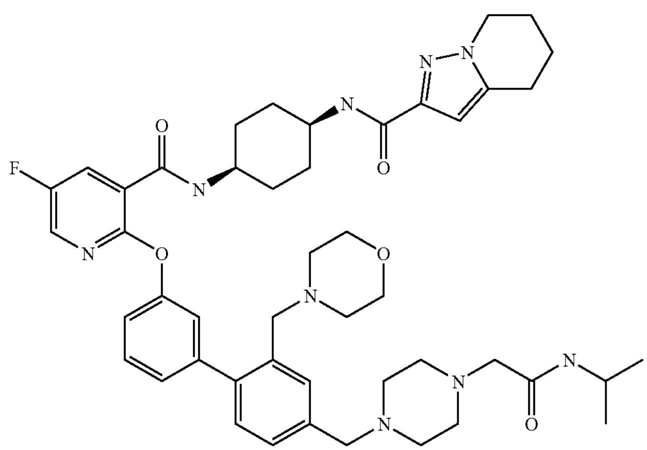 | ¹H NMR (400 MHz, CD₃OD) δ 8.46 (d, J = 8.1 Hz, 1H), 8.13 (d, J = 2.8 Hz, 1H), 8.03 (dd, J = 7.0, 3.0 Hz, 1H), 7.78 (s, 1H), 7.62-7.56 (m, 2H), 7.44 (d, J = 8.0 Hz, 1H), 7.33 (dd, J = 7.7, 2.8 Hz, 1H), 7.21 (d, J = 8.1 Hz, 1H), 7.15-7.14 (m, 1H), 6.41 (s, 1H), 4.43 (s, 2H), 4.12-4.05 (m, 5H), 4.03-3.94 (m, 2H), 3.84-3.63 (m, 4H), 3.49 (s, 2H), 3.16-2.99 (m, 10H), 2.80 (t, J = 5.5 Hz, 2H), 2.07-2.01 (m, 2H), 1.89-1.69 (m, 10H), 1.14 (d, J = 8.3 Hz, 6H). | 850 |
| 201 | N-((1s,4s)-4-(5-fluoro-2-(4'-((4-(2-(isopropylamino)-2-oxoethyl)piperazin-1-yl)methyl)-2'-(morpholinomethyl)biphenyl-3-yloxy)nicotinamido)cyclohexyl)-1H-benzo[d]imidazole-4-carboxamide | 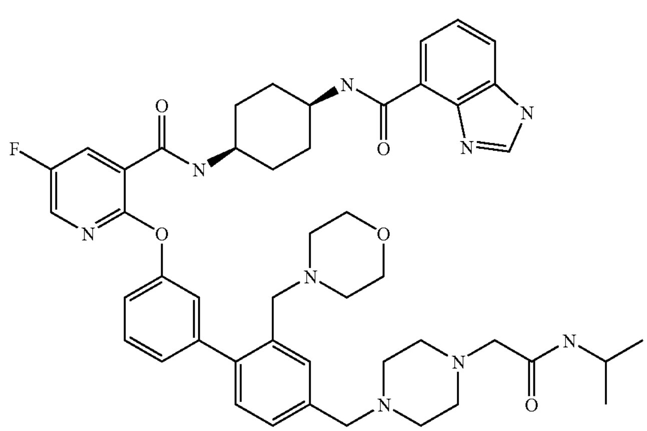 | ¹H NMR (400 MHz, CD₃OD) δ 8.94 (s, 1H), 8.13 (s, 1H), 8.04 (d, J = 8.0 Hz, 1H), 7.99 (d, J = 8.0 Hz, 1H), 7.90 (d, J = 7.0 Hz, 1H), 7.79 (s, 1H), 7.60-7.53 (m, 3H), 7.40 (d, J = 8.0 Hz, 1H), 7.32 (d, J = 8.0 Hz, 1H), 7.21-7.16 (m, 2H), 4.41 (s, 2H), 4.17-4.07 (m, 4H), 3.98 (quintet, J = 6.8 Hz, 1H), 3.80-3.67 (m, 5H), 3.43 (s, 2H), 3.09 (d, J = 18.8 Hz, 12H), 1.97-1.80 (m, 8H), 1.13 (d, J = 8.7 Hz, 6H). | 846 |

TABLE 1-continued

| Ex | Compound name | Structure | ¹H NMR Data | MS M+H+ |
|---|---|---|---|---|
| 202 | N-((1s,4s)-4-(2-(4'-(((3S,5R)-3,5-dimethylpiperazin-1-yl)methyl)-2'-(thiomorpholinomethyl)biphenyl-3-yloxy)-5-fluoronicotinamido)cyclohexyl)-1H-benzo[d]imidazole-4-carboxamide | 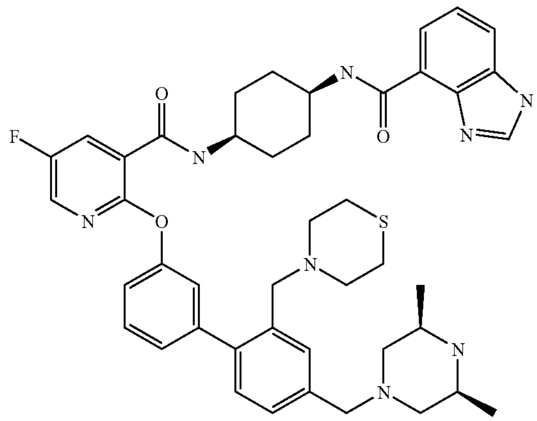 | ¹H NMR (400 MHz, CD$_3$OD) δ 8.72 (s, 1H), 8.51 (d, J = 8.9 Hz, 1H), 8.16 (d, J = 2.8 Hz, 1H), 8.04 (dd, J = 7.9, 3.1 Hz, 1H), 7.97 (d, J = 7.4 Hz, 1H), 7.86 (d, J = 7.9 Hz, 1H), 7.68 (s, 1H), 7.59-7.49 (m, 3H), 7.33-7.28 (m, 2H), 7.20-7.14 (m, 2H), 4.38 (s, 2H), 4.17-4.09 (m, 2H), 3.71 (s, 2H), 3.44-3.36 (m, 2H), 3.24-2.72 (m, 6H), 3.07 (d, J = 11.9 Hz, 2H), 2.19 (t, J = 12.0 Hz, 2H), 1.96-1.84 (m, 8H), 1.27 (d, J = 6.7 Hz, 6H). | 791 |

EXAMPLE A

Human Phosphodiesterase B2 Radiometric Assay

The assay uses recombinant Human Phosphodiesterase B2 (PDE4B2) produced in house (PrAZL0163), stored at −20° C. This assay is based on the observation that 5'AMP, the product of the reaction catalysed by PDE4, binds preferentially to yttrium silicate SPA beads (Amersham Biosciences, UK) compared to the substrate, cAMP. Compounds at the appropriate concentration were preincubated at 30 C for 30 min with an assay buffer containing 50 mM HEPES (pH 7.5), 8.3 mM MgCl2, 1.7 mM EGTA, 0.01% (w/v) Brij®35 and 0.1 µg/mL recombinant PDE4B2. The reaction was started by the addition of [3H]cyclic AMP to give a final concentration of 8 nM, and was stopped 20 min after the addition of the substrate by the addition of yttrium silicate SPA beads containing 18 mM Zn SO$_4$. Bound [3H]cyclic AMP was measured using a Topcount NXT (Packard Bioscience, UK). pIC50 values (presented in Table 2) were determined using Xlfit3 curve fitting, using model 205.

TABLE 2

| Ex | PDE4B2 pIC$_{50}$ |
|---|---|
| 1 | 9.9 |
| 2 | 10.8 |
| 3 | 8.9 |
| 4 | 7.2 |
| 5 | 8.3 |
| 6 | 8.5 |
| 7 | 8.2 |
| 8 | 9.2 |
| 9 | 10.5 |
| 10 | 10.5 |
| 11 | 10.3 |
| 12 | 10.3 |
| 13 | 10.7 |
| 14 | 10.7 |
| 15 | 10.7 |
| 16 | 10.5 |
| 17 | 8.8 |
| 18 | 10.8 |
| 19 | 11.0 |
| 20 | 10.5 |
| 21 | 10.3 |
| 22 | 10.4 |
| 23 | 9.5 |
| 24 | 10.0 |
| 25 | 8.5 |
| 26 | 9.7 |
| 27 | 9.2 |
| 28 | 10.6 |
| 29 | 10.4 |
| 30 | 10.4 |
| 31 | 9.3 |
| 32 | 9.5 |
| 33 | 9.2 |
| 34 | 10.6 |
| 35 | 9.9 |
| 36 | 10.0 |
| 37 | 9.7 |
| 38 | 10.4 |
| 39 | 10.7 |
| 40 | 9.1 |
| 41 | 10.0 |
| 42 | 10.3 |
| 43 | 9.9 |
| 44 | 10.0 |
| 45 | 10.8 |
| 46 | 9.9 |
| 47 | 9.1 |
| 48 | 10.2 |
| 49 | 10.6 |
| 50 | 9.5 |
| 51 | 10.0 |
| 52 | 10.3 |
| 53 | 9.4 |
| 54 | 10.2 |
| 55 | 10.0 |
| 56 | 10.6 |
| 57 | 10.2 |
| 58 | 10.2 |
| 59 | 10.1 |
| 60 | 10.3 |
| 61 | 10.7 |
| 62 | 10.6 |
| 63 | 9.9 |
| 64 | 9.9 |
| 65 | 10.4 |
| 66 | 10.5 |
| 67 | 10.0 |
| 68 | 10.6 |

TABLE 2-continued

| Ex | PDE4B2 pIC$_{50}$ |
|---|---|
| 69 | 9.4 |
| 70 | 10.1 |
| 71 | 10.6 |
| 72 | 10.2 |
| 73 | 10.2 |
| 74 | 10.6 |
| 75 | 10.5 |
| 76 | 10.2 |
| 77 | 10.2 |
| 78 | 10.1 |
| 79 | 10.5 |
| 80 | 10.4 |
| 81 | 10.5 |
| 82 | 10.7 |
| 83 | 10.6 |
| 84 | 9.8 |
| 85 | 10.2 |
| 86 | 10.5 |
| 87 | 10.6 |
| 88 | 10.5 |
| 89 | 10.1 |
| 90 | 9.7 |
| 91 | 9.6 |
| 92 | 9.9 |
| 93 | 10.0 |
| 94 | 10.2 |
| 95 | 9.7 |
| 96 | 9.7 |
| 97 | 9.9 |
| 98 | 10.0 |
| 99 | 10.1 |
| 100 | 9.8 |
| 101 | 10.2 |
| 102 | 10.4 |
| 103 | 10.5 |
| 104 | 10.5 |
| 105 | 9.2 |
| 106 | 9.6 |
| 107 | 9.8 |
| 108 | 10.7 |
| 109 | 10.2 |
| 110 | 9.7 |
| 111 | — |
| 112 | 10.4 |
| 113 | 10.3 |
| 114 | 9.8 |
| 115 | 9.2 |
| 116 | 10.5 |
| 117 | 10.0 |
| 118 | 10.4 |
| 119 | 10.1 |
| 120 | 10.3 |
| 121 | 10.2 |
| 122 | 10.4 |
| 123 | 10.2 |
| 124 | 10.3 |
| 125 | 10.2 |
| 126 | 10.3 |
| 127 | 10.1 |
| 128 | 9.9 |
| 129 | 10.5 |
| 130 | 10.5 |
| 131 | 9.9 |
| 132 | 10.4 |
| 133 | 10.3 |
| 134 | 10.2 |
| 135 | 10.3 |
| 136 | 10.0 |
| 137 | 10.3 |
| 138 | 10.6 |
| 139 | 10.1 |
| 140 | 10.5 |
| 141 | 10.2 |
| 142 | 10.6 |
| 143 | 10.1 |
| 144 | 10.5 |
| 145 | 10.7 |
| 146 | 10.5 |
| 147 | 10.3 |
| 148 | 10.4 |
| 149 | 10.5 |
| 150 | 10.1 |
| 151 | 10.2 |
| 152 | 10.4 |
| 153 | 10.5 |
| 154 | 10.5 |
| 155 | 10.4 |
| 156 | 9.9 |
| 157 | 10.1 |
| 158 | 10.5 |
| 159 | 10.3 |
| 160 | 11.0 |
| 161 | 10.9 |
| 162 | 10.4 |
| 163 | 10.4 |
| 164 | 9.9 |
| 165 | 10.2 |
| 166 | 10.4 |
| 167 | 10.3 |
| 168 | 10.3 |
| 169 | 10.7 |
| 170 | 10.3 |
| 171 | 10.1 |
| 172 | 10.2 |
| 173 | 10.4 |
| 174 | 10.0 |
| 175 | 10.7 |
| 176 | 10.3 |
| 177 | 10.3 |
| 178 | 10.4 |
| 179 | 10.3 |
| 180 | 10.8 |
| 181 | 9.6 |
| 182 | 10.4 |
| 183 | 9.7 |
| 184 | 10.4 |
| 185 | 10.7 |
| 186 | 10.4 |
| 187 | 9.7 |
| 188 | 10.7 |
| 189 | 10.8 |
| 190 | 10.4 |
| 191 | 10.7 |
| 192 | 10.7 |
| 193 | 10.6 |
| 194 | 10.5 |
| 195 | 10.7 |
| 196 | 10.6 |
| 197 | 10.7 |
| 198 | 10.6 |
| 199 | 10.7 |
| 200 | 10.6 |
| 201 | 10.8 |
| 202 | 10.9 |

The invention claimed is:
1. A compound of formula (I):

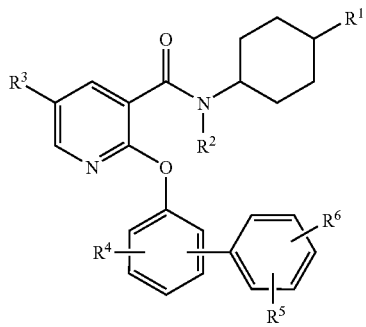

wherein:
R[1] is NR[7]C(O)R[8], NR[7]S(O)$_2$R[8] or NR[9]R[10];
R[2] is hydrogen or $C_{1-6}$ alkyl;
R[3] is hydrogen, halogen, $C_{1-4}$ alkyl or $C_{1-4}$ alkoxy;
R[4] is hydrogen, halogen, cyano, hydroxy, $C_{1-4}$ alkyl, $C_{1-4}$ alkoxy, $CF_3$, $OCF_3$, $C_{1-4}$ alkylthio, S(O)($C_{1-4}$ alkyl), S(O)$_2$($C_{1-4}$ alkyl), $CO_2H$ or $CO_2$($C_{1-4}$ alkyl);
R[5] is $C_{1-6}$ alkyl (substituted by NR[11]R[12] or heterocyclyl), $C_{1-6}$ alkoxy (substituted by NR[11]R[12] or heterocyclyl), $C_{3-6}$ cycloalkyl (substituted by NR[11]R[12] or heterocyclyl) or heterocyclyl; provided that if R[5] includes a heterocyclyl then said heterocyclyl comprises one or more ring nitrogen atoms; and that if said heterocyclyl is bonded directly via a ring nitrogen either: to the alkyl, alkoxy or cycloalkyl of R[5], or to the phenyl ring of formula (I) to which R[5] is directly bonded, then said heterocyclyl either has at least two ring heteroatoms, or has an NR[46]R[47] substituent;
R[6] is hydrogen, halogen, cyano, hydroxy, SH, $C_{1-4}$ alkyl, $C_{1-4}$ alkoxy, $CF_3$, $OCF_3$, C(O)H, $C_{1-6}$ alkylthio, S(O)($C_{1-6}$ alkyl), S(O)$_2$($C_{1-6}$ alkyl), $CO_2H$, $CO_2$($C_{1-6}$ alkyl), NR[13]R[14], $C_{1-6}$ alkyl (optionally substituted by halogen, OH, $CO_2H$, NR[15]R[16], NHC(O)O($C_{1-6}$ alkyl), OS(O)$_2$($C_{1-6}$ alkyl) or heterocyclyl), $C_{1-6}$ alkoxy (optionally substituted by halogen, OH, $CO_2H$, NR[15]R[16] or heterocyclyl), $C_{3-6}$ cycloalkyl (optionally substituted halogen, OH, $CO_2H$, NR[15]R[16] or heterocyclyl) or heterocyclyl;
R[7] is hydrogen or $C_{1-6}$ alkyl (optionally substituted by NR[26]R[27]);
R[8] is $C_{1-6}$ alkyl {optionally substituted by hydroxyl, $C_{1-6}$ alkoxy, NR[21]R[22], heterocyclyl {optionally substituted by oxo, hydroxy, $C_{1-6}$ alkyl, $CO_2$($C_{1-6}$ alkyl), aryl, heteroaryl, aryl($C_{1-4}$ alkyl), heterocyclyl or C(O)($C_{1-4}$ alkyl)phenyl}, aryl, heteroaryl, $C_{3-7}$ cycloalkyl, $C_{3-7}$ cycloalkyl($C_{1-4}$ alkyl), $CO_2H$, $CO_2$($C_{1-6}$ alkyl), aryl ($C_{1-4}$ alkoxy), aryl($C_{1-4}$ alkylthio), S(O)$_2$($C_{1-6}$ alkyl), NHC(O)heteroaryl or NHC(O)R[23]}, $C_{1-6}$ alkoxy, $C_{3-6}$ cycloalkyl {optionally substituted by hydroxyl, NR[24]R[25] or $C_{1-6}$ alkyl}, heterocyclyl {optionally substituted by oxo, hydroxy, $C_{1-6}$ alkyl, amino, aryl, heteroaryl, aryl($C_{1-4}$ alkyl), heteroaryl($C_{1-4}$ alkyl), heterocyclyl or C(O)($C_{1-4}$ alkyl)phenyl}, aryl($C_{1-4}$ alkyl) {substituted by amino($C_{1-4}$ alkyl)}, aryl or heteroaryl;
R[9] is hydrogen, $C_{1-6}$ alkyl (optionally substituted by aryl or heteroaryl), aryl or heteroaryl;
R[10] is hydrogen, $C_{1-6}$ alkyl (optionally substituted by hydroxyl, $C_{1-6}$ alkoxy, aryl, aryloxy, phenyl($C_{1-6}$ alkoxy), heteroaryl, $C_{3-10}$ cycloalkyl, $CO_2H$, $CO_2$($C_{1-6}$ alkyl), NHC(O)O($C_{1-6}$ alkyl) or NHC(O)R[23]), $C_{1-6}$ alkoxy, $C_{3-6}$ cycloalkyl (optionally substituted by hydroxy, $C_{1-6}$ alkyl, phenyl, phenyl ($C_{1-6}$ alkyl), heteroaryl or heteroaryl($C_{1-6}$ alkyl)), heterocyclyl (optionally substituted by $C_{1-6}$ alkyl, C(O)NH$_2$ or phenyl($C_{1-6}$ alkyl)), aryl or heteroaryl;
R[21] and R[22] are, independently, hydrogen, $C_{1-6}$ alkyl or phenyl($C_{1-4}$ alkyl);
R[23] is $C_{1-6}$ alkyl or phenyl;
the foregoing phenyl, aryl and heteroaryl moieties of R[5], R[8], R[9], R[10], R[23], R[21] and R[22] are independently, optionally substituted by: halogen, cyano, nitro, $CF_3$, hydroxy, S(O)$_q$R[26], OC(O)NR[27]R[28], NR[29]R[30], NR[31]C(O)R[32], NR[33]C(O)NR[34]R[35], S(O)$_2$NR[36]R[37], NR[38]S(O)$_2$R[39], C(O)NR[40]R[41], C(O)R[42], $CO_2$R[43], NR[44]$CO_2$R[45], OC(O)($C_{1-6}$ alkyl), $C_{1-6}$ alkyl, $C_{1-6}$ hydroxyalkyl, $C_{1-6}$ haloalkyl, $C_{1-6}$ alkoxy($C_{1-6}$)alkyl, amino($C_{1-4}$ alkyl), di($C_{1-6}$)alkylamino($C_{1-6}$)alkyl, $C_{1-6}$ alkoxy, $C_{1-6}$ haloalkoxy, hydroxyl ($C_{1-6}$ alkoxy), heterocyclyl($C_{1-6}$ alkoxy), $C_{1-6}$ alkoxy($C_{1-6}$)alkoxy, amino($C_{1-4}$ alkoxy), $C_{1-4}$ alkylamino($C_{1-4}$ alkoxy) (itself optionally substituted by phenyl), di($C_{1-4}$ alkyl)amino($C_{1-4}$ alkoxy), $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, heterocyclyl, heterocyclyl($C_{1-4}$ alkyl), phenyl, phenyl($C_{1-4}$)alkyl, phenoxy, phenylthio, phenyl($C_{1-4}$)alkoxy, heteroaryl, heteroaryl($C_{1-4}$)alkyl, heteroaryloxy or heteroaryl($C_{1-4}$) alkoxy; wherein any of the immediately foregoing phenyl and heteroaryl moieties are optionally substituted with halogen, hydroxy, nitro, S(O)$_r$($C_{1-4}$ alkyl), S(O)$_2$NH$_2$, S(O)$_2$NH($C_{1-4}$ alkyl), S(O)$_2$N($C_{1-4}$ alkyl)$_2$, cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$, $CO_2H$, $CO_2$($C_{1-4}$ alkyl), NHC(O)($C_{1-4}$ alkyl), NH(O)$_2$($C_{1-4}$ alkyl), C(O)($C_{1-4}$ alkyl), $CF_3$ or $OCF_3$;
q and r are, independently, 0, 1 or 2;
unless otherwise stated heterocyclyl is optionally substituted by OH, $C_{1-6}$ alkyl, $C_{3-7}$ cycloalkyl, NR[46]R[47], ($C_{1-6}$ alkyl)OH or ($C_{1-6}$ alkyl)NR[48]R[49], NR[50]$CO_2$($C_{1-6}$ alkyl), $CO_2$($C_{1-6}$ alkyl), C(O)($C_{1-6}$ alkyl), C(O)heterocyclyl, heteroaryl, ($C_{1-6}$ alkyl)C(O)NR[51]R[52], ($C_{1-6}$ alkyl)C(O)NR[53]R[54], ($C_{1-6}$ alkyl)C(O)heterocyclyl or heterocyclyl;
R[26], R[27], R[28], R[29], R[30], R[31], R[32], R[33], R[34], R[35], R[36], R[37], R[38], R[39], R[40], R[41], R[42], R[43], R[44] and R[45], are, independently, $C_{1-6}$ alkyl {optionally substituted by halogen, hydroxy or $C_{1-6}$ alkoxy}, $CH_2$($C_{2-6}$ alkenyl), phenyl {itself optionally substituted by halogen, hydroxy, nitro, NH$_2$, NH($C_{1-4}$ alkyl), N($C_{1-4}$ alkyl)$_2$, S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$, cyano, $C_{1-4}$ alkyl, $C_{1-4}$ alkoxy, C(O)NH$_2$, C(O)NH($C_{1-4}$ alkyl), C(O)N($C_{1-4}$ alkyl)$_2$, $CO_2H$, $CO_2$($C_{1-4}$ alkyl), NHC(O)($C_{1-4}$ alkyl), NH(O)$_2$($C_{1-4}$ alkyl), C(O)($C_{1-4}$ alkyl), $CF_3$ or $OCF_3$} or heteroaryl {itself optionally substituted by halogen, hydroxy, nitro, NH$_2$, NH($C_{1-4}$ alkyl), N($C_{1-4}$ alkyl)$_2$, S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$, cyano, $C_{1-4}$ alkyl, $C_{1-4}$ alkoxy, C(O)NH$_2$, C(O)NH($C_{1-4}$ alkyl), C(O) N($C_{1-4}$ alkyl)$_2$, $CO_2H$, $CO_2$($C_{1-4}$ alkyl), NHC(O)($C_{1-4}$ alkyl), NH(O)$_2$($C_{1-4}$ alkyl), C(O)($C_{1-4}$ alkyl), $CF_3$ or $OCF_3$};
R[27], R[28], R[29], R[30], R[31], R[32], R[33], R[34], R[35], R[36], R[37], R[38], R[40], R[41], R[42], R[43], R[44] and R[45] can also be hydrogen;
R[12], R[14], R[15], R[25], R[47] and R[49] are, independently, hydrogen, $C_{1-6}$ alkyl (optionally substituted by hydroxy, $C_{1-6}$ alkoxy, $C_{1-6}$ alkylthio, $C_{3-7}$ cycloalkyl (optionally substituted by hydroxy) or $NR^{55}R^{56}$), $C_{3-7}$ cycloalkyl (optionally substituted by hydroxy($C_{1-6}$ alkyl)) or heterocyclyl (optionally substituted by $C_{1-6}$ alkyl);

$R^{11}$, $R^{13}$, $R^{16}$, $R^{24}$, $R^{26}$, $R^{27}$, $R^{46}$, $R^{48}$, $R^{50}$, $R^{51}$, $R^{52}$, $R^{53}$, $R^{54}$ $R^{55}$ and $R^{56}$ are, independently, hydrogen or $C_{1-6}$ alkyl;

or a N-oxide thereof or a pharmaceutically acceptable salt thereof.

2. A compound of formula (I) as claimed in claim 1 wherein:

$R^1$ is $NR^7C(O)R^8$, $NR^7S(O)_2R^8$ or $NR^9R^{10}$;

$R^2$ is hydrogen or $C_{1-6}$ alkyl;

$R^3$ is hydrogen, halogen, $C_{1-4}$ alkyl or $C_{1-4}$ alkoxy;

$R^4$ is hydrogen, halogen, cyano, hydroxy, $C_{1-4}$ alkyl, $C_{1-4}$ alkoxy, $CF_3$, $OCF_3$, $C_{1-4}$ alkylthio, $S(O)(C_{1-4}$ alkyl), $S(O)_2(C_{1-4}$ alkyl), $CO_2H$ or $CO_2(C_{1-4}$ alkyl);

$R^5$ is $C_{1-6}$ alkyl (substituted by $NR^{11}R^{12}$ or heterocyclyl), $C_{1-6}$ alkoxy (substituted by $NR^{11}R^{12}$ or heterocyclyl), $C_{3-6}$ cycloalkyl (substituted by $NR^{11}R^{12}$ or heterocyclyl) or heterocyclyl; provided that if $R^5$ includes a heterocyclyl then said heterocyclyl comprises one or more ring nitrogen atoms; and that if said heterocyclyl is bonded directly via a ring nitrogen either: to the alkyl, alkoxy or cycloalkyl of $R^5$, or to the phenyl ring of formula (I) to which $R^5$ is directly bonded, then said heterocyclyl either has at least two ring heteroatoms, or has an $NR^{46}R^{47}$ substituent;

$R^6$ is hydrogen, halogen, cyano, hydroxy, SH, $C_{1-4}$ alkyl, $C_{1-4}$ alkoxy, $CF_3$, $OCF_3$, $C(O)H$, $C_{1-6}$ alkylthio, $S(O)(C_{1-6}$ alkyl), $S(O)_2(C_{1-6}$ alkyl), $CO_2H$, $CO_2(C_{1-6}$ alkyl), $NR^{13}R^{14}$, $C_{1-6}$ alkyl (optionally substituted by halogen, OH, $CO_2H$, $NR^{15}R^{16}$, $NHC(O)O(C_{1-6}$ alkyl), $OS(O)_2(C_{1-6}$ alkyl) or heterocyclyl), $C_{1-6}$ alkoxy (optionally substituted by halogen, OH, $CO_2H$, $NR^{15}R^{16}$ or heterocyclyl), $C_{3-6}$ cycloalkyl (optionally substituted halogen, OH, $CO_2H$, $NR^{15}R^{16}$ or heterocyclyl) or heterocyclyl;

$R^7$ is hydrogen or $C_{1-6}$ alkyl (optionally substituted by $NR^{26}R^{27}$);

$R^8$ is $C_{1-6}$ alkyl {optionally substituted by hydroxyl, $C_{1-6}$ alkoxy, $NR^{21}R^{22}$, heterocyclyl {optionally substituted by oxo, hydroxy, $C_{1-6}$ alkyl, $CO_2(C_{1-6}$ alkyl), aryl, heteroaryl, aryl($C_{1-4}$alkyl), heterocyclyl or $C(O)(C_{1-4}$ alkyl)phenyl}, aryl, heteroaryl, $C_{3-7}$ cycloalkyl, $C_{3-7}$ cycloalkyl($C_{1-4}$ alkyl), $CO_2H$, $CO_2(C_{1-6}$ alkyl), aryl ($C_{1-4}$ alkoxy), aryl($C_{1-4}$ alkylthio), $S(O)_2(C_{1-6}$ alkyl), NHC(O)heteroaryl or $NHC(O)R^{23}$}, $C_{1-6}$ alkoxy, $C_{3-6}$ cycloalkyl {optionally substituted by hydroxyl, $NR^{24}R^{25}$ or $C_{1-6}$ alkyl}, heterocyclyl {optionally substituted by oxo, hydroxy, $C_{1-6}$ alkyl, amino, aryl, heteroaryl, aryl($C_{1-4}$ alkyl), heteroaryl($C_{1-4}$ alkyl), heterocyclyl or $C(O)(C_{1-4}$ alkyl)phenyl}, aryl($C_{1-4}$ alkyl) {substituted by amino($C_{1-4}$ alkyl)}, aryl or heteroaryl;

$R^9$ is hydrogen, $C_{1-6}$ alkyl (optionally substituted by aryl or heteroaryl), aryl or heteroaryl;

$R^{10}$ is hydrogen, $C_{1-6}$ alkyl (optionally substituted by hydroxyl, $C_{1-6}$ alkoxy, aryl, aryloxy, phenyl($C_{1-6}$ alkoxy), heteroaryl, $C_{3-10}$ cycloalkyl, $CO_2H$, $CO_2(C_{1-6}$ alkyl), $NHC(O)O(C_{1-6}$ alkyl) or $NHC(O)R^{23}$), $C_{1-6}$ alkoxy, $C_{3-6}$ cycloalkyl (optionally substituted by hydroxy, $C_{1-6}$ alkyl, phenyl, phenyl($C_{1-6}$ alkyl), heteroaryl or heteroaryl($C_{1-6}$ alkyl)), heterocyclyl (optionally substituted by $C_{1-6}$ alkyl, $C(O)NH_2$ or phenyl($C_{1-6}$ alkyl)), aryl or heteroaryl;

$R^{21}$ and $R^{22}$ are, independently, hydrogen, $C_{1-6}$ alkyl or phenyl($C_{1-4}$ alkyl);

$R^{23}$ is $C_{1-6}$ alkyl or phenyl;

the foregoing phenyl, aryl and heteroaryl moieties of $R^8$, $R^9$, $R^{10}$, $R^{23}$, $R^{21}$ and $R^{22}$ are, independently, optionally substituted by: halogen, cyano, nitro, hydroxy, $S(O)_qR^{26}$, $OC(O)NR^{27}R^{28}$, $NR^{29}R^{30}$, $NR^{31}C(O)R^{32}$, $NR^{33}C(O)NR^{34}R^{35}$, $S(O)_2NR^{36}R^{37}$, $NR^{38}S(O)_2R^{39}$, $C(O)NR^{40}R^{41}$, $C(O)R^{42}$, $CO_2R^{43}$, $NR^{44}CO_2R^{45}$, $OC(O)(C_{1-6}$ alkyl), $C_{1-6}$ alkyl, $C_{1-6}$ hydroxyalkyl, $C_{1-6}$ haloalkyl, $C_{1-6}$ alkoxy($C_{1-6}$)alkyl, amino($C_{1-4}$ alkyl), di($C_{1-6}$)alkylamino($C_{1-6}$)alkyl, $C_{1-6}$ alkoxy, $C_{1-6}$ haloalkoxy, hydroxyl ($C_{1-6}$ alkoxy), heterocyclyl($C_{1-6}$ alkoxy), $C_{1-6}$ alkoxy($C_{1-6}$)alkoxy, amino($C_{1-4}$ alkoxy), $C_{1-4}$ alkylamino($C_{1-4}$ alkoxy) (itself optionally substituted by phenyl), di($C_{1-4}$ alkyl)amino($C_{1-4}$ alkoxy), $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, heterocyclyl, heterocyclyl($C_{1-4}$ alkyl), phenyl, phenyl($C_{1-4}$)alkyl, phenoxy, phenylthio, phenyl($C_{1-4}$ alkoxy, heteroaryl, heteroaryl($C_{1-4}$ alkyl, heteroaryloxy or heteroaryl($C_{1-4}$) alkoxy; wherein any of the immediately foregoing phenyl and heteroaryl moieties are optionally substituted with halogen, hydroxy, nitro, $S(O)_r(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NH(O)_2(C_{1-4}$ alkyl), $C(O)(C_{1-4}$ alkyl), $CF_3$ or $OCF_3$;

q and r are, independently, 0, 1 or 2;

unless otherwise stated heterocyclyl is optionally substituted by OH, $C_{1-6}$ alkyl, $C_{3-7}$ cycloalkyl, $NR^{46}R^{47}$, ($C_{1-6}$ alkyl)OH or ($C_{1-6}$ alkyl)$NR^{48}R^{49}$, $NR^{50}CO_2(C_{1-6}$ alkyl), $CO_2(C_{1-6}$ alkyl), $C(O)(C_{1-6}$ alkyl), C(O)heterocyclyl, heteroaryl, ($C_{1-6}$ alkyl)$C(O)NR^{51}R^{52}$, ($C_{1-6}$ alkyl)$C(O)NR^{53}R^{54}$, ($C_{1-6}$ alkyl)C(O)heterocyclyl or heterocyclyl;

$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$, are, independently, $C_{1-6}$ alkyl {optionally substituted by halogen, hydroxy or $C_{1-6}$ alkoxy}, $CH_2(C_{2-6}$ alkenyl), phenyl {itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NH(O)_2(C_{1-4}$ alkyl), $C(O)(C_{1-4}$ alkyl), $CF_3$ or $OCF_3$} or heteroaryl {itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NH(O)_2(C_{1-4}$ alkyl), $C(O)(C_{1-4}$ alkyl), $CF_3$ or $OCF_3$};

$R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{40}$, $R^{41}$, $R^{42}$, $R^{43}$, $R^{44}$ and $R^{45}$ can also be hydrogen;

$R^{12}$, $R^{14}$, $R^{15}$, $R^{25}$, $R^{47}$ and $R^{49}$ are, independently, hydrogen, $C_{1-6}$ alkyl (optionally substituted by hydroxy, $C_{1-6}$ alkoxy, $C_{1-6}$ alkylthio, $C_{3-7}$ cycloalkyl (optionally substituted by hydroxy) or $NR^{55}R^{56}$), $C_{3-7}$ cycloalkyl (optionally substituted by hydroxy($C_{1-6}$ alkyl)) or heterocyclyl (optionally substituted by $C_{1-6}$ alkyl);

$R^{11}$, $R^{13}$, $R^{16}$, $R^{24}$, $R^{26}$, $R^{27}$, $R^{46}$, $R^{48}$, $R^{50}$, $R^{51}$, $R^{52}$, $R^{53}$, $R^{54}$ $R^{55}$ and $R^{56}$ are, independently, hydrogen or $C_{1-6}$ alkyl;

or a N-oxide thereof or a pharmaceutically acceptable salt thereof.

3. A compound of formula (I) as claimed in claim 1 wherein $R^1$ is $NR^7C(O)R^8$.

4. A compound of formula (I) as claimed in claim 1 wherein $R^8$ is aryl or heteroaryl optionally substituted by halogen, cyano, nitro, hydroxy, $S(O)_qR^{26}$, $OC(O)NR^{27}R^{28}$, $NR^{29}R^{30}$, $NR^{31}C(O)R^{32}$, $NR^{33}C(O)NR^{34}R^{35}$, $S(O)_2NR^{36}R^{37}$, $NR^{38}S(O)_2R^{39}$, $C(O)NR^{40}R^{41}$, $C(O)R^{42}$, $CO_2R^{43}$, $NR^{44}CO_2R^{45}$, $OC(O)(C_{1-6}$ alkyl), $C_{1-6}$ alkyl, $C_{1-6}$ hydroxyalkyl, $C_{1-6}$ haloalkyl, $C_{1-6}$ alkoxy$(C_{1-6})$alkyl, amino$(C_{1-4}$ alkyl), di$(C_{1-6})$alkylamino$(C_{1-6})$alkyl, $C_{1-6}$ alkoxy, $C_{1-6}$ haloalkoxy, hydroxyl$(C_{1-6}$ alkoxy), heterocyclyl$(C_{1-6}$ alkoxy), $C_{1-6}$ alkoxy$(C_{1-6})$alkoxy, amino$(C_{1-4}$ alkoxy), $C_{1-4}$ alkylamino $(C_{1-4}$ alkoxy) (itself optionally substituted by phenyl), di$(C_{1-4}$ alkyl)amino$(C_{1-4}$ alkoxy), $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, heterocyclyl, heterocyclyl$(C_{1-4}$ alkyl), phenyl, phenyl$(C_{1-4})$alkyl, phenoxy, phenylthio, phenyl$(C_{1-4})$alkoxy, heteroaryl, heteroaryl$(C_{1-4})$alkyl, heteroaryloxy or heteroaryl$(C_{1-4})$alkoxy; wherein any of the immediately foregoing phenyl and heteroaryl moieties are optionally substituted with halogen, hydroxy, nitro, $S(O)_r(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NH(O)_2(C_{1-4}$ alkyl), $C(O)(C_{1-4}$ alkyl), $CF_3$ or $OCF_3$, or $R^8$ is $C_{3-6}$ cycloalkyl substituted by $NR^{24}R^{25}$.

5. A compound of formula (I) as claimed in claim 1 wherein $R^5$ is methyl, ethyl or propyl substituted by piperidinyl, piperazinyl, morpholinyl, homomorpholinyl or homopiperazinyl.

6. A compound of formula (I) as claimed in claim 1 wherein $R^6$ is hydroxy or $C_{1-6}$ alkyl optionally substituted by piperidinyl, piperazinyl, morpholinyl, homomorpholinyl or homopiperazinyl.

7. A pharmaceutical composition which comprises a compound of the formula (I), or a pharmaceutically acceptable salt thereof as claimed in any one of claims 1 to 6, and a pharmaceutically acceptable adjuvant, diluent or carrier.

8. A pharmaceutical product comprising, in combination, a first active ingredient which is a compound of formula (I) as claimed in claim 1, or a pharmaceutically acceptable salt thereof, as hereinbefore described, and at least one further active ingredient selected from:— a β2. adrenoceptor agonist, a modulator of chemokine receptor function, an inhibitor of kinase function, a protease inhibitor, a steroidal glucocorticoid receptor agonist, an anticholinergic agent, or a non-steroidal glucocorticoid receptor agonist.

9. A compound of formula (I) as claimed in claim 1 wherein the compound is 2-(4'-(((3S,5R)-3,5-dimethylpiperazin-1-yl)methyl)-2'-(morpholinomethyl)biphenyl-3-yloxy)-5-fluoro-N-((1s,4s)-4-(2-hydroxy-5-methylbenzamido)cyclohexyl)nicotinamide, which has the formula shown below:

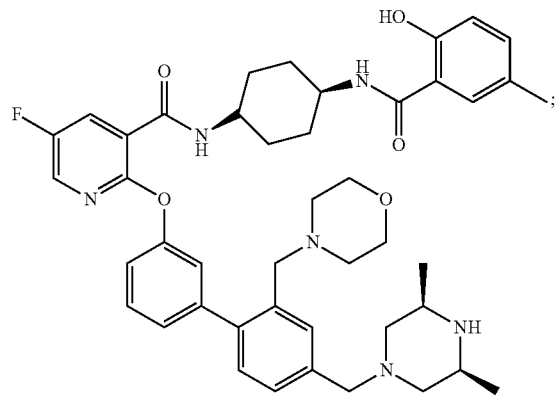

or a pharmaceutically acceptable salt thereof.

10. A pharmaceutical composition which comprises a compound, or a pharmaceutically acceptable salt thereof, as claimed in claim 9, and a pharmaceutically acceptable adjuvant, diluent or carrier.

11. A pharmaceutical product comprising, in combination, a first active ingredient which is a compound, or a pharmaceutically acceptable salt thereof, as claimed in claim 9, and at least one further active ingredient selected from:— a β2. adrenoceptor agonist, a modulator of chemokine receptor function, an inhibitor of kinase function, a protease inhibitor, a steroidal glucocorticoid receptor agonist, an anticholinergic agent, or a non-steroidal glucocorticoid receptor agonist.

12. A compound of formula (I) as claimed in claim 1 wherein the compound is N-((1s,4s)-4-(2-(4'-(((3S,5R)-3,5-dimethylpiperazin-1-yl)methyl)-2'-(morpholinomethyl)biphenyl-3-yloxy)-5-fluoronicotinamido)cyclohexyl)-4-methylthiazole-2-carboxamide, which has the formula shown below:

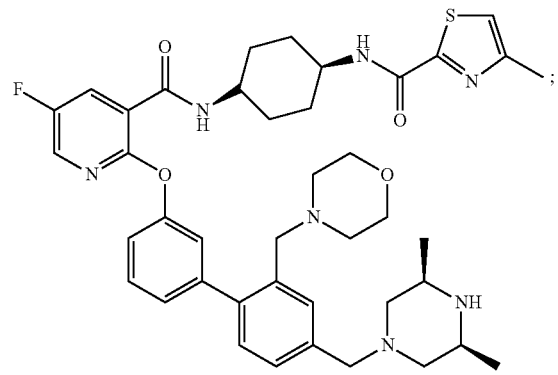

or a pharmaceutically acceptable salt thereof.

13. A pharmaceutical composition which comprises a compound, or a pharmaceutically acceptable salt thereof, as claimed in claim 12, and a pharmaceutically acceptable adjuvant, diluent or carrier.

14. A pharmaceutical product comprising, in combination, a first active ingredient which is a compound, or a pharmaceutically acceptable salt thereof, as claimed in claim 12, and at least one further active ingredient selected from:— a β2. adrenoceptor agonist,
a modulator of chemokine receptor function,
an inhibitor of kinase function,
a protease inhibitor,
a steroidal glucocorticoid receptor agonist,
an anticholinergic agent, or
a non-steroidal glucocorticoid receptor agonist.

15. A compound of formula (I) as claimed in claim 1 wherein the compound is N-((1s,4s)-4-(1,5-dimethyl-1H-pyrazole-3-carboxamido)cyclohexyl)-2-(4'-[((3S,5R)-3,5-dimethylpiperazin-1-yl)methyl)biphenyl-3-yloxy)-5-fluoronicotinamide, which has the formula shown below:

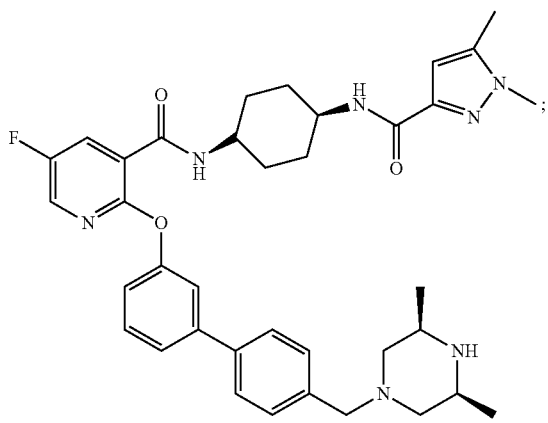

or a pharmaceutically acceptable salt thereof.

16. A pharmaceutical composition which comprises a compound, or a pharmaceutically acceptable salt thereof, as claimed in claim 15, and a pharmaceutically acceptable adjuvant, diluent or carrier.

17. A pharmaceutical product comprising, in combination, a first active ingredient which is a compound, or a pharmaceutically acceptable salt thereof, as claimed in claim 15, and at least one further active ingredient selected from:—
a β2. adrenoceptor agonist,
a modulator of chemokine receptor function,
an inhibitor of kinase function,
a protease inhibitor,
a steroidal glucocorticoid receptor agonist,
an anticholinergic agent, or
a non-steroidal glucocorticoid receptor agonist.

18. A compound of formula (I) as claimed in claim 1 wherein the compound is N-((1s,4s)-4-(1,5-dimethyl-1H-pyrazole-3-carboxamido)cyclohexyl)-2-(3'-[((3S,5R)-3,5-dimethylpiperazin-1-yl)methyl)biphenyl-3-yloxy)-5-fluoronicotinamide, which has the formula shown below:

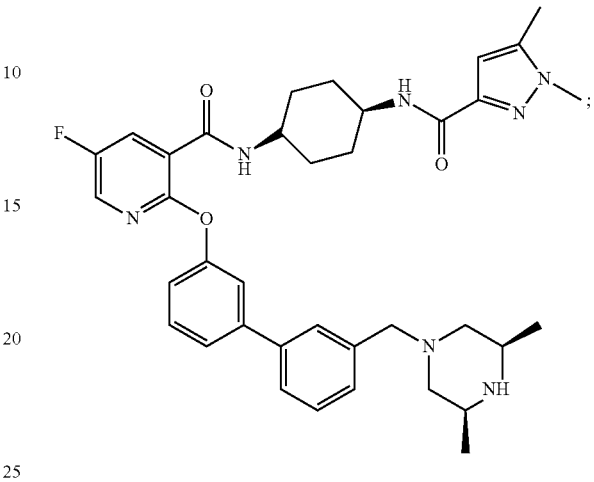

or a pharmaceutically acceptable salt thereof.

19. A pharmaceutical composition which comprises a compound, or a pharmaceutically acceptable salt thereof, as claimed in claim 18, and a pharmaceutically acceptable adjuvant, diluent or carrier.

20. A pharmaceutical product comprising, in combination, a first active ingredient which is a compound, or a pharmaceutically acceptable salt thereof, as claimed in claim 18, and at least one further active ingredient selected from:—
a β2. adrenoceptor agonist,
a modulator of chemokine receptor function,
an inhibitor of kinase function,
a protease inhibitor,
a steroidal glucocorticoid receptor agonist,
an anticholinergic agent, or
a non-steroidal glucocorticoid receptor agonist.

* * * * *

UNITED STATES PATENT AND TRADEMARK OFFICE
CERTIFICATE OF CORRECTION

PATENT NO. : 8,273,774 B2  Page 1 of 1
APPLICATION NO. : 12/471599
DATED : September 25, 2012
INVENTOR(S) : Glen Andrews et al.

It is certified that error appears in the above-identified patent and that said Letters Patent is hereby corrected as shown below:

Col. 250, line 19 and col. 252, line 10, "hydroxyl ($C_{1-6}$ alkoxy)," should read -- hydroxyl($C_{1-6}$ alkoxy), --.

Col. 250, line 46 and col. 252, line 38, "$R^{45}$," should read -- $R^{45}$ --.

Col. 251, line 5 and col. 252, line 64, "$R^{54}$ $R^{55}$" should read -- $R^{54}$, $R^{55}$ --.

Col. 251, line 7 and col. 252, line 66, "thereof" should read -- thereof; --.

Col. 252, line 19, "phenyl($C_{1-4}$ alkoxy," should read -- phenyl($C_{1-4}$alkoxy), --.

Col. 252, line 20, "heteroaryl($C_{1-4}$ alkyl," should read -- heteroaryl($C_{1-4}$alkyl), --.

Col. 253, line 46, "thereof" should read -- thereof, --.

Col. 255, line 10 and col. 256, line 3, "[((3S, 5R)" should read -- (((3S, 5R) --.

Signed and Sealed this
Twenty-second Day of January, 2013

David J. Kappos
*Director of the United States Patent and Trademark Office*